United States Patent
Anderson et al.

(10) Patent No.: US 11,649,227 B2
(45) Date of Patent: May 16, 2023

(54) ALLOSTERIC CHROMENONE INHIBITORS OF PHOSPHOINOSITIDE 3-KINASE (PI3K) FOR THE TREATMENT OF DISEASE

(71) Applicant: Petra Pharma Corporation, New York, NY (US)

(72) Inventors: Erin Danielle Anderson, Boulder, CO (US); Sean Douglas Aronow, Boulder, CO (US); Nicholas A. Boyles, Hillsboro, OR (US); Markus K. Dahlgren, Shelton, CT (US); Shulu Feng, Ridgewood, NJ (US); Aleksey I. Gerasyuto, Flemington, NJ (US); Eugene R. Hickey, Danbury, CT (US); Thomas Combs Irvin, Erie, CO (US); Edward A. Kesicki, New York, NY (US); Anke Klippel-Giese, Princeton, NJ (US); Jennifer Lynn Knight, Jersey City, NJ (US); Gabrielle R. Kolakowski, Longmont, CO (US); Manoj Kumar, Longmont, CO (US); Katelyn Frances Long, Lafayette, CO (US); Christopher Glenn Mayne, Boulder, CO (US); David L. McElligott, Bothell, WA (US); Johnathan Alexander McLean, Indianapolis, IN (US); Loredana Puca, New York, NY (US); Kannan Karukurichi Ravi, Fords, NJ (US); Daniel Lee Severance, San Diego, CA (US); Michael Brian Welch, Westminister, CO (US); Tien Widjaja, Lafayette, CO (US)

(73) Assignee: Petra Pharma Corporation, New York, NY (US)

(*) Notice: Subject to any disclaimer, the term of this patent is extended or adjusted under 35 U.S.C. 154(b) by 0 days.

(21) Appl. No.: 17/221,209

(22) Filed: Apr. 2, 2021

(65) Prior Publication Data
US 2022/0372023 A1  Nov. 24, 2022

Related U.S. Application Data

(60) Provisional application No. 63/005,096, filed on Apr. 3, 2020.

(51) Int. Cl.
*C07D 405/04* (2006.01)
*C07D 405/14* (2006.01)
*C07D 491/056* (2006.01)

(52) U.S. Cl.
CPC ......... *C07D 405/04* (2013.01); *C07D 405/14* (2013.01); *C07D 491/056* (2013.01)

(58) Field of Classification Search
CPC . C07D 405/04; C07D 405/14; C07D 491/056
See application file for complete search history.

(56) References Cited

U.S. PATENT DOCUMENTS

| | | | |
|---|---|---|---|
| 7,598,377 | B2 | 10/2009 | Jackson et al. |
| 7,872,011 | B2 | 1/2011 | Jackson et al. |
| 8,399,460 | B2 | 3/2013 | Barlaam et al. |
| 2007/0015802 | A1 | 1/2007 | Lal et al. |
| 2011/0098271 | A1 | 4/2011 | Barlaam et al. |

FOREIGN PATENT DOCUMENTS

| | | |
|---|---|---|
| CN | 108299365 A | 7/2018 |
| EP | 0223744 A2 | 5/1987 |
| EP | 0341104 A2 | 11/1989 |
| WO | 90/06921 A1 | 6/1990 |
| WO | 01/53266 A1 | 7/2001 |
| WO | 2004/004632 A2 | 1/2004 |
| WO | 2004/016607 A1 | 2/2004 |
| WO | 2010/037127 A1 | 4/2010 |
| WO | 2010/037129 A1 | 4/2010 |
| WO | 2011/051704 A1 | 5/2011 |

(Continued)

OTHER PUBLICATIONS

Science (1999), vol. 286, 531-537.*
Cancer and Metastasis Reviews (1998), 17(1), 91-106.*
Barlaam et al., Journal of Medical Chemistry, vol. 58, No. 2, Jan. 22, 2015, pp. 943-962.
Barlaam et al., Biorganic & Medicinal Chemistry Letters, vol. 26, No. 9, Mar. 11, 2016, pp. 2318-2323.
Fitzgerald et al., Annals of Oncology, v30, Supplement 5, Oct. 1, 2019, p. v110.

(Continued)

*Primary Examiner* — Rebecca L Anderson
(74) *Attorney, Agent, or Firm* — Joseph Pletcher

(57) ABSTRACT

The disclosure relates to compounds of Formula (I) as allosteric chromenone inhibitors of phosphoinositide 3-kinase (PI3K) useful in the treatment of diseases or disorders associated with PI3K modulation, Formula (I):

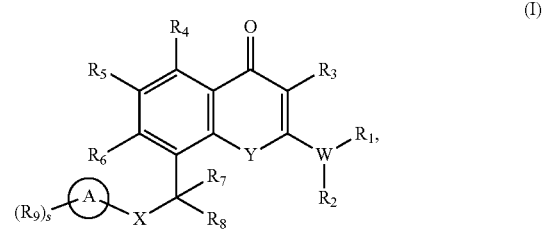

or a prodrug, solvate, enantiomer, stereoisomer, tautomer, or pharmaceutically acceptable salt thereof, wherein $R_1$, $R_2$, $R_3$, $R_4$, $R_5$, $R_6$, $R_7$, $R_8$, $R_9$, W, X, Y, s, and Ring A are as described herein.

20 Claims, No Drawings
Specification includes a Sequence Listing.

(56) References Cited

FOREIGN PATENT DOCUMENTS

WO 2017/156520 A1 9/2017
WO 2021/202964 A1 10/2021

OTHER PUBLICATIONS

Gaestel et al., Current Medicinal Chemistry, vol. 14, No. 21, Sep. 1, 2007, pp. 2214-2234.
Giordanetto et al., Bioorganic & Medicinal Chemistry Letters vol. 24, Issue 16, Aug. 15, 2014, pp. 3936-3943.
Hon et al., Oncogene (2012) 31, 3655-3666, published online Nov. 28, 2011.
Klippel, A. et al. Preclinical characterization of LOXO 783 (LOX-22783), a highly potent, mutantselective and brain-penetrant allosteric PI3Kα H1047R inhibitor. Presented at: 2021 AACR-NCI-EORTC Virtual International Conference on Molecular Targets and Cancer Therapeutics on: Oct. 7, 2021.
Li et al., Am J Clin Exp Urol 2014; 2(3):188-198; Epub 02 Oct. 2, 2014.
Written Opinion for PCT/US21/25521 (dated Jun. 28, 2021).
International Search Report for PCT/US21/25521 (dated Jun. 28, 2021).

\* cited by examiner

SEQUENCE LISTING

<160> NUMBER OF SEQ ID NOS: 2

<210> SEQ ID NO 1
<211> LENGTH: 1068
<212> TYPE: PRT
<213> ORGANISM: Homo sapiens

<400> SEQUENCE: 1

```
Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365
```

-continued

```
Asp Asn Val Asn Thr Gln Arg Val Pro Cys Ser Asn Pro Arg Trp Asn
370                 375                 380
Glu Trp Leu Asn Tyr Asp Ile Tyr Ile Pro Asp Leu Pro Arg Ala Ala
385                 390                 395                 400
Arg Leu Cys Leu Ser Ile Cys Ser Val Lys Gly Arg Lys Gly Ala Lys
                405                 410                 415
Glu Glu His Cys Pro Leu Ala Trp Gly Asn Ile Asn Leu Phe Asp Tyr
                420                 425                 430
Thr Asp Thr Leu Val Ser Gly Lys Met Ala Leu Asn Leu Trp Pro Val
            435                 440                 445
Pro His Gly Leu Glu Asp Leu Leu Asn Pro Ile Gly Val Thr Gly Ser
450                 455                 460
Asn Pro Asn Lys Glu Thr Pro Cys Leu Glu Leu Glu Phe Asp Trp Phe
465                 470                 475                 480
Ser Ser Val Val Lys Phe Pro Asp Met Ser Val Ile Glu Glu His Ala
                485                 490                 495
Asn Trp Ser Val Ser Arg Glu Ala Gly Phe Ser Tyr Ser His Ala Gly
                500                 505                 510
Leu Ser Asn Arg Leu Ala Arg Asp Asn Glu Leu Arg Glu Asn Asp Lys
            515                 520                 525
Glu Gln Leu Lys Ala Ile Ser Thr Arg Asp Pro Leu Ser Glu Ile Thr
530                 535                 540
Glu Gln Glu Lys Asp Phe Leu Trp Ser His Arg His Tyr Cys Val Thr
545                 550                 555                 560
Ile Pro Glu Ile Leu Pro Lys Leu Leu Leu Ser Val Lys Trp Asn Ser
                565                 570                 575
Arg Asp Glu Val Ala Gln Met Tyr Cys Leu Val Lys Asp Trp Pro Pro
                580                 585                 590
Ile Lys Pro Glu Gln Ala Met Glu Leu Leu Asp Cys Asn Tyr Pro Asp
            595                 600                 605
Pro Met Val Arg Gly Phe Ala Val Arg Cys Leu Glu Lys Tyr Leu Thr
610                 615                 620
Asp Asp Lys Leu Ser Gln Tyr Leu Ile Gln Leu Val Gln Val Leu Lys
625                 630                 635                 640
Tyr Glu Gln Tyr Leu Asp Asn Leu Leu Val Arg Phe Leu Leu Lys Lys
                645                 650                 655
Ala Leu Thr Asn Gln Arg Ile Gly His Phe Phe Phe Trp His Leu Lys
            660                 665                 670
Ser Glu Met His Asn Lys Thr Val Ser Gln Arg Phe Gly Leu Leu Leu
            675                 680                 685
Glu Ser Tyr Cys Arg Ala Cys Gly Met Tyr Leu Lys His Leu Asn Arg
690                 695                 700
Gln Val Glu Ala Met Glu Lys Leu Ile Asn Leu Thr Asp Ile Leu Lys
705                 710                 715                 720
Gln Glu Lys Lys Asp Glu Thr Gln Lys Val Gln Met Lys Phe Leu Val
                725                 730                 735
Glu Gln Met Arg Arg Pro Asp Phe Met Asp Ala Leu Gln Gly Phe Leu
                740                 745                 750
Ser Pro Leu Asn Pro Ala His Gln Leu Gly Asn Leu Arg Leu Glu Glu
            755                 760                 765
Cys Arg Ile Met Ser Ser Ala Lys Arg Pro Leu Trp Leu Asn Trp Glu
770                 775                 780
Asn Pro Asp Ile Met Ser Glu Leu Leu Phe Gln Asn Asn Glu Ile Ile
```

```
                785                 790                 795                 800
        Phe Lys Asn Gly Asp Asp Leu Arg Gln Asp Met Leu Thr Leu Gln Ile
                        805                 810                 815

Ile Arg Ile Met Glu Asn Ile Trp Gln Asn Gln Gly Leu Asp Leu Arg
                        820                 825                 830

Met Leu Pro Tyr Gly Cys Leu Ser Ile Gly Asp Cys Val Gly Leu Ile
                        835                 840                 845

Glu Val Val Arg Asn Ser His Thr Ile Met Gln Ile Gln Cys Lys Gly
                        850                 855                 860

Gly Leu Lys Gly Ala Leu Gln Phe Asn Ser His Thr Leu His Gln Trp
        865                 870                 875                 880

Leu Lys Asp Lys Asn Lys Gly Glu Ile Tyr Asp Ala Ala Ile Asp Leu
                        885                 890                 895

Phe Thr Arg Ser Cys Ala Gly Tyr Cys Val Ala Thr Phe Ile Leu Gly
                        900                 905                 910

Ile Gly Asp Arg His Asn Ser Asn Ile Met Val Lys Asp Asp Gly Gln
                        915                 920                 925

Leu Phe His Ile Asp Phe Gly His Phe Leu Asp His Lys Lys Lys Lys
            930                 935                 940

Phe Gly Tyr Lys Arg Glu Arg Val Pro Phe Val Leu Thr Gln Asp Phe
        945                 950                 955                 960

Leu Ile Val Ile Ser Lys Gly Ala Gln Glu Cys Thr Lys Thr Arg Glu
                        965                 970                 975

Phe Glu Arg Phe Gln Glu Met Cys Tyr Lys Ala Tyr Leu Ala Ile Arg
                        980                 985                 990

Gln His Ala Asn Leu Phe Ile Asn Leu Phe Ser Met Met Leu Gly Ser
                        995                 1000                1005

Gly Met Pro Glu Leu Gln Ser Phe Asp Asp Ile Ala Tyr Ile Arg
                        1010                1015                1020

Lys Thr Leu Ala Leu Asp Lys Thr Glu Gln Glu Ala Leu Glu Tyr
                        1025                1030                1035

Phe Met Lys Gln Met Asn Asp Ala His His Gly Gly Trp Thr Thr
                        1040                1045                1050

Lys Met Asp Trp Ile Phe His Thr Ile Lys Gln His Ala Leu Asn
                        1055                1060                1065

<210> SEQ ID NO 2
<211> LENGTH: 1068
<212> TYPE: PRT
<213> ORGANISM: Homo sapiens

<400> SEQUENCE: 2

Met Pro Pro Arg Pro Ser Ser Gly Glu Leu Trp Gly Ile His Leu Met
        1               5                   10                  15

Pro Pro Arg Ile Leu Val Glu Cys Leu Leu Pro Asn Gly Met Ile Val
                        20                  25                  30

Thr Leu Glu Cys Leu Arg Glu Ala Thr Leu Ile Thr Ile Lys His Glu
                        35                  40                  45

Leu Phe Lys Glu Ala Arg Lys Tyr Pro Leu His Gln Leu Leu Gln Asp
            50                  55                  60

Glu Ser Ser Tyr Ile Phe Val Ser Val Thr Gln Glu Ala Glu Arg Glu
        65                  70                  75                  80

Glu Phe Phe Asp Glu Thr Arg Arg Leu Cys Asp Leu Arg Leu Phe Gln
                        85                  90                  95
```

```
Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
            115                 120                 125

Asp Met Val Lys Asp Pro Glu Val Gln Asp Phe Arg Arg Asn Ile Leu
            130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                    165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
            195                 200                 205

Leu Lys Ile Asn His Asp Cys Val Pro Glu Gln Val Ile Ala Glu Ala
            210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                    245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
            275                 280                 285

Ala Lys Glu Ser Leu Tyr Ser Gln Leu Pro Met Asp Cys Phe Thr Met
            290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                    325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
            355                 360                 365

Asp Asn Val Asn Thr Gln Arg Val Pro Cys Ser Asn Pro Arg Trp Asn
            370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                    405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
            435                 440                 445

Pro His Gly Leu Glu Asp Leu Leu Asn Pro Ile Gly Val Thr Gly Ser
            450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                    485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
```

```
              515                 520                 525
Glu Gln Leu Lys Ala Ile Ser Thr Arg Asp Pro Leu Ser Glu Ile Thr
    530                 535                 540
Glu Gln Glu Lys Asp Phe Leu Trp Ser His Arg His Tyr Cys Val Thr
545                 550                 555                 560
Ile Pro Glu Ile Leu Pro Lys Leu Leu Leu Ser Val Lys Trp Asn Ser
                565                 570                 575
Arg Asp Glu Val Ala Gln Met Tyr Cys Leu Val Lys Asp Trp Pro Pro
            580                 585                 590
Ile Lys Pro Glu Gln Ala Met Glu Leu Leu Asp Cys Asn Tyr Pro Asp
        595                 600                 605
Pro Met Val Arg Gly Phe Ala Val Arg Cys Leu Glu Lys Tyr Leu Thr
    610                 615                 620
Asp Asp Lys Leu Ser Gln Tyr Leu Ile Gln Leu Val Gln Val Leu Lys
625                 630                 635                 640
Tyr Glu Gln Tyr Leu Asp Asn Leu Leu Val Arg Phe Leu Leu Lys Lys
                645                 650                 655
Ala Leu Thr Asn Gln Arg Ile Gly His Phe Phe Trp His Leu Lys
            660                 665                 670
Ser Glu Met His Asn Lys Thr Val Ser Gln Arg Phe Gly Leu Leu Leu
        675                 680                 685
Glu Ser Tyr Cys Arg Ala Cys Gly Met Tyr Leu Lys His Leu Asn Arg
    690                 695                 700
Gln Val Glu Ala Met Glu Lys Leu Ile Asn Leu Thr Asp Ile Leu Lys
705                 710                 715                 720
Gln Glu Lys Lys Asp Glu Thr Gln Lys Val Gln Met Lys Phe Leu Val
                725                 730                 735
Glu Gln Met Arg Arg Pro Asp Phe Met Asp Ala Leu Gln Gly Phe Leu
            740                 745                 750
Ser Pro Leu Asn Pro Ala His Gln Leu Gly Asn Leu Arg Leu Glu Glu
        755                 760                 765
Cys Arg Ile Met Ser Ser Ala Lys Arg Pro Leu Trp Leu Asn Trp Glu
    770                 775                 780
Asn Pro Asp Ile Met Ser Glu Leu Leu Phe Gln Asn Asn Glu Ile Ile
785                 790                 795                 800
Phe Lys Asn Gly Asp Asp Leu Arg Gln Asp Met Leu Thr Leu Gln Ile
                805                 810                 815
Ile Arg Ile Met Glu Asn Ile Trp Gln Asn Gln Gly Leu Asp Leu Arg
            820                 825                 830
Met Leu Pro Tyr Gly Cys Leu Ser Ile Gly Asp Cys Val Gly Leu Ile
        835                 840                 845
Glu Val Val Arg Asn Ser His Thr Ile Met Gln Ile Gln Cys Lys Gly
    850                 855                 860
Gly Leu Lys Gly Ala Leu Gln Phe Asn Ser His Thr Leu His Gln Trp
865                 870                 875                 880
Leu Lys Asp Lys Asn Lys Gly Glu Ile Tyr Asp Ala Ala Ile Asp Leu
                885                 890                 895
Phe Thr Arg Ser Cys Ala Gly Tyr Cys Val Ala Thr Phe Ile Leu Gly
            900                 905                 910
Ile Gly Asp Arg His Asn Ser Asn Ile Met Val Lys Asp Asp Gly Gln
        915                 920                 925
Leu Phe His Ile Asp Phe Gly His Phe Leu Asp His Lys Lys Lys Lys
    930                 935                 940
```

```
Phe Gly Tyr Lys Arg Glu Arg Val Pro Phe Val Leu Thr Gln Asp Phe
945                 950                 955                 960
Leu Ile Val Ile Ser Lys Gly Ala Gln Glu Cys Thr Lys Thr Arg Glu
                965                 970                 975
Phe Glu Arg Phe Gln Glu Met Cys Tyr Lys Ala Tyr Leu Ala Ile Arg
            980                 985                 990
Gln His Ala Asn Leu Phe Ile Asn Leu Phe Ser Met Met Leu Gly Ser
        995                 1000                1005
Gly Met Pro Glu Leu Gln Ser Phe Asp Asp Ile Ala Tyr Ile Arg
    1010            1015                1020
Lys Thr Leu Ala Leu Asp Lys Thr Glu Gln Glu Ala Leu Glu Tyr
1025            1030                1035
Phe Met Lys Gln Met Asn Asp Ala Arg His Gly Gly Trp Thr Thr
1040                1045                1050
Lys Met Asp Trp Ile Phe His Thr Ile Lys Gln His Ala Leu Asn
1055                1060                1065
```

ALLOSTERIC CHROMENONE INHIBITORS OF PHOSPHOINOSITIDE 3-KINASE (PI3K) FOR THE TREATMENT OF DISEASE

CROSS-REFERENCE

This application claims priority to U.S. Provisional Application No. 63/005,096, filed Apr. 3, 2020, the content of which is herein incorporated by reference in its entirety.

SEQUENCE LISTING

The instant application contains a Sequence Listing that has been submitted electronically in ASCII format and is hereby incorporated by reference in its entirety. Said ASCII copy, amended Aug. 18, 2022, is named X22826_18 Aug. 2022_ST25.txt and is 18200 bytes in size.

FIELD

The present disclosure is directed to allosteric chromenone inhibitors of phosphoinositide 3-kinase (PI3K) useful in the treatment of diseases or disorders associated with PI3K modulation. The disclosure is directed toward compounds and compositions which inhibit PI3K, methods of treating a disease or disorder associated with PI3K (e.g., CLOVES syndrome (congenital lipomatous overgrowth, vascular malformations, epidermal naevi, scoliosis/skeletal and spinal syndrome), PIK3CA-related overgrowth syndrome (PROS), breast cancer, brain cancer, prostate cancer, endometrial cancer, gastric cancer, leukemia, lymphoma, sarcoma, colorectal cancer, lung cancer, ovarian cancer, skin cancer, or head and neck cancer), and methods of using PI3K inhibitors in combination with one or more additional disorder or cancer therapy.

BACKGROUND

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids within cells. These enzymes, and the resulting phosphorylated lipids and lipid-derived biologically active organic molecules, play a role in many different physiological processes, including cell proliferation, migration, adhesion, and differentiation. A particular group of lipid kinases comprises membrane lipid kinases, i.e., kinases that catalyze the phosphorylation of lipids contained in or associated with cell membranes. Examples of such enzymes include phosphinositide(s) kinases (such as PI3-kinases, PI4-Kinases), diacylglycerol kinases, and sphingosine kinases.

The phosphoinositide 3-kinases (PI3Ks) signaling pathway is one of the most highly mutated systems in human cancers. PI3K signaling is involved in many other disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation (Katso et al., 2001). The class I PI3Ks (p110α, p110β, p110δ, and p110γ) are typically activated by tyrosine kinases or G-protein coupled receptors to generate PIP3, which engages downstream effectors such as those in the pathways of Akt/PDK1, mTOR, the Tec family kinases, and the Rho family GTPases. The class II and III PI3-Ks play a key role in intracellular trafficking through the synthesis of PI(3)P and $PI(3,4)P_2$.

The PI3K isoforms have been implicated, for example, in a variety of human cancers and disorders. Mutations in the gene coding for PI3K isoforms or mutations which lead to upregulation of a PI3K isoform are believed to occur in many human cancers. Mutations in the gene coding for a PI3K isoform are point mutations clustered within several hotspots in helical and kinase domains. Because of the high rate of PI3K mutations, targeting of this pathway may provide valuable therapeutic opportunities.

Genetic alterations in genes in PI3K signaling are believed to be involved in a range of cancers such as endometrial cancer, breast cancer, esophageal squamous-cell cancer, cervical squamous-cell carcinoma, cervical adenocarcinoma, colorectal adenocarcinoma, bladder urothelial carcinoma, glioblastoma, ovarian cancer, non-small-cell lung cancer, esophagogastric cancer, nerve-sheath tumor, head and neck squamous-cell carcinoma, melanoma, esophagogastric adenocarcinoma, soft-tissue sarcoma, prostate cancer, fibrolamellar carcinoma, hepatocellular carcinoma, diffuse glioma, colorectal cancer, pancreatic cancer, cholangiocarcinoma, B-cell lymphoma, mesothelioma, adrenocortical carcinoma, renal non-clear-cell carcinoma, renal clear-cell carcinoma, germ-cell carcinoma, thymic tumor, pheochromocytoma, miscellaneous neuroepithelial tumor, thyroid cancer, leukemia, and encapsulated glioma (Goncalves M D, Hopkins B D, Cantley L C. Phosphatidylinositol 3-Kinase, Growth Disorders, and Cancer. N Engl J Med. 2018 Nov. 22; 379(21):2052-2062).

The alpha (α) isoform of PI3K has been implicated, for example, in a variety of human cancers. Angiogenesis has been shown to selectively require the a isoform of PI3K in the control of endothelial cell migration. (Graupera et al, Nature 2008; 453; 662-6). Mutations in the gene coding for PI3Kα or mutations which lead to upregulation of PI3Kα are believed to occur in many human cancers such as lung, stomach, endometrial, ovarian, bladder, breast, colon, brain, prostate, and skin cancers. Mutations in the gene coding for PI3Kα are point mutations clustered within several hotspots in helical and kinase domains, such as E542K, E545K, and H1047R. Many of these mutations have been shown to be oncogenic gain-of-function mutations. Because of the high rate of PI3Kα mutations, targeting of this pathway may provide valuable therapeutic opportunities. While other PI3K isoforms such as PI3Kδ or PI3Kγ are expressed primarily in hematopoietic cells, PI3Kα, along with PI3Kβ, is expressed constitutively.

Due to the central role of PI3Kα in regulating organismal glucose homeostasis, PI3K inhibition in patients often gives rise to hyperglycemia and/or hyperinsulinemia (Busaidy N L, et al, Management of metabolic effects associated with anticancer agents targeting the PI3K-Akt-mTOR pathway. J Clin Oncol 2012; 30:2919-28). High levels of circulating insulin could potentially be mitogenic and/or antiapoptotic for cancer cells and thus negate the antiproliferative effects of PI3K inhibitors (Blouin M-J, et al, Abstract 4615: the hyperinsulinemia caused by PI3K inhibitors attenuates their antineoplastic efficacy, but can be minimized by co-administration of metformin. Cancer Res 2013; 73:4615).

In the setting of cancer with mutated PI3Kα, one way to overcome the problem of compensatory production of insulin and/or glucose upon systemic PI3Kα inhibition would be to develop inhibitors with enhanced selectivity for mutant PI3Kα over wild-type PI3Kα. This would create an increased window for drug dosing to selectively inhibit the pathologic signaling of mutant PI3Kα in the cancer cells without affecting the wild-type PI3Kα in the host tissues that control systemic metabolism (Okkenhaug K, Graupera M, Vanhaesebroeck B. Targeting PI3K in Cancer: Impact on Tumor Cells, Their Protective Stroma, Angiogenesis, and Immunotherapy. Cancer Discov. 2016 October; 6(10):1090-1105), thus limiting toxicities and permitting higher doses and more complete inhibition of the drug target (Ariella B. Hanker, et al, Challenges for the clinical development of PI3K inhibitors: Strategies to improve their impact in solid tumors. Cancer Discov. 2019 April; 9(4): 482-491).

Currently PI3Kα inhibitors are nearly equipotent to wild-type and mutant PI3Kα. Mutant selective inhibitors have been elusive due to the PI3Kα mutations location far from the active site. As such, inhibitors which target a second, peripheral binding pocket near a known mutation (e.g., H1047R) may provide a route to selective PI3Kα inhibition. Thus, targeting a mutated, peripheral binding pocket of PI3Kα, may in turn provide a valuable therapeutic target for drug development.

As such, kinases, for example lipid kinases such as PI3Ks, are prime targets for drug development. The present disclosure provides a new class of kinase inhibitors.

SUMMARY

In one aspect, the present disclosure relates to compounds of Formula (I) or pharmaceutically acceptable salts thereof, or prodrugs, solvates, hydrates, isomers, or tautomers thereof:

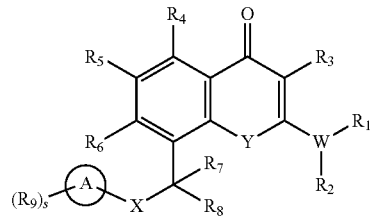

wherein:
X is —$NR_{12}$— or —O—;
Y is —$C(R_{11})_2$—, —O—, —$NR_{11}$—, or —S—;
W is —N—, —O—, or —S—, wherein when W is —O— or —S—, $R_1$ or $R_2$ is absent;
each $R_1$ and $R_2$ is independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle, aryl, or heteroaryl, wherein the cycloalkyl, heterocycle, aryl, and heteroaryl are optionally substituted with one or more oxo, =$NR_{12}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$, $C_3$-$C_6$ cycloalkyl, aryl, heteroaryl, or $R_{15}$; or
$R_1$ and $R_2$, together with the nitrogen to which they are attached, form a heterocycle comprising 1-4 heteroatoms selected from O, N, and S, wherein the heterocycle is optionally substituted with one or more $R_{10}$;
each $R_3$, $R_4$, $R_5$, and $R_6$ is independently H, halogen, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, aryl, heterocycle comprising 1-4 heteroatoms selected from O, N, and S, or heteroaryl comprising 1-4 heteroatoms selected from O, N, and S;
each $R_7$ and $R_8$ is independently H, halogen, —CN, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;
$R_9$ at each occurrence is independently oxo, =$NR_{11}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$N(R_{12})_2$, —$(CH_2)_m$—$OR_{12}$, —$(CH_2)_m$—$CR_{13}(OH)$—$R_{12}$, —$(CH_2)_m$—$C(O)R_{12}$, —$(CH_2)_m$—$C(O)OR_{12}$, —$(CH_2)_m$—$C(O)N(R_{12})_2$, —$(CH_2)_m$—$C(O)N(OH)R_{12}$, —$(CH_2)_m$—$SO_2R_{12}$, —$(CH_2)_m$—$SO_2$—$OR_{12}$, —$(CH_2)_m$—$SO_2N(R_{12})_2$, —$(CH_2)_m$—$P(O)(OR_{12})_2$, —$(CH_2)_m$—$P(O)(R_{12})_2$, —$(CH_2)_m$—$P(O)(OR_{13})R_{12}$, —$(CH_2)_m$—$B(OH)_2$, —$(CH_2)_m$—$B(R_{12})_2$, —$(CH_2)_m$—O—$(CH_2CH_2$—O$)_r R_{13}$, —$(CH_2)_m$—$NR_{12}$—$(CH_2CH_2$—O$)_r R_{13}$, —$(CH_2)_m$—C(O)—$(CH_2CH_2$—O$)_r R_{13}$, —$(CH_2)_m$—C(O)O—$(CH_2CH_2$—O$)_r R_{13}$, —$(CH_2)_m$—$C(O)NR_{12}$—$(CH_2CH_2$—O$)_r R_{13}$, —$(CH_2)_m$—C(O)—$NR_{12}$—$SO_2R_{13}$, —$(CH_2)_m$—$SO_2NR_{12}$—$C(O)R_{13}$, —$(CH_2)_m$—$S(O)(NR_{12})$—$R_{13}$, $C_3$-$C_{10}$ cycloalkyl, aryl, heterocycle comprising 1-4 heteroatoms selected from O, N, and S, or heteroaryl comprising 1-4 heteroatoms selected from N, O, and S, wherein the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, aryl, heterocycle, or heteroaryl is optionally substituted with one or more oxo, halogen, —CN, —OH, —$NH_2$, —$NO_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or two $R_9$, together with the atoms to which they are attached form a $C_3$-$C_{10}$ cycloalkyl, an aryl, or a heterocycle comprising 1-4 heteroatoms selected from O, N, and S, wherein the cycloalkyl, aryl, or heterocycle is optionally substituted with one or more oxo, halogen, —CN, —OH, —NH$_2$, =NH, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

$R_{10}$ at each occurrence is independently oxo, halogen, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_n$—OR$_{12}$, —(CH$_2$)$_n$—N(R$_{12}$)$_2$, —(CH$_2$)$_n$—C(O)R$_{12}$, —(CH$_2$)$_n$—C(O)OR$_{12}$, —(CH$_2$)$_n$—C(O)N(R$_{12}$)$_2$, —(CH$_2$)$_n$—SO$_2$R$_{12}$, —(CH$_2$)$_n$—O—(CH$_2$CH$_2$—O)$_r$R$_{13}$, $C_3$-$C_{10}$ cycloalkyl, heterocycle, —(CH$_2$)$_n$-aryl, or heteroaryl, wherein the cycloalkyl, heterocycle, aryl, and heteroaryl is optionally substituted with halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, —(CH$_2$)$_n$—SO$_2$R$_{12}$, —(CH$_2$)$_n$—C(O)R$_{12}$, —(CH$_2$)$_n$—C(O)OR$_{12}$, or —(CH$_2$)$_n$—C(O)N(R$_{12}$)$_2$, or two $R_{10}$, together with the atoms to which they are attached, form a $C_3$-$C_{10}$ cycloalkyl, an aryl, a heterocycle comprising 1-4 heteroatoms selected from O, N, and S, or a heteroaryl, wherein the cycloalkyl, aryl, heterocycle, and heteroaryl are optionally substituted with one or more oxo, =NR$_{12}$, halogen, —CN, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_n$—OR$_{12}$, —(CH$_2$)$_n$—N(R$_{12}$)$_2$, —(CH$_2$)$_n$—C(O)R$_{12}$, —(CH$_2$)$_n$—C(O)OR$_{12}$, —(CH$_2$)$_n$—C(O)N(R$_{12}$)$_2$, —(CH$_2$)$_n$—SO$_2$R$_{12}$, $C_3$-$C_6$ cycloalkyl, aryl, heteroaryl, or $R_{15}$;

$R_{11}$ is H, $C_1$-$C_6$ alkyl, $C_2$-$C_6$ alkenyl, or $C_2$-$C_6$ alkynyl;

each $R_{12}$ and $R_{13}$ at each occurrence is independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_q$—O—C(O)—(CH$_2$)$_r$—R$_{14}$, —(CH$_2$)$_q$—NH—C(O)—(CH$_2$)$_r$—R$_{14}$, —(CH$_2$)$_q$—O—C(O)—(CH$_2$)$_r$—OR$_{14}$, —(CH$_2$)$_q$—NH—C(O)—(CH$_2$)$_r$—OR$_{14}$, —(CH$_2$)$_q$—O—(CH$_2$)$_r$—R$_{14}$, —(CH$_2$)$_q$—NH—(CH$_2$)$_r$—R$_{14}$, —(CH$_2$)$_q$—O—(CH$_2$)$_r$—OR$_{14}$, —(CH$_2$)$_q$—NH—(CH$_2$)$_r$—OR$_{14}$, $C_3$-$C_{10}$ cycloalkyl, heterocycle comprising 1-4 heteroatoms selected from O, N, and S, —(CH$_2$)$_q$-aryl, or heteroaryl comprising 1-4 heteroatoms selected from N, O, and S, wherein the cycloalkyl, heterocycle, aryl, and heteroaryl are optionally substituted with one or more halogen, $C_1$-$C_6$ alkyl, $C_1$-$C_6$ haloalkyl, $C_1$-$C_6$ alkoxy, or $C_1$-$C_6$ haloalkoxy;

Ring A is $C_3$-$C_{10}$ cycloalkyl, aryl, heterocycle comprising 1-4 heteroatoms selected from N, O, and S, or heteroaryl comprising 1-4 heteroatoms selected from N, O, and S;

$R_{14}$ is

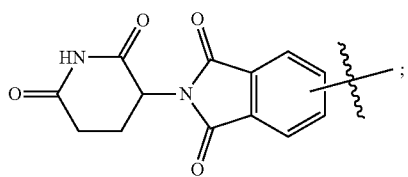

two $R_{15}$, together with the atoms to which they are attached form a cycloalkyl, an aryl, a heterocycle comprising 1-4 heteroatoms selected from O, N, and S, or a heteroaryl, wherein the cycloalkyl, aryl, heterocycle, and heteroaryl are optionally substituted with one or more $C_1$-$C_6$ alkyl, $C_1$-$C_6$ haloalkyl, $C_1$-$C_6$ alkoxy, —(CH$_2$)$_n$—OR$_{12}$, —(CH$_2$)$_n$—N(R$_{12}$)$_2$, —(CH$_2$)$_n$—C(O)R$_{12}$, —(CH$_2$)$_n$—C(O)OR$_{12}$, —(CH$_2$)$_n$—C(O)N(R$_{12}$)$_2$, or —(CH$_2$)$_n$—SO$_2$R$_{12}$; and each n, m, q, r, or s is independently at each occurrence 0, 1, 2, 3, 4, 5, or 6;

provided that when $R_1$ and $R_2$ together with the nitrogen atom to which they are attached form a morpholine and:
  i. when Y is —O—; $R_3$, $R_4$, and $R_6$ are hydrogen; $R_7$ is methyl; X is —NR$_{12}$— and Ring A is aryl; then $R_5$ is not —C(O)N(R$_{12}$)$_2$ or C(O)OR$_{12}$;
  ii. when Y is —O—, or —NR$_{11}$—; $R_3$, $R_4$, $R_6$ and $R_8$ are hydrogen; $R_7$ is H or $C_1$-$C_6$ alkyl; X is —NR$_{12}$— and Ring A is phenyl or pyridyl; then $R_5$ is not H, OH, OCH$_3$, OCF$_3$, F, Cl, CF$_3$, $C_1$-$C_6$ alkyl, or —(CH$_2$)$_m$-aryl; or
  iii. when $R_5$ is —CH$_3$, then either (a) the morpholine is substituted or (b) Ring A is not phenyl.

In a preferred embodiment of Formula (I), s is at least 1 and at least one $R_9$ is —C(O)OR$_{12}$.

In another preferred embodiment of Formula (I), W is —N—, and $R_1$ and $R_2$, together with the nitrogen to which they are attached, form a heterocycle comprising 1-4 heteroatoms selected from O, N, and S, wherein the heterocycle is optionally substituted with one or more $R_{10}$, and wherein said heterocycle is not an optionally substituted morpholine.

In another preferred embodiment of Formula (I), s is at least 1, at least one $R_9$ is —C(O)OR$_{12}$, W is —N—, and $R_1$ and $R_2$, together with the nitrogen to which they are attached, form a heterocycle comprising 1-4 heteroatoms selected from O, N, and S, wherein the heterocycle is optionally substituted with one or more $R_{10}$, and wherein said heterocycle is not an optionally substituted morpholine.

In another aspect, the present disclosure generally relates to methods for treating cancer. These methods comprise administering to a subject in need thereof, a therapeutically effective amount of a PI3K inhibitor (e.g., PI3Kα inhibitor or PI3KA H1047R mutant inhibitor).

In some embodiments, the PI3K inhibitor (e.g., PI3Kα inhibitor or PI3KA H1047R mutant inhibitor) is a compound of Formula (I), (Ia), (Ib), (Ic), (Id), (Ie), (If), (Ig), (Ih), or (II), or a pharmaceutically acceptable salt, prodrug, solvate, hydrate, isomer, or tautomer thereof.

In another aspect, the present disclosure provides a compound obtainable by, or obtained by, a method for preparing a compound as described herein (e.g., a method comprising one or more steps described in the Schemes).

In another aspect, the present disclosure provides a pharmaceutical composition comprising a compound of Formula (I), (Ia), (Ib), (Ic), (Id), (Ie), (If), (Ig), (Ih), or (II), or a pharmaceutically acceptable salt, prodrug, solvate, hydrate, isomer, or tautomer thereof, and a pharmaceutically acceptable diluent or carrier.

In another aspect, the present disclosure provides an intermediate as described herein, being suitable for use in a method for preparing a compound as described herein (e.g., the intermediate is selected from the intermediates described in the Examples).

In another aspect, the present disclosure provides a method of modulating PI3K (e.g., PI3Kα) activity (e.g., in vitro or in vivo), comprising contacting a cell with a therapeutically effective amount of a compound of Formula (I), (Ia), (Ib), (Ic), (Id), (Ie), (If), (Ig), (Ih), or (II), or a pharmaceutically acceptable salt, prodrug, solvate, hydrate, isomer, or tautomer thereof.

In some embodiments, the PI3Kα sequence correlates with NCBI Reference Sequence: NP_006209.2. In some embodiments, the PI3Kβ sequence correlates with NCBI Reference Sequence: NP_006210.1.

In some aspects, an amino acid sequence encoding PI3Kα comprises or consists of an amino acid sequence:

(SEQ ID NO: 1)
MPPRPSSGELWGIHLMPPRILVECLLPNGMIVTLECLREATLITIKHELFK

EARKYPLHQLLQDESSYIFVSVTQEAEREEFFDETRRLCDLRLFQPFLKVI

EPVGNREEKILNREIGFAIGMPVCEFDMVKDPEVQDFRRNILNVCKEAVDL

RDLNSPHSRAMYVYPPNVESSPELPKHIYNKLDKGQIIVVIWVIVSPNNDK

QKYTLKINHDCVPEQVIAEAIRKKTRSMLLSSEQLKLCVLEYQGKYILKVC

GCDEYFLEKYPLSQYKYIRSCIMLGRMPNLMLMAKESLYSQLPMDCFTMPS

YSRRISTATPYMNGETSTKSLWVINSALRIKILCATYVNVNIRDIDKIYVR

TGIYHGGEPLCDNVNTQRVPCSNPRWNEWLNYDIYIPDLPRAARLCLSICS

VKGRKGAKEEHCPLAWGNINLFDYTDTLVSGKMALNLWPVPHGLEDLLNPI

GVTGSNPNKETPCLELEFDWFSSVVKFPDMSVIEEHANWSVSREAGFSYSH

AGLSNRLARDNELRENDKEQLKAISTRDPLSEITEQEKDFLWSHRHYCVTI

PEILPKLLLSVKWNSRDEVAQMYCLVKDWPPIKPEQAMELLDCNYPDPMVR

GFAVRCLEKYLTDDKLSQYLIQLVQVLKYEQYLDNLLVRFLLKKALTNQRI

GHFFFWHLKSEMHNKTVSQRFGLLLESYCRACGMYLKHLNRQVEAMEKLIN

LTDILKQEKKDETQKVQMKFLVEQMRRPDFMDALQGFLSPLNPAHQLGNLR

LEECRIMSSAKRPLWLNWENPDIMSELLFQNNEIIFKNGDDLRQDMLTLQI

IRIMENIWQNQGLDLRMLPYGCLSIGDCVGLIEVVRNSHTIMQIQCKGGLK

GALQFNSHTLHQWLKDKNKGEIYDAAIDLFTRSCAGYCVATFILGIGDRHN

SNIMVKDDGQLFHIDFGHFLDHKKKKFGYKRERVPFVLTQDFLIVISKGAQ

ECTKTREFERFQEMCYKAYLAIRQHANLFINLFSMMLGSGMPELQSFDDIA

YIRKTLALDKTEQEALEYFMKQMNDAHHGGWTTKMDWIFHTIKQHALN.

In some aspects, an amino acid sequence encoding PI3Kα with a H1047R mutation comprises or consists of an amino acid sequence:

(SEQ ID NO: 2)
MPPRPSSGELWGIHLMPPRILVECLLPNGMIVTLECLREATLITIKHELFK

EARKYPLHQLLQDESSYIFVSVTQEAEREEFFDETRRLCDLRLFQPFLKVI

EPVGNREEKILNREIGFAIGMPVCEFDMVKDPEVQDFRRNILNVCKEAVDL

RDLNSPHSRAMYVYPPNVESSPELPKHIYNKLDKGQIIVVIWVIVSPNNDK

QKYTLKINHDCVPEQVIAEAIRKKTRSMLLSSEQLKLCVLEYQGKYILKVC

GCDEYFLEKYPLSQYKYIRSCIMLGRMPNLMLMAKESLYSQLPMDCFTMPS

YSRRISTATPYMNGETSTKSLWVINSALRIKILCATYVNVNIRDIDKIYVR

TGIYHGGEPLCDNVNTQRVPCSNPRWNEWLNYDIYIPDLPRAARLCLSICS

VKGRKGAKEEHCPLAWGNINLFDYTDTLVSGKMALNLWPVPHGLEDLLNPI

GVTGSNPNKETPCLELEFDWFSSVVKFPDMSVIEEHANWSVSREAGFSYSH

AGLSNRLARDNELRENDKEQLKAISTRDPLSEITEQEKDFLWSHRHYCVTI

PEILPKLLLSVKWNSRDEVAQMYCLVKDWPPIKPEQAMELLDCNYPDPMVR

GFAVRCLEKYLTDDKLSQYLIQLVQVLKYEQYLDNLLVRFLLKKALTNQRI

GHFFFWHLKSEMHNKTVSQRFGLLLESYCRACGMYLKHLNRQVEAMEKLIN

LTDILKQEKKDETQKVQMKFLVEQMRRPDFMDALQGFLSPLNPAHQLGNLR

LEECRIMSSAKRPLWLNWENPDIMSELLFQNNEIIFKNGDDLRQDMLTLQI

IRIMENIWQNQGLDLRMLPYGCLSIGDCVGLIEVVRNSHTIMQIQCKGGLK

GALQFNSHTLHQWLKDKNKGEIYDAAIDLFTRSCAGYCVATFILGIGDRHN

SNIMVKDDGQLFHIDFGHFLDHKKKKFGYKRERVPFVLTQDFLIVISKGAQ

ECTKTREFERFQEMCYKAYLAIRQHANLFINLFSMMLGSGMPELQSFDDIA

YIRKTLALDKTEQEALEYFMKQMNDARHGGWTTKMDWIFHTIKQHALN.

In some aspects, the present disclosure provides a method of treating or preventing a disease or disorder disclosed herein in a subject in need thereof, comprising administering to the subject a therapeutically effective amount of a compound of Formula (I), (Ia), (Ib), (Ic), (Id), (Ie), (If), (Ig), (Ih), or (II), or a pharmaceutically acceptable salt, prodrug, solvate, hydrate, isomer, or tautomer thereof.

In some aspects, the present disclosure provides a method of treating or preventing a disease or disorder disclosed herein in a subject in need thereof, comprising administering to the subject a therapeutically effective amount of a pharmaceutical composition of a compound of Formula (I), (Ia), (Ib), (Ic), (Id), (Ie), (If), (Ig), (Ih), or (II), or a pharmaceutically acceptable salt, prodrug, solvate, hydrate, isomer, or tautomer thereof.

In some aspects, the present disclosure provides a method of treating a disease or disorder disclosed herein in a subject in need thereof, comprising administering to the subject a therapeutically effective amount of a compound of Formula (I), (Ia), (Ib), (Ic), (Id), (Ie), (If), (Ig), (Ih), or (II), or a pharmaceutically acceptable salt, prodrug, solvate, hydrate, isomer, or tautomer thereof.

In some aspects, the present disclosure provides a method of treating a disease or disorder disclosed herein in a subject in need thereof, comprising administering to the subject a therapeutically effective amount of a pharmaceutical composition of a compound of Formula (I), (Ia), (Ib), (Ic), (Id), (Ie), (If), (Ig), (Ih), or (II), or a pharmaceutically acceptable salt, prodrug, solvate, hydrate, isomer, or tautomer thereof.

In another aspect, the present disclosure provides a compound of Formula (I), (Ia), (Ib), (Ic), (Id), (Ie), (If), (Ig), (Ih), or (II), or a pharmaceutically acceptable salt, prodrug, solvate, hydrate, isomer, or tautomer thereof for use in modulating PI3K (e.g., PI3Kα) activity (e.g., in vitro or in vivo).

In another aspect, the present disclosure provides a compound of Formula (I), (Ia), (Ib), (Ic), (Id), (Ie), (If), (Ig), (Ih), or (II), or a pharmaceutically acceptable salt, prodrug, solvate, hydrate, isomer, or tautomer thereof, for use in selective inhibition for mutant PI3Kα over wild-type PI3Kα.

In another aspect, the present disclosure provides a compound of Formula (I), (Ia), (Ib), (Ic), (Id), (Ie), (If), (Ig), (Ih), or (II), or a pharmaceutically acceptable salt, prodrug, solvate, hydrate, isomer, or tautomer thereof, for use in treating or preventing a disease or disorder disclosed herein.

In another aspect, the present disclosure provides a compound of Formula (I), (Ia), (Ib), (Ic), (Id), (Ie), (If), (Ig), (Ih), or (II), or a pharmaceutically acceptable salt, prodrug, solvate, hydrate, isomer, or tautomer thereof, for use in treating a disease or disorder disclosed herein.

In another aspect, the present disclosure provides use of a compound of Formula (I), (Ia), (Ib), (Ic), (Id), (Ie), (If), (Ig), (Ih), or (II), or a pharmaceutically acceptable salt, prodrug, solvate, hydrate, isomer, or tautomer thereof, in the manufacture of a medicament for modulating PI3K (e.g., PI3Kα) activity (e.g., in vitro or in vivo).

In another aspect, the present disclosure provides use of a compound of Formula (I), (Ia), (Ib), (Ic), (Id), (Ie), (If), (Ig), (Ih), or (II), or a pharmaceutically acceptable salt, prodrug, solvate, hydrate, isomer, or tautomer thereof, in the manufacture of a medicament for treating or preventing a disease or disorder disclosed herein.

In another aspect, the present disclosure provides use of a compound of Formula (I), (Ia), (Ib), (Ic), (Id), (Ie), (If), (Ig), (Ih), or (II), or a pharmaceutically acceptable salt, prodrug, solvate, hydrate, isomer, or tautomer thereof, in the manufacture of a medicament for treating a disease or disorder disclosed herein.

In another aspect, the present disclosure provides a method of preparing a compound of Formula (I), (Ia), (Ib), (Ic), (Id), (Ie), (If), (Ig), (Ih), or (II), or a pharmaceutically acceptable salt, prodrug, solvate, hydrate, isomer, or tautomer thereof.

In another aspect, the present disclosure provides a method of preparing a compound, comprising one or more steps described herein.

Other features and advantages of the disclosure will be apparent from the following detailed description and claims.

DETAILED DESCRIPTION

The present disclosure provides methods of treating, preventing, or ameliorating a disease or disorder in which PI3K plays a role by administering to a patient in need thereof a therapeutically effective amount of a PI3K inhibitor. The methods of the present disclosure can be used in the treatment of a variety of PI3K-dependent diseases and disorders.

In some embodiments, the disease of disorder is a cancer (e.g., breast cancer, brain cancers, prostate cancer, endometrial cancer, gastric cancer, leukemia, lymphoma, sarcoma, colorectal cancer, lung cancer, ovarian cancer, skin cancer, and head and neck cancer). In some embodiments, the disease or disorder associated with PI3K includes, but is not limited to, CLOVES syndrome (congenital lipomatous overgrowth, vascular malformations, epidermal naevi, scoliosis/skeletal and spinal syndrome), PIK3CA-related overgrowth syndrome (PROS), endometrial cancer, breast cancer, esophageal squamous-cell cancer, cervical squamous-cell carcinoma, cervical adenocarcinoma, colorectal adenocarcinoma, bladder urothelial carcinoma, glioblastoma, ovarian cancer, non-small-cell lung cancer, esophagogastric cancer, nerve-sheath tumor, head and neck squamous-cell carcinoma, melanoma, esophagogastric adenocarcinoma, soft-tissue sarcoma, prostate cancer, fibrolamellar carcinoma, hepatocellular carcinoma, diffuse glioma, colorectal cancer, pancreatic cancer, cholangiocarcinoma, B-cell lymphoma, mesothelioma, adrenocortical carcinoma, renal non-clear-cell carcinoma, renal clear-cell carcinoma, germ-cell carcinoma, thymic tumor, pheochromocytoma, miscellaneous neuroepithelial tumor, thyroid cancer, leukemia, and encapsulated glioma.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded to other substituents (e.g., heteroatoms). For instance, an alkyl group that is optionally substituted can be a fully saturated alkyl chain (i.e., a pure hydrocarbon). Alternatively, the same optionally substituted alkyl group can have one or more substituents different from hydrogen. For instance, it can, at any point along the chain be bonded to a halogen atom, a hydroxyl group, or any other substituent described herein. Thus, the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O ($C_1$-$C_6$) alkyl, —NH$_2$, —NH(($C_1$-$C_6$) alkyl), —N(($C_1$-$C_6$) alkyl)$_2$, —NHC(O)($C_1$-$C_6$) alkyl, —C(O)NH($C_1$-$C_6$) alkyl, —S(O)$_2$($C_1$-$C_6$) alkyl, —S(O)NH($C_1$-$C_6$)alkyl, and —S(O)N(($C_1$-$C_6$)alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$)alkyl, ($C_1$-$C_6$)alkyl, —O—($C_2$-$C_6$)alkenyl, —O—($C_2$-

$C_6$) alkynyl, ($C_2$-$C_6$)alkenyl, ($C_2$-$C_6$)alkynyl, —OH, —OP(O)(OH)$_2$, —OC(O)($C_1$-$C_6$)alkyl, —C(O)($C_1$-$C_6$) alkyl, —OC(O)O($C_1$-$C_6$)alkyl, —NH$_2$, —NH(($C_1$-$C_6$)alkyl), —N(($C_1$-$C_6$)alkyl)$_2$, —S(O)$_2$—($C_1$-$C_6$) alkyl, —S(O)NH($C_1$-$C_6$)alkyl, and —S(O)N(($C_1$-$C_6$)alkyl)$_2$. The substituents can themselves be optionally substituted. Furthermore, when containing two fused rings the aryl groups herein defined may have one or more saturated or partially unsaturated ring fused with a fully unsaturated aromatic ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic or a polycyclic aromatic radical of 5 to 24 ring atoms, preferably 5 to 10 rings atoms, containing one or more ring heteroatoms selected from N, O, S, P, or B, preferably 1, 2, 3, or 4 ring heteroatoms selected from N, O, or S, the remaining ring atoms being C. A polycyclic aromatic radical includes two or more fused rings and may further include two or more spiro-fused rings, e.g., bicyclic, tricyclic, tetracyclic, and the like. Unless otherwise specifically defined, "fused" means two rings sharing two ring atoms. Unless otherwise specifically defined, "spiro-fused" means two rings sharing one ring atom. Heteroaryl as herein defined also means a bicyclic heteroaromatic group wherein the heteroatom is selected from N, O, S, P, or B, preferably N, O, or S. Heteroaryl as herein defined also means a tricyclic heteroaromatic group containing one or more ring heteroatoms selected from N, O, S, P, or B, preferably N, O, or S. Heteroaryl as herein defined also means a tetracyclic heteroaromatic group containing one or more ring heteroatoms selected from N, O, S, P, or B, preferably N, O, or S. The aromatic radical is optionally substituted independently with one or more substituents described herein. Examples of heteroaromatic groups include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuranyl, chromanyl, thiochromanyl, tetrahydroquinolinyl, dihydrobenzothiazinyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1-pyrrolo[2,1-b]pyrimidine, dibenzo[b,d] thiophene, pyridin-2-one, furo[3,2-c]pyridinyl, furo[2,3-c]pyridinyl, 1H-pyrido[3,4-b][1,4] thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore, when containing two or more fused rings, the heteroaryl groups defined herein may have one or more saturated or partially unsaturated ring fused with one or more fully unsaturated aromatic ring. In heteroaryl ring systems containing more than two fused rings, a saturated or partially unsaturated ring may further be fused with a saturated or partially unsaturated ring described herein. Furthermore, when containing three or more fused rings, the heteroaryl groups defined herein may have one or more saturated or partially unsaturated ring spiro-fused. Any saturated or partially unsaturated ring described herein is optionally substituted with one or more oxo. Exemplary ring systems of these heteroaryl groups include, for example, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuranyl, benzofuranonyl, indolinyl, oxindolyl, indolyl, 1,6-dihydro-7H-pyrazolo[3,4-c]pyridin-7-onyl, 7,8-dihydro-6H-pyrido[3,2-b]pyrrolizinyl, 8H-pyrido[3,2-b]pyrrolizinyl, 1,5,6,7-tetrahydrocyclopenta[b]pyrazolo[4,3-e]pyridinyl, 7,8-dihydro-6H-pyrido[3,2-b]pyrrolizinyl, pyrazolo[1,5-a]pyrimidin-7(4H)-only, 3,4-dihydropyrazino[1,2-a]indol-1(2H)-onyl, benzo[c][1,2]oxaborol-1(3H)-olyl, 6,6a,7,8-tetrahydro-9H-pyrido[2,3-b]puyrrolo[1,2-d][1,4]oxazin-9-onyl, or 6a',7'-dihydro-6'H,9'H-spiro[cyclopropane-1,8'-pyrido[2,3-b]pyrrolo[1,2-d][1,4]oxazin]-9'-onyl.

Halogen or "halo" refers to fluorine, chlorine, bromine, or iodine.

Alkyl refers to a straight or branched chain saturated hydrocarbon containing 1-12 carbon atoms, preferably 1-6 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, i.e., —O(alkyl). Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

"Cycloalkyl" means mono or polycyclic saturated carbon rings containing 3-18 carbon atoms, preferably 3-10 carbon atoms. Examples of cycloalkyl groups include, without limitations, cyclopropyl, cyclobutyl, cyclopentyl, cyclohexyl, cycloheptanyl, cyclooctanyl, norbornyl, norborenyl, bicyclo[2.2.2]octanyl, or bicyclo[2.2.2]octenyl.

"Cycloalkylalkyl" means monocyclic saturated carbon rings containing 3-24 carbon atoms, preferably 3-10 carbon atoms, further substituted with ($C_1$-$C_6$) alkyl groups. In general, cycloalkylalkyl groups herein described display the following formula

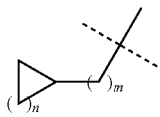

where m is an integer from 1 to 6 and n is an integer from 1 to 16. The cycloalkyl ring or carbocycle may be optionally substituted by one or more substituents, e.g., 1 to 5 substituents, at any point of attachment. The substituents can themselves be optionally substituted. Examples of cycloalkyl groups include, without limitations, cyclopropyl, cyclobutyl, cyclopentyl, cyclohexyl, cycloheptanyl, cyclooctanyl, norbornyl, norborenyl, bicyclo[2.2.2]octanyl, bicyclo[2.2.2]octenyl, decahydronaphthalenyl, octahydro-1H-indenyl, cyclopentenyl, cyclohexenyl, cyclohexa-1,4-dienyl, cyclohexa-1,3-dienyl, 1,2,3,4-tetrahydronaphthalenyl, octahydropentalenyl, 3a,4,5,6,7,7a-hexahydro-1H-indenyl, 1,2,3,3a-tetrahydropentalenyl, bicyclo[3.1.0]hexanyl, bicyclo[2.1.0]pentanyl, spiro[3.3]heptanyl, bicyclo[2.2.1]heptanyl, bicyclo[2.2.1]hept-2-enyl, bicyclo[2.2.2]octanyl, 6-methylbicyclo[3.1.1]heptanyl, 2,6,6-trimethylbicyclo[3.1.1]heptanyl, and derivatives thereof.

"Heterocyclyl", "heterocycle" or "heterocycloalkyl" means mono or polycyclic rings containing 3-24 atoms, preferably 3-10 atoms, which include carbon and one or more heteroatoms selected from N, O, S, P, or B, preferably 1, 2, 3, or 4 heteroatoms selected from N, O, and S, and wherein the rings are not aromatic. The heterocycloalkyl ring structure may be substituted by one or more substituents. The substituents can themselves be optionally substituted. Examples of heterocyclyl rings include, but are not limited to, oxetanyl, azetidinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

The term "aromatic" means a planar ring having 4n+2 electrons in a conjugated system. As used herein, "conjugated system" means a system of connected p-orbitals with delocalized electrons, and the system may include lone electron pairs.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted with one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N or —CN.

"Spirocycloalkyl" or "spirocyclyl" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A ($C_3$-$C_{12}$) spirocycloalkyl is a spirocycle containing between 3 and 12 carbon atoms. One or more of the carbon atoms can be substituted with a heteroatom.

The term "spiroheterocycloalkyl", "spiroheterocycle", or "spiroheterocyclyl" is understood to mean a spirocycle wherein at least one of the rings is a heterocycle (e.g., at least one of the rings is furanyl, morpholinyl, or piperidinyl).

The term "solvate" refers to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I), (Ia), (Ib), (Ic), (Id), (Ie), (If), (Ig), (Ih), or (II) may have one or more asymmetric carbon atom and may occur as racemates, racemic mixtures and as individual enantiomers or diastereomers.

The present disclosure also contemplates isotopically-labelled compounds of Formula (I), (Ia), (Ib), (Ic), (Id), (Ie), (If), (Ig), (Ih), or (II) (e.g., those labeled with $^2$H and $^{14}$C). Deuterated (i.e., $^2$H or D) and carbon-14 (i.e., $^{14}$C) isotopes are particularly preferred for their ease of preparation and detectability. Further, substitution with heavier isotopes such as deuterium may afford certain therapeutic advantages resulting from greater metabolic stability (e.g., increased in vivo half-life or reduced dosage requirements) and hence may be preferred in some circumstances. Isotopically labelled compounds of Formula (I), (Ia), (Ib), (Ic), (Id), (Ie), (If), (Ig), (Ih), or (II) can generally be prepared by following procedures analogous to those disclosed in the Schemes and/or in the Examples herein below, by substituting an appropriate isotopically labelled reagent for a non-isotopically labelled reagent.

The disclosure also includes pharmaceutical compositions comprising a therapeutically effective amount of a disclosed compound and a pharmaceutically acceptable carrier.

A "patient" or "subject" is a mammal, e.g., a human, mouse, rat, guinea pig, dog, cat, horse, cow, pig, or non-human primate, such as a monkey, chimpanzee, baboon or rhesus. Preferably, the mammal is human.

An "effective amount" when used in connection with a compound refers to the amount or dose of the compound which upon single or multiple dose administration to the patient, provides the desired effect in the patient under diagnosis or treatment. An effective amount can be determined by one skilled in the art by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, includes restraining, slowing, stopping, or reversing the progression or severity of an existing symptom or disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The term "salts" refers to pharmaceutically acceptable salts. Salt formation can occur upon the addition of a pharmaceutically acceptable acid to form the acid addition salt, or by the addition of a pharmaceutically acceptable base to form a base addition salt. Salts can also form simultaneously upon deprotection of a nitrogen or oxygen. Pharmaceutically acceptable salts and common methodology for preparing them are well known in the art (see, e.g., P. Stahl, et al. *Handbook of Pharmaceutical Salts: Properties, Selection and Use*, $2^{nd}$ Revised Edition (Wiley-VCH, 2011); S. M. Berge, et al., "Pharmaceutical Salts," *Journal of Pharmaceutical Sciences*, Vol. 66, No. 1, January 1977). Representative "pharmaceutically acceptable salts" include, e.g., water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium, calcium edetate, camsylate, carbonate, chloride, citrate, clavulanate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, pantothenate, phosphate/diphosphate, picrate, polygalacturonate, propionate, p-toluenesulfonate, salicylate, stearate, subacetate, succinate, sulfate, sulfosalicylate, tannate, tartrate, teoclate, tosylate, triethiodide, and valerate salts.

The term "pharmaceutically acceptable salt" also refers to a salt of the compositions of Formula (I), (Ia), (Ib), (Ic), (Id), (Ie), (If), (Ig), (Ih), or (II), having, for example, an acidic functional group, such as a carboxylic acid functional group, and a base.

The term "modulate", "modulation" or "modulating" as used herein refers to a biological activity of a compound or substrate that inhibits and/or activates PI3K.

"PI3K inhibitors" as used herein refer to compounds of Formula (I), (Ia), (Ib), (Ic), (Id), (Ie), (If), (Ig), (Ih), or (II) and/or compositions comprising a compound of Formula (I), (Ia), (Ib), (Ic), (Id), (Ie), (If), (Ig), (Ih), or (II) which inhibits PI3K.

The amount of compound of composition described herein needed for achieving a therapeutic effect may be determined empirically in accordance with conventional procedures for the particular purpose. Generally, for administering therapeutic agents (e.g. compounds or compositions of Formula (I), (Ia), (Ib), (Ic), (Id), (Ie), (If), (Ig), (Ih), or (II) (and/or additional agents) described herein) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. For example, administration of therapeutic agents to a patient suffering from cancer provides a therapeutic benefit not only when the underlying condition is eradicated or ameliorated, but also when the patient reports a decrease in the severity or duration of the symptoms associated with the disease, e.g., a decrease in tumor burden, a decrease in circulating tumor cells, an increase in progression free survival. Therapeutic benefit also includes halting or slowing the progression of the underlying disease or disorder, regardless of whether improvement is realized.

Compounds of the Present Disclosure

In one aspect, the present disclosure provides compounds of Formula (I) or pharmaceutically acceptable salts thereof, or prodrugs, solvates, hydrates, isomers, or tautomers thereof.

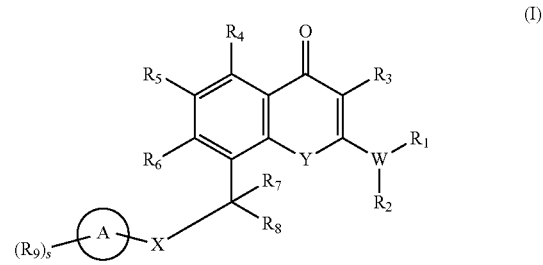

(I)

wherein $R_1$, $R_2$, $R_3$, $R_4$, $R_5$, $R_6$, $R_7$, $R_8$, $R_9$, W, X, Y, s, and Ring A are as described in the Summary for Formula (I).

In a preferred embodiment of Formula (I), X is —$NR_{12}$— or —O—; Y is —$C(R_{11})_2$—, —O—, —$NR_{11}$—, or —S—; $WR_1R_2$ is a group of the formula:

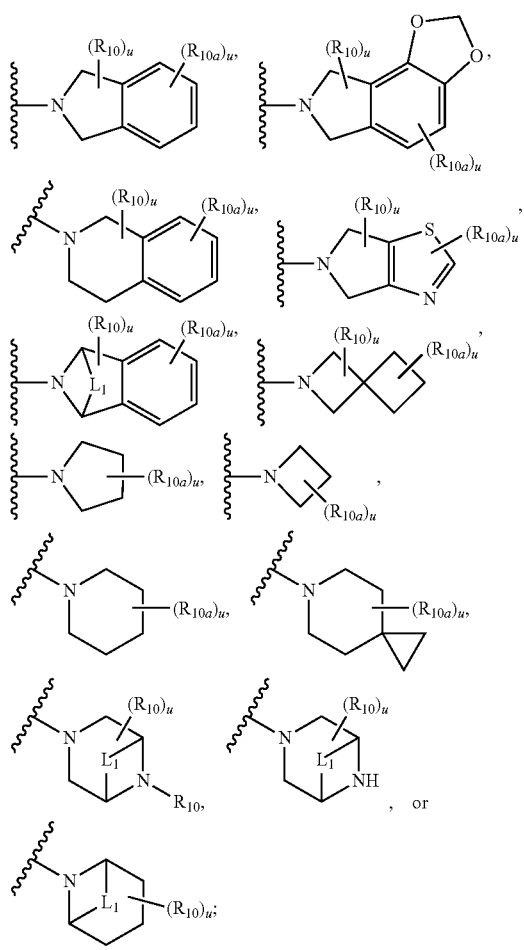

$R_{10}$ at each occurrence is independently oxo, halogen, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_n$—OR$_{12}$, —(CH$_2$)$_n$—N(R$_{12}$)$_2$, —(CH$_2$)$_n$—C(O)R$_{12}$, —(CH$_2$)$_n$—C(O)OR$_{12}$, —(CH$_2$)$_n$—C(O)N(R$_{12}$)$_2$, —(CH$_2$)$_n$—SO$_2$R$_{12}$, —(CH$_2$)$_n$—O—(CH$_2$CH$_2$—O)$_r$R$_{13}$, $C_3$-$C_{10}$ cycloalkyl, heterocycle, —(CH$_2$)$_n$-aryl, or heteroaryl, wherein the cycloalkyl, heterocycle, aryl, and heteroaryl is optionally substituted with halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, —(CH$_2$)$_n$—SO$_2$R$_{12}$, —(CH$_2$)$_n$—C(O)R$_{12}$, —(CH$_2$)$_n$—C(O)OR$_{12}$, or —(CH$_2$)$_n$—C(O)N(R$_{12}$)$_2$, or two R$_{10}$, together with the atoms to which they are attached, form a $C_3$-$C_{10}$ cycloalkyl, an aryl, a heterocycle comprising 1-4 heteroatoms selected from O, N, and S, or a heteroaryl, wherein the cycloalkyl, aryl, heterocycle, and heteroaryl are optionally substituted with one or more oxo, =NR$_{12}$, halogen, —CN, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_n$—OR$_{12}$, —(CH$_2$)$_n$—N(R$_{12}$)$_2$, —(CH$_2$)$_n$—C(O)R$_{12}$, —(CH$_2$)$_n$—C(O)OR$_{12}$, —(CH$_2$)$_n$—C(O)N(R$_{12}$)$_2$, —(CH$_2$)$_n$—SO$_2$R$_{12}$, $C_3$-$C_6$ cycloalkyl, aryl, heteroaryl, or R$_{15}$; R$_{10a}$ at each occurrence is independently halogen, —CN, $C_1$-$C_6$ alkyl, $C_1$-$C_6$ haloalkyl, $C_1$-$C_6$ alkoxy, or —(CH$_2$)$_n$—OR$_{12}$; -L$_1$- is absent, —(CH$_2$)— or —(CH$_2$)$_2$—; u at each occurrence is independently 0, 1, 2, 3 or 4; each R$_3$, R$_4$, R, and R$_6$ is independently H, halogen, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_m$—R$_{12}$, —(CH$_2$)$_m$—OR$_{12}$, —(CH$_2$)$_m$—N(R$_{12}$)$_2$, —(CH$_2$)$_m$—C(O)R$_{12}$, —(CH$_2$)$_m$—C(O)OR$_{12}$, —(CH$_2$)$_m$—C(O)N(R$_{12}$)$_2$, $C_3$-$C_{10}$ cycloalkyl, aryl, heterocycle comprising 1-4 heteroatoms selected from O, N, and S, or heteroaryl comprising 1-4 heteroatoms selected from O, N, and S; each R$_7$ and R$_8$ is independently H, halogen, —CN, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy; at least one R$_9$ is —C(O)OR$_{12}$ and each of the remaining R$_9$ at each occurrence is independently oxo, =NR$_{11}$, halogen, —CN, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_m$—N(R$_{12}$)$_2$, —(CH$_2$)$_m$—OR$_{12}$, —(CH$_2$)$_m$—CR$_{13}$(OH)—R$_{12}$, —(CH$_2$)$_m$—C(O)R$_{12}$, —(CH$_2$)$_m$—C(O)OR$_{12}$, —(CH$_2$)$_m$—C(O)N(R$_{12}$)$_2$, —(CH$_2$)$_m$—C(O)N(OH)R$_{12}$, —(CH$_2$)$_m$—SO$_2$R$_{12}$, —(CH$_2$)$_m$—SO$_2$—OR$_{12}$, —(CH$_2$)$_m$—SO$_2$N(R$_{12}$)$_2$, —(CH$_2$)$_m$—P(O)(OR$_{12}$)$_2$, —(CH$_2$)$_m$—P(O)(R$_{12}$)$_2$, —(CH$_2$)$_m$—P(O)(OR$_{13}$)R$_{12}$, —(CH$_2$)$_m$—B(OH)$_2$, —(CH$_2$)$_m$—B(R$_{12}$)$_2$, —(CH$_2$)$_m$—O—(CH$_2$CH$_2$—O)$_r$R$_{13}$, —(CH$_2$)$_m$—NR$_{12}$—(CH$_2$CH$_2$—O)$_r$R$_{13}$, —(CH$_2$)$_m$—C(O)—(CH$_2$CH$_2$—O)$_r$R$_{13}$, —(CH$_2$)$_m$—C(O)O—(CH$_2$CH$_2$—O)$_r$R$_{13}$, —(CH$_2$)$_m$—C(O)NR$_{12}$—(CH$_2$CH$_2$—O)$_r$R$_{13}$, —(CH$_2$)$_m$—C(O)—NR$_{12}$—SO$_2$R$_{13}$, —(CH$_2$)$_m$—SO$_2$NR$_{12}$—C(O)R$_{13}$, —(CH$_2$)$_m$—S(O)(NR$_{12}$)—R$_{13}$, $C_3$-$C_{10}$ cycloalkyl, aryl, heterocycle comprising 1-4 heteroatoms selected from O, N, and S, or heteroaryl comprising 1-4 heteroatoms selected from N, O, and S, wherein the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, aryl, heterocycle, or heteroaryl is optionally substituted with one or more oxo, halogen, —CN, —OH, —NH$_2$, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or two R$_9$, together with the atoms to which they are attached form a $C_3$-$C_{10}$ cycloalkyl, an aryl, or a heterocycle comprising 1-4 heteroatoms selected from O, N, and S, wherein the cycloalkyl, aryl, or heterocycle is optionally substituted with one or more oxo, halogen, —CN, —OH, —NH$_2$, =NH, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy; R$_{11}$ is H, $C_1$-$C_6$ alkyl, $C_2$-$C_6$ alkenyl, or $C_2$-$C_6$ alkynyl; each R$_{12}$ and R$_{13}$ at each occurrence is independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_q$—O—C(O)—(CH$_2$)$_r$—R$_{14}$, —(CH$_2$)$_q$—NH—C(O)—(CH$_2$)$_r$—R$_{14}$, —(CH$_2$)$_q$—O—C(O)—(CH$_2$)$_r$—OR$_{14}$, —(CH$_2$)$_q$—NH—C(O)—(CH$_2$)$_r$—OR$_{14}$, —(CH$_2$)$_q$—O—(CH$_2$)$_r$—R$_{14}$, —(CH$_2$)$_q$—NH—(CH$_2$)$_r$—R$_{14}$, —(CH$_2$)$_q$—O—(CH$_2$)$_r$—OR$_{14}$, —(CH$_2$)$_q$—NH—(CH$_2$)$_r$—OR$_{14}$, $C_3$-$C_{10}$ cycloalkyl, heterocycle comprising 1-4 heteroatoms selected from O, N, and S, —(CH$_2$)$_q$-aryl, or heteroaryl comprising 1-4 heteroatoms selected from N, O, and S, wherein the cycloalkyl, heterocycle, aryl, and heteroaryl are optionally substituted with one or more halogen, $C_1$-$C_6$ alkyl, $C_1$-$C_6$ haloalkyl, $C_1$-$C_6$ alkoxy, or $C_1$-$C_6$ haloalkoxy; Ring A is $C_3$-$C_{10}$ cycloalkyl, aryl, heterocycle comprising 1-4 heteroatoms selected from N, O, and S, or heteroaryl comprising 1-4 heteroatoms selected from N, O, and S; R$_{14}$ is

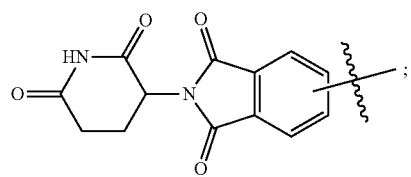

two R$_{15}$, together with the atoms to which they are attached form a cycloalkyl, an aryl, a heterocycle comprising 1-4 heteroatoms selected from O, N, and S, or a heteroaryl, wherein the cycloalkyl, aryl, heterocycle, and heteroaryl are optionally substituted with one or more $C_1$-$C_6$ alkyl, $C_1$-$C_6$ haloalkyl, $C_1$-$C_6$ alkoxy, —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, or —$(CH_2)_n$—$SO_2R_{12}$; each n, m, q, or r, is independently at each occurrence 0, 1, 2, 3, 4, 5, or 6; and s is 1, 2, 3, 4, 5, or 6.

In another preferred embodiment of Formula (I), X is —$NR_{12}$— or —O—; Y is —$C(R_{11})_2$—, —O—, —$NR_{11}$—, or —S—; $WR_1R_2$ is a group of the formula:

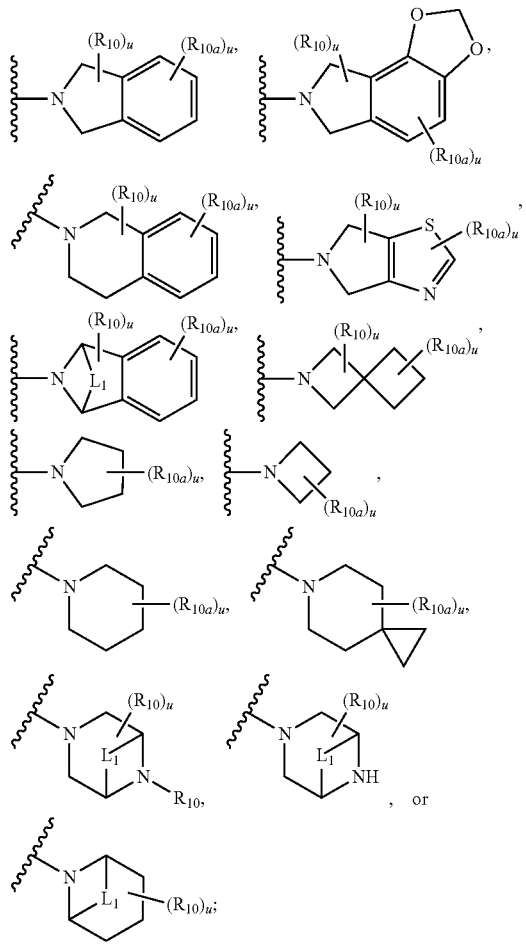

$R_{10}$ at each occurrence is independently oxo, halogen, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_n$—$OR_{12}$, —$(CH_2)_n$—$N(R_1)_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$, —$(CH_2)_n$—O—$(CH_2CH_2$—O$)_rR_{13}$, $C_3$-$C_{10}$ cycloalkyl, heterocycle, —$(CH_2)_n$-aryl, or heteroaryl, wherein the cycloalkyl, heterocycle, aryl, and heteroaryl is optionally substituted with halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, or —$(CH_2)_n$—$SO_2R_{12}$; $R_{10a}$ at each occurrence is independently halogen, —CN, $C_1$-$C_6$ alkyl, $C_1$-$C_6$ haloalkyl, $C_1$-$C_6$ alkoxy, or —$(CH_2)_n$—$OR_{12}$; -$L_1$- is —$(CH_2)$— or —$(CH_2)_2$—; u at each occurrence is independently 0, 1, 2, 3 or 4; each $R_3$, $R_4$, $R_5$, and $R_6$ is independently H, halogen, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, aryl, heterocycle comprising 1-4 heteroatoms selected from O, N, and S, or heteroaryl comprising 1-4 heteroatoms selected from O, N, and S; each $R_7$ and $R_8$ is independently H, halogen, —CN, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy; at least one $R_9$ is —$C(O)OR_{12}$ and each of the remaining $R_9$ at each occurrence is independently oxo, =$NR_{11}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$N(R_{12})_2$, —$(CH_2)_m$—$OR_{12}$, —$(CH_2)_m$—$CR_{13}(OH)$—$R_{12}$, —$(CH_2)_m$—$C(O)R_{12}$, —$(CH_2)_m$—$C(O)OR_{12}$, —$(CH_2)_m$—$C(O)N(R_{12})_2$, —$(CH_2)_m$—$C(O)N(OH)R_{12}$, —$(CH_2)_m$—$SO_2R_{12}$, —$(CH_2)_m$—$SO_2$—$OR_{12}$, —$(CH_2)_m$—$SO_2N(R_{12})_2$, —$(CH_2)_m$—$P(O)(OR_{12})_2$, —$(CH_2)_m$—$P(O)(R_{12})_2$, —$(CH_2)_m$—$P(O)(OR_{13})R_{12}$, —$(CH_2)_m$—$B(OH)_2$, —$(CH_2)_m$—$B(R_{12})_2$, —$(CH_2)_m$—O—$(CH_2CH_2$—O$)_rR_{13}$, —$(CH_2)_m$—$NR_{12}$—$(CH_2CH_2$—O$)_rR_{13}$, —$(CH_2)_m$—$C(O)$—$(CH_2CH_2$—O$)_rR_{13}$, —$(CH_2)_m$—$C(O)O$—$(CH_2CH_2$—O$)_rR_{13}$, —$(CH_2)_m$—$C(O)NR_{12}$—$(CH_2CH_2$—O$)_rR_{13}$, —$(CH_2)_m$—$C(O)$—$NR_{12}$—$SO_2R_{13}$, —$(CH_2)_m$—$SO_2NR_{12}$—$C(O)R_{13}$, —$(CH_2)_m$—$S(O)(NR_{12})$—$R_{13}$, $C_3$-$C_{10}$ cycloalkyl, aryl, heterocycle comprising 1-4 heteroatoms selected from O, N, and S, or heteroaryl comprising 1-4 heteroatoms selected from N, O, and S, wherein the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, aryl, heterocycle, or heteroaryl is optionally substituted with one or more oxo, halogen, —CN, —OH, —$NH_2$, —$NO_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy; or two $R_9$, together with the atoms to which they are attached form a $C_3$-$C_{10}$ cycloalkyl, an aryl, or a heterocycle comprising 1-4 heteroatoms selected from O, N, and S, wherein the cycloalkyl, aryl or heterocycle is optionally substituted with one or more oxo, halogen, —CN, —OH, —$NH_2$, =NH, —$NO_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy; Rn is H, $C_1$-$C_6$ alkyl, $C_2$-$C_6$ alkenyl, or $C_2$-$C_6$ alkynyl; each $R_{12}$ and $R_{13}$ at each occurrence is independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_q$—O—C(O)—$(CH_2)_r$—$R_{14}$, —$(CH_2)_q$—NH—C(O)—$(CH_2)_r$—$R_{14}$, —$(CH_2)_q$—O—C(O)—$(CH_2)_r$—$OR_{14}$, —$(CH_2)_q$—NH—C(O)—$(CH_2)_r$—$OR_{14}$, —$(CH_2)_q$—O—$(CH_2)_r$—$R_{14}$, —$(CH_2)_q$—NH—$(CH_2)_r$—$R_{14}$, —$(CH_2)_q$—O—$(CH_2)_r$—$OR_{14}$, —$(CH_2)_q$—NH—$(CH_2)_r$—$OR_{14}$, $C_3$-$C_{10}$ cycloalkyl, heterocycle comprising 1-4 heteroatoms selected from O, N, and S, —$(CH_2)_q$-aryl, or heteroaryl comprising 1-4 heteroatoms selected from N, O, and S, wherein the cycloalkyl, heterocycle, aryl, and heteroaryl are optionally substituted with one or more halogen, $C_1$-$C_6$ alkyl, $C_1$-$C_6$ haloalkyl, $C_1$-$C_6$ alkoxy, or $C_1$-$C_6$ haloalkoxy; Ring A is $C_3$-$C_{10}$ cycloalkyl, aryl, heterocycle comprising 1-4 heteroatoms selected from N, O, and S, or heteroaryl comprising 1-4 heteroatoms selected from N, O, and S; $R_{14}$ is

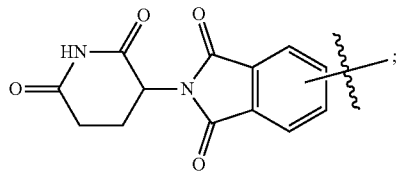

each n, m, q, or r, is independently at each occurrence 0, 1, 2, 3, 4, 5, or 6; and s is 1, 2, 3, 4, 5, or 6.

In a further aspect, the present disclosure provides compounds of Formula (Ia) or pharmaceutically acceptable salts thereof, or prodrugs, solvates, hydrates, isomers, or tautomers thereof.

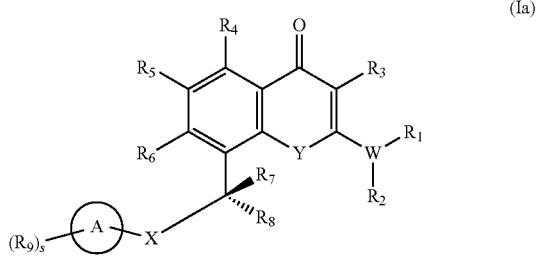

(Ia)

wherein $R_8$ is H and $R_7$ is not H, and $R_1$, $R_2$, $R_3$, $R_4$, $R_5$, $R_6$, $R_7$, $R_9$, W, X, Y, s, and Ring A are as otherwise described in the Summary for Formula (I).

In yet a further aspect, the present disclosure provides compounds of Formula (Ib) or pharmaceutically acceptable salts thereof, or prodrugs, solvates, hydrates, isomers, or tautomers thereof.

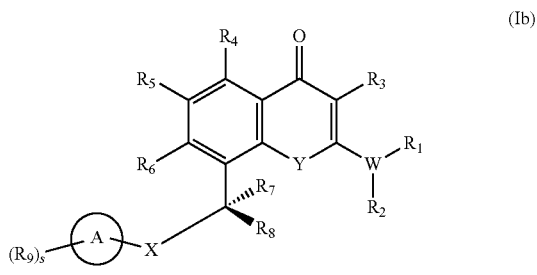

(Ib)

wherein $R_8$ is H and $R_7$ is not H, and $R_1$, $R_2$, $R_3$, $R_4$, $R_5$, $R_6$, $R_7$, $R_9$, W, X, Y, s, and Ring A are as otherwise described in the Summary for Formula (I).

In yet a further aspect, the present disclosure provides compounds of Formula (Ic) or pharmaceutically acceptable salts thereof, or prodrugs, solvates, hydrates, isomers, or tautomers thereof:

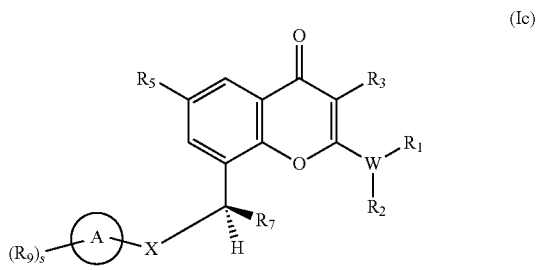

(Ic)

wherein $R_7$ is not H and $R_1$, $R_2$, $R_5$, $R_7$, $R_9$, W, X, s, and Ring A are as otherwise described in the Summary for Formula (I), and wherein $R_3$ is halogen, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_m$—R$_{12}$, —(CH$_2$)$_m$—OR$_{12}$, —(CH$_2$)$_m$—N(R$_{12}$)$_2$, —(CH$_2$)$_m$—C(O)R$_{12}$, —(CH$_2$)$_m$—C(O)OR$_{12}$, —(CH$_2$)$_m$—C(O)N(R$_{12}$)$_2$, $C_3$-$C_{10}$ cycloalkyl, aryl, heterocycle comprising 1-4 heteroatoms selected from O, N, and S, or heteroaryl comprising 1-4 heteroatoms selected from O, N, and S.

In yet a further aspect, the present disclosure provides compounds of Formula (Id) or pharmaceutically acceptable salts thereof, or prodrugs, solvates, hydrates, isomers, or tautomers thereof:

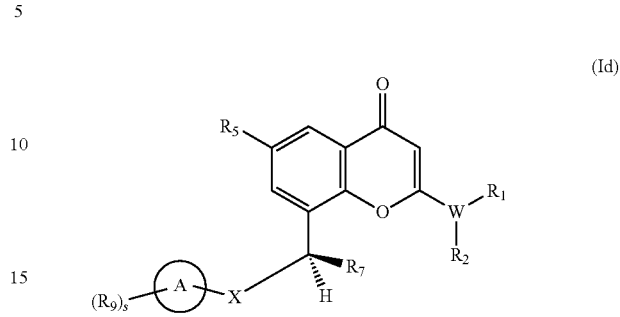

(Id)

wherein $R_7$ is not H and $R_1$, $R_2$, $R_5$, $R_7$, $R_9$, X, W, s, and Ring A are as otherwise described in the Summary for Formula (I).

In yet a further aspect, the present disclosure provides compounds of Formula (Ie) or pharmaceutically acceptable salts thereof, or prodrugs, solvates, hydrates, isomers, or tautomers thereof:

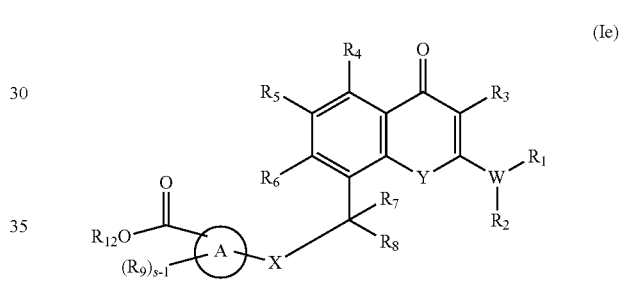

(Ie)

wherein $R_3$, $R_4$, $R_5$, $R_6$, $R_7$, $R_8$, $R_9$, $R_{10}$, $R_{12}$, X, Y, and Ring A are as described in the Summary for Formula (I), W is —N—, and $R_1$ and $R_2$, together with the nitrogen to which they are attached, form a heterocycle comprising 1-4 heteroatoms selected from O, N, and S, wherein the heterocycle is optionally substituted with one or more $R_{10}$, and wherein said heterocycle is not an optionally substituted morpholine, and s is 1, 2, 3, 4, 5, or 6.

In yet a further aspect, the present disclosure provides compounds of Formula (If) or pharmaceutically acceptable salts thereof, or prodrugs, solvates, hydrates, isomers, or tautomers thereof:

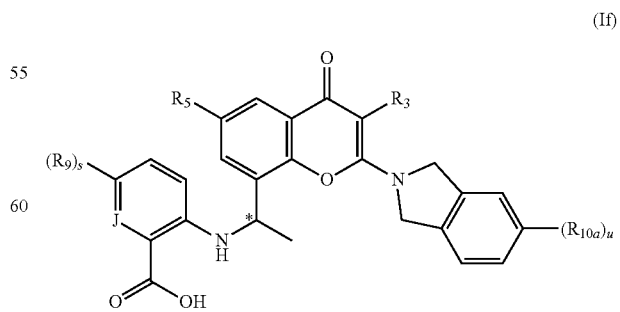

(If)

wherein $R_3$, $R_5$, and $R_9$ are as described in the Summary for Formula (I), $R_{10a}$ is halogen, —CN, $C_1$-$C_6$ alkyl, $C_1$-$C_6$ haloalkyl, $C_1$-$C_6$ alkoxy, or —$(CH_2)_n$—$OR_{12}$, s is 0 or 1, u is 0 or 1, J is C or N, and * indicates a stereocenter.

In yet a further aspect, the present disclosure provides compounds of Formula (Ig) or pharmaceutically acceptable salts thereof, or prodrugs, solvates, hydrates, isomers, or tautomers thereof:

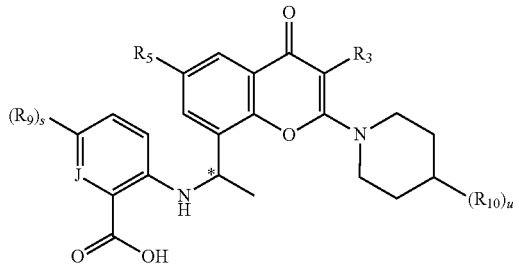

(Ig)

wherein $R_3$, $R_5$, $R_9$, $R_{10}$ are as described in the Summary for Formula (I), s is 0 or 1, u is 0, 1, or 2, J is C or N, and * indicates a stereocenter.

In yet a further aspect, the present disclosure provides compounds of Formula (Ih) or pharmaceutically acceptable salts thereof, or prodrugs, solvates, hydrates, isomers, or tautomers thereof:

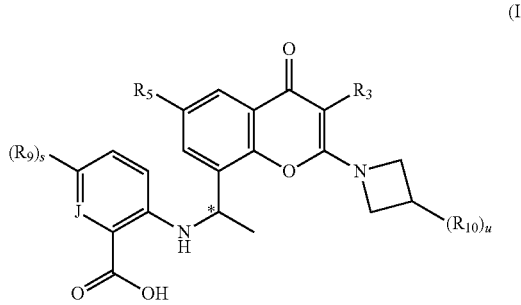

(Ih)

wherein $R_3$, $R_5$, $R_9$, $R_{10}$ are as described in the Summary for Formula (I), s is 0 or 1, u is 0, 1, or 2, J is C or N, and * indicates a stereocenter.

In yet a further aspect, the present disclosure provides compounds of Formula (II):

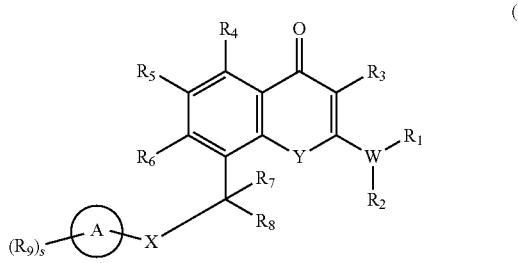

(II)

or a prodrug, solvate, enantiomer, stereoisomer, tautomer, or pharmaceutically acceptable salt thereof, wherein X is —$NR_{12}$— or —O—;
Y is —$C(R_{11})_2$—, —O—, —$NR_{11}$—, or —S—;
W is —N—, —O—, or —S—, wherein when W is —O— or —S—, $R_1$ or $R_2$ is absent; each $R_1$ and $R_2$ is independently absent, H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle, aryl, or heteroaryl, or $R_1$ and $R_2$, together with the nitrogen to which they are attached, form a heterocycle comprising 1-4 heteroatoms selected from O, N, and S, wherein the heterocycle is optionally substituted with one or more $R_{10}$;

each $R_3$, $R_4$, $R$, and $R_6$ is independently H, halogen, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle comprising 1-4 heteroatoms selected from O, N, and S, aryl, or heteroaryl comprising 1-4 heteroatoms selected from O, N, and S;

each $R_7$ and $R_8$ is independently H, halogen, —CN, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_9$ at each occurrence is independently oxo, =$NR_{11}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$N(R_{12})_2$, —$(CH_2)_m$—$OR_{12}$, —$(CH_2)_m$—$C(O)R_{12}$, —$(CH_2)_m$—$C(O)OR_{12}$, —$(CH_2)_m$—$C(O)N(R_{12})_2$, —$(CH_2)_m$—$SO_2R_{12}$, —$(CH_2)_m$—$SO_2$—$OR_{12}$, —$(CH_2)_m$—$SO_2N(R_{12})_2$, —$(CH_2)_m$—$CON(R_{12})_2$, —$(CH_2)_m$—$P(O)(OR_{12})_2$, —$(CH_2)_m$—$P(O)(R_{12})_2$, —$(CH_2)_m$—$B(OH)_2$, —$(CH_2)_m$—$B(R_{12})_2$, —$(CH_2)_m$—O—$(CH_2CH_2$—O$)_rR_{13}$, —$(CH_2)_m$—$NR_{12}$—$(CH_2CH_2$—O$)_rR_{13}$, —$(CH_2)_m$—C(O)—$(CH_2CH_2$—O$)_rR_{13}$, —$(CH_2)_m$—$C(O)O$—$(CH_2CH_2$—O$)_rR_{13}$, —$(CH_2)_m$—$C(O)NR_{12}$—$(CH_2CH_2$—O$)_rR_{13}$, —$(CH_2)_m$—C(O)—$NR_{12}$—$SO_2R_{13}$, —$(CH_2)_m$—$SO_2NR_{12}$—$C(O)R_{13}$, —$(CH_2)_m$—$S(O)(NR_{12})$—$R_{13}$, $C_3$-$C_{10}$ cycloalkyl, heterocycle comprising 1-4 heteroatoms selected from O, N, and S, aryl, or heteroaryl comprising 1-4 heteroatoms selected from N, O, and S, wherein the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, heterocycle, aryl, or heteroaryl is optionally substituted with one or more oxo, halogen, —CN, —OH, —$NH_2$, —$NO_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or two $R_9$ together with the atoms to which they are attached form a $C_3$-$C_{10}$ cycloalkyl or heterocycle comprising 1-4 heteroatoms selected from O, N, and S wherein the cycloalkyl or heterocycle is optionally substituted with one or more oxo, halogen, —CN, —OH, —$NH_2$, =NH, —$NO_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_{10}$ at each occurrence is independently oxo, halogen, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$, $C_3$-$C_{10}$ cycloalkyl, heterocycle, aryl, and heteroaryl, wherein the cycloalkyl, heterocycle, aryl, and heteroaryl is optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy, or two $R_{10}$, together with the atoms to which they are attached, form aryl or heteroaryl, wherein the aryl and heteroaryl are optionally substituted with one or more oxo, =$NR_{12}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$;

$R_{11}$ is H, $C_1$-$C_6$ alkyl, $C_2$-$C_6$ alkenyl, or $C_2$-$C_6$ alkynyl;

each $R_{12}$ and $R_{13}$ at each occurrence is independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_q$—O—C(O)—$(CH_2)_r$—$R_{14}$, —$(CH_2)_q$—NH—C(O)—$(CH_2)_r$—$R_{14}$, —$(CH_2)_q$—O—C(O)—$(CH_2)_r$—$OR_{14}$, —$(CH_2)_q$—NH—C(O)—$(CH_2)_r$—$OR_{14}$, —$(CH_2)_q$—O—$(CH_2)_r$—$R_{14}$, —$(CH_2)_q$—NH—$(CH_2)_r$—$R_{14}$, —$(CH_2)_q$—O—$(CH_2)_r$—$OR_{14}$, —$(CH_2)_q$—NH—$(CH_2)_r$—$OR_{14}$, $C_3$-$C_{10}$ cycloalkyl, heterocycle comprising 1-4 heteroatoms selected from O, N, and S, aryl, or heteroaryl comprising 1-4 heteroatoms selected from N, O, and S;

Ring A is $C_3$-$C_{10}$ cycloalkyl, heterocycle comprising 1-4 heteroatoms selected from N, O, and S, aryl, or heteroaryl comprising 1-4 heteroatoms selected from N, O, and S;

$R_{14}$ is

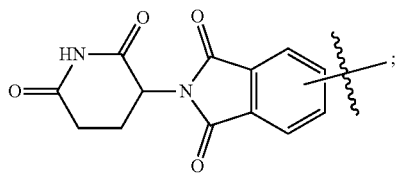

and each n, m, q, r, or s is independently at each occurrence 0, 1, 2, 3, 4, 5, or 6, provided that, when $R_1$ and $R_2$ together with the nitrogen atom to which they are attached form a heterocycle, wherein the heterocycle is morpholine and $R_5$ is —$CH_3$, then either (a) the morpholine is substituted or (b) Ring A is not phenyl.

In preferred embodiment (1) of Formula (I), (Ia), (Ib), or (II), s is at least 1 and at least one $R_9$ is —$C(O)OR_{12}$.

In preferred embodiment (2) of Formula (I), (Ia), (Ib), or (II), W is —N—, and $R_1$ and $R_2$, together with the nitrogen to which they are attached, form a heterocycle comprising 1-4 heteroatoms selected from O, N, and S, wherein the heterocycle is optionally substituted with one or more $R_{10}$, and wherein said heterocycle is not an optionally substituted morpholine.

In preferred embodiment (3) of Formula (I), (Ia), (Ib), or (II), s is at least 1, at least one $R_9$ is —$C(O)OR_{12}$, W is —N—, and $R_1$ and $R_2$, together with the nitrogen to which they are attached, form a heterocycle comprising 1-4 heteroatoms selected from O, N, and S, wherein the heterocycle is optionally substituted with one or more $R_{10}$, and wherein said heterocycle is not an optionally substituted morpholine.

It is understood that, for a compound of Formula (I), (Ia), (Ib), (Ic), (Id), (Ie), (If), (Ig), (Ih), or (II), $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, X, Y, W, s and Ring A can each be, where applicable, selected from the groups described herein, and any group described herein for any of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, X, Y, W, s and Ring A can be combined, where applicable, with any group described herein for one or more of the remainder of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, X, Y, W, s and Ring A.

In an embodiment of a compound of Formula (I), (Ia), (Ib), (Ie), or (II), or pharmaceutically acceptable salts thereof, or prodrugs, solvates, hydrates, isomers, or tautomers thereof, Y is —O—.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_3$ is H.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_3$ is —CN, $C_1$-$C_6$ alkyl, $C_1$-$C_6$ haloalkyl, —$(CH_2)_m$—$OR_{12}$, —$(CH_2)_m$—$C(O)R_{12}$, $C_3$-$C_{10}$ cycloalkyl, aryl, or 5 to 6 membered heteroaryl comprising 1-3 heteroatoms selected from O, N, and S; preferably $R_3$ is —CN, $C_1$-$C_3$ alkyl, —$(CH_2)_m$—OH, cyclopropyl or isoxazole; more preferably $R_3$ is —CN or $C_1$-$C_3$ alkyl; most preferably $R_3$ is —CN or methyl.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_4$ is H.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_5$ is H, halogen, $C_1$-$C_6$ alkyl, $C_1$-$C_6$ haloalkyl, or $C_1$-$C_6$ alkoxy; more preferably $R_5$ is H, halogen, methyl, or trifluoromethyl.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_6$ is H.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_3$ is —CN, $C_1$-$C_6$ alkyl, $C_1$-$C_6$ haloalkyl, —$(CH_2)_m$—$OR_{12}$, —$(CH_2)_m$—$C(O)R_{12}$, $C_3$-$C_{10}$ cycloalkyl, aryl, or 5 to 6 membered heteroaryl comprising 1-3 heteroatoms selected from O, N, and S, and $R_4$ is H; preferably $R_3$ is —CN, $C_1$-$C_3$ alkyl, —$(CH_2)_m$—OH, cyclopropyl, or isoxazole, and $R_4$ is H; more preferably $R_3$ is —CN or $C_1$-$C_3$ alkyl, and $R_4$ is H; most preferably $R_3$ is —CN or methyl, and $R_4$ is H.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_3$ is —CN, $C_1$-$C_6$ alkyl, $C_1$-$C_6$ haloalkyl, —$(CH_2)_m$—$OR_{12}$, —$(CH_2)_m$—$C(O)R_{12}$, $C_3$-$C_{10}$ cycloalkyl, aryl, or 5 to 6 membered heteroaryl comprising 1-3 heteroatoms selected from O, N, and S, $R_4$ is H, and $R_5$ is H, halogen, $C_1$-$C_6$ alkyl, $C_1$-$C_6$ haloalkyl, or $C_1$-$C_6$ alkoxy; preferably $R_3$ is —CN, $C_1$-$C_3$ alkyl, —$(CH_2)_m$—OH, cyclopropyl, or isoxazole, $R_4$ is H, and $R_5$ is H, halogen, $C_1$-$C_6$ alkyl, $C_1$-$C_6$ haloalkyl, or $C_1$-$C_6$ alkoxy; more preferably $R_3$ is —CN or $C_1$-$C_3$ alkyl, $R_4$ is H, and $R_5$ is H, halogen, $C_1$-$C_6$ alkyl, or $C_1$-$C_6$ haloalkyl; most preferably $R_3$ is —CN or methyl, $R_4$ is H, and $R_5$ is H, halogen, methyl, or trifluoromethyl.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_3$ is —CN, $C_1$-$C_6$ alkyl, $C_1$-$C_6$ haloalkyl, —$(CH_2)_m$—$OR_{12}$, —$(CH_2)_m$—$C(O)R_{12}$, $C_3$-$C_{10}$ cycloalkyl, aryl, or 5 to 6 membered heteroaryl comprising 1-3 heteroatoms selected from O, N, and S, and $R_4$ and $R_6$ are each H; preferably $R_3$ is —CN, $C_1$-$C_3$ alkyl, —$(CH_2)_m$—OH, cyclopropyl, or isoxazole, and $R_4$ and $R_6$ are each H; more preferably $R_3$ is —CN or $C_1$-$C_3$ alkyl, and $R_4$ and $R_6$ are each H; most preferably $R_3$ is —CN or methyl, and $R_4$ and $R_6$ are each H.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_3$ is —CN, $C_1$-$C_6$ alkyl, $C_1$-$C_6$ haloalkyl, —$(CH_2)_m$—$OR_{12}$, —$(CH_2)_m$—$C(O)R_{12}$, $C_3$-$C_{10}$ cycloalkyl, aryl, or 5 to 6 membered heteroaryl comprising 1-3 heteroatoms selected from O, N, and S, and $R_5$ is H, halogen, $C_1$-$C_6$ alkyl, $C_1$-$C_6$ haloalkyl, or $C_1$-$C_6$ alkoxy; preferably $R_3$ is —CN, $C_1$-$C_3$ alkyl, —(CH$_2$)$_m$—OH, cyclopropyl, or isoxazole, and $R_5$ is H, halogen, $C_1$-$C_6$ alkyl, $C_1$-$C_6$ haloalkyl, or $C_1$-$C_6$ alkoxy; more preferably $R_3$ is —CN or $C_1$-$C_3$ alkyl, and $R_5$ is H, halogen, $C_1$-$C_6$ alkyl, or $C_1$-$C_6$ haloalkyl; most preferably $R_3$ is —CN or methyl, and $R_5$ is H, halogen, methyl, or trifluoromethyl.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_3$ is —CN, $C_1$-$C_6$ alkyl, $C_1$-$C_6$ haloalkyl, —(CH$_2$)$_m$—OR$_{12}$, —(CH$_2$)$_m$—C(O)R$_{12}$, $C_3$-$C_{10}$ cycloalkyl, aryl, or 5 to 6 membered heteroaryl comprising 1-3 heteroatoms selected from O, N, and S, and $R_6$ is H; more preferably $R_3$ is —CN or $C_1$-$C_3$ alkyl, and $R_6$ is H; most preferably $R_3$ is —CN or methyl, and $R_6$ is H.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_3$ is —CN, $C_1$-$C_6$ alkyl, $C_1$-$C_6$ haloalkyl, —(CH$_2$)$_m$—OR$_{12}$, —(CH$_2$)$_m$—C(O)R$_{12}$, $C_3$-$C_{10}$ cycloalkyl, aryl, or 5 to 6 membered heteroaryl comprising 1-3 heteroatoms selected from O, N, and S, $R_5$ is H, halogen, $C_1$-$C_6$ alkyl, $C_1$-$C_6$ haloalkyl, or $C_1$-$C_6$ alkoxy, and $R_6$ is H; preferably $R_3$ is —CN, $C_1$-$C_3$ alkyl, —(CH$_2$)$_m$—OH, cyclopropyl, or isoxazole, $R_5$ is H, halogen, $C_1$-$C_6$ alkyl, $C_1$-$C_6$ haloalkyl, or $C_1$-$C_6$ alkoxy, and $R_6$ is H; more preferably $R_3$ is —CN or $C_1$-$C_3$ alkyl, $R_5$ is H, halogen, $C_1$-$C_6$ alkyl, or $C_1$-$C_6$ haloalkyl, and $R_6$ is H; most preferably $R_3$ is —CN or methyl, $R_5$ is H, halogen, methyl, or trifluoromethyl, and $R_6$ is H.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_3$ and $R_4$ are each H.

In yet a further embodiment of a compound of Formula (I), (Ia), (Ib), (Je), or (II), or pharmaceutically acceptable salts thereof, or prodrugs, solvates, hydrates, isomers, or tautomers thereof, $R_3$ and $R_4$ are each H, and $R_5$ is H, halogen, $C_1$-$C_6$ alkyl, $C_1$-$C_6$ haloalkyl, or $C_1$-$C_6$ alkoxy; preferably $R_3$ and $R_4$ are each H, and $R_5$ is H, halogen, methyl, or trifluoromethyl.

In yet a further embodiment of a compound of Formula (I), (Ia), (Ib), (Je), or (II), or pharmaceutically acceptable salts thereof, or prodrugs, solvates, hydrates, isomers, or tautomers thereof, $R_3$, $R_4$, and $R_6$ are each H.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_3$ is H, and $R_5$ is H, halogen, $C_1$-$C_6$ alkyl, $C_1$-$C_6$ haloalkyl, or $C_1$-$C_6$ alkoxy; preferably $R_3$ is H, and $R_5$ is H, halogen, methyl, or trifluoromethyl.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_3$ and $R_6$ are each H.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_3$ and $R_6$ are each H, and $R_5$ is H, halogen, $C_1$-$C_6$ alkyl, $C_1$-$C_6$ haloalkyl, or $C_1$-$C_6$ alkoxy; preferably $R_3$ and $R_6$ are each H, and $R_5$ is H, halogen, methyl, or trifluoromethyl.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_4$ is H, and $R_5$ is H, halogen, $C_1$-$C_6$ alkyl, $C_1$-$C_6$ haloalkyl, or $C_1$-$C_6$ alkoxy; preferably $R_5$ is H, halogen, methyl, or trifluoromethyl.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_5$ is H, halogen, $C_1$-$C_6$ alkyl, $C_1$-$C_6$ haloalkyl, or $C_1$-$C_6$ alkoxy, and $R_6$ is H; preferably $R_5$ is H, halogen, methyl, or trifluoromethyl, and $R_6$ is H.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_5$ is H, halogen, $C_1$-$C_6$ alkyl, $C_1$-$C_6$ haloalkyl, or $C_1$-$C_6$ alkoxy, and $R_4$ and $R_6$ are each H; preferably $R_5$ is H, halogen, methyl, or trifluoromethyl, and $R_4$ and $R_6$ are each H.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_3$ is —CN, $C_1$-$C_6$ alkyl, $C_1$-$C_6$ haloalkyl, —(CH$_2$)$_m$—OR$_{12}$, —(CH$_2$)$_m$—C(O)R$_{12}$, $C_3$-$C_{10}$ cycloalkyl, aryl, or 5 to 6 membered heteroaryl comprising 1-3 heteroatoms selected from O, N, and S, $R_4$ and $R_6$ are each H, and $R_5$ is H, halogen, $C_1$-$C_6$ alkyl, $C_1$-$C_6$ haloalkyl, or $C_1$-$C_6$ alkoxy; preferably $R_3$ is —CN, $C_1$-$C_3$ alkyl, —(CH$_2$)$_m$—OH, cyclopropyl, or isoxazole, $R_4$ and $R_6$ are each H, and $R_5$ is H, halogen, $C_1$-$C_6$ alkyl, $C_1$-$C_6$ haloalkyl, or $C_1$-$C_6$ alkoxy; more preferably $R_3$ is —CN or $C_1$-$C_3$ alkyl, $R_4$ and $R_6$ are each H, and $R_5$ is H, halogen, $C_1$-$C_6$ alkyl, or $C_1$-$C_6$ haloalkyl; most preferably $R_3$ is —CN or methyl, $R_4$ and $R_6$ are each H, and $R_5$ is H, halogen, methyl, or trifluoromethyl.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_3$, $R_4$, and $R_6$ are each H, and $R_5$ is H, halogen, $C_1$-$C_6$ alkyl, $C_1$-$C_6$ haloalkyl, or $C_1$-$C_6$ alkoxy; preferably $R_3$, $R_4$, and $R_6$ are each H, and $R_5$ is H, halogen, methyl, or trifluoromethyl.

In yet a further embodiment of a compound of Formula (I), (Ia), (Ib), (Ie), or (II), or pharmaceutically acceptable salts thereof, or prodrugs, solvates, hydrates, isomers, or tautomers thereof, X is —NR$_{12}$—, preferably —NH—.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_7$ is $C_1$-$C_6$ alkyl, or $C_1$-$C_6$ haloalkyl. In yet a further embodiment of a compound of Formula (I), (Ia), (Ib), (Ie), or (II), or pharmaceutically acceptable salts thereof, or prodrugs, solvates, hydrates, isomers, or tautomers thereof, $R_7$ is $C_1$-$C_3$ alkyl (preferably methyl).

In yet a further embodiment of a compound of Formula (I), (Ie), or (II), or pharmaceutically acceptable salts thereof, or prodrugs, solvates, hydrates, isomers, or tautomers thereof, $R_8$ is H.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_7$ is $C_1$-$C_6$ alkyl, or $C_1$-$C_6$ haloalkyl, and X is —NR$_{12}$—, preferably —NH—. In yet a further embodiment of a compound of Formula (I), (Ia), (Ib), (Ie), or (II), or pharmaceutically acceptable salts thereof, or prodrugs, solvates, hydrates, isomers, or tautomers thereof, $R_7$ is $C_1$-$C_3$ alkyl (preferably methyl) and X is —NR$_{12}$—, preferably —NH—.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_8$ is H and X is —$NR_{12}$—, preferably —NH—.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_7$ is $C_1$-$C_6$ alkyl, or $C_1$-$C_6$ haloalkyl, and $R_8$ is H. In yet a further embodiment of a compound of Formula (I), (Ia), (Ib), (Ie), or (II), or pharmaceutically acceptable salts thereof, or prodrugs, solvates, hydrates, isomers, or tautomers thereof, $R_7$ is $C_1$-$C_3$ alkyl (preferably methyl) and $R_8$ is H.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_7$ is $C_1$-$C_6$ alkyl, or $C_1$-$C_6$ haloalkyl, $R_8$ is H, and X is —$NR_{12}$—, preferably —NH—. In yet a further embodiment of a compound of Formula (I), (Ia), (Ib), (Ie), or (II), or pharmaceutically acceptable salts thereof, or prodrugs, solvates, hydrates, isomers, or tautomers thereof, $R_7$ is $C_1$-$C_3$ alkyl (preferably methyl), $R_8$ is H, and X is —$NR_{12}$—, preferably —NH—.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_7$ is $C_1$-$C_3$ alkyl. In yet a further embodiment of a compound of Formula (I), (Ia), (Ib), (Ie), or (II), or pharmaceutically acceptable salts thereof, or prodrugs, solvates, hydrates, isomers, or tautomers thereof, $R_7$ is $C_1$-$C_3$ alkyl, preferably $R_7$ is methyl.

In yet a further embodiment of a compound of Formula (I), (Ia), (Ib), (Ie), or (II), or pharmaceutically acceptable salts thereof, or prodrugs, solvates, hydrates, isomers, or tautomers thereof, each $R_9$ at each occurrence is independently halogen, —CN, $C_1$-$C_6$ alkyl, $C_1$-$C_6$ haloalkyl, $C_1$-$C_6$ alkoxy, —$(CH_2)_m$—$C(O)OR_{12}$, —$(CH_2)_m$—$C(O)N(R_{12})_2$, —$(CH_2)_m$—$SO_2R_{12}$, —$(CH_2)_m$—$SO_2N(R_{12})_2$, —$(CH_2)_m$—$CON(R_{12})_2$, —$(CH_2)_m$—$C(O)$—$NR_{12}$—$SO_2R_{13}$, —$(CH_2)_m$—$SO_2NR_{12}$—$C(O)R_{13}$, or tetrazole.

In yet a further embodiment of a compound of Formula (I), (Ia), (Ib), (Ie), or (II), or pharmaceutically acceptable salts thereof, or prodrugs, solvates, hydrates, isomers, or tautomers thereof, each $R_9$ at each occurrence is independently halogen, —CN, $C_1$-$C_6$ alkyl, $C_1$-$C_6$ haloalkyl, $C_1$-$C_6$ alkoxy, —$(CH_2)_m$—$C(O)OR_{12}$, —$(CH_2)_m$—$C(O)N(R_{12})_2$, —$(CH_2)_m$—$SO_2R_{12}$, —$(CH_2)_m$—$SO_2N(R_{12})_2$, —$(CH_2)_m$—$CON(R_{12})_2$, —$(CH_2)_m$—$C(O)$—$NR_{12}$—$SO_2R_{13}$, —$(CH_2)_m$—$SO_2NR_{12}$—$C(O)R_{13}$, $C_3$-$C_{10}$ cycloalkyl, or tetrazole, and each $R_{12}$ and $R_{13}$ at each occurrence is independently H, $C_1$-$C_6$ alkyl, $C_1$-$C_6$ haloalkyl, or —$(CH_2)_q$-phenyl.

In yet a further embodiment of a compound of Formula (I), (Ia), (Ib), (Ie), or (II), or pharmaceutically acceptable salts thereof, or prodrugs, solvates, hydrates, isomers, or tautomers thereof, $R_9$ is —$C(O)OR_{12}$ or —$CON(R_{12})_2$, preferably —$C(O)OH$ or —$CONHR_{12}$, most preferably —$C(O)OH$.

In yet a further embodiment of a compound of Formula (I), (Ia), (Ib), (Ie), or (II), or pharmaceutically acceptable salts thereof, or prodrugs, solvates, hydrates, isomers, or tautomers thereof, Ring A is phenyl, pyridine, pyridazine, pyrimidine, thiophene, furane, pyrazole, thiazole, imidazole, isoxazole, oxadiazole, indazole, benzothiophene, benzoxazole, benzimidazole, isoindole, indene or quinazoline; each of which is optionally substituted with $(R_9)_s$.

In yet a further embodiment of a compound of Formula (I), (Ia), (Ib), (Ie), or (II), or pharmaceutically acceptable salts thereof, or prodrugs, solvates, hydrates, isomers, or tautomers thereof, Ring A is phenyl, pyridine, pyrimidine, thiophene, pyrazole, benzothiophene, or benzoxazole, each of which is optionally substituted with $(R_9)_s$. In yet a further embodiment of a compound of Formula (I), (Ia), (Ib), (Ie), or (II), or pharmaceutically acceptable salts thereof, or prodrugs, solvates, hydrates, isomers, or tautomers thereof, Ring A is phenyl, pyridine, pyrimidine, thiophene, pyrazole, benzothiophene, or benzoxazole, each of which is optionally substituted with $(R_9)_s$, wherein s is at least 1 and at least one substituent $R_9$ is —$C(O)OR_{12}$ or —$CON(R_{12})_2$, preferably —$C(O)OH$ or —$CONHR_{12}$, most preferably —$C(O)OH$.

In yet a further embodiment of a compound of Formula (I), (Ia), (Ib), (Ie), or (II), or pharmaceutically acceptable salts thereof, or prodrugs, solvates, hydrates, isomers, or tautomers thereof, Ring A is a group of the formula:

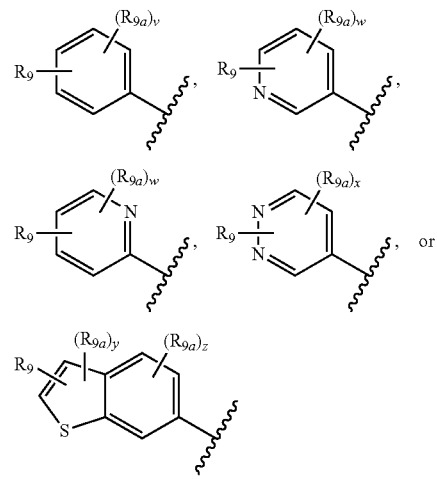

wherein $R_{9a}$ at each occurrence is independently halogen, —CN, $C_1$-$C_6$ alkyl, $C_1$-$C_6$ haloalkyl, $C_1$-$C_6$ alkoxy, or $C_3$-$C_{10}$ cycloalkyl, v is 0, 1, 2, 3, or 4, w is 0, 1, 2, or 3, x is 0, 1, or 2, y is 0 or 1, z is 0, 1, 2, or 3, and $R_9$ is —$(CH_2)_m$—$C(O)OR_{12}$, —$(CH_2)_m$—$C(O)N(R_{12})_2$, —$(CH_2)_m$—$SO_2R_{12}$, —$(CH_2)_m$—$SO_2N(R_{12})_2$, —$(CH_2)_m$—$CON(R_{12})_2$, —$(CH_2)_m$—$C(O)$—$NR_{12}$—$SO_2R_{13}$, —$(CH_2)_m$—$SO_2NR_{12}$—$C(O)R_{13}$, or heteroaryl comprising 1-4 heteroatoms selected from N, O, and S, wherein the heteroaryl is optionally substituted with one or more oxo, halogen, —CN, —OH, —$NH_2$, —$NO_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy; preferably $R_9$ is —$C(O)OR_{12}$ or —$C(O)NHR_{12}$. Most preferably $R_9$ is —$C(O)OH$.

In yet a further embodiment of a compound of Formula (I), (Ia), (Ib), (Ie), or (II), or pharmaceutically acceptable salts thereof, or prodrugs, solvates, hydrates, isomers, or tautomers thereof, Ring A is a group of the formula:

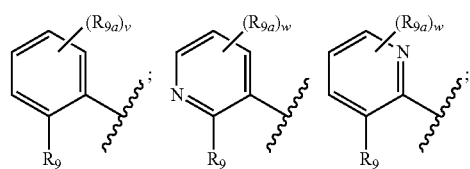

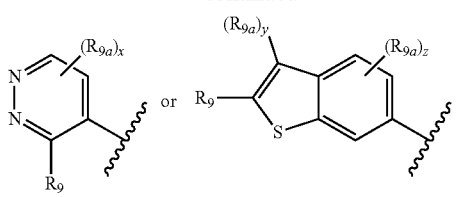

wherein $R_{9a}$ at each occurrence is independently halogen, —CN, $C_1$-$C_6$ alkyl, $C_1$-$C_6$ haloalkyl, $C_1$-$C_6$ alkoxy, or $C_3$-$C_{10}$ cycloalkyl, v is 0, 1, 2, 3, or 4, w is 0, 1, 2 or 3, x is 0, 1, or 2, y is 0 or 1, z is 0, 1, 2, or 3, and $R_9$ is —(CH$_2$)$_m$—C(O)OR$_{12}$, —(CH$_2$)$_m$—C(O)N(R$_{12}$)$_2$, —(CH$_2$)$_m$—SO$_2$R$_{12}$, —(CH$_2$)$_m$—SO$_2$N(R$_{12}$)$_2$, —(CH$_2$)$_m$—CON(R$_{12}$)$_2$, —(CH$_2$)$_m$—C(O)—NR$_{12}$—SO$_2$R$_{13}$, —(CH$_2$)$_m$—SO$_2$NR$_{12}$—C(O)R$_{13}$, or heteroaryl comprising 1-4 heteroatoms selected from N, O, and S, wherein the heteroaryl is optionally substituted with one or more oxo, halogen, —CN, —OH, —NH$_2$, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy; preferably $R_9$ is —C(O)OR$_{12}$ or —C(O)NHR$_{12}$. Most preferably $R_9$ is —C(O)OH.

In yet a further embodiment of a compound of Formula (I), (Ia), (Ib), (Ie), or (II), or pharmaceutically acceptable salts thereof, or prodrugs, solvates, hydrates, isomers, or tautomers thereof, Ring A is phenyl, pyridine, pyrimidine or benzothiophene, each of which is optionally substituted with $(R_9)_s$, preferably Ring A is a group of the formula:

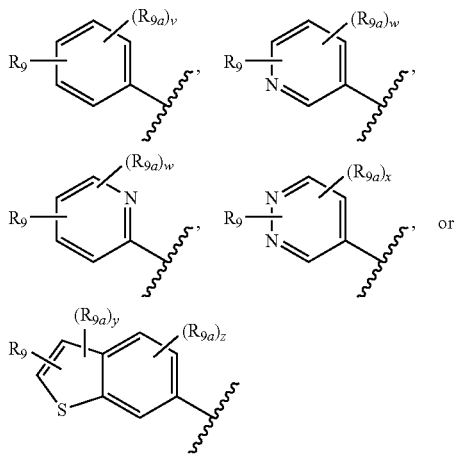

wherein $R_9$ is —C(O)OR$_{12}$; $R_{9a}$ is H, halogen, $C_1$-$C_3$ alkyl, $C_1$-$C_3$ haloalkyl, $C_1$-$C_3$ alkoxy, or $C_3$-$C_5$ cycloalkyl, v is 0, 1, 2, 3, or 4, w is 0, 1, 2, or 3, x is 0, 1, or 2, y is 0 or 1, and z is 0, 1, 2, or 3; preferably $R_9$ is —C(O)OH, $R_{9a}$ is halogen, $C_1$-$C_3$ alkyl, $C_1$-$C_3$ haloalkyl, $C_1$-$C_3$ alkoxy, or $C_3$-$C_5$ cycloalkyl, v is 0, 1, or 2, w is 0, 1, or 2, x is 0 or 1, y is 0 or 1, and z is 0, 1, or 2.

In yet a further embodiment of a compound of Formula (I), (Ia), (Ib), (Ie), or (II), or pharmaceutically acceptable salts thereof, or prodrugs, solvates, hydrates, isomers, or tautomers thereof, Ring A is a group of the formula:

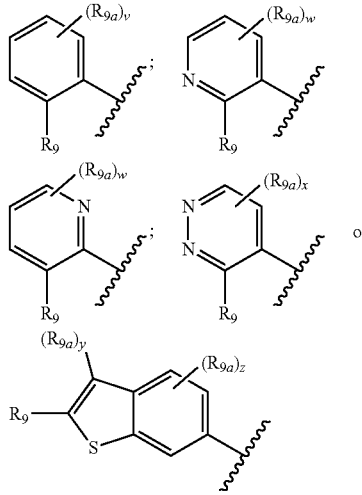

wherein $R_9$ is —C(O)OR$_{12}$; $R_{9a}$ is H, halogen, $C_1$-$C_3$ alkyl, $C_1$-$C_3$ haloalkyl, $C_1$-$C_3$ alkoxy, or $C_3$-$C_5$ cycloalkyl, v is 0, 1, 2, 3, or 4, w is 0, 1, 2, or 3, x is 0, 1, or 2, y is 0 or 1, and z is 0, 1, 2, or 3; preferably $R_9$ is —C(O)OH, $R_{9a}$ is halogen, $C_1$-$C_3$ alkyl, $C_1$-$C_3$ haloalkyl, $C_1$-$C_3$ alkoxy, or $C_3$-$C_5$ cycloalkyl, v is 0, 1, or 2, w is 0, 1, or 2, x is 0 or 1, y is 0 or 1, and z is 0, 1, or 2.

In yet a further embodiment of a compound of Formula (I), (Ia), (Ib), (Ie), or (II), or pharmaceutically acceptable salts thereof, or prodrugs, solvates, hydrates, isomers, or tautomers thereof, Ring A is a group of the formula:

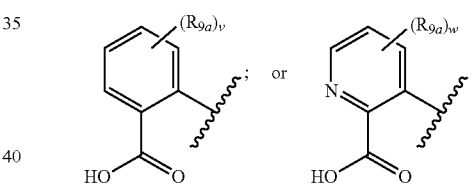

wherein $R_{9a}$ is halogen or trifluoromethyl; v is 0 or 1; and w is 0 or 1.

In yet a further embodiment of a compound of Formula (I), (Ia), (Ib), (Ie), or (II), or pharmaceutically acceptable salts thereof, or prodrugs, solvates, hydrates, isomers, or tautomers thereof, Ring A is a group of the formula:

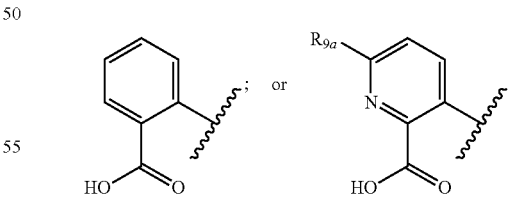

wherein $R_{9a}$ is halogen or trifluoromethyl, preferably chloro.

In yet a further embodiment of a compound of Formula (I), (Ia), (Ib), (Ie), or (II), or pharmaceutically acceptable salts thereof, or prodrugs, solvates, hydrates, isomers, or tautomers thereof, W is —N—, and $R_1$ and $R_2$, together with the nitrogen to which they are attached, form a heterocycle comprising 1-4 heteroatoms selected from O, N, and S, wherein the heterocycle is optionally substituted with 0, 1, 2, 3, 4 or 5 $R_{10}$, preferably 0, 1, 2, 3, or 4 $R_{10}$.

In yet a further embodiment of a compound of Formula (I), (Ia), (Ib), (Ie), or (II), or pharmaceutically acceptable salts thereof, or prodrugs, solvates, hydrates, isomers, or tautomers thereof, W is —N—, and $R_1$ and $R_2$, together with the nitrogen to which they are attached, form a heterocycle comprising 1-4 heteroatoms selected from O, N, and S, wherein the heterocycle is optionally substituted with one or more $R_{10}$, and two $R_{10}$, together with the atoms to which they are attached, form a $C_3$-$C_{10}$ cycloalkyl, a heterocycle comprising 1-4 heteroatoms selected from O, N, and S, an aryl, or a heteroaryl, wherein the cycloalkyl, heterocycle, aryl, and heteroaryl are optionally substituted with one or more oxo, =$NR_{12}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$, phenyl, $C_3$-$C_6$ cycloalkyl, or $R_{15}$.

In yet a further embodiment of a compound of Formula (I), (Ia), (Ib), (Ie), or (II), or pharmaceutically acceptable salts thereof, or prodrugs, solvates, hydrates, isomers, or tautomers thereof, W is —N—, and $R_1$ and $R_2$, together with the nitrogen to which they are attached, form a heterocycle comprising 1-4 heteroatoms selected from O, N, and S, wherein the heterocycle is optionally substituted with one or more $R_{10}$, and two $R_{10}$, together with the atoms to which they are attached, form a 4 to 6 membered heterocycle comprising 1-4 heteroatoms selected from O, N, and S, wherein the heterocycle is optionally substituted with one or more halogen, $C_1$-$C_6$ alkyl, $C_1$-$C_6$ haloalkyl, $C_1$-$C_6$ alkoxy, aryl, heteroaryl, or $R_{15}$.

In yet a further embodiment of a compound of Formula (I), (Ia), (Ib), (Ie), or (II), or pharmaceutically acceptable salts thereof, or prodrugs, solvates, hydrates, isomers, or tautomers thereof, W is —N—, and $R_1$ and $R_2$, together with the nitrogen to which they are attached, form a heterocycle comprising 1-4 heteroatoms selected from O, N, and S, wherein the heterocycle is optionally substituted with one or more $R_{10}$; two $R_{10}$, together with the atoms to which they are attached, form an aryl or a heteroaryl, wherein the aryl and heteroaryl are optionally substituted with one or more oxo, =$NR_{12}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$, phenyl, $C_3$-$C_6$ cycloalkyl, or $R_{15}$ and optionally a further two $R_{10}$, together with the atoms to which they are attached, form a $C_3$-$C_{10}$ cycloalkyl optionally substituted with one or more oxo, halogen, —CN, $C_1$-$C_6$ alkyl, $C_1$-$C_6$ haloalkyl, $C_1$-$C_6$ alkoxy, or —$(CH_2)_n$—$OR_{12}$.

In yet a further embodiment of a compound of Formula (I), (Ia), (Ib), (Ie), or (II), or pharmaceutically acceptable salts thereof, or prodrugs, solvates, hydrates, isomers, or tautomers thereof, $WR_1R_2$ is a group of the formula:

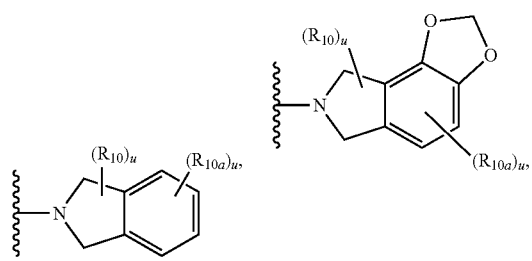

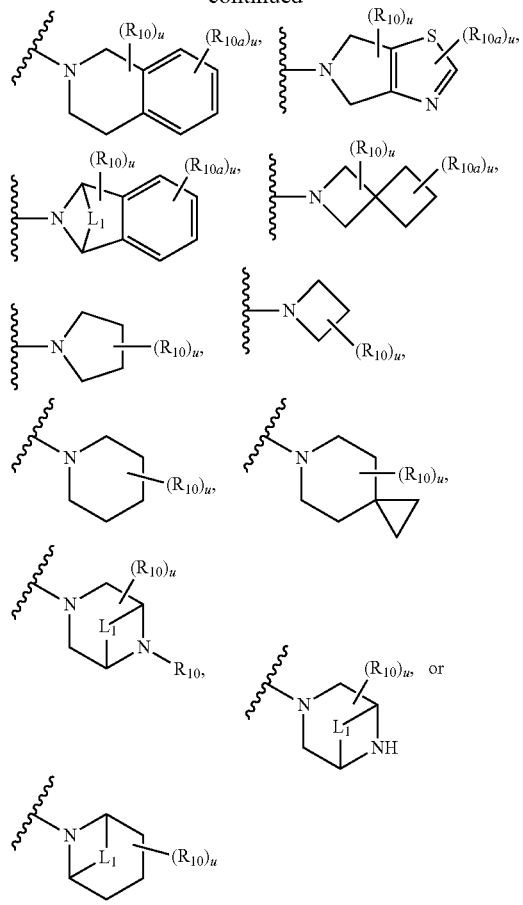

wherein $R_{10}$ at each occurrence is independently oxo, halogen, —CN, $C_1$-$C_6$ alkyl, $C_2$-$C_6$ alkenyl, $C_2$-$C_6$ alkynyl, G-$C_6$ haloalkyl, G-$C_6$ alkoxy, —$(CH_2)$—$OR_{12}$, —$(CH_2)_n$—$N(R_2)_2$, —$(CH_2)_n$—$C(O)R_{12}$, —$(CH_2)_n$—$C(O)OR_2$, —$(CH_2)_n$—$C(O)N(R_{12})_2$, —$(CH_2)$—$SO_2R_{12}$, —$(CH_2)_n$O—$(CH_2CH_2$—O$)_rR_{13}$, $C_3$-$C_{10}$ cycloalkyl, heterocycle, —$(CH_2)_n$-aryl, or heteroaryl, wherein the cycloalkyl, heterocycle, aryl, and heteroaryl is optionally substituted with halogen, G-$C_6$ alkyl, $C_2$-$C_6$ alkenyl, $C_2$-$C_6$ alkynyl, G-$C_6$ haloalkyl, G-$C_6$ alkoxy, G-$C_6$ haloalkoxy, or —$(CH_2)$—$SO_2R_{12}$; $R_{10a}$ at each occurrence is independently halogen, —CN, $C_1$-$C_6$ alkyl, $C_1$-$C_6$ haloalkyl, $C_1$-$C_6$ alkoxy, or —$(CH_2)_n$—$OR_{12}$, -$L_1$- is —$(CH_2)$— or —$(CH_2)_2$—, and u at each occurrence is independently 0, 1, 2, 3 or 4. Preferably $R_{10}$ is halogen, G-$C_6$ alkyl, G-$C_6$ haloalkyl or phenyl optionally substituted with halogen, -$L_1$- is —$(CH_2)$— or —$(CH_2)_2$—, and u at each occurrence is independently 0, 1 or 2.

In yet a further embodiment of a compound of Formula (I), (Ia), (Ib), (Ie), or (II), or pharmaceutically acceptable salts thereof, or prodrugs, solvates, hydrates, isomers, or tautomers thereof, $WR_1R_2$ is a group of the formula:

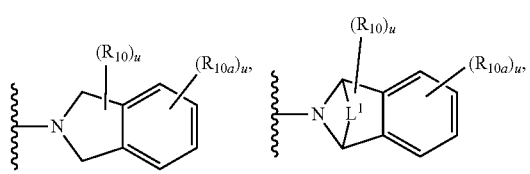

-continued

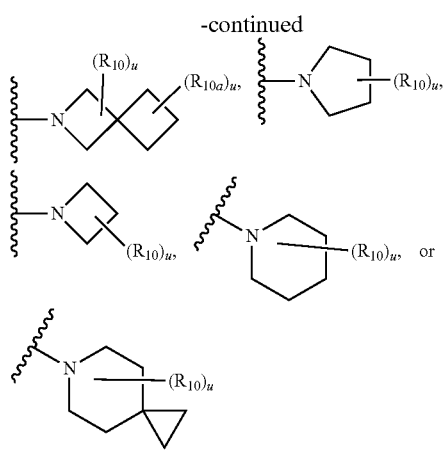

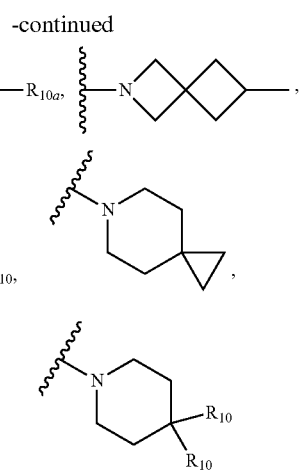

wherein $R_{10}$ at each occurrence is independently oxo, halogen, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)$—$OR_{12}$, —$(CH_2)_n$—$N(R_2)_2$, —$(CH_2)_n$—$C(O)R_{12}$, —$(CH_2)_n$—$C(O)OR_2$, —$(CH_2)_n$—$C(O)N(R_{12})_2$, —$(CH_2)$—$SO_2R_{12}$, —$(CH_2)_n$—O—$(CH_2CH_2$—O$)_rR_{13}$, $C_3$-$C_{10}$ cycloalkyl, heterocycle, —$(CH_2)_n$-aryl, or heteroaryl, wherein the cycloalkyl, heterocycle, aryl, and heteroaryl is optionally substituted with halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, or —$(CH_2)_n$—$SO_2R_{12}$; $R_{10a}$ at each occurrence is independently halogen, —CN, $C_1$-$C_6$ alkyl, $C_1$-$C_6$ haloalkyl, $C_1$-$C_6$ alkoxy, or —$(CH_2)_n$—$OR_{12}$; -$L_1$- is —$(CH_2)$— or —$(CH_2)_2$—, and u at each occurrence is independently 0, 1, 2, 3 or 4. Preferably $R_{10}$ is halogen, $C_1$-$C_6$ alkyl, $C_1$-$C_6$ haloalkyl or phenyl optionally substituted with halogen, -$L_1$- is —$(CH_2)$— or —$(CH_2)_2$—, and u at each occurrence is independently 0, 1 or 2.

In yet a further embodiment of a compound of Formula (I), (Ia), (Ib), (Ie), or (II), or pharmaceutically acceptable salts thereof, or prodrugs, solvates, hydrates, isomers, or tautomers thereof, $WR_1R_2$ is a group of the formula:

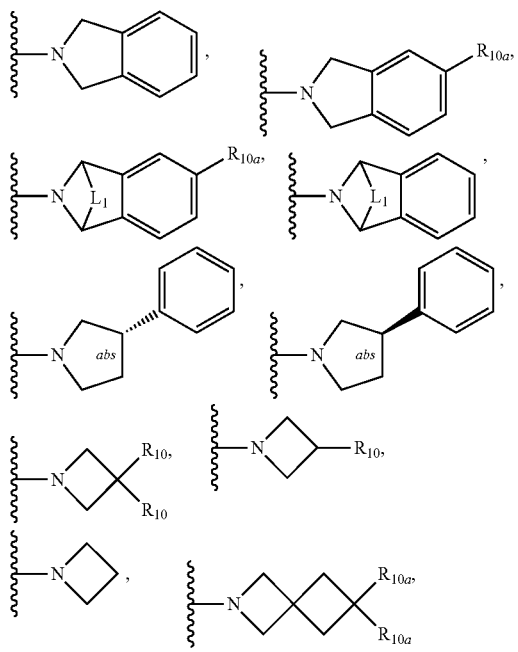

wherein $R_{10}$ at each occurrence is independently halogen, $C_1$-$C_6$ alkyl, $C_1$-$C_6$ haloalkyl or phenyl optionally substituted with halogen; $R_{10a}$ at each occurrence is independently halogen, —CN, $C_1$-$C_6$ alkyl, $C_1$-$C_6$ haloalkyl, $C_1$-$C_6$ alkoxy, or —$(CH_2)_n$—$OR_{12}$, and -$L_1$- is —$(CH_2)$— or —$(CH_2)_2$—.

In yet a further embodiment of a compound of Formula (I), (Ia), (Ib), (Ie), or (II), or pharmaceutically acceptable salts thereof, or prodrugs, solvates, hydrates, isomers, or tautomers thereof, $WR_1R_2$ is a group of the formula:

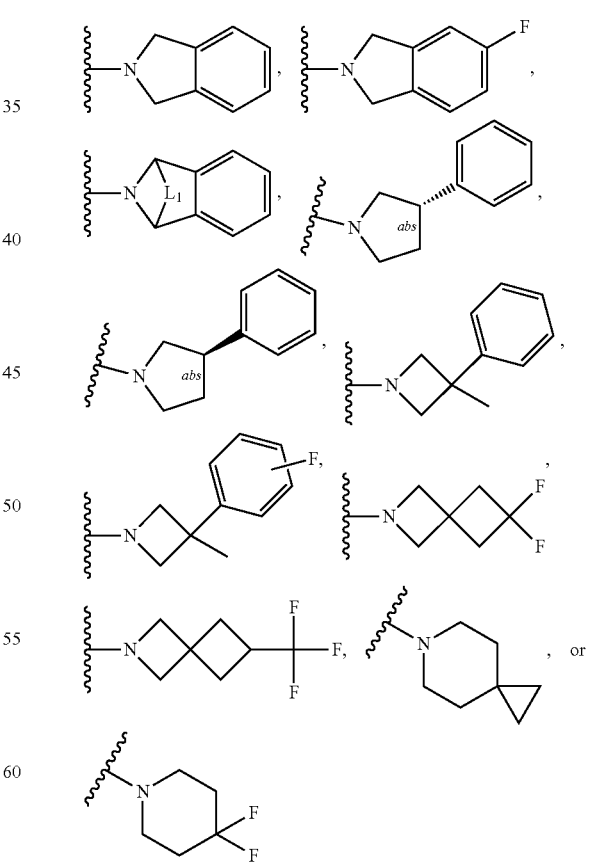

wherein -$L_1$- is —$(CH_2)$— or —$(CH_2)_2$—, preferably —$(CH_2)_2$—.

In yet a further embodiment of a compound of formula (Ic):

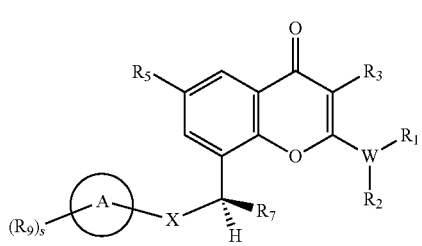

or a prodrug, solvate, enantiomer, stereoisomer, tautomer, or pharmaceutically acceptable salt thereof, $R_3$ is —CN, $C_1$-$C_6$ alkyl, $C_1$-$C_6$ haloalkyl, —$(CH_2)_m$—$OR_{12}$, —$(CH_2)_m$—$C(O)R_{12}$, $C_3$-$C_{10}$ cycloalkyl, aryl, or 5 to 6 membered heteroaryl comprising 1-3 heteroatoms selected from O, N, and S, $R_5$ is H, halogen, $C_1$-$C_6$ alkyl, $C_1$-$C_6$ haloalkyl, or $C_1$-$C_6$ alkoxy, and —X— is —$NR_{12}$—; preferably $R_3$ is —CN, $C_1$-$C_3$ alkyl, —$(CH_2)_m$—OH, cyclopropyl, or isoxazole, $R_5$ is H, halogen, $C_1$-$C_6$ alkyl, $C_1$-$C_6$ haloalkyl, or $C_1$-$C_6$ alkoxy and —X— is —NH—; more preferably $R_3$ is —CN or $C_1$-$C_3$ alkyl, $R_5$ is H, halogen, $C_1$-$C_6$ alkyl, or $C_1$-$C_6$ haloalkyl, $C_1$-$C_3$ alkyl and —X— is —NH—; most preferably $R_3$ is —CN or methyl, $R_5$ is H, halogen, methyl or trifluoromethyl and —X— is —NH—.

In yet a further embodiment of a compound of Formula (Ic) or pharmaceutically acceptable salts thereof, or prodrugs, solvates, hydrates, isomers, or tautomers thereof, $R_7$ is $C_1$-$C_6$ alkyl or $C_1$-$C_6$ haloalkyl; preferably $R_7$ is $C_1$-$C_3$ alkyl; most preferably methyl.

In yet a further embodiment of a compound of Formula (Ic) or pharmaceutically acceptable salts thereof, or prodrugs, solvates, hydrates, isomers, or tautomers thereof, $R_3$ is —CN, $C_1$-$C_6$ alkyl, $C_1$-$C_6$ haloalkyl, —$(CH_2)_m$—$OR_{12}$, —$(CH_2)_m$—$C(O)R_{12}$, $C_3$-$C_{10}$ cycloalkyl, aryl or 5 to 6 membered heteroaryl comprising 1-3 heteroatoms selected from O, N, and S, $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl and —X— is —$NR_{12}$—; preferably $R_3$ is —CN, $C_1$-$C_3$ alkyl, —$(CH_2)_m$—OH, cyclopropyl or isoxazole, $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl and —X— is —NH—; more preferably $R_3$ is —CN or $C_1$-$C_3$ alkyl, $R_5$ is H, halogen, $C_1$-$C_6$ alkyl, or $C_1$-$C_6$ haloalkyl, $R_7$ is $C_1$-$C_3$ alkyl and —X— is —NH—; most preferably $R_3$ is —CN or methyl, $R_5$ is H, halogen, methyl or trifluoromethyl, $R_7$ is methyl and —X— is —NH—.

In yet a further embodiment of a compound of Formula (Ic) or pharmaceutically acceptable salts thereof, or prodrugs, solvates, hydrates, isomers, or tautomers thereof, Ring A is phenyl, pyridine, thiophene, pyrazole, benzothiophene or benzoxazole, each of which is optionally substituted with $(R_9)_s$, wherein s is at least 1 and at least one substituent $R_9$ is —$C(O)OR_{12}$ or —$CON(R_{12})_2$, preferably —$C(O)OH$ or —$CONHR_{12}$, most preferably —$C(O)OH$.

In yet a further embodiment of a compound of Formula (Ic) or pharmaceutically acceptable salts thereof, or prodrugs, solvates, hydrates, isomers, or tautomers thereof, $R_3$ is —CN, $C_1$-$C_6$ alkyl, $C_1$-$C_6$ haloalkyl, —$(CH_2)_m$—$OR_{12}$, —$(CH_2)_m$—$C(O)R_{12}$, $C_3$-$C_{10}$ cycloalkyl, aryl or 5 to 6 membered heteroaryl comprising 1-3 heteroatoms selected from O, N, and S, $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl —X— is —$NR_{12}$— and Ring A is phenyl, pyridine, thiophene, pyrazole, benzothiophene or benzoxazole, each of which is optionally substituted with $(R_9)_s$, wherein s is at least 1 and at least one substituent $R_9$ is —$C(O)OR_{12}$ or —$CON(R_{12})_2$; preferably $R_3$ is —CN, $C_1$-$C_3$ alkyl, —$(CH_2)_m$—OH, cyclopropyl or isoxazole, $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl, —X— is —NH— and Ring A is phenyl, pyridine, thiophene, pyrazole, benzothiophene or benzoxazole, each of which is optionally substituted with $(R_9)_s$, wherein s is at least 1 and at least one substituent $R_9$ is —$C(O)OH$ or —$CONHR_{12}$; more preferably $R_3$ is —CN or $C_1$-$C_3$ alkyl, $R_5$ is H, halogen, $C_1$-$C_6$ alkyl, or $C_1$-$C_6$ haloalkyl, $R_7$ is $C_1$-$C_3$ alkyl, —X— is —NH— and Ring A is phenyl, pyridine, thiophene, pyrazole, benzothiophene or benzoxazole, each of which is optionally substituted with $(R_9)_s$, wherein s is at least 1 and at least one substituent $R_9$ is —$C(O)OH$; most preferably $R_3$ is —CN or methyl, $R_5$ is H, halogen, methyl or trifluoromethyl, $R_7$ is methyl, —X— is —NH— and Ring A is phenyl, pyridine, thiophene, pyrazole, benzothiophene or benzoxazole, each of which is optionally substituted with $(R_9)_s$, wherein s is at least 1 and at least one substituent $R_9$ is —$C(O)OH$.

In yet a further embodiment of a compound of Formula (Ic) or pharmaceutically acceptable salts thereof, or prodrugs, solvates, hydrates, isomers, or tautomers thereof, Ring A is a group of the formula:

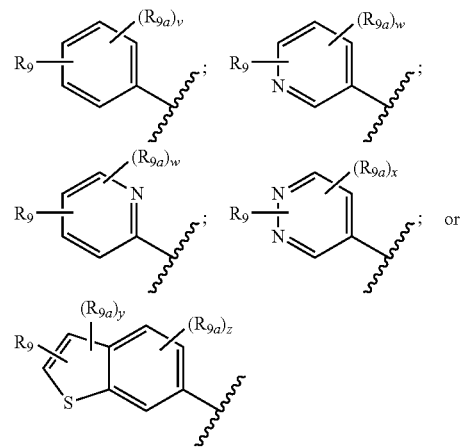

wherein $R_9$ is —$C(O)OH$, $R_{9a}$ at each occurrence is independently halogen, $C_1$-$C_3$ alkyl, $C_1$-$C_3$ haloalkyl, $C_1$-$C_3$ alkoxy or $C_3$-$C_5$ cycloalkyl, v is 0, 1 or 2, w is 0, 1, or 2, x is 0 or 1, y is 0 or 1, and z is 0, 1, or 2.

In yet a further embodiment of a compound of Formula (Ic) or pharmaceutically acceptable salts thereof, or prodrugs, solvates, hydrates, isomers, or tautomers thereof, Ring A is a group of the formula:

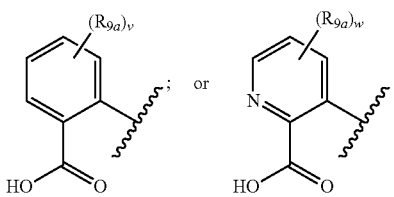

wherein $R_{9a}$ is halogen or trifluoromethyl; v is 0 or 1; and w is 0 or 1.

In yet a further embodiment of a compound of Formula (Ic) or pharmaceutically acceptable salts thereof, or prodrugs, solvates, hydrates, isomers, or tautomers thereof, Ring A is a group of the formula:

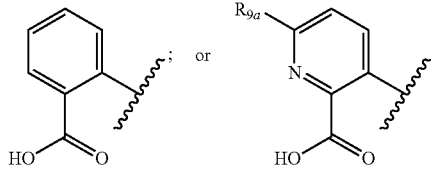

wherein $R_{9a}$ is halogen or trifluoromethyl; preferably $R_{9a}$ is chloro.

In yet a further embodiment of a compound of Formula (Ic) or pharmaceutically acceptable salts thereof, or prodrugs, solvates, hydrates, isomers, or tautomers thereof, $R_3$ is —CN, $C_1$-$C_6$ alkyl, $C_1$-$C_6$ haloalkyl, —$(CH_2)_m$—$OR_{12}$, —$(CH_2)_m$—$C(O)R_{12}$, $C_3$-$C_{10}$ cycloalkyl, aryl or a 5 to 6 membered heteroaryl comprising 1-3 heteroatoms selected from O, N, and S, $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl —X— is —$NR_{12}$—, and Ring A is a group of the formula:

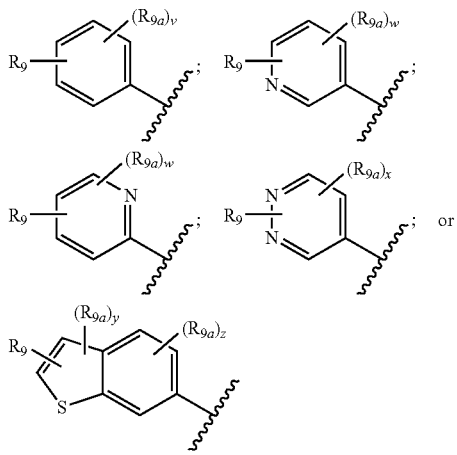

wherein $R_9$ is —C(O)OH, $R_{9a}$ at each occurrence is independently halogen, $C_1$-$C_3$ alkyl, $C_1$-$C_3$ haloalkyl, $C_1$-$C_3$ alkoxy or $C_3$-$C_5$ cycloalkyl, v is 0, 1 or 2, w is 0, 1 or 2, x is 0 or 1, y is 0 or 1, and z is 0, 1, or 2; preferably $R_3$ is —CN, $C_1$-$C_3$ alkyl, —$(CH_2)_m$—OH, cyclopropyl or isoxazole, $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl, —X— is —NH— and Ring A is a group of the formula:

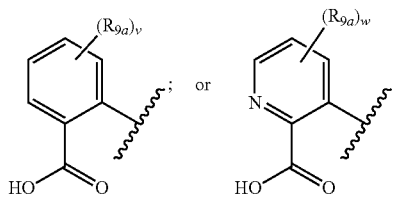

wherein $R_{9a}$ is halogen or trifluoromethyl; v is 0 or 1; and w is 0 or 1; more preferably $R_3$ is —CN or $C_1$-$C_3$ alkyl, $R_5$ is H, halogen, $C_1$-$C_6$ alkyl, or $C_1$-$C_6$ haloalkyl, $R_7$ is $C_1$-$C_3$ alkyl, —X— is —NH—, and Ring A is a group of the formula:

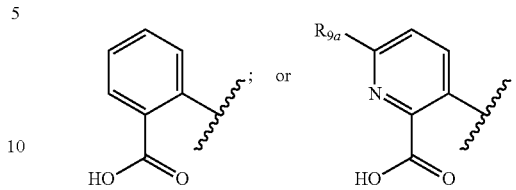

wherein $R_{9a}$ is halogen or trifluoromethyl, preferably $R_{9a}$ is chloro; most preferably $R_3$ is —CN or methyl, $R_5$ is H, halogen, methyl or trifluoromethyl, $R_7$ is methyl, —X— is —NH— and Ring A is a group of the formula:

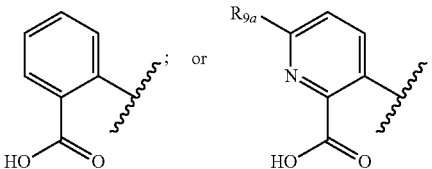

wherein $R_{9a}$ is halogen or trifluoromethyl, preferably $R_{9a}$ is chloro.

In yet a further embodiment of a compound of Formula (Ic) or pharmaceutically acceptable salts thereof, or prodrugs, solvates, hydrates, isomers, or tautomers thereof, W is —N— and $R_1$ and $R_2$, together with the nitrogen to which they are attached, form a heterocycle comprising 1-4 heteroatoms selected from O, N, and S, wherein the heterocycle is optionally substituted with one or more $R_{10}$ and two $R_{10}$, together with the atoms to which they are attached, form a 4 to 6 membered heterocycle comprising 1-4 heteroatoms selected from O, N, and S, wherein the heterocycle is optionally substituted with one or more halogen, $C_1$-$C_6$ alkyl, $C_1$-$C_6$ haloalkyl, $C_1$-$C_6$ alkoxy, aryl or heteroaryl, or $R_{15}$.

In yet a further embodiment of a compound of Formula (Ic) or pharmaceutically acceptable salts thereof, or prodrugs, solvates, hydrates, isomers, or tautomers thereof, $WR_1R_2$ is a group of the formula:

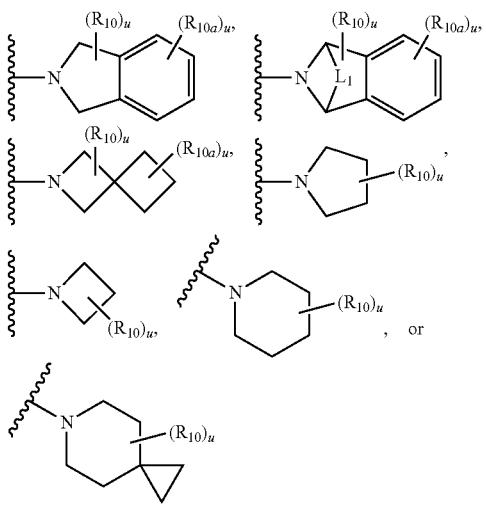

wherein $R_{10}$ at each occurrence is independently halogen, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$, —$(CH_2)_n$—O—$(CH_2CH_2$—O$)_rR_{13}$, $C_3$-$C_{10}$ cycloalkyl, heterocycle, —$(CH_2)_n$-aryl, or heteroaryl, wherein the cycloalkyl, heterocycle, aryl, and heteroaryl is optionally substituted with halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, or —$(CH_2)_n$—$SO_2R_{12}$; $R_{10a}$ at each occurrence is independently halogen, —CN, $C_1$-$C_6$ alkyl, $C_1$-$C_6$ haloalkyl, $C_1$-$C_6$ alkoxy, or —$(CH_2)_n$—$OR_{12}$, -$L_1$- is —$(CH_2)$— or —$(CH_2)_2$—, and u is at each occurrence independently 0, 1, 2, 3 or 4. Preferably $R_{10}$ is halogen, $C_1$-$C_6$ alkyl, $C_1$-$C_6$ haloalkyl or phenyl optionally substituted with halogen, -$L_1$- is —$(CH_2)$— or —$(CH_2)_2$—, and u is independently 0, 1 or 2.

In yet a further embodiment of a compound of Formula (Ic) or pharmaceutically acceptable salts thereof, or prodrugs, solvates, hydrates, isomers, or tautomers thereof, $WR_1R_2$ is a group of the formula:

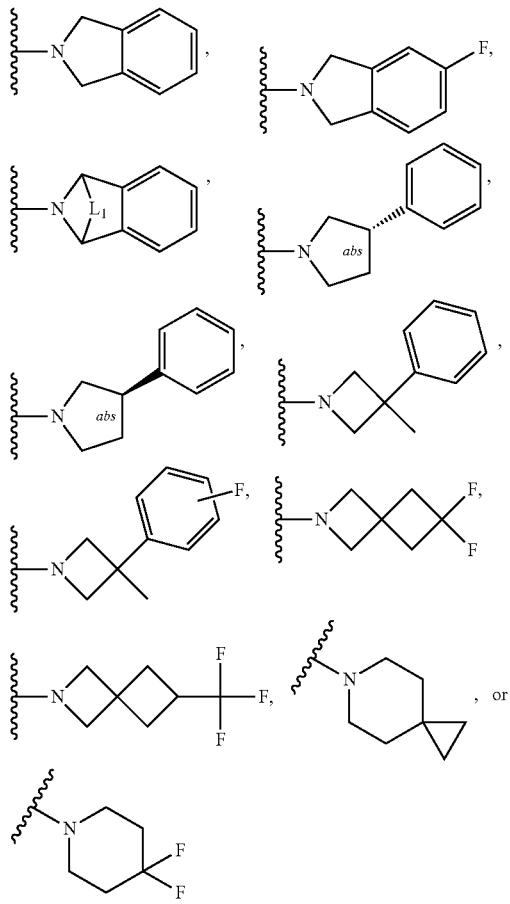

wherein -$L_1$- is —$(CH_2)$— or —$(CH_2)_2$—, preferably —$(CH_2)_2$—.

In yet a further embodiment of a compound of Formula (Ic) or pharmaceutically acceptable salts thereof, or prodrugs, solvates, hydrates, isomers, or tautomers thereof, $R_3$ is —CN, $C_1$-$C_6$ alkyl, $C_1$-$C_6$ haloalkyl, —$(CH_2)_m$—$OR_{12}$, —$(CH_2)_m$—$C(O)R_{12}$, $C_3$-$C_{10}$ cycloalkyl, aryl or 5 to 6 membered heteroaryl comprising 1-3 heteroatoms selected from O, N, and S, $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl, —X— is —$NR_{12}$— and W is —N— and $R_1$ and $R_2$, together with the nitrogen to which they are attached, form a heterocycle comprising 1-4 heteroatoms selected from O, N, and S, wherein the heterocycle is optionally substituted with one or more $R_{10}$ and two $R_{10}$, together with the atoms to which they are attached, form a 4 to 6 membered heterocycle comprising 1-4 heteroatoms selected from O, N, and S, wherein the heterocycle is optionally substituted with one or more halogen, $C_1$-$C_6$ alkyl, $C_1$-$C_6$ haloalkyl, $C_1$-$C_6$ alkoxy, aryl, heteroaryl, or $R_{15}$; preferably $R_3$ is —CN, $C_1$-$C_3$ alkyl, —$(CH_2)_m$—OH, cyclopropyl or isoxazole, $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl, —X— is —NH— and $WR_1R_2$ is a group of the formula:

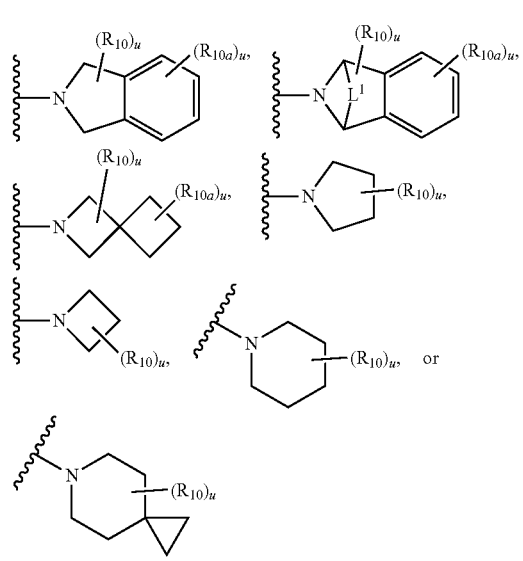

wherein $R_{10}$ at each occurrence is independently halogen, $C_1$-$C_6$ alkyl, $C_1$-$C_6$ haloalkyl or phenyl optionally substituted with halogen, $R_{10a}$ at each occurrence is independently halogen, —CN, $C_1$-$C_6$ alkyl, $C_1$-$C_6$ haloalkyl, $C_1$-$C_6$ alkoxy, or —$(CH_2)_n$—$OR_{12}$, -$L_1$- is —$(CH_2)$— or —$(CH_2)_2$—, and u is at each occurrence independently 0, 1 or 2; more preferably $R_3$ is —CN or $C_1$-$C_3$ alkyl, $R_5$ is H, halogen, $C_1$-$C_6$ alkyl, or $C_1$-$C_6$ haloalkyl, $R_7$ is $C_1$-$C_3$ alkyl and —X— is —NH—; most preferably $R_3$ is —CN or methyl, $R_5$ is H, halogen, methyl or trifluoromethyl, $R_7$ is methyl, —X— is —NH— and $WR_1R_2$ is a group of the formula:

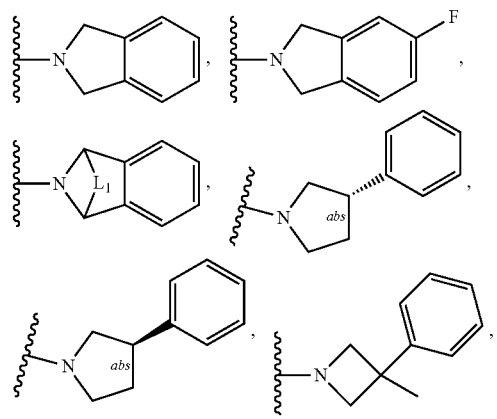

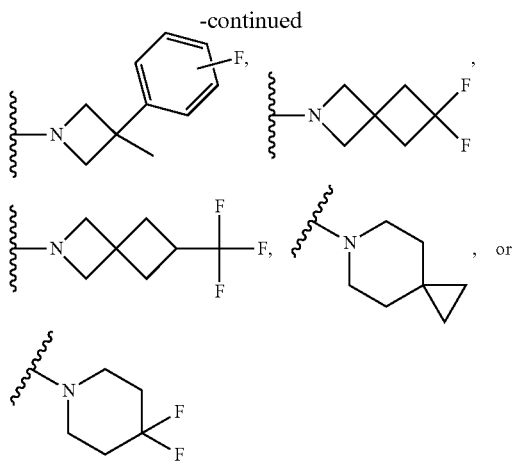

wherein -L$_1$- is —(CH$_2$)— or —(CH$_2$)$_2$—, preferably —(CH$_2$)$_2$—.

In yet a further embodiment of a compound of Formula (Ic) or pharmaceutically acceptable salts thereof, or prodrugs, solvates, hydrates, isomers, or tautomers thereof, R$_3$ is —CN, C$_1$-C$_6$ alkyl, C$_1$-C$_6$ haloalkyl, —(CH$_2$)$_m$—OR$_{12}$, —(CH$_2$)$_m$—C(O)R$_{12}$, C$_3$-C$_{10}$ cycloalkyl, aryl or 5 to 6 membered heteroaryl comprising 1-3 heteroatoms selected from O, N, and S, R$_5$ is H, halogen, C$_1$-C$_6$ alkyl, C$_1$-C$_6$ haloalkyl, or C$_1$-C$_6$ alkoxy, R$_7$ is C$_1$-C$_6$ alkyl or C$_1$-C$_6$ haloalkyl, —X— is —NR$_{12}$—, Ring A is phenyl, pyridine, thiophene, pyrazole, benzothiophene or benzoxazole, each of which is optionally substituted with (R$_9$)$_s$, wherein s is at least 1 and at least one substituent R$_9$ is —C(O)OR$_{12}$ or —CON(R$_{12}$)$_2$ and W is —N— and R$_1$ and R$_2$, together with the nitrogen to which they are attached, form a heterocycle comprising 1-4 heteroatoms selected from O, N, and S, wherein the heterocycle is optionally substituted with one or more R$_{10}$ and two R$_{10}$, together with the atoms to which they are attached, form a 4 to 6 membered heterocycle comprising 1-4 heteroatoms selected from O, N, and S, wherein the heterocycle is optionally substituted with one or more halogen, C$_1$-C$_6$ alkyl, C$_1$-C$_6$ haloalkyl, C$_1$-C$_6$ alkoxy, aryl or heteroaryl, or R$_{15}$; preferably R$_3$ is —CN, C$_1$-C$_3$ alkyl, —(CH$_2$)$_m$—OH, cyclopropyl or isoxazole, R$_5$ is H, halogen, C$_1$-C$_6$ alkyl, C$_1$-C$_6$ haloalkyl, or C$_1$-C$_6$ alkoxy, R$_7$ is C$_1$-C$_6$ alkyl or C$_1$-C$_6$ haloalkyl, —X— is —NH—, Ring A is phenyl, pyridine, thiophene, pyrazole, benzothiophene or benzoxazole, each of which is optionally substituted with (R$_9$)$_s$, wherein s is at least 1 and at least one substituent R$_9$ is —C(O)OH or —CONHR$_{12}$; and WR$_1$R$_2$ is a group of the formula:

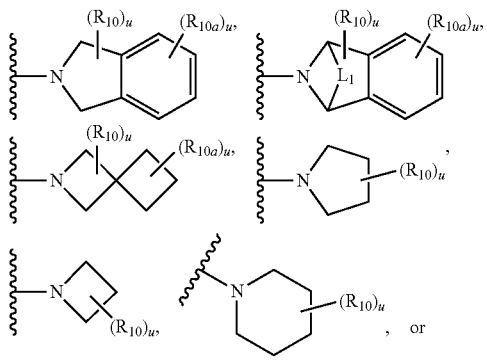

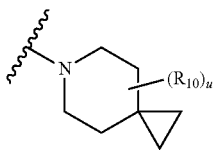

wherein R$_{10}$ at each occurrence is independently halogen, C$_1$-C$_6$ alkyl, C$_1$-C$_6$ haloalkyl or phenyl optionally substituted with halogen, R$_{10a}$ at each occurrence is independently halogen, —CN, C$_1$-C$_6$ alkyl, C$_1$-C$_6$ haloalkyl, C$_1$-C$_6$ alkoxy, or —(CH$_2$)$_n$—OR$_{12}$, -L$_1$- is —(CH$_2$)— or —(CH$_2$)$_2$—, and u is at each occurrence independently 0, 1 or 2; more preferably R$_3$ is —CN or C$_1$-C$_3$ alkyl, R$_5$ is H, halogen, C$_1$-C$_6$ alkyl, or C$_1$-C$_6$ haloalkyl, R$_7$ is C$_1$-C$_3$ alkyl, —X— is —NH—, Ring A is phenyl, pyridine, thiophene, pyrazole, benzothiophene or benzoxazole, each of which is optionally substituted with (R$_9$)$_s$, wherein s is at least 1 and at least one substituent R$_9$ is —C(O)OH and WR$_1$R$_2$ is a group of the formula:

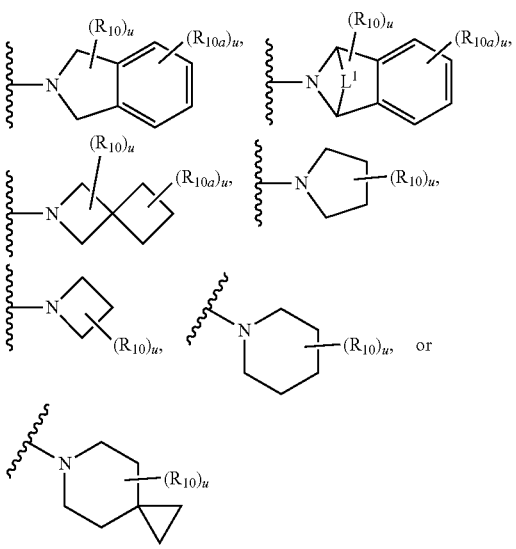

wherein R$_{10}$ at each occurrence is independently halogen, C$_1$-C$_6$ alkyl, C$_1$-C$_6$ haloalkyl or phenyl optionally substituted with halogen, R$_{10a}$ at each occurrence is independently halogen, —CN, C$_1$-C$_6$ alkyl, C$_1$-C$_6$ haloalkyl, C$_1$-C$_6$ alkoxy, or —(CH$_2$)$_n$—OR$_{12}$, -L$_1$- is —(CH$_2$)— or —(CH$_2$)$_2$—, and u is at each occurrence independently 0, 1 or 2; most preferably R$_3$ is —CN or methyl, R$_5$ is H, halogen, methyl or trifluoromethyl, R$_7$ is methyl, —X— is —NH—, Ring A is phenyl, pyridine, thiophene, pyrazole, benzothiophene or benzoxazole, each of which is optionally substituted with (R$_9$)$_s$, wherein s is at least 1 and at least one substituent R$_9$ is —C(O)OH and WR$_1$R$_2$ is a group of the formula:

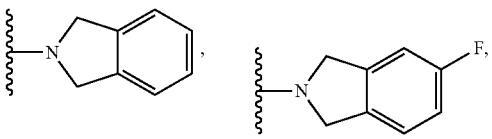

-continued

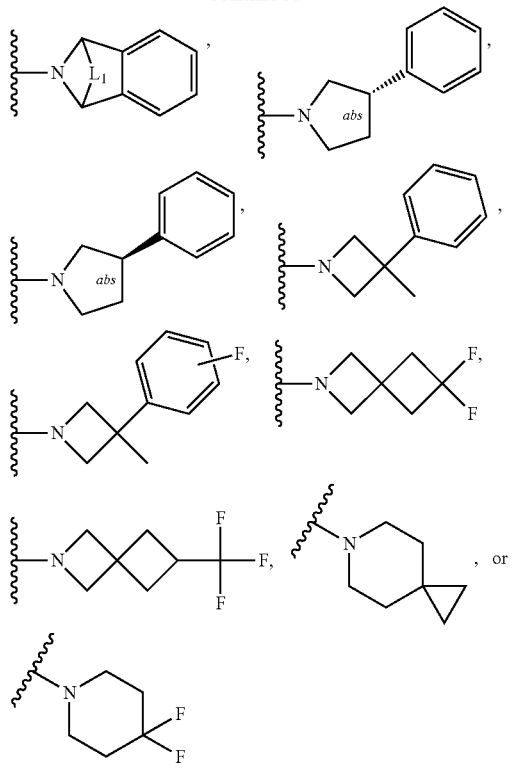

wherein, -L₁- is —(CH₂)— or —(CH₂)₂—, preferably —(CH₂)₂—.

In yet a further embodiment of a compound of Formula (Ic) or pharmaceutically acceptable salts thereof, or prodrugs, solvates, hydrates, isomers, or tautomers thereof, $R_3$ is —CN, $C_1$-$C_6$ alkyl, $C_1$-$C_6$ haloalkyl, —(CH₂)$_m$—OR$_{12}$, —(CH₂)$_m$—C(O)R₂, $C_3$-$C_{10}$ cycloalkyl, aryl or 5 to 6 membered heteroaryl comprising 1-3 heteroatoms selected from O, N, and S, $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl —X— is —NR$_{12}$—, Ring A is a group of the formula:

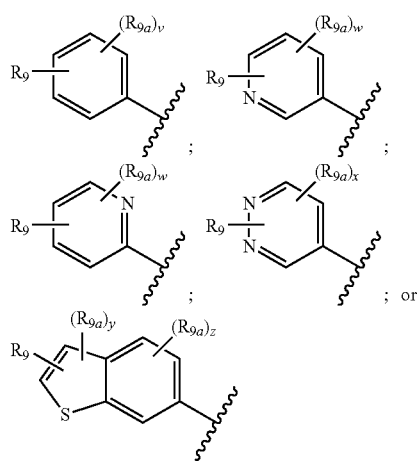

wherein $R_9$ is —C(O)OH, $R_{9a}$ at each occurrence is independently halogen, $C_1$-$C_3$ alkyl, $C_1$-$C_3$ haloalkyl, $C_1$-$C_3$ alkoxy or $C_3$-$C_5$ cycloalkyl, v is 0, 1 or 2, w is 0, 1 or 2, x is 0 or 1, y is 0 or 1, and z is 0, 1, or 2 and W is —N— and $R_1$ and $R_2$, together with the nitrogen to which they are attached, form a heterocycle comprising 1-4 heteroatoms selected from O, N, and S, wherein the heterocycle is optionally substituted with one or more R$_{10}$ and two R$_{10}$, together with the atoms to which they are attached, form a 4 to 6 membered heterocycle comprising 1-4 heteroatoms selected from O, N, and S, wherein the heterocycle is optionally substituted with one or more halogen, $C_1$-$C_6$ alkyl, $C_1$-$C_6$ haloalkyl, $C_1$-$C_6$ alkoxy, aryl or heteroaryl, or R$_{15}$; preferably $R_3$ is —CN, $C_1$-$C_3$ alkyl, —(CH₂)$_m$—OH, cyclopropyl or isoxazole, $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl, —X— is —NH—, Ring A is a group of the formula:

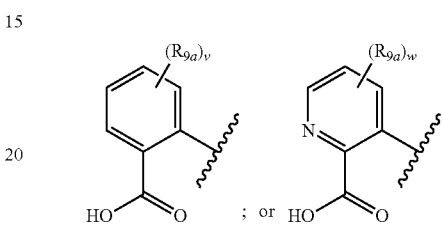

wherein $R_{9a}$ is halogen or trifluoromethyl; v is 0 or 1; and w is 0 or 1 and WR₁R₂ is a group of the formula:

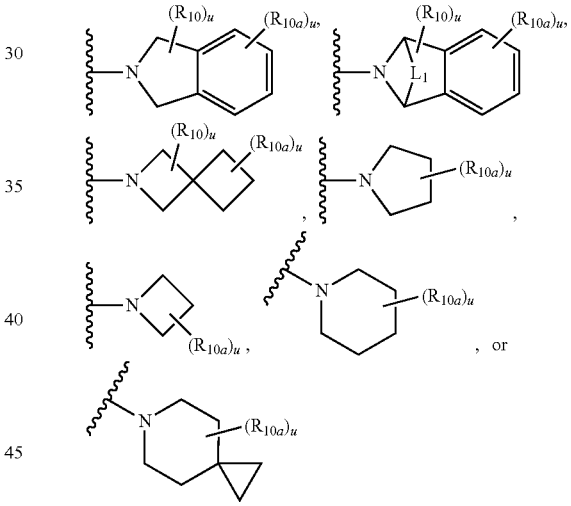

wherein R$_{10}$ at each occurrence is independently halogen, $C_1$-$C_6$ alkyl, $C_1$-$C_6$ haloalkyl or phenyl optionally substituted with halogen, R$_{10a}$ at each occurrence is independently halogen, —CN, $C_1$-$C_6$ alkyl, $C_1$-$C_6$ haloalkyl, $C_1$-$C_6$ alkoxy, or —(CH₂)$_n$—OR$_{12}$, -L₁- is —(CH₂)— or —(CH₂)₂—, and u is at each occurrence independently 0, 1 or 2; more preferably $R_3$ is —CN or $C_1$-$C_3$ alkyl, $R_5$ is H, halogen, $C_1$-$C_6$ alkyl, or $C_1$-$C_6$ haloalkyl, $R_7$ is $C_1$-$C_3$ alkyl, —X— is —NH—, Ring A is a group of the formula:

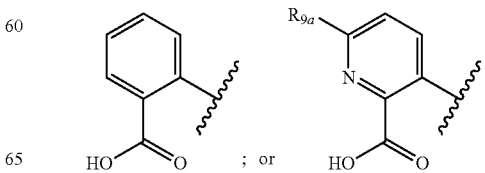

wherein $R_{9a}$ is halogen or trifluoromethyl, preferably chloro, and $WR_1R_2$ is a group of the formula:

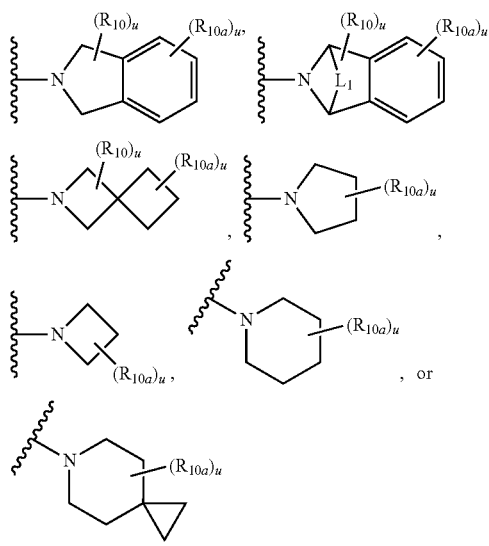

wherein $R_{10}$ at each occurrence is independently halogen, $C_1$-$C_6$ alkyl, $C_1$-$C_6$ haloalkyl or phenyl optionally substituted with halogen, $R_{10a}$ at each occurrence is independently halogen, —CN, $C_1$-$C_6$ alkyl, $C_1$-$C_6$ haloalkyl, $C_1$-$C_6$ alkoxy, or —$(CH_2)_n$—$OR_{12}$, -$L_1$- is —$(CH_2)$— or —$(CH_2)_2$—, and u is at each occurrence independently 0, 1 or 2; most preferably $R_3$ is —CN or methyl, $R_5$ is H, halogen, methyl or trifluoromethyl, $R_7$ is methyl, —X— is —NH—, Ring A is a group of the formula:

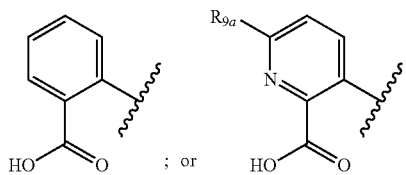

wherein $R_{9a}$ is halogen or trifluoromethyl, preferably chloro, and $WR_1R_2$ is a group of the formula:

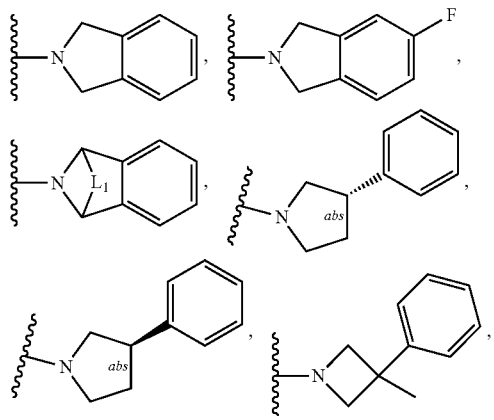

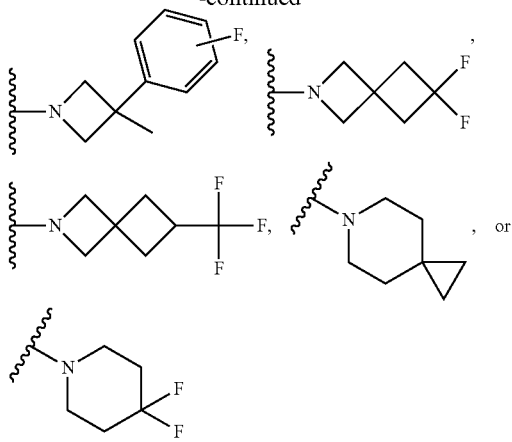

wherein -$L_1$- is —$(CH_2)$— or —$(CH_2)_2$—, preferably —$(CH_2)_2$—.

In yet a further embodiment of a compound of formula (Id):

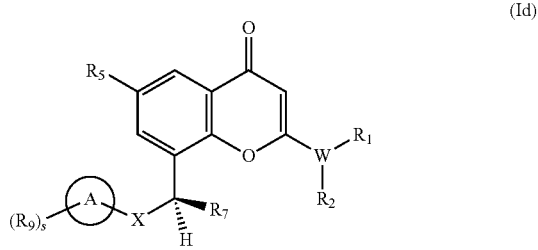

or a prodrug, solvate, enantiomer, stereoisomer, tautomer, or pharmaceutically acceptable salt thereof, wherein $R_5$ is H, halogen, $C_1$-$C_6$ alkyl, $C_1$-$C_6$ haloalkyl, or $C_1$-$C_6$ alkoxy, and —X— is —$NR_{12}$—; preferably $R_5$ is H, halogen, methyl or trifluoromethyl and —X— is —NH—.

In yet a further embodiment of a compound of Formula (Id) or pharmaceutically acceptable salts thereof, or prodrugs, solvates, hydrates, isomers, or tautomers thereof, $R_7$ is $C_1$-$C_6$ alkyl or $C_1$-$C_6$ haloalkyl; preferably $R_7$ is $C_1$-$C_3$ alkyl (most preferably methyl).

In yet a further embodiment of a compound of Formula (Id) or pharmaceutically acceptable salts thereof, or prodrugs, solvates, hydrates, isomers, or tautomers thereof, $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl and —X— is —$NR_{12}$—; preferably $R_5$ is H, halogen, $C_1$-$C_6$ alkyl, or $C_1$-$C_6$ haloalkyl, $R_7$ is $C_1$-$C_3$ alkyl and —X— is —NH—; more preferably $R_5$ is H, halogen, methyl or trifluoromethyl, $R_7$ is methyl and —X— is —NH—.

In yet a further embodiment of a compound of Formula (Id) or pharmaceutically acceptable salts thereof, or prodrugs, solvates, hydrates, isomers, or tautomers thereof, Ring A is phenyl, pyridine, thiophene, pyrazole, benzothiophene or benzoxazole, each of which is optionally substituted with $(R_9)_s$, wherein s is at least 1 and at least one substituent $R_9$ is —$C(O)OR_{12}$ or —$CON(R_{12})_2$, preferably —C(O)OH or —$CONHR_{12}$, most preferably —C(O)OH.

In yet a further embodiment of a compound of Formula (Id) or pharmaceutically acceptable salts thereof, or prodrugs, solvates, hydrates, isomers, or tautomers thereof, $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl —X— is —$NR_{12}$— and Ring A is phenyl, pyridine, thiophene, pyrazole, benzothiophene or benzoxazole, each of which is optionally substituted with $(R_9)_s$, wherein s is at least 1 and at least one substituent $R_9$ is —C(O)$OR_{12}$ or —CON($R_{12}$)$_2$; preferably $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl, —X— is —NH— and Ring A is phenyl, pyridine, thiophene, pyrazole, benzothiophene or benzoxazole, each of which is optionally substituted with $(R_9)_s$, wherein s is at least 1 and at least one substituent $R_9$ is —C(O)OH or —$CONHR_{12}$; more preferably $R_5$ is H, halogen, $C_1$-$C_6$ alkyl, or $C_1$-$C_6$ haloalkyl, $R_7$ is $C_1$-$C_3$ alkyl, —X— is —NH— and Ring A is phenyl, pyridine, thiophene, pyrazole, benzothiophene or benzoxazole, each of which is optionally substituted with $(R_9)_s$, wherein s is at least 1 and at least one substituent $R_9$ is —C(O)OH; most preferably $R_5$ is H, halogen, methyl or trifluoromethyl, $R_7$ is methyl, —X— is —NH— and Ring A is phenyl, pyridine, thiophene, pyrazole, benzothiophene or benzoxazole, each of which is optionally substituted with $(R_9)_s$, wherein s is at least 1 and at least one substituent $R_9$ is —C(O)OH.

In yet a further embodiment of a compound of Formula (Id) or pharmaceutically acceptable salts thereof, or prodrugs, solvates, hydrates, isomers, or tautomers thereof, Ring A is a group of the formula:

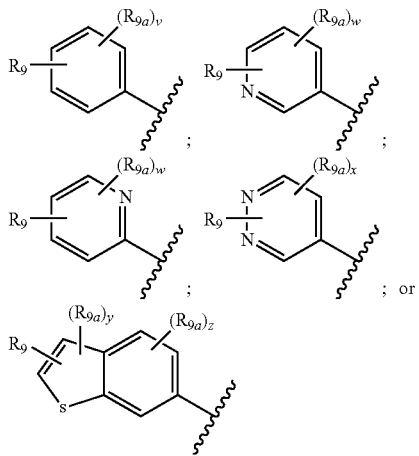

wherein $R_9$ at each occurrence is independently —C(O)OH, $R_{9a}$ is halogen, $C_1$-$C_3$ alkyl, $C_1$-$C_3$ haloalkyl, $C_1$-$C_3$ alkoxy or $C_3$-$C_5$ cycloalkyl, v is 0, 1 or 2, w is 0, 1, or 2, x is 0 or 1, y is 0 or 1, and z is 0, 1, or 2.

In yet a further embodiment of a compound of Formula (Id) or pharmaceutically acceptable salts thereof, or prodrugs, solvates, hydrates, isomers, or tautomers thereof, Ring A is a group of the formula:

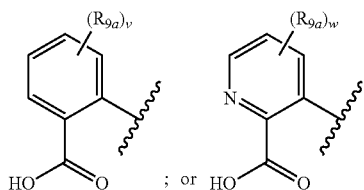

wherein $R_{9a}$ is halogen or trifluoromethyl; v is 0 or 1; and w is 0 or 1.

In yet a further embodiment of a compound of Formula (Id) or pharmaceutically acceptable salts thereof, or prodrugs, solvates, hydrates, isomers, or tautomers thereof, Ring A is a group of the formula:

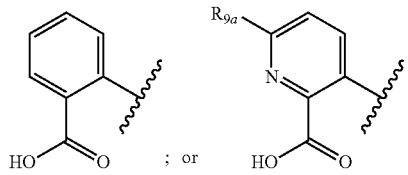

wherein $R_{9a}$ is halogen or trifluoromethyl, preferably chloro.

In yet a further embodiment of a compound of Formula (Id) or pharmaceutically acceptable salts thereof, or prodrugs, solvates, hydrates, isomers, or tautomers thereof, $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl —X— is —$NR_{12}$—, Ring A is a group of the formula:

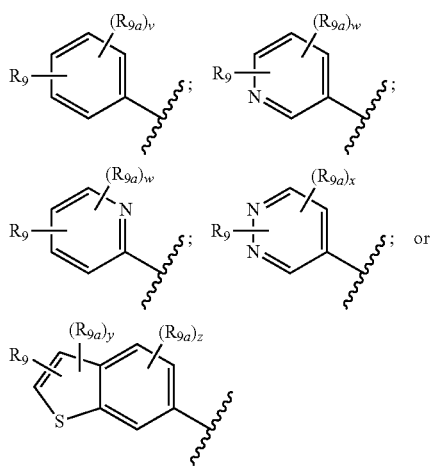

wherein $R_9$ at each occurrence is independently —C(O)OH, $R_{9a}$ is halogen, $C_1$-$C_3$ alkyl, $C_1$-$C_3$ haloalkyl, $C_1$-$C_3$ alkoxy or $C_3$-$C_5$ cycloalkyl, v is 0, 1 or 2, w is 0, 1, or 2, x is 0 or 1, y is 0 or 1, and z is 0, 1, or 2; preferably $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl, —X— is —NH— and Ring A is a group of the formula:

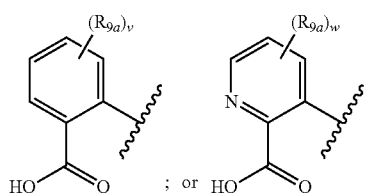

wherein $R_{9a}$ is halogen or trifluoromethyl; v is 0 or 1; and w is 0 or 1; more preferably $R_5$ is H, halogen, $C_1$-$C_6$ alkyl, or $C_1$-$C_6$ haloalkyl, $R_7$ is $C_1$-$C_3$ alkyl, —X— is —NH— and Ring A is a group of the formula:

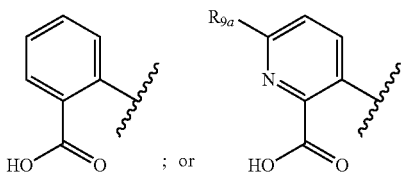

wherein $R_{9a}$ is halogen or trifluoromethyl, preferably chloro; most preferably $R_5$ is H, halogen, methyl or trifluoromethyl, $R_7$ is methyl, —X— is —NH—, and Ring A is a group of the formula:

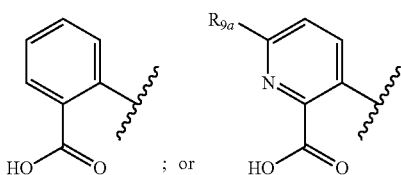

wherein $R_{9a}$ is halogen or trifluoromethyl, preferably chloro.

In yet a further embodiment of a compound of Formula (Id) or pharmaceutically acceptable salts thereof, or prodrugs, solvates, hydrates, isomers, or tautomers thereof, W is —N— and $R_1$ and $R_2$, together with the nitrogen to which they are attached, form a heterocycle comprising 1-4 heteroatoms selected from O, N, and S, wherein the heterocycle is optionally substituted with one or more $R_{10}$ and two $R_{10}$, together with the atoms to which they are attached, form a 4 to 6 membered heterocycle comprising 1-4 heteroatoms selected from O, N, and S, wherein the heterocycle is optionally substituted with one or more halogen, $C_1$-$C_6$ alkyl, $C_1$-$C_6$ haloalkyl, $C_1$-$C_6$ alkoxy, aryl or heteroaryl, or $R_{15}$.

In yet a further embodiment of a compound of Formula (Id) or pharmaceutically acceptable salts thereof, or prodrugs, solvates, hydrates, isomers, or tautomers thereof, $WR_1R_2$ is a group of the formula:

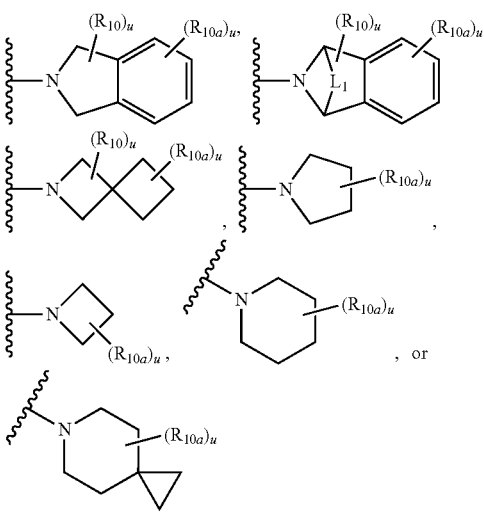

wherein $R_{10}$ at each occurrence is independently halogen, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_n$—OR$_{12}$, —(CH$_2$)$_n$—N(R$_{12}$)$_2$, —(CH$_2$)$_n$—C(O)R$_{12}$, —(CH$_2$)$_n$—C(O)OR$_{12}$, —(CH$_2$)$_n$—C(O)N(R$_{12}$)$_2$, —(CH$_2$)$_n$—SO$_2$R$_{12}$, —(CH$_2$)$_n$—O—(CH$_2$CH$_2$—O)$_r$R$_{13}$, $C_3$-$C_{10}$ cycloalkyl, heterocycle, —(CH$_2$)$_n$-aryl, or heteroaryl, wherein the cycloalkyl, heterocycle, aryl, and heteroaryl is optionally substituted with halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, or —(CH$_2$)$_n$—SO$_2$R$_{12}$; $R_{10a}$ at each occurrence is independently halogen, —CN, $C_1$-$C_6$ alkyl, $C_1$-$C_6$ haloalkyl, $C_1$-$C_6$ alkoxy, or —(CH$_2$)$_n$—OR$_{12}$, -L$_1$- is —(CH$_2$)— or —(CH$_2$)$_2$—, and u is at each occurrence independently 0, 1, 2, 3 or 4. Preferably $R_{10}$ is halogen, $C_1$-$C_6$ alkyl, $C_1$-$C_6$ haloalkyl or phenyl optionally substituted with halogen, $R_{10a}$ at each occurrence is independently halogen, —CN, $C_1$-$C_6$ alkyl, $C_1$-$C_6$ haloalkyl, $C_1$-$C_6$ alkoxy, or —(CH$_2$)$_n$—OR$_{12}$, -L$_1$- is —(CH$_2$)— or —(CH$_2$)$_2$—, and u is independently 0, 1 or 2.

In yet a further embodiment of a compound of Formula (Id) or pharmaceutically acceptable salts thereof, or prodrugs, solvates, hydrates, isomers, or tautomers thereof, $WR_1R_2$ is a group of the formula:

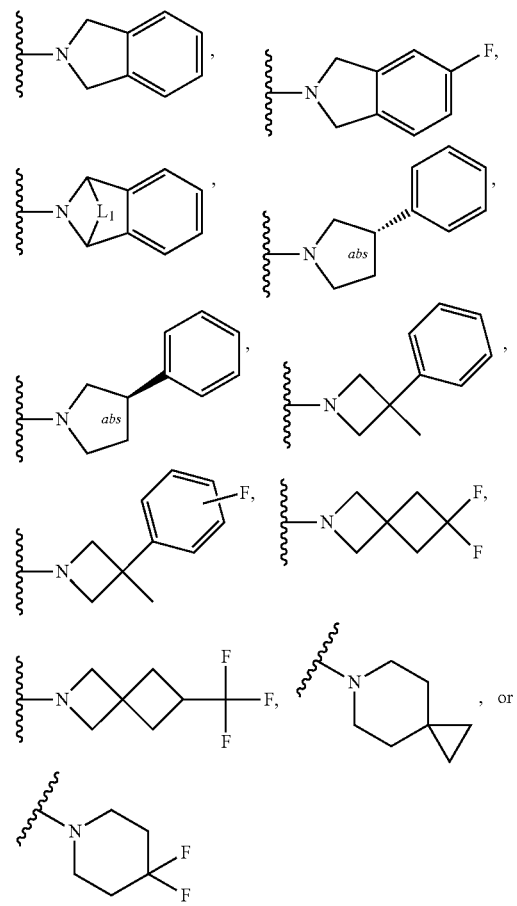

wherein -L$_1$- is —(CH$_2$)— or —(CH$_2$)$_2$—, preferably —(CH$_2$)$_2$—.

In yet a further embodiment of a compound of Formula (Id) or pharmaceutically acceptable salts thereof, or prodrugs, solvates, hydrates, isomers, or tautomers thereof, $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl, —X— is —NR$_{12}$— and W is —N— and $R_1$ and $R_2$, together with the nitrogen to which they are attached, form a heterocycle comprising 1-4 heteroatoms selected from O, N, and S, wherein the heterocycle is optionally substituted with one or more $R_{10}$ and two $R_{10}$, together with the atoms to which they are attached, form a 4 to 6 membered heterocycle comprising 1-4 heteroatoms selected from O, N, and S, wherein the heterocycle is optionally substituted with one or more halogen, $C_1$-$C_6$ alkyl, $C_1$-$C_6$ haloalkyl, $C_1$-$C_6$ alkoxy, aryl or heteroaryl, or $R_{15}$; preferably $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl, —X— is —NH— and $WR_1R_2$ is a group of the formula:

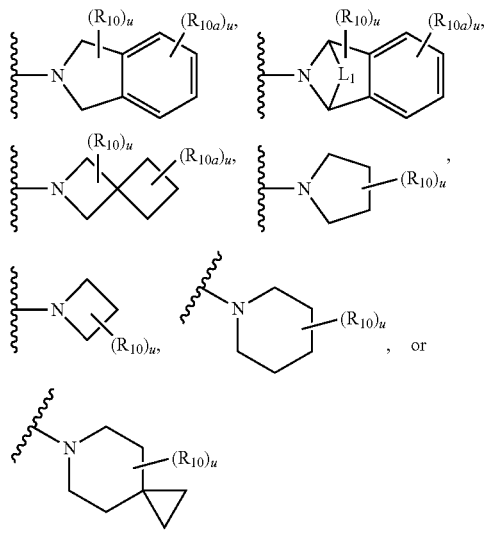

wherein $R_{10}$ at each occurrence is independently halogen, $C_1$-$C_6$ alkyl, $C_1$-$C_6$ haloalkyl or phenyl optionally substituted with halogen, $R_{10a}$ at each occurrence is independently halogen, —CN, $C_1$-$C_6$ alkyl, $C_1$-$C_6$ haloalkyl, $C_1$-$C_6$ alkoxy, or —$(CH_2)_n$—$OR_{12}$, -$L_1$- is —$(CH_2)$— or —$(CH_2)_2$—, and u is at each occurrence independently 0, 1 or 2; more preferably $R_5$ is H, halogen, $C_1$-$C_6$ alkyl, or $C_1$-$C_6$ haloalkyl, $R_7$ is $C_1$-$C_3$ alkyl and —X— is —NH—; most preferably $R_5$ is H, halogen, methyl or trifluoromethyl, $R_7$ is methyl, —X— is —NH— and $WR_1R_2$ is a group of the formula:

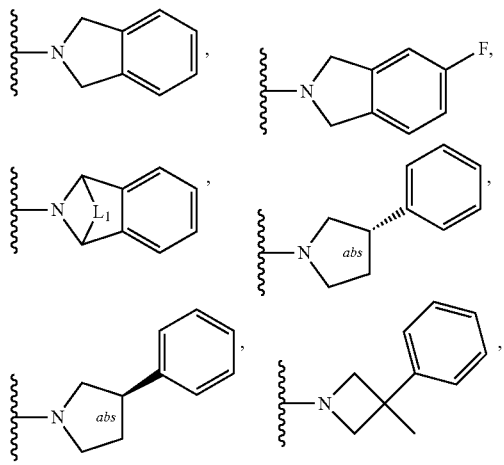

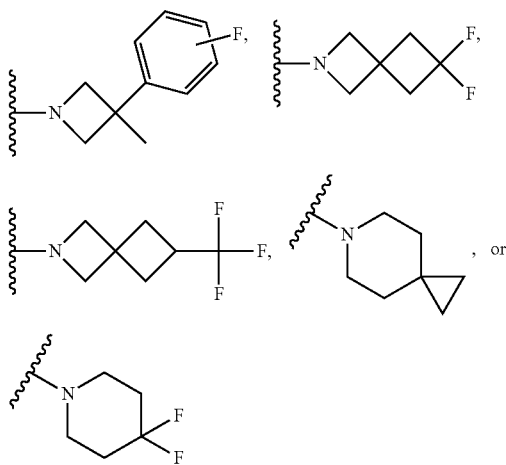

wherein -$L_1$- is —$(CH_2)$— or —$(CH_2)_2$—, preferably —$(CH_2)_2$—.

In yet a further embodiment of a compound of Formula (Id) or pharmaceutically acceptable salts thereof, or prodrugs, solvates, hydrates, isomers, or tautomers thereof, $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl —X— is —$NR_{12}$—, Ring A is phenyl, pyridine, thiophene, pyrazole, benzothiophene or benzoxazole, each of which is optionally substituted with $(R_9)_s$, wherein s is at least 1 and at least one substituent $R_9$ is —$C(O)OR_{12}$ or —$CON(R_{12})_2$ and W is —N— and $R_1$ and $R_2$, together with the nitrogen to which they are attached, form a heterocycle comprising 1-4 heteroatoms selected from O, N, and S, wherein the heterocycle is optionally substituted with one or more $R_{10}$ and two $R_{10}$, together with the atoms to which they are attached, form a 4 to 6 membered heterocycle comprising 1-4 heteroatoms selected from O, N, and S, wherein the heterocycle is optionally substituted with one or more halogen, $C_1$-$C_6$ alkyl, $C_1$-$C_6$ haloalkyl, $C_1$-$C_6$ alkoxy, aryl or heteroaryl, or $R_{15}$; preferably $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl, —X— is —NH—, Ring A is phenyl, pyridine, thiophene, pyrazole, benzothiophene or benzoxazole, each of which is optionally substituted with $(R_9)_s$, wherein s is at least 1 and at least one substituent $R_9$ is —$C(O)OH$ or —$CONHR_{12}$; and $WR_1R_2$ is a group of the formula:

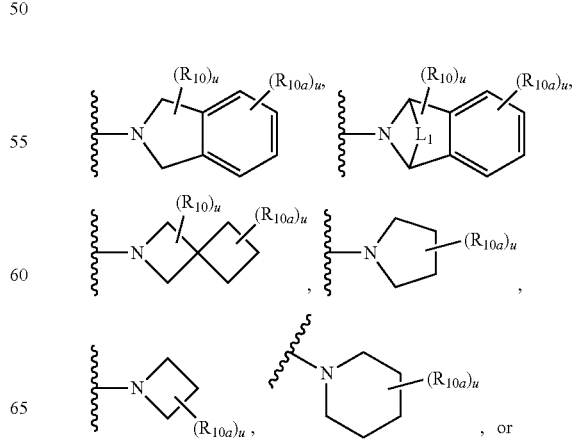

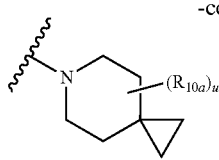

wherein $R_{10}$ at each occurrence is independently halogen, $C_1$-$C_6$ alkyl, $C_1$-$C_6$ haloalkyl or phenyl optionally substituted with halogen, $R_{10a}$ at each occurrence is independently halogen, —CN, $C_1$-$C_6$ alkyl, $C_1$-$C_6$ haloalkyl, $C_1$-$C_6$ alkoxy, or —(CH$_2$)$_n$—OR$_{12}$, -L$_1$- is —(CH$_2$)— or —(CH$_2$)$_2$—, and u is at each occurrence independently 0, 1 or 2; more preferably $R_5$ is H, halogen, $C_1$-$C_6$ alkyl, or $C_1$-$C_6$ haloalkyl, $R_7$ is $C_1$-$C_3$ alkyl, —X— is —NH—, Ring A is phenyl, pyridine, thiophene, pyrazole, benzothiophene or benzoxazole, each of which is optionally substituted with (R$_9$)$_s$, wherein s is at least 1 and at least one substituent $R_9$ is —C(O)OH and WR$_1$R$_2$ is a group of the formula:

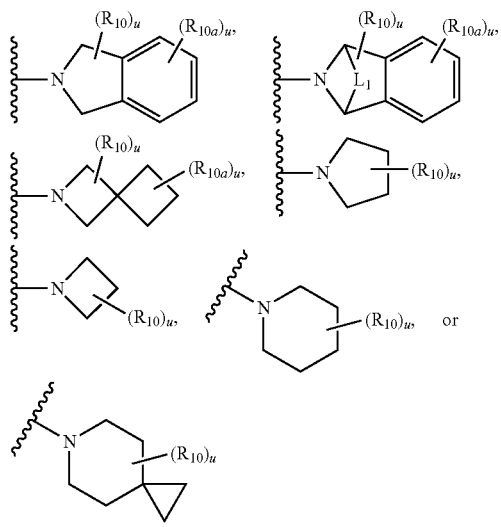

wherein $R_{10}$ at each occurrence is independently halogen, $C_1$-$C_6$ alkyl, $C_1$-$C_6$ haloalkyl or phenyl optionally substituted with halogen, $R_{10a}$ at each occurrence is independently halogen, —CN, $C_1$-$C_6$ alkyl, $C_1$-$C_6$ haloalkyl, $C_1$-$C_6$ alkoxy, or —(CH$_2$)$_n$—OR$_{12}$, -L$_1$- is —(CH$_2$)— or —(CH$_2$)$_2$—, and u is at each occurrence independently 0, 1 or 2; most preferably $R_7$ is methyl, —X— is —NH—, Ring A is phenyl, pyridine, thiophene, pyrazole, benzothiophene or benzoxazole, each of which is optionally substituted with (R$_9$)$_s$, wherein s is at least 1 and at least one substituent $R_9$ is —C(O)OH and WR$_1$R$_2$ is a group of the formula:

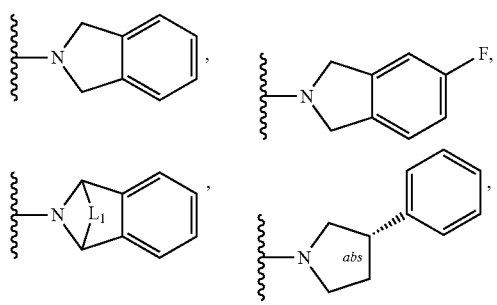

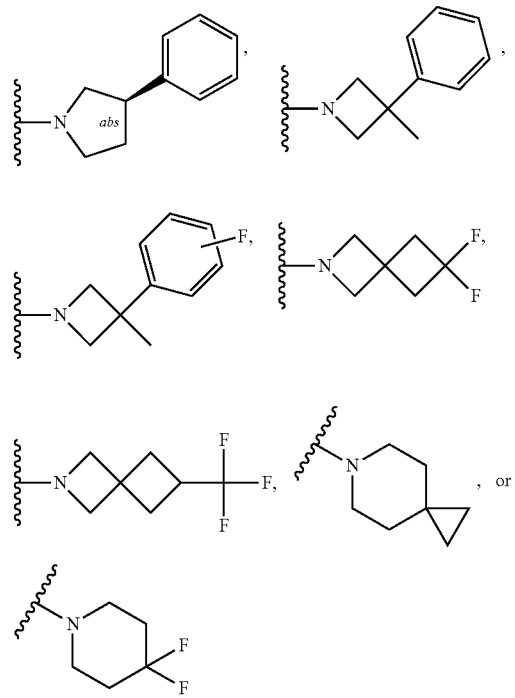

wherein -L$_1$- is —(CH$_2$)— or —(CH$_2$)$_2$—, preferably —(CH$_2$)$_2$—.

In yet a further embodiment of a compound of Formula (Id) or pharmaceutically acceptable salts thereof, or prodrugs, solvates, hydrates, isomers, or tautomers thereof, $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl —X— is —NR$_{12}$—, Ring A is a group of the formula:

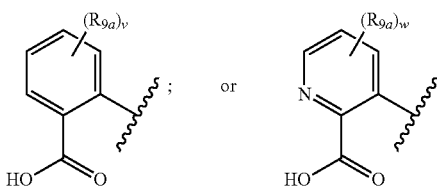

wherein $R_9$ at each occurrence is independently —C(O)OH, $R_{9a}$ is halogen, $C_1$-$C_3$ alkyl, $C_1$-$C_3$ haloalkyl, $C_1$-$C_3$ alkoxy or $C_3$-$C_5$ cycloalkyl, v is 0, 1 or 2, w is 0, 1, or 2, W is —N— and $R_1$ and $R_2$, together with the nitrogen to which they are attached, form a heterocycle comprising 1-4 heteroatoms selected from O, N, and S, wherein the heterocycle is optionally substituted with one or more $R_{10}$ and two $R_{10}$, together with the atoms to which they are attached, form a 4 to 6 membered heterocycle comprising 1-4 heteroatoms selected from O, N, and S, wherein the heterocycle is optionally substituted with one or more halogen, $C_1$-$C_6$ alkyl, $C_1$-$C_6$ haloalkyl, $C_1$-$C_6$ alkoxy, aryl or heteroaryl, or $R_{15}$; preferably $R_5$ is H, halogen, $C_1$-$C_6$ alkyl, $C_1$-$C_6$ haloalkyl, or $C_1$-$C_6$ alkoxy, $R_7$ is $C_1$-$C_6$ alkyl or $C_1$-$C_6$ haloalkyl, —X— is —NH—, Ring A is a group of the formula:

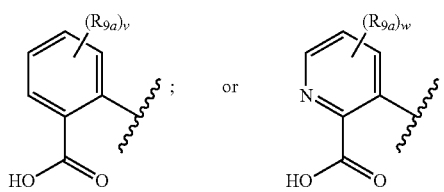

wherein $R_{9a}$ is halogen or trifluoromethyl; v is 0 or 1; and w is 0 or 1 and $WR_1R_2$ is a group of the formula:

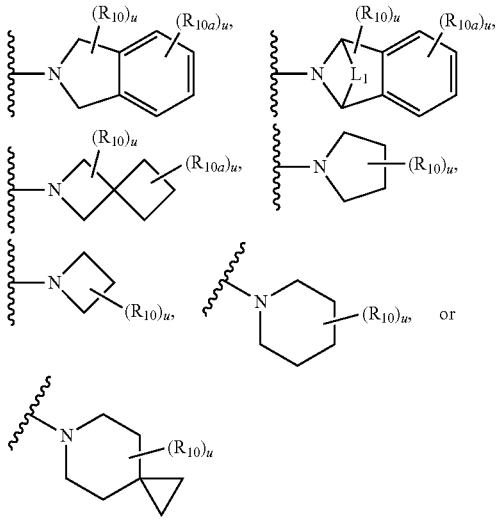

wherein $R_{10}$ at each occurrence is independently halogen, $C_1$-$C_6$ alkyl, $C_1$-$C_6$ haloalkyl or phenyl optionally substituted with halogen, $R_{10a}$ at each occurrence is independently halogen, —CN, $C_1$-$C_6$ alkyl, $C_1$-$C_6$ haloalkyl, $C_1$-$C_6$ alkoxy, or —(CH$_2$)$_n$—OR$_{12}$, -L$_1$- is —(CH$_2$)— or —(CH$_2$)$_2$—, and u is at each occurrence independently 0, 1 or 2; more preferably $R_5$ is H, halogen, $C_1$-$C_6$ alkyl, or $C_1$-$C_6$ haloalkyl, $R_7$ is $C_1$-$C_3$ alkyl, —X— is —NH—, Ring A is a group of the formula:

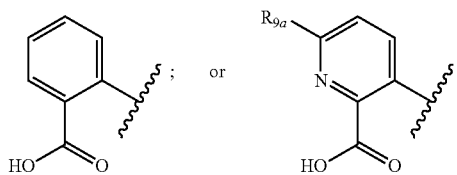

wherein $R_{9a}$ is halogen or trifluoromethyl, preferably chloro, and $WR_1R_2$ is a group of the formula:

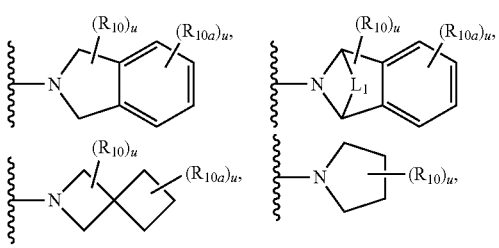

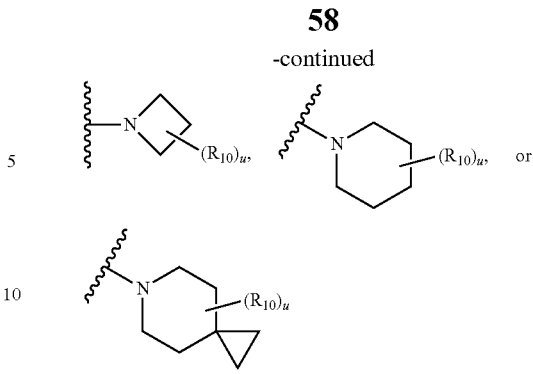

wherein $R_{10}$ at each occurrence is independently halogen, $C_1$-$C_6$ alkyl, $C_1$-$C_6$ haloalkyl or phenyl optionally substituted with halogen, $R_{10a}$ at each occurrence is independently halogen, —CN, $C_1$-$C_6$ alkyl, $C_1$-$C_6$ haloalkyl, $C_1$-$C_6$ alkoxy, or —(CH$_2$)$_n$—OR$_{12}$, -L$_1$- is —(CH$_2$)— or —(CH$_2$)$_2$—, and u is at each occurrence independently 0, 1 or 2; most preferably $R_5$ is H, halogen, methyl or trifluoromethyl, $R_7$ is methyl, —X— is —NH—, Ring A is a group of the formula:

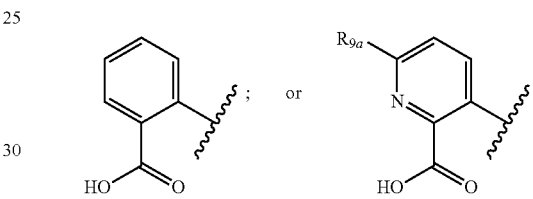

wherein $R_{9a}$ is halogen or trifluoromethyl, preferably chloro, and $WR_1R_2$ is a group of the formula:

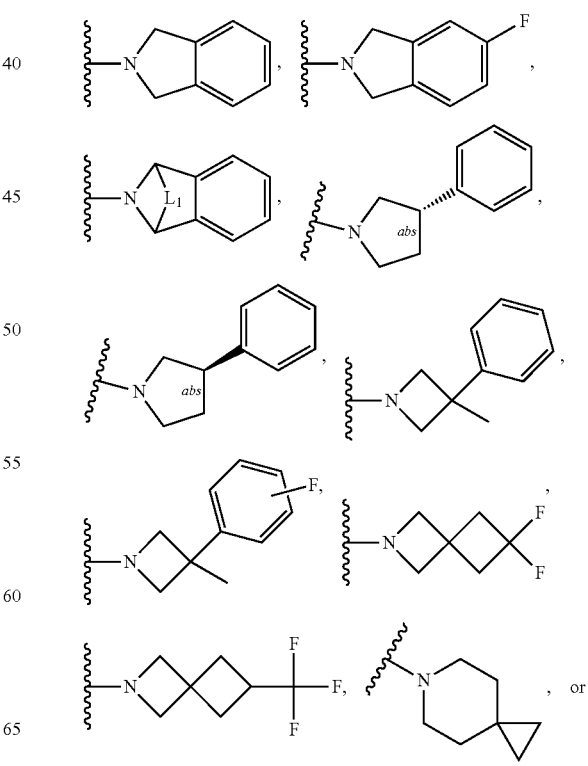

-continued

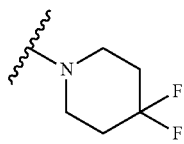

wherein $-L_1-$ is $—(CH_2)—$ or $—(CH_2)_2—$, preferably $—(CH_2)_2—$.

In yet a further embodiment of a compound of formula (If):

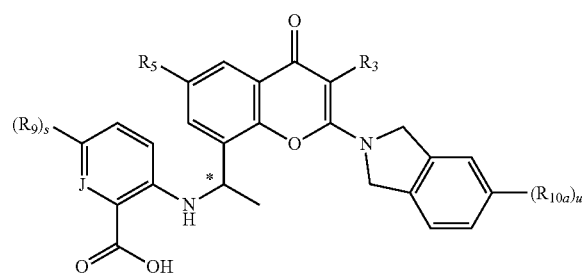

(If)

or pharmaceutically acceptable salts thereof, or prodrugs, solvates, hydrates, isomers, or tautomers thereof, wherein $R_3$ is H or $C_1$-$C_6$ alkyl, $R_5$ is halogen, $C_1$-$C_6$ alkyl, or $C_1$-$C_6$ haloalkyl, $R_9$ is halogen, $R_{10a}$ is halogen, s is 0 or 1, u is 0 or 1, J is C or N, and * indicates a stereocenter. In a preferred embodiment, $R_3$ is H or methyl, $R_5$ is fluoro, methyl, or trifluoromethyl, $R_9$ is chloro, $R_{10a}$ is fluoro, s is 0 or 1, u is 0 or 1, J is C or N, and the stereocenter has the (R)-configuration.

In yet a further embodiment of a compound of Formula (Ig):

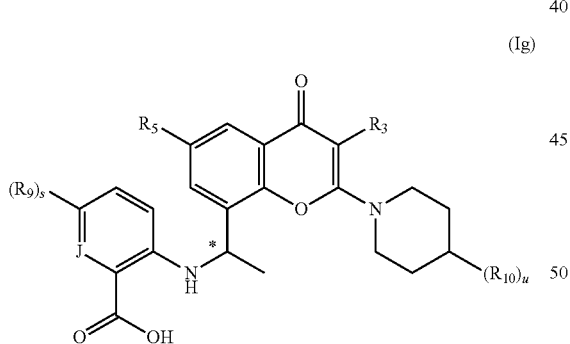

(Ig)

or pharmaceutically acceptable salts thereof, or prodrugs, solvates, hydrates, isomers, or tautomers thereof, wherein $R_3$ is H or $C_1$-$C_6$ alkyl, $R_5$ is halogen, $C_1$-$C_6$ alkyl, or $C_1$-$C_6$ haloalkyl, $R_9$ is halogen, $R_{10}$ is independently halogen, —CN, $C_1$-$C_6$ alkyl, or aryl, or two $R_{10}$ together with the carbon atom to which they are attached form a $C_3$-$C_{10}$ cycloalkyl, s is 0 or 1, u is 0, 1, or 2, J is C or N, and * indicates a stereocenter. In a preferred embodiment, $R_3$ is H or methyl, $R_5$ is fluoro, methyl, or trifluoromethyl, $R_9$ is chloro, $R_{10}$ is independently fluoro or methyl, or two $R_{10}$ together with the carbon atom to which they are attached form a cyclopropyl, s is 0 or 1, u is 0, 1, or 2, J is C or N, and the stereocenter has the (R)-configuration.

In yet a further embodiment of a compound of Formula (Ih):

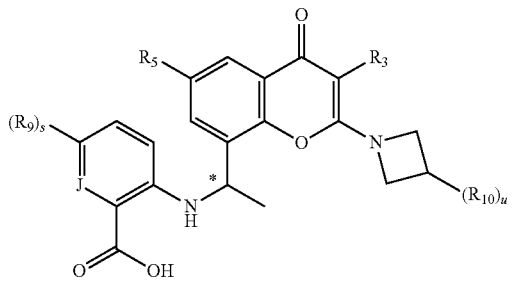

(Ih)

or pharmaceutically acceptable salts thereof, or prodrugs, solvates, hydrates, isomers, or tautomers thereof, wherein $R_3$ is H or $C_1$-$C_6$ alkyl, $R_5$ is halogen, $C_1$-$C_6$ alkyl, or $C_1$-$C_6$ haloalkyl, $R_9$ is halogen, $R_{10}$ is independently halogen, —CN, $C_1$-$C_6$ alkyl, or aryl, or two $R_{10}$ together with the carbon atom to which they are attached form a $C_3$-$C_{10}$ cycloalkyl, s is 0 or 1, u is 0, 1, or 2, J is C or N, and * indicates a stereocenter. In a preferred embodiment, $R_3$ is H or methyl, $R_5$ is fluoro, methyl, or trifluoromethyl, $R_9$ is chloro, $R_{10}$ is independently methyl or aryl, or two $R_{10}$ together with the carbon atom to which they are attached form a cyclobutyl, s is 0 or 1, u is 0, 1, or 2, J is C or N, and the stereocenter has the (R)-configuration.

In yet a further embodiment of a compound of Formula (I), (Ia), (Ib), (Ie), or (II), or pharmaceutically acceptable salts thereof, or prodrugs, solvates, hydrates, isomers, or tautomers thereof, the compound is selected from:

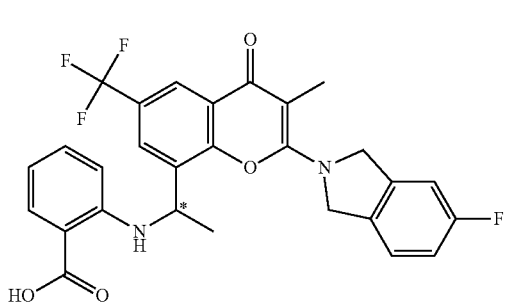

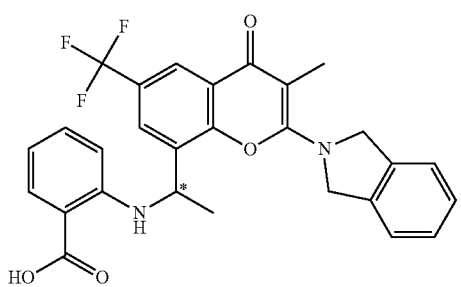

-continued
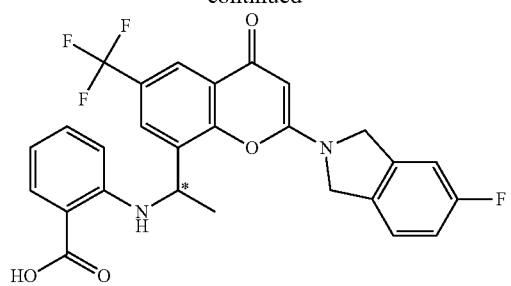
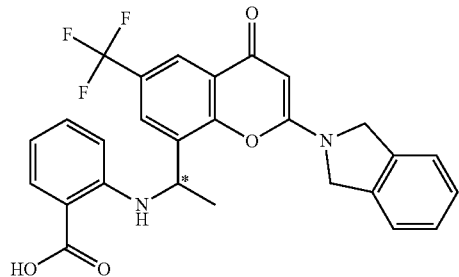
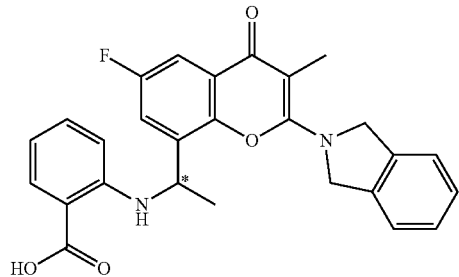
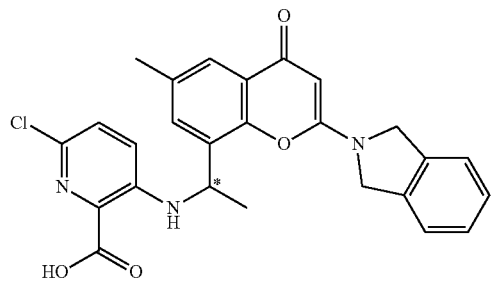
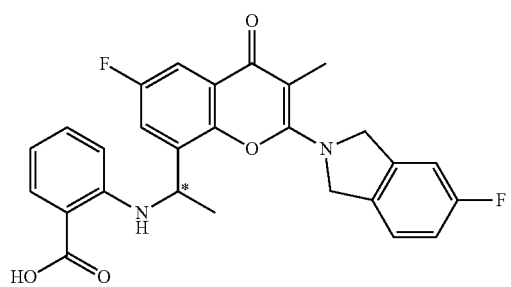
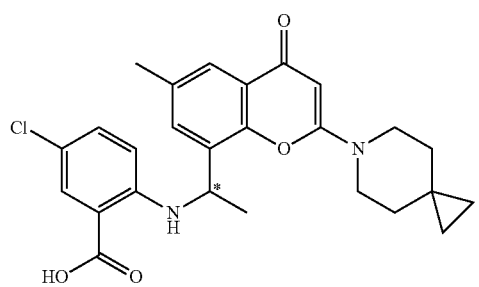
-continued
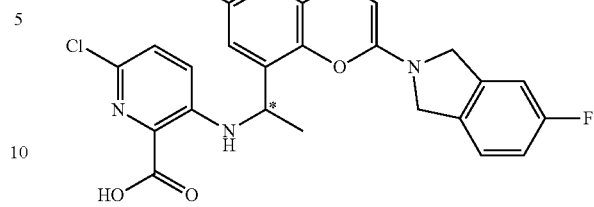
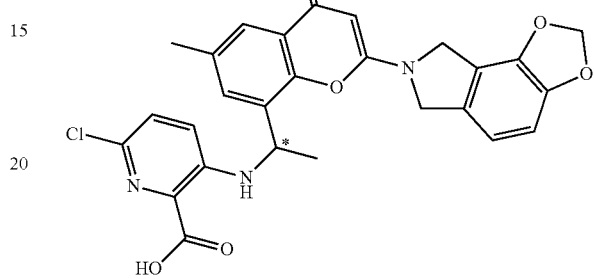
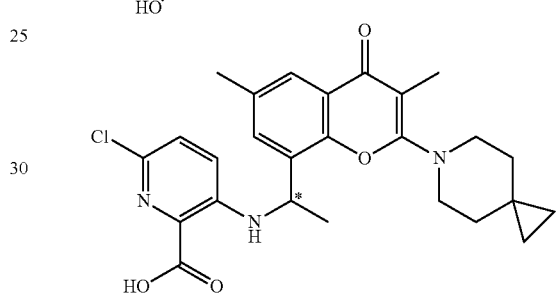
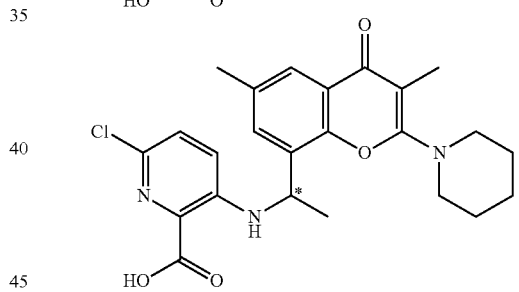
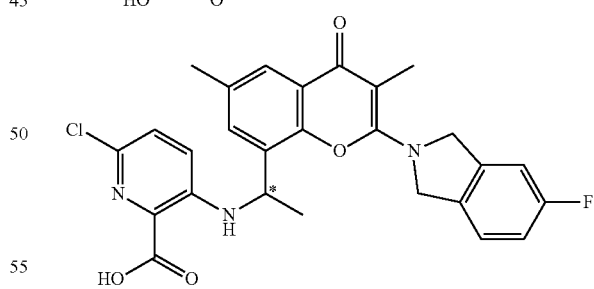
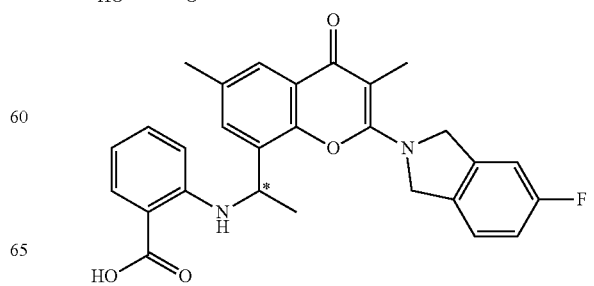

-continued
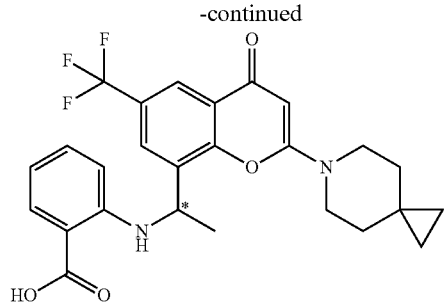
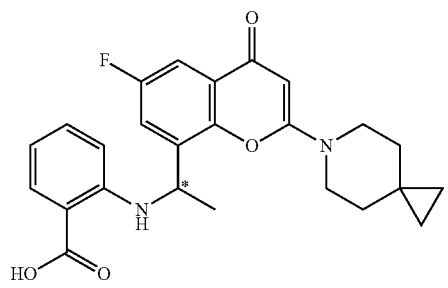
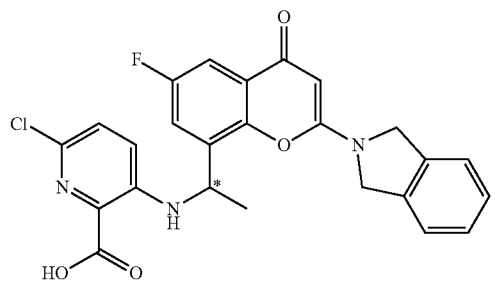
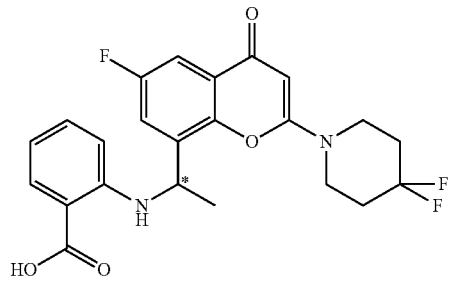
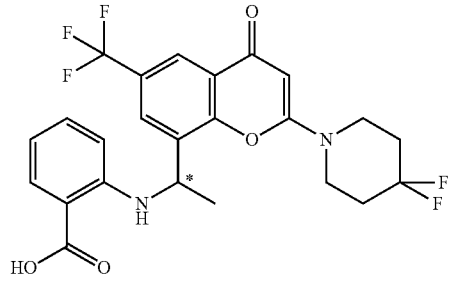
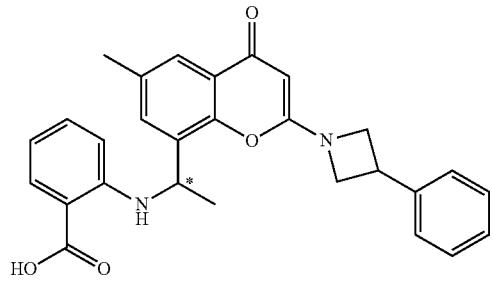
-continued
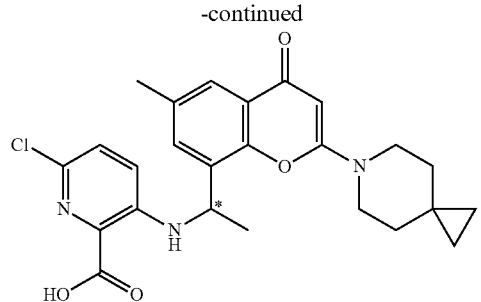
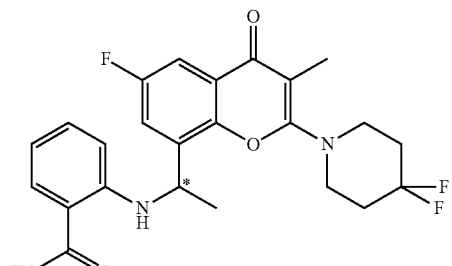
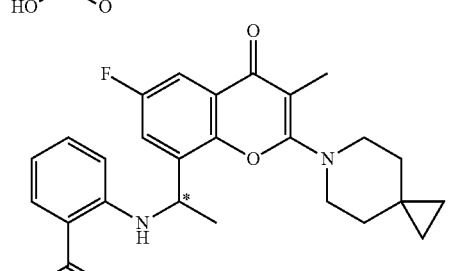
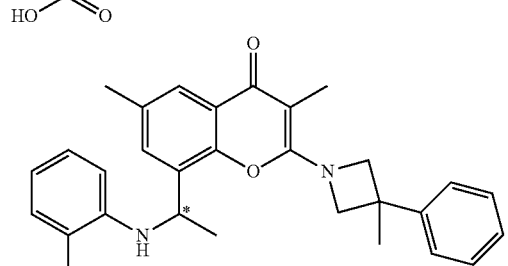
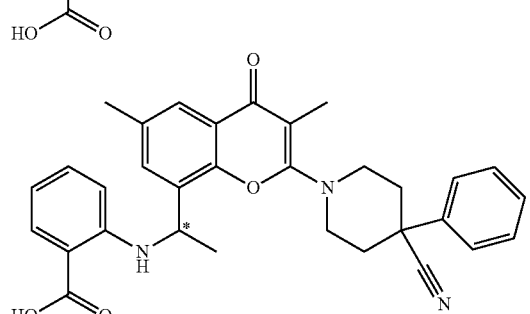
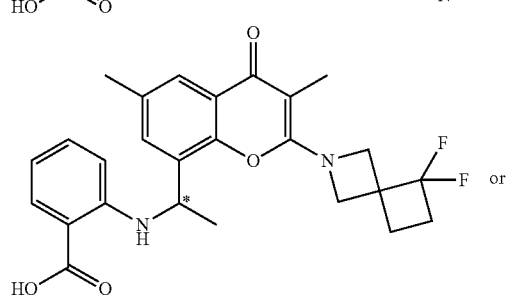 or -continued

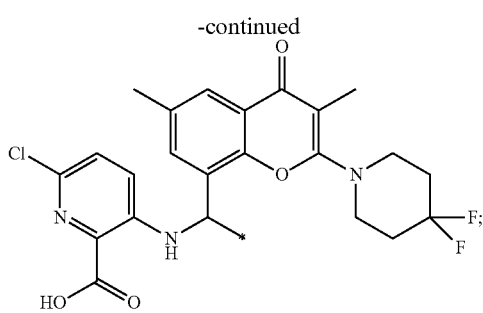

wherein the bond at the * position is as represented,

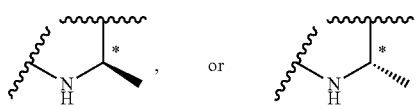

A further embodiment is a compound of Formula

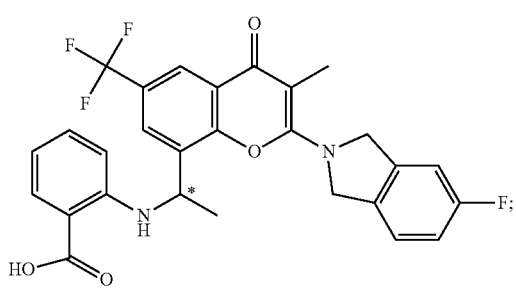 [SMILES: Cc1c(N2Cc3ccc(F)cc3C2)oc2c(C(C)Nc3ccccc3C(=O)O)cc(C(F)(F)F)cc2c1=O]

or a prodrug, solvate, enantiomer, stereoisomer, tautomer, or pharmaceutically acceptable salt thereof. In yet a further embodiment, the bond at the * position is

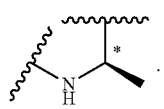

In yet a further embodiment, the bond at the * position is

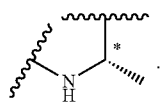 [SMILES: *N[C@H](*)C]

A further embodiment is a compound of Formula

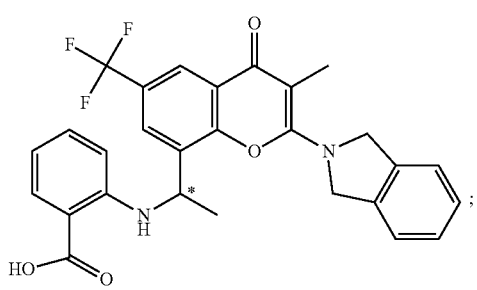 [SMILES: Cc1c(N2Cc3ccccc3C2)oc2c(C(C)Nc3ccccc3C(=O)O)cc(C(F)(F)F)cc2c1=O]

or a prodrug, solvate, enantiomer, stereoisomer, tautomer, or pharmaceutically acceptable salt thereof. In yet a further embodiment, the bond at the * position is

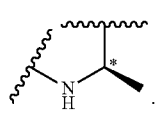

In yet a further embodiment, the bond at the * position is

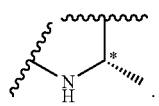

A further embodiment is a compound of Formula

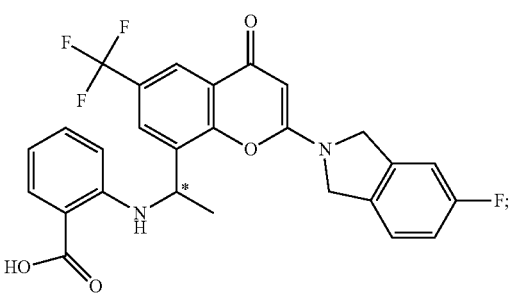 [SMILES: CC(Nc1ccccc1C(=O)O)c1cc(C(F)(F)F)cc2c(=O)cc(N3Cc4ccc(F)cc4C3)oc12]

or a prodrug, solvate, enantiomer, stereoisomer, tautomer, or pharmaceutically acceptable salt thereof. In yet a further embodiment, the bond at the * position is

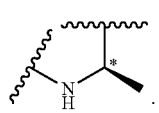

In yet a further embodiment, the bond at the * position is

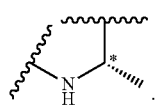

A further embodiment is a compound of Formula

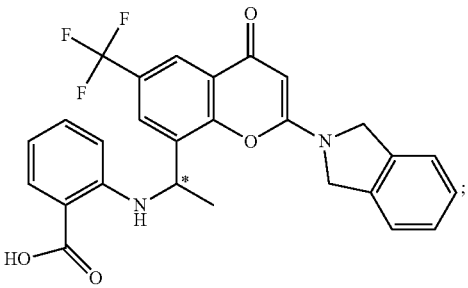 [SMILES: CC(Nc1ccccc1C(=O)O)c1cc(C(F)(F)F)cc2c(=O)cc(N3Cc4ccccc4C3)oc12]

or a prodrug, solvate, enantiomer, stereoisomer, tautomer, or pharmaceutically acceptable salt thereof. In yet a further embodiment, the bond at the * position is

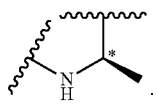 [SMILES: *N[C@@H](*)C]

In yet a further embodiment, the bond at the * position is

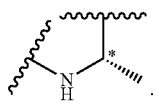

A further embodiment is a compound of Formula

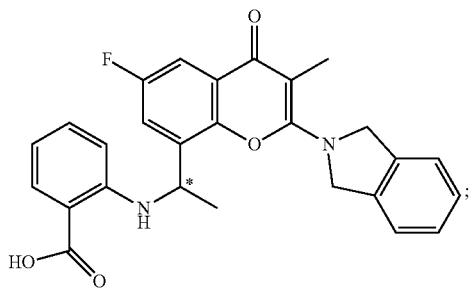 [SMILES: Cc1c(N2Cc3ccccc3C2)oc2c(C(C)Nc3ccccc3C(=O)O)cc(F)cc2c1=O]

or a prodrug, solvate, enantiomer, stereoisomer, tautomer, or pharmaceutically acceptable salt thereof. In yet a further embodiment, the bond at the * position is

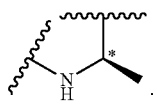

In yet a further embodiment, the bond at the * position is

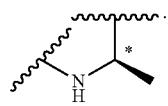

or a prodrug, solvate, enantiomer, stereoisomer, tautomer, or pharmaceutically acceptable salt thereof. In yet a further embodiment, the bond at the * position is

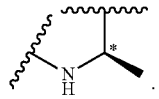

In yet a further embodiment, the bond at the * position is

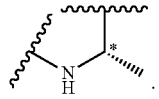

A further embodiment is a compound of Formula

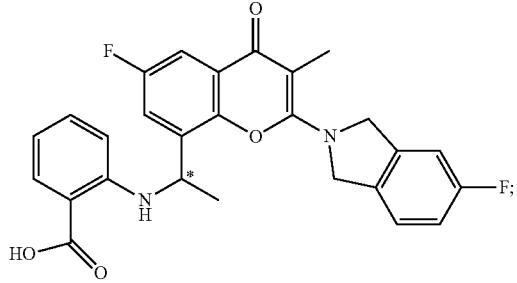

or a prodrug, solvate, enantiomer, stereoisomer, tautomer, or pharmaceutically acceptable salt thereof. In yet a further embodiment, the bond at the * position is In yet a further embodiment, the bond at the * position is A further embodiment is a compound of Formula

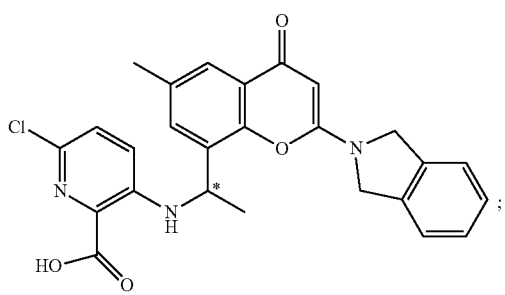 [SMILES: Cc1cc(C(C)Nc2ccc(Cl)nc2C(=O)O)c2oc(N3Cc4ccccc4C3)cc(=O)c2c1]

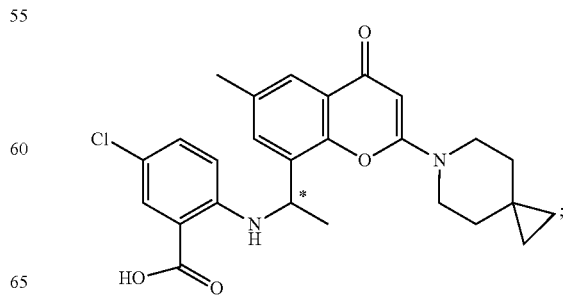

or a prodrug, solvate, enantiomer, stereoisomer, tautomer, or pharmaceutically acceptable salt thereof. In yet a further embodiment, the bond at the * position is

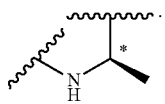

In yet a further embodiment, the bond at the * position is

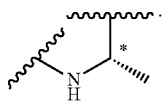

A further embodiment is a compound of Formula

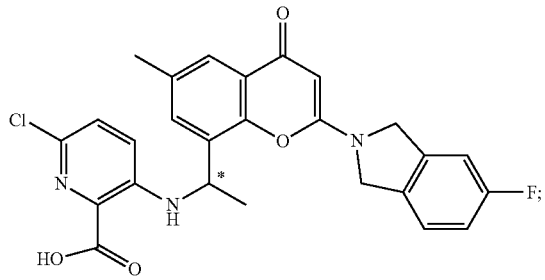 [SMILES: Cc1cc(C(C)Nc2ccc(Cl)nc2C(=O)O)c2oc(N3Cc4ccc(F)cc4C3)cc(=O)c2c1]

or a prodrug, solvate, enantiomer, stereoisomer, tautomer, or pharmaceutically acceptable salt thereof. In yet a further embodiment, the bond at the * position is

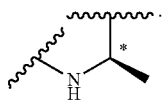

In yet a further embodiment, the bond at the * position is

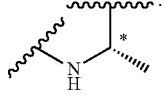

A further embodiment is a compound of Formula

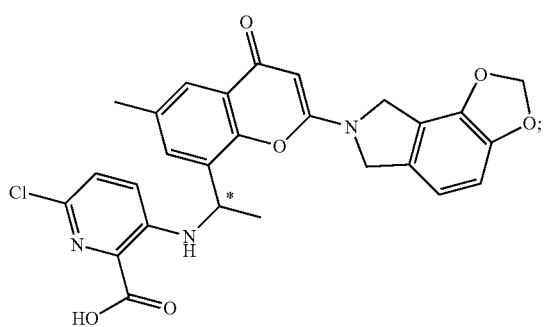 [SMILES: Cc1cc(C(C)Nc2ccc(Cl)nc2C(=O)O)c2oc(N3Cc4ccc5c(c4C3)OCO5)cc(=O)c2c1]

or a prodrug, solvate, enantiomer, stereoisomer, tautomer, or pharmaceutically acceptable salt thereof. In yet a further embodiment, the bond at the * position is

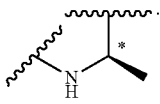 [SMILES: *N[C@@H](*)C]

In yet a further embodiment, the bond at the * position is

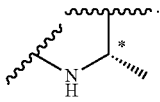

A further embodiment is a compound of Formula

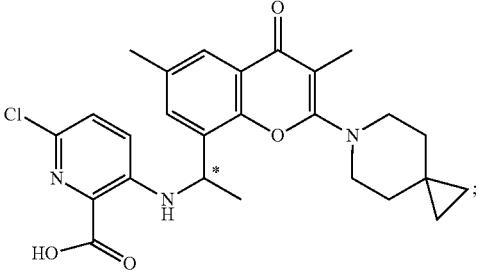 [SMILES: Cc1cc(C(C)Nc2ccc(Cl)nc2C(=O)O)c2oc(N3CCC4(CC3)CC4)c(C)c(=O)c2c1]

or a prodrug, solvate, enantiomer, stereoisomer, tautomer, or pharmaceutically acceptable salt thereof. In yet a further embodiment, the bond at the * position is

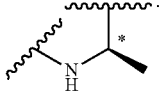

In yet a further embodiment, the bond at the * position is

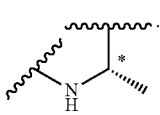 [SMILES: *N[C@H](*)C]

A further embodiment is a compound of Formula

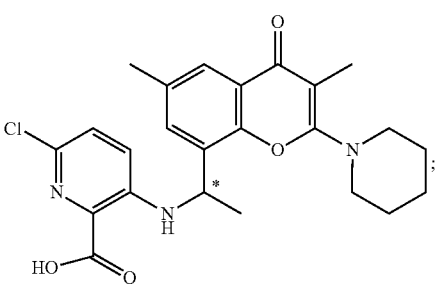 [SMILES: Cc1cc(C(C)Nc2ccc(Cl)nc2C(=O)O)c2oc(N3CCCCC3)c(C)c(=O)c2c1]

or a prodrug, solvate, enantiomer, stereoisomer, tautomer, or pharmaceutically acceptable salt thereof. In yet a further embodiment, the bond at the * position is

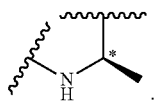

In yet a further embodiment, the bond at the * position is

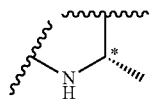

A further embodiment is a compound of Formula

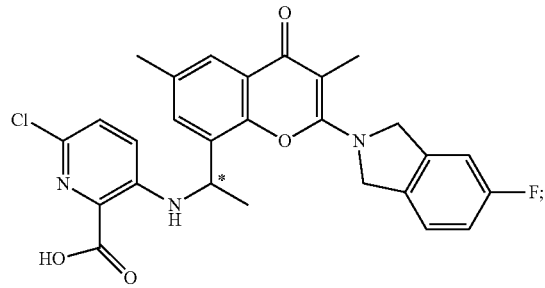 [SMILES: Cc1cc(C(C)Nc2ccc(Cl)nc2C(=O)O)c2oc(N3Cc4ccc(F)cc4C3)c(C)c(=O)c2c1]

or a prodrug, solvate, enantiomer, stereoisomer, tautomer, or pharmaceutically acceptable salt thereof. In yet a further embodiment, the bond at the * position is

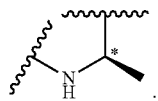

In yet a further embodiment, the bond at the * position is

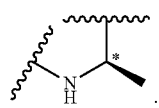

A further embodiment is a compound of Formula

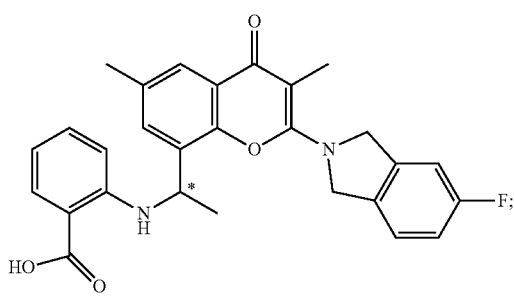 [SMILES: Cc1cc(C(C)Nc2ccccc2C(=O)O)c2oc(N3Cc4ccc(F)cc4C3)c(C)c(=O)c2c1]

or a prodrug, solvate, enantiomer, stereoisomer, tautomer, or pharmaceutically acceptable salt thereof. In yet a further embodiment, the bond at the * position is

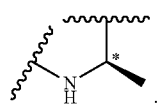 [SMILES: *N[C@@H](*)C]

In yet a further embodiment, the bond at the * position is

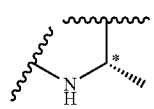

A further embodiment is a compound of Formula

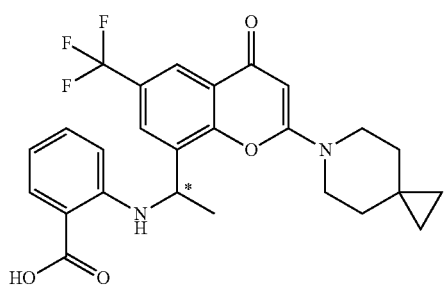

or a prodrug, solvate, enantiomer, stereoisomer, tautomer, or pharmaceutically acceptable salt thereof. In yet a further embodiment, the bond at the * position is

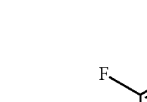

In yet a further embodiment, the bond at the * position is

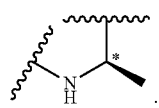

A further embodiment is a compound of Formula

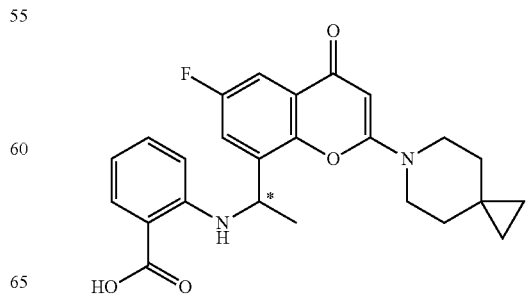

or a prodrug, solvate, enantiomer, stereoisomer, tautomer, or pharmaceutically acceptable salt thereof. In yet a further embodiment, the bond at the * position is

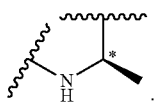

In yet a further embodiment, the bond at the * position is

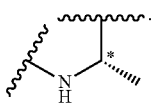

A further embodiment is a compound of Formula

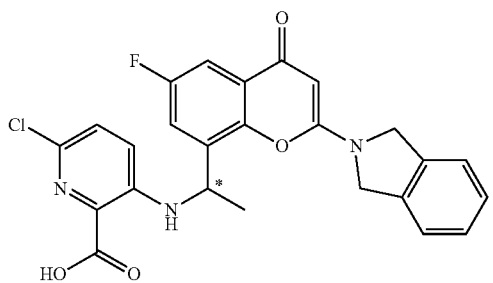

or a prodrug, solvate, enantiomer, stereoisomer, tautomer, or pharmaceutically acceptable salt thereof. In yet a further embodiment, the bond at the * position is

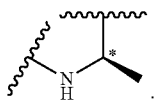

In yet a further embodiment, the bond at the * position is

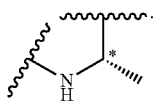

A further embodiment is a compound of Formula

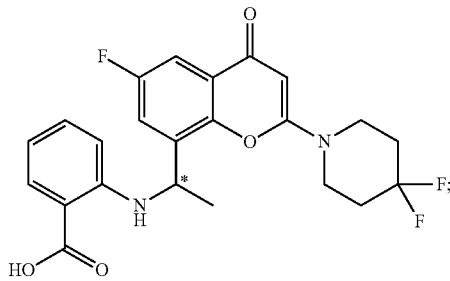 [SMILES: CC(Nc1ccccc1C(=O)O)c1cc(F)cc2c(=O)cc(N3CCC(F)(F)CC3)oc12]

or a prodrug, solvate, enantiomer, stereoisomer, tautomer, or pharmaceutically acceptable salt thereof. In yet a further embodiment, the bond at the * position is

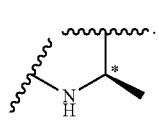

In yet a further embodiment, the bond at the * position is

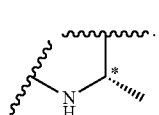

A further embodiment is a compound of Formula

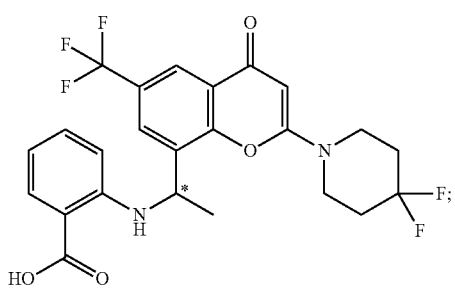 [SMILES: CC(Nc1ccccc1C(=O)O)c1cc(C(F)(F)F)cc2c(=O)cc(N3CCC(F)(F)CC3)oc12]

or a prodrug, solvate, enantiomer, stereoisomer, tautomer, or pharmaceutically acceptable salt thereof. In yet a further embodiment, the bond at the * position is

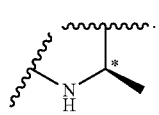

In yet a further embodiment, the bond at the * position is

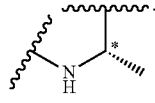

A further embodiment is a compound of Formula

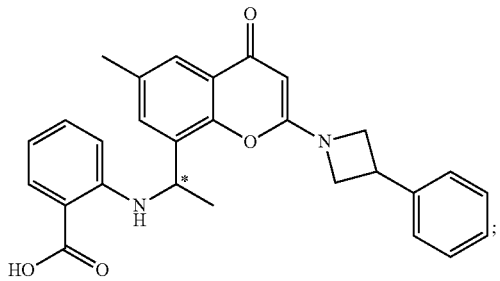 [SMILES: Cc1cc(C(C)Nc2ccccc2C(=O)O)c2oc(N3CC(c4ccccc4)C3)cc(=O)c2c1]

or a prodrug, solvate, enantiomer, stereoisomer, tautomer, or pharmaceutically acceptable salt thereof. In yet a further embodiment, the bond at the * position is

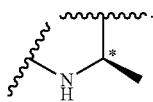

In yet a further embodiment, the bond at the * position is

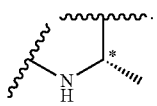

A further embodiment is a compound of Formula

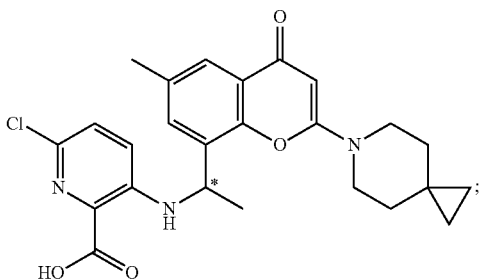 [SMILES: Cc1cc(C(C)Nc2ccc(Cl)nc2C(=O)O)c2oc(N3CCC4(CC3)CC4)cc(=O)c2c1]

or a prodrug, solvate, enantiomer, stereoisomer, tautomer, or pharmaceutically acceptable salt thereof. In yet a further embodiment, the bond at the * position is

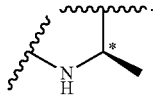

In yet a further embodiment, the bond at the * position is

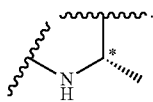 [SMILES: *N[C@H](*)C]

A further embodiment is a compound of Formula

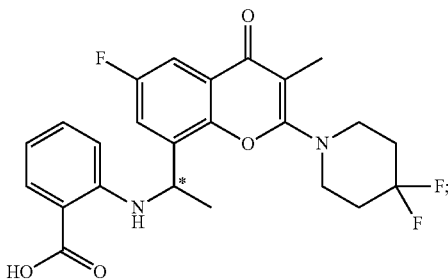 [SMILES: Cc1c(N2CCC(F)(F)CC2)oc2c(C(C)Nc3ccccc3C(=O)O)cc(F)cc2c1=O]

or a prodrug, solvate, enantiomer, stereoisomer, tautomer, or pharmaceutically acceptable salt thereof. In yet a further embodiment, the bond at the * position is

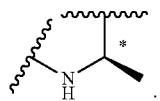

In yet a further embodiment, the bond at the * position is

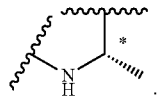

A further embodiment is a compound of Formula

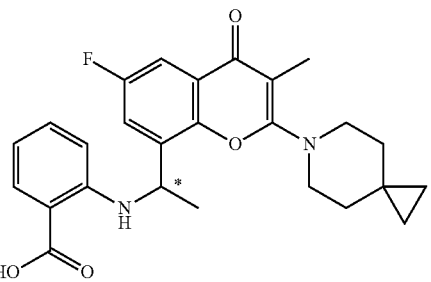

or a prodrug, solvate, enantiomer, stereoisomer, tautomer, or pharmaceutically acceptable salt thereof. In yet a further embodiment, the bond at the * position is

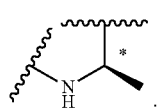

In yet a further embodiment, the bond at the * position is

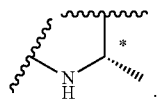

A further embodiment is a compound of Formula

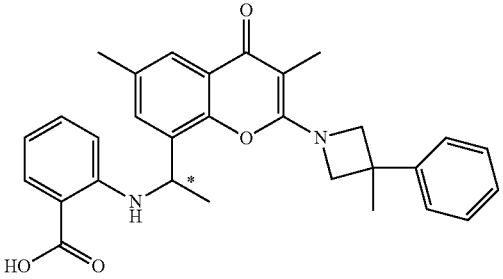

or a prodrug, solvate, enantiomer, stereoisomer, tautomer, or pharmaceutically acceptable salt thereof. In yet a further embodiment, the bond at the * position is

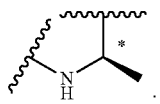

In yet a further embodiment, the bond at the * position is

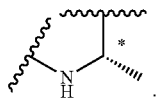

A further embodiment is a compound of Formula

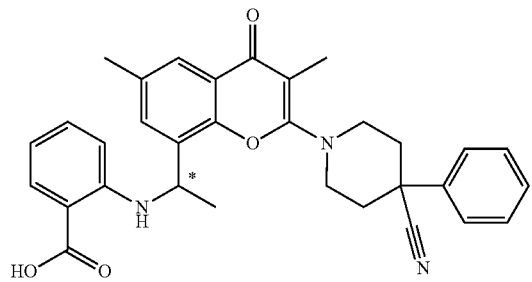

or a prodrug, solvate, enantiomer, stereoisomer, tautomer, or pharmaceutically acceptable salt thereof. In yet a further embodiment, the bond at the * position is

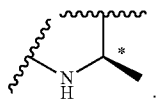

In yet a further embodiment, the bond at the * position is

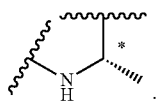

A further embodiment is a compound of Formula

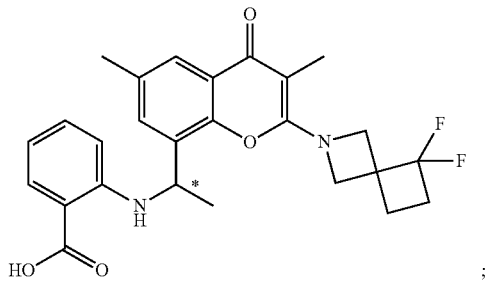 [SMILES: Cc1cc(C(C)Nc2ccccc2C(=O)O)c2oc(N3CC4(CCC4(F)F)C3)c(C)c(=O)c2c1]

or a prodrug, solvate, enantiomer, stereoisomer, tautomer, or pharmaceutically acceptable salt thereof. In yet a further embodiment, the bond at the * position is

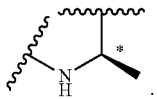

In yet a further embodiment, the bond at the * position is

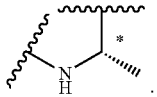

A further embodiment is a compound of Formula

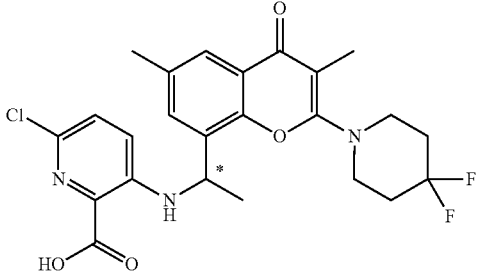

or a prodrug, solvate, enantiomer, stereoisomer, tautomer, or pharmaceutically acceptable salt thereof. In yet a further embodiment, the bond at the * position is

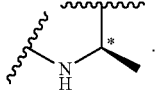

In yet a further embodiment, the bond at the * position is

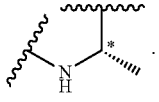

The embodiments in the following paragraphs, as applicable, refer to embodiments of compounds of Formula (I), (Ia), (Ib), (Ic), (Id), (Ie), (If), (Ig), (Ih), or (II), or a prodrug, solvate, enantiomer, stereoisomer, tautomer, or pharmaceutically acceptable salt thereof.

In some embodiments X is —NR$_{12}$— or —O—. In some embodiments X is —NR$_{12}$—. In some embodiments X is —O—.

In some embodiments, Y is —C(R$_{11}$)$_2$—, —O—, —NR$_{11}$—, or —S—.

In some embodiments, Y is —C(R$_{11}$)$_2$—. In some embodiments, Y is —O—. In some embodiments, Y is —NR$_{11}$—. In some embodiments, Y is —S—.

In some embodiments, W is —O—, —N—, or —S—.

In some embodiments, W is —O—. In some embodiments, W is —N—. In some embodiments, W is —S—.

In some embodiments, each $R_1$ and $R_2$ is independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle, aryl, or heteroaryl.

In some embodiments, each $R_1$ and $R_2$ is independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle, aryl, or heteroaryl.

In some embodiments, $R_1$ is absent, H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle, aryl, or heteroaryl.

In some embodiments, $R_1$ is H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle, aryl, or heteroaryl.

In some embodiments, $R_1$ is absent.

In some embodiments, $R_1$ is H.

In some embodiments, $R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle, aryl, or heteroaryl.

In some embodiments, $R_1$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_1$ is $C_1$-$C_6$ alkyl, $C_2$-$C_6$ alkenyl, or $C_2$-$C_6$ alkynyl.

In some embodiments, $R_1$ is $C_1$-$C_6$ alkyl.

In some embodiments, $R_1$ is methyl. In some embodiments, $R_1$ is ethyl. In some embodiments, $R_1$ is propyl. In some embodiments, $R_1$ is n-propyl. In some embodiments, $R_1$ is isopropyl. In some embodiments, $R_1$ is butyl. In some embodiments, $R_1$ is n-butyl. In some embodiments, $R_1$ is isobutyl. In some embodiments, $R_1$ is sec-butyl. In some embodiments, $R_1$ is tert-butyl. In some embodiments, $R_1$ is pentyl. In some embodiments, $R_1$ is hexyl.

In some embodiments, $R_1$ is $C_2$-$C_6$ alkenyl.

In some embodiments, $R_1$ is $C_2$ alkenyl. In some embodiments, $R_1$ is $C_3$ alkenyl. In some embodiments, $R_1$ is $C_4$ alkenyl. In some embodiments, $R_1$ is $C_5$ alkenyl. In some embodiments, $R_1$ is $C_6$ alkenyl.

In some embodiments, $R_1$ is $C_2$-$C_6$ alkynyl.

In some embodiments, $R_1$ is $C_2$ alkynyl. In some embodiments, $R_1$ is $C_3$ alkynyl. In some embodiments, $R_1$ is $C_4$ alkynyl. In some embodiments, $R_1$ is $C_5$ alkynyl. In some embodiments, $R_1$ is $C_6$ alkynyl.

In some embodiments, $R_1$ is $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle, aryl, or heteroaryl.

In some embodiments, $R_1$ is $C_1$-$C_6$ haloalkyl or $C_1$-$C_6$ alkoxy.

In some embodiments, $R_1$ is $C_1$-$C_6$ haloalkyl.

In some embodiments, $R_1$ is halomethyl. In some embodiments, $R_1$ is haloethyl. In some embodiments, $R_1$ is halopropyl. In some embodiments, $R_1$ is halobutyl. In some embodiments, $R_1$ is halopentyl. In some embodiments, $R_1$ is halohexyl.

In some embodiments, $R_1$ is $C_1$-$C_6$ alkoxy.

In some embodiments, $R_1$ is methoxy. In some embodiments, $R_1$ is ethoxy. In some embodiments, $R_1$ is propoxy. In some embodiments, $R_1$ is butoxy. In some embodiments, $R_1$ is pentoxy. In some embodiments, one $R_1$ is hexoxy.

In some embodiments, $R_1$ is —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, or —$(CH_2)_m$—$C(O)N(R_{12})_2$.

In some embodiments, $R_1$ is —$(CH_2)_m$—$R_{12}$, —$(CH_2)_m$—$OR_{12}$, or —$(CH_2)_m$—$N(R_{12})_2$.

In some embodiments, $R_1$ is —$(CH_2)_m$—$R_{12}$. In some embodiments, $R_1$ is —$(CH_2)_m$—$OR_{12}$. In some embodiments, $R_1$ is —$(CH_2)_m$—$N(R_{12})_2$.

In some embodiments, $R_1$ is —$R_{12}$. In some embodiments, $R_1$ is —$CH_2$—$R_{12}$. In some embodiments, $R_1$ is —$CH_2CH_2$—$R_{12}$. In some embodiments, $R_1$ is —$CH_2CH_2CH_2$—$R_{12}$. In some embodiments, $R_1$ is —$CH_2CH_2CH_2CH_2$—$R_{12}$. In some embodiments, $R_1$ is —$CH_2CH_2CH_2CH_2CH_2$—$R_{12}$. In some embodiments, $R_1$ is —$CH_2CH_2CH_2CH_2CH_2CH_2$—$R_{12}$.

In some embodiments, $R_1$ is —$OR_{12}$. In some embodiments, $R_1$ is —$CH_2$—$OR_{12}$. In some embodiments, $R_1$ is —$CH_2CH_2$—$OR_{12}$. In some embodiments, $R_1$ is —$CH_2CH_2CH_2$—$OR_{12}$. In some embodiments, $R_1$ is —$CH_2CH_2CH_2CH_2$—$OR_{12}$. In some embodiments, $R_1$ is —$CH_2CH_2CH_2CH_2CH_2$—$OR_{12}$. In some embodiments, $R_1$ is —$CH_2CH_2CH_2CH_2CH_2CH_2$—$OR_{12}$.

In some embodiments, $R_1$ is —$N(R_{12})_2$. In some embodiments, $R_1$ is —$CH_2$—$N(R_{12})_2$. In some embodiments, $R_1$ is —$CH_2CH_2$—$N(R_{12})_2$. In some embodiments, $R_1$ is —$CH_2CH_2CH_2$—$N(R_{12})_2$. In some embodiments, $R_1$ is —$CH_2CH_2CH_2CH_2$—$N(R_{12})_2$. In some embodiments, $R_1$ is —$CH_2CH_2CH_2CH_2CH_2$—$N(R_{12})_2$. In some embodiments, $R_1$ is —$CH_2CH_2CH_2CH_2CH_2CH_2$—$N(R_{12})_2$.

In some embodiments, $R_1$ is —$(CH_2)_m$—$C(O)R_{12}$, —$(CH_2)_m$—$C(O)OR_{12}$, or —$(CH_2)_m$—$C(O)N(R_{12})_2$.

In some embodiments, $R_1$ is —$(CH_2)_m$—$C(O)R_{12}$. In some embodiments, $R_1$ is —$(CH_2)_m$—$C(O)OR_{12}$. In some embodiments, $R_1$ is —$(CH_2)_m$—$C(O)N(R_{12})_2$.

In some embodiments, $R_1$ is —$C(O)R_{12}$. In some embodiments, $R_1$ is —$CH_2$—$C(O)R_{12}$. In some embodiments, $R_1$ is —$CH_2CH_2$—$C(O)R_{12}$. In some embodiments, $R_1$ is —$CH_2CH_2CH_2$—$C(O)R_{12}$. In some embodiments, $R_1$ is —$CH_2CH_2CH_2CH_2$—$C(O)R_{12}$. In some embodiments, $R_1$ is —$CH_2CH_2CH_2CH_2CH_2$—$C(O)R_{12}$. In some embodiments, $R_1$ is —$CH_2CH_2CH_2CH_2CH_2CH_2$—$C(O)R_{12}$.

In some embodiments, $R_1$ is —$C(O)OR_{12}$. In some embodiments, $R_1$ is —$CH_2$—$C(O)OR_{12}$. In some embodiments, $R_1$ is —$CH_2CH_2$—$C(O)OR_{12}$. In some embodiments, $R_1$ is —$CH_2CH_2CH_2$—$C(O)OR_{12}$. In some embodiments, $R_1$ is —$CH_2CH_2CH_2CH_2$—$C(O)OR_{12}$. In some embodiments, $R_1$ is —$CH_2CH_2CH_2CH_2CH_2$—$C(O)OR_{12}$. In some embodiments, $R_1$ is —$CH_2CH_2CH_2CH_2CH_2CH_2$—$C(O)OR_{12}$.

In some embodiments, $R_1$ is —$C(O)N(R_{12})_2$. In some embodiments, $R_1$ is —$CH_2$—$C(O)N(R_{12})_2$. In some embodiments, $R_1$ is —$CH_2CH_2$—$C(O)N(R_{12})_2$. In some embodiments, $R_1$ is —$CH_2CH_2CH_2$—$C(O)N(R_{12})_2$. In some embodiments, $R_1$ is —$CH_2CH_2CH_2CH_2$—$C(O)N(R_{12})_2$. In some embodiments, $R_1$ is —$CH_2CH_2CH_2CH_2CH_2$—$C(O)N(R_{12})_2$. In some embodiments, $R_1$ is —$CH_2CH_2CH_2CH_2CH_2CH_2$—$C(O)N(R_{12})_2$.

In some embodiments, $R_1$ is —$CH_2$—$C(O)NH_2$.

In some embodiments, $R_1$ is $C_3$-$C_{10}$ cycloalkyl, heterocycle, aryl, or heteroaryl.

In some embodiments, $R_1$ is $C_3$-$C_{10}$ cycloalkyl or heterocycle.

In some embodiments, $R_1$ is aryl or heteroaryl.

In some embodiments, $R_1$ is $C_3$-$C_{10}$ cycloalkyl.

In some embodiments, $R_1$ is a monocyclic $C_3$-$C_{10}$ cycloalkyl. In some embodiments, $R_1$ is a polycyclic $C_3$-$C_{10}$ cycloalkyl.

In some embodiments, $R_1$ is $C_5$-$C_6$ cycloalkyl.

In some embodiments, $R_1$ is cyclopropyl, cyclobutyl, cyclopentyl, cyclohexyl, cycloheptyl, cyclooctyl, cyclononyl, or cyclodecyl.

In some embodiments, $R_1$ is a fused polycyclic $C_3$-$C_{10}$ cycloalkyl. In some embodiments, $R_1$ is a bridged polycyclic $C_3$-$C_{10}$ cycloalkyl. In some embodiments, $R_1$ is a $C_3$-$C_{10}$ spirocycloalkyl.

In some embodiments, $R_1$ is heterocycle.

In some embodiments, $R_1$ is a monocyclic heterocycle. In some embodiments, $R_1$ is a polycyclic heterocycle.

In some embodiments, $R_1$ is 3-membered heterocycle. In some embodiments, $R_1$ is 4-membered heterocycle. In some embodiments, $R_1$ is 5-membered heterocycle. In some embodiments, $R_1$ is 6-membered heterocycle. In some embodiments, $R_1$ is 7-membered heterocycle. In some embodiments, $R_1$ is 8-membered heterocycle. In some embodiments, $R_1$ is 9-membered heterocycle. In some embodiments, $R_1$ is 10-membered heterocycle.

In some embodiments, $R_1$ is 5- to 6-membered heterocycle.

In some embodiments, $R_1$ is heterocycle comprising one, two, or three heteroatoms.

In some embodiments, $R_1$ is heterocycle comprising one, two, or three heteroatoms selected from N, O, and S.

In some embodiments, $R_1$ is heterocycle comprising one, two, or three heteroatoms selected from N and O.

In some embodiments, $R_1$ is heterocycle comprising one heteroatom selected from N and O. In some embodiments, $R_1$ is heterocycle comprising two heteroatoms selected from N and O. In some embodiments, $R_1$ is heterocycle comprising three heteroatoms selected from N and O.

In some embodiments, $R_1$ is aryl.

In some embodiments, $R_1$ is $C_6$ aryl (e.g., phenyl).

In some embodiments, $R_1$ is a heteroaryl.

In some embodiments, $R_1$ is 5- to 6-membered heteroaryl.

In some embodiments, $R_1$ is heteroaryl comprising one, two, or three heteroatoms.

In some embodiments, $R_1$ is heteroaryl comprising one, two, or three heteroatoms selected from N, O, and S.

In some embodiments, $R_1$ is heteroaryl comprising one, two, or three heteroatoms selected from N and O.

In some embodiments, $R_1$ is heteroaryl comprising one heteroatom selected from N and O. In some embodiments, $R_1$ is heteroaryl comprising two heteroatoms selected from N and O. In some embodiments, $R_1$ is heteroaryl comprising three heteroatoms selected from N and O.

In some embodiments, $R_1$ is ethyl, isobutyl, or —$CH_2$—$C(O)NH_2$.

In some embodiments, $R_2$ is absent, H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle, aryl, or heteroaryl.

In some embodiments, $R_2$ is H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle, aryl, or heteroaryl.

In some embodiments, $R_2$ is absent.

In some embodiments, $R_2$ is H.

In some embodiments, $R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle, aryl, or heteroaryl.

In some embodiments, $R_2$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_2$ is $C_1$-$C_6$ alkyl, $C_2$-$C_6$ alkenyl, or $C_2$-$C_6$ alkynyl.

In some embodiments, $R_2$ is $C_1$-$C_6$ alkyl (e.g. linear or branched).

In some embodiments, $R_2$ is methyl. In some embodiments, $R_2$ is ethyl. In some embodiments, $R_2$ is propyl. In some embodiments, $R_2$ is n-propyl. In some embodiments, $R_2$ is isopropyl. In some embodiments, $R_2$ is butyl. In some embodiments, $R_2$ is n-butyl. In some embodiments, $R_2$ is isobutyl. In some embodiments, $R_2$ is sec-butyl. In some embodiments, $R_2$ is tert-butyl. In some embodiments, $R_2$ is pentyl. In some embodiments, $R_2$ is hexyl.

In some embodiments, $R_2$ is $C_2$-$C_6$ alkenyl.

In some embodiments, $R_2$ is $C_2$ alkenyl. In some embodiments, $R_2$ is $C_3$ alkenyl. In some embodiments, $R_2$ is $C_4$ alkenyl. In some embodiments, $R_2$ is $C_5$ alkenyl. In some embodiments, $R_2$ is $C_6$ alkenyl.

In some embodiments, $R_2$ is $C_2$-$C_6$ alkynyl.

In some embodiments, $R_2$ is $C_2$ alkynyl. In some embodiments, $R_2$ is $C_3$ alkynyl. In some embodiments, $R_2$ is $C_4$ alkynyl. In some embodiments, $R_2$ is $C_5$ alkynyl. In some embodiments, $R_2$ is $C_6$ alkynyl.

In some embodiments, $R_2$ is $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle, aryl, or heteroaryl.

In some embodiments, $R_2$ is $C_1$-$C_6$ haloalkyl or $C_1$-$C_6$ alkoxy.

In some embodiments, $R_2$ is $C_1$-$C_6$ haloalkyl.

In some embodiments, $R_2$ is halomethyl. In some embodiments, $R_2$ is haloethyl. In some embodiments, $R_2$ is halopropyl. In some embodiments, $R_2$ is halobutyl. In some embodiments, $R_2$ is halopentyl. In some embodiments, $R_2$ is halohexyl.

In some embodiments, $R_2$ is $C_1$-$C_6$ alkoxy.

In some embodiments, $R_2$ is methoxy. In some embodiments, $R_2$ is ethoxy. In some embodiments, $R_2$ is propoxy. In some embodiments, $R_2$ is butoxy. In some embodiments, $R_2$ is pentoxy. In some embodiments, one $R_2$ is hexoxy.

In some embodiments, $R_2$ is —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, or —$(CH_2)_m$—$C(O)N(R_{12})_2$.

In some embodiments, $R_2$ is —$(CH_2)_m$—$R_{12}$, —$(CH_2)_m$—$OR_{12}$, or —$(CH_2)_m$—$N(R_{12})_2$.

In some embodiments, $R_2$ is —$(CH_2)_m$—$R_{12}$. In some embodiments, $R_2$ is —$(CH_2)_m$—$OR_{12}$. In some embodiments, $R_2$ is —$(CH_2)_m$—$N(R_{12})_2$.

In some embodiments, $R_2$ is —$CH_2$—$R_{12}$. In some embodiments, $R_2$ is —$CH_2CH_2$—$R_{12}$. In some embodiments, $R_2$ is —$CH_2CH_2CH_2$—$R_{12}$. In some embodiments, $R_2$ is —$CH_2CH_2CH_2CH_2$—$R_{12}$. In some embodiments, $R_2$ is —$CH_2CH_2CH_2CH_2CH_2$—$R_{12}$. In some embodiments, $R_2$ is —$CH_2CH_2CH_2CH_2CH_2CH_2$—$R_{12}$.

In some embodiments, $R_2$ is —$CH_2$—$OR_{12}$. In some embodiments, $R_2$ is —$CH_2CH_2$—$OR_{12}$. In some embodiments, $R_2$ is —$CH_2CH_2CH_2$—$OR_{12}$. In some embodiments, $R_2$ is —$CH_2CH_2CH_2CH_2$—$OR_{12}$. In some embodiments, $R_2$ is —$CH_2CH_2CH_2CH_2CH_2$—$OR_{12}$. In some embodiments, $R_2$ is —$CH_2CH_2CH_2CH_2CH_2CH_2$—$OR_{12}$.

In some embodiments, $R_2$ is —$CH_2$— $N(R_{12})_2$. In some embodiments, $R_2$ is —$CH_2CH_2$—$N(R_{12})_2$. In some embodiments, $R_2$ is —$CH_2CH_2CH_2$— $N(R_{12})_2$. In some embodiments, $R_2$ is —$CH_2CH_2CH_2CH_2$— $N(R_{12})_2$. In some embodiments, $R_2$ is —$CH_2CH_2CH_2CH_2CH_2$— $N(R_{12})_2$. In some embodiments, $R_2$ is —$CH_2CH_2CH_2CH_2CH_2CH_2$—$N(R_{12})_2$.

In some embodiments, $R_2$ is —$(CH_2)_m$—$C(O)R_{12}$, —$(CH_2)_m$—$C(O)OR_{12}$, or —$(CH_2)_m$—$C(O)N(R_{12})_2$.

In some embodiments, $R_2$ is —$(CH_2)_m$—$C(O)R_{12}$. In some embodiments, $R_2$ is —$(CH_2)_m$—$C(O)OR_{12}$. In some embodiments, $R_2$ is —$(CH_2)_m$—$C(O)N(R_{12})_2$.

In some embodiments, $R_2$ is —$CH_2$—$C(O)R_{12}$. In some embodiments, $R_2$ is —$CH_2CH_2$— $C(O)R_{12}$. In some embodiments, $R_2$ is —$CH_2CH_2CH_2$—$C(O)R_{12}$. In some embodiments, $R_2$ is —$CH_2CH_2CH_2CH_2$—$C(O)R_{12}$. In some embodiments, $R_2$ is —$CH_2CH_2CH_2CH_2CH_2$—$C(O)R_{12}$. In some embodiments, $R_2$ is —$CH_2CH_2CH_2CH_2CH_2CH_2$—$C(O)R_{12}$.

In some embodiments, $R_2$ is —$CH_2$—$C(O)OR_{12}$. In some embodiments, $R_2$ is —$CH_2CH_2$—$C(O)OR_{12}$. In some embodiments, $R_2$ is —$CH_2CH_2CH_2$—$C(O)OR_{12}$. In some embodiments, $R_2$ is —$CH_2CH_2CH_2CH_2$—$C(O)OR_{12}$. In some embodiments, $R_2$ is —$CH_2CH_2CH_2CH_2CH_2$—$C(O)OR_{12}$. In some embodiments, $R_2$ is —$CH_2CH_2CH_2CH_2CH_2CH_2$—$C(O)OR_{12}$.

In some embodiments, $R_2$ is —$CH_2$—$C(O)N(R_{12})_2$. In some embodiments, $R_2$ is —$CH_2CH_2$—$C(O)N(R_{12})_2$. In some embodiments, $R_2$ is —$CH_2CH_2CH_2$—$C(O)N(R_{12})_2$. In some embodiments, $R_2$ is —$CH_2CH_2CH_2CH_2$—$C(O)N(R_{12})_2$. In some embodiments, $R_2$ is —$CH_2CH_2CH_2CH_2CH_2$—$C(O)N(R_{12})_2$. In some embodiments, $R_2$ is —$CH_2CH_2CH_2CH_2CH_2CH_2$—$C(O)N(R_{12})_2$.

In some embodiments, $R_2$ is —$CH_2$—$C(O)NH_2$.

In some embodiments, $R_2$ is $C_3$-$C_{10}$ cycloalkyl, heterocycle, aryl, or heteroaryl.

In some embodiments, $R_2$ is $C_3$-$C_{10}$ cycloalkyl or heterocycle.

In some embodiments, $R_2$ is aryl or heteroaryl.

In some embodiments, $R_2$ is $C_3$-$C_{10}$ cycloalkyl.

In some embodiments, $R_2$ is a monocyclic $C_3$-$C_{10}$ cycloalkyl. In some embodiments, $R_2$ is a polycyclic $C_3$-$C_{10}$ cycloalkyl.

In some embodiments, $R_2$ is $C_5$-$C_6$ cycloalkyl.

In some embodiments, $R_2$ is cyclopropyl, cyclobutyl, cyclopentyl, cyclohexyl, cycloheptyl, cyclooctyl, cyclononyl, or cyclodecyl.

In some embodiments, $R_2$ is a fused polycyclic $C_3$-$C_{10}$ cycloalkyl. In some embodiments, $R_2$ is a bridged polycyclic $C_3$-$C_{10}$ cycloalkyl. In some embodiments, $R_2$ is a $C_3$-$C_{10}$ spirocycloalkyl.

In some embodiments, $R_2$ is heterocycle.

In some embodiments, $R_2$ is a monocyclic heterocycle. In some embodiments, $R_2$ is a polycyclic heterocycle.

In some embodiments, $R_2$ is 3-membered heterocycle. In some embodiments, $R_2$ is 4-membered heterocycle. In some embodiments, $R_2$ is 5-membered heterocycle. In some embodiments, $R_2$ is 6-membered heterocycle. In some embodiments, $R_2$ is 7-membered heterocycle. In some embodiments, $R_2$ is 8-membered heterocycle. In some embodiments, $R_2$ is 9-membered heterocycle. In some embodiments, $R_2$ is 10-membered heterocycle.

In some embodiments, $R_2$ is 5- to 6-membered heterocycle.

In some embodiments, $R_2$ is heterocycle comprising one, two, or three heteroatoms.

In some embodiments, $R_2$ is heterocycle comprising one, two, or three heteroatoms selected from N, O, and S.

In some embodiments, $R_2$ is heterocycle comprising one, two, or three heteroatoms selected from N and O.

In some embodiments, $R_2$ is heterocycle comprising one heteroatom selected from N and O. In some embodiments, $R_2$ is heterocycle comprising two heteroatoms selected from N and O. In some embodiments, $R_2$ is heterocycle comprising three heteroatoms selected from N and O.

In some embodiments, $R_2$ is aryl.

In some embodiments, $R_2$ is $C_6$ aryl (e.g., phenyl).

In some embodiments, $R_2$ is a heteroaryl.

In some embodiments, $R_2$ is 5- to 6-membered heteroaryl.

In some embodiments, $R_2$ is heteroaryl comprising one, two, or three heteroatoms.

In some embodiments, $R_2$ is heteroaryl comprising one, two, or three heteroatoms selected from N, O, and S.

In some embodiments, $R_2$ is heteroaryl comprising one, two, or three heteroatoms selected from N and O.

In some embodiments, $R_2$ is heteroaryl comprising one heteroatom selected from N and O. In some embodiments, $R_2$ is heteroaryl comprising two heteroatoms selected from N and O. In some embodiments, $R_2$ is heteroaryl comprising three heteroatoms selected from N and O.

In some embodiments, $R_2$ is ethyl, isobutyl, or —$CH_2$—$C(O)NH_2$.

In some embodiments, $R_1$ and $R_2$, together with the nitrogen to which they are attached, form a heterocycle comprising 1-4 heteroatoms selected from O, N, and S, wherein the heterocycle is optionally substituted with one or more $R_{10}$.

In some embodiments $R_1$ and $R_2$, together with the nitrogen to which they are attached, form a saturated heterocycle comprising 1-4 heteroatoms selected from O, N, and S, wherein the heterocycle is optionally substituted with one or more $R_{10}$. In some embodiments $R_1$ and $R_2$, together with the nitrogen to which they are attached, form a partially unsaturated heterocycle comprising 1-4 heteroatoms selected from O, N, and S, wherein the heterocycle is optionally substituted with one or more $R_{10}$.

In some embodiments, $R_1$ and $R_2$, together with the nitrogen to which they are attached, form a heterocycle comprising one heteroatom which is N, wherein the heterocycle is unsubstituted. In some embodiments, $R_1$ and $R_2$, together with the nitrogen to which they are attached, form a heterocycle comprising one N heteroatom, wherein the heterocycle is optionally substituted with one or more $R_{10}$. In some embodiments, $R_1$ and $R_2$, together with the nitrogen to which they are attached, form a heterocycle comprising two heteroatoms selected from O, N, and S, wherein the heterocycle is optionally substituted with one or more $R_{10}$. In some embodiments, $R_1$ and $R_2$, together with the nitrogen to which they are attached, form a heterocycle comprising three heteroatoms selected from O, N, and S, wherein the heterocycle is optionally substituted with one or more $R_{10}$. In some embodiments, $R_1$ and $R_2$, together with the nitrogen to which they are attached, form a heterocycle comprising four heteroatoms selected from O, N, and S, wherein the heterocycle is optionally substituted with one or more $R_{10}$.

In some embodiments, $R_1$ and $R_2$, together with the nitrogen to which they are attached, form a heterocycle comprising one N heteroatom, wherein the heterocycle is substituted with one or more $R_{10}$. In some embodiments, $R_1$ and $R_2$, together with the nitrogen to which they are attached, form a heterocycle comprising two heteroatoms selected from O, N, and S, wherein the heterocycle is substituted with one or more $R_{10}$. In some embodiments, $R_1$ and $R_2$, together with the nitrogen to which they are attached, form a heterocycle comprising three heteroatoms selected from O, N, and S, wherein the heterocycle is substituted with one or more $R_{10}$. In some embodiments, $R_1$ and $R_2$, together with the nitrogen to which they are attached, form a heterocycle comprising four heteroatoms selected from O, N, and S, wherein the heterocycle is substituted with one or more $R_{10}$.

In some embodiments, $R_1$ and $R_2$, together with the nitrogen to which they are attached, form a 3- to 10-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 3- to 9-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 3- to 8-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 3- to 7-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 3- to 6-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 3- to 5-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 4- to 10-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 4- to 9-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 4- to 8-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 4- to 7-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 4- to 6-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 4- to 5-membered saturated or partially unsaturated heterocycle comprising 1-4 heteroatoms selected from O, N, and S, wherein the heterocycle is optionally substituted with one or more $R_{10}$.

In some embodiments, $R_1$ and $R_2$, together with the nitrogen to which they are attached, form a 5- to 6-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 5- to 7-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 5- to 8-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 5- to 9-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 5- to 10-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 6- to 10-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 6- to 9-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 6- to 8-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 6- to 7-membered saturated or partially unsaturated heterocycle comprising 1-4 heteroatoms selected from O, N, and S, wherein the heterocycle is optionally substituted with one or more $R_{10}$.

In some embodiments, $R_1$ and $R_2$, together with the nitrogen to which they are attached, form a 7- to 8-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 7- to 9-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 7- to 10-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 8- to 10-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 8- to 9-membered saturated or partially unsaturated heterocycle comprising 1-4 heteroatoms selected from O, N, and S, wherein the heterocycle is optionally substituted with one or more $R_{10}$.

In some embodiments, $R_1$ and $R_2$, together with the nitrogen to which they are attached, form a 9- to 10-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 3- to 15-membered saturated or partially unsaturated monocyclic heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 3- to 15-membered saturated or partially unsaturated polycyclic heterocycle comprising 1-4 heteroatoms selected from O, N, and S, wherein the heterocycle is optionally substituted with one or more $R_{10}$.

In some embodiments, $R_1$ and $R_2$, together with the nitrogen to which they are attached, form a fused polycyclic heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a bridged polycyclic heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a spiroheterocycle comprising 1-4 heteroatoms selected from O, N, and S, wherein the heterocycle is optionally substituted with one or more $R_{10}$.

In some embodiments, $R_1$ and $R_2$, together with the nitrogen to which they are attached, form a heterocycle comprising 1-4 heteroatoms selected from O, N, and S, wherein the heterocycle is optionally substituted with one $R_{10}$. In some embodiments, $R_1$ and $R_2$, together with the nitrogen to which they are attached, form a heterocycle comprising 1-4 heteroatoms selected from O, N, and S, wherein the heterocycle is optionally substituted with two $R_{10}$. In some embodiments, $R_1$ and $R_2$, together with the nitrogen to which they are attached, form a heterocycle comprising 1-4 heteroatoms selected from O, N, and S, wherein the heterocycle is optionally substituted with three $R_{10}$. In some embodiments, $R_1$ and $R_2$, together with the nitrogen to which they are attached, form a heterocycle comprising 1-4 heteroatoms selected from O, N, and S, wherein the heterocycle is optionally substituted with four $R_{10}$.

In some embodiments, $R_1$ and $R_2$, together with the nitrogen to which they are attached, form a 3-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 4-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 5-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 6-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 7-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 8-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 9-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 10-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 11-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 12-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 13-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 14-membered saturated or partially unsaturated heterocycle comprising 1-4 heteroatoms selected from O, N, and S, wherein the heterocycle is optionally substituted with one or more $R_{10}$. In some embodiments, $R_1$ and $R_2$, together with the nitrogen to which they are attached, form a 15-membered saturated or partially unsaturated heterocycle comprising 1-4 heteroatoms selected from O, N, and S, wherein the heterocycle is optionally substituted with one or more $R_{10}$.

In some embodiments, $R_3$ is H, halogen, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle comprising 1-4 heteroatoms selected from O, N, and S, aryl, or heteroaryl comprising 1-4 heteroatoms selected from O, N, and S.

In some embodiments, $R_3$ is H.

In some embodiments, $R_3$ is halogen, —CN, $C_1C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle comprising 1-4 heteroatoms selected from O, N, and S, aryl, or heteroaryl comprising 1-4 heteroatoms selected from O, N, and S.

In some embodiments, $R_3$ is halogen. In some embodiments, $R_3$ is F, Cl, Br, or I. In some embodiments, $R_3$ is F, Cl, or Br. In some embodiments, $R_3$ is F. In some embodiments, $R_3$ is Cl. In some embodiments, $R_3$ is Br. In some embodiments, $R_3$ is I.

In some embodiments, $R_3$ is —CN.

In some embodiments, $R_3$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—C(O)$R_{12}$, —$(CH_2)_m$—C(O)O$R_{12}$, —$(CH_2)_m$—C(O)N($R_{12})_2$, $C_3$-$C_{10}$ cycloalkyl, heterocycle comprising 1-4 heteroatoms selected from O, N, and S, aryl, or heteroaryl comprising 1-4 heteroatoms selected from O, N, and S.

In some embodiments, $R_3$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_3$ is $C_1$-$C_6$ alkyl, $C_2$-$C_6$ alkenyl, or $C_2$-$C_6$ alkynyl.

In some embodiments, $R_3$ is $C_1$-$C_6$ alkyl (e.g. linear or branched).

In some embodiments, $R_3$ is methyl. In some embodiments, $R_3$ is ethyl. In some embodiments, $R_3$ is propyl. In some embodiments, $R_3$ is n-propyl. In some embodiments, $R_3$ is isopropyl. In some embodiments, $R_3$ is butyl. In some embodiments, $R_3$ is n-butyl. In some embodiments, $R_3$ is isobutyl. In some embodiments, $R_3$ is sec-butyl. In some embodiments, $R_3$ is tert-butyl. In some embodiments, $R_3$ is pentyl. In some embodiments, $R_3$ is hexyl.

In some embodiments, $R_3$ is $C_2$-$C_6$ alkenyl.

In some embodiments, $R_3$ is $C_2$ alkenyl. In some embodiments, $R_3$ is $C_3$ alkenyl. In some embodiments, $R_3$ is $C_4$ alkenyl. In some embodiments, $R_3$ is $C_5$ alkenyl. In some embodiments, $R_3$ is $C_6$ alkenyl.

In some embodiments, $R_3$ is $C_2$-$C_6$ alkynyl.

In some embodiments, $R_3$ is $C_2$ alkynyl. In some embodiments, $R_3$ is $C_3$ alkynyl. In some embodiments, $R_3$ is $C_4$ alkynyl. In some embodiments, $R_3$ is $C_5$ alkynyl. In some embodiments, $R_3$ is $C_6$ alkynyl.

In some embodiments, $R_3$ is $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—N($R_{12})_2$, —$(CH_2)_m$—C(O)$R_{12}$, —$(CH_2)_m$—C(O)O$R_{12}$, —$(CH_2)_m$—C(O)N($R_{12})_2$, $C_3$-$C_{10}$ cycloalkyl, heterocycle, aryl, or heteroaryl.

In some embodiments, $R_3$ is $C_1$-$C_6$ haloalkyl or $C_1$-$C_6$ alkoxy.

In some embodiments, $R_3$ is $C_1$-$C_6$ haloalkyl.

In some embodiments, $R_3$ is halomethyl. In some embodiments, $R_3$ is haloethyl. In some embodiments, $R_3$ is halopropyl. In some embodiments, $R_3$ is halobutyl. In some embodiments, $R_3$ is halopentyl. In some embodiments, $R_3$ is halohexyl.

In some embodiments, $R_3$ is $CH_2F$. In some embodiments, $R_3$ is $CHF_2$. In some embodiments, $R_3$ is $CF_3$.

In some embodiments, $R_3$ is $C_1$-$C_6$ alkoxy.

In some embodiments, $R_3$ is methoxy. In some embodiments, $R_3$ is ethoxy. In some embodiments, $R_3$ is propoxy. In some embodiments, $R_3$ is butoxy. In some embodiments, $R_3$ is pentoxy. In some embodiments, one $R_3$ is hexoxy.

In some embodiments, $R_3$ is —$(CH_2)_m$—$R_{12}$, —$(CH_2)_m$—$OR_{12}$, —$(CH_2)_m$—$N(R_{12})_2$, —$(CH_2)_m$—C(O)$R_{12}$, —$(CH_2)_m$—C(O)O$R_{12}$, or —$(CH_2)_m$—C(O)N($R_{12})_2$.

In some embodiments, $R_3$ is —$(CH_2)_m$—$R_{12}$, —$(CH_2)_m$—$OR_{12}$, or —$(CH_2)_m$—N($R_{12})_2$.

In some embodiments, $R_3$ is —$(CH_2)_m$—$R_{12}$. In some embodiments, $R_3$ is —$(CH_2)_m$—$OR_{12}$. In some embodiments, $R_3$ is —$(CH_2)_m$—N($R_{12})_2$.

In some embodiments, $R_3$ is —$CH_2$—$R_{12}$. In some embodiments, $R_3$ is —$R_{12}$. In some embodiments, $R_3$ is —$CH_2CH_2$—$R_{12}$. In some embodiments, $R_3$ is —$CH_2CH_2CH_2$—$R_{12}$. In some embodiments, $R_3$ is —$CH_2CH_2CH_2CH_2$—$R_{12}$. In some embodiments, $R_3$ is —$CH_2CH_2CH_2CH_2CH_2$—$R_{12}$. In some embodiments, $R_3$ is —$CH_2CH_2CH_2CH_2CH_2CH_2$—$R_{12}$.

In some embodiments, $R_3$ is —$OR_{12}$. In some embodiments, $R_3$ is —$CH_2$—$OR_{12}$. In some embodiments, $R_3$ is —$CH_2CH_2$—$OR_{12}$. In some embodiments, $R_3$ is —$CH_2CH_2CH_2$—$OR_{12}$. In some embodiments, $R_3$ is —$CH_2CH_2CH_2CH_2$—$OR_{12}$. In some embodiments, $R_3$ is —$CH_2CH_2CH_2CH_2CH_2$—$OR_{12}$. In some embodiments, $R_3$ is —$CH_2CH_2CH_2CH_2CH_2CH_2$—$OR_{12}$.

In some embodiments, $R_3$ is —$OR_{12}$, wherein $R_{12}$ is H. In some embodiments, $R_3$ is —$OR_{12}$, wherein $R_{12}$ is $C_{3-10}$ cycloalkyl. In some embodiments, $R_3$ is.

In some embodiments, $R_3$ is —N($R_{12})_2$. In some embodiments, $R_3$ is —$CH_2$—N($R_{12})_2$. In some embodiments, $R_3$ is —$CH_2CH_2$—N($R_{12})_2$. In some embodiments, $R_3$ is —$CH_2CH_2CH_2$—N($R_{12})_2$. In some embodiments, $R_3$ is —$CH_2CH_2CH_2CH_2$—N($R_{12})_2$. In some embodiments, $R_3$ is —$CH_2CH_2CH_2CH_2CH_2$—N($R_{12})_2$. In some embodiments, $R_3$ is —$CH_2CH_2CH_2CH_2CH_2CH_2$—N($R_{12})_2$.

In some embodiments, $R_3$ is —N($CH_3)_2$.

In some embodiments, $R_3$ is —$(CH_2)_m$—C(O)$R_{12}$, —$(CH_2)_m$—C(O)O$R_{12}$, or —$(CH_2)_m$—C(O)N($R_{12})_2$.

In some embodiments, $R_3$ is —$(CH_2)_m$—C(O)$R_{12}$. In some embodiments, $R_3$ is —$(CH_2)_m$—C(O)O$R_{12}$. In some embodiments, $R_3$ is —$(CH_2)_m$—C(O)N($R_{12})_2$.

In some embodiments, $R_3$ is —$CH_2$—C(O)$R_{12}$. In some embodiments, $R_3$ is —$CH_2CH_2$—C(O)$R_{12}$. In some embodiments, $R_3$ is —$CH_2CH_2CH_2$—C(O)$R_{12}$. In some embodiments, $R_3$ is —$CH_2CH_2CH_2CH_2$—C(O)$R_{12}$. In some embodiments, $R_3$ is —$CH_2CH_2CH_2CH_2CH_2$—C(O)$R_{12}$. In some embodiments, $R_3$ is —$CH_2CH_2CH_2CH_2CH_2CH_2$—C(O)$R_{12}$.

In some embodiments, $R_3$ is —$CH_2$—C(O)O$R_{12}$. In some embodiments, $R_3$ is —$CH_2CH_2$—C(O)O$R_{12}$. In some embodiments, $R_3$ is —$CH_2CH_2CH_2$—C(O)O$R_{12}$. In some embodiments, $R_3$ is —$CH_2CH_2CH_2CH_2$—C(O)O$R_{12}$. In some embodiments, $R_3$ is —$CH_2CH_2CH_2CH_2CH_2$—C(O)O$R_{12}$. In some embodiments, $R_3$ is —$CH_2CH_2CH_2CH_2CH_2CH_2$—C(O)O$R_{12}$.

In some embodiments, $R_3$ is —$CH_2$—C(O)N($R_{12})_2$. In some embodiments, $R_3$ is —$CH_2CH_2$—C(O)N($R_{12})_2$. In some embodiments, $R_3$ is —$CH_2CH_2CH_2$—C(O)N($R_{12})_2$. In some embodiments, $R_3$ is —$CH_2CH_2CH_2CH_2$—C(O)N($R_{12})_2$. In some embodiments, $R_3$ is —$CH_2CH_2CH_2CH_2CH_2$—C(O)N($R_{12})_2$. In some embodiments, $R_3$ is —$CH_2CH_2CH_2CH_2CH_2CH_2$—C(O)N($R_{12})_2$.

In some embodiments, $R_3$ is —$CH_2$—C(O)$NH_2$.

In some embodiments, $R_3$ is $C_3$-$C_{10}$ cycloalkyl, heterocycle, aryl, or heteroaryl.

In some embodiments, $R_3$ is $C_3$-$C_{10}$ cycloalkyl or heterocycle.

In some embodiments, $R_3$ is aryl or heteroaryl.

In some embodiments, R₃ is C₃-C₁₀ cycloalkyl.
In some embodiments, R₃ is a monocyclic C₃-C₁₀ cycloalkyl. In some embodiments, R₃ is a polycyclic C₃-C₁₀ cycloalkyl.
In some embodiments, R₃ is C₅-C₆ cycloalkyl.
In some embodiments, R₃ is cyclopropyl, cyclobutyl, cyclopentyl, cyclohexyl, cycloheptyl, cyclooctyl, cyclononyl, or cyclodecyl.
In some embodiments, R₃ is a fused polycyclic C₃-C₁₀ cycloalkyl. In some embodiments, R₃ is a bridged polycyclic C₃-C₁₀ cycloalkyl. In some embodiments, R₃ is a C₃-C₁₀ spirocycloalkyl.
In some embodiments, R₃ is heterocycle comprising 1-4 heteroatoms selected from O, N, and S.
In some embodiments, R₃ is a monocyclic heterocycle comprising 1-4 heteroatoms selected from O, N, and S. In some embodiments, R₃ is a polycyclic heterocycle comprising 1-4 heteroatoms selected from O, N, and S.
In some embodiments, R₃ is 3-membered heterocycle comprising 1-4 heteroatoms selected from O, N, and S. In some embodiments, R₃ is 4-membered heterocycle comprising 1-4 heteroatoms selected from O, N, and S. In some embodiments, R₃ is 5-membered heterocycle comprising 1-4 heteroatoms selected from O, N, and S. In some embodiments, R₃ is 6-membered heterocycle comprising 1-4 heteroatoms selected from O, N, and S. In some embodiments, R₃ is 7-membered heterocycle comprising 1-4 heteroatoms selected from O, N, and S. In some embodiments, R₃ is 8-membered heterocycle comprising 1-4 heteroatoms selected from O, N, and S. In some embodiments, R₃ is 9-membered heterocycle comprising 1-4 heteroatoms selected from O, N, and S. In some embodiments, R₃ is 10-membered heterocycle comprising 1-4 heteroatoms selected from O, N, and S.
In some embodiments, R₃ is 3-membered heterocycle comprising one N heteroatom. In some embodiments, R₃ is 4-membered heterocycle comprising one N heteroatom. In some embodiments, R₃ is 5-membered heterocycle comprising one N heteroatom. In some embodiments, R₃ is 6-membered heterocycle comprising one N heteroatom. In some embodiments, R₃ is 7-membered heterocycle comprising one N heteroatom. In some embodiments, R₃ is 8-membered heterocycle comprising one N heteroatom. In some embodiments, R₃ is 9-membered heterocycle comprising one N heteroatom. In some embodiments, R₃ is 10-membered heterocycle comprising one N heteroatom.
In some embodiments, R₃ is heterocycle comprising one heteroatom selected from O, N, and S. In some embodiments, R₃ is heterocycle comprising two heteroatoms selected from O, N, and S. In some embodiments, R₃ is heterocycle comprising three heteroatoms selected from O, N, and S. In some embodiments, R₃ is heterocycle comprising four heteroatoms selected from O, N, and S.
In some embodiments, R₃ is aryl.
In some embodiments, R₃ is C₆ aryl (e.g., phenyl).
In some embodiments, R₃ is a heteroaryl comprising 1-4 heteroatoms selected from O, N, and S
In some embodiments, R₃ is 5- to 6-membered heteroaryl comprising 1-4 heteroatoms selected from O, N, and S.
In some embodiments, R₃ is 5-membered heteroaryl comprising 1-4 heteroatoms selected from O, N, and S. In some embodiments, R₃ is 6-membered heteroaryl comprising 1-4 heteroatoms selected from O, N, and S. In some embodiments, R₃ is 7-membered heteroaryl comprising 1-4 heteroatoms selected from O, N, and S. In some embodiments, R₃ is 8-membered heteroaryl comprising 1-4 heteroatoms selected from O, N, and S. In some embodiments, R₃ is 9-membered heteroaryl comprising 1-4 heteroatoms selected from O, N, and S. In some embodiments, R₃ is 10-membered heteroaryl comprising 1-4 heteroatoms selected from O, N, and S.
In some embodiments, R₃ is heteroaryl comprising one heteroatom selected from O, N, and S. In some embodiments, R₃ is heteroaryl comprising two heteroatoms selected from O, N, and S. In some embodiments, R₃ is heteroaryl comprising three heteroatoms selected from O, N, and S. In some embodiments, R₃ is heteroaryl comprising four heteroatoms selected from O, N, and S.
In some embodiments, R₃ is a monocyclic heterocycle. In some embodiments, R₃ is a 5-membered monocyclic heterocycle. In some embodiments, R₃ is

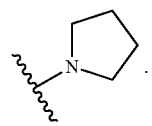 [SMILES: *N1CCCC1]

In some embodiments, R₄ is a 6-membered monocyclic heterocycle. In some embodiments, R₃ is

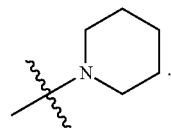

In some embodiments, R₄ is H, halogen, —CN, C₁-C₆ alkyl, C₂-C₆ alkenyl, C₂-C₆ alkynyl, C₁-C₆ haloalkyl, C₁-C₆ alkoxy, —(CH₂)$_m$—R₁₂, —(CH₂)$_m$—OR₁₂, —(CH₂)$_m$—N(R₁₂)₂, —(CH₂)$_m$—C(O)R₁₂, —(CH₂)$_m$—C(O)OR₁₂, —(CH₂)$_m$—C(O)N(R₁₂)₂, C₃-C₁₀ cycloalkyl, heterocycle comprising 1-4 heteroatoms selected from O, N, and S, Aryl, or heteroaryl comprising 1-4 heteroatoms selected from O, N, and S.
In some embodiments, R₄ is H.
In some embodiments, R₄ is halogen, C₁C₁-C₆ alkyl, C₂-C₆ alkenyl, C₂-C₆ alkynyl, C₁-C₆ haloalkyl, C₁-C₆ alkoxy, —(CH₂)$_m$—R₁₂, —(CH₂)$_m$—OR₁₂, —(CH₂)$_m$—N(R₁₂)₂, —(CH₂)$_m$—C(O)R₁₂, —(CH₂)$_m$—C(O)OR₁₂, —(CH₂)$_m$—C(O)N(R₁₂)₂, C₃-C₁₀ cycloalkyl, heterocycle comprising 1-4 heteroatoms selected from O, N, and S, aryl, or heteroaryl comprising 1-4 heteroatoms selected from O, N, and S.
In some embodiments, R₄ is halogen. In some embodiments, R₄ is F, Cl, Br, or I. In some embodiments, R₄ is F, Cl, or Br. In some embodiments, R₄ is F. In some embodiments, R₄ is Cl. In some embodiments, R₄ is Br. In some embodiments, R₄ is I.
In some embodiments, R₄ is —CN.
In some embodiments, R₄ is C₁-C₆ alkyl, C₂-C₆ alkenyl, C₂-C₆ alkynyl, C₁-C₆ haloalkyl, C₁-C₆ alkoxy, —(CH₂)$_m$—R₁₂, —(CH₂)$_m$—OR₁₂, —(CH₂)$_m$—N(R₁₂)₂, —(CH₂)$_m$—C(O)R₁₂, —(CH₂)$_m$—C(O)OR₁₂, —(CH₂)$_m$—C(O)N(R₁₂)₂, C₃-C₁₀ cycloalkyl, heterocycle comprising 1-4 heteroatoms selected from O, N, and S, aryl, or heteroaryl comprising 1-4 heteroatoms selected from O, N, and S.
In some embodiments, R₄ is C₁-C₆ alkyl, C₂-C₆ alkenyl, C₂-C₆ alkynyl, C₁-C₆ haloalkyl, or C₁-C₆ alkoxy.
In some embodiments, R₄ is C₁-C₆ alkyl, C₂-C₆ alkenyl, or C₂-C₆ alkynyl.

In some embodiments, $R_4$ is $C_1$-$C_6$ alkyl (e.g. linear or branched).

In some embodiments, $R_4$ is methyl. In some embodiments, $R_4$ is ethyl. In some embodiments, $R_4$ is propyl. In some embodiments, $R_4$ is n-propyl. In some embodiments, $R_4$ is isopropyl. In some embodiments, $R_4$ is butyl. In some embodiments, $R_4$ is n-butyl. In some embodiments, $R_4$ is isobutyl. In some embodiments, $R_4$ is sec-butyl. In some embodiments, $R_4$ is tert-butyl. In some embodiments, $R_4$ is pentyl. In some embodiments, $R_4$ is hexyl.

In some embodiments, $R_4$ is $C_2$-$C_6$ alkenyl.

In some embodiments, $R_4$ is $C_3$-$C_6$ alkenyl. In some embodiments, $R_4$ is $C_4$-$C_6$ alkenyl. In some embodiments, $R_4$ is $C_5$-$C_6$ alkenyl. In some embodiments, $R_4$ is $C_2$-$C_5$ alkenyl. In some embodiments, $R_4$ is $C_2$-$C_4$ alkenyl. In some embodiments, $R_4$ is $C_2$-$C_3$ alkenyl. In some embodiments, $R_4$ is $C_3$-$C_4$ alkenyl. In some embodiments, $R_4$ is $C_3$-$C_5$ alkenyl. In some embodiments, $R_4$ is $C_3$-$C_6$ alkenyl. In some embodiments, $R_4$ is $C_4$-$C_6$ alkenyl. In some embodiments, $R_4$ is $C_4$-$C_5$ alkenyl. In some embodiments, $R_4$ is $C_5$-$C_6$ alkenyl.

In some embodiments, $R_4$ is $C_2$ alkenyl. In some embodiments, $R_4$ is $C_3$ alkenyl. In some embodiments, $R_4$ is $C_4$ alkenyl. In some embodiments, $R_4$ is $C_5$ alkenyl. In some embodiments, $R_4$ is $C_6$ alkenyl.

In some embodiments, $R_4$ is $C_2$-$C_6$ alkynyl.

In some embodiments, $R_4$ is $C_3$-$C_6$ alkynyl. In some embodiments, $R_4$ is $C_4$-$C_6$ alkynyl. In some embodiments, $R_4$ is $C_5$-$C_6$ alkynyl. In some embodiments, $R_4$ is $C_2$-$C_5$ alkynyl. In some embodiments, $R_4$ is $C_2$-$C_4$ alkynyl. In some embodiments, $R_4$ is $C_2$-$C_3$ alkynyl. In some embodiments, $R_4$ is $C_3$-$C_4$ alkynyl. In some embodiments, $R_4$ is $C_3$-$C_5$ alkynyl. In some embodiments, $R_4$ is $C_3$-$C_6$ alkynyl. In some embodiments, $R_4$ is $C_4$-$C_6$ alkynyl. In some embodiments, $R_4$ is $C_4$-$C_5$ alkynyl. In some embodiments, $R_4$ is $C_5$-$C_6$ alkynyl.

In some embodiments, $R_4$ is $C_2$ alkynyl. In some embodiments, $R_4$ is $C_3$ alkynyl. In some embodiments, $R_4$ is $C_4$ alkynyl. In some embodiments, $R_4$ is $C_5$ alkynyl. In some embodiments, $R_4$ is $C_6$ alkynyl.

In some embodiments, $R_4$ is $C_1$-$C_6$ haloalkyl, $C_1$-$C_6$ alkoxy, $-(CH_2)_m-R_{12}$, $-(CH_2)_m-OR_{12}$, $-(CH_2)_m-N(R_{12})_2$, $-(CH_2)_m-C(O)R_{12}$, $-(CH_2)_m-C(O)OR_{12}$, $-(CH_2)_m-C(O)N(R_{12})_2$, $C_3$-$C_{10}$ cycloalkyl, heterocycle, aryl, or heteroaryl.

In some embodiments, $R_4$ is $C_1$-$C_6$ haloalkyl or $C_1$-$C_6$ alkoxy.

In some embodiments, $R_4$ is $C_1$-$C_6$ haloalkyl.

In some embodiments, $R_4$ is halomethyl. In some embodiments, $R_4$ is haloethyl. In some embodiments, $R_4$ is halopropyl. In some embodiments, $R_4$ is halobutyl. In some embodiments, $R_4$ is halopentyl. In some embodiments, $R_4$ is halohexyl.

In some embodiments, $R_4$ is $CH_2F$. In some embodiments, $R_4$ is $CHF_2$. In some embodiments, $R_4$ is $CF_3$.

In some embodiments, $R_4$ is $C_1$-$C_6$ alkoxy.

In some embodiments, $R_4$ is $C_1$-$C_6$ alkoxy. In some embodiments, $R_4$ is methoxy. In some embodiments, $R_4$ is ethoxy. In some embodiments, $R_4$ is propoxy. In some embodiments, $R_4$ is butoxy. In some embodiments, $R_4$ is pentoxy. In some embodiments, one $R_4$ is hexoxy.

In some embodiments, $R_4$ is $-(CH_2)_m-R_{12}$, $-(CH_2)_m-OR_{12}$, $-(CH_2)_m-N(R_{12})_2$, $-(CH_2)_m-C(O)R_{12}$, $-(CH_2)_m-C(O)OR_{12}$, or $-(CH_2)_m-C(O)N(R_{12})_2$.

In some embodiments, $R_4$ is $-(CH_2)_m-R_{12}$, $-(CH_2)_m-OR_{12}$, or $-(CH_2)_m-N(R_{12})_2$.

In some embodiments, $R_4$ is $-(CH_2)_m-R_{12}$. In some embodiments, $R_4$ is $-(CH_2)_m-OR_{12}$. In some embodiments, $R_4$ is $-(CH_2)_m-N(R_{12})_2$.

In some embodiments, $R_4$ is $-R_{12}$. In some embodiments, $R_4$ is $-CH_2-R_{12}$. In some embodiments, $R_4$ is $-CH_2CH_2-R_{12}$. In some embodiments, $R_4$ is $-CH_2CH_2CH_2-R_{12}$. In some embodiments, $R_4$ is $-CH_2CH_2CH_2CH_2-R_{12}$. In some embodiments, $R_4$ is $-CH_2CH_2CH_2CH_2CH_2-R_{12}$. In some embodiments, $R_4$ is $-CH_2CH_2CH_2CH_2CH_2CH_2-R_{12}$.

In some embodiments, $R_4$ is $-OR_{12}$. In some embodiments, $R_4$ is $-CH_2-OR_{12}$. In some embodiments, $R_4$ is $-CH_2CH_2-OR_{12}$. In some embodiments, $R_4$ is $-CH_2CH_2CH_2-OR_{12}$. In some embodiments, $R_4$ is $-CH_2CH_2CH_2CH_2-OR_{12}$. In some embodiments, $R_4$ is $-CH_2CH_2CH_2CH_2CH_2-OR_{12}$. In some embodiments, $R_4$ is $-CH_2CH_2CH_2CH_2CH_2CH_2-OR_{12}$.

In some embodiments, $R_4$ is $-OR_{12}$, wherein $R_{12}$ is H. In some embodiments, $R_4$ is $-OR_{12}$, wherein $R_{12}$ is $C_{3-10}$ cycloalkyl. In some embodiments, $R_4$ is

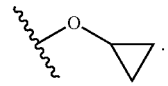 [SMILES: *OC1CC1]

In some embodiments, $R_4$ is $-N(R_{12})_2$. In some embodiments, $R_4$ is $-CH_2-N(R_{12})_2$. In some embodiments, $R_4$ is $-CH_2CH_2-N(R_{12})_2$. In some embodiments, $R_4$ is $-CH_2CH_2CH_2-N(R_{12})_2$. In some embodiments, $R_4$ is $-CH_2CH_2CH_2CH_2-N(R_{12})_2$. In some embodiments, $R_4$ is $-CH_2CH_2CH_2CH_2CH_2-N(R_{12})_2$. In some embodiments, $R_4$ is $-CH_2CH_2CH_2CH_2CH_2CH_2-N(R_{12})_2$.

In some embodiments, $R_4$ is $-N(CH_3)_2$.

In some embodiments, $R_4$ is $-(CH_2)_m-C(O)R_{12}$, $-(CH_2)_m-C(O)OR_{12}$, or $-(CH_2)_m-C(O)N(R_{12})_2$.

In some embodiments, $R_4$ is $-(CH_2)_m-C(O)R_{12}$. In some embodiments, $R_4$ is $-(CH_2)_m-C(O)OR_{12}$. In some embodiments, $R_4$ is $-(CH_2)_m-C(O)N(R_{12})_2$.

In some embodiments, $R_4$ is $-CH_2-C(O)R_{12}$. In some embodiments, $R_4$ is $-CH_2CH_2-C(O)R_{12}$. In some embodiments, $R_4$ is $-CH_2CH_2CH_2-C(O)R_{12}$. In some embodiments, $R_4$ is $-CH_2CH_2CH_2CH_2-C(O)R_{12}$. In some embodiments, $R_4$ is $-CH_2CH_2CH_2CH_2CH_2-C(O)R_{12}$. In some embodiments, $R_4$ is $-CH_2CH_2CH_2CH_2CH_2CH_2-C(O)R_{12}$.

In some embodiments, $R_4$ is $-CH_2-C(O)OR_{12}$. In some embodiments, $R_4$ is $-CH_2CH_2-C(O)OR_{12}$. In some embodiments, $R_4$ is $-CH_2CH_2CH_2-C(O)OR_{12}$. In some embodiments, $R_4$ is $-CH_2CH_2CH_2CH_2-C(O)OR_{12}$. In some embodiments, $R_4$ is $-CH_2CH_2CH_2CH_2CH_2-C(O)OR_{12}$. In some embodiments, $R_4$ is $-CH_2CH_2CH_2CH_2CH_2CH_2-C(O)OR_{12}$.

In some embodiments, $R_4$ is $-CH_2-C(O)N(R_{12})_2$. In some embodiments, $R_4$ is $-CH_2CH_2-C(O)N(R_{12})_2$. In some embodiments, $R_4$ is $-CH_2CH_2CH_2-C(O)N(R_{12})_2$. In some embodiments, $R_4$ is $-CH_2CH_2CH_2CH_2-C(O)N(R_{12})_2$. In some embodiments, $R_4$ is $-CH_2CH_2CH_2CH_2CH_2-C(O)N(R_{12})_2$. In some embodiments, $R_4$ is $-CH_2CH_2CH_2CH_2CH_2CH_2-C(O)N(R_{12})_2$.

In some embodiments, $R_4$ is $-CH_2-C(O)NH_2$.

In some embodiments, $R_4$ is $C_3$-$C_{10}$ cycloalkyl, heterocycle, aryl, or heteroaryl.

In some embodiments, $R_4$ is $C_3$-$C_{10}$ cycloalkyl or heterocycle.

In some embodiments, $R_4$ is aryl or heteroaryl.

In some embodiments, $R_4$ is $C_3$-$C_{10}$ cycloalkyl.

In some embodiments, $R_4$ is a monocyclic $C_3$-$C_{10}$ cycloalkyl. In some embodiments, $R_4$ is a polycyclic $C_3$-$C_{10}$ cycloalkyl.

In some embodiments, $R_4$ is $C_5$-$C_6$ cycloalkyl.

In some embodiments, $R_4$ is cyclopropyl, cyclobutyl, cyclopentyl, cyclohexyl, cycloheptyl, cyclooctyl, cyclononyl, or cyclodecyl.

In some embodiments, $R_4$ is a fused polycyclic $C_3$-$C_{10}$ cycloalkyl. In some embodiments, $R_4$ is a bridged polycyclic $C_3$-$C_{10}$ cycloalkyl. In some embodiments, $R_4$ is a $C_3$-$C_{10}$ spirocycloalkyl.

In some embodiments, $R_4$ is heterocycle comprising 1-4 heteroatoms selected from O, N, and S.

In some embodiments, $R_4$ is a monocyclic heterocycle comprising 1-4 heteroatoms selected from O, N, and S. In some embodiments, $R_4$ is a polycyclic heterocycle comprising 1-4 heteroatoms selected from O, N, and S.

In some embodiments, $R_4$ is 3-membered heterocycle comprising 1-4 heteroatoms selected from O, N, and S. In some embodiments, $R_4$ is 4-membered heterocycle comprising 1-4 heteroatoms selected from O, N, and S. In some embodiments, $R_4$ is 5-membered heterocycle comprising 1-4 heteroatoms selected from O, N, and S. In some embodiments, $R_4$ is 6-membered heterocycle comprising 1-4 heteroatoms selected from O, N, and S. In some embodiments, $R_4$ is 7-membered heterocycle comprising 1-4 heteroatoms selected from O, N, and S. In some embodiments, $R_4$ is 8-membered heterocycle comprising 1-4 heteroatoms selected from O, N, and S. In some embodiments, $R_4$ is 9-membered heterocycle comprising 1-4 heteroatoms selected from O, N, and S. In some embodiments, $R_4$ is 10-membered heterocycle comprising 1-4 heteroatoms selected from O, N, and S.

In some embodiments, $R_4$ is 3-membered heterocycle comprising one N heteroatom. In some embodiments, $R_4$ is 4-membered heterocycle comprising one N heteroatom. In some embodiments, $R_4$ is 5-membered heterocycle comprising one N heteroatom. In some embodiments, $R_4$ is 6-membered heterocycle comprising one N heteroatom. In some embodiments, $R_4$ is 7-membered heterocycle comprising one N heteroatom. In some embodiments, $R_4$ is 8-membered heterocycle comprising one N heteroatom. In some embodiments, $R_4$ is 9-membered heterocycle comprising one N heteroatom. In some embodiments, $R_3$ is 10-membered heterocycle comprising one N heteroatom.

In some embodiments, $R_4$ is heterocycle comprising one heteroatom selected from O, N, and S. In some embodiments, $R_4$ is heterocycle comprising two heteroatoms selected from O, N, and S. In some embodiments, $R_4$ is heterocycle comprising three heteroatoms selected from O, N, and S. In some embodiments, $R_4$ is heterocycle comprising four heteroatoms selected from O, N, and S.

In some embodiments, $R_4$ is aryl. In some embodiments, $R_4$ is $C_6$ aryl (e.g., phenyl).

In some embodiments, $R_4$ is a heteroaryl comprising 1-4 heteroatoms selected from O, N, and S In some embodiments, $R_4$ is 5- to 6-membered heteroaryl comprising 1-4 heteroatoms selected from O, N, and S.

In some embodiments, $R_4$ is 5-membered heteroaryl comprising 1-4 heteroatoms selected from O, N, and S. In some embodiments, $R_4$ is 6-membered heteroaryl comprising 1-4 heteroatoms selected from O, N, and S. In some embodiments, $R_4$ is 7-membered heteroaryl comprising 1-4 heteroatoms selected from O, N, and S. In some embodiments, $R_4$ is 8-membered heteroaryl comprising 1-4 heteroatoms selected from O, N, and S. In some embodiments, $R_4$ is 9-membered heteroaryl comprising 1-4 heteroatoms selected from O, N, and S. In some embodiments, $R_5$ is 10-membered heteroaryl comprising 1-4 heteroatoms selected from O, N, and S.

In some embodiments, $R_4$ is heteroaryl comprising one heteroatom selected from O, N, and S. In some embodiments, $R_4$ is heteroaryl comprising two heteroatoms selected from O, N, and S. In some embodiments, $R_4$ is heteroaryl comprising three heteroatoms selected from O, N, and S. In some embodiments, $R_4$ is heteroaryl comprising four heteroatoms selected from O, N, and S.

In some embodiments, $R_4$ is a monocyclic heterocycle. In some embodiments, $R_4$ is a 5-membered monocyclic heterocycle. In some embodiments, $R_4$ is

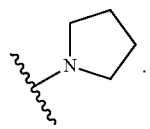 [SMILES: *N1CCCC1]

In some embodiments, $R_4$ is a 6-membered monocyclic heterocycle. In some embodiments, $R_4$ is

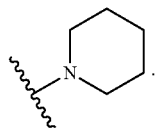 [SMILES: *N1CCCCC1]

In some embodiments, $R_5$ is H, halogen, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle comprising 1-4 heteroatoms selected from O, N, and S, aryl, or heteroaryl comprising 1-4 heteroatoms selected from O, N, and S.

In some embodiments, $R_5$ is H.

In some embodiments, $R_5$ is halogen, —CN, $C_1C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle comprising 1-4 heteroatoms selected from O, N, and S, aryl, or heteroaryl comprising 1-4 heteroatoms selected from O, N, and S.

In some embodiments, $R_5$ is halogen. In some embodiments, $R_5$ is F, Cl, Br, or I. In some embodiments, $R_5$ is F, Cl, or Br. In some embodiments, $R_5$ is F. In some embodiments, $R_5$ is Cl. In some embodiments, $R_5$ is Br. In some embodiments, $R_5$ is I.

In some embodiments, $R_5$ is —CN.

In some embodiments, $R_5$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle comprising 1-4 heteroatoms selected from O, N, and S, aryl, or heteroaryl comprising 1-4 heteroatoms selected from O, N, and S.

In some embodiments, $R_5$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_5$ is $C_1$-$C_6$ alkyl, $C_2$-$C_6$ alkenyl, or $C_2$-$C_6$ alkynyl.

In some embodiments, $R_5$ is $C_1$-$C_6$ alkyl (e.g. linear or branched).

In some embodiments, $R_5$ is methyl. In some embodiments, $R_5$ is ethyl. In some embodiments, $R_5$ is propyl. In some embodiments, $R_5$ is n-propyl. In some embodiments, $R_5$ is isopropyl. In some embodiments, $R_5$ is butyl. In some embodiments, $R_5$ is n-butyl. In some embodiments, $R_5$ is isobutyl. In some embodiments, $R_5$ is sec-butyl. In some embodiments, $R_5$ is tert-butyl. In some embodiments, $R_5$ is pentyl. In some embodiments, $R_5$ is hexyl.

In some embodiments, $R_5$ is $C_2$-$C_6$ alkenyl.

In some embodiments, $R_5$ is $C_2$ alkenyl. In some embodiments, $R_5$ is $C_3$ alkenyl. In some embodiments, $R_5$ is $C_4$ alkenyl. In some embodiments, $R_5$ is $C_5$ alkenyl. In some embodiments, R is $C_6$ alkenyl.

In some embodiments, $R_5$ is $C_2$-$C_6$ alkynyl.

In some embodiments, $R_5$ is $C_2$ alkynyl. In some embodiments, $R_5$ is $C_3$ alkynyl. In some embodiments, $R_5$ is $C_4$ alkynyl. In some embodiments, $R_5$ is $C_5$ alkynyl. In some embodiments, R is $C_6$ alkynyl.

In some embodiments, $R_5$ is $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—N$(R_{12})_2$, —$(CH_2)_m$—C(O)$R_{12}$, —$(CH_2)_m$—C(O)O$R_{12}$, —$(CH_2)_m$—C(O)N$(R_{12})_2$, $C_3$-$C_{10}$ cycloalkyl, heterocycle, aryl, or heteroaryl.

In some embodiments, $R_5$ is $C_1$-$C_6$ haloalkyl or $C_1$-$C_6$ alkoxy.

In some embodiments, $R_5$ is $C_1$-$C_6$ haloalkyl.

In some embodiments, $R_5$ is halomethyl. In some embodiments, $R_5$ is haloethyl. In some embodiments, $R_5$ is halopropyl. In some embodiments, $R_5$ is halobutyl. In some embodiments, $R_5$ is halopentyl. In some embodiments, $R_5$ is halohexyl.

In some embodiments, $R_5$ is $CH_2F$. In some embodiments, $R_5$ is $CHF_2$. In some embodiments, $R_5$ is $CF_3$.

In some embodiments, $R_5$ is $C_1$-$C_6$ alkoxy.

In some embodiments, $R_5$ is $C_1$-$C_6$ alkoxy. In some embodiments, $R_5$ is methoxy. In some embodiments, $R_5$ is ethoxy. In some embodiments, $R_5$ is propoxy. In some embodiments, $R_5$ is butoxy. In some embodiments, $R_5$ is pentoxy. In some embodiments, one $R_5$ is hexoxy.

In some embodiments, $R_5$ is —$(CH_2)_m$—$R_{12}$, —$(CH_2)_m$—$OR_{12}$, —$(CH_2)_m$—N$(R_{12})_2$, —$(CH_2)_m$—C(O)$R_{12}$, —$(CH_2)_m$—C(O)O$R_{12}$, or —$(CH_2)_m$—C(O)N$(R_{12})_2$.

In some embodiments, $R_5$ is —$(CH_2)_m$—$R_{12}$, —$(CH_2)_m$—$OR_{12}$, or —$(CH_2)_m$—N$(R_{12})_2$.

In some embodiments, $R_5$ is —$(CH_2)_m$—$R_{12}$. In some embodiments, $R_5$ is —$(CH_2)_m$—$OR_{12}$. In some embodiments, $R_5$ is —$(CH_2)_m$—N$(R_{12})_2$.

In some embodiments, $R_5$ is —$R_{12}$. In some embodiments, $R_5$ is —$CH_2$—$R_{12}$. In some embodiments, $R_5$ is —$CH_2CH_2$—$R_{12}$. In some embodiments, $R_5$ is —$CH_2CH_2CH_2$—$R_{12}$. In some embodiments, $R_5$ is —$CH_2CH_2CH_2CH_2$—$R_{12}$. In some embodiments, $R_5$ is —$CH_2CH_2CH_2CH_2CH_2$—$R_{12}$. In some embodiments, $R_5$ is —$CH_2CH_2CH_2CH_2CH_2CH_2$—$R_{12}$.

In some embodiments, $R_5$ is —$OR_{12}$. In some embodiments, $R_5$ is —$CH_2$—$OR_{12}$. In some embodiments, $R_5$ is —$CH_2CH_2$—$OR_{12}$. In some embodiments, $R_5$ is —$CH_2CH_2CH_2$—$OR_{12}$. In some embodiments, $R_5$ is —$CH_2CH_2CH_2CH_2$—$OR_{12}$. In some embodiments, $R_5$ is —$CH_2CH_2CH_2CH_2CH_2$—$OR_{12}$. In some embodiments, $R_5$ is —$CH_2CH_2CH_2CH_2CH_2CH_2$—$OR_{12}$.

In some embodiments, $R_5$ is —$OR_{12}$, wherein $R_{12}$ is H. In some embodiments, $R_5$ is —$OR_{12}$, wherein $R_{12}$ is $C_{3-10}$ cycloalkyl. In some embodiments, $R_{15}$ is

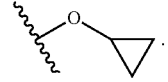 [SMILES: *OC1CC1]

In some embodiments, $R_5$ is —N$(R_{12})_2$. In some embodiments, $R_5$ is —$CH_2$—N$(R_{12})_2$. In some embodiments, $R_5$ is —$CH_2CH_2$—N$(R_{12})_2$. In some embodiments, $R_5$ is —$CH_2CH_2CH_2$—N$(R_{12})_2$. In some embodiments, $R_5$ is —$CH_2CH_2CH_2CH_2$—N$(R_{12})_2$. In some embodiments, $R_5$ is —$CH_2CH_2CH_2CH_2CH_2$—N$(R_{12})_2$. In some embodiments, $R_5$ is —$CH_2CH_2CH_2CH_2CH_2CH_2$—N$(R_{12})_2$.

In some embodiments, $R_{15}$ is —N$(CH_3)_2$.

In some embodiments, $R_5$ is —$(CH_2)_m$—C(O)$R_{12}$, —$(CH_2)_m$—C(O)O$R_{12}$, or —$(CH_2)_m$—C(O)N$(R_{12})_2$.

In some embodiments, $R_5$ is —$(CH_2)_m$—C(O)$R_{12}$. In some embodiments, $R_5$ is —$(CH_2)_m$—C(O)O$R_{12}$. In some embodiments, $R_5$ is —$(CH_2)_m$—C(O)N$(R_{12})_2$.

In some embodiments, $R_5$ is —$CH_2$—C(O)$R_{12}$. In some embodiments, $R_5$ is —$CH_2CH_2$—C(O)$R_{12}$. In some embodiments, $R_5$ is —$CH_2CH_2CH_2$—C(O)$R_{12}$. In some embodiments, $R_5$ is —$CH_2CH_2CH_2CH_2$—C(O)$R_{12}$. In some embodiments, $R_5$ is —$CH_2CH_2CH_2CH_2CH_2$—C(O)$R_{12}$. In some embodiments, $R_5$ is —$CH_2CH_2CH_2CH_2CH_2CH_2$—C(O)$R_{12}$.

In some embodiments, $R_5$ is —$CH_2$—C(O)O$R_{12}$. In some embodiments, $R_5$ is —$CH_2CH_2$—C(O)O$R_{12}$. In some embodiments, $R_5$ is —$CH_2CH_2CH_2$—C(O)O$R_{12}$. In some embodiments, $R_5$ is —$CH_2CH_2CH_2CH_2$—C(O)O$R_{12}$. In some embodiments, $R_5$ is —$CH_2CH_2CH_2CH_2CH_2$—C(O)O$R_{12}$. In some embodiments, $R_5$ is —$CH_2CH_2CH_2CH_2CH_2CH_2$—C(O)O$R_{12}$.

In some embodiments, $R_5$ is —$CH_2$—C(O)N$(R_{12})_2$. In some embodiments, $R_5$ is —$CH_2CH_2$—C(O)N$(R_{12})_2$. In some embodiments, $R_5$ is —$CH_2CH_2CH_2$—C(O)N$(R_{12})_2$. In some embodiments, $R_5$ is —$CH_2CH_2CH_2CH_2$—C(O)N$(R_{12})_2$. In some embodiments, $R_5$ is —$CH_2CH_2CH_2CH_2CH_2$—C(O)N$(R_{12})_2$. In some embodiments, $R_5$ is —$CH_2CH_2CH_2CH_2CH_2CH_2$—C(O)N$(R_{12})_2$.

In some embodiments, $R_5$ is —$CH_2$—C(O)$NH_2$.

In some embodiments, $R_5$ is $C_3$-$C_{10}$ cycloalkyl, heterocycle, aryl, or heteroaryl.

In some embodiments, $R_5$ is $C_3$-$C_{10}$ cycloalkyl or heterocycle.

In some embodiments, $R_5$ is aryl or heteroaryl.

In some embodiments, $R_5$ is $C_3$-$C_{10}$ cycloalkyl.

In some embodiments, $R_5$ is a monocyclic $C_3$-$C_{10}$ cycloalkyl. In some embodiments, $R_5$ is a polycyclic $C_3$-$C_{10}$ cycloalkyl.

In some embodiments, $R_5$ is $C_5$-$C_6$ cycloalkyl.

In some embodiments, $R_5$ is cyclopropyl, cyclobutyl, cyclopentyl, cyclohexyl, cycloheptyl, cyclooctyl, cyclononyl, or cyclodecyl.

In some embodiments, $R_5$ is a fused polycyclic $C_3$-$C_{10}$ cycloalkyl. In some embodiments, R is a bridged polycyclic $C_3$-$C_{10}$ cycloalkyl. In some embodiments, $R_5$ is a $C_3$-$C_{10}$ spirocycloalkyl.

In some embodiments, $R_5$ is heterocycle comprising 1-4 heteroatoms selected from O, N, and S.

In some embodiments, $R_5$ is a monocyclic heterocycle comprising 1-4 heteroatoms selected from O, N, and S. In some embodiments, $R_5$ is a polycyclic heterocycle comprising 1-4 heteroatoms selected from O, N, and S.

In some embodiments, $R_5$ is 3-membered heterocycle comprising 1-4 heteroatoms selected from O, N, and S. In some embodiments, $R_5$ is 4-membered heterocycle comprising 1-4 heteroatoms selected from O, N, and S. In some embodiments, $R_5$ is 5-membered heterocycle comprising 1-4 heteroatoms selected from O, N, and S. In some embodiments, $R_5$ is 6-membered heterocycle comprising 1-4 heteroatoms selected from O, N, and S. In some embodiments, $R_5$ is 7-membered heterocycle comprising 1-4 heteroatoms selected from O, N, and S. In some embodiments, $R_5$ is 8-membered heterocycle comprising 1-4 heteroatoms selected from O, N, and S. In some embodiments, $R_5$ is 9-membered heterocycle comprising 1-4 heteroatoms selected from O, N, and S. In some embodiments, $R_5$ is 10-membered heterocycle comprising 1-4 heteroatoms selected from O, N, and S.

In some embodiments, $R_5$ is 3-membered heterocycle comprising one N heteroatom. In some embodiments, $R_5$ is 4-membered heterocycle comprising one N heteroatom. In some embodiments, $R_5$ is 5-membered heterocycle comprising one N heteroatom. In some embodiments, $R_5$ is 6-membered heterocycle comprising one N heteroatom. In some embodiments, $R_5$ is 7-membered heterocycle comprising one N heteroatom. In some embodiments, $R_5$ is 8-membered heterocycle comprising one N heteroatom. In some embodiments, $R_5$ is 9-membered heterocycle comprising one N heteroatom. In some embodiments, $R_5$ is 10-membered heterocycle comprising one N heteroatom.

In some embodiments, $R_5$ is heterocycle comprising one heteroatom selected from O, N, and S. In some embodiments, $R_5$ is heterocycle comprising two heteroatoms selected from O, N, and S. In some embodiments, $R_5$ is heterocycle comprising three heteroatoms selected from O, N, and S. In some embodiments, $R_5$ is heterocycle comprising four heteroatoms selected from O, N, and S.

In some embodiments, $R_5$ is aryl. In some embodiments, $R_5$ is $C_6$ aryl (e.g., phenyl).

In some embodiments, $R_5$ is a heteroaryl comprising 1-4 heteroatoms selected from O, N, and S In some embodiments, $R_5$ is 5- to 6-membered heteroaryl comprising 1-4 heteroatoms selected from O, N, and S.

In some embodiments, $R_5$ is 5-membered heteroaryl comprising 1-4 heteroatoms selected from O, N, and S. In some embodiments, $R_5$ is 6-membered heteroaryl comprising 1-4 heteroatoms selected from O, N, and S. In some embodiments, $R_5$ is 7-membered heteroaryl comprising 1-4 heteroatoms selected from O, N, and S. In some embodiments, $R_5$ is 8-membered heteroaryl comprising 1-4 heteroatoms selected from O, N, and S. In some embodiments, $R_5$ is 9-membered heteroaryl comprising 1-4 heteroatoms selected from O, N, and S. In some embodiments, $R_5$ is 10-membered heteroaryl comprising 1-4 heteroatoms selected from O, N, and S.

In some embodiments, $R_5$ is heteroaryl comprising one heteroatom selected from O, N, and S. In some embodiments, $R_5$ is heteroaryl comprising two heteroatoms selected from O, N, and S. In some embodiments, $R_5$ is heteroaryl comprising three heteroatoms selected from O, N, and S. In some embodiments, $R_5$ is heteroaryl comprising four heteroatoms selected from O, N, and S.

In some embodiments, $R_5$ is a monocyclic heterocycle. In some embodiments, $R_5$ is a 5-membered monocyclic heterocycle. In some embodiments, $R_5$ is

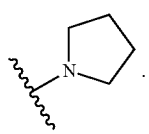

In some embodiments, $R_5$ is a 6-membered monocyclic heterocycle. In some embodiments, $R_5$ is

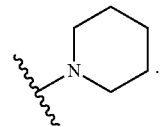 [SMILES: *N1CCCCC1]

In some embodiments, $R_6$ is H, halogen, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—N$(R_{12})_2$, —$(CH_2)_m$—C(O)$R_{12}$, —$(CH_2)_m$—C(O)O$R_{12}$, —$(CH_2)_m$—C(O)N$(R_{12})_2$, $C_3$-$C_{10}$ cycloalkyl, heterocycle comprising 1-4 heteroatoms selected from O, N, and S, aryl, or heteroaryl comprising 1-4 heteroatoms selected from O, N, and S.

In some embodiments, $R_6$ is H.

In some embodiments, $R_6$ is halogen, —CN, $C_1C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—N$(R_{12})_2$, —$(CH_2)_m$—C(O)$R_{12}$, —$(CH_2)_m$—C(O)O$R_{12}$, —$(CH_2)_m$—C(O)N$(R_{12})_2$, $C_3$-$C_{10}$ cycloalkyl, heterocycle comprising 1-4 heteroatoms selected from O, N, and S, aryl, or heteroaryl comprising 1-4 heteroatoms selected from O, N, and S.

In some embodiments, $R_6$ is halogen. In some embodiments, $R_6$ is F, Cl, Br, or I. In some embodiments, $R_6$ is F, Cl, or Br. In some embodiments, $R_6$ is F. In some embodiments, $R_6$ is Cl. In some embodiments, $R_6$ is Br. In some embodiments, $R_6$ is I.

In some embodiments, $R_6$ is —CN.

In some embodiments, $R_6$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—N$(R_{12})_2$, —$(CH_2)_m$—C(O)$R_{12}$, —$(CH_2)_m$—C(O)O$R_{12}$, —$(CH_2)_m$—C(O)N$(R_{12})_2$, $C_3$-$C_{10}$ cycloalkyl, heterocycle comprising 1-4 heteroatoms selected from O, N, and S, aryl, or heteroaryl comprising 1-4 heteroatoms selected from O, N, and S.

In some embodiments, $R_6$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_6$ is $C_1$-$C_6$ alkyl, $C_2$-$C_6$ alkenyl, or $C_2$-$C_6$ alkynyl.

In some embodiments, $R_6$ is $C_1$-$C_6$ alkyl (e.g. linear or branched).

In some embodiments, $R_6$ is methyl. In some embodiments, $R_6$ is ethyl. In some embodiments, $R_6$ is propyl. In some embodiments, $R_6$ is n-propyl. In some embodiments, $R_6$ is isopropyl. In some embodiments, $R_6$ is butyl. In some embodiments, $R_6$ is n-butyl. In some embodiments, $R_6$ is isobutyl. In some embodiments, $R_6$ is sec-butyl. In some embodiments, $R_6$ is tert-butyl. In some embodiments, $R_6$ is pentyl. In some embodiments, $R_6$ is hexyl.

In some embodiments, $R_6$ is $C_2$-$C_6$ alkenyl.

In some embodiments, $R_6$ is $C_3$-$C_6$ alkenyl. In some embodiments, $R_6$ is $C_4$-$C_6$ alkenyl. In some embodiments, $R_6$ is $C_5$-$C_6$ alkenyl. In some embodiments, $R_6$ is $C_2$-$C_5$ alkenyl. In some embodiments, $R_6$ is $C_2$-$C_4$ alkenyl. In some embodiments, $R_6$ is $C_2$-$C_3$ alkenyl. In some embodiments, $R_6$ is $C_3$-$C_4$ alkenyl. In some embodiments, $R_6$ is $C_3$-$C_5$ alkenyl. In some embodiments, $R_6$ is $C_3$-$C_6$ alkenyl. In some embodiments, $R_6$ is $C_4$-$C_6$ alkenyl. In some embodiments, $R_6$ is $C_4$-$C_5$ alkenyl. In some embodiments, $R_6$ is $C_5$-$C_6$ alkenyl.

In some embodiments, $R_6$ is $C_2$ alkenyl. In some embodiments, $R_6$ is $C_3$ alkenyl. In some embodiments, $R_6$ is $C_4$ alkenyl. In some embodiments, $R_6$ is $C_5$ alkenyl. In some embodiments, $R_6$ is $C_6$ alkenyl.

In some embodiments, $R_6$ is $C_2$-$C_6$ alkynyl.

In some embodiments, $R_6$ is $C_3$-$C_6$ alkynyl. In some embodiments, $R_6$ is $C_4$-$C_6$ alkynyl. In some embodiments, $R_6$ is $C_5$-$C_6$ alkynyl. In some embodiments, $R_6$ is $C_2$-$C_5$ alkynyl. In some embodiments, $R_6$ is $C_2$-$C_4$ alkynyl. In some embodiments, $R_6$ is $C_2$-$C_3$ alkynyl. In some embodiments, $R_6$ is $C_3$-$C_4$ alkynyl. In some embodiments, $R_6$ is $C_3$-$C_5$ alkynyl. In some embodiments, $R_6$ is $C_3$-$C_6$ alkynyl. In some embodiments, $R_6$ is $C_4$-$C_6$ alkynyl. In some embodiments, $R_6$ is $C_4$-$C_5$ alkynyl. In some embodiments, $R_6$ is $C_5$-$C_6$ alkynyl.

In some embodiments, $R_6$ is $C_2$ alkynyl. In some embodiments, $R_6$ is $C_3$ alkynyl. In some embodiments, $R_6$ is $C_4$ alkynyl. In some embodiments, $R_6$ is $C_5$ alkynyl. In some embodiments, $R_6$ is $C_6$ alkynyl.

In some embodiments, $R_6$ is $C_1$-$C_6$ haloalkyl, $C_1$-$C_6$ alkoxy, —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, —$(CH_2)_m$—$C(O)N(R_{12})_2$, $C_3$-$C_{10}$ cycloalkyl, heterocycle, aryl, or heteroaryl.

In some embodiments, $R_6$ is $C_1$-$C_6$ haloalkyl or $C_1$-$C_6$ alkoxy.

In some embodiments, $R_6$ is $C_1$-$C_6$ haloalkyl.

In some embodiments, $R_6$ is halomethyl. In some embodiments, $R_6$ is haloethyl. In some embodiments, $R_6$ is halopropyl. In some embodiments, $R_6$ is halobutyl. In some embodiments, $R_6$ is halopentyl. In some embodiments, $R_6$ is halohexyl.

In some embodiments, $R_6$ is $CH_2F$. In some embodiments, $R_6$ is $CHF_2$. In some embodiments, $R_6$ is $CF_3$.

In some embodiments, $R_6$ is $C_1$-$C_6$ alkoxy.

In some embodiments, $R_6$ is $C_1$-$C_6$ alkoxy. In some embodiments, $R_6$ is methoxy. In some embodiments, $R_6$ is ethoxy. In some embodiments, $R_6$ is propoxy. In some embodiments, $R_6$ is butoxy. In some embodiments, $R_6$ is pentoxy. In some embodiments, one $R_6$ is hexoxy.

In some embodiments, $R_6$ is —$(CH_2)_m$—$R_{12}$, —$(CH_2)_m$—$OR_{12}$, —$(CH_2)_m$—$N(R_{12})_2$, —$(CH_2)_m$—$C(O)R_{12}$, —$(CH_2)_m$—$C(O)OR_{12}$, or —$(CH_2)_m$—$C(O)N(R_{12})_2$.

In some embodiments, $R_6$ is —$(CH_2)_m$—$R_{12}$, —$(CH_2)_m$—$OR_{12}$, or —$(CH_2)_m$—$N(R_{12})_2$.

In some embodiments, $R_6$ is —$(CH_2)_m$—$R_{12}$. In some embodiments, $R_6$ is —$(CH_2)_m$—$OR_{12}$. In some embodiments, $R_6$ is —$(CH_2)_m$—$N(R_{12})_2$.

In some embodiments, $R_6$ is —$R_{12}$. In some embodiments, $R_6$ is —$CH_2$—$R_{12}$. In some embodiments, $R_6$ is —$CH_2CH_2$—$R_{12}$. In some embodiments, $R_6$ is —$CH_2CH_2CH_2$—$R_{12}$. In some embodiments, $R_6$ is —$CH_2CH_2CH_2CH_2$—$R_{12}$. In some embodiments, $R_6$ is —$CH_2CH_2CH_2CH_2CH_2$—$R_{12}$. In some embodiments, $R_6$ is —$CH_2CH_2CH_2CH_2CH_2CH_2$—$R_{12}$.

In some embodiments, $R_6$ is —$OR_{12}$. In some embodiments, $R_6$ is —$CH_2$—$OR_{12}$. In some embodiments, $R_6$ is —$CH_2CH_2$—$OR_{12}$. In some embodiments, $R_6$ is —$CH_2CH_2CH_2$—$OR_{12}$. In some embodiments, $R_6$ is —$CH_2CH_2CH_2CH_2$—$OR_{12}$. In some embodiments, $R_6$ is —$CH_2CH_2CH_2CH_2CH_2$—$OR_{12}$. In some embodiments, $R_6$ is —$CH_2CH_2CH_2CH_2CH_2CH_2$—$OR_{12}$.

In some embodiments, $R_6$ is —$OR_{12}$, wherein $R_{12}$ is H. In some embodiments, $R_6$ is —$OR_{12}$, wherein $R_{12}$ is $C_{3-10}$ cycloalkyl. In some embodiments, $R_6$ is

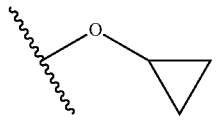

In some embodiments, $R_6$ is —$N(R_{12})_2$. In some embodiments, $R_6$ is —$CH_2$—$N(R_{12})_2$. In some embodiments, $R_6$ is —$CH_2CH_2$—$N(R_{12})_2$. In some embodiments, $R_6$ is —$CH_2CH_2CH_2$—$N(R_{12})_2$. In some embodiments, $R_6$ is —$CH_2CH_2CH_2CH_2$—$N(R_{12})_2$. In some embodiments, $R_6$ is —$CH_2CH_2CH_2CH_2CH_2$—$N(R_{12})_2$. In some embodiments, $R_6$ is —$CH_2CH_2CH_2CH_2CH_2CH_2$—$N(R_{12})_2$.

In some embodiments, $R_6$ is —$N(CH_3)_2$.

In some embodiments, $R_6$ is —$(CH_2)_m$—$C(O)R_{12}$, —$(CH_2)_m$—$C(O)OR_{12}$, or —$(CH_2)_m$—$C(O)N(R_{12})_2$.

In some embodiments, $R_6$ is —$(CH_2)_m$—$C(O)R_{12}$. In some embodiments, $R_6$ is —$(CH_2)_m$—$C(O)OR_{12}$. In some embodiments, $R_6$ is —$(CH_2)_m$—$C(O)N(R_{12})_2$.

In some embodiments, $R_6$ is —$CH_2$—$C(O)R_{12}$. In some embodiments, $R_6$ is —$CH_2CH_2$—$C(O)R_{12}$. In some embodiments, $R_6$ is —$CH_2CH_2CH_2$—$C(O)R_{12}$. In some embodiments, $R_6$ is —$CH_2CH_2CH_2CH_2$—$C(O)R_{12}$. In some embodiments, $R_6$ is —$CH_2CH_2CH_2CH_2CH_2$—$C(O)R_{12}$. In some embodiments, $R_6$ is —$CH_2CH_2CH_2CH_2CH_2CH_2$—$C(O)R_{12}$.

In some embodiments, $R_6$ is —$CH_2$—$C(O)OR_{12}$. In some embodiments, $R_6$ is —$CH_2CH_2$—$C(O)OR_{12}$. In some embodiments, $R_6$ is —$CH_2CH_2CH_2$—$C(O)OR_{12}$. In some embodiments, $R_6$ is —$CH_2CH_2CH_2CH_2$—$C(O)OR_{12}$. In some embodiments, $R_6$ is —$CH_2CH_2CH_2CH_2CH_2$—$C(O)OR_{12}$. In some embodiments, $R_6$ is —$CH_2CH_2CH_2CH_2CH_2CH_2$—$C(O)OR_{12}$.

In some embodiments, $R_6$ is —$CH_2$—$C(O)N(R_{12})_2$. In some embodiments, $R_6$ is —$CH_2CH_2$—$C(O)N(R_{12})_2$. In some embodiments, $R_6$ is —$CH_2CH_2CH_2$—$C(O)N(R_{12})_2$. In some embodiments, $R_6$ is —$CH_2CH_2CH_2CH_2$—$C(O)N(R_{12})_2$. In some embodiments, $R_6$ is —$CH_2CH_2CH_2CH_2CH_2$—$C(O)N(R_{12})_2$. In some embodiments, $R_6$ is —$CH_2CH_2CH_2CH_2CH_2CH_2$—$C(O)N(R_{12})_2$.

In some embodiments, $R_6$ is —$CH_2$—$C(O)NH_2$.

In some embodiments, $R_6$ is $C_3$-$C_{10}$ cycloalkyl, heterocycle, aryl, or heteroaryl.

In some embodiments, $R_6$ is $C_3$-$C_{10}$ cycloalkyl or heterocycle.

In some embodiments, $R_6$ is aryl or heteroaryl.

In some embodiments, $R_6$ is $C_3$-$C_{10}$ cycloalkyl.

In some embodiments, $R_6$ is a monocyclic $C_3$-$C_{10}$ cycloalkyl. In some embodiments, $R_6$ is a polycyclic $C_3$-$C_{10}$ cycloalkyl.

In some embodiments, $R_6$ is $C_5$-$C_6$ cycloalkyl.

In some embodiments, $R_6$ is cyclopropyl, cyclobutyl, cyclopentyl, cyclohexyl, cycloheptyl, cyclooctyl, cyclononyl, or cyclodecyl.

In some embodiments, $R_6$ is a fused polycyclic $C_3$-$C_{10}$ cycloalkyl. In some embodiments, $R_6$ is a bridged polycyclic $C_3$-$C_{10}$ cycloalkyl. In some embodiments, $R_6$ is a $C_3$-$C_{10}$ spirocycloalkyl.

In some embodiments, $R_6$ is heterocycle comprising 1-4 heteroatoms selected from O, N, and S.

In some embodiments, $R_6$ is a monocyclic heterocycle comprising 1-4 heteroatoms selected from O, N, and S. In some embodiments, $R_6$ is a polycyclic heterocycle comprising 1-4 heteroatoms selected from O, N, and S.

In some embodiments, $R_6$ is 3-membered heterocycle comprising 1-4 heteroatoms selected from O, N, and S. In some embodiments, $R_6$ is 4-membered heterocycle comprising 1-4 heteroatoms selected from O, N, and S. In some embodiments, $R_6$ is 5-membered heterocycle comprising 1-4 heteroatoms selected from O, N, and S. In some embodiments, $R_6$ is 6-membered heterocycle comprising 1-4 heteroatoms selected from O, N, and S. In some embodiments, $R_6$ is 7-membered heterocycle comprising 1-4 heteroatoms selected from O, N, and S. In some embodiments, $R_6$ is 8-membered heterocycle comprising 1-4 heteroatoms selected from O, N, and S. In some embodiments, $R_6$ is 9-membered heterocycle comprising 1-4 heteroatoms selected from O, N, and S. In some embodiments, $R_6$ is 10-membered heterocycle comprising 1-4 heteroatoms selected from O, N, and S.

In some embodiments, $R_6$ is 3-membered heterocycle comprising one N heteroatom. In some embodiments, $R_6$ is 4-membered heterocycle comprising one N heteroatom. In some embodiments, $R_6$ is 5-membered heterocycle comprising one N heteroatom. In some embodiments, $R_6$ is 6-membered heterocycle comprising one N heteroatom. In some embodiments, $R_6$ is 7-membered heterocycle comprising one N heteroatom. In some embodiments, $R_6$ is 8-membered heterocycle comprising one N heteroatom. In some embodiments, $R_6$ is 9-membered heterocycle comprising one N heteroatom. In some embodiments, $R_6$ is 10-membered heterocycle comprising one N heteroatom.

In some embodiments, $R_6$ is heterocycle comprising one heteroatom selected from O, N, and S. In some embodiments, $R_6$ is heterocycle comprising two heteroatoms selected from O, N, and S. In some embodiments, $R_6$ is heterocycle comprising three heteroatoms selected from O, N, and S. In some embodiments, $R_6$ is heterocycle comprising four heteroatoms selected from O, N, and S.

In some embodiments, $R_6$ is aryl. In some embodiments, $R_6$ is $C_6$ aryl (e.g., phenyl).

In some embodiments, $R_6$ is a heteroaryl comprising 1-4 heteroatoms selected from O, N, and S In some embodiments, $R_6$ is 5- to 6-membered heteroaryl comprising 1-4 heteroatoms selected from O, N, and S.

In some embodiments, $R_6$ is 5-membered heteroaryl comprising 1-4 heteroatoms selected from O, N, and S. In some embodiments, $R_6$ is 6-membered heteroaryl comprising 1-4 heteroatoms selected from O, N, and S. In some embodiments, $R_6$ is 7-membered heteroaryl comprising 1-4 heteroatoms selected from O, N, and S. In some embodiments, $R_6$ is 8-membered heteroaryl comprising 1-4 heteroatoms selected from O, N, and S. In some embodiments, $R_6$ is 9-membered heteroaryl comprising 1-4 heteroatoms selected from O, N, and S. In some embodiments, $R_6$ is 10-membered heteroaryl comprising 1-4 heteroatoms selected from O, N, and S.

In some embodiments, $R_6$ is heteroaryl comprising one heteroatom selected from O, N, and S. In some embodiments, $R_6$ is heteroaryl comprising two heteroatoms selected from O, N, and S. In some embodiments, $R_6$ is heteroaryl comprising three heteroatoms selected from O, N, and S. In some embodiments, $R_6$ is heteroaryl comprising four heteroatoms selected from O, N, and S.

In some embodiments, $R_6$ is a monocyclic heterocycle. In some embodiments, $R_6$ is a 5-membered monocyclic heterocycle. In some embodiments, $R_6$ is

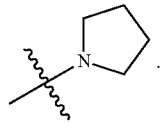 [SMILES: *N1CCCC1]

In some embodiments, $R_6$ is a 6-membered monocyclic heterocycle. In some embodiments, $R_6$ is

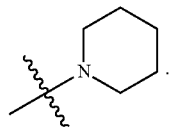

In some embodiments, each $R_7$ and $R_8$ is independently H, halogen, —CN, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_7$ and $R_8$ is independently H.

In some embodiments, each $R_7$ and $R_8$ is independently halogen, —CN, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_7$ is H, halogen, —CN, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_7$ is H.

In some embodiments, $R_7$ is halogen. In some embodiments, $R_7$ is F, Cl, Br, or I. In some embodiments, $R_7$ is F, Cl, or Br. In some embodiments, $R_7$ is F. In some embodiments, $R_7$ is Cl. In some embodiments, $R_7$ is Br. In some embodiments, $R_7$ is I.

In some embodiments, $R_7$ is —CN.

In some embodiments, $R_7$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_7$ is $C_1$-$C_6$ alkyl, $C_2$-$C_6$ alkenyl, or $C_2$-$C_6$ alkynyl.

In some embodiments, $R_7$ is $C_1$-$C_6$ alkyl (e.g. linear or branched).

In some embodiments, $R_7$ is methyl. In some embodiments, $R_7$ is ethyl. In some embodiments, $R_7$ is propyl. In some embodiments, $R_7$ is n-propyl. In some embodiments, $R_7$ is isopropyl. In some embodiments, $R_7$ is butyl. In some embodiments, $R_7$ is n-butyl. In some embodiments, $R_7$ is isobutyl. In some embodiments, $R_7$ is sec-butyl. In some embodiments, $R_7$ is tert-butyl. In some embodiments, $R_7$ is pentyl. In some embodiments, $R_7$ is hexyl.

In some embodiments, $R_7$ is $C_2$-$C_6$ alkenyl.

In some embodiments, $R_7$ is $C_2$ alkenyl. In some embodiments, $R_7$ is $C_3$ alkenyl. In some embodiments, $R_7$ is $C_4$ alkenyl. In some embodiments, $R_7$ is $C_5$ alkenyl. In some embodiments, $R_7$ is $C_6$ alkenyl.

In some embodiments, $R_7$ is $C_2$-$C_6$ alkynyl.

In some embodiments, $R_7$ is $C_2$ alkynyl. In some embodiments, $R_7$ is $C_3$ alkynyl. In some embodiments, $R_7$ is $C_4$ alkynyl. In some embodiments, $R_7$ is $C_5$ alkynyl. In some embodiments, $R_7$ is $C_6$ alkynyl.

In some embodiments, $R_7$ is $C_1$-$C_6$ haloalkyl or $C_1$-$C_6$ alkoxy.

In some embodiments, $R_7$ is $C_1$-$C_6$ haloalkyl.

In some embodiments, $R_7$ is halomethyl. In some embodiments, $R_7$ is haloethyl. In some embodiments, $R_7$ is halopropyl. In some embodiments, $R_7$ is halobutyl. In some embodiments, $R_7$ is halopentyl. In some embodiments, $R_7$ is halohexyl.

In some embodiments, $R_7$ is $CH_2F$. In some embodiments, $R_7$ is $CHF_2$. In some embodiments, $R_7$ is $CF_3$.

In some embodiments, $R_7$ is $C_1$-$C_6$ alkoxy.

In some embodiments, $R_7$ is methoxy. In some embodiments, $R_7$ is ethoxy. In some embodiments, $R_7$ is propoxy. In some embodiments, $R_7$ is butoxy. In some embodiments, $R_7$ is pentoxy. In some embodiments, one $R_7$ is hexoxy.

In some embodiments, $R_8$ is H, halogen, —CN, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_8$ is H.

In some embodiments, $R_8$ is halogen. In some embodiments, $R_8$ is F, Cl, Br, or I. In some embodiments, $R_8$ is F, Cl, or Br. In some embodiments, $R_8$ is F. In some embodiments, $R_8$ is Cl. In some embodiments, $R_8$ is Br. In some embodiments, $R_8$ is I.

In some embodiments, $R_8$ is —CN.

In some embodiments, $R_8$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_8$ is $C_1$-$C_6$ alkyl, $C_2$-$C_6$ alkenyl, or $C_2$-$C_6$ alkynyl.

In some embodiments, $R_8$ is $C_1$-$C_6$ alkyl (e.g. linear or branched).

In some embodiments, $R_8$ is methyl. In some embodiments, $R_8$ is ethyl. In some embodiments, $R_8$ is propyl. In some embodiments, $R_8$ is n-propyl. In some embodiments, $R_8$ is isopropyl. In some embodiments, $R_8$ is butyl. In some embodiments, $R_8$ is n-butyl. In some embodiments, $R_8$ is isobutyl. In some embodiments, $R_8$ is sec-butyl. In some embodiments, $R_8$ is tert-butyl. In some embodiments, $R_8$ is pentyl. In some embodiments, $R_8$ is hexyl.

In some embodiments, $R_8$ is $C_2$-$C_6$ alkenyl.

In some embodiments, $R_8$ is $C_2$ alkenyl. In some embodiments, $R_8$ is $C_3$ alkenyl. In some embodiments, $R_8$ is $C_4$ alkenyl. In some embodiments, $R_8$ is $C_5$ alkenyl. In some embodiments, $R_8$ is $C_6$ alkenyl.

In some embodiments, $R_8$ is $C_2$-$C_6$ alkynyl.

In some embodiments, $R_8$ is $C_2$ alkynyl. In some embodiments, $R_8$ is $C_3$ alkynyl. In some embodiments, $R_8$ is $C_4$ alkynyl. In some embodiments, $R_8$ is $C_5$ alkynyl. In some embodiments, $R_8$ is $C_6$ alkynyl.

In some embodiments, $R_8$ is $C_1$-$C_6$ haloalkyl or $C_1$-$C_6$ alkoxy.

In some embodiments, $R_8$ is $C_1$-$C_6$ haloalkyl.

In some embodiments, $R_8$ is halomethyl. In some embodiments, $R_8$ is haloethyl. In some embodiments, $R_8$ is halopropyl. In some embodiments, $R_8$ is halobutyl. In some embodiments, $R_8$ is halopentyl. In some embodiments, $R_8$ is halohexyl.

In some embodiments, $R_8$ is $CH_2F$. In some embodiments, $R_8$ is $CHF_2$. In some embodiments, $R_8$ is $CF_3$.

In some embodiments, $R_8$ is $C_1$-$C_6$ alkoxy.

In some embodiments, $R_8$ is methoxy. In some embodiments, $R_8$ is ethoxy. In some embodiments, $R_8$ is propoxy. In some embodiments, $R_8$ is butoxy. In some embodiments, $R_8$ is pentoxy. In some embodiments, one $R_8$ is hexoxy.

In some embodiments, at least one $R_9$ is oxo, $=NR_{11}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$N(R_{12})_2$, —$(CH_2)_m$—$OR_{12}$, —$(CH_2)_m$—$C(O)R_{12}$, —$(CH_2)_m$—$C(O)OR_{12}$, —$(CH_2)_m$—$C(O)N(R_{12})_2$, —$(CH_2)_m$—$SO_2R_{12}$, —$(CH_2)_m$—$SO_2$—$OR_{12}$, —$(CH_2)_m$—$SO_2N(R_{12})_2$, —$(CH_2)_m$—$CON(R_{12})_2$, —$(CH_2)_m$—$P(O)(OR_{12})_2$, —$(CH_2)_m$—$P(O)(R_{12})_2$, —$(CH_2)_m$—$B(OH)_2$, —$(CH_2)_m$—$B(R_{12})_2$, —$(CH_2)_m$—O—$(CH_2CH_2$—O$)_rR_{13}$, —$(CH_2)_m$—$NR_{12}$—$(CH_2CH_2$—O$)_rR_{13}$, —$(CH_2)_m$—C(O)—$(CH_2CH_2$—O$)_rR_{12}$, —$(CH_2)_m$—C(O)O—$(CH_2CH_2$—O$)_rR_{12}$, —$(CH_2)_m$—$C(O)NR_{12}$—$(CH_2CH_2$—O$)_rR_{13}$, —$(CH_2)_m$—C(O)—$NR_{12}$—$SO_2R_{13}$, —$(CH_2)_m$—$SO_2NR_{12}$—$C(O)R_{13}$, —$(CH_2)_m$—$S(O)(NR_{12})$—$R_{13}$, $C_3$-$C_{10}$ cycloalkyl, heterocycle comprising 1-4 heteroatoms selected from O, N, and S, aryl, or 5- to 6-membered heteroaryl comprising 1-4 heteroatoms selected from N, O, and S.

In some embodiments, at least one $R_9$ is oxo, $=NR_{11}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_m$—$N(R_{12})_2$, —$(CH_2)_m$—$OR_{12}$, —$(CH_2)_m$—$C(O)R_{12}$, —$(CH_2)_m$—$C(O)OR_{12}$, —$(CH_2)_m$—$C(O)N(R_{12})_2$, —$(CH_2)_m$—$SO_2R_{12}$, —$(CH_2)_m$—$SO_2$—$OR_{12}$, —$(CH_2)_m$—$SO_2N(R_{12})_2$, —$(CH_2)_m$—$CON(R_{12})_2$, —$(CH_2)_m$—$P(O)(OR_{12})_2$, —$(CH_2)_m$—$P(O)(R_{12})_2$, —$(CH_2)_m$—$B(OH)_2$, —$(CH_2)_m$—$B(R_{12})_2$, —$(CH_2)_m$—O—$(CH_2CH_2$—O$)_rR_{13}$, —$(CH_2)_m$—$NR_{12}$—$(CH_2CH_2$—O$)_rR_{13}$, —$(CH_2)_m$—C(O)—$(CH_2CH_2$—O$)_rR_{12}$, —$(CH_2)_m$—C(O)O—$(CH_2CH_2$—O$)_rR_{12}$, —$(CH_2)_m$—$C(O)NR_{12}$—$(CH_2CH_2$—O$)_rR_{13}$, —$(CH_2)_m$—C(O)—$NR_{12}$—$SO_2R_{13}$, —$(CH_2)_m$—$SO_2NR_{12}$—$C(O)R_{13}$, —$(CH_2)_m$—$S(O)(NR_{12})$—$R_{13}$, $C_3$-$C_{10}$ cycloalkyl, heterocycle comprising 1-4 heteroatoms selected from O, N, and S, aryl, or 5- to 6-membered heteroaryl comprising 1-4 heteroatoms selected from N, O, and S, wherein the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, heterocycle, aryl, or 5- to 6-membered heteroaryl is optionally substituted with one or more oxo, halogen, —CN, —OH, —$NH_2$, —$NO_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, at least one $R_9$ is oxo, $=NR_{11}$, halogen, —CN, or —$NO_2$.

In some embodiments, at least one $R_9$ is oxo.

In some embodiments, at least one $R_9$ is $=NR_{11}$.

In some embodiments, at least one $R_9$ is halogen. In some embodiments, at least one $R_9$ is F, Cl, Br, or I. In some embodiments, at least one $R_9$ is F, Cl, or Br. In some embodiments, $R_9$ is F. In some embodiments, $R_9$ is Cl. In some embodiments, $R_9$ is Br. In some embodiments, $R_9$ is I.

In some embodiments, at least one $R_9$ is —CN.

In some embodiments, at least one $R_9$ is $NO_2$.

In some embodiments, at least one $R_9$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, wherein the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy is optionally substituted with one or more oxo, halogen, —CN, —OH, —$NH_2$, —$NO_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_9$ is $C_1$-$C_6$ alkyl, $C_2$-$C_6$ alkenyl, or $C_2$-$C_6$ alkynyl.

In some embodiments, $R_9$ is $C_1$-$C_6$ alkyl (e.g. linear or branched).

In some embodiments, $R_9$ is methyl. In some embodiments, $R_9$ is ethyl. In some embodiments, $R_9$ is propyl. In some embodiments, $R_9$ is n-propyl. In some embodiments, $R_9$ is isopropyl. In some embodiments, $R_9$ is butyl. In some embodiments, $R_9$ is n-butyl. In some embodiments, $R_9$ is isobutyl. In some embodiments, $R_9$ is sec-butyl. In some embodiments, $R_9$ is tert-butyl. In some embodiments, $R_9$ is pentyl. In some embodiments, $R_9$ is hexyl.

In some embodiments, $R_9$ is $C_1$-$C_6$ alkyl optionally substituted with one or more oxo, halogen, —CN, —OH, —$NH_2$, —$NO_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_9$ is $C_2$-$C_6$ alkenyl.

In some embodiments, $R_9$ is $C_2$ alkenyl. In some embodiments, $R_9$ is $C_3$ alkenyl. In some embodiments, $R_9$ is $C_4$ alkenyl. In some embodiments, $R_9$ is $C_5$ alkenyl. In some embodiments, $R_9$ is $C_6$ alkenyl.

In some embodiments, $R_9$ is $C_2$-$C_6$ alkenyl optionally substituted with one or more oxo, halogen, —CN, —OH, —NH$_2$, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_9$ is $C_2$-$C_6$ alkynyl.

In some embodiments, $R_9$ is $C_2$ alkynyl. In some embodiments, $R_9$ is $C_3$ alkynyl. In some embodiments, $R_9$ is $C_4$ alkynyl. In some embodiments, $R_9$ is $C_5$ alkynyl. In some embodiments, $R_9$ is $C_6$ alkynyl.

In some embodiments, $R_9$ is $C_2$-$C_6$ alkynyl optionally substituted with one or more oxo, halogen, —CN, —OH, —NH$_2$, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_9$ is $C_1$-$C_6$ haloalkyl or $C_1$-$C_6$ alkoxy.

In some embodiments, $R_9$ is $C_1$-$C_6$ haloalkyl.

In some embodiments, $R_9$ is halomethyl. In some embodiments, $R_9$ is haloethyl. In some embodiments, $R_9$ is halopropyl. In some embodiments, $R_9$ is halobutyl. In some embodiments, $R_9$ is halopentyl. In some embodiments, $R_9$ is halohexyl.

In some embodiments, $R_9$ is CH$_2$F. In some embodiments, $R_9$ is CHF$_2$. In some embodiments, $R_9$ is CF$_3$.

In some embodiments, $R_9$ is $C_1$-$C_6$ haloalkyl optionally substituted with one or more oxo, halogen, —CN, —OH, —NH$_2$, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy In some embodiments, $R_9$ is $C_1$-$C_6$ alkoxy.

In some embodiments, $R_9$ is methoxy. In some embodiments, $R_9$ is ethoxy. In some embodiments, $R_9$ is propoxy. In some embodiments, $R_9$ is butoxy. In some embodiments, $R_9$ is pentoxy. In some embodiments, one $R_9$ is hexoxy.

In some embodiments, $R_9$ is $C_1$-$C_6$ alkoxy optionally substituted with one or more oxo, halogen, —CN, —OH, —NH$_2$, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy. In some embodiments, at least one $R_9$ is —(CH$_2$)$_m$—N(R$_{12}$)$_2$, —(CH$_2$)$_m$—OR$_{12}$, —(CH$_2$)$_m$—C(O)R$_{12}$, —(CH$_2$)$_m$—C(O)OR$_{12}$, —(CH$_2$)$_m$—C(O)N(R$_{12}$)$_2$, —(CH$_2$)$_m$—SO$_2$R$_{12}$, —(CH$_2$)$_m$—SO$_2$—OR$_{12}$, —(CH$_2$)$_m$—SO$_2$N(R$_{12}$)$_2$, —(CH$_2$)$_m$—CON(R$_{12}$)$_2$, —(CH$_2$)$_m$—P(O)(OR$_{12}$)$_2$, —(CH$_2$)$_m$—P(O)(R$_{12}$)$_2$, —(CH$_2$)$_m$—B(OH)$_2$, —(CH$_2$)$_m$—B(R$_{12}$)$_2$, —(CH$_2$)$_m$—O—(CH$_2$CH$_2$—O)$_r$R$_{13}$, —(CH$_2$)$_m$—NR$_{12}$—(CH$_2$CH$_2$—O)$_r$R$_{13}$, —(CH$_2$)$_m$—C(O)—(CH$_2$CH$_2$—O)$_r$R$_{12}$, —(CH$_2$)$_m$—C(O)O—(CH$_2$CH$_2$—O)$_r$R$_{12}$, —(CH$_2$)$_m$—C(O)NR$_{12}$—(CH$_2$CH$_2$—O)$_r$R$_{13}$, —(CH$_2$)$_m$—C(O)—NR$_{12}$—SO$_2$R$_{13}$, —(CH$_2$)$_m$—SO$_2$NR$_{12}$—C(O)R$_{13}$, or —(CH$_2$)$_m$—S(O)(NR$_{12}$)—R$_{13}$.

In some embodiments, at least one $R_9$ is —(CH$_2$)$_m$—N(R$_{12}$)$_2$ or —(CH$_2$)$_m$—OR$_{12}$.

In some embodiments, at least one $R_9$ is —(CH$_2$)$_m$—N(R$_{12}$)$_2$. In some embodiments, at least one $R_9$ is —(CH$_2$)$_m$—OR$_{12}$.

In some embodiments, at least one $R_9$ is -CH$_2$—N(R$_{12}$)$_2$.

In some embodiments, at least one $R_9$ is —(CH$_2$)$_m$—C(O)R$_{12}$, —(CH$_2$)$_m$—C(O)OR$_{12}$, —(CH$_2$)$_m$—C(O)N(R$_{12}$)$_2$, or —(CH$_2$)$_m$—CON(R$_{12}$)$_2$.

In some embodiments, at least one $R_9$ is —(CH$_2$)$_m$—C(O)R$_{12}$. In some embodiments, at least one $R_9$ is —(CH$_2$)$_m$—C(O)OR$_{12}$. In some embodiments, at least one $R_9$ is —(CH$_2$)$_m$—C(O)N(R$_{12}$)$_2$. In some embodiments, at least one $R_9$ is —(CH$_2$)$_m$—CON(R$_{12}$)$_2$.

In some embodiments, at least one $R_9$ is —C(O)R$_{12}$. In some embodiments, at least one $R_9$ is —CH$_2$—C(O)R$_{12}$. In some embodiments, at least one $R_9$ is —CH$_2$CH$_2$—C(O)R$_{12}$. In some embodiments, at least one $R_9$ is —CH$_2$CH$_2$CH$_2$—C(O)R$_{12}$. In some embodiments, at least one $R_9$ is —CH$_2$CH$_2$CH$_2$CH$_2$—C(O)R$_{12}$. In some embodiments, at least one $R_9$ is —CH$_2$CH$_2$CH$_2$CH$_2$CH$_2$—C(O)R$_{12}$. In some embodiments, at least one $R_9$ is —CH$_2$CH$_2$CH$_2$CH$_2$CH$_2$CH$_2$—C(O)R$_{12}$.

In some embodiments, at least one $R_9$ is —C(O)OR$_{12}$. In some embodiments, at least one $R_9$ is —CH$_2$—C(O)OR$_{12}$. In some embodiments, at least one $R_9$ is —CH$_2$CH$_2$—C(O)OR$_{12}$. In some embodiments, at least one $R_9$ is —CH$_2$CH$_2$CH$_2$—C(O)OR$_{12}$. In some embodiments, at least one $R_9$ is —CH$_2$CH$_2$CH$_2$CH$_2$—C(O)OR$_{12}$. In some embodiments, at least one $R_9$ is —CH$_2$CH$_2$CH$_2$CH$_2$CH$_2$—C(O)OR$_{12}$. In some embodiments, at least one $R_9$ is —CH$_2$CH$_2$CH$_2$CH$_2$CH$_2$CH$_2$—C(O)OR$_{12}$.

In some embodiments, at least one $R_9$ is —(CH$_2$)$_m$—CON(R$_{12}$)$_2$.

In some embodiments, at least one $R_9$ is —C(O)N(R$_{12}$)$_2$. In some embodiments, at least one $R_9$ is —CH$_2$—C(O)N(R$_{12}$)$_2$. In some embodiments, at least one $R_9$ is —CH$_2$CH$_2$—C(O)N(R$_{12}$)$_2$. In some embodiments, at least one $R_9$ is —CH$_2$CH$_2$CH$_2$—C(O)N(R$_{12}$)$_2$. In some embodiments, at least one $R_9$ is —CH$_2$CH$_2$CH$_2$CH$_2$—C(O)N(R$_{12}$)$_2$. In some embodiments, at least one $R_9$ is —CH$_2$CH$_2$CH$_2$ CH$_2$CH$_2$CH$_2$—C(O)N(R$_{12}$)$_2$.

In some embodiments, at least one $R_9$ is —(CH$_2$)$_m$—SO$_2$R$_{12}$, —(CH$_2$)$_m$—SO$_2$—OR$_{12}$, or —(CH$_2$)$_m$—SO$_2$N(R$_{12}$)$_2$.

In some embodiments, at least one $R_9$ is —(CH$_2$)$_m$—SO$_2$R$_{12}$. In some embodiments, at least one $R_9$ is —(CH$_2$)$_m$—SO$_2$—OR$_{12}$. In some embodiments, at least one $R_9$ is —(CH$_2$)$_m$—SO$_2$N(R$_{12}$)$_2$.

In some embodiments, at least one $R_9$ is —SO$_2$R$_{12}$. In some embodiments, at least one $R_9$ is —CH$_2$—SO$_2$R$_{12}$. In some embodiments, at least one $R_9$ is —CH$_2$CH$_2$—SO$_2$R$_{12}$. In some embodiments, at least one $R_9$ is —CH$_2$CH$_2$CH$_2$—SO$_2$R$_{12}$. In some embodiments, at least one $R_9$ is —CH$_2$CH$_2$CH$_2$CH$_2$—SO$_2$R$_{12}$. In some embodiments, at least one $R_9$ is —CH$_2$CH$_2$CH$_2$CH$_2$CH$_2$—SO$_2$R$_{12}$. In some embodiments, at least one $R_9$ is —CH$_2$CH$_2$CH$_2$CH$_2$CH$_2$CH$_2$—SO$_2$R$_{12}$.

In some embodiments, at least one $R_9$ is —SO$_2$—OR$_{12}$. In some embodiments, at least one $R_9$ is —CH$_2$—SO$_2$—OR$_{12}$. In some embodiments, at least one $R_9$ is —CH$_2$CH$_2$—SO$_2$—OR$_{12}$. In some embodiments, at least one $R_9$ is —CH$_2$CH$_2$CH$_2$—SO$_2$—OR$_{12}$. In some embodiments, at least one $R_9$ is —CH$_2$CH$_2$CH$_2$CH$_2$—SO$_2$—OR$_{12}$. In some embodiments, at least one $R_9$ is —CH$_2$ CH$_2$CH$_2$CH$_2$CH$_2$—SO$_2$—OR$_{12}$. In some embodiments, at least one $R_9$ is —CH$_2$CH$_2$CH$_2$CH$_2$CH$_2$CH$_2$—SO$_2$R$_{12}$.

In some embodiments, at least one $R_9$ is —SO$_2$N(R$_{12}$)$_2$. In some embodiments, at least one $R_9$ is —CH$_2$—SO$_2$N(R$_{12}$)$_2$. In some embodiments, at least one $R_9$ is —CH$_2$CH$_2$—SO$_2$N(R$_{12}$)$_2$. In some embodiments, at least one $R_9$ is —CH$_2$CH$_2$CH$_2$—SO$_2$N(R$_{12}$)$_2$. In some embodiments, at least one $R_9$ is —CH$_2$CH$_2$CH$_2$CH$_2$—SO$_2$N(R$_{12}$)$_2$. In some embodiments, at least one $R_9$ is —CH$_2$—CH$_2$CH$_2$CH$_2$CH$_2$—SO$_2$N(R$_{12}$)$_2$. In some embodiments, at least one $R_9$ is —CH$_2$CH$_2$CH$_2$CH$_2$CH$_2$CH$_2$—SO$_2$N(R$_{12}$)$_2$.

In some embodiments, at least one $R_9$ is —(CH$_2$)$_m$—P(O)(OR$_{12}$)$_2$, or —(CH$_2$)$_m$—P(O)(R$_{12}$)$_2$.

In some embodiments, at least one $R_9$ is —(CH$_2$)$_m$—P(O)(OR$_{12}$)$_2$. In some embodiments, at least one $R_9$ is —(CH$_2$)$_m$—P(O)(R$_{12}$)$_2$.

In some embodiments, at least one $R_9$ is —P(O)(OR$_{12}$)$_2$. In some embodiments, at least one $R_9$ is —CH$_2$—P(O)(OR$_{12}$)$_2$. In some embodiments, at least one $R_9$ is —CH$_2$CH$_2$—P(O)(OR$_{12}$)$_2$. In some embodiments, at least one $R_9$ is —CH$_2$CH$_2$CH$_2$—P(O)(OR$_{12}$)$_2$. In some embodiments, at least one $R_9$ is —CH$_2$CH$_2$CH$_2$CH$_2$—P(O)(OR$_{12}$)$_2$. In some embodiments, at least one $R_9$ is —CH$_2$—CH$_2$CH$_2$CH$_2$CH$_2$—P(O)(OR$_{12}$)$_2$. In some embodiments, at least one $R_9$ is —CH$_2$CH$_2$CH$_2$CH$_2$CH$_2$CH$_2$—P(O)(OR$_{12}$)$_2$.

In some embodiments, at least one $R_9$ is —P(O)(R$_{12}$)$_2$. In some embodiments, at least one $R_9$ is —CH$_2$—P(O)(R$_{12}$)$_2$. In some embodiments, at least one $R_9$ is —CH$_2$CH$_2$—P(O)(R$_{12}$)$_2$. In some embodiments, at least one $R_9$ is —CH$_2$CH$_2$CH$_2$—P(O)(R$_{12}$)$_2$. In some embodiments, at least one $R_9$ is —CH$_2$CH$_2$CH$_2$CH$_2$—P(O)(R$_{12}$)$_2$. In some embodiments, at least one $R_9$ is —CH$_2$—CH$_2$CH$_2$CH$_2$CH$_2$—P(O)(R$_{12}$)$_2$. In some embodiments, at least one $R_9$ is —CH$_2$CH$_2$CH$_2$CH$_2$CH$_2$CH$_2$—P(O)(R$_{12}$)$_2$.

In some embodiments, at least one $R_9$ is —(CH$_2$)$_m$—B(OH)$_2$, or —(CH$_2$)$_m$—B(R$_{12}$)$_2$.

In some embodiments, at least one $R_9$ is —(CH$_2$)$_m$—B(OH)$_2$. In some embodiments, at least one $R_9$ is —(CH$_2$)$_m$—B(R$_{12}$)$_2$.

In some embodiments, at least one $R_9$ is —B(OH)$_2$. In some embodiments, at least one $R_9$ is —CH$_2$—B(OH)$_2$. In some embodiments, at least one $R_9$ is —CH$_2$CH$_2$—B(OH)$_2$. In some embodiments, at least one $R_9$ is —CH$_2$CH$_2$CH$_2$—B(OH)$_2$. In some embodiments, at least one $R_9$ is —CH$_2$CH$_2$CH$_2$CH$_2$—B(OH)$_2$. In some embodiments, at least one $R_9$ is —CH$_2$—CH$_2$CH$_2$CH$_2$CH$_2$—B(OH)$_2$. In some embodiments, at least one $R_9$ is —CH$_2$CH$_2$CH$_2$CH$_2$CH$_2$CH$_2$—B(OH)$_2$.

In some embodiments, at least one $R_9$ is —B(R$_{12}$)$_2$. In some embodiments, at least one $R_9$ is —CH$_2$—B(R$_{12}$)$_2$. In some embodiments, at least one $R_9$ is —CH$_2$CH$_2$—B(R$_{12}$)$_2$. In some embodiments, at least one $R_9$ is —CH$_2$CH$_2$CH$_2$—B(R$_{12}$)$_2$. In some embodiments, at least one $R_9$ is —CH$_2$CH$_2$CH$_2$CH$_2$—B(R$_{12}$)$_2$. In some embodiments, at least one $R_9$ is —CH$_2$— CH$_2$CH$_2$CH$_2$CH$_2$—B(R$_{12}$)$_2$. In some embodiments, at least one $R_9$ is —CH$_2$CH$_2$CH$_2$CH$_2$CH$_2$CH$_2$.

In some embodiments, at least one $R_9$ is —(CH$_2$)$_m$—O—(CH$_2$CH$_2$—O)$_r$R$_{13}$, —(CH$_2$)$_m$—NR$_{12}$—(CH$_2$CH$_2$—O)$_r$R$_{13}$, —(CH$_2$)$_m$—C(O)—(CH$_2$CH$_2$—O)$_r$R$_{13}$, —(CH$_2$)$_m$—C(O)O—(CH$_2$CH$_2$—O)$_r$R$_{13}$, —(CH$_2$)$_m$—C(O)NR$_{12}$—(CH$_2$CH$_2$—O)$_r$R$_{13}$, —(CH$_2$)$_m$—C(O)—NR$_{12}$—SO$_2$R$_{13}$, —(CH$_2$)$_m$—SO$_2$NR$_{12}$—C(O)R$_{13}$, or —(CH$_2$)$_m$—S(O)(NR$_{12}$)—R$_{13}$.

In some embodiments, at least one $R_9$ is —(CH$_2$)$_m$—O—(CH$_2$CH$_2$—O)$_r$R$_{13}$. In some embodiments, at least one $R_9$ is —(CH$_2$)$_m$—NR$_{12}$—(CH$_2$CH$_2$—O)$_r$R$_{13}$. In some embodiments, at least one $R_9$ is —(CH$_2$)$_m$—C(O)—(CH$_2$CH$_2$—O)$_r$R$_{13}$. In some embodiments, at least one $R_9$ is —(CH$_2$)$_m$—C(O)O—(CH$_2$CH$_2$—O)$_r$R$_{13}$. In some embodiments, at least one $R_9$ is —(CH$_2$)$_m$—C(O)NR$_{12}$—(CH$_2$CH$_2$—O)$_r$R$_{13}$. In some embodiments, at least one $R_9$ is —(CH$_2$)$_m$—C(O)—NR$_{12}$—SO$_2$R$_{13}$. In some embodiments, at least one $R_9$ is —(CH$_2$)$_m$—SO$_2$NR$_{12}$—C(O)R$_{13}$. In some embodiments, at least one $R_9$ is —(CH$_2$)$_m$—S(O)(NR$_{12}$)—R$_{13}$.

In some embodiments, at least one $R_9$ is —C(O)NR$_{12}$—R$_{13}$. In some embodiments, at least one $R_9$ is —C(O)NR$_{12}$—CH$_2$CH$_2$—OR$_{13}$. In some embodiments, at least one $R_9$ is —C(O)NR$_{12}$—(CH$_2$CH$_2$—O)$_2$R$_{13}$. In some embodiments, at least one $R_9$ is —C(O)NR$_{12}$—(CH$_2$CH$_2$—O)$_3$R$_{13}$. In some embodiments, at least one $R_9$ is —C(O)NR$_{12}$—(CH$_2$CH$_2$—O)$_4$R$_{13}$. In some embodiments, at least one $R_9$ is —C(O)NR$_{12}$—(CH$_2$CH$_2$—O)$_5$R$_{13}$. In some embodiments, at least one $R_9$ is —C(O)NR$_{12}$—(CH$_2$CH$_2$—O)$_6$R$_{13}$.

In some embodiments, at least one $R_9$ is —C(O)R$_{12}$—R$_{13}$. In some embodiments, at least one $R_9$ is —C(O)R$_{12}$—CH$_2$CH$_2$—OR$_{13}$. In some embodiments, at least one $R_9$ is —C(O)R$_{12}$—(CH$_2$CH$_2$—O)$_2$R$_{13}$. In some embodiments, at least one $R_9$ is —C(O)R$_{12}$—(CH$_2$CH$_2$—O)$_3$R$_{13}$. In some embodiments, at least one $R_9$ is —C(O)R$_{12}$—(CH$_2$CH$_2$—O)$_4$R$_{13}$. In some embodiments, at least one $R_9$ is —C(O)R$_{12}$—(CH$_2$CH$_2$—O)$_5$R$_{13}$. In some embodiments, at least one $R_9$ is —C(O)R$_{12}$—(CH$_2$CH$_2$—O)$_6$R$_{13}$.

In some embodiments, at least one $R_9$ is $C_3$-$C_{10}$ cycloalkyl, heterocycle comprising 1-4 heteroatoms selected from O, N, and S, Aryl, or 5- to 6-membered heteroaryl comprising 1-4 heteroatoms selected from N, O, and S, wherein the $C_3$-$C_{10}$ cycloalkyl, heterocycle, Aryl, or 5- to 6-membered heteroaryl is optionally substituted with one or more oxo, halogen, —CN, —OH, —NH$_2$, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, at least one $R_9$ is $C_3$-$C_{10}$ cycloalkyl, wherein the $C_3$-$C_{10}$ cycloalkyl is optionally substituted with one or more oxo, halogen, —CN, —OH, —NH$_2$, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy. In some embodiments, at least one $R_9$ is heterocycle comprising 1-4 heteroatoms selected from O, N, and S, wherein the heterocycle is optionally substituted with one or more oxo, halogen, —CN, —OH, —NH$_2$, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy. In some embodiments, at least one $R_9$ is aryl wherein the aryl is optionally substituted with one or more oxo, halogen, —CN, —OH, —NH$_2$, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy. In some embodiments, at least one $R_9$ is 5- to 6-membered heteroaryl comprising 1-4 heteroatoms selected from N, O, and S, wherein the 5- to 6-membered heteroaryl is optionally substituted with one or more oxo, halogen, —CN, —OH, —NH$_2$, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, at least one $R_{10}$ is $C_3$-$C_{10}$ cycloalkyl.

In some embodiments, at least one $R_{10}$ is $C_3$-$C_{10}$ cycloalkyl optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, at least one $R_9$ is a monocyclic $C_3$-$C_{10}$ cycloalkyl. In some embodiments, at least one $R_9$ is a monocyclic $C_3$-$C_{10}$ cycloalkyl optionally substituted with one or more oxo, halogen, —CN, —OH, —NH$_2$, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy. In some embodiments, at least one $R_9$ is a polycyclic $C_3$-$C_{10}$ cycloalkyl. In some embodiments, at least one $R_9$ is a polycyclic $C_3$-$C_{10}$ cycloalkyl optionally substituted with one or more oxo, halogen, —CN, —OH, —NH$_2$, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, at least one $R_9$ is $C_5$-$C_6$ cycloalkyl. In some embodiments, at least one $R_9$ is $C_5$-$C_6$ cycloalkyl optionally substituted with one or more oxo, halogen, —CN, —OH, —NH$_2$, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, at least one $R_9$ is cyclopropyl, cyclobutyl, cyclopentyl, cyclohexyl, cycloheptyl, cyclooctyl, cyclononyl, or cyclodecyl. In some embodiments, at least one $R_9$ is cyclopropyl, cyclobutyl, cyclopentyl, cyclohexyl, cycloheptyl, cyclooctyl, cyclononyl, or cyclodecyl, wherein the cyclopropyl, cyclobutyl, cyclopentyl, cyclohexyl, cycloheptyl, cyclooctyl, cyclononyl, or cyclodecyl is optionally substituted with one or more oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is heterocycle comprising 1-4 heteroatoms selected from O, N, and S.

In some embodiments, at least one R$_9$ is heterocycle comprising 1-4 heteroatoms selected from O, N, and S, substituted with one substituent selected from oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, R$_9$ is 5- to 6-membered heterocycle comprising 1-4 heteroatoms selected from O, N, and S.

In some embodiments, R$_9$ is 5- to 6-membered heterocycle comprising 1-4 heteroatoms selected from O, N, and S, optionally substituted with one or more oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, R$_9$ is 5- to 6-membered heterocycle comprising 1-4 heteroatoms selected from O, N, and S, substituted with one oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is heterocycle comprising 1-4 heteroatoms selected from O, N, and S, substituted with two substituents selected from oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is heterocycle comprising 1-4 heteroatoms selected from O, N, and S, substituted with three substituents selected from oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is heterocycle comprising 1-4 heteroatoms selected from O, N, and S, substituted with four substituents selected from oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is heterocycle comprising three heteroatoms selected from N and S, optionally substituted with one or more oxo.

In some embodiments, at least one R$_9$ is 4-membered heterocycle comprising 1-3 heteroatoms selected from N, O, and S, optionally substituted with one or more oxo. In some embodiments, at least one R$_9$ is 5-membered heterocycle comprising 1-3 heteroatoms selected from N, O, and S, optionally substituted with one or more oxo. In some embodiments, at least one R$_9$ is 6-membered heterocycle comprising 1-3 heteroatoms selected from N, O, and S, optionally substituted with one or more oxo. In some embodiments, at least one R$_9$ is 7-membered heterocycle comprising 1-3 heteroatoms selected from N, O, and S, optionally substituted with one or more oxo. In some embodiments, at least one R$_9$ is 8-membered heterocycle comprising 1-3 heteroatoms selected from N, O, and S, optionally substituted with one or more oxo. In some embodiments, at least one R$_9$ is 9-membered heterocycle comprising 1-3 heteroatoms selected from N, O, and S, optionally substituted with one or more oxo. In some embodiments, at least one R$_9$ is 10-membered heterocycle comprising 1-3 heteroatoms selected from N, O, and S, optionally substituted with one or more oxo.

In some embodiments, at least one R$_9$ is

In some embodiments, at least one R$_9$ is 5- to 6-membered heteroaryl comprising 1-4 heteroatoms selected from O, N, and S. In some embodiments, at least one R$_9$ is 5- to 6-membered heteroaryl comprising 1-4 heteroatoms selected from O, N, and S, wherein the heteroaryl is optionally substituted with one or more substituents selected from oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is 5- to 6-membered heteroaryl comprising one heteroatom selected from O, N, and S. In some embodiments, at least one R$_9$ is 5- to 6-membered heteroaryl comprising one heteroatom selected from O, N, and S, wherein the heteroaryl is optionally substituted with one or more substituents selected from oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is 5- to 6-membered heteroaryl comprising two heteroatoms selected from O, N, and S. In some embodiments, at least one R$_9$ is 5- to 6-membered heteroaryl comprising two heteroatoms selected from O, N, and S, wherein the heteroaryl is optionally substituted with one or more substituents selected from oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is 5- to 6-membered heteroaryl comprising three heteroatoms selected from O, N, and S. In some embodiments, at least one R$_9$ is 5- to 6-membered heteroaryl comprising three heteroatoms selected from O, N, and S, wherein the heteroaryl is optionally substituted with one or more substituents selected from oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is 5- to 6-membered heteroaryl comprising 1-4 heteroatoms selected from O, N, and S. In some embodiments, at least one R$_9$ is 5- to 6-membered heteroaryl comprising 1-4 heteroatoms selected from O, N, and S, wherein the heteroaryl is optionally substituted with one or more substituents selected from oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is 5-membered heteroaryl comprising 1-4 heteroatoms selected from N, O, and S. In some embodiments, at least one R$_9$ is 5-membered heteroaryl comprising 1-4 heteroatoms selected from N, O, and S, wherein the 5-membered heteroaryl is optionally substituted with one or more oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is 5-membered heteroaryl comprising one heteroatom selected from N, O, and S, optionally substituted with one or more oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy. In some embodiments, at least one R$_9$ is 5-membered heteroaryl comprising two heteroatoms selected from N, O, and S, optionally substituted with one or more oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy. In some embodiments, at least one R$_9$ is 5-membered heteroaryl comprising three heteroatoms selected from N, O, and S, optionally substituted with one or more oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy. In some embodiments, at least one R$_9$ is 5-membered heteroaryl comprising four heteroatoms selected from N, O, and S, optionally substituted with one or more oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is 5-membered heteroaryl comprising 1-4 heteroatoms selected from N, O, and S, substituted with one oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is 5-membered heteroaryl comprising 1-4 heteroatoms selected from N, O, and S, substituted with two substituents selected from oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is 5-membered heteroaryl comprising 1-4 heteroatoms selected from N, O, and S, substituted with three substituents selected oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is

[chemical structures shown]

In some embodiments, at least one R$_9$ is 6-membered heteroaryl comprising 1-4 heteroatoms selected from N, O, and S. In some embodiments, at least one R$_9$ is 6-membered heteroaryl comprising 1-4 heteroatoms selected from N, O, and S, optionally substituted with one or more oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is 6-membered heteroaryl comprising one heteroatom selected from N, O, and S, optionally substituted with one or more oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy. In some embodiments, at least one R$_9$ is 6-membered heteroaryl comprising two heteroatoms selected from N, O, and S, optionally substituted with one or more oxo, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy. In some embodiments, at least one R$_9$ is 6-membered heteroaryl comprising three heteroatoms selected from N, O, and S, optionally substituted with one or more oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy. In some embodiments, at least one R$_9$ is 6-membered heteroaryl comprising four heteroatoms selected from N, O, and S, optionally substituted with one or more oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is 6-membered heteroaryl comprising 1-4 heteroatoms selected from N, O, and S, substituted with one oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is 6-membered heteroaryl comprising 1-4 heteroatoms selected from N, O, and S, substituted with two substituents selected from oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is 6-membered heteroaryl comprising 1-4 heteroatoms selected from N, O, and S, substituted with three substituents selected from oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, at least one R$_9$ is 6-membered heteroaryl comprising 1-4 heteroatoms selected from N, O, and S, substituted with four substituents selected from oxo, halogen, —CN, —OH, —NH$_2$, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, two R$_9$ together with the atoms to which they are attached form a C$_3$-C$_{10}$ cycloalkyl or a 3- to 15-membered saturated or partially saturated heterocycle comprising 1-4 heteroatoms selected from O, N, and S.

In some embodiments, two R$_9$ together with the atoms to which they are attached form a C$_3$-C$_{10}$ cycloalkyl or a 3- to 15-membered saturated or partially saturated heterocycle comprising 1-4 heteroatoms selected from O, N, and S, wherein the cycloalkyl or heterocycle is optionally substituted with one or more oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, two R$_9$ together with the atoms to which they are attached form a C$_3$-C$_{10}$ cycloalkyl.

In some embodiments, two R$_9$ together with the atoms to which they are attached form a cyclopropyl, cyclobutyl, cyclopentyl, cyclohexyl, cycloheptyl, cyclooctyl, cyclononyl, or cyclodecyl.

In some embodiments, two R$_9$ together with the atoms to which they are attached form a C$_3$-C$_{10}$ cycloalkyl optionally substituted with one or more oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, two R$_9$ together with the atoms to which they are attached form a C$_5$-C$_6$ cycloalkyl.

In some embodiments, two R$_9$ together with the atoms to which they are attached form a C$_5$-C$_6$ cycloalkyl wherein the cycloalkyl is optionally substituted with one or more oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, two R$_9$ together with the atoms to which they are attached form a C$_3$-C$_{10}$ cycloalkyl substituted with one oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, two R$_9$ together with the atoms to which they are attached form a C$_3$-C$_{10}$ cycloalkyl substituted with two substituents selected from oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, two R$_9$ together with the atoms to which they are attached form a C$_3$-C$_{10}$ cycloalkyl substituted with three substituents selected from oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, two R$_9$ together with the atoms to which they are attached form a C$_3$-C$_{10}$ cycloalkyl substituted with four substituents selected from oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, two R$_9$ together with the atoms to which they are attached form a cyclopropyl, cyclobutyl, cyclopentyl, cyclohexyl, cycloheptyl, cyclooctyl, cyclononyl, or cyclodecyl, wherein the cyclopropyl, cyclobutyl, cyclopentyl, cyclohexyl, cycloheptyl, cyclooctyl, cyclononyl, or cyclodecyl is optionally substituted with four substituents selected from oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

some embodiments, two R$_9$ together with the atoms to which they are attached form a C$_3$-C$_{10}$ cycloalkyl wherein the cycloalkyl is optionally substituted with one or more oxo or =NH.

In some embodiments, two R$_9$ together with the atoms to which they are attached form 3 to 15-membered saturated or partially unsaturated heterocycle comprising 1-4 heteroatoms selected from O, N, and S.

In some embodiments, two R$_9$ together with the atoms to which they are attached form heterocycle comprising 1-4 heteroatoms selected from O, N, and S, optionally substituted with one or more oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, two R$_9$ together with the atoms to which they are attached form 3- to 15-membered saturated heterocycle comprising 1-4 heteroatoms selected from O, N, and S, optionally substituted with one or more oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy. In some embodiments, two R$_9$ together with the atoms to which they are attached form 3-15-membered partially unsaturated heterocycle comprising 1-4 heteroatoms selected from O, N, and S, optionally substituted with one or more oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, two R$_9$ together with the atoms to which they are attached form a heterocycle comprising one heteroatom selected from O, N, and S, optionally substituted with one or more oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy. In some embodiments, two R$_9$ together with the atoms to which they are attached form a heterocycle comprising two heteroatoms selected from O, N, and S, optionally substituted with one or more oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy. In some embodiments, two R$_9$ together with the atoms to which they are attached form a heterocycle comprising three heteroatoms selected from O, N, and S, optionally substituted with one or more oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy. In some embodiments, two R$_9$ together with the atoms to which they are attached form a heterocycle comprising four heteroatoms selected from O, N, and S, optionally substituted with one or more oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, two R$_9$ together with the atoms to which they are attached form heterocycle comprising 1-4 heteroatoms selected from O, N, and S, substituted with one or more oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, two R$_9$ together with the atoms to which they are attached form a 5- to 6-membered saturated or partially unsaturated heterocycle comprising 1-4 heteroatoms selected from O, N, and S.

In some embodiments, two R$_9$ together with the atoms to which they are attached form a 5- to 6-membered saturated or partially unsaturated heterocycle comprising 1-4 heteroatoms selected from O, N, and S, wherein the heterocycle is optionally substituted with one or more oxo, halogen, —CN, —OH, —NH$_2$, =NH, —NO$_2$, C$_1$-C$_6$ alkyl, C$_2$-C$_6$ alkenyl, C$_2$-C$_6$ alkynyl, C$_1$-C$_6$ haloalkyl, or C$_1$-C$_6$ alkoxy.

In some embodiments, two R$_9$ together with the atoms to which they are attached form heterocycle comprising 1-4 heteroatoms selected from O, N, and S, wherein the heterocycle is optionally substituted with one or more oxo or =NH.

In some embodiments, two R$_9$ together with the atoms to which they are attached form 5-membered saturated or partially unsaturated heterocycle comprising 1-4 heteroatoms selected from O, N, and S.

In some embodiments, two R$_9$ together with the atoms to which they are attached form 5-membered saturated or partially unsaturated heterocycle comprising 1-4 heteroatoms selected from O, N, and S, wherein the heterocycle is optionally substituted with one or more oxo or =NH. In some embodiments, two R$_9$ together with the atoms to which they are attached form 5-membered saturated or partially unsaturated heterocycle comprising 1-4 heteroatoms selected from O, N, and S, wherein the heterocycle is optionally substituted with one or more oxo. In some embodiments, two R$_9$ together with the atoms to which they are attached form 5-membered saturated or partially unsaturated heterocycle comprising 1-4 heteroatoms selected from O, N, and S, wherein the heterocycle is optionally substituted with one or more =NH.

In some embodiments, two R$_9$ together with the atoms to which they are attached form 6-membered saturated or partially unsaturated heterocycle comprising 1-4 heteroatoms selected from O, N, and S.

In some embodiments, two R$_9$ together with the atoms to which they are attached form 6-membered saturated or partially unsaturated heterocycle comprising 1-4 heteroatoms selected from O, N, and S, wherein the heterocycle is optionally substituted with one or more oxo or =NH. In some embodiments, two R$_9$ together with the atoms to which they are attached form 6-membered saturated or partially unsaturated heterocycle comprising 1-4 heteroatoms selected from O, N, and S, wherein the heterocycle is optionally substituted with one or more oxo. In some embodiments, two R$_9$ together with the atoms to which they are attached form 6-membered saturated or partially unsaturated heterocycle comprising 1-4 heteroatoms selected from O, N, and S, wherein the heterocycle is optionally substituted with one or more =NH.

In some embodiments, two R$_9$ together with the atoms to which they are attached form

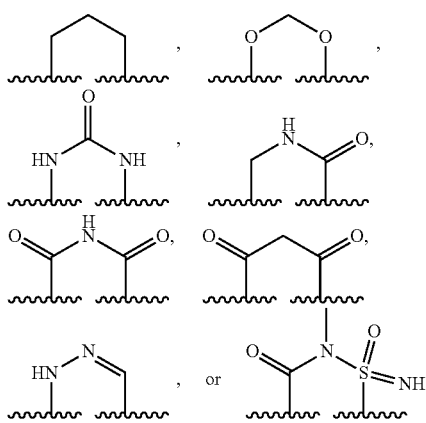

wherein " $\sim$ " signifies the point at which the two $R_9$ attach to different atoms of ring A.

In some embodiments, two $R_9$ together with the atoms to which they are attached form

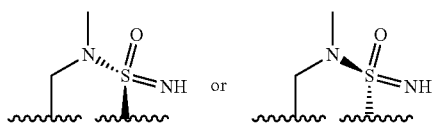

wherein " $\sim$ " signifies the point at which the two $R_9$ attach to different atoms of ring A.

In some embodiments, at least one $R_{10}$ is oxo, halogen, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$, $C_3$-$C_{10}$ cycloalkyl, heterocycle, aryl, and heteroaryl, wherein the cycloalkyl, heterocycle, aryl, and heteroaryl is optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, at least one $R_{10}$ is oxo, halogen, or —CN.

In some embodiments, at least one $R_{10}$ is oxo.

In some embodiments, at least one $R_{10}$ is halogen. In some embodiments, at least one $R_{10}$ is F, Cl, Br, or I. In some embodiments, at least one $R_{10}$ is F, Cl, or Br. In some embodiments, at least one $R_{10}$ is F. In some embodiments, at least one $R_{10}$ is Cl. In some embodiments, at least one $R_{10}$ is Br. In some embodiments, at least one $R_{10}$ is I.

In some embodiments, at least one $R_{10}$ is —CN.

In some embodiments, at least one $R_{10}$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, at least one $R_{10}$ is $C_1$-$C_6$ alkyl.

In some embodiments, at least one $R_{10}$ is methyl. In some embodiments, at least one $R_{10}$ is ethyl. In some embodiments, at least one $R_{10}$ is propyl. In some embodiments, at least one $R_{10}$ is n-propyl. In some embodiments, at least one $R_{10}$ is isopropyl. In some embodiments, at least one $R_{10}$ is butyl. In some embodiments, at least one $R_{10}$ is n-butyl. In some embodiments, at least one $R_{10}$ is isobutyl. In some embodiments, at least one $R_{10}$ is sec-butyl. In some embodiments, at least one $R_{10}$ is tert-butyl. In some embodiments, at least one $R_{10}$ is pentyl. In some embodiments, at least one $R_{10}$ is hexyl.

In some embodiments, at least one $R_{10}$ is $C_2$-$C_6$ alkenyl.

In some embodiments, at least one $R_{10}$ is $C_2$ alkenyl. In some embodiments, at least one $R_{10}$ is $C_3$ alkenyl. In some embodiments, at least one $R_{10}$ is $C_4$ alkenyl. In some embodiments, at least one $R_{10}$ is $C_5$ alkenyl. In some embodiments, at least one $R_{10}$ is $C_6$ alkenyl.

In some embodiments, at least one $R_{10}$ is $C_2$-$C_6$ alkynyl.

In some embodiments, at least one $R_{10}$ is $C_2$ alkynyl. In some embodiments, at least one $R_{10}$ is $C_3$ alkynyl. In some embodiments, at least one $R_{10}$ is $C_4$ alkynyl. In some embodiments, at least one $R_{10}$ is $C_5$ alkynyl. In some embodiments, at least one $R_{10}$ is $C_6$ alkynyl.

In some embodiments, at least one $R_{10}$ is $C_1$-$C_6$ haloalkyl or $C_1$-$C_6$ alkoxy.

In some embodiments, at least one $R_{10}$ is $C_1$-$C_6$ haloalkyl.

In some embodiments, at least one $R_{10}$ is $C_1$-$C_6$ haloalkyl. In some embodiments, at least one $R_{10}$ is halomethyl. In some embodiments, at least one $R_{10}$ is haloethyl. In some embodiments, at least one $R_{10}$ is halopropyl. In some embodiments, at least one $R_{10}$ is halobutyl. In some embodiments, at least one $R_{10}$ is halopentyl. In some embodiments, at least one $R_{10}$ is halohexyl.

In some embodiments, at least one $R_{10}$ is $C_1$-$C_6$ alkoxy.

In some embodiments, at least one $R_{10}$ is $C_1$-$C_6$ alkoxy. In some embodiments, at least one $R_{10}$ is methoxy. In some embodiments, at least one $R_{10}$ is ethoxy. In some embodiments, at least one $R_{10}$ is propoxy. In some embodiments, at least one $R_{10}$ is butoxy. In some embodiments, at least one $R_{10}$ is pentoxy. In some embodiments, at least one $R_{10}$ is hexoxy.

In some embodiments, at least one $R_{10}$ is —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$.

In some embodiments, at least one $R_{10}$ is —$(CH_2)_n$—$OR_{12}$.

In some embodiments, at least one $R_{10}$ is —$OR_{12}$. In some embodiments, at least one $R_{10}$ is —$CH_2$—$OR_{12}$. In some embodiments, at least one $R_{10}$ is —$CH_2CH_2$—$OR_{12}$. In some embodiments, at least one $R_{10}$ is —$CH_2CH_2CH_2$—$OR_{12}$. In some embodiments, at least one $R_{10}$ is —$CH_2CH_2CH_2CH_2$—$OR_{12}$. In some embodiments, at least one $R_{10}$ is —$CH_2CH_2CH_2CH_2CH_2$—$OR_{12}$. In some embodiments, at least one $R_{10}$ is —$CH_2CH_2CH_2CH_2CH_2CH_2$—$OR_{12}$.

In some embodiments, at least one $R_{10}$ is —$(CH_2)_n$—$N(R_{12})_2$.

In some embodiments, at least one $R_{10}$ is —$N(R_{12})$. In some embodiments, at least one $R_{10}$ is —$CH_2$—$N(R_{12})$. In some embodiments, at least one $R_{10}$ is —$CH_2CH_2$—$N(R_{12})$. In some embodiments, at least one $R_{10}$ is —$CH_2CH_2CH_2$—$N(R_{12})$. In some embodiments, at least one $R_{10}$ is —$CH_2CH_2CH_2CH_2$—$N(R_{12})$. In some embodiments, at least one $R_{10}$ is —$CH_2CH_2CH_2CH_2CH_2$—$N(R_{12})$. In some embodiments, at least one $R_{10}$ is —$CH_2CH_2CH_2CH_2CH_2CH_2$—$N(R_{12})$.

In some embodiments, at least one $R_{10}$ is —$(CH_2)_n$—$C(O)R_{12}$.

In some embodiments, at least one $R_{10}$ is —$C(O)R_{12}$. In some embodiments, at least one $R_{10}$ is —$CH_2$—$C(O)R_{12}$. In some embodiments, at least one $R_{10}$ is —$CH_2CH_2$—$C(O)R_{12}$. In some embodiments, at least one $R_{10}$ is —$CH_2CH_2CH_2$—$C(O)R_{12}$. In some embodiments, at least one $R_{10}$ is —$CH_2CH_2CH_2CH_2$—$C(O)R_{12}$. In some embodiments, at least one $R_{10}$ is —$CH_2CH_2CH_2CH_2CH_2$—$C(O)R_{12}$. In some embodiments, at least one $R_{10}$ is —$CH_2CH_2CH_2CH_2CH_2CH_2$—$C(O)R_{12}$.

In some embodiments, at least one $R_{10}$ is —$(CH_2)_n$—C(O)O$R_{12}$.

In some embodiments, at least one $R_{10}$ is —C(O)O$R_{12}$. In some embodiments, at least one $R_{10}$ is —$CH_2$—C(O)O$R_{12}$. In some embodiments, at least one $R_{10}$ is —$CH_2CH_2$—C(O)O$R_{12}$. In some embodiments, at least one $R_{10}$ is —$CH_2CH_2CH_2$—C(O)O$R_{12}$. In some embodiments, at least one $R_{10}$ is —$CH_2CH_2CH_2CH_2$—C(O)O$R_{12}$. In some embodiments, at least one $R_{10}$ is —$CH_2CH_2CH_2CH_2CH_2$—C(O)O$R_{12}$. In some embodiments, at least one $R_{10}$ is —$CH_2CH_2CH_2CH_2CH_2CH_2$—C(O)O$R_{12}$.

In some embodiments, at least one $R_{10}$ is —$(CH_2)_n$—C(O)N$(R_{12})_2$.

In some embodiments, at least one $R_{10}$ is —C(O)N$(R_{12})_2$. In some embodiments, at least one $R_{10}$ is —$CH_2$—C(O)N$(R_{12})_2$. In some embodiments, at least one $R_{10}$ is —$CH_2CH_2$—C(O)N$(R_{12})_2$. In some embodiments, at least one $R_{10}$ is —$CH_2CH_2CH_2$—C(O)N$(R_{12})_2$. In some embodiments, at least one $R_{10}$ is —$CH_2CH_2CH_2CH_2$—C(O)N$(R_{12})_2$. In some embodiments, at least one $R_{10}$ is —$CH_2CH_2CH_2CH_2CH_2$—C(O)N$(R_{12})_2$. In some embodiments, at least one $R_{10}$ is —$CH_2CH_2CH_2CH_2CH_2CH_2$—C(O)N$(R_{12})_2$.

In some embodiments, at least one $R_{10}$ is —$(CH_2)_n$—SO$_2R_{12}$.

In some embodiments, at least one $R_{10}$ is —SO$_2R_{12}$. In some embodiments, at least one $R_{10}$ is —$CH_2$—SO$_2R_{12}$. In some embodiments, at least one $R_{10}$ is —$CH_2CH_2$—SO$_2R_{12}$. In some embodiments, at least one $R_{10}$ is —$CH_2CH_2CH_2$—SO$_2R_{12}$. In some embodiments, at least one $R_{10}$ is —$CH_2CH_2CH_2CH_2$—SO$_2R_{12}$. In some embodiments, at least one $R_{10}$ is —$CH_2CH_2CH_2CH_2CH_2$—SO$_2R_{12}$. In some embodiments, at least one $R_{10}$ is —$CH_2CH_2CH_2CH_2CH_2CH_2$—SO$_2R_{12}$.

In some embodiments, at least one $R_{10}$ is $C_3$-$C_{10}$ cycloalkyl, heterocycle, aryl, and heteroaryl.

In some embodiments, at least one $R_{10}$ is $C_3$-$C_{10}$ cycloalkyl, heterocycle, Aryl, and heteroaryl, wherein the $C_3$-$C_{10}$ cycloalkyl, heterocycle, aryl, and heteroaryl is optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, at least one $R_{10}$ is $C_3$-$C_{10}$ cycloalkyl. In some embodiments, at least one $R_{10}$ is $C_3$-$C_{10}$ cycloalkyl optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, at least one $R_{10}$ is a monocyclic $C_3$-$C_{10}$ cycloalkyl. In some embodiments, at least one $R_{10}$ is a monocyclic $C_3$-$C_{10}$ cycloalkyl optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy. In some embodiments, at least one $R_{10}$ is a polycyclic $C_3$-$C_{10}$ cycloalkyl. In some embodiments, at least one $R_{10}$ is a polycyclic $C_3$-$C_{10}$ cycloalkyl optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, at least one $R_{10}$ is $C_5$-$C_6$ cycloalkyl. In some embodiments, at least one $R_{10}$ is $C_5$-$C_6$ cycloalkyl optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, at least one $R_{10}$ is cyclopropyl, cyclobutyl, cyclopentyl, cyclohexyl, cycloheptyl, cyclooctyl, cyclononyl, or cyclodecyl. In some embodiments, at least one $R_{10}$ is cyclopropyl, cyclobutyl, cyclopentyl, cyclohexyl, cycloheptyl, cyclooctyl, cyclononyl, or cyclodecyl, wherein the cyclopropyl, cyclobutyl, cyclopentyl, cyclohexyl, cycloheptyl, cyclooctyl, cyclononyl, or cyclodecyl is optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, at least one $R_{10}$ is a fused polycyclic $C_3$-$C_{10}$ cycloalkyl. In some embodiments, at least one $R_{10}$ is a fused polycyclic $C_3$-$C_{10}$ cycloalkyl optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy. In some embodiments, at least one $R_{10}$ is a bridged polycyclic $C_3$-$C_{10}$ cycloalkyl. In some embodiments, at least one $R_{10}$ is a bridged polycyclic $C_3$-$C_{10}$ cycloalkyl optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy. In some embodiments, at least one $R_{10}$ is a $C_3$-$C_{10}$ spirocycloalkyl. In some embodiments, at least one $R_{10}$ is a $C_3$-$C_{10}$ spirocycloalkyl optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, at least one $R_{10}$ is $C_3$-$C_{10}$ cycloalkyl optionally substituted with $C_1$-$C_6$ alkyl. In some embodiments, at least one $R_{10}$ is $C_3$-$C_{10}$ cycloalkyl optionally substituted with $C_2$-$C_6$ alkenyl. In some embodiments, at least one $R_{10}$ is $C_3$-$C_{10}$ cycloalkyl optionally substituted with $C_2$-$C_6$ alkynyl. In some embodiments, at least one $R_{10}$ is $C_3$-$C_{10}$ cycloalkyl optionally substituted with $C_1$-$C_6$ haloalkyl. In some embodiments, at least one $R_{10}$ is $C_3$-$C_{10}$ cycloalkyl optionally substituted with $C_1$-$C_6$ alkoxy. In some embodiments, at least one $R_{10}$ is $C_3$-$C_{10}$ cycloalkyl optionally substituted with $C_1$-$C_6$ haloalkoxy.

In some embodiments, at least one $R_{10}$ is heterocycle comprising 1-4 heteroatoms selected from O, N, and S. In some embodiments, at least one $R_{10}$ is heterocycle comprising 1-4 heteroatoms selected from O, N, and S, optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, at least one $R_{10}$ is a monocyclic heterocycle comprising 1-4 heteroatoms selected from O, N, and S. In some embodiments, at least one $R_{10}$ is a monocyclic heterocycle comprising 1-4 heteroatoms selected from O, N, and S, optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy. In some embodiments, at least one $R_{10}$ is a polycyclic heterocycle comprising 1-4 heteroatoms selected from O, N, and S. In some embodiments, at least one $R_{10}$ is a polycyclic heterocycle comprising 1-4 heteroatoms selected from O, N, and S, optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, at least one $R_{10}$ is 3-membered heterocycle comprising 1-4 heteroatoms selected from O, N, and S, optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy. In some embodiments, at least one $R_{10}$ is 4-membered heterocycle comprising 1-4 heteroatoms selected from O, N, and S, optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy. In some embodiments, at least one $R_{10}$ is 5-membered heterocycle comprising 1-4 heteroatoms selected from O, N, and S, optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy. In some embodiments, at least one $R_{10}$ is 6-membered heterocycle comprising 1-4 heteroatoms selected from O, N, and S, optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy. In some embodiments, at least one $R_{10}$ is 7-membered heterocycle comprising 1-4 heteroatoms selected from O, N, and S, optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy. In some embodiments, at least one $R_{10}$ is 8-membered heterocycle comprising 1-4 heteroatoms selected from O, N, and S, optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy. In some embodiments, at least one $R_{10}$ is 9-membered heterocycle comprising 1-4 heteroatoms selected from O, N, and S, optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy. In some embodiments, at least one $R_{10}$ is 10-membered heterocycle comprising 1-4 heteroatoms selected from O, N, and S, optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, at least one $R_{10}$ is 5- to 6-membered heterocycle comprising 1-4 heteroatoms selected from O, N, and S. In some embodiments, at least one $R_{10}$ is 5- to 6-membered heterocycle comprising 1-4 heteroatoms selected from O, N, and S, optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, at least one $R_{10}$ is heterocycle comprising one, two, or three heteroatoms selected from N and O.

In some embodiments, at least one $R_{10}$ is heterocycle comprising 1-4 heteroatoms selected from O, N, and S, optionally substituted with $C_1$-$C_6$ alkyl. In some embodiments, at least one $R_{10}$ is heterocycle comprising 1-4 heteroatoms selected from O, N, and S, optionally substituted with $C_2$-$C_6$ alkenyl. In some embodiments, at least one $R_{10}$ is heterocycle comprising 1-4 heteroatoms selected from O, N, and S, optionally substituted with $C_2$-$C_6$ alkynyl. In some embodiments, at least one $R_{10}$ is heterocycle comprising 1-4 heteroatoms selected from O, N, and S, optionally substituted with $C_1$-$C_6$ haloalkyl. In some embodiments, at least one $R_{10}$ is heterocycle comprising 1-4 heteroatoms selected from O, N, and S, optionally substituted with $C_1$-$C_6$ alkoxy. In some embodiments, at least one $R_{10}$ is heterocycle comprising 1-4 heteroatoms selected from O, N, and S, optionally substituted with $C_1$-$C_6$ haloalkoxy.

In some embodiments, at least one $R_{10}$ is aryl. In some embodiments, at least one $R_{10}$ is aryl optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, at least one $R_{10}$ is $C_6$ aryl (e.g., phenyl). In some embodiments, at least one $R_{10}$ is $C_6$ aryl (e.g., phenyl) optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, at least one $R_{10}$ is aryl optionally substituted with $C_1$-$C_6$ alkyl. In some embodiments, at least one $R_{10}$ is aryl optionally substituted with $C_2$-$C_6$ alkenyl. In some embodiments, at least one $R_{10}$ is aryl optionally substituted with $C_2$-$C_6$ alkynyl. In some embodiments, at least one $R_{10}$ is aryl optionally substituted with $C_1$-$C_6$ haloalkyl. In some embodiments, at least one $R_{10}$ is aryl optionally substituted with $C_1$-$C_6$ alkoxy. In some embodiments, at least one $R_{10}$ is aryl optionally substituted with $C_1$-$C_6$ haloalkoxy.

In some embodiments, at least one $R_{10}$ is heteroaryl comprising 1-4 heteroatoms selected from O, N, and S. In some embodiments, at least one $R_{10}$ is heteroaryl comprising 1-4 heteroatoms selected from O, N, and S, optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, at least one $R_{10}$ is 5- to 6-membered heteroaryl comprising 1-4 heteroatoms selected from O, N, and S. In some embodiments, at least one $R_{10}$ is 5- to 6-membered heteroaryl comprising 1-4 heteroatoms selected from O, N, and S, optionally substituted with $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, at least one $R_{10}$ is heteroaryl comprising 1-4 heteroatoms selected from O, N, and S optionally substituted with $C_1$-$C_6$ alkyl. In some embodiments, at least one $R_{10}$ is heteroaryl comprising 1-4 heteroatoms selected from O, N, and S optionally substituted with $C_2$-$C_6$ alkenyl. In some embodiments, at least one $R_{10}$ is heteroaryl comprising 1-4 heteroatoms selected from O, N, and S optionally substituted with $C_2$-$C_6$ alkynyl. In some embodiments, at least one $R_{10}$ is heteroaryl comprising 1-4 heteroatoms selected from O, N, and S optionally substituted with $C_1$-$C_6$ haloalkyl. In some embodiments, at least one $R_{10}$ is heteroaryl comprising 1-4 heteroatoms selected from O, N, and S optionally substituted with $C_1$-$C_6$ alkoxy. In some embodiments, at least one $R_{10}$ is heteroaryl comprising 1-4 heteroatoms selected from O, N, and S optionally substituted with $C_1$-$C_6$ haloalkoxy.

In some embodiments, at least one $R_{10}$ is

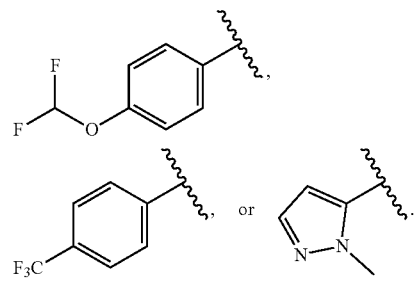

In some embodiments, two $R_{10}$, together with the atoms to which they are attached, form a $C_{6-10}$ aryl or heteroaryl. In some embodiments, two $R_{10}$, together with the atoms to which they are attached, form a $C_{6-10}$ aryl or heteroaryl, wherein the aryl and heteroaryl are optionally substituted with one or more oxo, $=NR_{12}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$.

In some embodiments, two $R_{10}$, together with the atoms to which they are attached, form aryl. In some embodiments, two $R_{10}$, together with the atoms to which they are attached, form aryl, wherein the aryl is optionally substituted with one or more oxo, $=NR_{12}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$.

In some embodiments, two $R_{10}$, together with the atoms to which they are attached, form a $C_6$ aryl (e.g., phenyl). In some embodiments, two $R_{10}$, together with the atoms to which they are attached, form a $C_6$ aryl (e.g., phenyl), wherein the aryl is optionally substituted with one or more oxo, $=NR_{12}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$.

In some embodiments, two $R_{10}$, together with the atoms to which they are attached, form aryl, wherein the aryl is substituted with one oxo, $=NR_{12}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$.

In some embodiments, two $R_{10}$, together with the atoms to which they are attached, form aryl, wherein the aryl is substituted with two substituents selected from oxo, $=NR_{12}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$.

In some embodiments, two $R_{10}$, together with the atoms to which they are attached, form aryl, wherein the aryl is substituted with three substituents selected from oxo, $=NR_{12}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$.

In some embodiments, two $R_{10}$, together with the atoms to which they are attached, form aryl, wherein the aryl is substituted with four substituents selected from oxo, $=NR_{12}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$.

In some embodiments, two $R_{10}$, together with the atoms to which they are attached, form aryl optionally substituted with one or more oxo, $=NR_{12}$, halogen, —CN, or —$NO_2$.

In some embodiments, two $R_{10}$, together with the atoms to which they are attached, form aryl optionally substituted with one or more oxo.

In some embodiments, two $R_{10}$, together with the atoms to which they are attached, form aryl optionally substituted with one or more $=NR_{12}$.

In some embodiments, two $R_{10}$, together with the atoms to which they are attached, form aryl optionally substituted with one or more halogen. In some embodiments, two $R_{10}$, together with the atoms to which they are attached, form aryl optionally substituted with one or more F. In some embodiments, two $R_{10}$, together with the atoms to which they are attached, form aryl is optionally substituted with one or more Cl. In some embodiments, two $R_{10}$, together with the atoms to which they are attached, form aryl optionally substituted with one or more Br. In some embodiments, two $R_{10}$, together with the atoms to which they are attached, form aryl optionally substituted with one or more I.

In some embodiments, two $R_{10}$, together with the atoms to which they are attached, form aryl, wherein the aryl is optionally substituted with one or more —CN.

In some embodiments, two $R_{10}$, together with the atoms to which they are attached, form aryl optionally substituted with one or more —$NO_2$.

In some embodiments, two $R_{10}$, together with the atoms to which they are attached, form aryl optionally substituted with one or more $C_1$-$C_6$ alkyl, $C_2$-$C_6$ alkenyl, $C_2$-$C_6$ alkynyl, $C_1$-$C_6$ haloalkyl, $C_1$-$C_6$ alkoxy.

In some embodiments, two $R_{10}$, together with the atoms to which they are attached, form aryl optionally substituted with one or more $C_1$-$C_6$ alkyl In some embodiments, two $R_{10}$, together with the atoms to which they are attached, form aryl optionally substituted with one or more $C_2$-$C_6$ alkenyl.

In some embodiments, two $R_{10}$, together with the atoms to which they are attached, form aryl optionally substituted with one or more $C_2$-$C_6$ alkynyl.

In some embodiments, two $R_{10}$, together with the atoms to which they are attached, form aryl optionally substituted with one or more $C_1$-$C_6$ haloalkyl.

In some embodiments, two $R_{10}$, together with the atoms to which they are attached, form aryl optionally substituted with one or more $C_1$-$C_6$ alkoxy.

In some embodiments, two $R_{10}$, together with the atoms to which they are attached, form aryl optionally substituted with one or more —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$.

In some embodiments, two $R_{10}$, together with the atoms to which they are attached, form aryl optionally substituted with one or more —$(CH_2)_n$—$OR_{12}$. In some embodiments, two $R_{10}$, together with the atoms to which they are attached, form aryl optionally substituted with one or more —$OR_{12}$.

In some embodiments, two $R_{10}$, together with the atoms to which they are attached, form aryl optionally substituted with one or more —$(CH_2)_n$—$N(R_{12})_2$. In some embodiments, two $R_{10}$, together with the atoms to which they are attached, form aryl optionally substituted with one or more —$N(R_{12})_2$.

In some embodiments, two $R_{10}$, together with the atoms to which they are attached, form aryl optionally substituted with one or more —$(CH_2)_n$—$C(O)R_{12}$. In some embodiments, two $R_{10}$, together with the atoms to which they are attached, form aryl optionally substituted with one or more —$C(O)R_{12}$.

In some embodiments, two $R_{10}$, together with the atoms to which they are attached, form aryl optionally substituted with one or more —$(CH_2)_n$—$C(O)OR_{12}$. In some embodiments, two $R_{10}$, together with the atoms to which they are attached, form aryl optionally substituted with one or more —$C(O)OR_{12}$.

In some embodiments, two $R_{10}$, together with the atoms to which they are attached, form aryl optionally substituted with one or more —$(CH_2)_n$—$C(O)N(R_{12})_2$. In some embodiments, two $R_{10}$, together with the atoms to which they are attached, form aryl optionally substituted with one or more —$C(O)N(R_{12})_2$.

In some embodiments, two $R_{10}$, together with the atoms to which they are attached, form aryl optionally substituted with one or more —$(CH_2)_n$—$SO_2R_{12}$. In some embodiments, two $R_{10}$, together with the atoms to which they are attached, form aryl optionally substituted with one or more —$SO_2R_{12}$.

In some embodiments, two $R_{10}$, together with the atoms to which they are attached, form a heteroaryl comprising 1-4 heteroatoms selected from O, N, and S. In some embodiments, two $R_{10}$, together with the atoms to which they are attached, form a heteroaryl comprising 1-4 heteroatoms selected from O, N, and S, optionally substituted with one or more oxo, $=NR_{12}$, halogen, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_n$—$OR_{12}$, —$(CH_2)_n$—$N(R_{12})_2$, —$(CH_2)_n$—$C(O)R_{12}$, —$(CH_2)_n$—$C(O)OR_{12}$, —$(CH_2)_n$—$C(O)N(R_{12})_2$, —$(CH_2)_n$—$SO_2R_{12}$.

In some embodiments, two $R_{10}$, together with the atoms to which they are attached, form a 5- to 6-membered heteroaryl comprising 1-4 heteroatoms selected from O, N, and S. In some embodiments, two $R_{10}$, together with the atoms to which they are attached, form a 5- to 6-membered heteroaryl comprising 1-4 heteroatoms selected from O, N, and S, optionally substituted with one or more oxo, $=NR_{12}$, halogen, —CN, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_n$—OR$_{12}$, —(CH$_2$)$_n$—N(R$_{12}$)$_2$, —(CH$_2$)$_n$—C(O)R$_{12}$, —(CH$_2$)$_n$—C(O)OR$_{12}$, —(CH$_2$)$_n$—C(O)N(R$_{12}$)$_2$, —(CH$_2$)$_n$—SO$_2$R$_{12}$.

In some embodiments, two R$_{10}$, together with the atoms to which they are attached, form a heteroaryl comprising 1-4 heteroatoms selected from O, N, and S, optionally substituted with one or more oxo, $=NR_{12}$, halogen, —CN, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_n$—OR$_{12}$, —(CH$_2$)$_n$—N(R$_{12}$)$_2$, —(CH$_2$)$_n$—C(O)R$_{12}$, —(CH$_2$)$_n$—C(O)OR$_{12}$, —(CH$_2$)$_n$—C(O)N(R$_{12}$)$_2$, —(CH$_2$)$_n$—SO$_2$R$_{12}$.

In some embodiments, two R$_{10}$, together with the atoms to which they are attached, form a heteroaryl comprising 1-4 heteroatoms selected from O, N, and S, substituted with one oxo, $=NR_{12}$, halogen, —CN, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_n$—OR$_{12}$, —(CH$_2$)$_n$—N(R$_{12}$)$_2$, —(CH$_2$)$_n$—C(O)R$_{12}$, —(CH$_2$)$_n$—C(O)OR$_{12}$, —(CH$_2$)$_n$—C(O)N(R$_{12}$)$_2$, —(CH$_2$)$_n$—SO$_2$R$_{12}$.

In some embodiments, two R$_{10}$, together with the atoms to which they are attached, form a heteroaryl comprising 1-4 heteroatoms selected from O, N, and S, substituted with two substituents selected from oxo, $=NR_{12}$, halogen, —CN, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_n$—OR$_{12}$, —(CH$_2$)$_n$—N(R$_{12}$)$_2$, —(CH$_2$)$_n$—C(O)R$_{12}$, —(CH$_2$)$_n$—C(O)OR$_{12}$, —(CH$_2$)$_n$—C(O)N(R$_{12}$)$_2$, —(CH$_2$)$_n$—SO$_2$R$_{12}$.

In some embodiments, two R$_{10}$, together with the atoms to which they are attached, form a heteroaryl comprising 1-4 heteroatoms selected from O, N, and S, substituted with three substituents selected from oxo, $=NR_{12}$, halogen, —CN, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_n$—OR$_{12}$, —(CH$_2$)$_n$—N(R$_{12}$)$_2$, —(CH$_2$)$_n$—C(O)R$_{12}$, —(CH$_2$)$_n$—C(O)OR$_{12}$, —(CH$_2$)$_n$—C(O)N(R$_{12}$)$_2$, —(CH$_2$)$_n$—SO$_2$R$_{12}$.

In some embodiments, two R$_{10}$, together with the atoms to which they are attached, form a heteroaryl comprising 1-4 heteroatoms selected from O, N, and S, substituted with four substituents selected from oxo, $=NR_{12}$, halogen, —CN, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_n$—OR$_{12}$, —(CH$_2$)$_n$—N(R$_{12}$)$_2$, —(CH$_2$)$_n$—C(O)R$_{12}$, —(CH$_2$)$_n$—C(O)OR$_{12}$, —(CH$_2$)$_n$—C(O)N(R$_{12}$)$_2$, —(CH$_2$)$_n$—SO$_2$R$_{12}$.

In some embodiments, two R$_{10}$, together with the atoms to which they are attached, form a heteroaryl comprising 1-4 heteroatoms selected from O, N, and S, optionally substituted with one or more oxo, $=NR_{12}$, halogen, —CN, or —NO$_2$.

In some embodiments, two R$_{10}$, together with the atoms to which they are attached, form a heteroaryl comprising 1-4 heteroatoms selected from O, N, and S, optionally substituted with one or more oxo.

In some embodiments, two R$_{10}$, together with the atoms to which they are attached, form a heteroaryl comprising 1-4 heteroatoms selected from O, N, and S, optionally substituted with one or more $=NR_{12}$.

In some embodiments, two R$_{10}$, together with the atoms to which they are attached, form a heteroaryl comprising 1-4 heteroatoms selected from O, N, and S, optionally substituted with one or more halogen. In some embodiments, two R$_{10}$, together with the atoms to which they are attached, form a heteroaryl comprising 1-4 heteroatoms selected from O, N, and S, optionally substituted with one or more F.

In some embodiments, two R$_{10}$, together with the atoms to which they are attached, form a heteroaryl comprising 1-4 heteroatoms selected from O, N, and S, optionally substituted with one or more Cl. In some embodiments, two R$_{10}$, together with the atoms to which they are attached, form a heteroaryl comprising 1-4 heteroatoms selected from O, N, and S, optionally substituted with one or more Br. In some embodiments, two R$_{10}$, together with the atoms to which they are attached, form a heteroaryl comprising 1-4 heteroatoms selected from O, N, and S, optionally substituted with one or more I.

In some embodiments, two R$_{10}$, together with the atoms to which they are attached, form a heteroaryl comprising 1-4 heteroatoms selected from O, N, and S, optionally substituted with one or more —CN.

In some embodiments, two R$_{10}$, together with the atoms to which they are attached, form a heteroaryl comprising 1-4 heteroatoms selected from O, N, and S, optionally substituted with one or more —NO$_2$.

In some embodiments, two R$_{10}$, together with the atoms to which they are attached, form a heteroaryl comprising 1-4 heteroatoms selected from O, N, and S, optionally substituted with one or more $C_1$-$C_6$ alkyl, $C_2$-$C_6$ alkenyl, $C_2$-$C_6$ alkynyl, $C_1$-$C_6$ haloalkyl, $C_1$-$C_6$ alkoxy.

In some embodiments, two R$_{10}$, together with the atoms to which they are attached, form a heteroaryl comprising 1-4 heteroatoms selected from O, N, and S, optionally substituted with one or more $C_1$-$C_6$ alkyl.

In some embodiments, two R$_{10}$, together with the atoms to which they are attached, form a heteroaryl comprising 1-4 heteroatoms selected from O, N, and S, optionally substituted with one or more $C_2$-$C_6$ alkenyl.

In some embodiments, two R$_{10}$, together with the atoms to which they are attached, form a heteroaryl comprising 1-4 heteroatoms selected from O, N, and S, optionally substituted with one or more $C_2$-$C_6$ alkynyl.

In some embodiments, two R$_{10}$, together with the atoms to which they are attached, form a heteroaryl comprising 1-4 heteroatoms selected from O, N, and S, optionally substituted with one or more $C_1$-$C_6$ haloalkyl.

In some embodiments, two R$_{10}$, together with the atoms to which they are attached, form a heteroaryl comprising 1-4 heteroatoms selected from O, N, and S, optionally substituted with one or more $C_1$-$C_6$ alkoxy.

In some embodiments, two R$_{10}$, together with the atoms to which they are attached, form a heteroaryl comprising 1-4 heteroatoms selected from O, N, and S, optionally substituted with one or more —(CH$_2$)$_n$—OR$_{12}$, —(CH$_2$)$_n$—N(R$_{12}$)$_2$, —(CH$_2$)$_n$—C(O)R$_{12}$, —(CH$_2$)$_n$—C(O)OR$_{12}$, —(CH$_2$)$_n$—C(O)N(R$_{12}$)$_2$, —(CH$_2$)$_n$—SO$_2$R$_{12}$.

In some embodiments, two R$_{10}$, together with the atoms to which they are attached, form a heteroaryl comprising 1-4 heteroatoms selected from O, N, and S, optionally substituted with one or more —(CH$_2$)$_n$—OR$_{12}$. In some embodiments, two R$_{10}$, together with the atoms to which they are attached, form a heteroaryl comprising 1-4 heteroatoms selected from O, N, and S, optionally substituted with one or more —OR$_{12}$.

In some embodiments, two R$_{10}$, together with the atoms to which they are attached, form a heteroaryl comprising 1-4 heteroatoms selected from O, N, and S, optionally substituted with one or more —(CH$_2$)$_n$—N(R$_{12}$)$_2$. In some embodiments, two R$_{10}$, together with the atoms to which they are attached, form a heteroaryl comprising 1-4 heteroatoms selected from O, N, and S, optionally substituted with one or more —N(R$_{12}$)$_2$.

In some embodiments, two $R_{10}$, together with the atoms to which they are attached, form a heteroaryl comprising 1-4 heteroatoms selected from O, N, and S, optionally substituted with one or more —$(CH_2)_n$—$C(O)R_{12}$. In some embodiments, two $R_{10}$, together with the atoms to which they are attached, form a heteroaryl comprising 1-4 heteroatoms selected from O, N, and S, optionally substituted with one or more —$C(O)R_{12}$.

In some embodiments, two $R_{10}$, together with the atoms to which they are attached, form a heteroaryl comprising 1-4 heteroatoms selected from O, N, and S, optionally substituted with one or more —$(CH_2)_n$—$C(O)OR_{12}$. In some embodiments, two $R_{10}$, together with the atoms to which they are attached, form a heteroaryl comprising 1-4 heteroatoms selected from O, N, and S, optionally substituted with one or more —$C(O)OR_{12}$.

In some embodiments, two $R_{10}$, together with the atoms to which they are attached, form a heteroaryl comprising 1-4 heteroatoms selected from O, N, and S, optionally substituted with one or more —$(CH_2)_n$—$C(O)N(R_{12})_2$. In some embodiments, two $R_{10}$, together with the atoms to which they are attached, form a heteroaryl comprising 1-4 heteroatoms selected from O, N, and S, optionally substituted with one or more —$C(O)N(R_{12})_2$.

In some embodiments, two $R_{10}$, together with the atoms to which they are attached, form a heteroaryl comprising 1-4 heteroatoms selected from O, N, and S, optionally substituted with one or more —$(CH_2)_n$—$SO_2R_{12}$. In some embodiments, two $R_{10}$, together with the atoms to which they are attached, form a heteroaryl comprising 1-4 heteroatoms selected from O, N, and S, optionally substituted with one or more —$SO_2R_{12}$.

In some embodiments, two $R_{10}$, together with the atoms to which they are attached, form

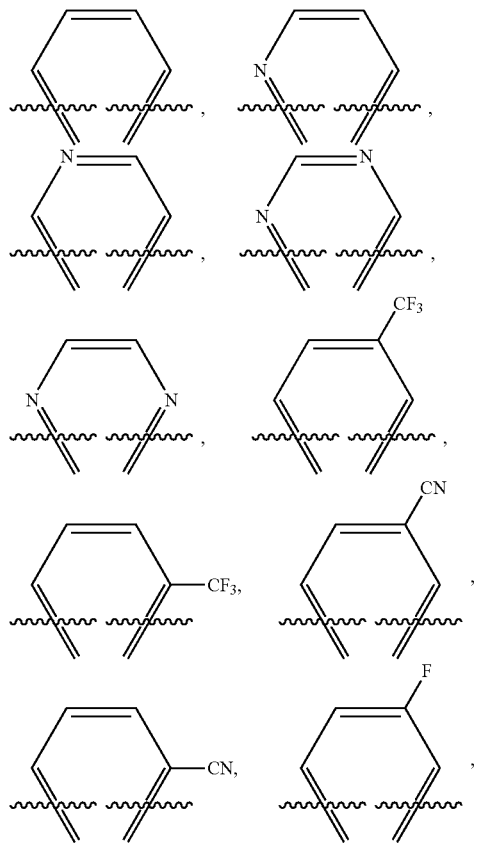

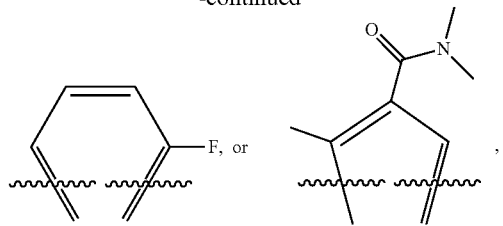

wherein " $\sim\!\sim\!\sim$ " signifies the point at which the two $R_{10}$ attach to the ring atoms of the heterocycle formed by $R_1$ and $R_2$.

In some embodiments, two $R_{10}$, together with the atoms to which they are attached, form

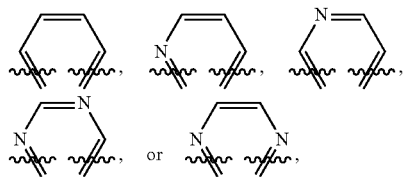

wherein " $\sim\!\sim\!\sim$ " signifies the point at which the two $R_{10}$ attach to the ring atoms of the heterocycle formed by $R_1$ and $R_2$.

In some embodiments, two $R_{10}$, together with the atoms to which they are attached, form

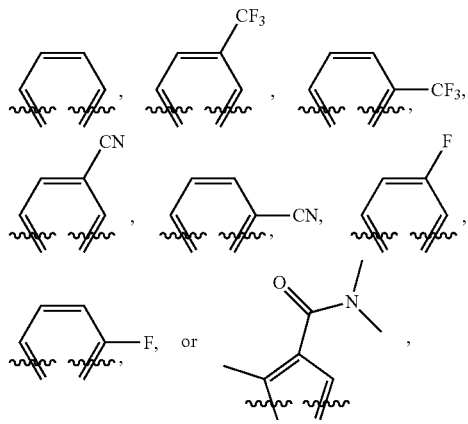

wherein " $\sim\!\sim\!\sim$ " signifies the point at which the two $R_{10}$ attach to the ring atoms of the heterocycle formed by $R_1$ and $R_2$.

In some embodiments, two $R_{10}$, together with the atoms to which they are attached, form

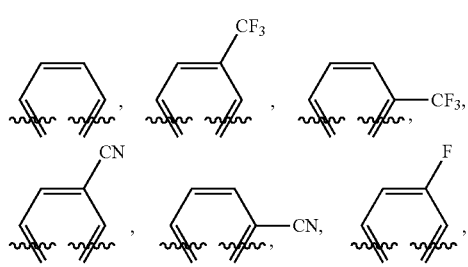

-continued

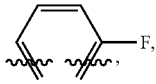

wherein " ⌇ " signifies the point at which the two $R_{10}$ attach to the ring atoms of the heterocycle formed by $R_1$ and $R_2$.

In some embodiments, two $R_{10}$, together with the atoms to which they are attached, form

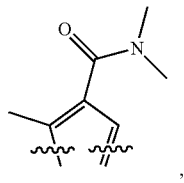

wherein " ⌇ " signifies the point at which the two $R_{10}$ attach to the ring atoms of the heterocycle formed by $R_1$ and $R_2$.

In some embodiments, two $R_{10}$, together with the atoms to which they are attached, form,

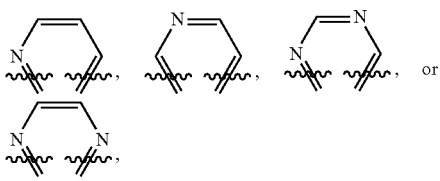

wherein " ⌇ " signifies the point at which the two $R_{10}$ attach to the ring atoms of the heterocycle formed by $R_1$ and $R_2$.

In some embodiments, $R_{11}$ is H, $C_1$-$C_6$ alkyl, $C_2$-$C_6$ alkenyl, or $C_2$-$C_6$ alkynyl.

In some embodiments, $R_{11}$ is H.

In some embodiments, $R_{11}$ is $C_1$-$C_6$ alkyl, $C_2$-$C_6$ alkenyl, or $C_2$-$C_6$ alkynyl.

In some embodiments, $R_{11}$ is $C_1$-$C_6$ alkyl.

In some embodiments, $R_{11}$ is methyl. In some embodiments, $R_{11}$ is ethyl. In some embodiments, $R_{11}$ is propyl. In some embodiments, $R_{11}$ is n-propyl. In some embodiments, $R_{11}$ is isopropyl. In some embodiments, $R_{11}$ is butyl. In some embodiments, $R_{11}$ is n-butyl. In some embodiments, $R_{11}$ is isobutyl. In some embodiments, $R_{11}$ is sec-butyl. In some embodiments, $R_{11}$ is tert-butyl. In some embodiments, $R_{11}$ is pentyl. In some embodiments, $R_{11}$ is hexyl.

In some embodiments, $R_{11}$ is $C_2$-$C_6$ alkenyl.

In some embodiments, $R_{11}$ is $C_2$-$C_6$ alkynyl.

In some embodiments, each $R_{12}$ and $R_{13}$ at each occurrence is independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_q$—O—C(O)—$(CH_2)_r$—$R_{14}$, —$(CH_2)_q$—NH—C(O)—$(CH_2)_r$—$R_{14}$, —$(CH_2)_q$—O—C(O)—$(CH_2)_r$—$OR_{14}$, —$(CH_2)_q$—NH—C(O)—$(CH_2)_r$—$OR_{14}$, —$(CH_2)_q$—O—$(CH_2)_r$—$R_{14}$, —$(CH_2)_q$—NH—$(CH_2)_r$—$R_{14}$, —$(CH_2)_q$—O—$(CH_2)_r$—$OR_{14}$, —$(CH_2)_q$—NH—$(CH_2)_r$—$OR_{14}$, $C_3$-$C_{10}$ cycloalkyl, heterocycle comprising 1-4 heteroatoms selected from O, N, and S, aryl, or heteroaryl comprising 1-4 heteroatoms selected from N, O, and S.

In some embodiments, each $R_{12}$ and $R_{13}$ at each occurrence is independently $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_q$—O—C(O)—$(CH_2)_r$—$R_{14}$, —$(CH_2)_q$—NH—C(O)—$(CH_2)_r$—$R_{14}$, —$(CH_2)_q$—O—C(O)—$(CH_2)_r$—$OR_{14}$, —$(CH_2)_q$—NH—C(O)—$(CH_2)_r$—$OR_{14}$, —$(CH_2)_q$—O—$(CH_2)_r$—$R_{14}$, —$(CH_2)_q$—NH—$(CH_2)_r$—$R_{14}$, —$(CH_2)_q$—O—$(CH_2)_r$—$OR_{14}$, —$(CH_2)_q$—NH—$(CH_2)_r$—$OR_{14}$, $C_3$-$C_{10}$ cycloalkyl, heterocycle comprising 1-4 heteroatoms selected from O, N, and S, aryl, or heteroaryl comprising 1-4 heteroatoms selected from N, O, and S.

In some embodiments, each $R_{12}$ and $R_{13}$ at each occurrence is independently H.

In some embodiments, $R_{12}$ is H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_q$—O—C(O)—$(CH_2)_r$—$R_{14}$, —$(CH_2)_q$—NH—C(O)—$(CH_2)_r$—$R_{14}$, —$(CH_2)_q$—O—C(O)—$(CH_2)_r$—$OR_{14}$, —$(CH_2)_q$—NH—C(O)—$(CH_2)_r$—$OR_{14}$, —$(CH_2)_q$—O—$(CH_2)_r$—$R_{14}$, —$(CH_2)_q$—NH—$(CH_2)_r$—$R_{14}$, —$(CH_2)_q$—O—$(CH_2)_r$—$OR_{14}$, —$(CH_2)_q$—NH—$(CH_2)_r$—$OR_{14}$, $C_3$-$C_{10}$ cycloalkyl, heterocycle comprising 1-4 heteroatoms selected from O, N, and S, aryl, or heteroaryl comprising 1-4 heteroatoms selected from N, O, and S.

In some embodiments, $R_{12}$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_q$—O—C(O)—$(CH_2)_r$—$R_{14}$, —$(CH_2)_q$—NH—C(O)—$(CH_2)_r$—$R_{14}$, —$(CH_2)_q$—O—C(O)—$(CH_2)_r$—$OR_{14}$, —$(CH_2)_q$—NH—C(O)—$(CH_2)_r$—$OR_{14}$, —$(CH_2)_q$—O—$(CH_2)_r$—$R_{14}$, —$(CH_2)_q$—NH—$(CH_2)_r$—$R_{14}$, —$(CH_2)_q$—O—$(CH_2)_r$—$OR_{14}$, —$(CH_2)_q$—NH—$(CH_2)_r$—$OR_{14}$, $C_3$-$C_{10}$ cycloalkyl, heterocycle comprising 1-4 heteroatoms selected from O, N, and S, aryl, or heteroaryl comprising 1-4 heteroatoms selected from N, O, and S.

In some embodiments, $R_{12}$ is H.

In some embodiments, $R_{12}$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_{12}$ is $C_1$-$C_6$ alkyl.

In some embodiments, $R_{12}$ is methyl. In some embodiments, $R_{12}$ is ethyl. In some embodiments, $R_{12}$ is propyl. In some embodiments, $R_{12}$ is n-propyl. In some embodiments, $R_{12}$ is isopropyl. In some embodiments, $R_{12}$ is butyl. In some embodiments, $R_{12}$ is n-butyl. In some embodiments, $R_{12}$ is isobutyl. In some embodiments, $R_{12}$ is sec-butyl. In some embodiments, $R_{12}$ is tert-butyl. In some embodiments, $R_{12}$ is pentyl. In some embodiments, $R_{12}$ is hexyl.

In some embodiments, $R_{12}$ is $C_2$-$C_6$ alkenyl. In some embodiments, $R_{12}$ is $C_2$-$C_6$ alkynyl.

In some embodiments, $R_{12}$ is $C_1$-$C_6$ haloalkyl or $C_1$-$C_6$ alkoxy.

In some embodiments, $R_{12}$ is $C_1$-$C_6$ haloalkyl. In some embodiments, $R_{12}$ is halomethyl. In some embodiments, $R_{12}$ is haloethyl. In some embodiments, $R_{12}$ is halopropyl. In some embodiments, $R_{12}$ is halobutyl. In some embodiments, $R_{12}$ is halopentyl. In some embodiments, $R_{12}$ is halohexyl.

In some embodiments, $R_{12}$ is $C_1$-$C_6$ alkoxy. In some embodiments, $R_{12}$ is $C_1$-$C_6$ alkoxy. In some embodiments, $R_{12}$ is methoxy. In some embodiments, $R_{12}$ is ethoxy. In some embodiments, $R_{12}$ is propoxy. In some embodiments, $R_{12}$ is butoxy. In some embodiments, $R_{12}$ is pentoxy. In some embodiments, $R_{12}$ is hexoxy.

In some embodiments, $R_{12}$ is —$(CH_2)_q$—O—C(O)—$(CH_2)_r$—$R_{14}$, —$(CH_2)_q$—NH—C(O)—$(CH_2)_r$—$R_{14}$, —$(CH_2)_q$—O—C(O)—$(CH_2)_r$—$OR_{14}$, —$(CH_2)_q$—NH—C(O)—$(CH_2)_r$—$OR_{14}$, —$(CH_2)_q$—O—$(CH_2)_r$—$R_{14}$, —$(CH_2)_q$—NH—$(CH_2)_r$—$R_{14}$, —$(CH_2)_q$—O—$(CH_2)_r$—$OR_{14}$, or —$(CH_2)_q$—NH—$(CH_2)_r$—$OR_{14}$.

In some embodiments, $R_{12}$ is —$(CH_2)_q$—O—C(O)—$(CH_2)_r$—$R_{14}$. In some embodiments, $R_{12}$ is —O—C(O)—$(CH_2)_r$—$R_{14}$. In some embodiments, $R_{12}$ is —$(CH_2)_q$—O—C(O)—$R_{14}$.

In some embodiments, $R_{12}$ is —$(CH_2)_q$—NH—C(O)—$(CH_2)_r$—$R_{14}$. In some embodiments, $R_{12}$ is —NH—C(O)—$(CH_2)_r$—$R_{14}$. In some embodiments, $R_{12}$ is —$(CH_2)_q$—NH—C(O)—$R_{14}$.

In some embodiments, $R_{12}$ is —$(CH_2)_q$—O—C(O)—$(CH_2)_r$—$OR_{14}$. In some embodiments, $R_{12}$ is —O—C(O)—$(CH_2)_r$—$R_{14}$. In some embodiments, $R_{12}$ is —$(CH_2)_q$—O—C(O)—$R_{14}$.

In some embodiments, $R_{12}$ is —$(CH_2)_q$—NH—C(O)—$(CH_2)_r$—$OR_{14}$. In some embodiments, $R_{12}$ is —NH—$(CH_2)_r$—$R_{14}$. In some embodiments, $R_{12}$ is —$(CH_2)_q$—NH—$R_{14}$.

In some embodiments, $R_{12}$ is —$(CH_2)_q$—O—$(CH_2)_r$—$R_{14}$. In some embodiments, $R_{12}$ is —O—$(CH_2)_r$—$R_{14}$. In some embodiments, $R_{12}$ is —$(CH_2)_q$—O—$R_{14}$.

In some embodiments, $R_{12}$ is —$(CH_2)_q$—NH—$(CH_2)_r$—$R_{14}$. In some embodiments, $R_{12}$ is —NH—$(CH_2)_r$—$R_{14}$. In some embodiments, $R_{12}$ is —$(CH_2)_q$—NH—$R_{14}$.

In some embodiments, $R_{12}$ is —$(CH_2)_q$—O—$(CH_2)_r$—$OR_{14}$. In some embodiments, $R_{12}$ is —O—$(CH_2)_r$—$OR_{14}$. In some embodiments, $R_{12}$ is —$(CH_2)_q$—O—$OR_{14}$.

In some embodiments, $R_{12}$ is —$(CH_2)_q$—NH—$(CH_2)_r$—$OR_{14}$. In some embodiments, $R_{12}$ is —NH—$(CH_2)_r$—$OR_{14}$. In some embodiments, $R_{12}$ is —$(CH_2)_q$—NH—$OR_{14}$.

In some embodiments, $R_{12}$ is $C_3$-$C_{10}$ cycloalkyl, heterocycle comprising 1-4 heteroatoms selected from O, N, and S, aryl, or heteroaryl comprising 1-4 heteroatoms selected from N, O, and S.

In some embodiments, $R_{12}$ is $C_3$-$C_{10}$ cycloalkyl or a heterocycle comprising 1-4 heteroatoms selected from O, N, and S.

In some embodiments, $R_{12}$ is $C_3$-$C_{10}$ cycloalkyl.
In some embodiments, $R_{12}$ is $C_5$-$C_6$ cycloalkyl.
In some embodiments, $R_{12}$ is cyclopropyl, cyclobutyl, cyclopentyl, cyclohexyl, cycloheptyl, cyclooctyl, cyclononyl, or cyclodecyl.

In some embodiments, $R_{12}$ is a fused polycyclic $C_3$-$C_{10}$ cycloalkyl. In some embodiments, $R_{12}$ is a bridged polycyclic $C_3$-$C_{10}$ cycloalkyl. In some embodiments, $R_{12}$ is a $C_3$-$C_{10}$ spirocycloalkyl.

In some embodiments, $R_{12}$ is heterocycle comprising 1-4 heteroatoms selected from O, N, and S.

In some embodiments, $R_{12}$ is a heterocycle comprising one heteroatom selected from O, N, and S. In some embodiments, $R_{12}$ is a heterocycle comprising one heteroatom which is N. In some embodiments, $R_{12}$ is a heterocycle comprising two heteroatoms selected from O, N, and S. In some embodiments, $R_{12}$ is a heterocycle comprising three heteroatoms selected from O, N, and S. In some embodiments, $R_{12}$ is a heterocycle comprising four heteroatoms selected from O, N, and S.

In some embodiments, $R_{12}$ is a 5- to 6-membered saturated or partially unsaturated heterocycle comprising 1-4 heteroatoms selected from O, N, and S.

In some embodiments, $R_{12}$ is a monocyclic heterocycle comprising 1-4 heteroatoms selected from O, N, and S. In some embodiments, $R_{12}$ is a polycyclic heterocycle comprising 1-4 heteroatoms selected from O, N, and S.

In some embodiments, $R_{12}$ is a fused polycyclic heterocycle comprising 1-4 heteroatoms selected from O, N, and S. In some embodiments, $R_{12}$ is a bridged polycyclic heterocycle comprising 1-4 heteroatoms selected from O, N, and S. In some embodiments, $R_{12}$ is a spiroheterocycle comprising 1-4 heteroatoms selected from O, N, and S.

In some embodiments, $R_{12}$ is aryl. In some embodiments, $R_{12}$ is $C_6$ aryl (e.g., phenyl).

In some embodiments, $R_{12}$ is a heteroaryl comprising 1-4 heteroatoms selected from O, N, and S In some embodiments, $R_{12}$ is 5- to 6-membered heteroaryl comprising 1-4 heteroatoms selected from O, N, and S.

In some embodiments, $R_{12}$ is heteroaryl comprising one heteroatom selected from O, N, and S. In some embodiments, $R_{12}$ is heteroaryl comprising two heteroatoms selected from O, N, and S. In some embodiments, $R_{12}$ is heteroaryl comprising three heteroatoms selected from O, N, and S. In some embodiments, $R_{12}$ is heteroaryl comprising four heteroatoms selected from O, N, and S.

In some embodiments, $R_{13}$ is H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_q$—O—C(O)—$(CH_2)_r$—$R_{14}$, —$(CH_2)_q$—NH—C(O)—$(CH_2)_r$—$R_{14}$, —$(CH_2)_q$—O—C(O)—$(CH_2)_r$—$OR_{14}$, —$(CH_2)_q$—NH—C(O)—$(CH_2)_r$—$OR_{14}$, —$(CH_2)_q$—O—$(CH_2)_r$—$R_{14}$, —$(CH_2)_q$—NH—$(CH_2)_r$—$R_{14}$, —$(CH_2)_q$—O—$(CH_2)_r$—$OR_{14}$, —$(CH_2)_q$—NH—$(CH_2)_r$—$OR_{14}$, $C_3$-$C_{10}$ cycloalkyl, heterocycle comprising 1-4 heteroatoms selected from O, N, and S, aryl, or heteroaryl comprising 1-4 heteroatoms selected from N, O, and S.

In some embodiments, $R_{13}$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —$(CH_2)_q$—O—C(O)—$(CH_2)_r$—$R_{14}$, —$(CH_2)_q$—NH—C(O)—$(CH_2)_r$—$R_{14}$, —$(CH_2)_q$—O—C(O)—$(CH_2)_r$—$OR_{14}$, —$(CH_2)_q$—NH—C(O)—$(CH_2)_r$—$OR_{14}$, —$(CH_2)_q$—O—$(CH_2)_r$—$R_{14}$, —$(CH_2)_q$—NH—$(CH_2)_r$—$R_{14}$, —$(CH_2)_q$—O—$(CH_2)_r$—$OR_{14}$, —$(CH_2)_q$—NH—$(CH_2)_r$—$OR_{14}$, $C_3$-$C_{10}$ cycloalkyl, heterocycle comprising 1-4 heteroatoms selected from O, N, and S, aryl, or heteroaryl comprising 1-4 heteroatoms selected from N, O, and S.

In some embodiments, $R_{13}$ is H.
In some embodiments, $R_{13}$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_{13}$ is $C_1$-$C_6$ alkyl.

In some embodiments, $R_{13}$ is methyl. In some embodiments, $R_{13}$ is ethyl. In some embodiments, $R_{13}$ is propyl. In some embodiments, $R_{13}$ is n-propyl. In some embodiments, $R_{13}$ is isopropyl. In some embodiments, $R_{13}$ is butyl. In some embodiments, $R_{13}$ is n-butyl. In some embodiments, $R_{13}$ is isobutyl. In some embodiments, $R_{13}$ is sec-butyl. In some embodiments, $R_{13}$ is tert-butyl. In some embodiments, $R_{13}$ is pentyl. In some embodiments, $R_{13}$ is hexyl.

In some embodiments, $R_{13}$ is $C_2$-$C_6$ alkenyl. In some embodiments, $R_{13}$ is $C_2$-$C_6$ alkynyl.

In some embodiments, $R_{13}$ is $C_1$-$C_6$ haloalkyl or $C_1$-$C_6$ alkoxy.

In some embodiments, $R_{13}$ is $C_1$-$C_6$ haloalkyl. In some embodiments, $R_{13}$ is halomethyl. In some embodiments, $R_{13}$ is haloethyl. In some embodiments, $R_{13}$ is halopropyl. In some embodiments, $R_{13}$ is halobutyl. In some embodiments, $R_{13}$ is halopentyl. In some embodiments, $R_{13}$ is halohexyl.

In some embodiments, $R_{13}$ is $C_1$-$C_6$ alkoxy. In some embodiments, $R_{13}$ is $C_1$-$C_6$ alkoxy. In some embodiments, $R_{13}$ is methoxy. In some embodiments, $R_{13}$ is ethoxy. In some embodiments, $R_{13}$ is propoxy. In some embodiments, $R_{13}$ is butoxy. In some embodiments, $R_{13}$ is pentoxy. In some embodiments, $R_{13}$ is hexoxy.

In some embodiments, $R_{13}$ is —$(CH_2)_q$—O—C(O)—$(CH_2)_r$—$R_{14}$, —$(CH_2)_q$—NH—C(O)—$(CH_2)_r$—$R_{14}$, —$(CH_2)_q$—O—C(O)—$(CH_2)_r$—$OR_{14}$, —$(CH_2)_q$—NH—C(O)—$(CH_2)_r$—$OR_{14}$, —$(CH_2)_q$—O—$(CH_2)_r$—$R_{14}$, —$(CH_2)_q$—NH—$(CH_2)_r$—$R_{14}$, —$(CH_2)_q$—O—$(CH_2)_r$—$OR_{14}$, or —$(CH_2)_q$—NH—$(CH_2)_r$—$OR_{14}$.

In some embodiments, $R_{13}$ is —$(CH_2)_q$—O—C(O)—$(CH_2)_r$—$R_{14}$. In some embodiments, $R_{13}$ is —O—C(O)—$(CH_2)_r$—$R_{14}$. In some embodiments, $R_{13}$ is —$(CH_2)_q$—O—C(O)—$R_{14}$.

In some embodiments, $R_{13}$ is —$(CH_2)_q$—NH—C(O)—$(CH_2)_r$—$R_{14}$. In some embodiments, $R_{13}$ is —NH—C(O)—$(CH_2)_r$—$R_{14}$. In some embodiments, $R_{13}$ is —$(CH_2)_q$—NH—C(O)—$R_{14}$.

In some embodiments, $R_{13}$ is —$(CH_2)_q$—O—C(O)—$(CH_2)_r$—$OR_{14}$. In some embodiments, $R_{13}$ is —O—C(O)—$(CH_2)_r$—$R_{14}$. In some embodiments, $R_{13}$ is —$(CH_2)_q$—O—C(O)—$R_{14}$.

In some embodiments, $R_{13}$ is —$(CH_2)_q$—NH—C(O)—$(CH_2)_r$—$OR_{14}$. In some embodiments, $R_{13}$ is —NH—$(CH_2)_r$—$R_{14}$. In some embodiments, $R_{13}$ is —$(CH_2)_q$—NH—$R_{14}$.

In some embodiments, $R_{13}$ is —$(CH_2)_q$—O—$(CH_2)_r$—$R_{14}$. In some embodiments, $R_{13}$ is —O—$(CH_2)_r$—$R_{14}$. In some embodiments, $R_{13}$ is —$(CH_2)_q$—O—$R_{14}$.

In some embodiments, $R_{13}$ is —$(CH_2)_q$—NH—$(CH_2)_r$—$R_{14}$. In some embodiments, $R_{13}$ is —NH—$(CH_2)_r$—$R_{14}$. In some embodiments, $R_{13}$ is —$(CH_2)_q$—NH—$R_{14}$.

In some embodiments, $R_{13}$ is —$(CH_2)_q$—O—$(CH_2)_r$—$OR_{14}$. In some embodiments, $R_{13}$ is —O—$(CH_2)_r$—$OR_{14}$. In some embodiments, $R_{13}$ is —$(CH_2)_q$—O—$OR_{14}$.

In some embodiments, $R_{13}$ is —$(CH_2)_q$—NH—$(CH_2)_r$—$OR_{14}$. In some embodiments, $R_{13}$ is —NH—$(CH_2)_r$—$OR_{14}$. In some embodiments, $R_{13}$ is —$(CH_2)_q$—NH—$OR_{14}$.

In some embodiments, $R_{13}$ is $C_3$-$C_{10}$ cycloalkyl, heterocycle comprising 1-4 heteroatoms selected from O, N, and S, aryl, or heteroaryl comprising 1-4 heteroatoms selected from N, O, and S.

In some embodiments, $R_{13}$ is $C_3$-$C_{10}$ cycloalkyl or a heterocycle comprising 1-4 heteroatoms selected from O, N, and S.

In some embodiments, $R_{13}$ is $C_3$-$C_{10}$ cycloalkyl.

In some embodiments, $R_{13}$ is $C_5$-$C_6$ cycloalkyl.

In some embodiments, $R_{13}$ is cyclopropyl, cyclobutyl, cyclopentyl, cyclohexyl, cycloheptyl, cyclooctyl, cyclononyl, or cyclodecyl.

In some embodiments, $R_{13}$ is a fused polycyclic $C_3$-$C_{10}$ cycloalkyl. In some embodiments, $R_{13}$ is a bridged polycyclic $C_3$-$C_{10}$ cycloalkyl. In some embodiments, $R_{13}$ is a $C_3$-$C_{10}$ spirocycloalkyl.

In some embodiments, $R_{13}$ is heterocycle comprising 1-4 heteroatoms selected from O, N, and S.

In some embodiments, $R_{13}$ is a heterocycle comprising 1-4 heteroatoms selected from O, N, and S.

In some embodiments, $R_{13}$ is a heterocycle comprising one heteroatom selected from O, N, and S. In some embodiments, $R_{13}$ is a heterocycle comprising one heteroatom which is N. In some embodiments, $R_{13}$ is a heterocycle comprising two heteroatoms selected from O, N, and S. In some embodiments, $R_{13}$ is a heterocycle comprising three heteroatoms selected from O, N, and S. In some embodiments, $R_{13}$ is a heterocycle comprising four heteroatoms selected from O, N, and S.

In some embodiments, $R_{13}$ is a 5- to 6-membered saturated or partially unsaturated heterocycle comprising 1-4 heteroatoms selected from O, N, and S.

In some embodiments, $R_{13}$ is a monocyclic heterocycle comprising 1-4 heteroatoms selected from O, N, and S. In some embodiments, $R_{13}$ is a polycyclic heterocycle comprising 1-4 heteroatoms selected from O, N, and S.

In some embodiments, $R_{13}$ is a fused polycyclic heterocycle comprising 1-4 heteroatoms selected from O, N, and S. In some embodiments, $R_{13}$ is a bridged polycyclic heterocycle comprising 1-4 heteroatoms selected from O, N, and S. In some embodiments, $R_{13}$ is a spiroheterocycle comprising 1-4 heteroatoms selected from O, N, and S.

In some embodiments, $R_{13}$ is aryl. In some embodiments, $R_{13}$ is $C_6$ aryl (e.g., phenyl).

In some embodiments, $R_{13}$ is a heteroaryl comprising 1-4 heteroatoms selected from O, N, and S In some embodiments, $R_{13}$ is 5- to 6-membered heteroaryl comprising 1-4 heteroatoms selected from O, N, and S.

In some embodiments, $R_{13}$ is heteroaryl comprising one heteroatom selected from O, N, and S. In some embodiments, $R_{13}$ is heteroaryl comprising two heteroatoms selected from O, N, and S. In some embodiments, $R_{13}$ is heteroaryl comprising three heteroatoms selected from O, N, and S. In some embodiments, $R_{13}$ is heteroaryl comprising four heteroatoms selected from O, N, and S.

In some embodiments, Ring A is $C_3$-$C_{10}$ cycloalkyl, heterocycle comprising 1-4 heteroatoms selected from N, O, and S, aryl, or heteroaryl comprising 1-4 heteroatoms selected from N, O, and S.

In some embodiments, Ring A is $C_3$-$C_{10}$ cycloalkyl or heterocycle comprising 1-4 heteroatoms selected from N, O, and S.

In some embodiments, Ring A is $C_3$-$C_{10}$ cycloalkyl.

In some embodiments, Ring A is $C_5$-$C_6$ cycloalkyl. In some embodiments, Ring A is cyclopropyl, cyclobutyl, cyclopentyl, cyclohexyl, cycloheptyl, cyclooctyl, cyclononyl, or cyclodecyl.

In some embodiments, Ring A is a fused polycyclic $C_3$-$C_{10}$ cycloalkyl. In some embodiments, Ring A is a bridged polycyclic $C_3$-$C_{10}$ cycloalkyl. In some embodiments, Ring A is a $C_3$-$C_{10}$ spirocycloalkyl.

In some embodiments, Ring A is heterocycle comprising 1-4 heteroatoms selected from N, O, and S.

In some embodiments, Ring A is a monocyclic heterocycle comprising 1-4 heteroatoms selected from N, O, and S. In some embodiments, Ring A is a polycyclic heterocycle comprising 1-4 heteroatoms selected from N, O, and S.

In some embodiments, Ring A is 5- to 6-membered heterocycle comprising 1-4 heteroatoms selected from N, O, and S.

In some embodiments, Ring A is heterocycle comprising one heteroatom selected from N, O, and S. In some embodiments, Ring A is heterocycle comprising two heteroatoms selected from N, O, and S. In some embodiments, Ring A is heterocycle comprising three heteroatoms selected from N, O, and S. In some embodiments, Ring A is heterocycle comprising four heteroatoms selected from N, O, and S.

In some embodiments, Ring A is aryl. In some embodiments, Ring A is $C_6$ aryl (e.g., phenyl). In some embodiments, Ring A is phenyl.

In some embodiments, Ring A is a heteroaryl comprising 1-4 heteroatoms selected from N, O, and S.

In some embodiments, Ring A is 5- to 6-membered heteroaryl comprising 1-4 heteroatoms selected from N, O, and S.

In some embodiments, Ring A is heteroaryl comprising one heteroatom selected from N, O, and S. In some embodiments, Ring A is heteroaryl comprising two heteroatoms selected from N, O, and S. In some embodiments, Ring A is heteroaryl comprising three heteroatoms selected from N, O, and S. In some embodiments, Ring A is heteroaryl comprising four heteroatoms selected from N, O, and S.

In some embodiments, Ring A is
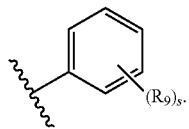
In some embodiments, Ring A is
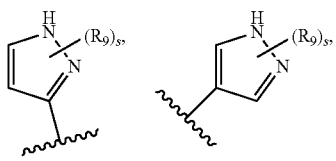
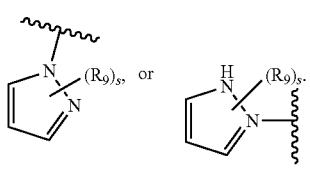
In some embodiments, Ring A is
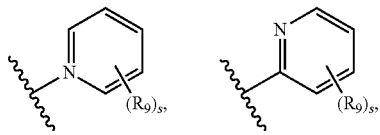
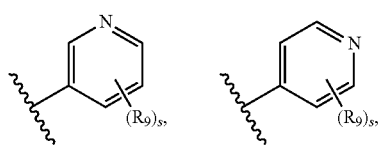
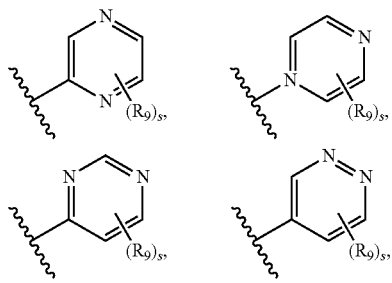
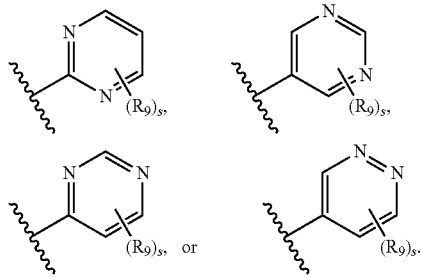
In some embodiments, Ring A is
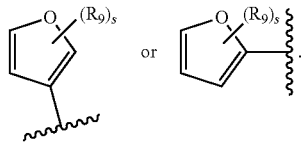
In some embodiments, Ring A is
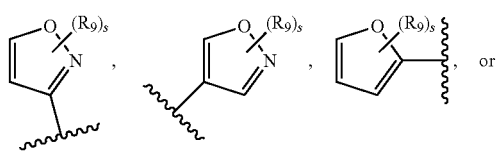
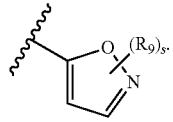
In some embodiments, Ring A is
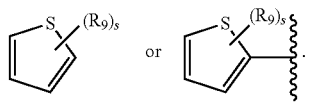
In some embodiments, Ring A is
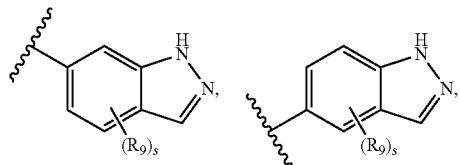
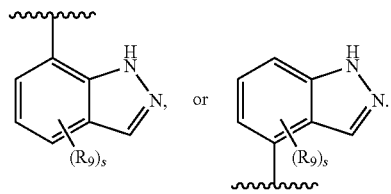
In some embodiments, Ring A is
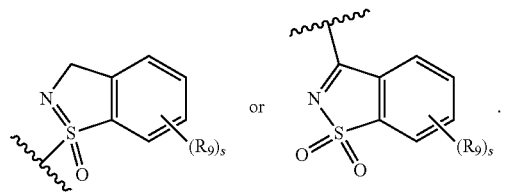

In some embodiments $R_{14}$ is

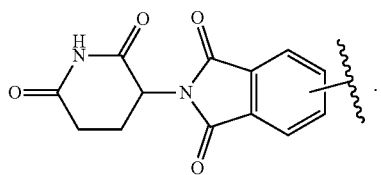

In some embodiments $R_{14}$ is

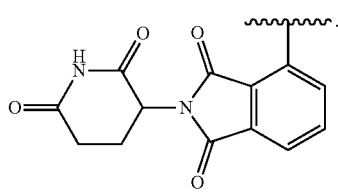 [SMILES: *c1cccc2c1C(=O)N(C1CCC(=O)NC1=O)C2=O]

In some embodiments $R_{14}$ is

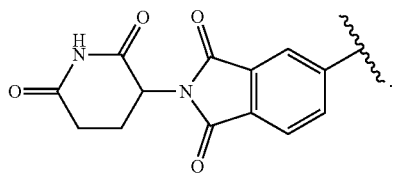 [SMILES: *c1ccc2c(c1)C(=O)N(C1CCC(=O)NC1=O)C2=O]

In some embodiments, each n, m, q, r, or s is independently at each occurrence 0, 1, 2, 3, 4, 5, or 6.

In some embodiments, n is 0, 1, 2, 3, 4, 5, or 6. In some embodiments, n is 0. In some embodiments, n is 1. In some embodiments, n is 2. In some embodiments, n is 3. In some embodiments, n is 4. In some embodiments, n is 5. In some embodiments, n is 6.

In some embodiments, m is 0, 1, 2, 3, 4, 5, or 6. In some embodiments, m is 0. In some embodiments, m is 1. In some embodiments, m is 2. In some embodiments, m is 3. In some embodiments, m is 4. In some embodiments, m is 5. In some embodiments, m is 6.

In some embodiments, q is 0, 1, 2, 3, 4, 5, or 6. In some embodiments, q is 0. In some embodiments, q is 1. In some embodiments, q is 2. In some embodiments, q is 3. In some embodiments, q is 4. In some embodiments, q is 5. In some embodiments, q is 6.

In some embodiments, r is 0, 1, 2, 3, 4, 5, or 6. In some embodiments, r is 0. In some embodiments, r is 1. In some embodiments, r is 2. In some embodiments, r is 3. In some embodiments, r is 4. In some embodiments, r is 5. In some embodiments, r is 6.

In some embodiments, s is 0, 1, 2, 3, 4, 5, or 6. In some embodiments, s is 0. In some embodiments, s is 1. In some embodiments, s is 2. In some embodiments, s is 3. In some embodiments, s is 4. In some embodiments, s is 5. In some embodiments, s is 6.

In some embodiments, when $R_1$ and $R_2$ together with the nitrogen atom to which they are attached form a heterocycle, wherein if the heterocycle is morpholine and $R_5$ is —$CH_3$ then either (a) the morpholine is substituted or (b) Ring A is not phenyl.

In some embodiments, when $R_1$ and $R_2$ together with the nitrogen atom to which they are attached form a heterocycle, wherein if the heterocycle is morpholine and $R_5$ is —$CH_3$, then the morpholine is substituted.

In some embodiments, when $R_1$ and $R_2$ together with the nitrogen atom to which they are attached form a heterocycle, wherein if the heterocycle is morpholine and $R_5$ is —$CH_3$, then Ring A is not phenyl.

In some embodiments, the compound is of Formula (II'):

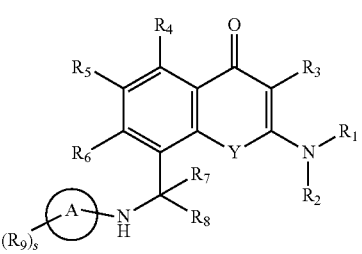

(II')

or a prodrug, solvate, enantiomer, stereoisomer, tautomer, or pharmaceutically acceptable salt thereof, wherein Y, $R_1$, $R_2$, $R_3$, $R_4$, $R_5$, $R_6$, $R_7$, $R_8$, $R_9$, Ring A, and s are as described herein.

In some embodiments, the compound is of Formula (II') or a prodrug, solvate, enantiomer, stereoisomer, tautomer, or pharmaceutically acceptable salt thereof.

In some embodiments, the compound is of Formula (IIa):

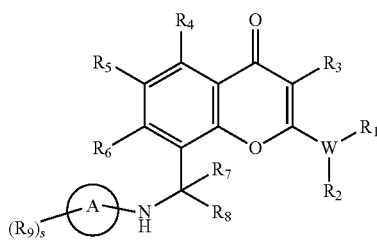

(IIa)

or a prodrug, solvate, enantiomer, stereoisomer, tautomer, or pharmaceutically acceptable salt thereof, wherein W, $R_1$, $R_2$, $R_3$, $R_4$, $R_5$, $R_6$, $R_7$, $R_8$, $R_9$, Ring A, and s are as described herein.

In some embodiments, the compound is of Formula (IIa) or a prodrug, solvate, enantiomer, stereoisomer, tautomer, or pharmaceutically acceptable salt thereof.

In some embodiments, the compound is of Formula (IIa'):

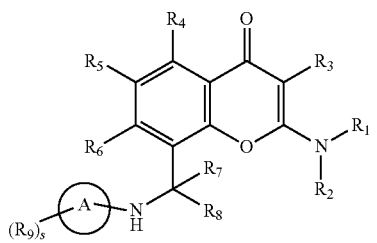

(IIa')

or a prodrug, solvate, enantiomer, stereoisomer, tautomer, or pharmaceutically acceptable salt thereof, wherein $R_1$, $R_2$, $R_3$, $R_4$, $R_5$, $R_6$, $R_7$, $R_8$, $R_9$, Ring A, and s are as described herein.

In some embodiments, the compound is of Formula (IIa') or a prodrug, solvate, enantiomer, stereoisomer, tautomer, or pharmaceutically acceptable salt thereof.

In some embodiments, the compound is of Formula (IIb):

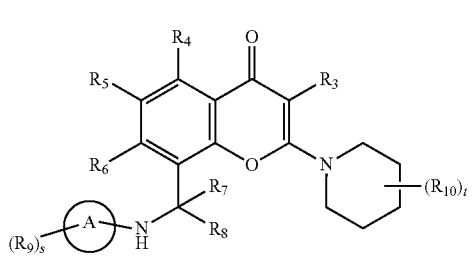

(IIb)

or a prodrug, solvate, enantiomer, stereoisomer, tautomer, or pharmaceutically acceptable salt thereof, wherein $R_3$, $R_4$, $R_5$, $R_6$, $R_7$, $R_8$, $R_9$, Ring A, and s are as described herein and t is 1, 2, 3, or 4.

In some embodiments, the compound is of Formula (IIb) or a prodrug, solvate, enantiomer, stereoisomer, tautomer, or pharmaceutically acceptable salt thereof.

In some embodiments, the compound is of Formula (IIc):

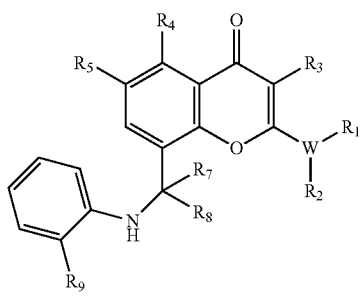

(IIc)

or a prodrug, solvate, enantiomer, stereoisomer, tautomer, or pharmaceutically acceptable salt thereof, wherein W, $R_1$, $R_2$, $R_3$, $R_4$, $R_5$, $R_7$, $R_8$, and $R_9$ are as described herein.

In some embodiments, the compound is of Formula (IIc) or a prodrug, solvate, enantiomer, stereoisomer, tautomer, or pharmaceutically acceptable salt thereof.

In some embodiments, the compound is of Formula (IIc'):

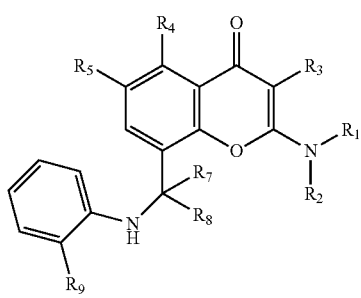

(IIc')

or a prodrug, solvate, enantiomer, stereoisomer, tautomer, or pharmaceutically acceptable salt thereof, wherein $R_1$, $R_2$, $R_3$, $R_4$, $R_5$, $R_7$, $R_8$, and $R_9$ are as described herein.

In some embodiments, the compound is of Formula (IIc') or a prodrug, solvate, enantiomer, stereoisomer, tautomer, or pharmaceutically acceptable salt thereof.

In some embodiments, the compound is of Formula (IId):

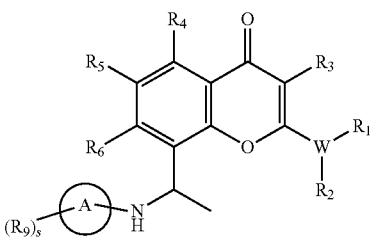

(IId)

or a prodrug, solvate, enantiomer, stereoisomer, tautomer, or pharmaceutically acceptable salt thereof, wherein W, $R_1$, $R_2$, $R_3$, $R_4$, $R_5$, $R_6$, $R_9$, Ring A, and s are as described herein.

In some embodiments, the compound is of Formula (IId) or a prodrug, solvate, enantiomer, stereoisomer, tautomer, or pharmaceutically acceptable salt thereof.

In some embodiments, the compound is of Formula (IId'):

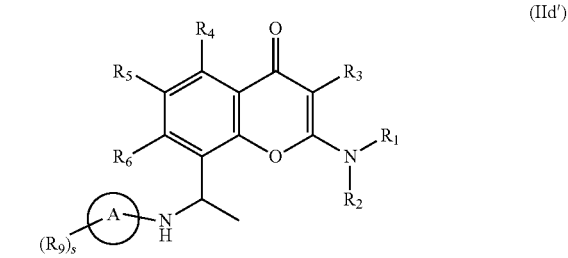

(IId')

or a prodrug, solvate, enantiomer, stereoisomer, tautomer, or pharmaceutically acceptable salt thereof, wherein $R_1$, $R_2$, $R_3$, $R_4$, $R_5$, $R_6$, $R_9$, Ring A, and s are as described herein.

In some embodiments, the compound is of Formula (IId') or a prodrug, solvate, enantiomer, stereoisomer, tautomer, or pharmaceutically acceptable salt thereof.

In some embodiments, the compound is of Formula (IId-1):

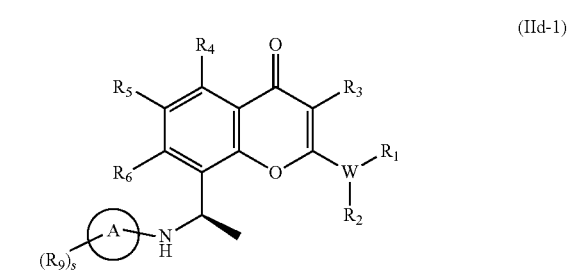

(IId-1)

or a prodrug, solvate, enantiomer, stereoisomer, tautomer, or pharmaceutically acceptable salt thereof, wherein W, $R_1$, $R_2$, $R_3$, $R_4$, $R_5$, $R_6$, $R_9$, Ring A, and s are as described herein.

In some embodiments, the compound is of Formula (IId-1) or a prodrug, solvate, enantiomer, stereoisomer, tautomer, or pharmaceutically acceptable salt thereof.

In some embodiments, the compound is of Formula (IId'-1):

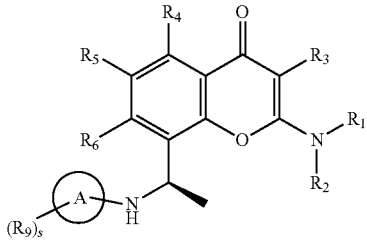

(IId'-1)

or a prodrug, solvate, enantiomer, stereoisomer, tautomer, or pharmaceutically acceptable salt thereof, wherein $R_1$, $R_2$, $R_3$, $R_4$, $R_5$, $R_6$, $R_9$, Ring A, and s are as described herein.

In some embodiments, the compound is of Formula (IId'-1) or a prodrug, solvate, enantiomer, stereoisomer, tautomer, or pharmaceutically acceptable salt thereof.

In some embodiments, the compound is of Formula (IIe):

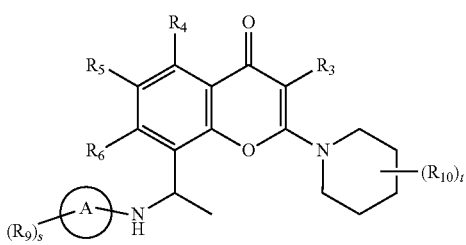

(IIe)

or a prodrug, solvate, enantiomer, stereoisomer, tautomer, or pharmaceutically acceptable salt thereof, wherein $R_3$, $R_4$, $R_5$, $R_6$, $R_9$, Ring A, and s are as described herein and t is 1, 2, 3, or 4.

In some embodiments, the compound is of Formula (IIe) or a prodrug, solvate, enantiomer, stereoisomer, tautomer, or pharmaceutically acceptable salt thereof.

In some embodiments, the compound is of Formula (IIe-1):

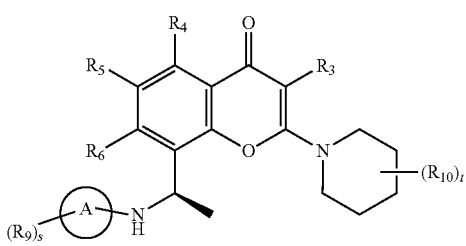

(IIe-1)

or a prodrug, solvate, enantiomer, stereoisomer, tautomer, or pharmaceutically acceptable salt thereof, wherein $R_3$, $R_4$, $R_5$, $R_6$, $R_9$, Ring A, and s are as described herein and t is 1, 2, 3, or 4.

In some embodiments, the compound is of Formula (IIe-1) or a prodrug, solvate, enantiomer, stereoisomer, tautomer, or pharmaceutically acceptable salt thereof.

In some embodiments, the compound is of Formula (IIf):

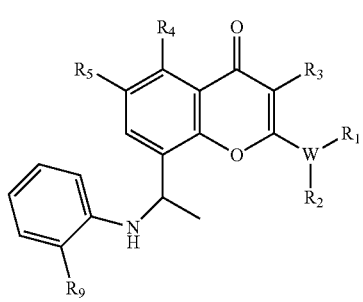

(IIf)

or a prodrug, solvate, enantiomer, stereoisomer, tautomer, or pharmaceutically acceptable salt thereof, wherein W, $R_1$, $R_2$, $R_3$, $R_4$, $R_5$, and $R_9$ are as described herein.

In some embodiments, the compound is of Formula (IIf) or a prodrug, solvate, enantiomer, stereoisomer, tautomer, or pharmaceutically acceptable salt thereof.

In some embodiments, the compound is of Formula (IIf'):

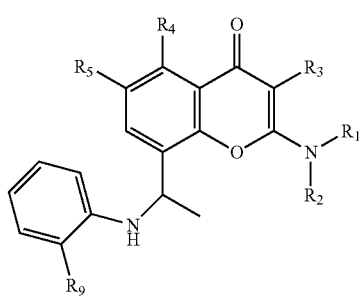

(IIf')

or a prodrug, solvate, enantiomer, stereoisomer, tautomer, or pharmaceutically acceptable salt thereof, wherein $R_1$, $R_2$, $R_3$, $R_4$, $R_5$, and $R_9$ are as described herein.

In some embodiments, the compound is of Formula (IIf') or a prodrug, solvate, enantiomer, stereoisomer, tautomer, or pharmaceutically acceptable salt thereof.

In some embodiments, the compound is of Formula (IIf-1):

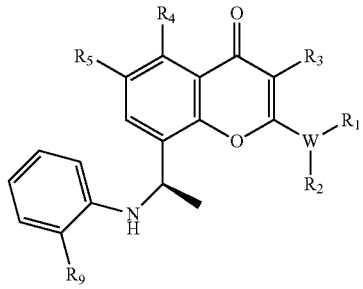

(IIf-1)

or a prodrug, solvate, enantiomer, stereoisomer, tautomer, or pharmaceutically acceptable salt thereof, wherein W, $R_1$, $R_2$, $R_3$, $R_4$, $R_5$, and $R_9$ are as described herein.

In some embodiments, the compound is of Formula (IIf-1) or a prodrug, solvate, enantiomer, stereoisomer, tautomer, or pharmaceutically acceptable salt thereof.

In some embodiments, the compound is of Formula (IIf'-1):

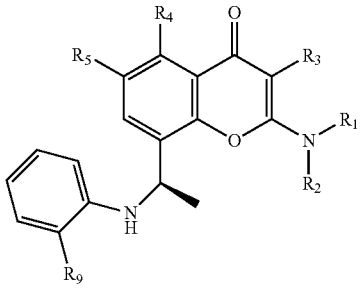

(IIf'-1)

or a prodrug, solvate, enantiomer, stereoisomer, tautomer, or pharmaceutically acceptable salt thereof, wherein $R_1$, $R_2$, $R_3$, $R_4$, $R_5$, and $R_9$ are as described herein.

In some embodiments, the compound is of Formula (IIf'-1) or a prodrug, solvate, enantiomer, stereoisomer, tautomer, or pharmaceutically acceptable salt thereof.

In some embodiments, the compound is of Formula (IIg):

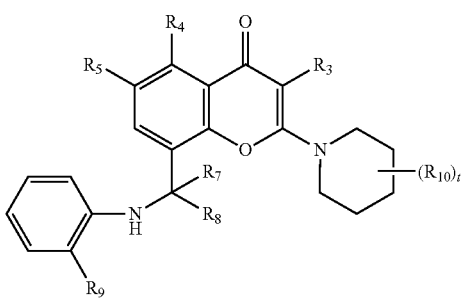

(IIg)

or a prodrug, solvate, enantiomer, stereoisomer, tautomer, or pharmaceutically acceptable salt thereof, wherein $R_3$, $R_4$, $R_5$, $R_7$, $R_8$, $R_9$, and $R_{10}$ are as described herein and t is 1, 2, 3, or 4.

In some embodiments, the compound is of Formula (IIg) or a prodrug, solvate, enantiomer, stereoisomer, tautomer, or pharmaceutically acceptable salt thereof.

In some embodiments, the compound is of Formula (IIh):

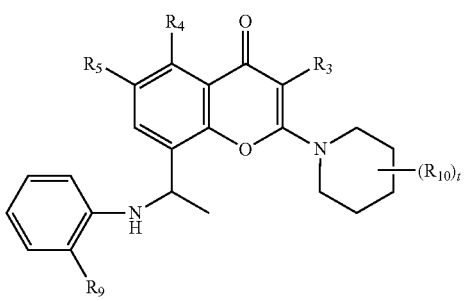

(IIh)

or a prodrug, solvate, enantiomer, stereoisomer, tautomer, or pharmaceutically acceptable salt thereof, wherein $R_3$, $R_4$, $R_5$, $R_9$, and $R_{10}$ are as described herein and t is 1, 2, 3, or 4.

In some embodiments, the compound is of Formula (IIh) or a prodrug, solvate, enantiomer, stereoisomer, tautomer, or pharmaceutically acceptable salt thereof.

In some embodiments, the compound is of Formula (IIh-1):

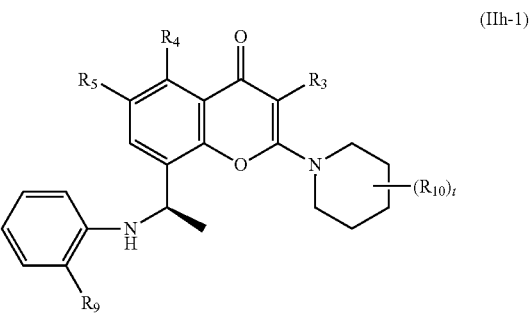

(IIh-1)

or a prodrug, solvate, enantiomer, stereoisomer, tautomer, or pharmaceutically acceptable salt thereof, wherein $R_3$, $R_4$, $R_5$, $R_9$, and $R_{10}$ are as described herein and t is 1, 2, 3, or 4.

In some embodiments, the compound is of Formula (IIh-1) or a prodrug, solvate, enantiomer, stereoisomer, tautomer, or pharmaceutically acceptable salt thereof.

In some embodiments, the compound is of Formula (IIa), (IIc), (IId), or (IIf), or a prodrug, solvate, enantiomer, stereoisomer, tautomer, or pharmaceutically acceptable salt thereof.

In some embodiments, the compound is of Formula (IIb), (IIe), (IIg), or (IIh), or a prodrug, solvate, enantiomer, stereoisomer, tautomer, or pharmaceutically acceptable salt thereof.

In some embodiments, the compound is of Formula (IIc), (IIf), (IIg), or (IIh), or a prodrug, solvate, enantiomer, stereoisomer, tautomer, or pharmaceutically acceptable salt thereof.

In some embodiments, the compound is selected from the compounds described in Table 1 and prodrugs and pharmaceutically acceptable salts thereof.

In some embodiments, the compound is selected from the compounds described in Table 1 and pharmaceutically acceptable salts thereof.

In some embodiments, the compound is selected from the prodrugs of the compounds described in Table 1 and pharmaceutically acceptable salts thereof.

In some embodiments, the compound is selected from the compounds described in Table 1.

TABLE 1

| Compound Name |
| --- |
| (2-((1-(2-(4,4-dimethylpiperidin-1-yl)-6-methyl-4-oxo-4H-chromen-8-yl)ethyl)amino)phenyl)boronic acid |
| 5-borono-2-((1-(2-(4,4-dimethylpiperidin-1-yl)-6-methyl-4-oxo-4H-chromen-8-yl)ethyl)amino)benzoic acid |
| 2-(4,4-dimethylpiperidin-1-yl)-6-methyl-8-(1-((1-methyl-1H-pyrazol-5-yl)amino)ethyl)-4H-chromen-4-one |
| 1-(8-(1-((2-carboxyphenyl)amino)ethyl)-6-methyl-4-oxo-4H-chromen-2-yl)-3-methylazetidine-3-carboxylic acid |
| 2-((1-(6-methyl-4-oxo-2-(3-oxo-2,7-diazaspiro[4.5]decan-7-yl)-4H-chromen-8-yl)ethyl)amino)benzoic acid |
| 2-((1-(2-(4,4-dimethylpiperidin-1-yl)-6-methyl-4-oxo-4H-chromen-8-yl)ethyl)amino)-5-(trifluoromethyl)benzoic acid |
| 2-((1-(2-(3-carbamoyl-3-methylazetidin-1-yl)-6-methyl-4-oxo-4H-chromen-8-yl)ethyl)amino)benzoic acid |
| 2-((1-(2-((S)-3-methoxypiperidin-1-yl)-6-methyl-4-oxo-4H-chromen-8-yl)ethyl)amino)benzoic acid |
| 2-((1-(6-methyl-4-oxo-2-(1-oxo-2,8-diazaspiro[4.5]decan-8-yl)-4H-chromen-8-yl)ethyl)amino)benzoic acid |
| 2-((1-(2-(8-oxa-3-azabicyclo[3.2.1]octan-3-yl)-6-methyl-4-oxo-4H-chromen-8-yl)ethyl)amino)benzoic acid |
| 2-((1-(2-(4-isobutyl-4-methylpiperidin-1-yl)-6-methyl-4-oxo-4H-chromen-8-yl)ethyl)amino)benzoic acid |
| 2-((1-(2-(4-cyano-4-methylpiperidin-1-yl)-6-methyl-4-oxo-4H-chromen-8-yl)ethyl)amino)benzoic acid |
| 2-((1-(6-methyl-2-(2-(4-(methylsulfonyl)phenyl)morpholino)-4-oxo-4H-chromen-8-yl)ethyl)amino)benzoic acid |
| 2-((1-(2-(9-acetyl-3,9-diazaspiro[5.5]undecan-3-yl)-6-methyl-4-oxo-4H-chromen-8-yl)ethyl)amino)benzoic acid |
| 2-((1-(2-(4-isobutyrylpiperazin-1-yl)-6-methyl-4-oxo-4H-chromen-8-yl)ethyl)amino)benzoic acid |
| (S)-2-((1-(2-(4,4-dimethylpiperidin-1-yl)-3,6-dimethyl-4-oxo-4H-chromen-8-yl)ethyl)amino)benzoic acid |
| (R)-2-((1-(2-(4,4-dimethylpiperidin-1-yl)-3,6-dimethyl-4-oxo-4H-chromen-8-yl)ethyl)amino)benzoic acid |
| 2-((1-(2-(3-chloroazetidin-1-yl)-6-methyl-4-oxo-4H-chromen-8-yl)ethyl)amino)benzoic acid |
| 2-((1-(6-methyl-4-oxo-2-(6-azaspiro[2.5]octan-6-yl)-4H-chromen-8-yl)ethyl)amino)benzoic acid |
| 2-((1-(2-(3,3-dimethylpiperidin-1-yl)-6-methyl-4-oxo-4H-chromen-8-yl)ethyl)amino)benzoic acid |
| 2-((1-(2-(4-ethyl-4-methylpiperidin-1-yl)-6-methyl-4-oxo-4H-chromen-8-yl)ethyl)amino)benzoic acid |
| 2-((1-(6-methyl-4-oxo-2-(5-oxo-4,5-dihydro-3H-spiro[benzo[f][1,4]oxazepine-2,4'-piperidin]-1'-yl)-4H-chromen-8-yl)ethyl)amino)benzoic acid |
| 6-((1-(2-(4,4-dimethylpiperidin-1-yl)-6-methyl-4-oxo-4H-chromen-8-yl)ethyl)amino)benzo[d][1,3]dioxole-5-carboxylic acid |
| N-((2-((1-(2-(4,4-dimethylpiperidin-1-yl)-6-methyl-4-oxo-4H-chromen-8-yl)ethyl)amino)phenyl)sulfonyl)acetamide |
| 2-((1-(2-(isoindolin-2-yl)-6-methyl-4-oxo-4H-chromen-8-yl)ethyl)amino)benzoic acid |
| 2-((1-(2-(4,4-dimethylpiperidin-1-yl)-6-methyl-4-oxo-4H-chromen-8-yl)ethyl)amino)benzoic acid |
| 2-((1-(2-(4,4-dimethylpiperidin-1-yl)-6-methyl-4-oxo-4H-chromen-8-yl)ethyl)amino)-5-ethylbenzoic acid |
| 2-((1-(2-(3-(dimethylamino)azetidin-1-yl)-6-methyl-4-oxo-4H-chromen-8-yl)ethyl)amino)benzoic acid |
| 2-((1-(2-(3-fluoroazetidin-1-yl)-6-methyl-4-oxo-4H-chromen-8-yl)ethyl)amino)benzoic acid |
| 2-((1-(2-(3,3-dimethylazetidin-1-yl)-6-methyl-4-oxo-4H-chromen-8-yl)ethyl)amino)benzoic acid |
| 2-((1-(2-(4-isopropyl-4-methylpiperidin-1-yl)-6-methyl-4-oxo-4H-chromen-8-yl)ethyl)amino)benzoic acid |
| 2-((1-(6-methyl-4-oxo-2-(2-oxa-8-azaspiro[4.5]decan-8-yl)-4H-chromen-8-yl)ethyl)amino)benzoic acid |
| 2-((1-(2-(4-(methoxymethyl)-4-methylpiperidin-1-yl)-6-methyl-4-oxo-4H-chromen-8-yl)ethyl)amino)benzoic acid |
| 2-((1-(6-methyl-4-oxo-2-(4-(trifluoromethyl)piperidin-1-yl)-4H-chromen-8-yl)ethyl)amino)benzoic acid |
| 2-((1-(2-(6,6-dimethyl-3-azabicyclo[3.1.0]hexan-3-yl)-6-methyl-4-oxo-4H-chromen-8-yl)ethyl)amino)benzoic acid |
| 6-((1-(2-(4,4-dimethylpiperidin-1-yl)-6-methyl-4-oxo-4H-chromen-8-yl)ethyl)amino)-3-fluoro-2-methylbenzoic acid |
| 2-((1-(6-methyl-4-oxo-2-(9-oxa-2-azaspiro[5.5]undecan-2-yl)-4H-chromen-8-yl)ethyl)amino)benzoic acid |
| 2-((1-(2-(4,4-dimethylpiperidin-1-yl)-6-methyl-4-oxo-4H-chromen-8-yl)ethyl)amino)benzenesulfonic acid |
| (S)-2-((1-(2-(isoindolin-2-yl)-6-methyl-4-oxo-4H-chromen-8-yl)ethyl)amino)benzoic acid |
| 2-((1-(2-(4,4-dimethylpiperidin-1-yl)-6-methyl-4-oxo-4H-chromen-8-yl)ethyl)(methyl)amino)benzoic acid |
| 5-cyano-2-((1-(2-(4,4-dimethylpiperidin-1-yl)-6-methyl-4-oxo-4H-chromen-8-yl)ethyl)amino)benzoic acid |

TABLE 1-continued

| Compound Name |
|---|
| 5-bromo-2-((1-(2-(4,4-dimethylpiperidin-1-yl)-6-methyl-4-oxo-4H-chromen-8-yl)ethyl)amino)benzoic acid |
| 2-((1-(2-(isobutylamino)-6-methyl-4-oxo-4H-chromen-8-yl)ethyl)amino)benzoic acid |
| 2-((1-(2-(dimethylamino)-6-methyl-4-oxo-4H-chromen-8-yl)ethyl)amino)benzoic acid |
| 2-((1-(6-methyl-2-(3-methylpiperidin-1-yl)-4-oxo-4H-chromen-8-yl)ethyl)amino)benzoic acid |
| 2-((1-(2-(3-ethylpiperidin-1-yl)-6-methyl-4-oxo-4H-chromen-8-yl)ethyl)amino)benzoic acid |
| 2-(4,4-dimethylpiperidin-1-yl)-8-(1-((5-fluoro-2-nitrophenyl)amino)ethyl)-6-methyl-4H-chromen-4-one |
| 4-((1-(2-(4,4-dimethylpiperidin-1-yl)-6-methyl-4-oxo-4H-chromen-8-yl)ethyl)amino)-1,3-dihydro-2H-benzo[d]imidazol-2-one |
| 2-(4,4-dimethylpiperidin-1-yl)-6-methyl-8-(1-((2-(2,2,2-trifluoro-1-hydroxyethyl)phenyl)amino)ethyl)-4H-chromen-4-one |
| 2-(4,4-dimethylpiperidin-1-yl)-6-methyl-8-(1-((2-(2,2,2-trifluoroacetyl)phenyl)amino)ethyl)-4H-chromen-4-one |
| 2-((1-(6-methyl-4-oxo-2-(2-azaspiro[3.5]nonan-2-yl)-4H-chromen-8-yl)ethyl)amino)benzoic acid |
| (S)-2-((1-(2-(4,4-dimethylpiperidin-1-yl)-6-methyl-4-oxo-4H-chromen-8-yl)ethyl)amino)benzoic acid |
| 2-((1-(6-methyl-4-oxo-2-(3,9-diazaspiro[5.5]undecan-3-yl)-4H-chromen-8-yl)ethyl)amino)benzoic acid |
| 2-((1-(2-(4-(tert-butoxycarbonyl)piperazin-1-yl)-6-methyl-4-oxo-4H-chromen-8-yl)ethyl)amino)benzoic acid |
| 2-((1-(6-methyl-4-oxo-2-(piperazin-1-yl)-4H-chromen-8-yl)ethyl)amino)benzoic acid |
| 2-((1-(6-methyl-2-(4-methylpiperazin-1-yl)-4-oxo-4H-chromen-8-yl)ethyl)amino)benzoic acid |
| 2-((1-(6-methyl-4-oxo-2-(1-oxa-9-azaspiro[5.5]undecan-9-yl)-4H-chromen-8-yl)ethyl)amino)benzoic acid |
| 2-((1-(6-methyl-4-oxo-2-(3-oxa-9-azaspiro[5.5]undecan-9-yl)-4H-chromen-8-yl)ethyl)amino)benzoic acid |
| 2-((1-(6-methyl-4-oxo-2-(1-oxo-2,7-diazaspiro[4.5]decan-7-yl)-4H-chromen-8-yl)ethyl)amino)benzoic acid |
| 2-((1-(2-(ethylamino)-6-methyl-4-oxo-4H-chromen-8-yl)ethyl)amino)benzoic acid |
| 2-((1-(6-methyl-4-oxo-2-(pyrrolidin-1-yl)-4H-chromen-8-yl)ethyl)amino)benzoic acid |
| 2-((1-(2-(4,4-dimethylpiperidin-1-yl)-6-methyl-4-oxo-4H-chromen-8-yl)ethyl)amino)-4-fluoro-5-methoxybenzoic acid |
| 4-chloro-2-((1-(2-(4,4-dimethylpiperidin-1-yl)-6-methyl-4-oxo-4H-chromen-8-yl)ethyl)amino)benzoic acid |
| 3-chloro-2-((1-(2-(4,4-dimethylpiperidin-1-yl)-6-methyl-4-oxo-4H-chromen-8-yl)ethyl)amino)benzoic acid |
| 2-((1-(2-(4,4-dimethylpiperidin-1-yl)-6-methyl-4-oxo-4H-chromen-8-yl)ethyl)amino)-4,5-dimethylbenzoic acid |
| 2-((1-(2-(4,4-dimethylpiperidin-1-yl)-6-methyl-4-oxo-4H-chromen-8-yl)ethyl)amino)-4,5-difluorobenzoic acid |
| 2-((1-(2-(4,4-dimethylpiperidin-1-yl)-6-methyl-4-oxo-4H-chromen-8-yl)ethyl)amino)-4-fluorobenzoic acid |
| 2-((1-(2-(4,4-dimethylpiperidin-1-yl)-6-methyl-4-oxo-4H-chromen-8-yl)ethyl)amino)-5-methylbenzoic acid |
| 2-((1-(2-(4,4-dimethylpiperidin-1-yl)-6-methyl-4-oxo-4H-chromen-8-yl)ethyl)amino)-5-fluorobenzoic acid |
| 2-((1-(2-(4,4-dimethylpiperidin-1-yl)-6-methyl-4-oxo-4H-chromen-8-yl)ethyl)amino)-5-methoxybenzoic acid |
| 2-((1-(2-(4,4-dimethylpiperidin-1-yl)-6-methyl-4-oxo-4H-chromen-8-yl)ethyl)amino)-4,5-dimethoxybenzoic acid |
| 2-((1-(2-(4,4-dimethylpiperidin-1-yl)-6-methyl-4-oxo-4H-chromen-8-yl)ethyl)amino)-3-methylbenzoic acid |
| 2-((1-(2-(4,4-dimethylpiperidin-1-yl)-6-methyl-4-oxo-4H-chromen-8-yl)ethyl)amino)-4-fluoro-5-methylbenzoic acid |
| 2-((1-(2-(4,4-dimethylpiperidin-1-yl)-6-methyl-4-oxo-4H-chromen-8-yl)ethyl)amino)-N-methoxybenzamide |
| 2-(((2-(4,4-dimethylpiperidin-1-yl)-6-methyl-4-oxo-4H-chromen-8-yl)methyl)amino)benzoic acid |
| 8-(1-((2-(1H-tetrazol-5-yl)phenyl)amino)ethyl)-2-(4,4-dimethylpiperidin-1-yl)-6-methyl-4H-chromen-4-one |
| 2-((1-(2-(4,4-dimethylpiperidin-1-yl)-6-methyl-4-oxo-4H-chromen-8-yl)ethyl)amino)benzenesulfonamide |
| 8-(1-((2,3-dihydro-1H-inden-4-yl)amino)ethyl)-2-(4,4-dimethylpiperidin-1-yl)-6-methyl-4H-chromen-4-one |
| 2-((1-(2-(4,4-dimethylpiperidin-1-yl)-6-methyl-4-oxo-4H-chromen-8-yl)ethyl)amino)-6-fluorobenzoic acid |
| 2-chloro-6-((1-(2-(4,4-dimethylpiperidin-1-yl)-6-methyl-4-oxo-4H-chromen-8-yl)ethyl)amino)benzoic acid |
| 2-((1-(6-methyl-4-oxo-2-(8-azaspiro[4.5]decan-8-yl)-4H-chromen-8-yl)ethyl)amino)benzoic acid |
| 2-((1-(2-(3-carbamoylpiperidin-1-yl)-6-methyl-4-oxo-4H-chromen-8-yl)ethyl)amino)benzoic acid |
| 2-((1-(6-methyl-2-(4-methylpiperidin-1-yl)-4-oxo-4H-chromen-8-yl)ethyl)amino)benzoic acid |
| 2-((1-(6-methyl-2-(4-(methylcarbamoyl)piperidin-1-yl)-4-oxo-4H-chromen-8-yl)ethyl)amino)benzoic acid |

TABLE 1-continued

| Compound Name |
| --- |
| 2-((1-(6-methyl-4-oxo-2-(piperidin-1-yl)-4H-chromen-8-yl)ethyl)amino)benzamide |
| 2-((1-(2-(4,4-dimethylpiperidin-1-yl)-6-methyl-4-oxo-4H-chromen-8-yl)ethyl)amino)-6-methylbenzoic acid |
| 2-((1-(2-(4,4-dimethylpiperidin-1-yl)-6-methyl-4-oxo-4H-chromen-8-yl)ethyl)amino)-3-methoxybenzoic acid |
| 2-((1-(2-(4,4-dimethylpiperidin-1-yl)-6-methyl-4-oxo-4H-chromen-8-yl)ethyl)amino)-4-methylbenzoic acid |
| 5-chloro-2-((1-(2-(4,4-dimethylpiperidin-1-yl)-6-methyl-4-oxo-4H-chromen-8-yl)ethyl)amino)benzoic acid |
| 7-((1-(2-(4,4-dimethylpiperidin-1-yl)-6-methyl-4-oxo-4H-chromen-8-yl)ethyl)amino)isoindolin-1-one |
| 2-((1-(2-(4,4-dimethylpiperidin-1-yl)-6-methyl-4-oxo-4H-chromen-8-yl)ethyl)amino)benzonitrile |
| methyl 2-((1-(2-(4,4-dimethylpiperidin-1-yl)-6-methyl-4-oxo-4H-chromen-8-yl)ethyl)amino)benzoate |
| 2-((1-(2-(4-methoxypiperidin-1-yl)-6-methyl-4-oxo-4H-chromen-8-yl)ethyl)amino)benzoic acid |
| 2-((1-(2-(4-cyanopiperidin-1-yl)-6-methyl-4-oxo-4H-chromen-8-yl)ethyl)amino)benzoic acid |
| 2-((1-(2-(4,4-dimethylpiperidin-1-yl)-3,6-dimethyl-4-oxo-4H-chromen-8-yl)ethyl)amino)benzoic acid |
| 4-((1-(2-(4,4-dimethylpiperidin-1-yl)-6-methyl-4-oxo-4H-chromen-8-yl)ethyl)amino)isoindoline-1,3-dione |
| 2-((1-(2-(azetidin-1-yl)-6-methyl-4-oxo-4H-chromen-8-yl)ethyl)amino)benzoic acid |
| 2-(2-methoxyethoxy)ethyl (R)-2-((1-(6-methyl-4-oxo-2-(piperidin-1-yl)-4H-chromen-8-yl)ethyl)amino)benzoate |
| 2-((1-(2-(4-acetylpiperazin-1-yl)-6-methyl-4-oxo-4H-chromen-8-yl)ethyl)amino)benzoic acid |
| 2-((1-(6-methyl-4-oxo-2-(2-oxa-7-azaspiro[3.5]nonan-7-yl)-4H-chromen-8-yl)ethyl)amino)benzoic acid |
| methyl (R)-2-((1-(6-methyl-4-oxo-2-(piperidin-1-yl)-4H-chromen-8-yl)ethyl)amino)benzoate |
| 2-((1-(6-methyl-2-(3-methyl-2-oxo-1-oxa-3,8-diazaspiro[4.5]decan-8-yl)-4-oxo-4H-chromen-8-yl)ethyl)amino)benzoic acid |
| 2-((1-(6-methyl-2-(2-methyl-1-oxo-2,8-diazaspiro[4.5]decan-8-yl)-4-oxo-4H-chromen-8-yl)ethyl)amino)benzoic acid |
| (R)-N-(2-(2-methoxyethoxy)ethyl)-2-((1-(6-methyl-4-oxo-2-(piperidin-1-yl)-4H-chromen-8-yl)ethyl)amino)benzamide |
| 2-((1-(2-(4-chloropiperidin-1-yl)-6-methyl-4-oxo-4H-chromen-8-yl)ethyl)amino)benzoic acid |
| (R)-2-((1-(2-(isoindolin-2-yl)-6-methyl-4-oxo-4H-chromen-8-yl)ethyl)amino)benzoic acid |
| (R)-2-((1-(2-(4,4-difluoropiperidin-1-yl)-6-methyl-4-oxo-4H-chromen-8-yl)ethyl)amino)benzoic acid |
| (R)-2-((1-(2-(4,4-dimethylpiperidin-1-yl)-6-methyl-4-oxo-4H-chromen-8-yl)ethyl)amino)benzoic acid |
| (R)-2-((1-(6-methyl-4-oxo-2-thiomorpholino-4H-chromen-8-yl)ethyl)amino)benzoic acid |
| 2-(((R)-1-(2-((2S,6R)-2,6-dimethylmorpholino)-6-methyl-4-oxo-4H-chromen-8-yl)ethyl)amino)benzoic acid |
| (R)-2-((1-(6-methyl-4-oxo-2-(piperidin-1-yl)-4H-chromen-8-yl)ethyl)amino)benzoic acid |
| (R)-2-(4,4-dimethylpiperidin-1-yl)-6-methyl-8-(1-(phenylamino)ethyl)-4H-chromen-4-one |
| 2-((2S,6R)-2,6-dimethylmorpholino)-6-methyl-8-((R)-1-(phenylamino)ethyl)-4H-chromen-4-one |
| (R)-6-methyl-8-(1-(phenylamino)ethyl)-2-(piperidin-1-yl)-4H-chromen-4-one |
| (R)-6-methyl-8-(1-(phenylamino)ethyl)-2-thiomorpholino-4H-chromen-4-one |

In some embodiments, the compound is selected from the 50 compounds described in Table 2.

TABLE 2

| Compound Structure | Compound Name |
| --- | --- |
| 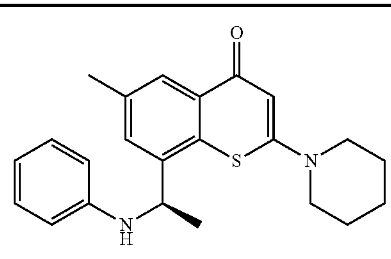 | (R)-6-methyl-8-(1-(phenylamino)ethyl)-2-(piperidin-1-yl)-4H-thiochromen-4-one |

TABLE 2-continued

| Compound Structure | Compound Name |
|---|---|
| 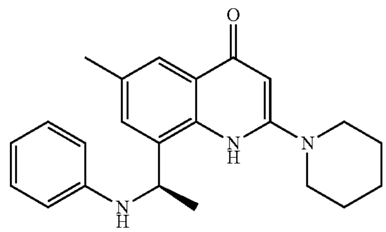 [SMILES: Cc1cc([C@@H](C)Nc2ccccc2)c2[nH]c(N3CCCCC3)cc(=O)c2c1] | (R)-6-methyl-8-(1-(phenylamino)ethyl)-2-(piperidin-1-yl)quinolin-4(1H)-one |
| 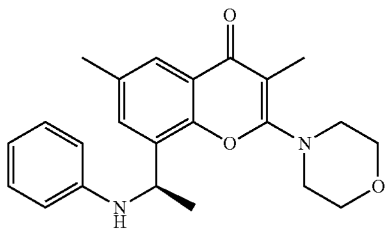 [SMILES: Cc1cc([C@@H](C)Nc2ccccc2)c2oc(N3CCOCC3)c(C)c(=O)c2c1] | (R)-3,6-dimethyl-2-morpholino-8-(1-(phenylamino)ethyl)-4H-chromen-4-one |
| 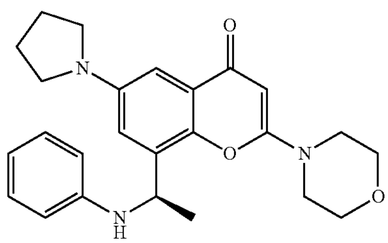 [SMILES: C[C@@H](Nc1ccccc1)c1cc(N2CCCC2)cc2c(=O)cc(N3CCOCC3)oc12] | (R)-2-morpholino-8-(1-(phenylamino)ethyl)-6-(pyrrolidin-1-yl)-4H-chromen-4-one |
| 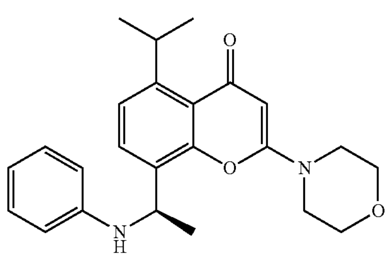 [SMILES: CC(C)c1ccc([C@@H](C)Nc2ccccc2)c2oc(N3CCOCC3)cc(=O)c12] | (R)-5-isopropyl-2-morpholino-8-(1-(phenylamino)ethyl)-4H-chromen-4-one |
| 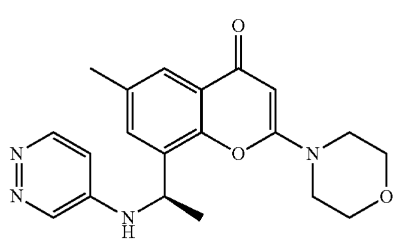 [SMILES: Cc1cc([C@@H](C)Nc2ccnnc2)c2oc(N3CCOCC3)cc(=O)c2c1] | (R)-6-methyl-2-morpholino-8-(1-(pyridazin-4-ylamino)ethyl)-4H-chromen-4-one |
| 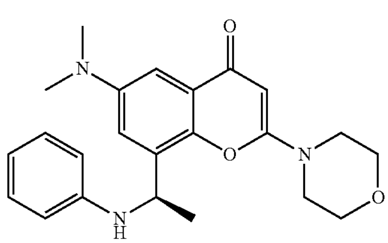 [SMILES: C[C@@H](Nc1ccccc1)c1cc(N(C)C)cc2c(=O)cc(N3CCOCC3)oc12] | (R)-6-(dimethylamino)-2-morpholino-8-(1-(phenylamino)ethyl)-4H-chromen-4-one |

TABLE 2-continued

| Compound Structure | Compound Name |
| --- | --- |
| 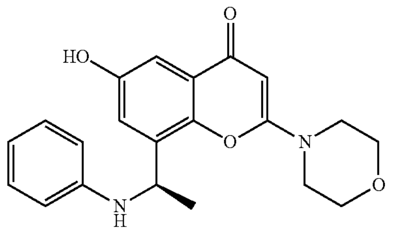 [SMILES: C[C@@H](Nc1ccccc1)c1cc(O)cc2c(=O)cc(N3CCOCC3)oc12] | (R)-6-hydroxy-2-morpholino-8-(1-(phenylamino)ethyl)-4H-chromen-4-one |
| 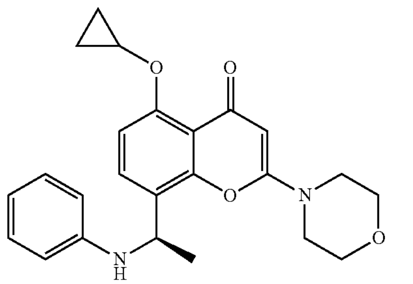 [SMILES: C[C@@H](Nc1ccccc1)c1ccc(OC2CC2)c2c(=O)cc(N3CCOCC3)oc12] | (R)-5-cyclopropoxy-2-morpholino-8-(1-(phenylamino)ethyl)-4H-chromen-4-one |
| 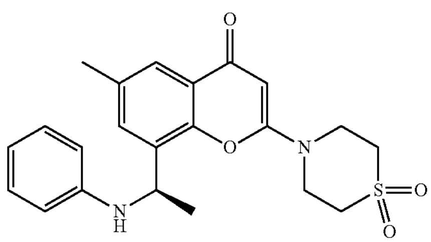 [SMILES: Cc1cc([C@@H](C)Nc2ccccc2)c2oc(N3CCS(=O)(=O)CC3)cc(=O)c2c1] | (R)-2-((1-(2-(1,1-dioxidothiomorpholino)-6-methyl-4-oxo-4H-chromen-8-yl)ethyl)amino)benzoic acid |
| 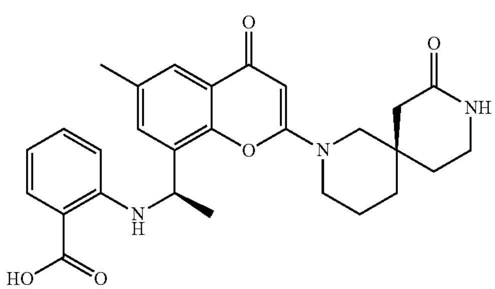 [SMILES: Cc1cc([C@@H](C)Nc2ccccc2C(=O)O)c2oc(N3CCC[C@@]4(CCNC(=O)C4)C3)cc(=O)c2c1] | 2-(((R)-1-(6-methyl-4-oxo-2-((S)-8-oxo-2,9-diazaspiro[5.5]undecan-2-yl)-4H-chromen-8-yl)ethyl)amino)benzoic acid |
| 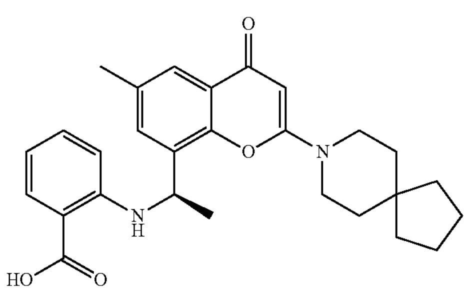 [SMILES: Cc1cc([C@@H](C)Nc2ccccc2C(=O)O)c2oc(N3CCC4(CCCC4)CC3)cc(=O)c2c1] | (R)-2-((1-(6-methyl-4-oxo-2-(8-azaspiro[4.5]decan-8-yl)-4H-chromen-8-yl)ethyl)amino)benzoic acid |

TABLE 2-continued

| Compound Structure | Compound Name |
|---|---|
| 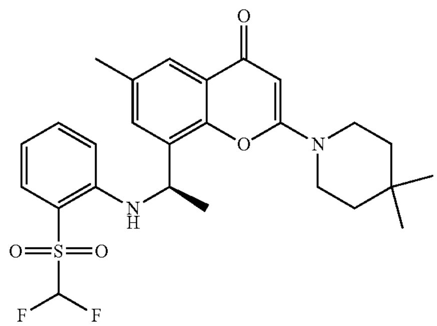 [SMILES: Cc1cc([C@@H](C)Nc2ccccc2S(=O)(=O)C(F)F)c2oc(N3CCC(C)(C)CC3)cc(=O)c2c1] | (R)-8-(1-((2-((difluoromethyl)sulfonyl)phenyl)amino)ethyl)-2-(4,4-dimethylpiperidin-1-yl)-6-methyl-4H-chromen-4-one |
| 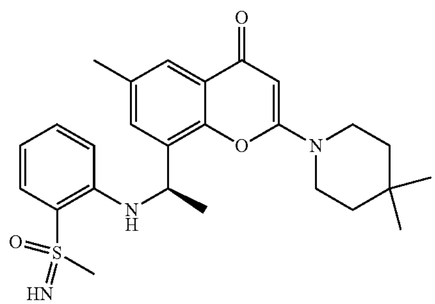 [SMILES: Cc1cc([C@@H](C)Nc2ccccc2S(C)(=N)=O)c2oc(N3CCC(C)(C)CC3)cc(=O)c2c1] | 2-(4,4-dimethylpiperidin-1-yl)-6-methyl-8-((1R)-1-((2-(S-methylsulfonimidoyl)phenyl)amino)ethyl)-4H-chromen-4-one |
| 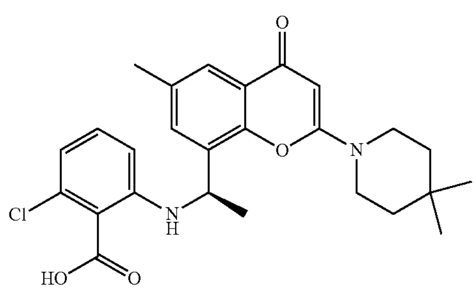 [SMILES: Cc1cc([C@@H](C)Nc2cccc(Cl)c2C(=O)O)c2oc(N3CCC(C)(C)CC3)cc(=O)c2c1] | (R)-2-chloro-6-((1-(2-(4,4-dimethylpiperidin-1-yl)-6-methyl-4-oxo-4H-chromen-8-yl)ethyl)amino)benzoic acid |
| 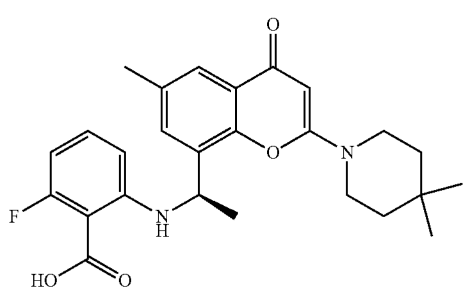 [SMILES: Cc1cc([C@@H](C)Nc2cccc(F)c2C(=O)O)c2oc(N3CCC(C)(C)CC3)cc(=O)c2c1] | (R)-2-((1-(2-(4,4-dimethylpiperidin-1-yl)-6-methyl-4-oxo-4H-chromen-8-yl)ethyl)amino)-6-fluorobenzoic acid |
| 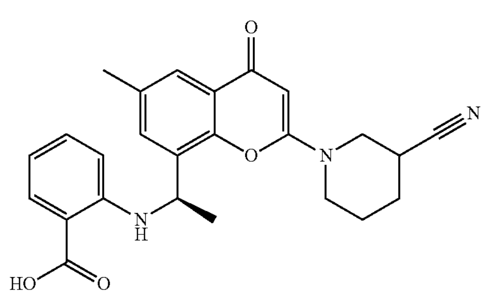 [SMILES: Cc1cc([C@@H](C)Nc2ccccc2C(=O)O)c2oc(N3CCCC(C#N)C3)cc(=O)c2c1] | 2-(((1R)-1-(2-(3-cyanopiperidin-1-yl)-6-methyl-4-oxo-4H-chromen-8-yl)ethyl)amino)benzoic acid |

TABLE 2-continued

| Compound Structure | Compound Name |
|---|---|
| 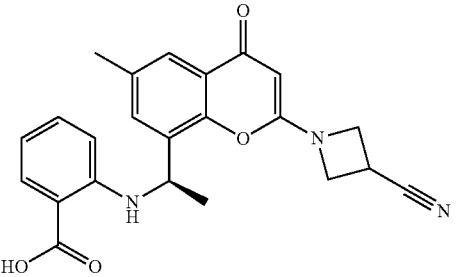 [SMILES: Cc1cc([C@@H](C)Nc2ccccc2C(=O)O)c2oc(N3CC(C#N)C3)cc(=O)c2c1] | (R)-2-((1-(2-(3-cyanoazetidin-1-yl)-6-methyl-4-oxo-4H-chromen-8-yl)ethyl)amino)benzoic acid |
| 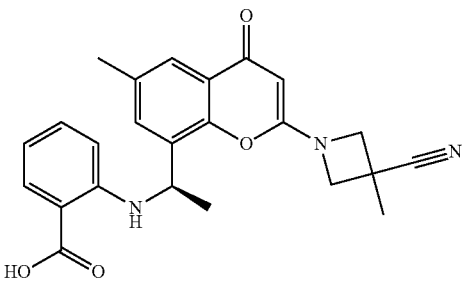 [SMILES: Cc1cc([C@@H](C)Nc2ccccc2C(=O)O)c2oc(N3CC(C)(C#N)C3)cc(=O)c2c1] | (R)-2-((1-(2-(3-cyano-3-methylazetidin-1-yl)-6-methyl-4-oxo-4H-chromen-8-yl)ethyl)amino)benzoic acid |
| 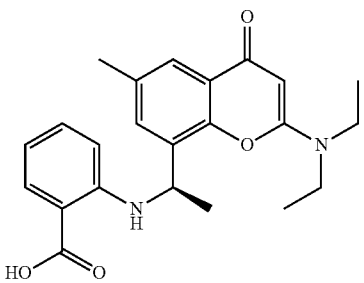 [SMILES: CCN(CC)c1cc(=O)c2cc(C)cc([C@@H](C)Nc3ccccc3C(=O)O)c2o1] | (R)-2-((1-(2-(diethylamino)-6-methyl-4-oxo-4H-chromen-8-yl)ethyl)amino)benzoic acid |
| 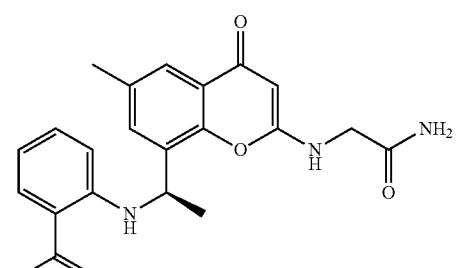 | (R)-2-((1-(2-((2-amino-2-oxoethyl)amino)-6-methyl-4-oxo-4H-chromen-8-yl)ethyl)amino)benzoic acid |
| 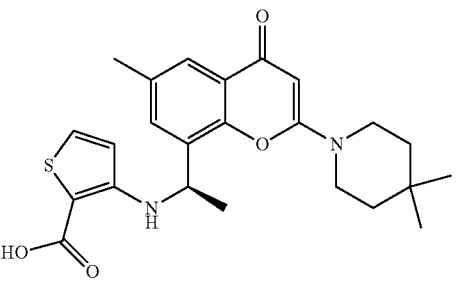 | (R)-3-((1-(2-(4,4-dimethylpiperidin-1-yl)-6-methyl-4-oxo-4H-chromen-8-yl)ethyl)amino)thiophene-2-carboxylic acid |

TABLE 2-continued

| Compound Structure | Compound Name |
|---|---|
| 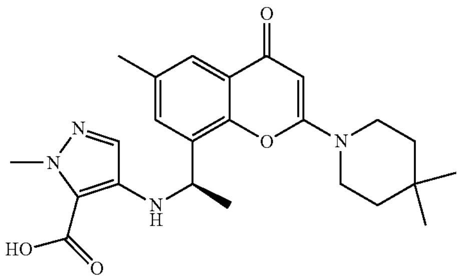 | (R)-4-((1-(2-(4,4-dimethylpiperidin-1-yl)-6-methyl-4-oxo-4H-chromen-8-yl)ethyl)amino)-1-methyl-1H-pyrazole-5-carboxylic acid |
| 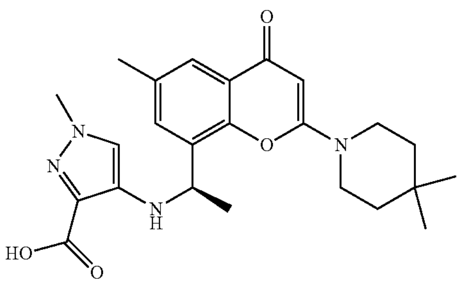 [SMILES: Cc1cc([C@@H](C)Nc2cn(C)nc2C(=O)O)c2oc(N3CCC(C)(C)CC3)cc(=O)c2c1] | (R)-4-((1-(2-(4,4-dimethylpiperidin-1-yl)-6-methyl-4-oxo-4H-chromen-8-yl)ethyl)amino)-1-methyl-1H-pyrazole-3-carboxylic acid |
| 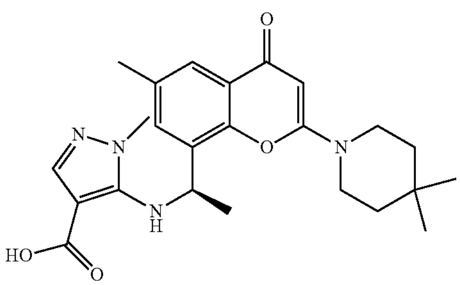 [SMILES: Cc1cc([C@@H](C)Nc2c(C(=O)O)cnn2C)c2oc(N3CCC(C)(C)CC3)cc(=O)c2c1] | (R)-5-((1-(2-(4,4-dimethylpiperidin-1-yl)-6-methyl-4-oxo-4H-chromen-8-yl)ethyl)amino)-1-methyl-1H-pyrazole-4-carboxylic acid |
| 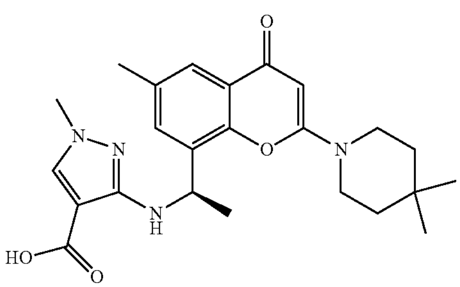 [SMILES: Cc1cc([C@@H](C)Nc2nn(C)cc2C(=O)O)c2oc(N3CCC(C)(C)CC3)cc(=O)c2c1] | (R)-3-((1-(2-(4,4-dimethylpiperidin-1-yl)-6-methyl-4-oxo-4H-chromen-8-yl)ethyl)amino)-1-methyl-1H-pyrazole-4-carboxylic acid |
| 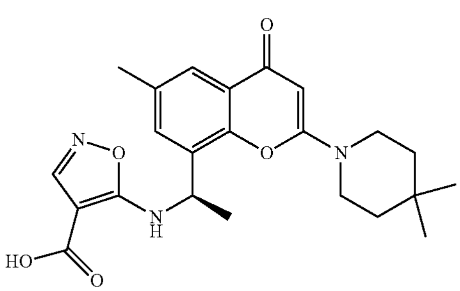 [SMILES: Cc1cc([C@@H](C)Nc2oncc2C(=O)O)c2oc(N3CCC(C)(C)CC3)cc(=O)c2c1] | (R)-5-((1-(2-(4,4-dimethylpiperidin-1-yl)-6-methyl-4-oxo-4H-chromen-8-yl)ethyl)amino)isoxazole-4-carboxylic acid |

TABLE 2-continued

| Compound Structure | Compound Name |
| --- | --- |
| 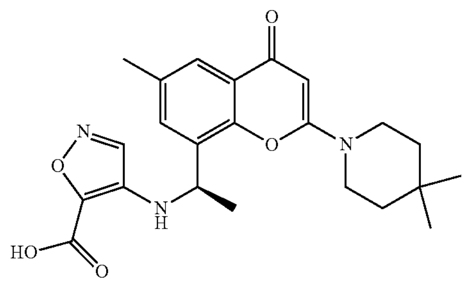 [SMILES: Cc1cc([C@@H](C)Nc2cnoc2C(=O)O)c2oc(N3CCC(C)(C)CC3)cc(=O)c2c1] | (R)-4-((1-(2-(4,4-dimethylpiperidin-1-yl)-6-methyl-4-oxo-4H-chromen-8-yl)ethyl)amino)isoxazole-5-carboxylic acid |
| 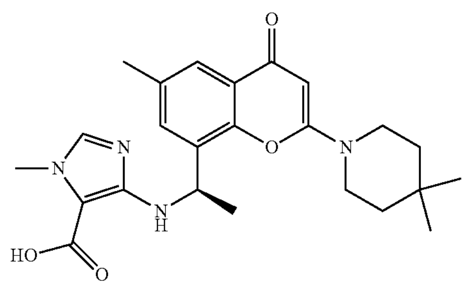 | (R)-4-((1-(2-(4,4-dimethylpiperidin-1-yl)-6-methyl-4-oxo-4H-chromen-8-yl)ethyl)amino)-1-methyl-1H-imidazole-5-carboxylic acid |
| 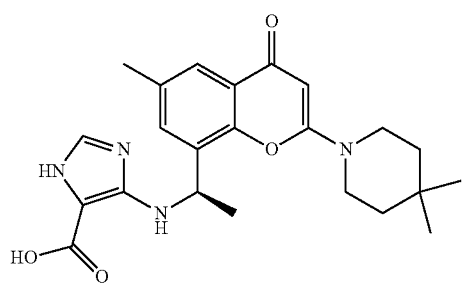 [SMILES: Cc1cc([C@@H](C)Nc2nc[nH]c2C(=O)O)c2oc(N3CCC(C)(C)CC3)cc(=O)c2c1] | (R)-4-((1-(2-(4,4-dimethylpiperidin-1-yl)-6-methyl-4-oxo-4H-chromen-8-yl)ethyl)amino)-1H-imidazole-5-carboxylic acid |
| 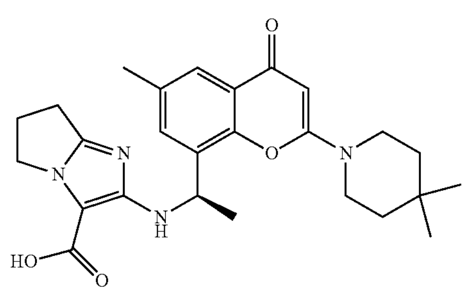 [SMILES: Cc1cc([C@@H](C)Nc2nc3n(c2C(=O)O)CCC3)c2oc(N3CCC(C)(C)CC3)cc(=O)c2c1] | (R)-2-((1-(2-(4,4-dimethylpiperidin-1-yl)-6-methyl-4-oxo-4H-chromen-8-yl)ethyl)amino)-6,7-dihydro-5H-pyrrolo[1,2-a]imidazole-3-carboxylic acid |
| 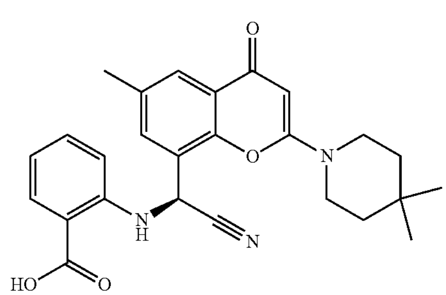 [SMILES: Cc1cc([C@@H](C#N)Nc2ccccc2C(=O)O)c2oc(N3CCC(C)(C)CC3)cc(=O)c2c1] | (S)-2-((cyano(2-(4,4-dimethylpiperidin-1-yl)-6-methyl-4-oxo-4H-chromen-8-yl)methyl)amino)benzoic acid |

TABLE 2-continued

| Compound Structure | Compound Name |
| --- | --- |
| 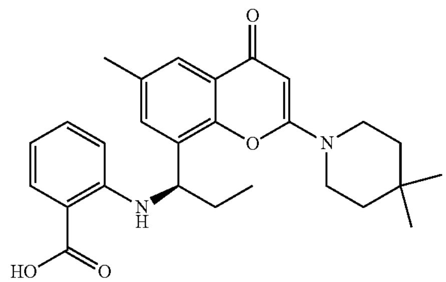 [SMILES: CC[C@@H](Nc1ccccc1C(=O)O)c1cc(C)cc2c(=O)cc(N3CCC(C)(C)CC3)oc12] | (R)-2-((1-(2-(4,4-dimethylpiperidin-1-yl)-6-methyl-4-oxo-4H-chromen-8-yl)propyl)amino)benzoic acid |
| 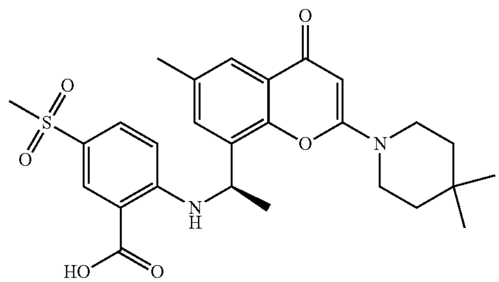 | (R)-2-((1-(2-(4,4-dimethylpiperidin-1-yl)-6-methyl-4-oxo-4H-chromen-8-yl)ethyl)amino)-5-(methylsulfonyl)benzoic acid |
| 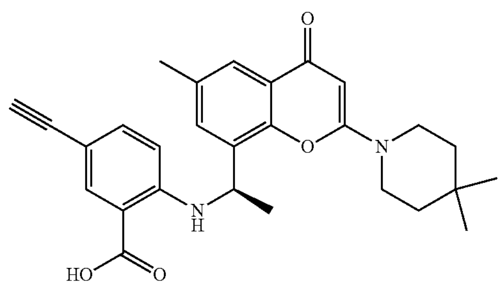 [SMILES: C#Cc1ccc(N[C@H](C)c2cc(C)cc3c(=O)cc(N4CCC(C)(C)CC4)oc23)c(C(=O)O)c1] | (R)-2-((1-(2-(4,4-dimethylpiperidin-1-yl)-6-methyl-4-oxo-4H-chromen-8-yl)ethyl)amino)-5-ethynylbenzoic acid |
| 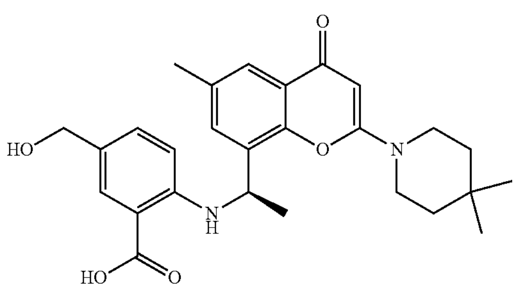 [SMILES: Cc1cc([C@@H](C)Nc2ccc(CO)cc2C(=O)O)c2oc(N3CCC(C)(C)CC3)cc(=O)c2c1] | (R)-2-((1-(2-(4,4-dimethylpiperidin-1-yl)-6-methyl-4-oxo-4H-chromen-8-yl)ethyl)amino)-5-(hydroxymethyl)benzoic acid |
| 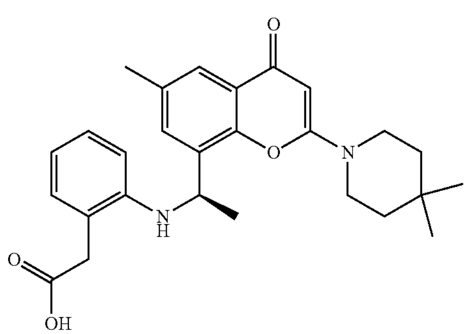 [SMILES: Cc1cc([C@@H](C)Nc2ccccc2CC(=O)O)c2oc(N3CCC(C)(C)CC3)cc(=O)c2c1] | (R)-2-(2-((1-(2-(4,4-dimethylpiperidin-1-yl)-6-methyl-4-oxo-4H-chromen-8-yl)ethyl)amino)phenyl)acetic acid |

TABLE 2-continued

| Compound Structure | Compound Name |
|---|---|
| 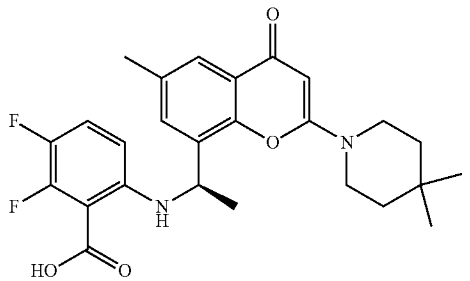 [SMILES: Cc1cc([C@@H](C)Nc2ccc(F)c(F)c2C(=O)O)c2oc(N3CCC(C)(C)CC3)cc(=O)c2c1] | (R)-6-((1-(2-(4,4-dimethylpiperidin-1-yl)-6-methyl-4-oxo-4H-chromen-8-yl)ethyl)amino)-2,3-difluorobenzoic acid |
| 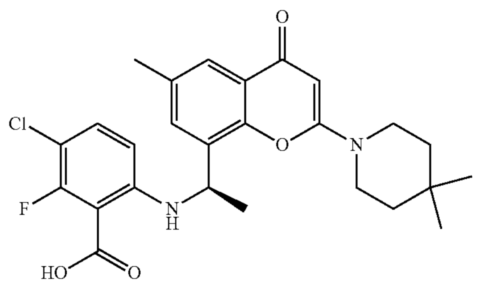 [SMILES: Cc1cc([C@@H](C)Nc2ccc(Cl)c(F)c2C(=O)O)c2oc(N3CCC(C)(C)CC3)cc(=O)c2c1] | (R)-3-chloro-6-((1-(2-(4,4-dimethylpiperidin-1-yl)-6-methyl-4-oxo-4H-chromen-8-yl)ethyl)amino)-2-fluorobenzoic acid |
| 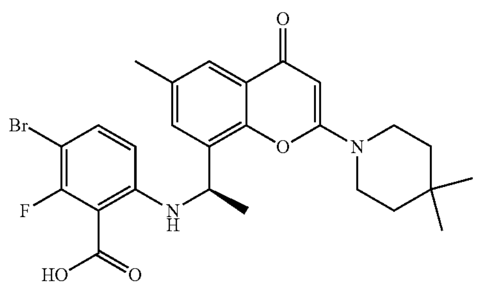 [SMILES: Cc1cc([C@@H](C)Nc2ccc(Br)c(F)c2C(=O)O)c2oc(N3CCC(C)(C)CC3)cc(=O)c2c1] | (R)-3-bromo-6-((1-(2-(4,4-dimethylpiperidin-1-yl)-6-methyl-4-oxo-4H-chromen-8-yl)ethyl)amino)-2-fluorobenzoic acid |
| 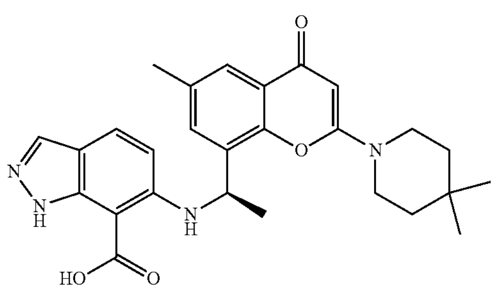 [SMILES: Cc1cc([C@@H](C)Nc2ccc3cn[nH]c3c2C(=O)O)c2oc(N3CCC(C)(C)CC3)cc(=O)c2c1] | (R)-6-((1-(2-(4,4-dimethylpiperidin-1-yl)-6-methyl-4-oxo-4H-chromen-8-yl)ethyl)amino)-1H-indazole-7-carboxylic acid |
| 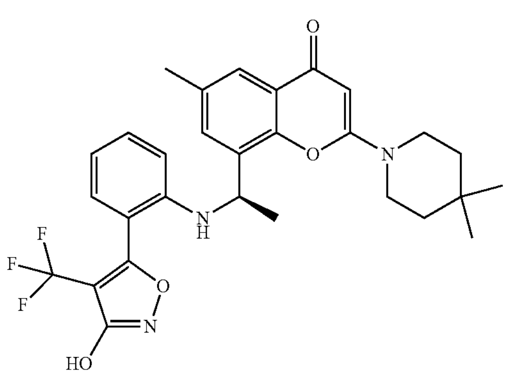 [SMILES: Cc1cc([C@@H](C)Nc2ccccc2-c2onc(O)c2C(F)(F)F)c2oc(N3CCC(C)(C)CC3)cc(=O)c2c1] | (R)-2-(4,4-dimethylpiperidin-1-yl)-8-(1-((2-(3-hydroxy-4-(trifluoromethyl)isoxazol-5-yl)phenyl)amino)ethyl)-6-methyl-4H-chromen-4-one |

TABLE 2-continued

| Compound Structure | Compound Name |
|---|---|
| 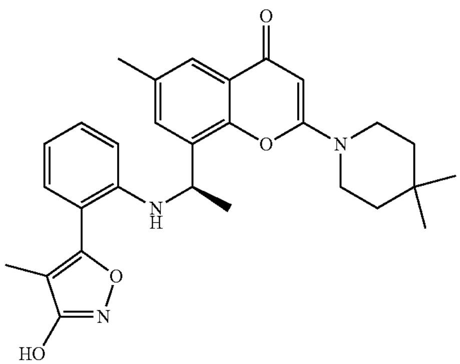 | (R)-2-(4,4-dimethylpiperidin-1-yl)-8-(1-((2-(3-hydroxy-4-methylisoxazol-5-yl)phenyl)amino)ethyl)-6-methyl-4H-chromen-4-one |
| 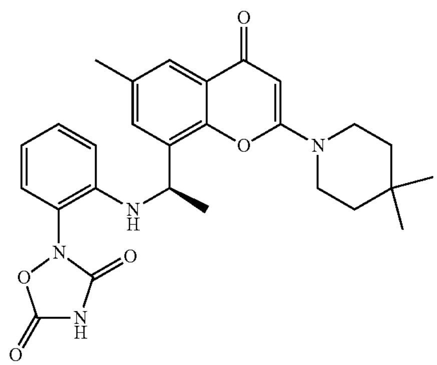 [SMILES: Cc1cc([C@@H](C)Nc2ccccc2-n2oc(=O)[nH]c2=O)c2oc(N3CCC(C)(C)CC3)cc(=O)c2c1] | (R)-2-(2-((1-(2-(4,4-dimethylpiperidin-1-yl)-6-methyl-4-oxo-4H-chromen-8-yl)ethyl)amino)phenyl)-1,2,4-oxadiazolidine-3,5-dione |
| 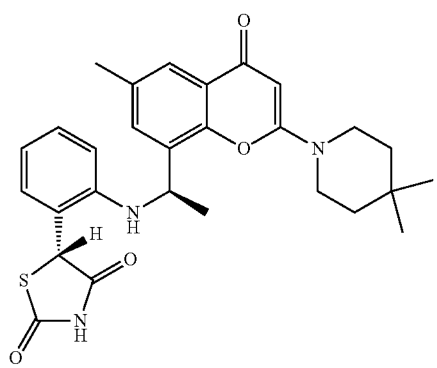 [SMILES: Cc1cc([C@@H](C)Nc2ccccc2[C@H]2SC(=O)NC2=O)c2oc(N3CCC(C)(C)CC3)cc(=O)c2c1] | (R)-5-(2-(((R)-1-(2-(4,4-dimethylpiperidin-1-yl)-6-methyl-4-oxo-4H-chromen-8-yl)ethyl)amino)phenyl)thiazolidine-2,4-dione |
| 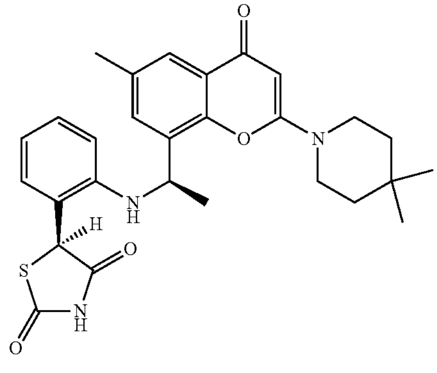 [SMILES: Cc1cc([C@@H](C)Nc2ccccc2[C@@H]2SC(=O)NC2=O)c2oc(N3CCC(C)(C)CC3)cc(=O)c2c1] | (S)-5-(2-(((R)-1-(2-(4,4-dimethylpiperidin-1-yl)-6-methyl-4-oxo-4H-chromen-8-yl)ethyl)amino)phenyl)thiazolidine-2,4-dione |

TABLE 2-continued

| Compound Structure | Compound Name |
| --- | --- |
| 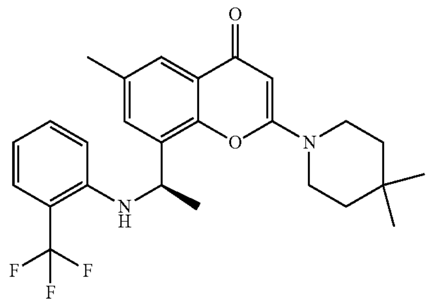 [SMILES: Cc1cc([C@@H](C)Nc2ccccc2C(F)(F)F)c2oc(N3CCC(C)(C)CC3)cc(=O)c2c1] | (R)-2-(4,4-dimethylpiperidin-1-yl)-6-methyl-8-(1-((2-(trifluoromethyl)phenyl)amino)ethyl)-4H-chromen-4-one |
| 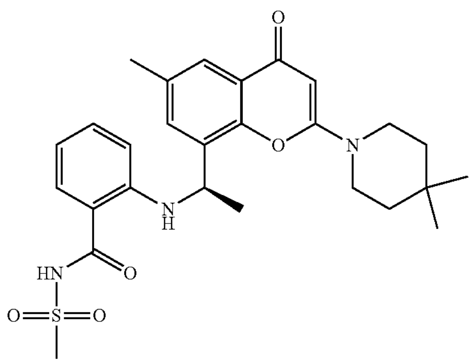 [SMILES: Cc1cc([C@@H](C)Nc2ccccc2C(=O)NS(C)(=O)=O)c2oc(N3CCC(C)(C)CC3)cc(=O)c2c1] | (R)-2-((1-(2-(4,4-dimethylpiperidin-1-yl)-6-methyl-4-oxo-4H-chromen-8-yl)ethyl)amino)-N-(methylsulfonyl)benzamide |
| 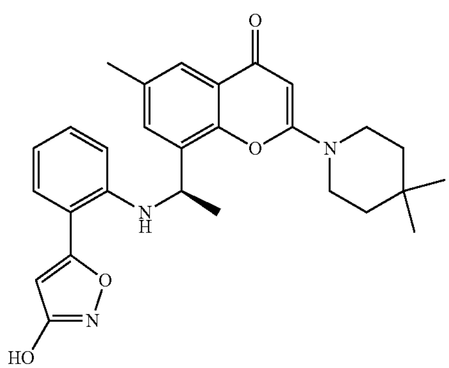 [SMILES: Cc1cc([C@@H](C)Nc2ccccc2-c2cc(O)no2)c2oc(N3CCC(C)(C)CC3)cc(=O)c2c1] | (R)-2-(4,4-dimethylpiperidin-1-yl)-8-(1-((2-(3-hydroxyisoxazol-5-yl)phenyl)amino)ethyl)-6-methyl-4H-chromen-4-one |
| 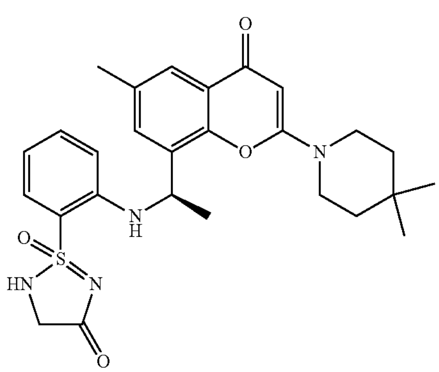 [SMILES: Cc1cc([C@@H](C)Nc2ccccc2S2(=O)=NC(=O)CN2)c2oc(N3CCC(C)(C)CC3)cc(=O)c2c1] | 1-(2-(((R)-1-(2-(4,4-dimethylpiperidin-1-yl)-6-methyl-4-oxo-4H-chromen-8-yl)ethyl)amino)phenyl)-4,5-dihydro-3H-1l6,2,5-thiadiazol-3-one 1-oxide |

TABLE 2-continued

| Compound Structure | Compound Name |
|---|---|
| 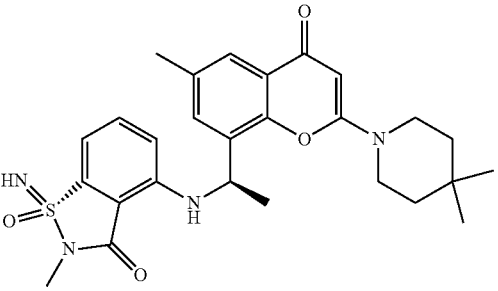 [SMILES: Cc1cc([C@@H](C)Nc2cccc3c2C(=O)N(C)[S@]3(=N)=O)c2oc(N3CCC(C)(C)CC3)cc(=O)c2c1] | (S)-4-(((R)-1-(2-(4,4-dimethylpiperidin-1-yl)-6-methyl-4-oxo-4H-chromen-8-yl)ethyl)amino)-1-imino-2-methyl-1,2-dihydro-3H-1l4-benzo[d]isothiazol-3-one 1-oxide |
| 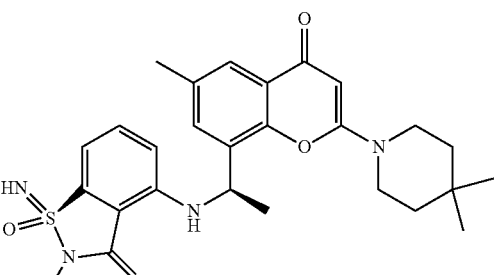 | (R)-4-(((R)-1-(2-(4,4-dimethylpiperidin-1-yl)-6-methyl-4-oxo-4H-chromen-8-yl)ethyl)amino)-1-imino-2-methyl-1,2-dihydro-3H-1l4-benzo[d]isothiazol-3-one 1-oxide |
| 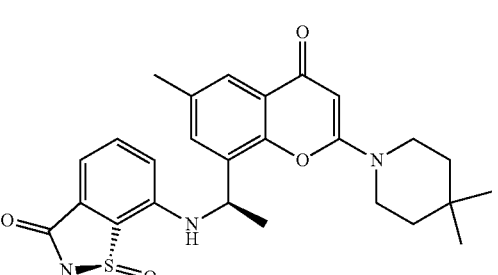 | (S)-7-(((R)-1-(2-(4,4-dimethylpiperidin-1-yl)-6-methyl-4-oxo-4H-chromen-8-yl)ethyl)amino)-1-imino-2-methyl-1,2-dihydro-3H-1l4-benzo[d]isothiazol-3-one 1-oxide |
| 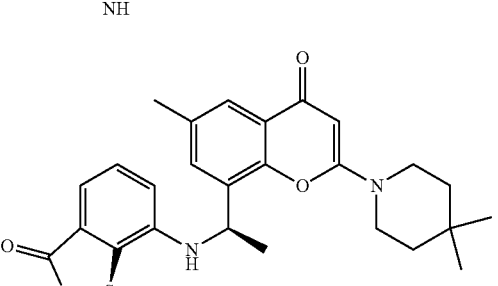 | (R)-7-(((R)-1-(2-(4,4-dimethylpiperidin-1-yl)-6-methyl-4-oxo-4H-chromen-8-yl)ethyl)amino)-1-imino-2-methyl-1,2-dihydro-3H-1l4-benzo[d]isothiazol-3-one 1-oxide |
| 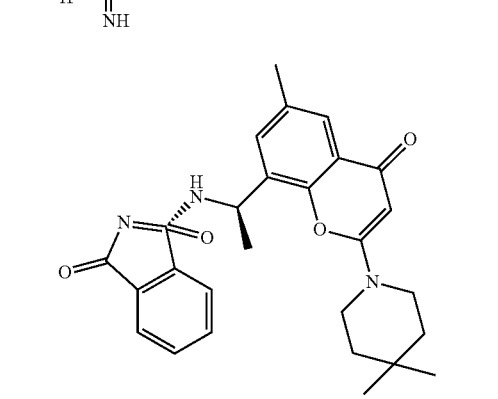 | (S)-1-(((R)-1-(2-(4,4-dimethylpiperidin-1-yl)-6-methyl-4-oxo-4H-chromen-8-yl)ethyl)amino)-3H-1l4-benzo[d]isothiazol-3-one 1-oxide |

TABLE 2-continued

| Compound Structure | Compound Name |
|---|---|
| | (R)-1-(((R)-1-(2-(4,4-dimethylpiperidin-1-yl)-6-methyl-4-oxo-4H-chromen-8-yl)ethyl)amino)-3H-1λ4-benzo[d]isothiazol-3-one 1-oxide |
| 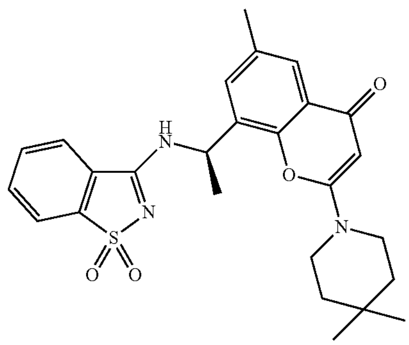 [SMILES: Cc1cc([C@@H](C)NC2=NS(=O)(=O)c3ccccc32)c2oc(N3CCC(C)(C)CC3)cc(=O)c2c1] | (R)-2-(4,4-dimethylpiperidin-1-yl)-8-(1-((1,1-dioxidobenzo[d]isothiazol-3-yl)amino)ethyl)-6-methyl-4H-chromen-4-one |
| 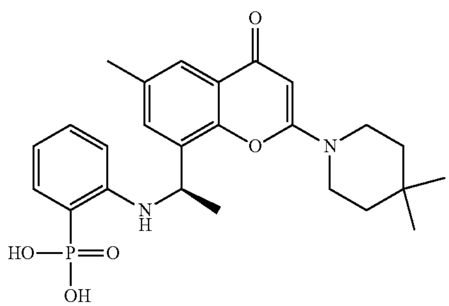 [SMILES: Cc1cc([C@@H](C)Nc2ccccc2P(=O)(O)O)c2oc(N3CCC(C)(C)CC3)cc(=O)c2c1] | (R)-(2-((1-(2-(4,4-dimethylpiperidin-1-yl)-6-methyl-4-oxo-4H-chromen-8-yl)ethyl)amino)phenyl)phosphonic acid |
| 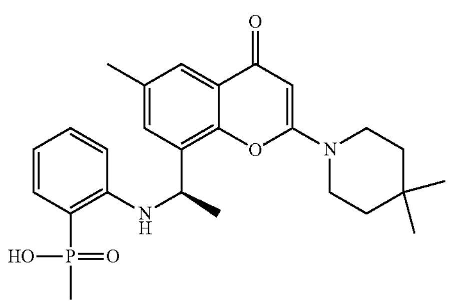 [SMILES: Cc1cc([C@@H](C)Nc2ccccc2P(C)(=O)O)c2oc(N3CCC(C)(C)CC3)cc(=O)c2c1] | (2-(((R)-1-(2-(4,4-dimethylpiperidin-1-yl)-6-methyl-4-oxo-4H-chromen-8-yl)ethyl)amino)phenyl)(methyl)phosphinic acid |
| 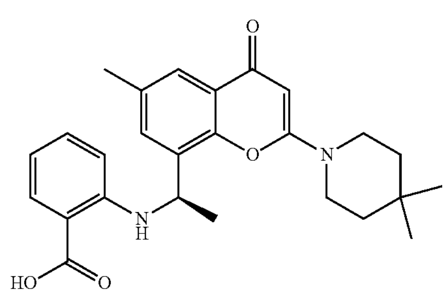 | (R)-2-(1-(2-(4,4-dimethylpiperidin-1-yl)-6-methyl-4-oxo-4H-chromen-8-yl)ethoxy)benzoic acid |

TABLE 2-continued

| Compound Structure | Compound Name |
|---|---|
| 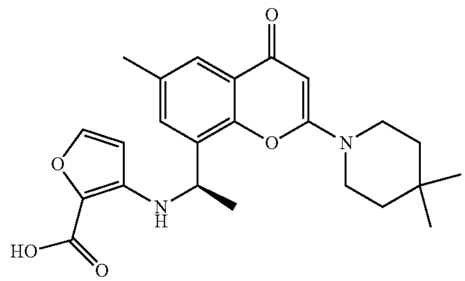 | (R)-3-((1-(2-(4,4-dimethylpiperidin-1-yl)-6-methyl-4-oxo-4H-chromen-8-yl)ethyl)amino)furan-2-carboxylic acid |
| 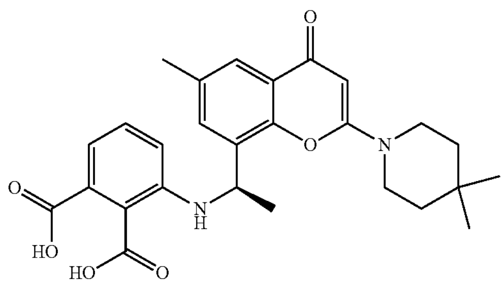 [SMILES: Cc1cc([C@@H](C)Nc2cccc(C(=O)O)c2C(=O)O)c2oc(N3CCC(C)(C)CC3)cc(=O)c2c1] | (R)-3-((1-(2-(4,4-dimethylpiperidin-1-yl)-6-methyl-4-oxo-4H-chromen-8-yl)ethyl)amino)phthalic acid |
| 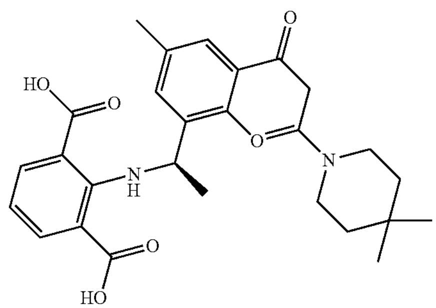 | (R)-2-((1-(2-(4,4-dimethylpiperidin-1-yl)-6-methyl-4-oxo-4H-chromen-8-yl)ethyl)amino)isophthalic acid |
| 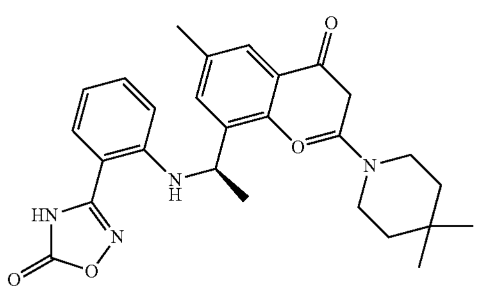 | (R)-3-(2-((1-(2-(4,4-dimethylpiperidin-1-yl)-6-methyl-4-oxo-4H-chromen-8-yl)ethyl)amino)phenyl)-1,2,4-oxadiazol-5(4H)-one |
| 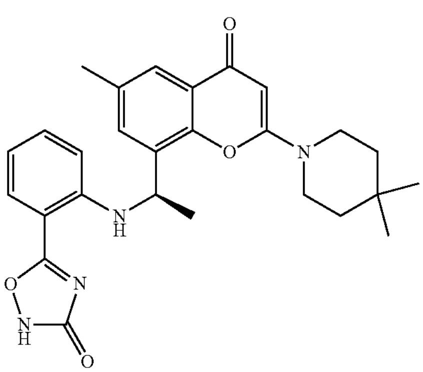 [SMILES: Cc1cc([C@@H](C)Nc2ccccc2-c2nc(=O)[nH]o2)c2oc(N3CCC(C)(C)CC3)cc(=O)c2c1] | (R)-5-(2-((1-(2-(4,4-dimethylpiperidin-1-yl)-6-methyl-4-oxo-4H-chromen-8-yl)ethyl)amino)phenyl)-1,2,4-oxadiazol-3(2H)-one |

TABLE 2-continued

| Compound Structure | Compound Name |
|---|---|
| 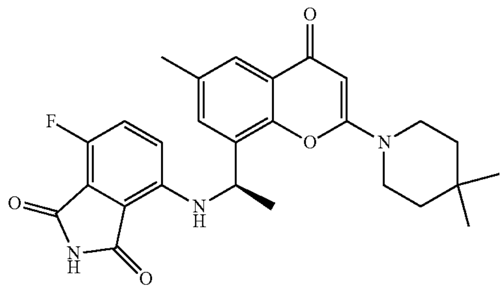 [SMILES: Cc1cc([C@@H](C)Nc2ccc(F)c3c2C(=O)NC3=O)c2oc(N3CCC(C)(C)CC3)cc(=O)c2c1] | (R)-4-((1-(2-(4,4-dimethylpiperidin-1-yl)-6-methyl-4-oxo-4H-chromen-8-yl)ethyl)amino)-7-fluoroisoindoline-1,3-dione |
| 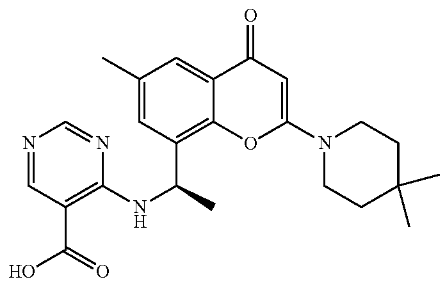 [SMILES: Cc1cc([C@@H](C)Nc2ncncc2C(=O)O)c2oc(N3CCC(C)(C)CC3)cc(=O)c2c1] | (R)-4-((1-(2-(4,4-dimethylpiperidin-1-yl)-6-methyl-4-oxo-4H-chromen-8-yl)ethyl)amino)pyrimidine-5-carboxylic acid |
| 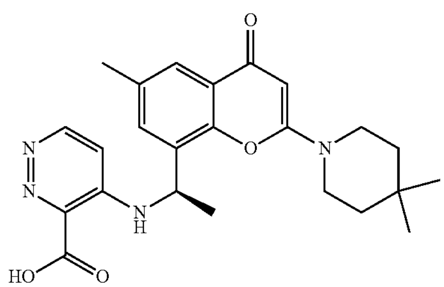 [SMILES: Cc1cc([C@@H](C)Nc2ccnnc2C(=O)O)c2oc(N3CCC(C)(C)CC3)cc(=O)c2c1] | (R)-4-((1-(2-(4,4-dimethylpiperidin-1-yl)-6-methyl-4-oxo-4H-chromen-8-yl)ethyl)amino)pyridazine-3-carboxylic acid |
| 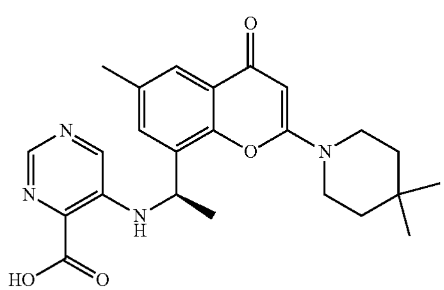 [SMILES: Cc1cc([C@@H](C)Nc2cncnc2C(=O)O)c2oc(N3CCC(C)(C)CC3)cc(=O)c2c1] | (R)-5-((1-(2-(4,4-dimethylpiperidin-1-yl)-6-methyl-4-oxo-4H-chromen-8-yl)ethyl)amino)pyrimidine-4-carboxylic acid |
| 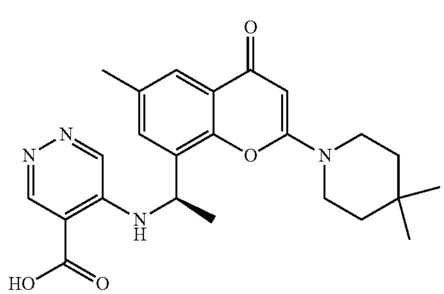 [SMILES: Cc1cc([C@@H](C)Nc2cnncc2C(=O)O)c2oc(N3CCC(C)(C)CC3)cc(=O)c2c1] | (R)-5-((1-(2-(4,4-dimethylpiperidin-1-yl)-6-methyl-4-oxo-4H-chromen-8-yl)ethyl)amino)pyridazine-4-carboxylic acid |

TABLE 2-continued

| Compound Structure | Compound Name |
| --- | --- |
| 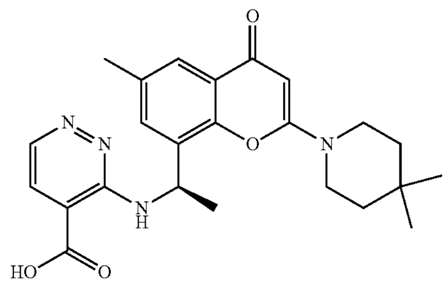 [SMILES: Cc1cc([C@@H](C)Nc2nnccc2C(=O)O)c2oc(N3CCC(C)(C)CC3)cc(=O)c2c1] | (R)-3-((1-(2-(4,4-dimethylpiperidin-1-yl)-6-methyl-4-oxo-4H-chromen-8-yl)ethyl)amino)pyridazine-4-carboxylic acid |
| 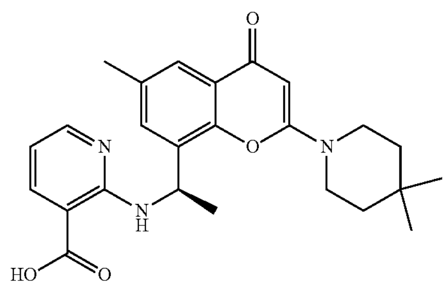 [SMILES: Cc1cc([C@@H](C)Nc2ncccc2C(=O)O)c2oc(N3CCC(C)(C)CC3)cc(=O)c2c1] | (R)-2-((1-(2-(4,4-dimethylpiperidin-1-yl)-6-methyl-4-oxo-4H-chromen-8-yl)ethyl)amino)nicotinic acid |
| 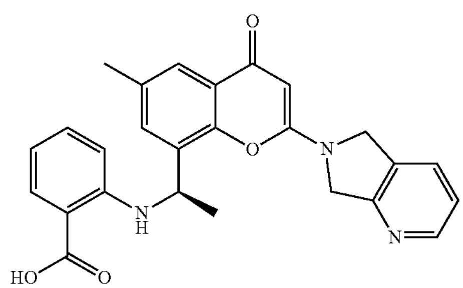 [SMILES: Cc1cc([C@@H](C)Nc2ccccc2C(=O)O)c2oc(N3Cc4cccnc4C3)cc(=O)c2c1] | (R)-2-((1-(2-(5,7-dihydro-6H-pyrrolo[3,4-b]pyridin-6-yl)-6-methyl-4-oxo-4H-chromen-8-yl)ethyl)amino)benzoic acid |
| 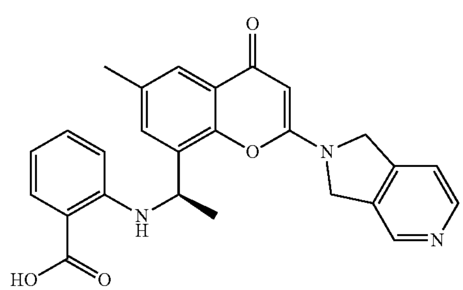 [SMILES: Cc1cc([C@@H](C)Nc2ccccc2C(=O)O)c2oc(N3Cc4ccncc4C3)cc(=O)c2c1] | (R)-2-((1-(2-(1,3-dihydro-2H-pyrrolo[3,4-c]pyridin-2-yl)-6-methyl-4-oxo-4H-chromen-8-yl)ethyl)amino)benzoic acid |
| 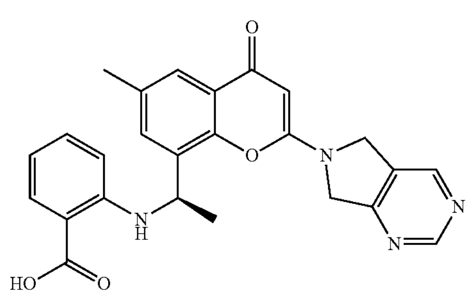 [SMILES: Cc1cc([C@@H](C)Nc2ccccc2C(=O)O)c2oc(N3Cc4cncnc4C3)cc(=O)c2c1] | (R)-2-((1-(2-(5,7-dihydro-6H-pyrrolo[3,4-d]pyrimidin-6-yl)-6-methyl-4-oxo-4H-chromen-8-yl)ethyl)amino)benzoic acid |

TABLE 2-continued

| Compound Structure | Compound Name |
|---|---|
| 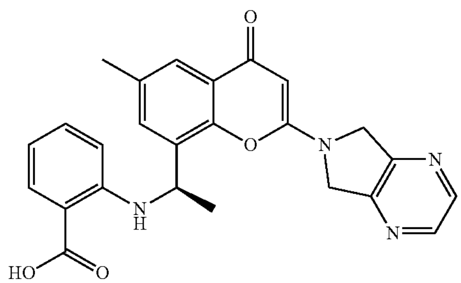 [SMILES: Cc1cc([C@@H](C)Nc2ccccc2C(=O)O)c2oc(N3Cc4nccnc4C3)cc(=O)c2c1] | (R)-2-((1-(2-(5,7-dihydro-6H-pyrrolo[3,4-b]pyrazin-6-yl)-6-methyl-4-oxo-4H-chromen-8-yl)ethyl)amino)benzoic acid |
| 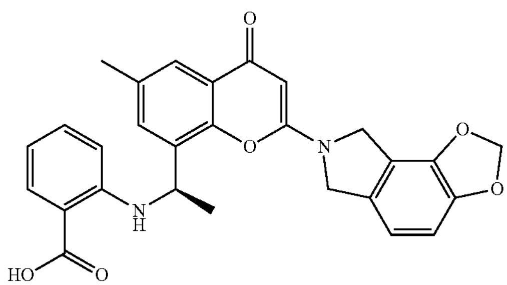 [SMILES: Cc1cc([C@@H](C)Nc2ccccc2C(=O)O)c2oc(N3Cc4ccc5c(c4C3)OCO5)cc(=O)c2c1] | (R)-2-((1-(2-(6,8-dihydro-7H-[1,3]dioxolo[4,5-e]isoindol-7-yl)-6-methyl-4-oxo-4H-chromen-8-yl)ethyl)amino)benzoic acid |
| 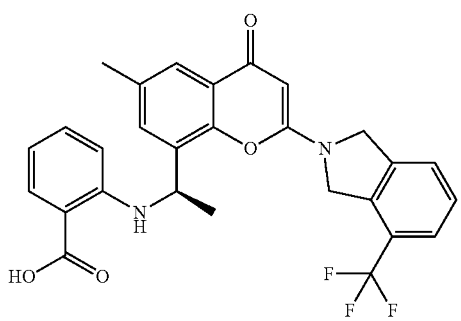 [SMILES: Cc1cc([C@@H](C)Nc2ccccc2C(=O)O)c2oc(N3Cc4cccc(C(F)(F)F)c4C3)cc(=O)c2c1] | (R)-2-((1-(6-methyl-4-oxo-2-(4-(trifluoromethyl)isoindolin-2-yl)-4H-chromen-8-yl)ethyl)amino)benzoic acid |
| 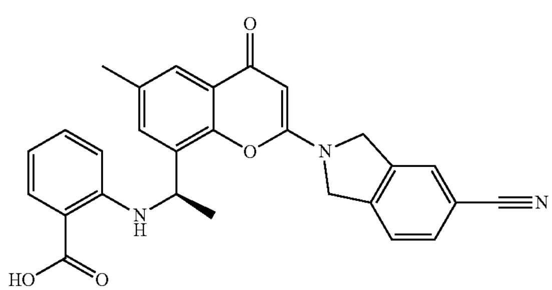 [SMILES: Cc1cc([C@@H](C)Nc2ccccc2C(=O)O)c2oc(N3Cc4ccc(C#N)cc4C3)cc(=O)c2c1] | (R)-2-((1-(2-(5-cyanoisoindolin-2-yl)-6-methyl-4-oxo-4H-chromen-8-yl)ethyl)amino)benzoic acid |
| 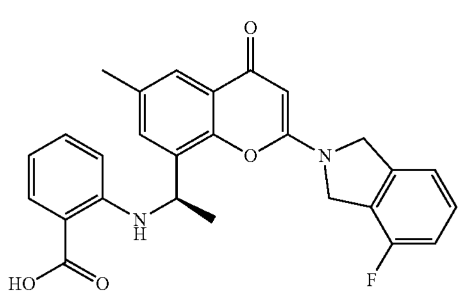 [SMILES: Cc1cc([C@@H](C)Nc2ccccc2C(=O)O)c2oc(N3Cc4cccc(F)c4C3)cc(=O)c2c1] | (R)-2-((1-(2-(4-fluoroisoindolin-2-yl)-6-methyl-4-oxo-4H-chromen-8-yl)ethyl)amino)benzoic acid |

TABLE 2-continued

| Compound Structure | Compound Name |
| --- | --- |
| 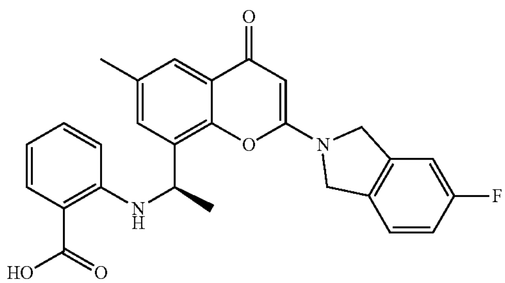 [SMILES: Cc1cc([C@@H](C)Nc2ccccc2C(=O)O)c2oc(N3Cc4ccc(F)cc4C3)cc(=O)c2c1] | (R)-2-((1-(2-(5-fluoroisoindolin-2-yl)-6-methyl-4-oxo-4H-chromen-8-yl)ethyl)amino)benzoic acid |
| 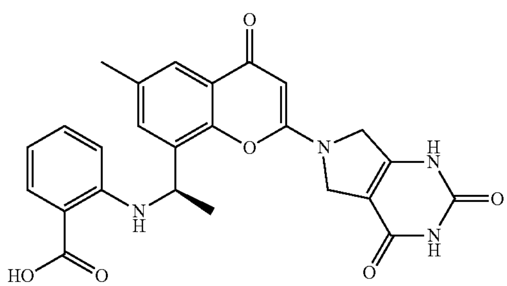 [SMILES: Cc1cc([C@@H](C)Nc2ccccc2C(=O)O)c2oc(N3Cc4[nH]c(=O)[nH]c(=O)c4C3)cc(=O)c2c1] | (R)-2-((1-(2-(2,4-dioxo-1,2,3,4,5,7-hexahydro-6H-pyrrolo[3,4-d]pyrimidin-6-yl)-6-methyl-4-oxo-4H-chromen-8-yl)ethyl)amino)benzoic acid |
| 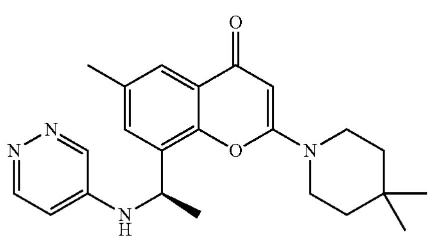 [SMILES: Cc1cc([C@@H](C)Nc2ccnnc2)c2oc(N3CCC(C)(C)CC3)cc(=O)c2c1] | (R)-2-(4,4-dimethylpiperidin-1-yl)-6-methyl-8-(1-(pyridazin-4-ylamino)ethyl)-4H-chromen-4-one |
| 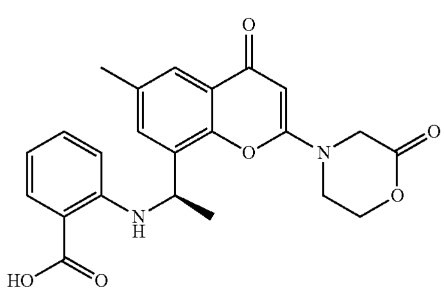 [SMILES: Cc1cc([C@@H](C)Nc2ccccc2C(=O)O)c2oc(N3CCOC(=O)C3)cc(=O)c2c1] | (R)-2-((1-(6-methyl-4-oxo-2-(2-oxomorpholino)-4H-chromen-8-yl)ethyl)amino)benzoic acid |
| 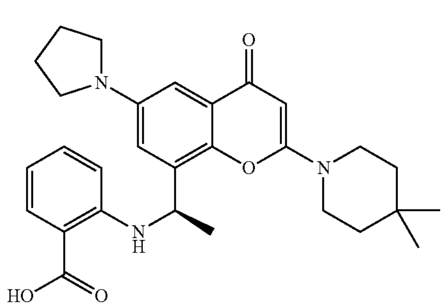 [SMILES: C[C@@H](Nc1ccccc1C(=O)O)c1cc(N2CCCC2)cc2c(=O)cc(N3CCC(C)(C)CC3)oc12] | (R)-2-((1-(2-(4,4-dimethylpiperidin-1-yl)-4-oxo-6-(pyrrolidin-1-yl)-4H-chromen-8-yl)ethyl)amino)benzoic acid |

TABLE 2-continued

| Compound Structure | Compound Name |
| --- | --- |
| 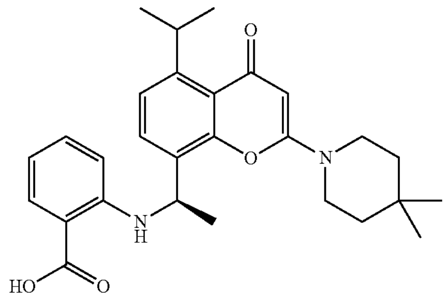 [SMILES: CC(C)c1ccc([C@@H](C)Nc2ccccc2C(=O)O)c2oc(N3CCC(C)(C)CC3)cc(=O)c12] | (R)-2-((1-(2-(4,4-dimethylpiperidin-1-yl)-5-isopropyl-4-oxo-4H-chromen-8-yl)ethyl)amino)benzoic acid |
| 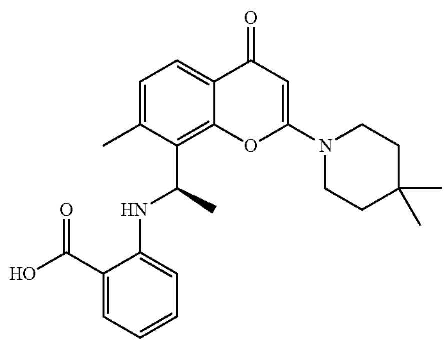 [SMILES: Cc1ccc2c(=O)cc(N3CCC(C)(C)CC3)oc2c1[C@@H](C)Nc1ccccc1C(=O)O] | (R)-2-((1-(2-(4,4-dimethylpiperidin-1-yl)-7-methyl-4-oxo-4H-chromen-8-yl)ethyl)amino)benzoic acid |
| 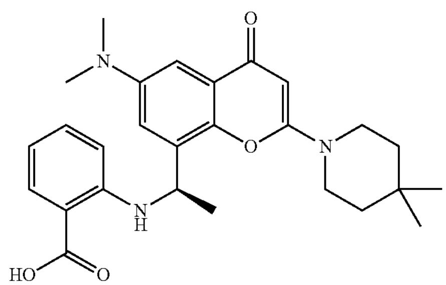 [SMILES: C[C@@H](Nc1ccccc1C(=O)O)c1cc(N(C)C)cc2c(=O)cc(N3CCC(C)(C)CC3)oc12] | (R)-2-((1-(6-(dimethylamino)-2-(4,4-dimethylpiperidin-1-yl)-4-oxo-4H-chromen-8-yl)ethyl)amino)benzoic acid |
| 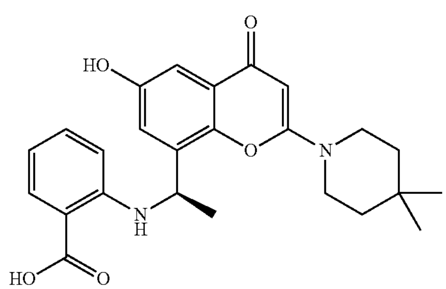 [SMILES: C[C@@H](Nc1ccccc1C(=O)O)c1cc(O)cc2c(=O)cc(N3CCC(C)(C)CC3)oc12] | (R)-2-((1-(2-(4,4-dimethylpiperidin-1-yl)-6-hydroxy-4-oxo-4H-chromen-8-yl)ethyl)amino)benzoic acid |
| 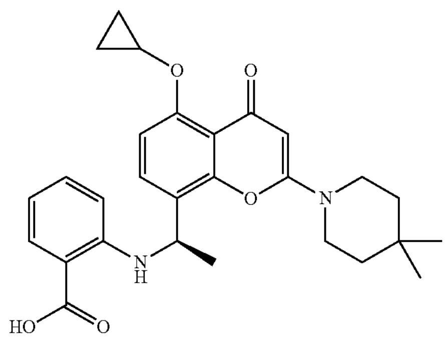 [SMILES: C[C@@H](Nc1ccccc1C(=O)O)c1ccc(OC2CC2)c2c(=O)cc(N3CCC(C)(C)CC3)oc12] | (R)-2-((1-(5-cyclopropoxy-2-(4,4-dimethylpiperidin-1-yl)-4-oxo-4H-chromen-8-yl)ethyl)amino)benzoic acid |

TABLE 2-continued

| Compound Structure | Compound Name |
| --- | --- |
| 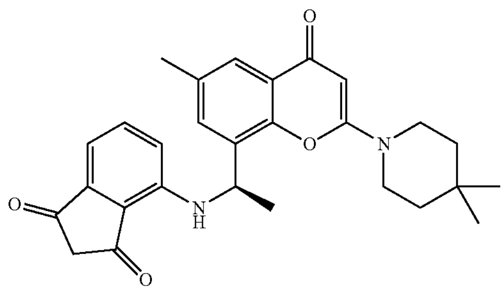 [SMILES: Cc1cc([C@@H](C)Nc2cccc3c2C(=O)CC3=O)c2oc(N3CCC(C)(C)CC3)cc(=O)c2c1] | (R)-4-((1-(2-(4,4-dimethylpiperidin-1-yl)-6-methyl-4-oxo-4H-chromen-8-yl)ethyl)amino)-1H-indene-1,3-(2H)-dione |
| 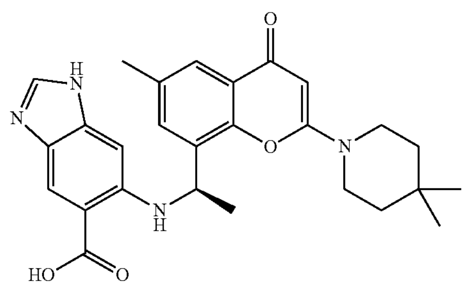 [SMILES: Cc1cc([C@@H](C)Nc2cc3[nH]cnc3cc2C(=O)O)c2oc(N3CCC(C)(C)CC3)cc(=O)c2c1] | (R)-5-((1-(2-(4,4-dimethylpiperidin-1-yl)-6-methyl-4-oxo-4H-chromen-8-yl)ethyl)amino)-1H-benzo[d]imidazole-6-carboxylic acid |
| 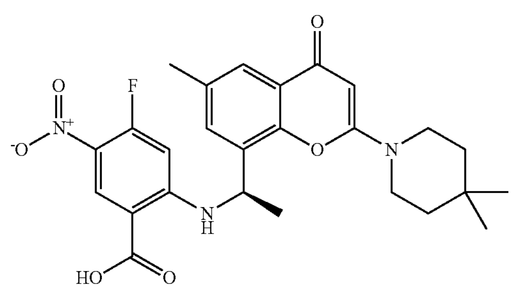 | (R)-2-((1-(2-(4,4-dimethylpiperidin-1-yl)-6-methyl-4-oxo-4H-chromen-8-yl)ethyl)amino)-4-fluoro-5-nitrobenzoic acid |
| 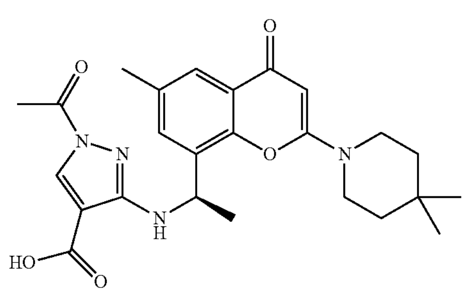 [SMILES: CC(=O)n1cc(C(=O)O)c(N[C@H](C)c2cc(C)cc3c(=O)cc(N4CCC(C)(C)CC4)oc23)n1] | (R)-1-acetyl-3-((1-(2-(4,4-dimethylpiperidin-1-yl)-6-methyl-4-oxo-4H-chromen-8-yl)ethyl)amino)-1H-pyrazole-4-carboxylic acid |
| 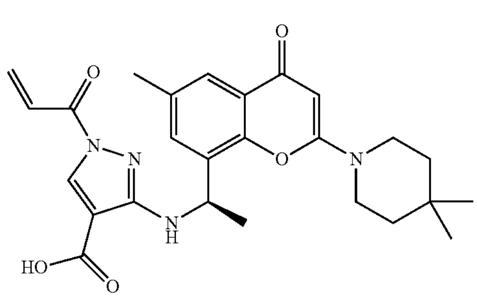 [SMILES: C=CC(=O)n1cc(C(=O)O)c(N[C@H](C)c2cc(C)cc3c(=O)cc(N4CCC(C)(C)CC4)oc23)n1] | (R)-1-acrylol-3-((1-(2-(4,4-dimethylpiperidin-1-yl)-6-methyl-4-oxo-4H-chromen-8-yl)ethyl)amino)-1H-pyrazole-4-carboxylic acid |

TABLE 2-continued

| Compound Structure | Compound Name |
| --- | --- |
| 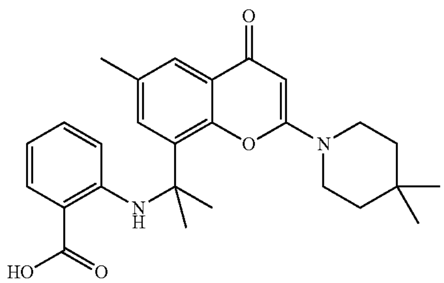 [SMILES: Cc1cc(C(C)(C)Nc2ccccc2C(=O)O)c2oc(N3CCC(C)(C)CC3)cc(=O)c2c1] | 2-((2-(2-(4,4-dimethylpiperidin-1-yl)-6-methyl-4-oxo-4H-chromen-8-yl)propan-2-yl)amino)benzoic acid |
| 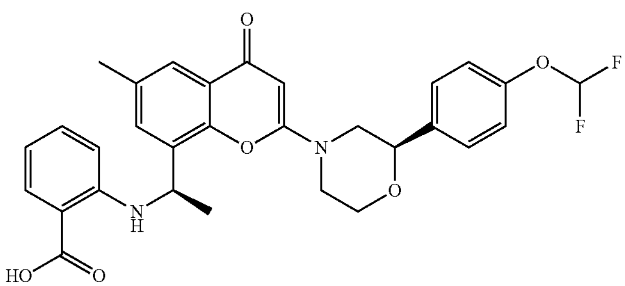 [SMILES: Cc1cc([C@@H](C)Nc2ccccc2C(=O)O)c2oc(N3CCO[C@H](c4ccc(OC(F)F)cc4)C3)cc(=O)c2c1] | 2-(((R)-1-(2-((R)-2-(4-(difluoromethoxy)phenyl)morpholino)-6-methyl-4-oxo-4H-chromen-8-yl)ethyl)amino)benzoic acid |
| 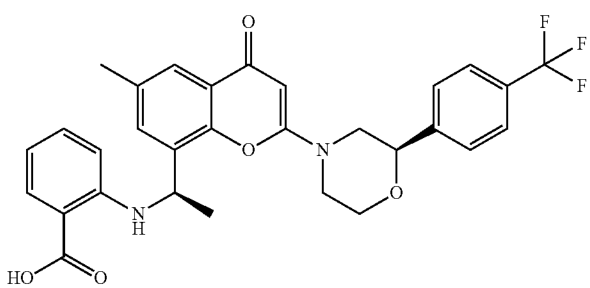 [SMILES: Cc1cc([C@@H](C)Nc2ccccc2C(=O)O)c2oc(N3CCO[C@H](c4ccc(C(F)(F)F)cc4)C3)cc(=O)c2c1] | 2-(((R)-1-(6-methyl-4-oxo-2-((R)-2-(4-(trifluoromethyl)phenyl)morpholino)-4H-chromen-8-yl)ethyl)amino)benzoic acid |
| 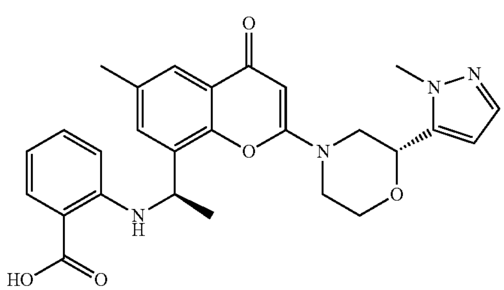 [SMILES: Cc1cc([C@@H](C)Nc2ccccc2C(=O)O)c2oc(N3CCO[C@@H](c4ccnn4C)C3)cc(=O)c2c1] | 2-(((R)-1-(6-methyl-2-((R)-2-(1-methyl-1H-pyrazol-5-yl)morpholino)-4-oxo-4H-chromen-8-yl)ethyl)amino)benzoic acide |
| 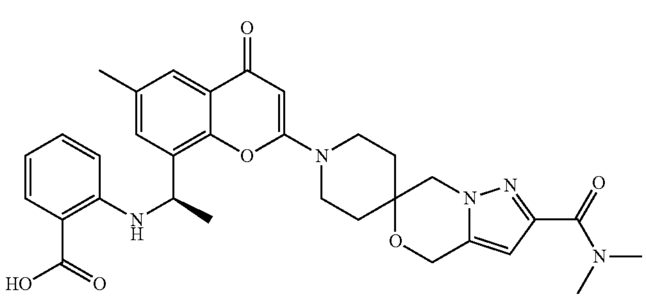 [SMILES: Cc1cc([C@@H](C)Nc2ccccc2C(=O)O)c2oc(N3CCC4(CC3)Cn3nc(C(=O)N(C)C)cc3CO4)cc(=O)c2c1] | (R)-2-((1-(2-(2'-(dimethylcarbamoyl)-4'H,7'H-spiro[piperidine-4,6'-pyrazolo[5,1-c][1,4]oxazin]-1-yl)-6-methyl-4-oxo-4H-chromen-8-yl)ethyl)amino)benzoic acid |

TABLE 2-continued

| Compound Structure | Compound Name |
|---|---|
| 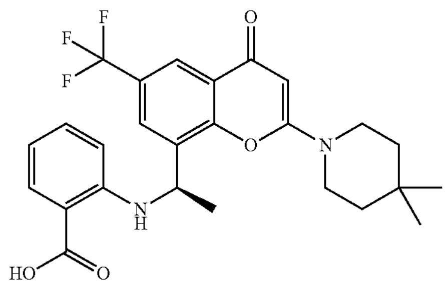 [SMILES: C[C@@H](Nc1ccccc1C(=O)O)c1cc(C(F)(F)F)cc2c(=O)cc(N3CCC(C)(C)CC3)oc12] | (R)-2-((1-(2-(4,4-dimethylpiepridin-1-yl)-4-oxo-6-(trifluoromethyl)-4H-chromen-8-yl)ethyl)amino)benzoic acid |
| 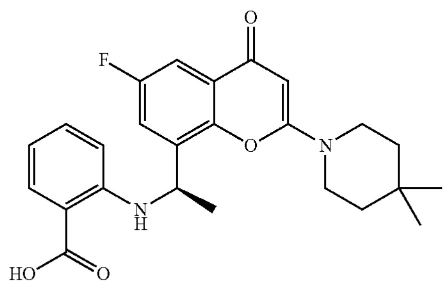 [SMILES: C[C@@H](Nc1ccccc1C(=O)O)c1cc(F)cc2c(=O)cc(N3CCC(C)(C)CC3)oc12] | (R)-2-((1-(2-(4,4-dimethylpiperidin-1-yl)-6-fluoro-4-oxo-4H-chromen-8-yl)ethyl)amino)benzoic acid |
| 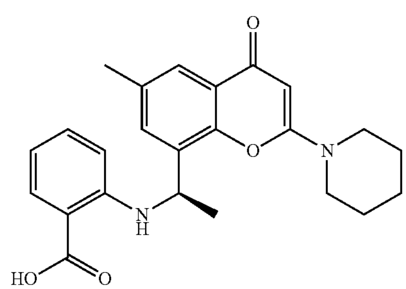 [SMILES: Cc1cc([C@@H](C)Nc2ccccc2C(=O)O)c2oc(N3CCCCC3)cc(=O)c2c1] | (R)-2-(methyl(1-(6-methyl-4-oxo-2-(piperidin-1-yl)-4H-chromen-8-yl)ethyl)amino)benzoic acid |

In some embodiments, the compound is selected from the compounds described in Table 3.

TABLE 3

| Compound Structure | Compound Name |
|---|---|
| 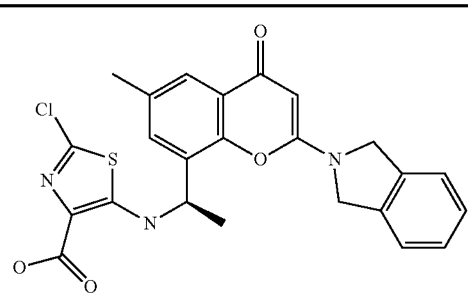 | 2-chloro-5-[[(1R)-1-(2-isoindolin-2-yl-6-methyl-4-oxo-chromen-8-yl)ethyl]amino]thiazole-4-carboxylic acid |

TABLE 3-continued

| Compound Structure | Compound Name |
|---|---|
| 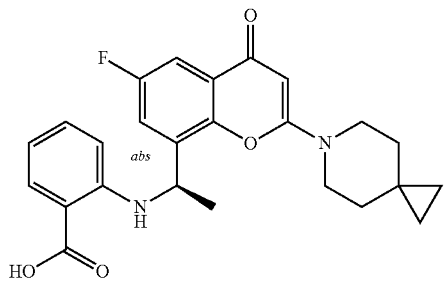 [SMILES: C[C@@H](Nc1ccccc1C(=O)O)c1cc(F)cc2c(=O)cc(N3CCC4(CC3)CC4)oc12] | 2-[[(1R)-1-[2-(6-azaspiro[2.5]octan-6-yl)-6-fluoro-4-oxo-chromen-8-yl]ethyl]amino]benzoic acid |
| 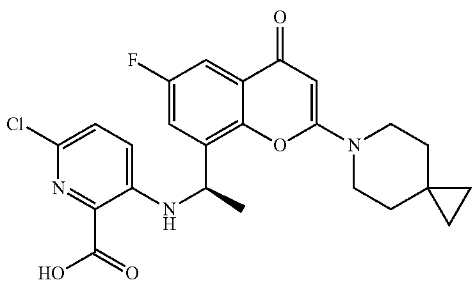 [SMILES: C[C@@H](Nc1ccc(Cl)nc1C(=O)O)c1cc(F)cc2c(=O)cc(N3CCC4(CC3)CC4)oc12] | 3-[[(1R)-1-[2-(6-azaspiro[2.5]octan-6-yl)-6-fluoro-4-oxo-chromen-8-yl]ethyl]amino]-6-chloro-pyridine-2-carboxlic acid |
| 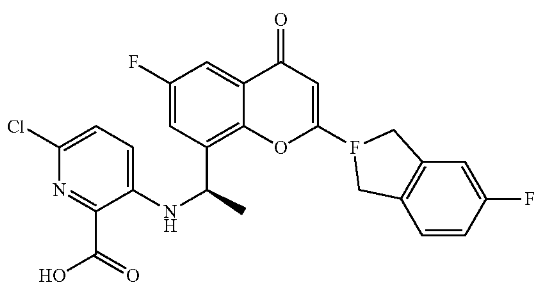 | 6-chloro-3-[[(1R)-1-[6-fluoro-2-(5-fluoroisoindolin-2-yl)-4-oxo-chromen-8-yl]ethyl]amino]pyridine-2-carboxylic acid |
| 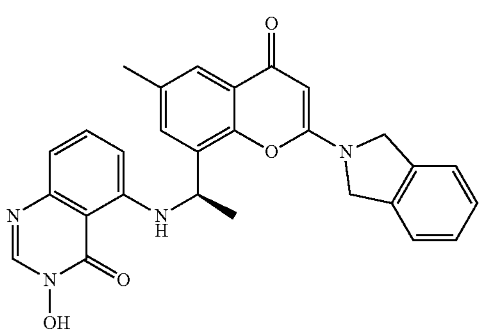 [SMILES: Cc1cc([C@@H](C)Nc2cccc3ncn(O)c(=O)c23)c2oc(N3Cc4ccccc4C3)cc(=O)c2c1] | 3-hydroxy-5-[[(1R)-1-(2-isoindolin-2-yl-6-methyl-4-oxo-chromen-8-yl)ethyl]amino]quinazolin-4-one |
| 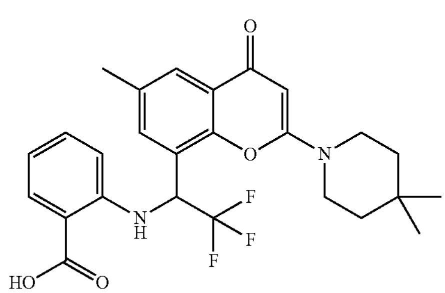 [SMILES: Cc1cc(C(Nc2ccccc2C(=O)O)C(F)(F)F)c2oc(N3CCC(C)(C)CC3)cc(=O)c2c1] | 2-[[1-[2-(4,4-dimethyl-1-piperidyl)-6-methyl-4-oxo-chromen-8-yl]-2,2,2-trifluoro-ethyl]amino]benzoic acid |

TABLE 3-continued

| Compound Structure | Compound Name |
| --- | --- |
| 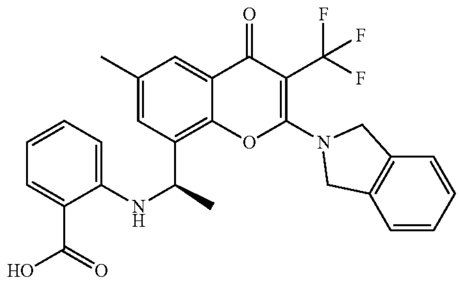 [SMILES: Cc1cc([C@@H](C)Nc2ccccc2C(=O)O)c2oc(N3Cc4ccccc4C3)c(C(F)(F)F)c(=O)c2c1] | 2-[[(1R)-1-[2-isoindolin-2-yl-6-methyl-4-oxo-3-(trifluoromethyl)chromen-8-yl]ethyl]amino]benzoic acid |
| 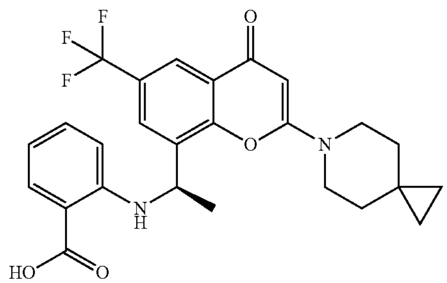 [SMILES: C[C@@H](Nc1ccccc1C(=O)O)c1cc(C(F)(F)F)cc2c(=O)cc(N3CCC4(CC3)CC4)oc12] | 2-[[(1R)-1-[2-(6-azaspiro[2.5]octan-6-yl)-4-oxo-6-(trifluoromethyl)chromen-8-yl]ethyl]amino]benzoic acid |
| 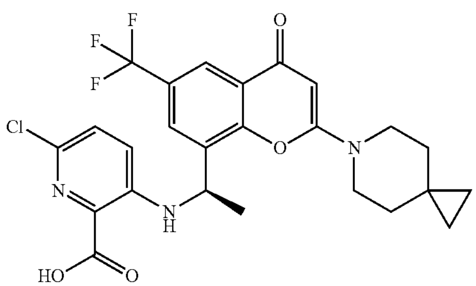 [SMILES: C[C@@H](Nc1ccc(Cl)nc1C(=O)O)c1cc(C(F)(F)F)cc2c(=O)cc(N3CCC4(CC3)CC4)oc12] | 3-[[(1R)-1-[2-(6-azaspiro[2.5]octan-6-yl)-4-oxo-6-(trifluoromethyl)chromen-8-yl]ethyl]amino]-6-chloro-pyridine-2-carboxylic acid |
| 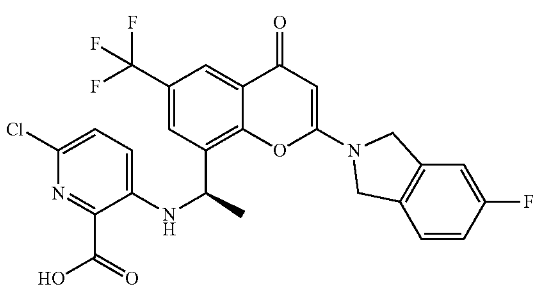 [SMILES: C[C@@H](Nc1ccc(Cl)nc1C(=O)O)c1cc(C(F)(F)F)cc2c(=O)cc(N3Cc4ccc(F)cc4C3)oc12] | 6-chloro-3-[[(1R)-1-[2-(5-fluoroisoindolin-2-yl)-4-oxo-6-(trifluoromethyl)chromen-8-yl]ethyl]amino]pyridine-2-carboxylic acid |
| 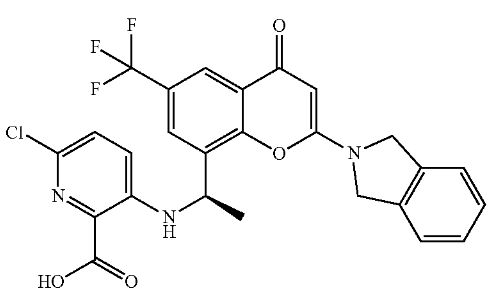 [SMILES: C[C@@H](Nc1ccc(Cl)nc1C(=O)O)c1cc(C(F)(F)F)cc2c(=O)cc(N3Cc4ccccc4C3)oc12] | 6-chloro-3-[[(1R)-1-[2-isoindolin-2-yl-4-oxo-6-(trifluoromethyl)chromen-8-yl]ethyl]amino]pyridine-2-carboxylic acid |

TABLE 3-continued

| Compound Structure | Compound Name |
|---|---|
| 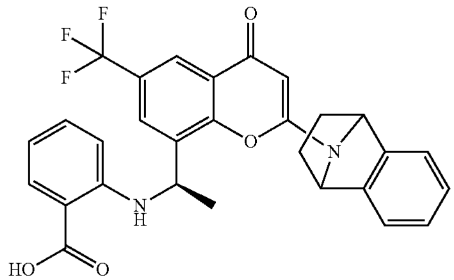 [SMILES: C[C@@H](Nc1ccccc1C(=O)O)c1cc(C(F)(F)F)cc2c(=O)cc(N3C4CCC3c3ccccc34)oc12] | 2-[[(1R)-1-[2-(11-azatricyclo[6.2.1.02,7]undeca-2(7),3,5-trien-11-yl)-4-oxo-6-(trifluoromethyl)chromen-8-yl]ethyl]amino]benzoic acid |
| 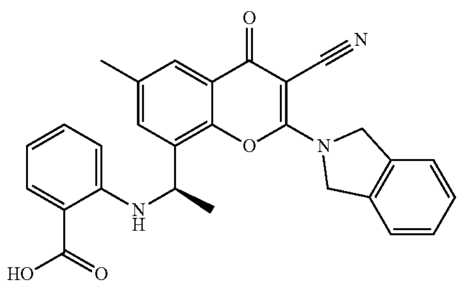 [SMILES: Cc1cc([C@@H](C)Nc2ccccc2C(=O)O)c2oc(N3Cc4ccccc4C3)c(C#N)c(=O)c2c1] | 2-[[(1R)-1-(3-cyano-2-isoindolin-2-yl-6-methyl-4-oxo-chromen-8-yl)ethyl]amino]benzoic acid |
| 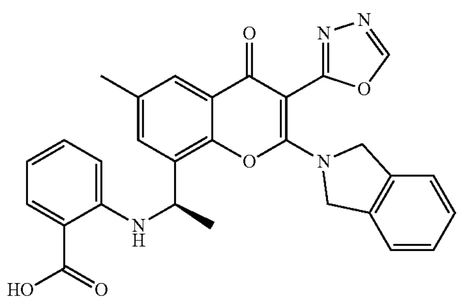 [SMILES: Cc1cc([C@@H](C)Nc2ccccc2C(=O)O)c2oc(N3Cc4ccccc4C3)c(-c3nnco3)c(=O)c2c1] | 2-[[(1R)-1-[2-isoindolin-2-yl-6-methyl-3-(1,3,4-oxadiazol-2-yl)-4-oxo-chromen-8-yl]ethyl]amino]benzoic acid |
| 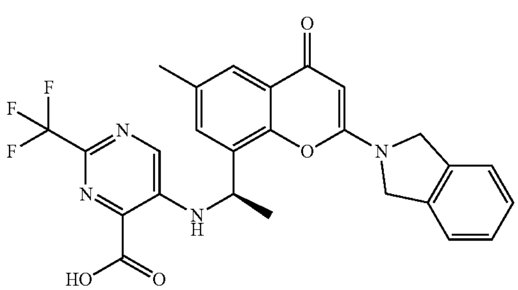 [SMILES: Cc1cc([C@@H](C)Nc2cnc(C(F)(F)F)nc2C(=O)O)c2oc(N3Cc4ccccc4C3)cc(=O)c2c1] | 5-[[(1R)-1-(2-isoindolin-2-yl-6-methyl-4-oxo-chromen-8-yl)ethyl]amino]-2-(trifluoromethyl)pyrimidine-4-carboxylic acid |
| 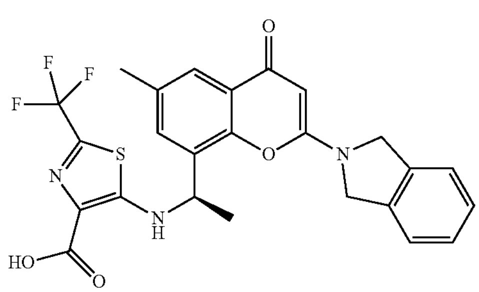 [SMILES: Cc1cc([C@@H](C)Nc2sc(C(F)(F)F)nc2C(=O)O)c2oc(N3Cc4ccccc4C3)cc(=O)c2c1] | 5-[[(1R)-1-(2-isoindolin-2-yl-6-methyl-4-oxo-chromen-8-yl)ethyl]amino]-2-(trifluoromethyl)thiazole-4-carboxylic acid |

In some embodiments, the compound is a pharmaceutically acceptable salt of any one of the compounds described in Table 1, Table 2, or Table 3.

In some embodiments, the compound is a lithium salt, sodium salt, potassium salt, calcium salt, or magnesium salt of any one of the compounds described in Table 1, Table 2, or Table 3.

In some embodiments, the compound is a sodium salt or potassium salt of any one of the compounds described in Table 1, Table 2, or Table 3.

In some embodiments, the compound is a sodium salt of any one of the compounds described in Table 1, Table 2, or Table 3.

In some embodiments, the compound is a potassium salt of any one of the compounds described in Table 1, Table 2, or Table 3.

In some aspects, the present disclosure provides a compound being an isotopic derivative (e.g., isotopically labeled compound) of any one of the compounds of the Formulae disclosed herein.

In some embodiments, the compound is an isotopic derivative of any one of the compounds described in Table 1, Table 2, or Table 3 and prodrugs and pharmaceutically acceptable salts thereof.

In some embodiments, the compound is an isotopic derivative of any one of the compounds described in Table 1, Table 2, or Table 3 and pharmaceutically acceptable salts thereof.

In some embodiments, the compound is an isotopic derivative of any one of prodrugs of the compounds described in Table 1, Table 2, or Table 3 and pharmaceutically acceptable salts thereof.

In some embodiments, the compound is an isotopic derivative of any one of the compounds described in Table 1, Table 2, or Table 3.

It is understood that the isotopic derivative can be prepared using any of a variety of art-recognized techniques. For example, the isotopic derivative can generally be prepared by carrying out the procedures disclosed in the Schemes and/or in the Examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

The term "isotopic derivative", as used herein, refers to a derivative of a compound in which one or more atoms are isotopically enriched or labelled. For example, an isotopic derivative of a compound of Formula (I), (Ia), (Ib), (Ic), (Id), (Ie), (If), (Ig), (Ih), or (II) is isotopically enriched with regard to, or labelled with, one or more isotopes as compared to the corresponding compound of Formula (I), (Ia), (Ib), (Ic), (Id), (Ie), (If), (Ig), (Ih), or (II). In some embodiments, the isotopic derivative is enriched with regard to, or labelled with, one or more atoms selected from $^{2}H$, $^{13}C$, $^{14}C$, $^{15}N$, $^{18}O$, $^{29}Si$, $^{31}P$, and $^{34}S$. In some embodiments, the isotopic derivative is a deuterium labeled compound (i.e., being enriched with $^{2}H$ with regard to one or more atoms thereof).

In some embodiments, the compound is a deuterium labeled compound of any one of the compounds described in Table 1, Table 2, or Table 3 and prodrugs and pharmaceutically acceptable salts thereof.

In some embodiments, the compound is a deuterium labeled compound of any one of the compounds described in Table 1, Table 2, or Table 3 and pharmaceutically acceptable salts thereof.

In some embodiments, the compound is a deuterium labeled compound of any one of the prodrugs of the compounds described in Table 1, Table 2, or Table 3 and pharmaceutically acceptable salts thereof.

In some embodiments, the compound is a deuterium labeled compound of any one of the compounds described in Table 1, Table 2, or Table 3.

It is understood that the deuterium labeled compound comprises a deuterium atom having an abundance of deuterium that is substantially greater than the natural abundance of deuterium, which is 0.015%.

In some embodiments, the deuterium labeled compound has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). As used herein, the term "deuterium enrichment factor" means the ratio between the deuterium abundance and the natural abundance of a deuterium.

It is understood that the deuterium labeled compound can be prepared using any of a variety of art-recognized techniques. For example, the deuterium labeled compound can generally be prepared by carrying out the procedures disclosed in the Schemes and/or in the Examples described herein, by substituting a deuterium labeled reagent for a non-deuterium labeled reagent.

A compound of the disclosure or a pharmaceutically acceptable salt or solvate thereof that contains the aforementioned deuterium atom(s) is within the scope of the disclosure. Further, substitution with deuterium (i.e., $^{2}H$) may afford certain therapeutic advantages resulting from greater metabolic stability, e.g., increased in vivo half-life or reduced dosage requirements.

In some embodiments, the compound is a $^{18}F$ labeled compound.

In some embodiments, the compound is a $^{123}I$ labeled compound, a $^{124}I$ labeled compound, a $^{125}I$ labeled compound, a $^{129}I$ labeled compound, a $^{131}I$ labeled compound, a $^{135}I$ labeled compound, or any combination thereof.

In some embodiments, the compound is a $^{33}S$ labeled compound, a $^{34}S$ labeled compound, a $^{35}S$ labeled compound, a $^{36}S$ labeled compound, or any combination thereof.

It is understood that the $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$ labeled compound, can be prepared using any of a variety of art-recognized techniques. For example, the deuterium labeled compound can generally be prepared by carrying out the procedures disclosed in the Schemes and/or in the Examples described herein, by substituting a $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$ labeled reagent for a non-isotope labeled reagent.

A compound of the disclosure or a pharmaceutically acceptable salt or solvate thereof that contains one or more of the aforementioned $^{18}F$, $^{123}I$, $^{124}I$, $^{125}I$, $^{129}I$, $^{131}I$, $^{135}I$, $^{3}S$, $^{34}S$, $^{35}S$, and $^{36}S$ atom(s) is within the scope of the disclosure. Further, substitution with isotope (e.g., $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$) may afford certain therapeutic advantages resulting from greater metabolic stability, e.g., increased in vivo half-life or reduced dosage requirements.

For the avoidance of doubt it is to be understood that, where in this specification a group is qualified by "described herein", the said group encompasses the first occurring and broadest definition as well as each and all of the particular definitions for that group.

The various functional groups and substituents making up the compounds of the Formula (I), (Ia), (Ib), (Ic), (Id), (Ie), (If), (Ig), (Ih), or (II) are typically chosen such that the molecular weight of the compound does not exceed 1000 daltons. More usually, the molecular weight of the compound will be less than 900, for example less than 800, or less than 750, or less than 700, or less than 650 daltons. More conveniently, the molecular weight is less than 600 and, for example, is 550 daltons or less.

A suitable pharmaceutically acceptable salt of a compound of the disclosure is, for example, an acid-addition salt of a compound of the disclosure, which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, diethylamine, trimethylamine, piperidine, morpholine or tris-(2-hydroxyethyl)amine.

It will be understood that the compounds of any one of the Formulae disclosed herein and any pharmaceutically acceptable salts thereof, comprise stereoisomers, mixtures of stereoisomers, polymorphs of all isomeric forms of said compounds.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral center" refers to a carbon atom bonded to four nonidentical substituents.

As used herein, the term "chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

The compounds of the present disclosure may be depicted as different chiral isomers or geometric isomers. When compounds have chiral isomeric or geometric isomeric forms, all isomeric forms are intended to be included in the scope of the present disclosure, and the naming of the compounds does not exclude any isomeric forms, it being understood that not all isomers may have the same level of activity.

The structures and other compounds discussed in this disclosure include all atropic isomers thereof. Not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerizations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

The compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterised by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this disclosure may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. The designations "Isomer 1" and "Isomer 2" refer to the separated stereoisomers that elute from chiral chromatography separations under the stated conditions as specified in the examples. Some of the compounds of the disclosure may have geometric isomeric centers (E- and Z-isomers). It is to be understood that the present disclosure encompasses all optical, diastereoisomers and geometric isomers and mixtures thereof.

The present disclosure also encompasses compounds of the disclosure as defined herein which comprise one or more isotopic substitutions.

It is to be understood that the compounds of any Formula described herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted compound disclosed herein. Suitable cations include sodium ion, potassium ion, magnesium ion, calcium ion, and an ammonium cation such as tetramethylammonium ion or diethylamine ion. The substituted compounds disclosed herein also include those salts containing quaternary nitrogen atoms.

The compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure and are substituted with various groups as described herein.

It is also to be understood that certain compounds of any one of the Formulae disclosed herein may exist in solvated as well as unsolvated forms such as, for example, hydrated forms. A suitable pharmaceutically acceptable solvate is, for example, a hydrate such as hemi-hydrate, a mono-hydrate, a di-hydrate or a tri-hydrate. It is to be understood that the disclosure encompasses all such solvated forms that possess inflammasome inhibitory activity.

It is also to be understood that certain compounds of any one of the Formulae disclosed herein may exhibit polymorphism, and that the disclosure encompasses all such forms, or mixtures thereof, which possess inflammasome inhibitory activity. It is generally known that crystalline materials may be analysed using conventional techniques such as X-Ray Powder Diffraction analysis, Differential Scanning Calorimetry, Thermal Gravimetric Analysis, Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

Compounds of any one of the Formulae disclosed herein may exist in a number of different tautomeric forms and references to compounds of Formula (I), (Ia), (Ib), (Ic), (Id), (Je), (If), (Ig), (Ih), or (II) include all such forms. For the avoidance of doubt, where a compound can exist in one of several tautomeric forms, and only one is specifically described or shown, all others are nevertheless embraced by Formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

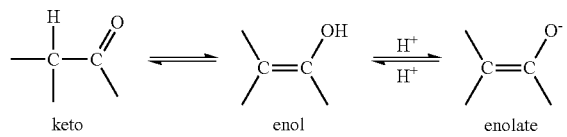

keto          enol          enolate

Compounds of any one of the Formulae disclosed herein containing an amine function may also form N-oxides. A reference herein to a compound of Formula (I), (Ia), (Ib), (Ic), (Id), (Je), (If), (Ig), (Ih), or (II) that contains an amine function also includes the N-oxide. Where a compound contains several amine functions, one or more than one nitrogen atom may be oxidized to form an N-oxide. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a peracid (e.g., a peroxycarboxylic acid), see for example Advanced Organic Chemistry, by Jerry March, 4th Edition, Wiley Interscience. More particularly, N-oxides can be made by the procedure of L. W. Deady (Syn. Comm. 1977, 7, 509-514) in which the amine compound is reacted with meta-chloroperoxybenzoic acid (mCPBA), for example, in an inert solvent such as dichloromethane.

The compounds of any one of the Formulae disclosed herein may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include derivatives containing in vivo cleavable alkyl or acyl substituents at the ester or amide group in any one of the Formulae disclosed herein.

Accordingly, the present disclosure includes those compounds of any one of the Formulae disclosed herein as defined hereinbefore when made available by organic synthesis and when made available within the human or animal body by way of cleavage of a prodrug thereof. Accordingly, the present disclosure includes those compounds of any one of the Formulae disclosed herein that are produced by organic synthetic means and also such compounds that are produced in the human or animal body by way of metabolism of a precursor compound, that is a compound of any one of the Formulae disclosed herein may be a synthetically-produced compound or a metabolically-produced compound.

A suitable pharmaceutically acceptable prodrug of a compound of any one of the Formulae disclosed herein is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Prodrugs, edited by H. Bundgaard, (Elsevier, 1985); c) A Textbook of Drug Design and Development, edited by Krogsgaard-Larsen and H. Bundgaard, Chapter 5 "Design and Application of Pro-drugs", by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pharm. Bull., 32, 692 (1984); g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable prodrug of a compound of any one of the Formulae disclosed herein that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl.

The in vivo effects of a compound of any one of the Formulae disclosed herein may be exerted in part by one or more metabolites that are formed within the human or animal body after administration of a compound of any one of the Formulae disclosed herein. As stated hereinbefore, the in vivo effects of a compound of any one of the Formulae disclosed herein may also be exerted by way of metabolism of a precursor compound (a prodrug).

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention can be synthesized by following the steps outlined in General Schemes 1 and 2 which comprise different sequences of assembling intermediates or compounds. Starting materials are either commercially available or made by known procedures in the reported literature or as illustrated below.

Scheme 1

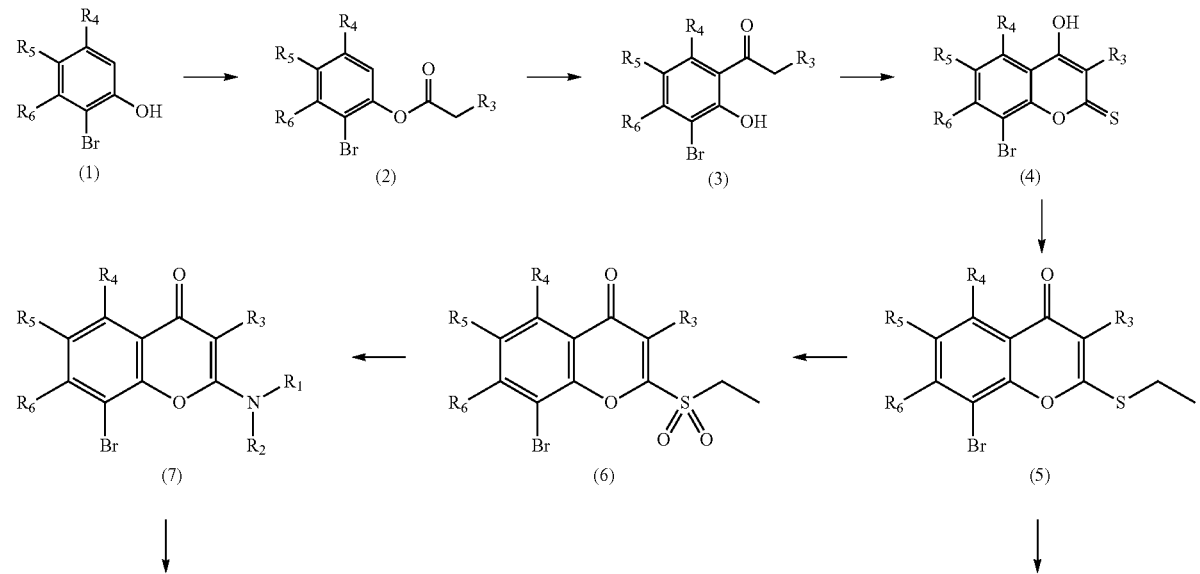

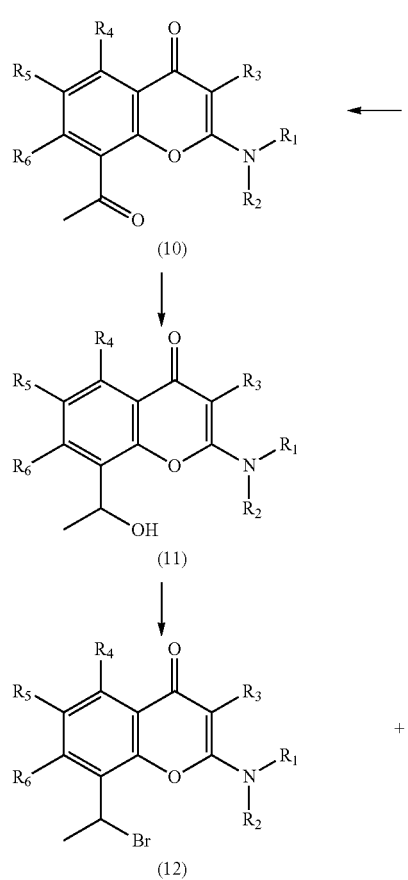
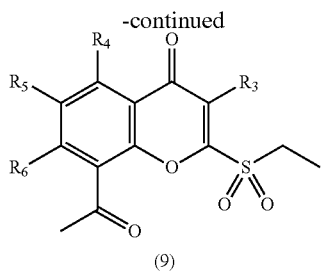
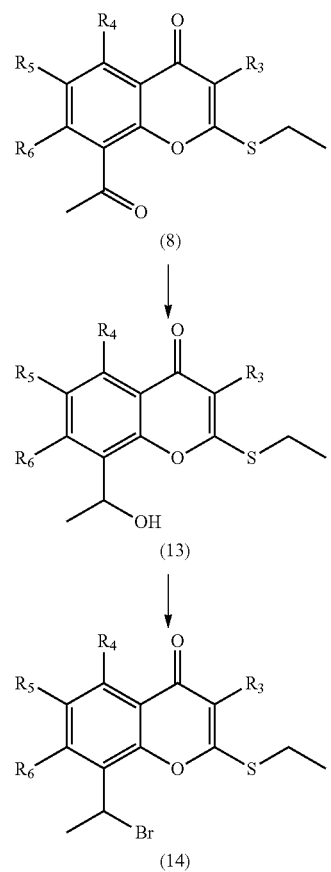
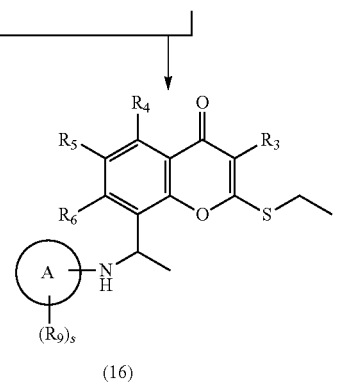

Scheme 1 depicts the preparation of compounds of Formula (I), where W is N, X is NH, Y is O, $R_7$ is methyl, and $R_8$ is H. A person of ordinary skill in the art will recognize that acylation of substituted phenol (1) may provide ester (2). Ester (2) may undergo rearrangement under Lewis acid conditions to the hydroxy aryl ketone (3). Basic deprotonation of ketone (3) in the presence of carbon disulfide gives the bicyclic chromene-2-thione (4). Alkylation of thione (4) under basic conditions affords thiolether (5).

Oxidation of thiolether (5) with an oxidant such as m-CPBA may give sulfone (6). Substitution of sulfone (6) with various primary and secondary amines may then produce amino substituted chromen-4-one (7). Palladium-catalyzed acylation of bromide (7) may give the acyl chromen-4-one (10).

Alternatively, phenyl bromide (5) can be acylated via palladium catalysis to produce acyl chromen-4-one (8). This thiolether (8) can be oxidized with an oxidant such as m-CPBA to produce sulfone (9). Substitution of sulfone (9) with various primary and secondary amines may then produce amino substituted chromen-4-one (10). The ketone (10) can be reduced to hydroxy chromen-4-one (11) with a reducing agent such as sodium borohydride. Use of a halogenating agent such as phosphorus tribromide can be used to convert hydroxy compound (11) to the halo compound (12).

Alternatively, ketone (8) can be reduced to hydroxy compound (13) with a reagent such as sodium borohydride. This hydroxy compound (13) can be converted to halo compound (14) in a similar manner to the synthesis of bromide (12).

Substitution of bromide (12) with a substituted amine (15) produces compounds of Formula (I). Alternatively, bromide (14) can be substituted with amine (15) to produce thiolether (16). This thiolether can be oxidized to sulfoxide (17) followed by substitution with a primary or secondary amine to also produce compounds of Formula (I).
Scheme 2
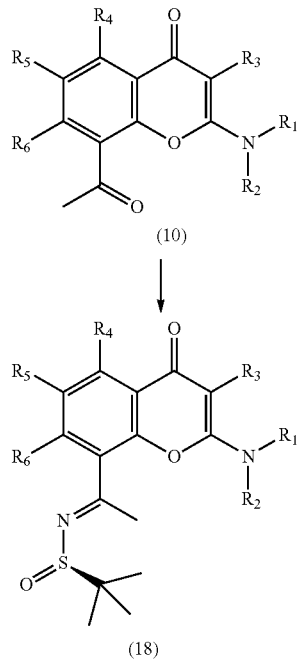
(10)
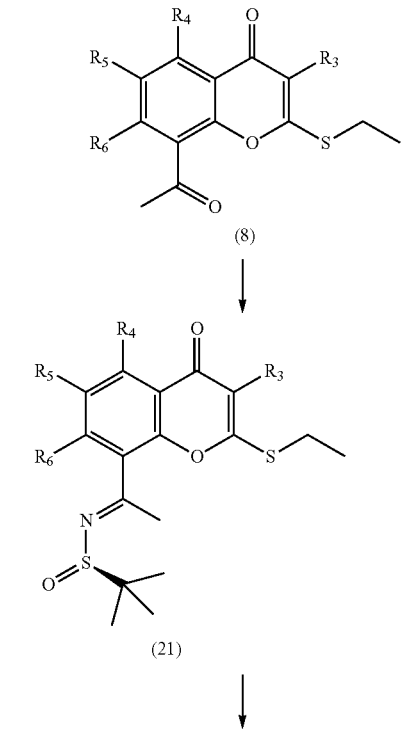
(8)
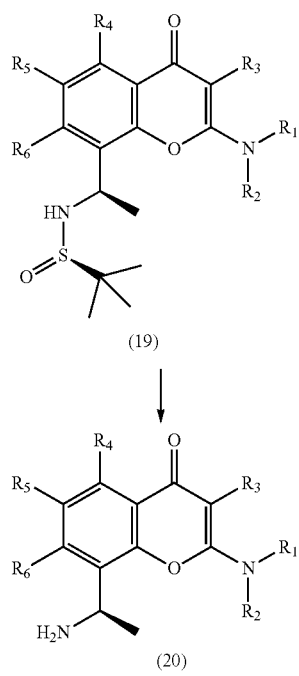
(18)
(21)
(19)
(22)
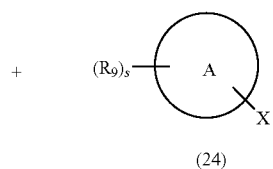
(24)
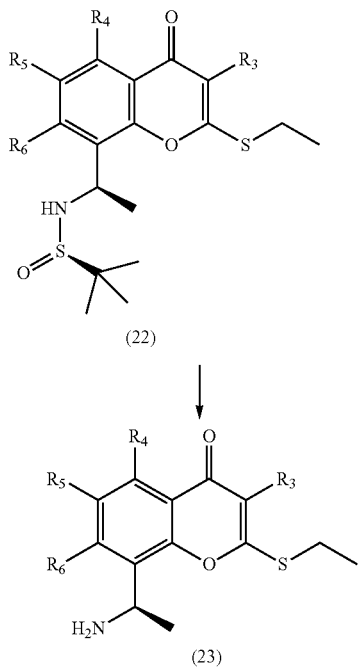
(20)
(23)

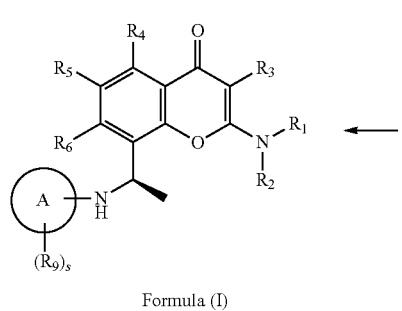

Formula (I)

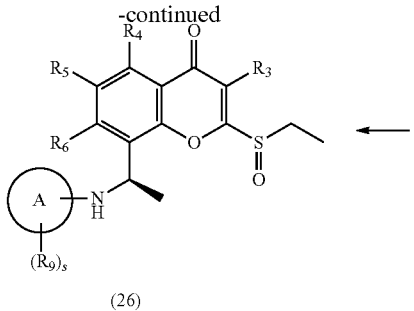

(26)

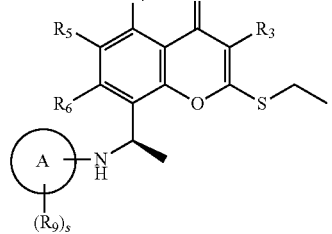

(25)

Scheme 2 depicts additional preparation of compounds of Formula (I), where W is N, X is NH, Y is O, $R_7$ is methyl, and $R_8$ is H. Condensation of ketone (10) with tert-butanesulfinamide using a Lewis acidic dehydrating agent such as a titanium(IV) alkoxide may afford ketimine (18). Asymmetric reduction of sulfinimine (18) may be effected with a borohydride reagent in the presence of a transition metal catalyst such as cerium (III) chloride to yield chirally enriched sulfinamide (19). Removal of the sulfinyl group under acidic conditions may be used to transform sulfinamide (19) to benzylamine (20) which can be alkylated with aryl halide (24) under Finkelstein or Ullmann-type conditions to give compounds of Formula (I).

A similar synthetic route allowing for access to different intermediates may also achieved. For instance, ketone (8) may be converted to benzylamine (23), using conditions previously described for the metal-catalyzed condensation, stereoselective reduction, and acid hydrolysis. Alkylation of benzylamine (23) with aryl halide (24) may be used to provide thioether (25). This thioether (25) can be oxidized to sulfoxide (26) followed by substitution with a primary or secondary amine to also produce compounds of Formula (I).

Biological Assays

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

Various in vitro or in vivo biological assays may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

Pharmaceutical Compositions

In some aspects, the present disclosure provides a pharmaceutical composition comprising a compound of Formula (I), (Ia), (Ib), (Ic), (Id), (Ie), (If), (Ig), (Ih), or (II) as an active ingredient. In some embodiments, the present disclosure provides a pharmaceutical composition comprising a compound of Formula (I), (Ia), (Ib), (Ic), (Id), (Ie), (If), (Ig), (Ih), or (II), or a pharmaceutically acceptable salt or solvate thereof, and one or more pharmaceutically acceptable carriers or excipients. In some embodiments, the present disclosure provides a pharmaceutical composition comprising at least one compound selected from Table 1, Table 2, or Table 3.

As used herein, the term "composition" is intended to encompass a product comprising the specified ingredients in the specified amounts, as well as any product which results, directly or indirectly, from combination of the specified ingredients in the specified amounts.

The compounds of Formula (I), (Ia), (Ib), (Ic), (Id), (Ie), (If), (Ig), (Ih), or (II) can be formulated for oral administration in forms such as tablets, capsules (each of which includes sustained release or timed release formulations), pills, powders, granules, elixirs, tinctures, suspensions, syrups and emulsions. The compounds of Formula (I), (Ia), (Ib), (Ic), (Id), (Ie), (If), (Ig), (Ih), or (II) can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulfated β-cyclodextrin (S-β-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, butyl-p-hydroxybenzoate, and sorbic acid, and mixtures thereof.

In some embodiments, examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, merthiolate, methylparaben, propylparaben, sorbic acid, potassium sorbate, sodium benzoate, sodium propionate, ethyl p-hydroxybenzoate, propylaminopropyl biguanide, butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof. In some embodiments, the tonicity agent is selected from the group consisting of a glycol (such as propylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilize the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and F-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotex; a glidant such as colloidal silicon dioxide; a sweetening agent such as sucrose or saccharin; or a flavoring agent such as peppermint, methyl salicylate, or orange flavoring.

According to a further aspect of the disclosure there is provided a pharmaceutical composition which comprises a compound any one of the Formulae disclosed herein, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more coloring, sweetening, flavoring and/or preservative agents.

A therapeutically effective amount of a compound of any one of the Formulae disclosed herein for use in therapy is an amount sufficient to treat or prevent a PI3K related condition referred to herein, slow its progression and/or reduce the symptoms associated with the condition.

A therapeutically effective amount of a compound of Formula (I), (Ia), (Ib), (Ic), (Id), (Ie), (If), (Ig), (Ih), or (II) for use in therapy is an amount sufficient to treat an PI3K related condition referred to herein, slow its progression and/or reduce the symptoms associated with the condition.

The size of the dose for therapeutic or prophylactic purposes of a compound of Formula (I), (Ia), (Ib), (Ic), (Id), (Ie), (If), (Ig), (Ih), or (II) will naturally vary according to the nature and severity of the conditions, the age and sex of the animal or patient and the route of administration, according to well-known principles of medicine. Methods of Use In some aspects, the present disclosure provides a method of modulating PI3K (e.g., PI3Kα) activity (e.g., in vitro or in vivo), comprising contacting a cell with a therapeutically effective amount of a compound of Formula (I), (Ia), (Ib), (Ic), (Id), (Ie), (If), (Ig), (Ih), or (II) or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of Formula (I), (Ia), (Ib), (Ic), (Id), (Ie), (If), (Ig), (Ih), or (II) or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a therapeutically effective amount of a compound of Formula (I), (Ia), (Ib), (Ic), (Id), (Ie), (If), (Ig), (Ih), or (II) or a pharmaceutically acceptable salt thereof, or a pharmaceutical composition of the present disclosure.

In some embodiments, the disease or disorder is associated with an implicated PI3K activity. In some embodiments, the disease or disorder is a disease or disorder in which PI3K activity is implicated.

In some embodiments, the disease or disorder is a cancer.

In some embodiments, the cancer is selected from acute lymphoblastic leukemia (ALL), acute myeloid leukemia (AML), adrenocortical carcinoma, aids-related cancers, aids-related lymphoma, anal cancer, astrocytoma, basal cell carcinoma, bile duct cancer, bladder cancer, bone cancer, osteosarcoma, malignant fibrous histiocytoma, brain tumors, breast cancer, bronchial tumors, Burkitt lymphoma, carcinoid tumor, cancer of unknown primary, cardiac (heart) tumors, atypical teratoid/rhabdoid tumor, primary CNS lymphoma, cervical cancer, cholangiocarcinoma, chordoma, chronic lymphocytic leukemia (CLL), chronic myelogenous leukemia (CML), colorectal cancer, craniopharyngioma, cutaneous t-cell lymphoma, mycosis fungoides, Sezary syndrome, ductal carcinoma in situ (DCIS), embryonal tumors, medulloblastoma, endometrial cancer, ependymoma, esophageal cancer, esthesioneuroblastoma, Ewing sarcoma, extracranial germ cell tumor, extragonadal germ cell tumor, fallopian tube cancer, gallbladder cancer, gastric cancer, gastrointestinal carcinoid tumor, malignant gastrointestinal stromal tumors (GIST), germ cell tumors, gestational trophoblastic disease, hairy cell leukemia, head and neck cancer, hepatocellular cancer, Langerhans cell histiocytosis, Hodgkin lymphoma, islet cell tumors, pancreatic neuroendocrine tumors, Kaposi sarcoma, kidney cancer, laryngeal cancer, leukemia, liver cancer, lung cancer, lymphoma, male breast cancer, intraocular melanoma, Merkel cell carcinoma, malignant mesothelioma, metastatic cancer, metastatic squamous neck cancer, midline tract carcinoma with nut gene changes, mouth cancer, multiple endocrine neoplasia syndromes, multiple myeloma/plasma cell neoplasms, myelodysplastic syndromes, myelodysplastic neoplasms, myeloproliferative neoplasms, chronic myeloproliferative neoplasm, nasal cavity and paranasal sinus cancer, nasopharyngeal cancer, neuroblastoma, non-Hodgkin lymphoma, non-small cell lung cancer, oral cancer, lip and oral cavity cancer, oropharyngeal cancer, malignant fibrous histiocytoma of bone, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, multiple myeloma, pleuropulmonary blastoma, primary central nervous system (CNS) lymphoma, primary peritoneal cancer, prostate cancer, rectal cancer, recurrent cancer, renal cell (kidney) cancer, retinoblastoma, rhabdomyosarcoma, salivary gland cancer, sarcoma, childhood vascular tumors, skin cancer, small cell lung cancer, small intestine cancer, soft tissue sarcoma, squamous cell carcinoma of the skin, testicular cancer, oropharyngeal cancer, hypopharyngeal cancer, thymoma, thymic carcinoma, thyroid cancer, tracheobronchial tumors, transitional cell cancer of the renal pelvis and ureter, urethral cancer, uterine sarcoma, vaginal cancer, vascular tumors, vulvar cancer, and Wilms tumor.

In some embodiments, the cancer is Endometrial cancer, Breast cancer, Oesophageal squamous-cell cancer, Cervical squamous-cell carcinoma, Cervical adenocarcinoma, Colorectal adenocarcinoma, Bladder Urothelial Carcinoma, Glioblastoma, Ovarian cancer, Non-small-cell Lung cancer, Esophagogastric cancer, Nerve-sheath tumor, Head and neck squamous-cell carcinoma, Melanoma, Esophagogastric adenocarcinoma, Soft-tissue sarcoma, Prostate cancer, Fibrolamellar carcinoma, Hepatocellular carcinoma, Diffuse glioma, Colorectal cancer, Pancreatic cancer, Cholangiocarcinoma, B-cell lymphoma, Mesothelioma, Adrenocortical carcinoma, Renal non-clear-cell carcinoma, Renal clear-cell carcinoma, Germ-cell carcinoma, Thymic tumor, Pheochromocytoma, Miscellaneous neuroepithelial tumor, thyroid cancer, leukemia, or encapsulated glioma.

In some embodiments, the cancer is a breast cancer, a prostate cancer, or a brain cancer.

In some embodiments, the cancer is a breast cancer. In some embodiments, the cancer is a prostate cancer. In some embodiments, the cancer is a brain cancer.

In some embodiments, the breast cancer is metastatic breast cancer. In some embodiments, the breast cancer is ductal carcinoma in situ (DCIS). In some embodiments, the breast cancer is invasive ductal carcinoma. In some embodiments, the breast cancer is triple negative breast cancer. In some embodiments, the breast cancer is medullary carcinoma. In some embodiments, the breast cancer is tubular carcinoma. In some embodiments, the breast cancer is mucinous carcinoma. In some embodiments, the breast cancer is Paget disease of the breast or nipple. In some embodiments, the breast cancer is inflammatory breast cancer (IBC).

In some embodiments, the prostate cancer is an adenocarcinoma. In some embodiments, the prostate cancer is a small cell carcinoma. In some embodiments, the prostate cancer is a neuroendocrine tumor. In some embodiments, the prostate cancer is a transitional cell carcinoma. In some embodiments, the prostate cancer is a sarcoma.

In some embodiments, the brain cancer is an acoustic neuroma. In some embodiments, the brain cancer is an astrocytoma. In some embodiments, the brain cancer is a brain metastasis. In some embodiments, the brain cancer is choroid plexus carcinoma. In some embodiments, the brain cancer is craniopharyngioma. In some embodiments, the brain cancer is an embryonal tumor. In some embodiments, the brain cancer is an ependymoma. In some embodiments, the brain cancer is a glioblastoma. In some embodiments, the brain cancer is a glioma. In some embodiments, the brain cancer is a medulloblastoma. In some embodiments, the brain cancer is a meningioma. In some embodiments, the brain cancer is an oligodendroglioma. In some embodiments, the brain cancer is a pediatric brain tumor. In some embodiments, the brain cancer is a pineoblastoma. In some embodiments, the brain cancer is a pituitary tumor.

In some embodiments, the disease or disorder associated with PI3K includes, but is not limited to, CLOVES syndrome (congenial lipomatous overgrowth, vascular malformations, epidermal naevi, scoliosis/skeletal and spinal syndrome), PIK3CA-related overgrowth syndrome (PROS), breast cancer, brain cancer, prostate cancer, endometrial cancer, gastric cancer, leukemia, lymphoma, sarcoma, colorectal cancer, lung cancer, ovarian cancer, skin cancer, or head and neck cancer.

In some embodiments, the diseases or disorder associated with PI3K is CLOVES syndrome (congenital lipomatous overgrowth, vascular malformations, epidermal naevi, scoliosis/skeletal and spinal syndrome).

In some embodiments, the disease or disorder associated with PI3K is PIK3CA-related overgrowth syndrome (PROS).

In some embodiments, the disease or disorder associated with PI3K is breast cancer, brain cancer, prostate cancer, endometrial cancer, gastric cancer, leukemia, lymphoma, sarcoma, colorectal cancer, lung cancer, ovarian cancer, skin cancer, or head and neck cancer.

In some embodiments, the disease or disorder associated with PI3K is breast cancer, brain cancer, prostate cancer, endometrial cancer, gastric cancer, colorectal cancer, lung cancer, ovarian cancer, skin cancer, or head and neck cancer.

In some embodiments, the disease or disorder associated with PI3K is leukemia, lymphoma, or sarcoma.

In some embodiments, the cancer is endometrial cancer, head and neck cancer, or a sarcoma.

In some embodiments, the cancer is endometrial cancer. In some embodiments the cancer is head and neck cancer. In some embodiments, the cancer is a sarcoma.

In some embodiments, the sarcoma is soft tissue sarcoma, osteosarcoma, chondrosarcoma, Ewing sarcoma, hemangioendothelioma, angiosarcoma, fibrosarcoma, myofibrosarcoma, chordoma, adamantinoma, liposarcoma, leiomyosarcoma, malignant peripheral nerve sheath tumor, rhabdomyosarcoma, synovial sarcoma, or malignant solitary fibrous tumor.

In some embodiments, the sarcoma is soft tissue sarcoma. In some embodiments the soft tissue sarcoma is liposarcoma, atypical lipomatous tumor, dermatofibrosarcoma protuberans, malignant solitary fibrous tumor, inflammatory myofibroblastic tumor, low-grade myofibroblastic sarcoma, fibrosarcoma, myxofibrosarcoma, low-grade fibromyxoid sarcoma, giant cell tumor of soft tissues, leiomyosarcoma, malignant glomus tumor, rhabdomyosarcoma, hemangioendothelioma, angiosarcoma of soft tissue, extraskeletal osteosarcoma, gastrointestinal stromal tumor, malignant gastrointestinal stromal tumor (GIST), malignant peripheral nerve sheath tumor, malignant Triton tumor, malignant granular cell tumor, malignant ossifying fibromyxoid tumor, stromal sarcoma, myoepithelial carcinoma, malignant phosphaturic mesenchymal tumor, synovial sarcoma, epithelioid sarcoma, alveolar soft part sarcoma, clear cell sarcoma of soft tissue, extraskeletal myxoid chondrosarcoma, extraskeletal Ewing sarcoma, desmoplastic small round cell tumor, extrarenal rhabdoid tumor, perivascular epithelioid cell tumor, intimal sarcoma, undifferentiated spindle cell sarcoma, undifferentiated pleomorphic sarcoma, undifferentiated round cell sarcoma, undifferentiated epithelioid sarcoma, or undifferentiated sarcoma, not otherwise specified.

In some aspects, the present disclosure provides a method of treating or preventing a cancer in a subject in need thereof, comprising administering to the subject a therapeutically effective amount of a compound of Formula (I), (Ia), (Ib), (Ic), (Id), (Ie), (If), (Ig), (Ih), or (II) or a pharmaceutically acceptable salt thereof, or a pharmaceutical composition of the present disclosure.

In some aspects, the present disclosure provides a method of treating a cancer in a subject in need thereof, comprising administering to the subject a therapeutically effective amount of a compound of Formula (I), (Ia), (Ib), (Ic), (Id), (Ie), (If), (Ig), (Ih), or (II) or a pharmaceutically acceptable salt thereof, or a pharmaceutical composition of the present disclosure.

In some aspects, the present disclosure provides a method of treating or preventing a breast cancer in a subject in need thereof, comprising administering to the subject a therapeutically effective amount of a compound of Formula (I), (Ia), (Ib), (Ic), (Id), (Ie), (If), (Ig), (Ih), or (II) or a pharmaceutically acceptable salt thereof, or a pharmaceutical composition of the present disclosure.

In some aspects, the present disclosure provides a method of treating a breast cancer in a subject in need thereof, comprising administering to the subject a therapeutically effective amount of a compound of Formula (I), (Ia), (Ib), (Ic), (Id), (Ie), (If), (Ig), (Ih), or (II) or a pharmaceutically acceptable salt thereof, or a pharmaceutical composition of the present disclosure.

In some aspects, the present disclosure provides a method of treating or preventing a prostate cancer in a subject in need thereof, comprising administering to the subject a therapeutically effective amount of a compound of Formula (I), (Ia), (Ib), (Ic), (Id), (Ie), (If), (Ig), (Ih), or (II) or a pharmaceutically acceptable salt thereof, or a pharmaceutical composition of the present disclosure.

In some aspects, the present disclosure provides a method of treating a prostate cancer in a subject in need thereof, comprising administering to the subject a therapeutically effective amount of a compound of Formula (I), (Ia), (Ib), (Ic), (Id), (Ie), (If), (Ig), (Ih), or (II) or a pharmaceutically acceptable salt thereof, or a pharmaceutical composition of the present disclosure.

In some aspects, the present disclosure provides a method of treating or preventing a brain cancer in a subject in need thereof, comprising administering to the subject a therapeutically effective amount of a compound of Formula (I), (Ia), (Ib), (Ic), (Id), (Ie), (If), (Ig), (Ih), or (II) or a pharmaceutically acceptable salt thereof, or a pharmaceutical composition of the present disclosure.

In some aspects, the present disclosure provides a method of treating a brain cancer in a subject in need thereof, comprising administering to the subject a therapeutically effective amount of a compound of Formula (I), (Ia), (Ib), (Ic), (Id), (Ie), (If), (Ig), (Ih), or (II) or a pharmaceutically acceptable salt thereof, or a pharmaceutical composition of the present disclosure.

In some aspects, the present disclosure provides a compound of Formula (I), (Ia), (Ib), (Ic), (Id), (Ie), (If), (Ig), (Ih), or (II) or a pharmaceutically acceptable salt thereof for use in modulating PI3K (e.g., PI3Kα) activity (e.g., in vitro or in vivo).

In some aspects, the present disclosure provides a compound of Formula (I), (Ia), (Ib), (Ic), (Id), (Ie), (If), (Ig), (Ih), or (II) or a pharmaceutically acceptable salt thereof for use in treating or preventing a disease or disorder disclosed herein.

In some aspects, the present disclosure provides a compound of Formula (I), (Ia), (Ib), (Ic), (Id), (Ie), (If), (Ig), (Ih), or (II) or a pharmaceutically acceptable salt thereof for use in treating a disease or disorder disclosed herein.

In some aspects, the present disclosure provides a compound of Formula (I), (Ia), (Ib), (Ic), (Id), (Ie), (If), (Ig), (Ih), or (II) or a pharmaceutically acceptable salt thereof for use in treating or preventing a cancer in a subject in need thereof.

In some aspects, the present disclosure provides a compound of Formula (I), (Ia), (Ib), (Ic), (Id), (Ie), (If), (Ig), (Ih), or (II) or a pharmaceutically acceptable salt thereof for use in treating a cancer in a subject in need thereof.

In some aspects, the present disclosure provides a compound of Formula (I), (Ia), (Ib), (Ic), (Id), (Ie), (If), (Ig), (Ih), or (II) or a pharmaceutically acceptable salt thereof for use in treating or preventing a breast cancer in a subject in need thereof.

In some aspects, the present disclosure provides a compound of Formula (I), (Ia), (Ib), (Ic), (Id), (Ie), (If), (Ig), (Ih), or (II) or a pharmaceutically acceptable salt thereof for use in treating a breast cancer in a subject in need thereof.

In some aspects, the present disclosure provides a compound of Formula (I), (Ia), (Ib), (Ic), (Id), (Ie), (If), (Ig), (Ih), or (II) or a pharmaceutically acceptable salt thereof for use in treating or preventing a prostate cancer in a subject in need thereof.

In some aspects, the present disclosure provides a compound of Formula (I), (Ia), (Ib), (Ic), (Id), (Ie), (If), (Ig), (Ih), or (II) or a pharmaceutically acceptable salt thereof for use in treating a prostate cancer in a subject in need thereof.

In some aspects, the present disclosure provides a compound of Formula (I), (Ia), (Ib), (Ic), (Id), (Ie), (If), (Ig), (Ih), or (II) or a pharmaceutically acceptable salt thereof for use in treating or preventing a brain cancer in a subject in need thereof.

In some aspects, the present disclosure provides a compound of Formula (I), (Ia), (Ib), (Ic), (Id), (Ie), (If), (Ig), (Ih), or (II) or a pharmaceutically acceptable salt thereof for use in treating a brain cancer in a subject in need thereof.

In some aspects, the present disclosure provides use of a compound of Formula (I), (Ia), (Ib), (Ic), (Id), (Ie), (If), (Ig), (Ih), or (II) or a pharmaceutically acceptable salt thereof in the manufacture of a medicament for modulating PI3K (e.g., PI3Kα) activity (e.g., in vitro or in vivo).

In some aspects, the present disclosure provides use of a compound of Formula (I), (Ia), (Ib), (Ic), (Id), (Ie), (If), (Ig), (Ih), or (II) or a pharmaceutically acceptable salt thereof in the manufacture of a medicament for treating or preventing a disease or disorder disclosed herein.

In some aspects, the present disclosure provides use of a compound of Formula (I), (Ia), (Ib), (Ic), (Id), (Ie), (If), (Ig), (Ih), or (II) or a pharmaceutically acceptable salt thereof in the manufacture of a medicament for treating a disease or disorder disclosed herein.

In some aspects, the present disclosure provides use of a compound of Formula (I), (Ia), (Ib), (Ic), (Id), (Ie), (If), (Ig), (Ih), or (II) or a pharmaceutically acceptable salt thereof in the manufacture of a medicament for treating or preventing a cancer in a subject in need thereof.

In some aspects, the present disclosure provides use of a compound of Formula (I), (Ia), (Ib), (Ic), (Id), (Ie), (If), (Ig), (Ih), or (II) or a pharmaceutically acceptable salt thereof in the manufacture of a medicament for treating a cancer in a subject in need thereof.

In some aspects, the present disclosure provides use of a compound of Formula (I), (Ia), (Ib), (Ic), (Id), (Ie), (If), (Ig), (Ih), or (II) or a pharmaceutically acceptable salt thereof in the manufacture of a medicament for treating or preventing a breast cancer in a subject in need thereof.

In some aspects, the present disclosure provides use of a compound of Formula (I), (Ia), (Ib), (Ic), (Id), (Ie), (If), (Ig), (Ih), or (II) or a pharmaceutically acceptable salt thereof in the manufacture of a medicament for treating a breast cancer in a subject in need thereof.

In some aspects, the present disclosure provides use of a compound of Formula (I), (Ia), (Ib), (Ic), (Id), (Ie), (If), (Ig), (Ih), or (II) or a pharmaceutically acceptable salt thereof in the manufacture of a medicament for treating or preventing a prostate cancer in a subject in need thereof.

In some aspects, the present disclosure provides use of a compound of Formula (I), (Ia), (Ib), (Ic), (Id), (Ie), (If), (Ig), (Ih), or (II) or a pharmaceutically acceptable salt thereof in the manufacture of a medicament for treating a prostate cancer in a subject in need thereof.

In some aspects, the present disclosure provides use of a compound of Formula (I), (Ia), (Ib), (Ic), (Id), (Ie), (If), (Ig), (Ih), or (II) or a pharmaceutically acceptable salt thereof in the manufacture of a medicament for treating or preventing a brain cancer in a subject in need thereof.

In some aspects, the present disclosure provides use of a compound of Formula (I), (Ia), (Ib), (Ic), (Id), (Ie), (If), (Ig), (Ih), or (II) or a pharmaceutically acceptable salt thereof in the manufacture of a medicament for treating a brain cancer in a subject in need thereof.

The present disclosure provides compounds that function as modulators of PI3K activity. The present disclosure therefore provides a method of modulating PI3K activity in vitro or in vivo, said method comprising contacting a cell with a therapeutically effective amount of a compound, or a pharmaceutically acceptable salt thereof, as defined herein.

In some embodiments, PI3K is modulation is inhibition of PI3K.

In some embodiments, the PI3K inhibitor is a compound of Formula (I), (Ia), (Ib), (Ic), (Id), (Ie), (If), (Ig), (Ih), or (II), or a pharmaceutically acceptable salt thereof. In some embodiments, the PI3K inhibitor is a PI3Kα inhibitor. In some embodiments, the PI3K inhibitor is a PI3KA H1047R mutant inhibitor. In some embodiments, the PI3K inhibitor is alpha/beta non-selective. In some embodiments, the PI3K inhibitor is alpha selective. In some embodiments, the PI3K inhibitor is beta selective.

Effectiveness of compounds of the disclosure can be determined by industry-accepted assays/disease models according to standard practices of elucidating the same as described in the art and are found in the current general knowledge.

The present disclosure also provides a method of treating a disease or disorder in which PI3K activity is implicated in a patient in need of such treatment, said method comprising administering to said patient a therapeutically effective amount of a compound, or a pharmaceutically acceptable salt thereof, or a pharmaceutical composition as defined herein.

The disclosure provides a method of modulating the activity of the PI3Kα allosteric active site, wherein the modulation is induced through peripheral site targeting. In some embodiments, the peripheral site is targeted with an agent selected from a small molecule, a peptide, a peptidomimetic, a protein, a protein mimetic, a nucleic acid, an antibody, an antibody-drug conjugate, a nucleoprotein complex, an immunotherapy, or a combination thereof.

In some embodiments, the agent binds an epitope of the peripheral site selected from: (a) a) an epitope that comprises at least two contiguous or non-contiguous residues of SEQ ID NO: 1 or (b) an epitope that comprises at least two contiguous or non-contiguous residues of SEQ ID NO: 2.

In some embodiments, the agent binds an epitope of the peripheral site selected from: (a) an epitope that comprises at least one residue of SEQ ID NO: 1 wherein the at least one residue is: Cys901, Cys905, Thr908, Phe909, Phe954, Thr957, Phe960, Leu961, Ile964, Phe977, Phe980, Gln981, Cys984, Met1043, Ala1046, or His1047; or (b) an epitope that comprises at least one residue of SEQ ID NO: 2 wherein the at least one residue is: Cys901, Cys905, Thr908, Phe909, Phe954, Thr957, Phe960, Leu961, Ile964, Phe977, Phe980, Gln981, Cys984, Met1043, Ala1046, or Arg1047.

Routes of Administration

The compounds of Formula (I), (Ia), (Ib), (Ic), (Id), (Ie), (If), (Ig), (Ih), or (II) or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

EXAMPLES

Exemplary compounds of Formula (I) are synthesized and tested in the examples. It is understood that compounds of Formula (I) may be converted to the corresponding pharmaceutically acceptable salts of the compounds using routine techniques in the art (e.g., by saponification of an ester to the carboxylic acid salt, or by hydrolyzing an amide to form a corresponding carboxylic acid and then converting the carboxylic acid to a carboxylic acid salt).

Nuclear magnetic resonance (NMR) spectra were recorded at 400 MHz or 300 MHz as stated and at 300.3 K unless otherwise stated; the chemical shifts (δ) are reported in parts per million (ppm). Spectra were recorded using a Bruker or Varian instrument with 8, 16 or 32 scans.

LC-MS chromatograms and spectra were recorded using an Agilent 1200 or Shimadzu LC-20 AD&MS 2020 instrument using a C-18 column such as a Luna-C18 2.0×30 mm or Xbridge Shield RPC18 2.1×50 mm. Injection volumes were 0.7-8.0 μl and the flow rates were typically 0.8 or 1.2 ml/min. Detection methods were diode array (DAD) or evaporative light scattering (ELSD) as well as positive ion electrospray ionization. MS range was 100-1000 Da. Solvents were gradients of water and acetonitrile both containing a modifier (typically 0.01-0.04%) such as trifluoroacetic acid or ammonium carbonate.

ABBREVIATIONS

4A MS 4 angstrom molecular sieves
ACN Acetonitrile
AcOH or (OAc) Acetic Acid
aq. Aqueous
ADP Adenosine diphosphate
ATP Adenosine triphosphate
CDCl$_3$ Chloroform-d
CHCl$_3$ Chloroform
CO Carbon monoxide
CuI Copper(I) iodide
DCE 1,2-Dichloroethane
DCM Dichloromethane
DIPEA, DIEA N,N-Diisopropylethylamine
DMAP 4-Dimethylaminopyridine
DMF N,N-dimethylformamide
DMSO Dimethylsulfoxide
DMSO-d$_6$ Hexadeuterodimethylsulfoxide
DPPF or dppf 1,1'-bis(diphenylphosphino)ferrocene
EDCI N-(3-dimethylaminopropyl)-N'-ethylcarbodiimide
ee Enantiomeric excess
eq. Equivalents
ES/MS Electrospray mass spectrometry
EtI Ethyl iodide
EtOAc Ethyl acetate
EtOH Ethanol
FA Formic acid
h, hr(s) Hour(s)
HEPES 4-(2-Hydroxyethyl)-1-piperazineethanesulfonic acid
$^1$H NMR Proton nuclear magnetic resonance spectroscopy
HPLC High performance liquid chromatography
LC-MS Liquid chromatography-mass spectrometry
LiHMDS Lithium bis(trimethylsilyl)amide
m-CPBA meta-Chloroperoxybenzoic acid
MeCN Acetonitrile
MeOH Methanol
min(s) Minute(s)
n-BuLi n-Butyllithium
NaOAc Sodium acetate
NaHMDS Sodium bis(trimethylsilyl)amide
pet. ether or PE Petroleum ether
PIP2 Phosphatidylinositol 4,5-bisphosphate
PPh$_3$ Triphenylphosphine
ppm Parts per million
RM Reaction mixture
rt Room temperature
sat. Saturated
SFC Supercritical fluid chromatography
t-BuOK Potassium tert-butoxide
TEA Triethylamine
Tf$_2$O Trifluoromethanesulfonic anhydride
TFA Trifluoroacetic acid
THF Tetrahydrofuran
Ti(i-Pr)$_4$ Titanium(IV) isopropoxide
TLC Thin layer chromatography Tables 4 & 5—Columns & Eluents for Chiral SFC Purifications

TABLE 4

Chiral SFC Columns

| | Column Description |
|---|---|
| A | Daicel Chiracel OD-H, 21 × 250 mm, 5 um |
| B | Daicel Chiralcel OD-H, 21 × 150 mm, 5 um |
| C | Daicel Chiralcel OJ-H, 21 × 150 mm, 5 um |
| D | Daicel Chiralpak AD-H, 21 × 150 mm, 5 um |
| E | Daicel Chiralpak AS-H, 21 × 150 mm, 5 um |
| F | Daicel Chiralpak IH, 20 × 250 mm, 5 um |
| G | Lux Cellulose-2 AD-H, 21 × 250 mm |
| H | Lux Cellulose-2, 21 × 250 mm |
| I | Daicel Chiralpak AD-H, 20 × 250 mm, 5 um |
| J | Daicel Chiralpak AD-H, 30 × 250 mm, 5 um |
| K | Daicel Chiralpak AS-H, 20 × 250 mm, 5 um |
| L | Daicel Chiralpak IA, 20 × 250 mm, 5 um |
| M | Daicel Chiralpak IC, 20 × 250 mm, 5 um |
| N | Daicel Chiralpak ID, 20 × 250 mm, 5 um |
| O | Daicel Chiralpak IG, 30 × 250 mm, 5 um |
| P | Daicel Chiralpak OD-H, 20 × 250 mm, 5 um |

TABLE 4-continued

Chiral SFC Columns

| | Column Description |
|---|---|
| Q | Daicel Chiralpak OJ-H, 20 × 250 mm, 5 um |
| R | Daicel Chiralpak AD, 50 × 250 mm, 10 um |
| S | Daicel Chiralpak AS, 50 × 250 mm, 10 um |
| T | Regis(S,S)Whelk-O1, 25 × 250 mm, 10 um |
| U | Daicel Chiralpak AS, 30 × 250 mm, 10 um |
| V | Daicel Chiralpak AD-H, 30 × 250 mm, 5 um |
| W | Daicel Chiralpak OD-H, 30 × 250 mm, 5 um |
| X | Daicel Chiralpak AD, 30 × 250 mm, 10 um |
| Y | Daicel ChiralCel OD, 30 × 250 mm, 10 um |
| Z | Daicel ChiralCel OD-H, 30 × 250 mm, 5 um |
| AA | Daicel ChiralCel OJ, 30 × 250 mm; 10 um |
| AB | Daicel ChiralCel OJ-H, 30 × 250 mm; 5 um |
| AC | Daicel Chiralpak IC, 30 × 250 mm, 10 um |
| AD | Daicel Chiralpak OJ, 30 × 250 mm, 10 um |
| AE | Daicel ChiralCel AS, 30 × 250 mm, 10 um |
| AF | Daicel Chiralpak OD, 30 × 250 mm, 10 um |
| AG | (s,s) WHELK-O1 (250 × 30 mm, 5 um) |

TABLE 5

SFC Eluents

| | Chromatography Eluent |
|---|---|
| 1 | 15% MeOH:85% CO2 |
| 2 | 20% MeOH:80% CO2 |
| 3 | 25% MeOH:75% CO2 |
| 4 | 30% MeOH:70% CO2 |
| 5 | 40% MeOH:60% CO2 |
| 6 | 5-50% MeOH (w/0.1% aq NH3) in CO2 |
| 7 | 35% MeOH (w/0.1% aq NH3):65% CO2 |
| 8 | 50% MeOH (w/0.1% aq NH3):50% CO2 |
| 9 | 55% MeOH (w/0.1% aq NH3):45% CO2 |
| 10 | 25% MeOH (w/0.2% DMEA):75% CO2 |
| 11 | 30% MeOH (w/0.2% DMEA):70% CO2 |
| 12 | 35% MeOH (w/0.2% DMEA):65% CO2 |
| 13 | 40% MeOH (w/0.2% DMEA):60% CO2 |
| 14 | 15% MeOH (w/0.5% DMEA):85% CO2 |
| 15 | 20% MeOH (w/0.5% DMEA):80% CO2 |
| 16 | 25% MeOH (w/0.5% DMEA):75% CO2 |
| 17 | 30% MeOH (w/0.5% DMEA):70% CO2 |
| 18 | 35% MeOH (w/0.5% DMEA):65% CO2 |
| 19 | 40% MeOH (w/0.5% DMEA):60% CO2 |
| 20 | 50% MeOH (w/0.5% DMEA):50% CO2 |
| 21 | 20% EtOH (w/0.1% aq NH3):80% CO2 |
| 22 | 25% EtOH (w/0.1% aq NH3):75% CO2 |
| 23 | 30% EtOH (w/0.1% aq NH3):70% CO2 |
| 24 | 35% EtOH (w/0.1% aq NH3):65% CO2 |
| 25 | 40% EtOH (w/0.1% aq NH3):60% CO2 |
| 26 | 45% EtOH (w/0.1% aq NH3):55% CO2 |
| 27 | 55% EtOH (w/0.1% aq NH3):45% CO2 |
| 28 | 60% EtOH (w/0.1% aq NH3):40% CO2 |
| 29 | 10% EtOH (w/0.2% DMEA):90% CO2 |
| 30 | 35% EtOH (w/0.2% DMEA):65% CO2 |
| 31 | 30% EtOH (w/0.5% DMEA):70% CO2 |
| 32 | 40% EtOH (w/0.5% DMEA):60% CO2 |
| 33 | 35% IPA (w/0.2% DMEA):65% CO2 |
| 34 | 40% IPA (w/0.2% DMEA):60% CO2 |
| 35 | 30% IPA (w/0.5% DMEA):70% CO2 |
| 36 | 35% IPA (w/0.5% DMEA):65% CO2 |
| 37 | 55% IPA (w/0.1% aq NH3):45% CO2 |
| 38 | 40% MeOH (w/0.1% aq NH3):60% CO2 |

Intermediate 1:
8-Bromo-2-ethylsulfanyl-6-methyl-chromen-4-one

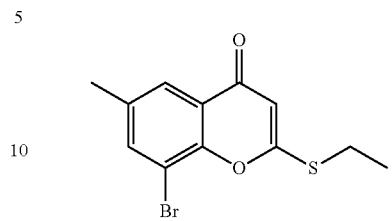

Step 1: 2-bromo-4-methylphenyl acetate. A mixture of 2-bromo-4-methyl-phenol (300 g, 1.60 mol) and pyridine (152 g, 1.92 mol) in DCM (2.4 L) was added acetyl chloride (151 g, 1.92 mol) at 0° C., and stirred at 25° C. for 16 h. The mixture was diluted with water (1500 mL) and adjusted to pH=5 with HCl (2 M), then extracted with DCM (500 mL×3). The combined extract was washed with brine (250 mL×2), dried over anhydrous $Na_2SO_4$, filtered and concentrated to give the product as oil (400 g, crude). $^1$H NMR (400 MHz, $CDCl_3$) δ ppm 2.24 (s, 3H), 2.25 (s, 3H), 6.91 (d, J=8.4 Hz, 2H), 7.01-7.02 (m, 2H), 7.33 (s, 1H).

Step 2: 1-(3-bromo-2-hydroxy-5-methyl-phenyl)ethanone. A mixture of (2-bromo-4-methyl-phenyl) acetate (50 g, 218 mmol) and $AlCl_3$ (102 g, 764 mmol) was degassed and purged with $N_2$ for 3 times and stirred at 140° C. for 1 h. When cooled to rt the reaction was diluted with DCM (30 mL), dropped in $H_2O$ (150 mL) at 0° C. The mixture was filtered, aqueous phase was extracted with DCM (150 mL×2). The combined extract was washed with brine (100 mL), dried over anhydrous $Na_2SO_4$, filtered and concentrated. The residue was triturated with petroleum ether (150 mL×2) to give the product as a solid (30 g, 52%). $^1$H NMR (400 MHz, $CDCl_3$) δ ppm 2.30 (s, 3H), 2.68 (s, 3H), 7.73 (s, 1H), 7.33 (s, 1H), 12.64 (s, 1H).

Step 3: 8-bromo-4-hydroxy-6-methyl-chromene-2-thione. A solution of 1-(3-bromo-2-hydroxy-5-methyl-phenyl)ethanone (65 g, 284 mmol) in THF (800 mL) was added NaHMDS (851 mL, 1 M) at −50° C. over 30 min, warmed to −5 to 0° C. and stirred for 1 h. To the mixture was added $CS_2$ (64.8 g, 851 mmol) at −20° C. dropwise over 1 h, warmed to 25° C. and stirred for another 16 h. The reaction was quenched with $H_2SO_4$ (800 mL, 15%) at −50° C. over 1 h, warmed to rt and extracted with EtOAc (1 L×2). The combined extract was washed with brine (1 L), dried over anhydrous $Na_2SO_4$, filtered and concentrated. The residue was triturated with EtOAc (0.5 L) to give the product as a solid (210 g crude, yield: 64%, purity: 76%).

Step 4: 8-bromo-2-ethylsulfanyl-6-methyl-chromen-4-one. A mixture of 8-bromo-4-hydroxy-6-methyl-chromene-2-thione (20.0 g, 73.8 mmol), EtI (46.0 g, 295 mmol) and $K_2CO_3$ (12.2 g, 88.5 mmol) in acetone (200 mL) was stirred at 60° C. for 3 h. When cooled to rt the mixture was diluted with water (200 mL), extracted with DCM (200 mL×2). The combined extract was concentrated and purified by silica gel chromatography eluted with 20%-40% EtOAc in petroleum ether to give 8-bromo-2-ethylsulfanyl-6-methyl-chromen-4-one (14.6 g, 66%) as gum. $^1$H NMR (400 MHz, $CDCl_3$) δ ppm 1.51 (t, J=7.2 Hz, 3H), 2.45 (s, 3H), 3.22 (q, J=7.2 Hz, 2H), 6.32 (s, 1H), 7.70 (s, 1H), 7.93 (s, 1H). MS ES+ m/z 301 [M+H]$^+$.

Intermediate 2:
8-Bromo-2-ethylsulfonyl-6-methyl-chromen-4-one

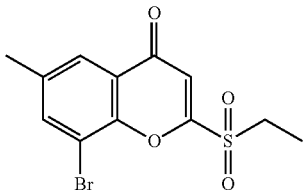 [SMILES: CCS(=O)(=O)c1cc(=O)c2cc(C)cc(Br)c2o1]

A mixture of 8-bromo-2-ethylsulfanyl-6-methyl-chromen-4-one (9.5 g, 31.7 mmol) in DCM (150 mL) was added m-CPBA (13.7 g, 63.5 mmol, 80% purity) in portions at 10° C., then warmed to 25° C. and stirred for 16 h. The mixture and another batch (5.1 g) were cooled to −15° C. and filtered. The filter cake was washed with cold DCM (20 mL×3). The filtrate was washed with sat.Na$_2$S$_2$O$_4$ (300 mL×2), sat.NaHCO$_3$ (300 mL×2) and concentrated to give 8-bromo-2-ethylsulfonyl-6-methyl-chromen-4-one (16.1 g, crude) as a solid. MS ES+ m/z 333 [M+H]$^+$.

Intermediate 3: 8-(1-Bromoethyl)-2-(4,4-dimethyl-1-piperidyl)-6-methyl-chromen-4-one

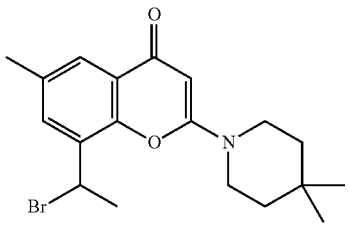

Step 1: 8-bromo-2-(4,4-dimethyl-1-piperidyl)-6-methyl-chromen-4-one. A mixture of 8-bromo-2-ethylsulfonyl-6-methyl-chromen-4-one (11.0 g, crude) and 4,4-dimethylpiperidine (7.46 g, 49.8 mmol, HCl salt) in DCM (200 mL) was added DIPEA (17.2 g, 133 mmol) dropwise at 5-10° C. and stirred at 20° C. for 16 h. The mixture was combined with another batch (5 g) and washed with water (300 mL×2), followed by brine (250 mL×2). The extract was dried over anhydrous Na$_2$SO$_4$, filtered and concentrated. The residue was purified by silica gel chromatography eluted with 25%-80% EtOAc in pet. ether to give the product as gum (14.2 g, 84%). $^1$H NMR (400 MHz, CDCl$_3$) δ ppm 1.06 (s, 6H), 1.50-1.55 (m, 4H), 2.42 (s, 3H), 3.55-3.64 (m, 4H), 5.53 (s, 1H), 7.58 (d, J=1.6 Hz, 1H), 7.90 (d, J=1.6 Hz, 1H).

Step 2: 8-acetyl-2-(4,4-dimethyl-1-piperidyl)-6-methyl-chromen-4-one. A mixture of 8-bromo-2-(4,4-dimethyl-1-piperidyl)-6-methyl-chromen-4-one (9.0 g, 25.7 mmol), Pd(PPh$_3$)$_2$Cl$_2$ (902 mg, 1.28 mmol) and tributyl(1-ethoxyvinyl)stannane (11.1 g, 30.8 mmol) in dioxane (100 mL) was stirred at 95° C. under N$_2$ atmosphere for 16 h. HCl (12 mL, 2 M) was added into the mixture and stirred at 50° C. for 0.5 h. The mixture was combined with another batch (5 g), added sat. KF (200 mL) and stirred at 20° C. for 0.5 h. The gray suspension was filtered. The filter cake was washed with EtOAc (50 mL×3). The aqueous phase was extracted with EtOAc (200 mL×2). The combined organic layer was washed with brine (250 mL), filtered, concentrated and triturated with PE/EtOAc (200 mL/15 mL) to give the product (8.2 g). The mother liquor was concentrated and triturated with PE/EtOAc (100 mL/5 mL) to give the product (3.53 g), combined to provide a total product (11.73 g, 92%). $^1$H NMR (400 MHz, DMSO-d$_4$) δ ppm 0.99 (s, 6H), 1.40-1.45 (m, 4H), 2.43 (s, 3H), 2.67 (s, 3H), 3.52-3.60 (m, 4H), 5.54 (s, 1H), 7.89-7.95 (m, 2H). MS ES+ m/z 314 [M+H]$^+$.

Step 3: 2-(4,4-dimethyl-1-piperidyl)-8-(1-hydroxyethyl)-6-methyl-chromen-4-one. A mixture of 8-acetyl-2-(4,4-dimethyl-1-piperidyl)-6-methyl-chromen-4-one (8.2 g, 26.2 mmol) in DCM (50 mL) and MeOH (50 mL) was added NaBH$_4$ (1.19 g, 31.4 mmol) in portions at −10° C., then stirred at 20° C. for 16 h. The mixture was quenched with sat.NH$_4$Cl (120 mL) and extracted with DCM (150 mL×2). The combined extract was washed with brine (150 mL×2), dried over anhydrous Na$_2$SO$_4$, filtered and concentrated. The residue was triturated with PE/EtOAc (120 mL/10 mL) to give the product as a solid (8.2 g, 99%). $^1$H NMR (400 MHz, DMSO-d$_4$) δ ppm 0.99 (s, 6H), 1.30-1.45 (m, 7H), 2.38 (s, 3H), 3.46-3.54 (m, 4H), 5.10-5.20 (m, 1H), 5.35 (d, J=4.4 Hz, 1H), 5.48 (s, 1H), 7.55 (d, J=2.0 Hz, 1H), 7.58 (d, J=2.0 Hz, 1H). MS ES+ m/z 316 [M+H]$^+$.

Step 4: 8-(1-bromoethyl)-2-(4,4-dimethyl-1-piperidyl)-6-methyl-chromen-4-one. A mixture of 2-(4,4-dimethyl-1-piperidyl)-8-(1-hydroxyethyl)-6-methyl-chromen-4-one (7.60 g, 24.1 mmol) in DCM (150 mL) was added PBr$_3$ (9.78 g, 36.1 mmol) dropwise at 0° C., and stirred at 25° C. for 16 h. The mixture was adjusted to pH=8 with sat.NaHCO$_3$ slowly and stirred for 0.5 h. The mixture was filtered. The filter cake was washed with DCM (20 mL×2). The filtrate was extracted with DCM (200 mL×2). The combined extract was washed with brine (300 mL), dried over anhydrous Na$_2$SO$_4$, filtered, concentrated and triturated with PE/EtOAc (200 mL/15 mL) to give the product as a solid (6.85 g). The mother liquor was combined with another batch (4 g) and purified by silica gel chromatography eluted with 50%-100% EtOAc in pet. ether to give the product as a solid (1.5 g). Total amount of 8-(1-bromoethyl)-2-(4,4-dimethyl-1-piperidyl)-6-methyl-chromen-4-one (8.35 g, 89%). $^1$H NMR (400 MHz, DMSO-d$_4$) δ ppm 1.00 (s, 6H), 1.40-1.49 (m, 4H), 2.11 (d, J=6.8 Hz, 3H), 2.40 (s, 3H), 3.54-3.65 (m, 4H), 5.53 (s, 1H), 5.80-5.88 (m, 1H), 7.60-7.71 (m, 2H). MS ES+ m/z 380 [M+H]$^+$.

Intermediate 4: 8-(1-Bromoethyl)-2-(4,4-dimethyl-1-piperidyl)-3,6-dimethyl-chromen-4-one

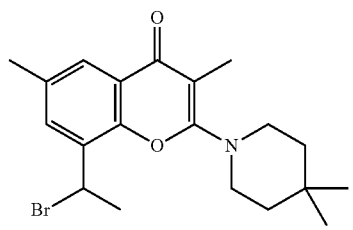

Step 1: (2-bromo-4-methyl-phenyl) propanoate. A mixture of 2-bromo-4-methyl-phenol (10.0 g, 53.5 mmol) and pyridine (6.34 g, 80.2 mmol) in DCM (100 mL) was added propanoyl chloride (5.44 g, 58.8 mmol) at 0° C., and stirred at 25° C. for 16 h. Then the mixture was diluted with water (100 mL), adjusted to pH=5 with HCl (2 M) and extracted with DCM (100 mL×2). The combined extract was washed with brine (150 mL×2), dried over anhydrous Na₂SO₄, filtered and concentrated to give the product as oil (13 g, crude). ¹H NMR (400 MHz, DMSO-d₆) δ ppm 1.17 (t, J=7.6 Hz, 3H), 2.30 (s, 3H), 2.62 (q, J=7.6 Hz, 2H), 7.11-7.18 (m, 1H), 7.19-7.26 (m, 1H), 7.50-7.55 (m, 1H).

Step 2: 1-(3-bromo-2-hydroxy-5-methyl-phenyl)propan-1-one. A mixture of (2-bromo-4-methyl-phenyl) propanoate (12.5 g, 51.4 mmol) and AlCl₃ (24.0 g, 180 mmol) was stirred at 140° C. for 1 h. When cooled to rt the mixture was quenched with water (80 mL) dropwise and stirred for 30 min. Then the mixture was extracted with EtOAc (100 mL×3). The combined extract was washed with brine (200 mL×2), dried over anhydrous Na₂SO₄ and filtered. The filtrate was concentrated and triturated with petroleum ether (20 mL) to give the product as a solid (9.82 g, 79%). ¹H NMR (400 MHz, DMSO-d₆) δ ppm 1.10 (t, J=7.2 Hz, 3H), 2.28 (s, 3H), 3.15 (q, J=7.2 Hz, 2H), 7.66-7.73 (m, 1H), 7.77-7.83 (m, 1H), 12.66 (s, 1H).

Step 3: 8-bromo-4-hydroxy-3,6-dimethyl-chromene-2-thione. A mixture of 1-(3-bromo-2-hydroxy-5-methyl-phenyl)propan-1-one (5.0 g, 21 mmol) in THF (80 mL) was added NaHMDS (1 M, 72 mL) at −50° C. dropwise, then warmed to −5-0° C. and stirred for 1 h, then added CS₂ (2.51 g, 32.9 mmol) at −20° C. and stirred at 25° C. for another 16 h. When cooled to −50° C. the mixture was quenched with 15% H₂SO₄ (50 mL) and extracted with DCM (100 mL×3). The combined extract was washed with brine (150 mL×2), dried over anhydrous Na₂SO₄ and filtered. The filtrate was concentrated and triturated with DCM (10 mL) to give the product as a solid (4.1 g, 70%). ¹H NMR (400 MHz, DMSO-d₆) δ ppm 2.24 (s, 3H), 2.39 (s, 3H), 7.80 (s, 2H).

Step 4: 8-bromo-2-ethylsulfanyl-3,6-dimethyl-chromen-4-one. A mixture of 9-bromo-2-hydroxy-7-methyl-pyrido[1,2-a]pyrimidin-4-one (4.1 g, 14 mmol), EtI (9.0 g, 58 mmol) and K₂CO₃ (2.38 g, 17.2 mmol) in acetone (80 mL) was stirred at 60° C. for 2 h. When cooled to rt the mixture was quenched with water (100 mL), extracted with DCM (150 mL×3), dried over anhydrous Na₂SO₄ and filtered. The filtrate was concentrated and purified on a silica gel column eluted with 0-20% EtOAc in petroleum ether to give the product as a solid (3.25 g, 71%). MS ES+ m/z 315 [M+H]⁺.

Step 5: 8-bromo-2-ethylsulfonyl-3,6-dimethyl-chromen-4-one. A mixture of 8-bromo-2-ethylsulfanyl-3,6-dimethyl-chromen-4-one (1.5 g, 4.8 mmol) in DCM (15 mL) was added m-CPBA (2.92 g, 14.4 mmol, 85% purity) at 10° C., and stirred at 20° C. for 16 h. The mixture was diluted with sat.aq.Na₂SO₃ (40 mL), extracted with DCM (40 mL×3). The combined extract was washed with sat.aq.NaHCO₃ (60 mL×2), dried over anhydrous Na₂SO₄ and filtered. The filtrate was concentrated and purified on a silica gel column eluted with 0-20% EtOAc in petroleum ether to give the product as a solid (1.5 g, 91%). MS ES+ m/z 347 [M+H]⁺.

Step 6: 8-bromo-2-(4,4-dimethyl-1-piperidyl)-3,6-dimethyl-chromen-4-one. A mixture of 8-bromo-2-ethylsulfonyl-3,6-dimethyl-chromen-4-one (1.5 g, 4.3 mmol) in DCM (15 mL) was added 4,4-dimethylpiperidine (1.95 g, 13.0 mmol, HCl) and DIPEA (4.49 g, 34.8 mmol) at 10° C., stirred at 20° C. for 15 h. The mixture was diluted with water (30 mL), extracted with DCM (40 mL×3), washed with brine (50 mL×2), dried over anhydrous Na₂SO₄ and filtered. The filtrate was concentrated and purified on a silica gel column eluted with 0-15% EtOAc in petroleum ether to give the product as a solid (1.4 g, 88%). MS ES+ m/z 364 [M+H]⁺.

Step 7: 8-acetyl-2-(4,4-dimethyl-1-piperidyl)-3,6-dimethyl-chromen-4-one. A mixture of 8-bromo-2-(4,4-dimethyl-1-piperidyl)-3,6-dimethyl-chromen-4-one (1.4 g, 3.8 mmol), Pd(PPh₃)₂Cl₂ (270 mg, 0.384 mmol) and tributyl(1-ethoxyvinyl)stannane (1.67 g, 4.61 mmol) in dioxane (15 mL) was stirred at 95° C. under N₂ for 16 h. To the mixture was added HCl (2 mL, 1 M) and stirred for 0.5 h. When cooled to rt the mixture was added sat.aq. KF (30 mL) and stirred for 1 h, filtered and the filter cake was rinsed with DCM (20 mL). The aqueous phase was extracted with DCM (50 mL×3). The combined extract was dried over anhydrous Na₂SO₄, filtered, concentrated and triturated with PE/EtOAc (5/1, 12 mL) to give the product as a solid (1.2 g, crude). MS ES+ m/z 328 [M+H]⁺.

Step 8: 2-(4,4-dimethyl-1-piperidyl)-8-(1-hydroxyethyl)-3,6-dimethyl-chromen-4-one. A mixture of 8-acetyl-2-(4,4-dimethyl-1-piperidyl)-3,6-dimethyl-chromen-4-one (1.2 g, 3.7 mmol) in DCM (6 mL) and MeOH (6 mL) was added NaBH₄ (166.38 mg, 4.40 mmol) at −10° C., and stirred at −10° C. for 1.5 h. The reaction mixture was quenched with water (30 mL), extracted with DCM/MeOH (40 mL×3, 10/1). The combined extract was washed with brine (50 mL×2), dried over anhydrous Na₂SO₄ and filtered. The filtrate was concentrated to give the product as a solid (1.2 g, crude). MS ES+ m/z 330 [M+H]⁺.

Step 9: 8-(1-bromoethyl)-2-(4,4-dimethyl-1-piperidyl)-3,6-dimethyl-chromen-4-one. A mixture of 2-(4,4-dimethyl-1-piperidyl)-8-(1-hydroxyethyl)-3,6-dimethyl-chromen-4-one (1.2 g, 3.6 mmol) in DCM (12 mL) was added PBr₃ (1.48 g, 5.46 mmol) at 0° C., and stirred at 20° C. for 2 h. The reaction mixture was quenched with sat.aq.NaHCO₃ (50 mL), extracted with DCM (60 mL×3). The combined extract was washed with brine (80 mL×2), dried over anhydrous Na₂SO₄ and filtered. The filtrate was concentrated and purified on a silica gel column eluted with 0-25% EtOAc in petroleum ether to give 8-(1-bromoethyl)-2-(4,4-dimethyl-1-piperidyl)-3,6-dimethyl-chromen-4-one as a solid (930 mg, 65%). ¹H NMR (400 MHz, DMSO-d₆) δ ppm 1.01 (s, 6H), 1.46-1.51 (m, 4H), 1.91 (s, 3H), 2.11 (d, J=6.8 Hz, 3H), 2.40 (s, 3H), 3.42-3.51 (m, 4H), 5.84 (q, J=6.8 Hz, 1H), 7.72 (d, J=7.2 Hz, 2H).

Intermediate 5: 8-(1-Bromoethyl)-6-methyl-2-(1-piperidyl)chromen-4-one

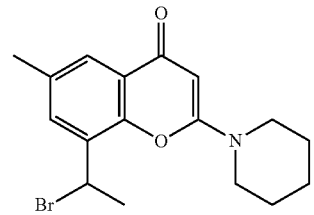 [SMILES: Cc1cc(C(C)Br)c2oc(N3CCCCC3)cc(=O)c2c1]

Step 1: 8-bromo-6-methyl-2-(1-piperidyl)chromen-4-one. A mixture of piperidine (340 mg, 3.99 mmol) and DIPEA (937 mg, 7.25 mmol) in DCM (5 mL) was added dropwise to a solution of 8-bromo-2-ethylsulfonyl-6-methyl-chromen-4-one (600 mg, 1.81 mmol) in DCM (10 mL) at 10° C. and stirred at 20° C. for 2 h. The mixture was diluted with H₂O (20 mL), quenched with HCl (2M, 1 mL), then extracted with DCM (20 mL×2). The combined extract was washed with brine (20 mL×2), dried over anhydrous Na₂SO₄, filtered and concentrated to give the product as a solid (550 mg, 96%). MS ES+ m/z 324 [M+H]⁺.

Step 2: 8-acetyl-6-methyl-2-(1-piperidyl)chromen-4-one. A mixture of 8-bromo-6-methyl-2-(1-piperidyl)chromen-4-one (550 mg, 1.71 mmol), Pd(PPh$_3$)$_2$Cl$_2$ (240 mg, 0.341 mmol) and tributyl(1-ethoxyvinyl)stannane (863 mg, 2.39 mmol) in dioxane (10 mL) was stirred at 95° C. for 16 h under N$_2$ atmosphere. Then HCl (1 M, 1.71 mL) was added into the mixture and stirred at 50° C. for 4 h. When cooled to rt the mixture was added aq. KF (10 mL) and stirred at 25° C. for 0.5 h, then filtered. The filtrate was extracted with DCM (30 mL×2). The combined extract was washed with brine (30 mL×2), dried over anhydrous Na$_2$SO$_4$, filtered and concentrated to give the product as a solid (480 mg, crude). MS ES+ m/z 286 [M+H]$^+$.

Step 3: 8-(1-hydroxyethyl)-6-methyl-2-(1-piperidyl)chromen-4-one. A mixture of 8-acetyl-6-methyl-2-(1-piperidyl)chromen-4-one (480 mg, 1.68 mmol) in DCM (3 mL) and MeOH (3 mL) was added NaBH$_4$ (76.4 mg, 2.02 mmol) at −10° C., and stirred at −10° C. for 1 h. The reaction mixture was quenched with water (15 mL), the aqueous layer was extracted with DCM/MeOH (20 mL×2, 10/1). The combined extract was washed with brine (20 mL), dried over anhydrous Na$_2$SO$_4$, filtered and concentrated. The residue was purified by silica gel chromatography eluted with 0%-10% MeOH in DCM to give the product as a solid (360 mg, 75%). MS ES+ m/z 288 [M+H]$^+$.

Step 4: 8-(1-bromoethyl)-6-methyl-2-(1-piperidyl)chromen-4-one. A mixture of 8-(1-hydroxyethyl)-6-methyl-2-(1-piperidyl)chromen-4-one (300 mg, 1.04 mmol) in DCM (5 mL) was added PBr$_3$ (283 mg, 1.04 mmol) dropwise at 0° C. and stirred at 20° C. for 2 h. The reaction mixture was quenched with sat. aq. NaHCO$_3$ (20 mL), the aqueous phase was extracted with DCM (20 mL×2). The combined extract was washed with brine (30 mL×2), dried over anhydrous Na$_2$SO$_4$, filtered and concentrated to give 8-(1-bromoethyl)-6-methyl-2-(1-piperidyl)chromen-4-one as a solid (300 mg, crude). MS ES+ m/z 352 [M+H]$^+$.

Intermediate 6: Methyl 2-[1-(2-ethylsulfanyl-6-methyl-4-oxo-chromen-8-yl)ethylamino]benzoate

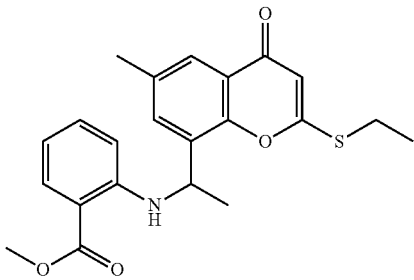 [SMILES: CCSc1cc(=O)c2cc(C)cc(C(C)Nc3ccccc3C(=O)OC)c2o1]

Step 1: 8-acetyl-2-ethylsulfanyl-6-methyl-chromen-4-one. A mixture of 8-bromo-2-ethylsulfanyl-6-methyl-chromen-4-one (9.00 g, 30.0 mmol), tributyl(1-ethoxyvinyl)tin (13.3 g, 36.8 mmol) and Pd(PPh$_3$)$_2$Cl$_2$ (2.11 g, 3.01 mmol) in dioxane (90 mL) was stirred at 95° C. for 16 h. HCl (30 mL, 1 M) was added to the mixture and stirred at 50° C. for 0.5 h. When cooled to rt the mixture and added sat. KF (100 mL) and stirred for 0.5 h, then filtered. The filter cake was washed with EtOAc (40 mL×3). The filtrate was extracted with EtOAc (80 mL×2). The combined extract was concentrated and purified on a silica gel column eluted with 0-60% EtOAc in petroleum ether to give the product as a solid (5.8 g, 60%). MS ES+ m/z 263 [M+H]$^+$.

Step 2: 2-ethylsulfanyl-8-(1-hydroxyethyl)-6-methyl-chromen-4-one. A solution of 8-acetyl-2-ethylsulfanyl-6-methyl-chromen-4-one (8.30 g, 31.6 mmol) in DCM (30 mL) and MeOH (30 mL) was added NaBH$_4$ (1.32 g, 34.8 mmol) in portions at 0° C., and stirred at 15° C. for 1 h. The mixture was diluted with water (50 mL), then extracted with DCM (100 mL×2). The combined extract was washed with brine (80 mL), dried over anhydrous Na$_2$SO$_4$, filtered, concentrated. The residue was purified on a silica gel column eluted with 0-4% MeOH in DCM to give the product as a solid (6.0 g, 60%). MS ES+ m/z 265 [M+H]$^+$.

Step 3: 8-(1-bromoethyl)-2-ethylsulfanyl-6-methyl-chromen-4-one. A mixture of 2-ethylsulfanyl-8-(1-hydroxyethyl)-6-methyl-chromen-4-one (5.50 g, 20.8 mmol) in DCM (50 mL) was added PBr$_3$ (16.9 g, 62.4 mmol) dropwise at 0° C., then stirred at 30° C. for 4 h. The reaction mixture was added water (20 mL) at 0° C., and then adjusted with sat.NaHCO$_3$ to pH=8. The mixture was extracted with DCM (80 mL×2). The combined extract was washed with brine (100 mL), dried over anhydrous Na$_2$SO$_4$, filtered and concentrated to give the product as oil (4.7 g, 61%). MS ES+ m/z 329 [M+2+H]$^+$.

Step 4: methyl 2-[1-(2-ethylsulfanyl-6-methyl-4-oxo-chromen-8-yl)ethylamino]benzoate. A mixture of 8-(1-bromoethyl)-2-ethylsulfanyl-6-methyl-chromen-4-one (4.00 g, 12.2 mmol) and methyl 2-aminobenzoate (3.70 g, 24.5 mmol) in DMF (30 mL) was stirred at 80° C. for 8 h. When cooled to rt the mixture was diluted with water (100 mL), extracted with EtOAc (80 mL×3). The combined extract was washed with brine (100 mL×3), dried over anhydrous Na$_2$SO$_4$, filtered, concentrated. The residue was purified by silica gel chromatography eluted with 0%-27% EtOAc in petroleum ether to give methyl 2-[1-(2-ethylsulfanyl-6-methyl-4-oxo-chromen-8-yl)ethylamino]benzoate (4.5 g, 84%) as a solid. MS ES+ m/z 398 [M+H]$^+$.

Intermediate 7: Methyl 2-[1-(2-ethylsulfinyl-6-methyl-4-oxo-chromen-8-yl)ethylamino]benzoate

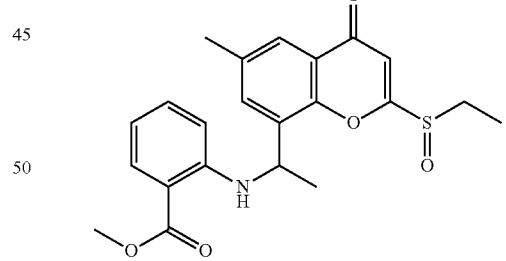

A mixture of methyl 2-[1-(2-ethylsulfanyl-6-methyl-4-oxo-chromen-8-yl)ethylamino]benzoate (4.80 g, 12.1 mmol) in DCM (50 mL) was added m-CPBA (3.39 g, 15.7 mmol, 80% purity) in portions at 0° C., and stirred at 15° C. for 2 h. The mixture was filtered, the filter cake was washed with DCM (10 mL×3). The filtrate was washed with sat. Na$_2$S$_2$O$_4$ (100 mL) and followed by sat.NaHCO$_3$ (100 mL). The organic phase was concentrated and purified by silica gel chromatography eluted with 0%-68% EtOAc in petroleum ether to give methyl 2-[1-(2-ethylsulfinyl-6-methyl-4-oxo-chromen-8-yl)ethylamino]benzoate (3.7 g, 70%) as a solid. MS ES+ m/z 414 [M+H]$^+$.

Intermediate 8: 2-[1-(2-Ethylsulfinyl-6-methyl-4-oxo-chromen-8-yl)ethylamino]benzoic acid

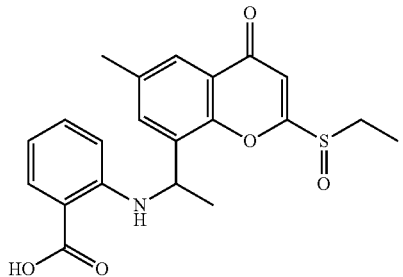 [SMILES: CCS(=O)c1cc(=O)c2cc(C)cc(C(C)Nc3ccccc3C(=O)O)c2o1]

Step 1: 2-[1-(2-ethylsulfanyl-6-methyl-4-oxo-chromen-8-yl)ethylamino]benzoic acid. A mixture of 8-(1-bromoethyl)-2-ethylsulfanyl-6-methyl-chromen-4-one (200 mg, 611 µmol) and 2-aminobenzoic acid (167 mg, 1.22 mmol) in DMF (2 mL) was stirred at 80° C. for 14 h. When cooled to rt the mixture was diluted with water (20 mL), extracted with EtOAc (20 mL×3). The combined extract was washed with brine (40 mL×3), dried over anhydrous $Na_2SO_4$, filtered, concentrated. The residue was purified on a silica gel column eluted with 0-2% MeOH in DCM to give the product as a solid (160 mg, 57%). MS ES+ m/z 384 [M+H]+.

Step 2: 2-[1-(2-ethylsulfinyl-6-methyl-4-oxo-chromen-8-yl)ethylamino]benzoic acid. A mixture of 2-[1-(2-ethylsulfanyl-6-methyl-4-oxo-chromen-8-yl)ethylamino]benzoic acid (160 mg, 350 µmol) in DCM (5 mL) was added m-CPBA (98.0 mg, 456 µmol, 80% purity) in portions at 0° C., then stirred at 15° C. for 2 h. The mixture was diluted with DCM (20 mL), and washed with sat.$Na_2S_2O_4$ (15 mL). The organic phase was concentrated and purified on a silica gel column eluted with 0-2% MeOH in DCM to give 2-[1-(2-ethylsulfinyl-6-methyl-4-oxo-chromen-8-yl)ethylamino]benzoic acid as oil (100 mg, 64%). MS ES+ m/z 400 [M+H]+.

Intermediate 9: 2-[1-(2-Ethylsulfinyl-6-methyl-4-oxo-chromen-8-yl)ethylamino]benzoic acid, Isomer 1

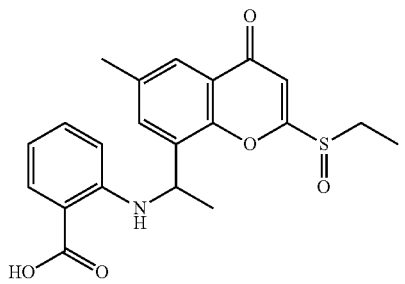 [SMILES: CCS(=O)c1cc(=O)c2cc(C)cc(C(C)Nc3ccccc3C(=O)O)c2o1]

Step 1: 2-[1-(2-ethylsulfanyl-6-methyl-4-oxo-chromen-8-yl)ethylamino]benzoic acid, Isomer 1. The mixture of 8-(1-bromoethyl)-2-ethylsulfanyl-6-methyl-chromen-4-one (10 g, 31 mmol) and 2-aminobenzoic acid (8.38 g, 61.1 mmol) in DMF (70 mL) was stirred at 80° C. for 2 h. The reaction mixture was diluted with DCM (200 mL) and water (500 mL), then adjusted to pH=11 with aq. NaOH (2 M). The aqueous layer was washed with MTBE (200 mL×2) and adjusted to pH=3 with aq. HCl (2 M) to give a solid. After stirring 0.5 h, the mixture was filtered and the filter cake was purified by chiral SFC (AB, 6; See Tables 4 and 5 for chiral columns and eluents) to give the product as a solid (4.7 g, yield: 47%, ee: 93%). MS ES+ m/z 383 [M+H]+.

Step 2: 2-[1-(2-ethylsulfinyl-6-methyl-4-oxo-chromen-8-yl)ethylamino]benzoic acid, Isomer 1. To a mixture of 2-[1-(2-ethylsulfanyl-6-methyl-4-oxo-chromen-8-yl)ethylamino]benzoic acid, Isomer 1 (850 mg, 2.22 mmol) and DCM (10 mL) was added m-CPBA (585 mg, 2.88 mmol, 85% purity) under $N_2$ at 0° C., and stirred at 25° C. for 2 h. The mixture was quenched with sat.$Na_2S_2O_3$ (10 mL) at 0° C., the aqueous layer was extracted with EtOAc (20 mL×2). The combined organic layer was washed with brine (20 mL×3), dried over anhydrous $Na_2SO_4$, filtered and concentrated. The residue was purified by column chromatography ($SiO_2$, Petroleum ether/Ethyl acetate=1/0 to 1/4) to give 2-[1-(2-ethylsulfinyl-6-methyl-4-oxo-chromen-8-yl)ethylamino]benzoic acid, Isomer 1 as a solid. (410 mg, yield: 42%). MS ES+ m/z 400 [M+H]+.

Intermediate 10: 8-Acetyl-2-ethylsulfanyl-3,6-dimethyl-chromen-4-one

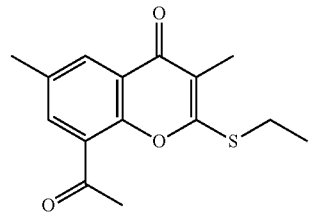 [SMILES: CCSc1oc2c(C(C)=O)cc(C)cc2c(=O)c1C]

Prepared in the same manner as 8-acetyl-2-ethylsulfanyl-6-methyl-chromen-4-one to give 8-acetyl-2-ethylsulfanyl-3,6-dimethyl-chromen-4-one as a solid (yield: 57%). MS ES+ m/z 277 [M+H]+.

Intermediate 11: 8-(1-Bromoethyl)-2-ethylsulfanyl-3,6-dimethyl-chromen-4-one

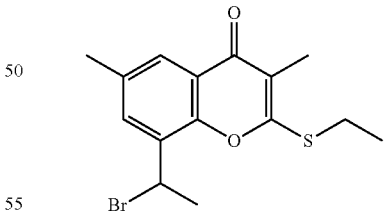

Step 1: 2-ethylsulfanyl-8-(1-hydroxyethyl)-3,6-dimethyl-chromen-4-one. Prepared in the same manner as 2-ethylsulfanyl-8-(1-hydroxyethyl)-6-methyl-chromen-4-one to give the product as a solid (yield: 61%). MS ES+ m/z 278 [M+H]+.

Step 2: 8-(1-bromoethyl)-2-ethylsulfanyl-3,6-dimethyl-chromen-4-one. Prepared in the same manner as 8-(1-bromoethyl)-2-ethylsulfanyl-6-methyl-chromen-4-one to give 8-(1-bromoethyl)-2-ethylsulfanyl-3,6-dimethyl-chromen-4-one as a solid (yield: 95%). MS ES+ m/z 342 [M+H]+.

Intermediate 12: 2-[1-(2-Ethylsulfonyl-6-methyl-4-oxo-chromen-8-yl)ethylamino]benzoic acid

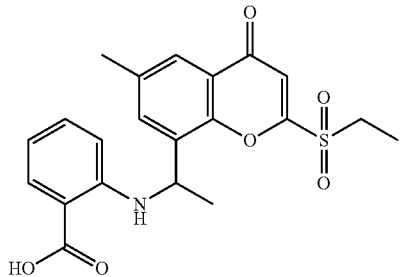 [SMILES: CCS(=O)(=O)c1cc(=O)c2cc(C)cc(C(C)Nc3ccccc3C(=O)O)c2o1]

To a solution of 2-[1-(2-ethylsulfanyl-6-methyl-4-oxo-chromen-8-yl)ethylamino]benzoic acid (199 g, 519 mmol) in DCM (3 L) was added m-CPBA (142 g, 701 mmol, 85% purity) at 0° C., and stirred at rt for 2 h. The mixture was added sat.Na$_2$S$_2$O$_3$ (1000 mL) and extracted with DCM (600 mL×3). The combined organic phase was washed with brine (1000 mL), dried over anhydrous Na$_2$SO$_4$, filtered and concentrated. The residue was purified by column chromatography on silica gel (PE to PE:EtOAc=1:1 to DCM:EtOAc=2:1) to give 2-[1-(2-ethylsulfonyl-6-methyl-4-oxo-chromen-8-yl)ethylamino]benzoic acid as a solid (70 g, crude). MS ES+ m/z 438 [M+Na].

Intermediate 13: Methyl 2-[1-(2-ethylsulfonyl-6-methyl-4-oxo-chromen-8-yl)ethylamino]benzoate

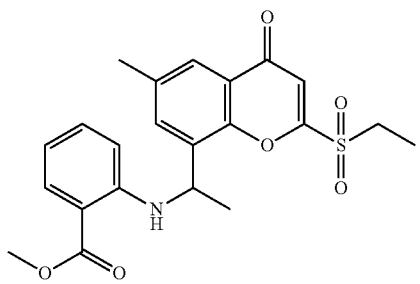 [SMILES: CCS(=O)(=O)c1cc(=O)c2cc(C)cc(C(C)Nc3ccccc3C(=O)OC)c2o1]

To a solution of methyl 2-[1-(2-ethylsulfanyl-6-methyl-4-oxo-chromen-8-yl)ethylamino]benzoate (1.0 g, 2.5 mmol) in DCM (10 mL) was added m-CPBA (1.3 g, 6.4 mmol, 85% purity) at 0° C., and stirred at rt for 16 h. The mixture was quenched with sat.Na$_2$S$_2$O$_3$ (10 mL), the aqueous layer was extracted with DCM (20 mL×3). The combined organic phase was washed with brine (20 mL), dried over anhydrous Na$_2$SO$_4$, filtered and concentrated. The residue was purified by column chromatography on silica gel (PE:EtOAc=1:0 to 1:1, then DCM:EtOAc=2:1) to give methyl 2-[1-(2-ethylsulfonyl-6-methyl-4-oxo-chromen-8-yl)ethylamino]benzoate as a solid (650 mg, yield: 65%).

Intermediate 14: 8-[(1R)-1-Aminoethyl]-2-(4,4-dimethyl-1-piperidyl)-6-methyl-chromen-4-one

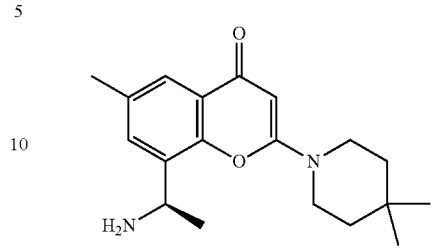

Step 1: 8-acetyl-2-ethylsulfonyl-6-methyl-chromen-4-one. To a mixture of 8-acetyl-2-ethylsulfanyl-6-methyl-chromen-4-one (10.0 g, 38.1 mmol) in DCM (100 mL) was added m-CPBA (23.2 g, 114 mmol, 85% purity) at 0° C., and stirred at 25° C. for 16 h. The mixture was cooled to −10° C. and filtrated, the filter cake was washed with DCM (100 mL×2). The filtrate was diluted with sat.Na$_2$S$_2$O$_3$ (150 mL), the aqueous layer was extracted with DCM (100 mL×3). The combined extracts were washed with sat.NaHCO$_3$ (100 mL×3), brine (200 mL), dried over anhydrous Na$_2$SO$_4$, filtrated and concentrated to give the product as a solid (11.3 g, crude). MS ES+ m/z 295 [M+H]$^+$.

Step 2: 8-acetyl-2-(4,4-dimethyl-1-piperidyl)-6-methyl-chromen-4-one. To a mixture of 8-acetyl-2-ethylsulfonyl-6-methyl-chromen-4-one (10.3 g, 35.0 mmol) and 4,4-dimethylpiperidine (6.28 g, 42.0 mmol, HCl salt) in DCM (100 mL) was added DIEA (22.6 g, 175 mmol) at 0° C., and stirred at rt for 16 h. The reaction mixture was diluted with H$_2$O (100 mL), the aqueous layer was extracted with DCM (100 mL×3). The combined extracts were washed with HCl (1 M, 100 mL) and brine (100 mL), dried over anhydrous Na$_2$SO$_4$, filtrated and concentrated to give the product as a solid (11 g, crude). MS ES+ m/z 314 [M+H]$^+$.

Step 3: (NE,R)—N-[1-[2-(4,4-dimethyl-1-piperidyl)-6-methyl-4-oxo-chromen-8-yl]ethylidene]-2-methyl-propane-2-sulfinamide. To a mixture of 8-acetyl-2-(4,4-dimethyl-1-piperidyl)-6-methyl-chromen-4-one (11.0 g, 35.1 mmol) and (R)-2-methylpropane-2-sulfinamide (8.51 g, 70.2 mmol) in THF (100 mL) was added Ti(i-PrO)$_4$ (39.9 g, 140 mmol), and stirred at 75° C. for 16 h. When cooled to rt, the mixture was quenched with brine (200 mL), stirred for 0.5 h and filtered. The filter cake was washed with EtOAc (300 mL). The aqueous layer was extracted with EtOAc (300 mL×2). The combined extracts were washed with brine (200 mL), dried over anhydrous Na$_2$SO$_4$, filtered and concentrated to give the product as a solid (13 g, crude). MS ES+ m/z 417 [M+H]$^+$.

Step 4: (R)—N-[(1R)-1-[2-(4,4-dimethyl-1-piperidyl)-6-methyl-4-oxo-chromen-8-yl]ethyl]-2-methyl-propane-2-sulfinamide. To a mixture of (NE,R)—N-[1-[2-(4,4-dimethyl-1-piperidyl)-6-methyl-4-oxo-chromen-8-yl]ethylidene]-2-methyl-propane-2-sulfinamide (13.0 g, 31.2 mmol) and CeCl$_3$.7H$_2$O (5.81 g, 15.6 mmol) in MeOH (120 mL) was added NaBH$_4$ (2.36 g, 62.4 mmol) in portions at −78° C., and stirred at 20° C. for 16 h. The reaction mixture was quenched with sat.NH$_4$Cl (200 mL) and filtered. The filter cake was washed with DCM (500 mL). The aqueous layer was extracted with DCM (300 mL×2). The combined extracts were washed with brine (300 mL), dried over anhydrous Na$_2$SO$_4$, filtered and concentrated. The residue was purified by preparative HPLC to give the product as a solid (3.8 g, yield: 27%). MS ES+ m/z 419 [M+H]$^+$.

Step 5: 8-[(1R)-1-aminoethyl]-2-(4,4-dimethyl-1-piperidyl)-6-methyl-chromen-4-one. To a mixture of (R)—N-[(1R)-1-[2-(4,4-dimethyl-1-piperidyl)-6-methyl-4-oxo-chromen-8-yl]ethyl]-2-methyl-propane-2-sulfinamide (3.8 g, 9.08 mmol) in EtOAc (30 mL) was added HCl (8.65 mL, 4 M in EtOAc), and stirred at rt for 16 h. The reaction mixture was diluted with H₂O (50 mL) and washed with EtOAc (50 mL×2). The aqueous phase was adjusted to pH=12 with aq.NH₃.H₂O (25%) and extracted with DCM (50 mL×2). The combined extracts were washed with brine (30 mL), dried over anhydrous Na₂SO₄, filtered and concentrated to give 8-[(1R)-1-aminoethyl]-2-(4,4-dimethyl-1-piperidyl)-6-methyl-chromen-4-one as a solid (2.2 g, yield: 76%). MS ES+ m/z 315 [M+H]⁺.

Intermediate 15: 8-[(1R)-1-Aminoethyl]-2-(5-fluoroisoindolin-2-yl)-6-methyl-chromen-4-one

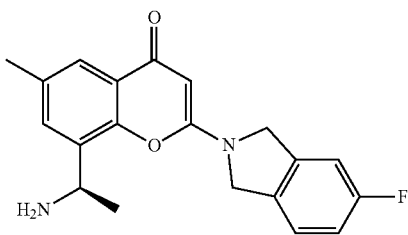 [SMILES: Cc1cc([C@@H](C)N)c2oc(N3Cc4ccc(F)cc4C3)cc(=O)c2c1]

Step 1: 8-acetyl-2-(5-fluoroisoindolin-2-yl)-6-methyl-chromen-4-one. Prepared in the same manner as 8-acetyl-2-(4,4-dimethyl-1-piperidyl)-6-methyl-chromen-4-one to give the product as a solid (yield: 87%). MS ES+ m/z 338 [M+H]⁺.

Step 2: (NE,R)—N-[1-[2-(5-fluoroisoindolin-2-yl)-6-methyl-4-oxo-chromen-8-yl]ethylidene]-2-methyl-propane-2-sulfinamide. Prepared in the same manner as (NE,R)—N-[1-[2-(4,4-dimethyl-1-piperidyl)-6-methyl-4-oxo-chromen-8-yl]ethylidene]-2-methyl-propane-2-sulfinamide to give the product as oil (crude). MS ES+ m/z 441 [M+H]⁺.

Step 3: (R)—N-[(1R)-1-[2-(5-fluoroisoindolin-2-yl)-6-methyl-4-oxo-chromen-8-yl]ethyl]-2-methyl-propane-2-sulfinamide. Prepared in the same manner as (R)—N-[(1R)-1-[2-(4,4-dimethyl-1-piperidyl)-6-methyl-4-oxo-chromen-8-yl]ethyl]-2-methyl-propane-2-sulfinamide to give the product as a solid (yield: 31%). MS ES+ m/z 443 [M+H]⁺.

Step 4: 8-[(1R)-1-aminoethyl]-2-(5-fluoroisoindolin-2-yl)-6-methyl-chromen-4-one. Prepared in the same manner as 8-[(1R)-1-aminoethyl]-2-(4,4-dimethyl-1-piperidyl)-6-methyl-chromen-4-one to give 8-[(1R)-1-aminoethyl]-2-(5-fluoroisoindolin-2-yl)-6-methyl-chromen-4-one as yellow oil (crude). MS ES+ m/z 339 [M+H]⁺.

Intermediate 16: Methyl 2-[1-(2-ethylsulfinyl-3,6-dimethyl-4-oxo-chromen-8-yl)ethylamino]benzoate

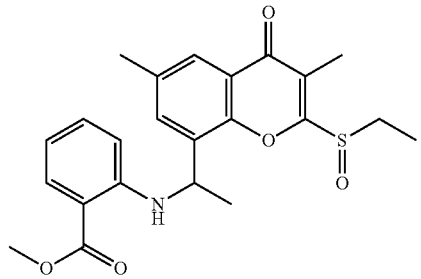 [SMILES: CCS(=O)c1oc2c(C(C)Nc3ccccc3C(=O)OC)cc(C)cc2c(=O)c1C]

Step 1: methyl 2-[1-(2-ethylsulfanyl-3,6-dimethyl-4-oxo-chromen-8-yl)ethylamino]benzoate. To a mixture of 8-(1-bromoethyl)-2-ethylsulfanyl-3,6-dimethyl-chromen-4-one (780 mg, 2.29 mmol) in DMF (10 mL) was added methyl 2-aminobenzoate (691 mg, 4.57 mmol), and stirred at 80° C. for 16 h. The reaction mixture was diluted with H₂O (30 mL), extracted with EtOAc (40 mL×3), washed with brine (40 mL×3), dried over anhydrous Na₂SO₄, filtered and concentrated. The residue was purified by flash silica gel chromatography eluent of 0~15% EtOAc in petroleum ether to give the product as a solid (940 mg, yield: 93%). MS ES+ m/z 412 [M+H]⁺.

Step 2: methyl 2-[1-(2-ethylsulfinyl-3,6-dimethyl-4-oxo-chromen-8-yl)ethylamino]benzoate. To a mixture of methyl 2-[1-(2-ethylsulfanyl-3,6-dimethyl-4-oxo-chromen-8-yl)ethylamino]benzoate (940 mg, 2.28 mmol) in DCM (10 mL) was added m-CPBA (557 mg, 2.74 mmol, 85% purity) at 0° C., and stirred at 25° C. for 15 h. The mixture was quenched with sat.Na₂SO₃ (30 mL), extracted with DCM (30 mL×3), washed with sat.NaHCO₃ (50 mL×2), dried over anhydrous Na₂SO₄, filtered and concentrated. The residue was purified by silica gel chromatography eluted with 0%-35% EtOAc in petroleum ether to give methyl 2-[1-(2-ethylsulfinyl-3,6-dimethyl-4-oxo-chromen-8-yl)ethylamino]benzoate as a solid (760 mg, yield: 78%). MS ES+ m/z 428 [M+H]⁺.

Intermediate 17: 2-[1-(2-Ethylsulfinyl-3,6-dimethyl-4-oxo-chromen-8-yl)ethylamino]benzoic acid

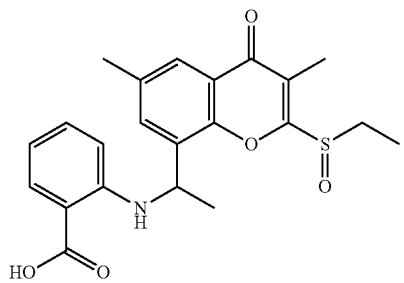

Step 1: 2-[1-(2-ethylsulfanyl-3,6-dimethyl-4-oxo-chromen-8-yl)ethylamino]benzoic acid. A mixture of 8-(1-bromoethyl)-2-ethylsulfanyl-3,6-dimethyl-chromen-4-one (37.0 g, 108 mmol) and 2-aminobenzoic acid (29.7 g, 216 mmol) in DMF (300 mL) was stirred at 80° C. for 16 h. The mixture was diluted with H₂O (400 mL), adjusted to pH=12 with NaOH (2 M) and washed with MTBE (200 mL×2). The aqueous layer was adjusted to pH=2 with HCl (2 M) to give a white solid and filtered. The filter cake was dried in vacuum to give the product as a solid (51 g, crude). MS ES+ m/z 398 [M+H]⁺.

Step 2: 2-[1-(2-ethylsulfinyl-3,6-dimethyl-4-oxo-chromen-8-yl)ethylamino]benzoic acid. To a mixture of 2-[1-(2-ethylsulfanyl-3,6-dimethyl-4-oxo-chromen-8-yl)ethylamino]benzoic acid (46.0 g, 116 mmol) in DCM (300 mL) was added m-CPBA (58.7 g, 289 mmol, 85% purity) at 0° C., and stirred at 25° C. for 2 h. The mixture was quenched with sat.Na₂S₂O₃ (400 mL) and extracted with DCM (300 mL×3). The combined organic phase was washed with brine (300 mL), dried over anhydrous Na₂SO₄, filtered and concentrated. The residue was purified by silica gel chromatography eluted with 0%-3% MeOH in DCM to give 2-[1-(2-ethylsulfinyl-3,6-dimethyl-4-oxo-chromen-8-yl)ethylamino]benzoic acid as oil (24 g, crude). MS ES+ m/z 414 [M+H]⁺.

Intermediate 18: 2-[[(1R)-1-(2-Ethylsulfinyl-3,6-dimethyl-4-oxo-chromen-8-yl)ethyl]amino]benzoic acid

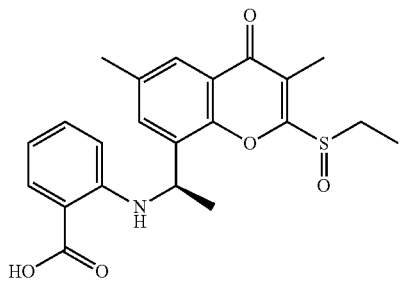 [SMILES: CCS(=O)c1oc2c([C@@H](C)Nc3ccccc3C(=O)O)cc(C)cc2c(=O)c1C]

Step 1: (NE,R)—N-[1-(2-ethylsulfanyl-3,6-dimethyl-4-oxo-chromen-8-yl)ethylidene]-2-methyl-propane-2-sulfinamide. Prepared in the same manner as (NE,R)—N-[1-[2-(4,4-dimethyl-1-piperidyl)-6-methyl-4-oxo-chromen-8-yl]ethylidene]-2-methyl-propane-2-sulfinamide to give the product as a yellow oil (crude). MS ES+ m/z 380 [M+H]⁺.

Step 2: (R)—N-[(1R)-1-(2-ethylsulfanyl-3,6-dimethyl-4-oxo-chromen-8-yl)ethyl]-2-methyl-propane-2-sulfinamide. To a mixture of (NE,R)—N-[1-(2-ethylsulfanyl-3,6-dimethyl-4-oxo-chromen-8-yl)ethylidene]-2-methyl-propane-2-sulfinamide (100 g, 179 mmol) and CeCl₃.7H₂O (33.3 g, 89.5 mmol) in MeOH (500 mL) was added NaBH₄ (13.5 g, 358. mmol) at −70° C. under N₂, then the mixture was warmed up to 25° C. slowly and stirred for 16 h. The residue was triturated with EtOAc (400 mL). The mixture was filtered, the filtrate was concentrated under reduced pressure to give a residue. This was recrystallized by adding 200 mL EtOAc to obtain a filtrate, which was concentrated to give the product as yellow oil (30 g, yield: 33%). MS ES+ m/z 382 [M+H]⁺.

Step 3: 8-[(1R)-1-aminoethyl]-2-ethylsulfanyl-3,6-dimethyl-chromen-4-one. Prepared in the same manner as 8-[(1R)-1-aminoethyl]-2-(4,4-dimethyl-1-piperidyl)-6-methyl-chromen-4-one to give the product as a yellow solid (7.8 g, yield: 78%, ee: 97.57%). MS ES+ m/z 278 [M+H]⁺.

Step 4: 2-[[(1R)-1-(2-ethylsulfanyl-3,6-dimethyl-4-oxo-chromen-8-yl)ethyl]amino]benzoic acid. The mixture of 8-[(1R)-1-aminoethyl]-2-ethylsulfanyl-3,6-dimethyl-chromen-4-one (6.44 g, 23.2 mmol), 2-iodobenzoic acid (8.64 g, 34.8 mmol), N,N-diethylethanamine (4.70 g, 46.4 mmol) and copper (885 mg, 13.9 mmol) in dimethylacetamide (120 mL) was stirred at 110° C. for 3 h. The mixture was added H₂O (400 mL) and adjusted pH to 12 with NaOH (aq., 2M), let stand for 10 minutes to filter and wash the filtrate with EtOAc (200 mL), the mixture was adjusted pH to 2 with HCl (aq., 2M), the mixture was filtered and concentrated to give the product as yellow oil (8 g, crude). MS ES+ m/z 398 [M+H]⁺.

Step 5: 2-[[(1R)-1-(2-ethylsulfinyl-3,6-dimethyl-4-oxo-chromen-8-yl)ethyl]amino]benzoic acid. To a mixture of 2-[[(1R)-1-(2-ethylsulfanyl-3,6-dimethyl-4-oxo-chromen-8-yl)ethyl]amino]benzoic acid (8.00 g, 14.8 mmol) in DCM (80 mL) was added m-CPBA (3.02 g, 14.8 mmol) at 0° C., then the mixture was stirred at 25° C. for 1 h. The mixture was added with sat.Na₂S₂O₃ (100 mL) and extracted with DCM (100 mL×3). The combined organic phase was washed with brine (100 mL), dried with anhydrous Na₂SO₄, filtered and concentrated in vacuum to give 2-[[(1R)-1-(2-ethylsulfinyl-3,6-dimethyl-4-oxo-chromen-8-yl)ethyl]amino]benzoic acid as yellow oil (9 g, crude). MS ES+ m/z 414 [M+H]⁺.

Intermediate 19: 8-(1-Bromoethyl)-2-(5-fluoroisoindolin-2-yl)-6-methyl-chromen-4-one

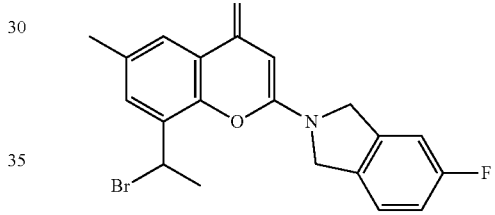

Step 1: 8-bromo-2-(5-fluoroisoindolin-2-yl)-6-methyl-chromen-4-one. A mixture of 5-fluoroisoindoline; hydrochloride (2.00 g, 9.52 mmol, HCl salt) and DIPEA (3.28 g, 25.4 mmol, 4.42 mL) in DCM (10 mL) was added dropwise to a stirred solution of 8-bromo-2-ethylsulfonyl-6-methyl-chromen-4-one (2 g, 6.35 mmol) in DCM (10 mL) at 10° C. under N₂ atmosphere. The resulting solution was stirred at 45° C. for 16 h. The reaction mixture was diluted with water (40 mL) and extracted with DCM (50 mL×2). The combined organic layer was washed with brine (50 mL×2), dried over anhydrous Na₂SO₄, filtered and concentrated. The residue was triturated with 20% EtOAc in petroleum ether (60 mL) to give the product as a solid (2.37 g, crude). MS ES+ m/z 374 [M+H]⁺.

Step 2: 8-acetyl-2-(5-fluoroisoindolin-2-yl)-6-methyl-chromen-4-one. A mixture of 8-bromo-2-(5-fluoroisoindolin-2-yl)-6-methyl-chromen-4-one (1.67 g, 4.46 mmol) in dioxane (30 mL) was added Pd(PPh₃)₂Cl₂ (313 mg, 0.446 mmol) and tributyl(1-ethoxyvinyl)stannane (1.93 g, 5.36 mmol) under N₂ atmosphere, and stirred at 95° C. for 16 h. The reaction was added HCl (1 M, 2.23 mL) and stirred at 50° C. for 0.5 h. When cooled to rt, the mixture was added sat. KF (50 mL), stirred for 0.5 h and filtered. The filtrate was extracted with DCM (50 mL×2). The combined organic layer was washed with brine (7 mL×2), dried over anhydrous Na₂SO₄, filtered and concentrated. The residue was purified by a silica gel chromatography eluted with 0-5% MeOH in DCM to give the product as a solid (2 g, crude). MS ES+ m/z 337.9 [M+H]⁺.

Step 3: 2-(5-fluoroisoindolin-2-yl)-8-(1-hydroxyethyl)-6-methyl-chromen-4-one. A mixture of 8-acetyl-2-(5-fluoroisoindolin-2-yl)-6-methyl-chromen-4-one (1.50 g, 4.45 mmol) in DCM (15 mL) and MeOH (10 mL) was added NaBH$_4$ (185 mg, 4.89 mmol) at 0° C., and stirred at 25° C. for 1 h. The mixture was diluted with water (40 mL), extracted with a DCM/MeOH=10:1 (100 mL×4). The combined extracts were washed with brine (200 mL), dried over anhydrous Na$_2$SO$_4$, filtered and concentrated. The residue was purified by silica gel column eluted with 0-4% MeOH in DCM to give the product as a solid (1.3 g, yield: 86%). MS ES+ m/z 340 [M+H]$^+$.

Step 4: 8-(1-bromoethyl)-2-(5-fluoroisoindolin-2-yl)-6-methyl-chromen-4-one. To a mixture of 2-(5-fluoroisoindolin-2-yl)-8-(1-hydroxyethyl)-6-methyl-chromen-4-one (1.10 g, 3.24 mmol) in DCM (30 mL) was added PBr$_3$ (2.63 g, 9.72 mmol) dropwise at 0° C., then warmed to 25° C. and stirred for 14 h. The reaction mixture was added water (20 mL) at 0° C. and adjusted to pH=8 with sat.NaHCO$_3$. The mixture was extracted with a DCM/MeOH=10:1 (110 mL×2). The combined organic layer was washed with brine (60 mL), dried over anhydrous Na$_2$SO$_4$, filtered and concentrated to give 8-(1-bromoethyl)-2-(5-fluoroisoindolin-2-yl)-6-methyl-chromen-4-one as a solid (1 g, yield: 67%). MS ES+ m/z 402 [M+H]$^+$.

Intermediate 20: 6-Chloro-3-[1-(2-ethylsulfinyl-6-methyl-4-oxo-chromen-8-yl)ethylamino]pyridine-2-carboxylic acid

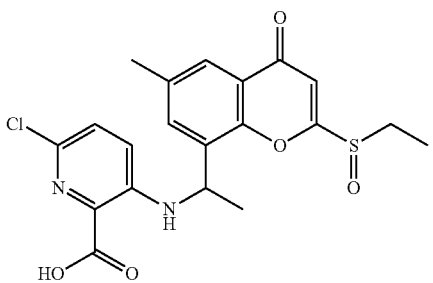 [SMILES: CCS(=O)c1cc(=O)c2cc(C)cc(C(C)Nc3ccc(Cl)nc3C(=O)O)c2o1]

Step 1: (NE,R)—N-[1-(2-ethylsulfanyl-6-methyl-4-oxo-chromen-8-yl)ethylidene]-2-methyl-propane-2-sulfinamide. To a mixture of 8-acetyl-2-ethylsulfanyl-6-methyl-chromen-4-one (9.49 g, 36.2 mmol) and (R)-2-methylpropane-2-sulfinamide (8.77 g, 72.4 mmol) in THF (100 mL) was added Ti(i-PrO)$_4$ (41.1 g, 145 mmol), and stirred at 75° C. for 16 h. The reaction was added (R)-2-methylpropane-2-sulfinamide (6.58 g, 54.3 mmol) and Ti(i-PrO)$_4$ (30.9 g, 109 mmol) and stirred at 75° C. for another 16 h. The mixture was added brine (200 mL), stirred for 0.5 h and filtered. The filter cake was washed with EtOAc (300 mL). The aqueous layer was extracted with EtOAc (300 mL×2). The combined extracts were washed with brine (200 mL×2), dried over anhydrous Na$_2$SO$_4$, filtered and concentrated to give the product as a solid (13 g, crude). MS ES+ m/z 366 [M+H]$^+$.

Step 2: (R)—N-[(1R)-1-(2-ethylsulfanyl-6-methyl-4-oxo-chromen-8-yl)ethyl]-2-methyl-propane-2-sulfinamide. To a mixture of (NE,R)—N-[1-(2-ethylsulfanyl-6-methyl-4-oxo-chromen-8-yl)ethylidene]-2-methyl-propane-2-sulfinamide (12.0 g, 32.8 mmol) in DCM (100 mL) and MeOH (100 mL) was added AcOH (15.8 g, 262 mmol) and NaBH$_3$CN (6.19 g, 98.5 mmol) at -10° C., and stirred at 25° C. for 16 h. The mixture was quenched with NH$_3$H$_2$O (250 mL), extracted with DCM (200 mL×3). The combined extracts were washed with brine (300 mL), dried over anhydrous Na$_2$SO$_4$, filtered and concentrated to give the product as a solid (11 g, isomer ratio: 3/2, crude). MS ES+ m/z 368 [M+H]$^+$.

Step 3: 8-(1-aminoethyl)-2-ethylsulfanyl-6-methyl-chromen-4-one. To a mixture of (R)—N-[(1R)-1-(2-ethylsulfanyl-3,6-dimethyl-4-oxo-chromen-8-yl)ethyl]-2-methyl-propane-2-sulfinamide (6.00 g, 16.3 mmol) in EtOAc (40 mL) was added HCl (82 mL, 4 M in EtOAc), and stirred at 25° C. for 16 h. The mixture was concentrated, diluted with H$_2$O (100 mL) and washed with EtOAc (100 mL). The aqueous phase was adjusted to pH=8 with NH$_3$.H$_2$O (25%) and extracted with DCM (100 mL×3). The combined organic phase was washed with brine (100 mL), dried over anhydrous Na$_2$SO$_4$, filtered and concentrated to give the product as oil (2.4 g, crude). MS ES+m/z 264 [M+H]$^+$.

Step 4: 6-chloro-3-[1-(2-ethylsulfanyl-6-methyl-4-oxo-chromen-8-yl)ethylamino]pyridine-2-carboxylic acid. A mixture of 8-(1-aminoethyl)-2-ethylsulfanyl-6-methyl-chromen-4-one (2.70 g, 10.3 mmol) and 6-chloro-3-fluoro-pyridine-2-carboxylic acid (3.60 g, 20.5 mmol) in DMSO (10 mL) was stirred at 120° C. for 17 h. The mixture was added 6-chloro-3-fluoro-pyridine-2-carboxylic acid (900 mg, 5.13 mmol) and stirred at 120° C. for another 3 h. When cooled to rt, the mixture was poured into water (30 mL), adjusted to pH=2 with HCl (1M) and extracted with DCM (30 mL×3). The combined organic layer was washed with brine (40 mL×3), dried over anhydrous Na$_2$SO$_4$, filtered and concentrated. The residue was purified by silica gel chromatography eluted with 0%-87% EtOAc:DCM=2:1 in petroleum ether to give the product as a gum (710 mg, yield: 12%). MS ES+ m/z 419 [M+H]$^+$.

Step 5: 6-chloro-3-[1-(2-ethylsulfinyl-6-methyl-4-oxo-chromen-8-yl)ethylamino]pyridine-2-carboxylic acid. A mixture of 6-chloro-3-[1-(2-ethylsulfanyl-6-methyl-4-oxo-chromen-8-yl)ethylamino]pyridine-2-carboxylic acid (710 mg, 1.69 mmol) in DCM (10 mL) was added m-CPBA (475 mg, 2.20 mmol) at 0° C., and stirred at 25° C. for 2 h. The mixture was added m-CPBA (110 mg, 0.508 mmol) and stirred at 25° C. for another 2 h. The reaction mixture was quenched with sat.Na$_2$S$_2$O$_3$ (40 mL) and extracted with DCM (40 mL×3). The combined organic phase was washed with brine (40 mL), dried over anhydrous Na$_2$SO$_4$, filtered and concentrated. The residue was purified by silica gel chromatography eluted with 0%-6% MeOH in dichloromethane to give 6-chloro-3-[1-(2-ethylsulfinyl-6-methyl-4-oxo-chromen-8-yl)ethylamino]pyridine-2-carboxylic acid as a solid (620 mg, yield: 54%). MS ES+ m/z 319 [M+H]$^+$.

Intermediate 21: Methyl 6-chloro-3-[[(1R)-1-(2-ethylsulfinyl-6-methyl-4-oxo-chromen-8-yl)ethyl]amino]pyridine-2-carboxylate

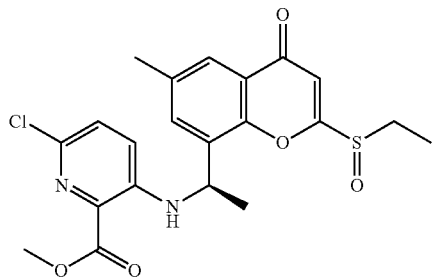 [SMILES: CCS(=O)c1cc(=O)c2cc(C)cc([C@@H](C)Nc3ccc(Cl)nc3C(=O)OC)c2o1]

Step 1: (R)—N-[(1R)-1-(2-ethylsulfanyl-6-methyl-4-oxo-chromen-8-yl)ethyl]-2-methyl-propane-2-sulfinamide. Prepared in the same manner as (R)—N-[(1R)-1-(2-ethylsulfanyl-6-methyl-4-oxo-chromen-8-yl)ethyl]-2-methyl-propane-2-sulfinamide (Intermediate 20, Step 2) to give the product as brown gum (18.8 g, isomer ratio: 3/2, crude). The crude product was purified by preparative HPLC to give the product as oil (5.33 g, yield: 17%). MS ES+ m/z 368 [M+H]+.

Step 2: 8-[(1R)-1-aminoethyl]-2-ethylsulfanyl-6-methyl-chromen-4-one. Prepared in the same manner as 8-(1-aminoethyl)-2-ethylsulfanyl-6-methyl-chromen-4-one to give the product as a solid (yield: 87%). MS ES+ m/z 264 [M+H]+.

Step 3: methyl 6-chloro-3-[[(1R)-1-(2-ethylsulfanyl-6-methyl-4-oxo-chromen-8-yl)ethyl]amino]pyridine-2-carboxylate. A mixture of 8-[(1R)-1-aminoethyl]-2-ethylsulfanyl-6-methyl-chromen-4-one (880 mg, 3.34 mmol), methyl 6-chloro-3-fluoro-pyridine-2-carboxylate (950 mg, 5.01 mmol) and DIEA (2.16 g, 16.7 mmol) in DMF (10 mL) was stirred at 100° C. for 21 h. The mixture was diluted with water (30 mL) and extracted with EtOAc (30 mL×2). The combined extracts were washed with brine (10 mL), dried over anhydrous Na$_2$SO$_4$, filtered and concentrated. The residue was purified by silica gel chromatography eluted with 0%-35% EtOAc in petroleum ether to give the product as a solid (1.08 g, yield: 75%). MS ES+ m/z 433 [M+H]+.

Step 4: methyl 6-chloro-3-[[(1R)-1-(2-ethylsulfinyl-6-methyl-4-oxo-chromen-8-yl)ethyl]amino]pyridine-2-carboxylate. A mixture of methyl 6-chloro-3-[[(1R)-1-(2-ethylsulfanyl-6-methyl-4-oxo-chromen-8-yl)ethyl]amino]pyridine-2-carboxylate (0.98 g, 2.26 mmol) in DCM (10 mL) was added m-CPBA (597 mg, 2.94 mmol, 85% purity) at 0° C., and stirred at 10° C. for 2 h. The mixture was added m-CPBA (46.0 mg, 0.226 mmol, 85% purity) and stirred at 25° C. for another 18 h. The mixture was added m-CPBA (46.0 mg, 0.226 mmol, 85% purity) and stirred at 25° C. for another 1 h. The mixture was quenched with sat.Na$_2$S$_2$O$_3$ (50 mL) and extracted with DCM (40 mL×3). The combined organic phase was washed with brine (50 mL), dried over anhydrous Na$_2$SO$_4$, filtered and concentrated. The residue was purified by silica gel chromatography eluted with 0%-60% EtOAc in petroleum ether to give methyl 6-chloro-3-[[(1R)-1-(2-ethylsulfinyl-6-methyl-4-oxo-chromen-8-yl)ethyl]amino]pyridine-2-carboxylate as a solid (600 mg, yield: 59%). MS ES+ m/z 449 [M+H]+.

Intermediate 22: 6-Chloro-3-[1-(2-ethylsulfinyl-3,6-dimethyl-4-oxo-chromen-8-yl)ethylamino]pyridine-2-carboxylic acid

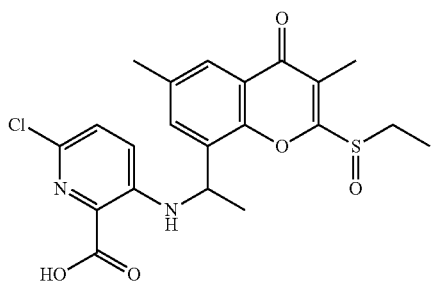 [SMILES: CCS(=O)c1oc2c(C(C)Nc3ccc(Cl)nc3C(=O)O)cc(C)cc2c(=O)c1C]

Step 1: (NE,R)—N-[1-(2-ethylsulfanyl-3,6-dimethyl-4-oxo-chromen-8-yl)ethylidene]-2-methyl-propane-2-sulfinamide. Prepared in the same manner as (NE,R)—N-[1-(2-ethylsulfanyl-6-methyl-4-oxo-chromen-8-yl)ethylidene]-2-methyl-propane-2-sulfinamide to give the product as a solid (crude).

Step 2: (R)—N-[(1R)-1-(2-ethylsulfanyl-3,6-dimethyl-4-oxo-chromen-8-yl)ethyl]-2-methyl-propane-2-sulfinamide. Prepared in the same manner as (R)—N-[(1R)-1-(2-ethylsulfanyl-6-methyl-4-oxo-chromen-8-yl)ethyl]-2-methyl-propane-2-sulfinamide to give the product as a solid (crude, isomer ratio: 3/1). MS ES+ m/z 398 [M+H]+.

Step 3: 8-(1-aminoethyl)-2-ethylsulfanyl-3,6-dimethyl-chromen-4-one. Prepared in the same manner as 8-(1-aminoethyl)-2-ethylsulfanyl-6-methyl-chromen-4-one to give the product as a solid (yield: 69%). MS ES+ m/z 294 [M+H]+.

Step 4: 6-chloro-3-[1-(2-ethylsulfanyl-3,6-dimethyl-4-oxo-chromen-8-yl)ethylamino]pyridine-2-carboxylic acid. Prepared in the same manner as 6-chloro-3-[1-(2-ethylsulfanyl-6-methyl-4-oxo-chromen-8-yl)ethylamino]pyridine-2-carboxylic acid to give the product as a solid (yield: 39%). MS ES+ m/z 433 [M+H]+.

Step 5: 6-chloro-3-[1-(2-ethylsulfinyl-3,6-dimethyl-4-oxo-chromen-8-yl)ethylamino]pyridine-2-carboxylic acid. Prepared in the same manner as 6-chloro-3-[1-(2-ethylsulfinyl-6-methyl-4-oxo-chromen-8-yl)ethylamino]pyridine-2-carboxylic acid to give 6-chloro-3-[1-(2-ethylsulfinyl-3,6-dimethyl-4-oxo-chromen-8-yl)ethylamino]pyridine-2-carboxylic acid as a solid (yield: 89%). MS ES+ m/z 449 [M+H]+.

Intermediate 23: Methyl 6-chloro-3-[[(1R)-1-(2-ethylsulfinyl-3,6-dimethyl-4-oxo-chromen-8-yl)ethyl]amino]pyridine-2-carboxylate

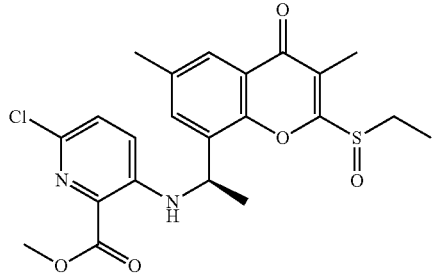 [SMILES: CCS(=O)c1oc2c([C@@H](C)Nc3ccc(Cl)nc3C(=O)OC)cc(C)cc2c(=O)c1C]

Step 1: (R)—N-[(1R)-1-(2-ethylsulfanyl-3,6-dimethyl-4-oxo-chromen-8-yl)ethyl]-2-methyl-propane-2-sulfinamide. Prepared in the same manner as (R)—N-[(1R)-1-(2-ethylsulfanyl-6-methyl-4-oxo-chromen-8-yl)ethyl]-2-methyl-propane-2-sulfinamide to give the product as a yellow solid (crude, isomer ratio: 3/1). The crude product (6 g) was purified by preparative HPLC to give the product as a solid (yield: 63%, de: 94.8%). MS ES+ m/z 382 [M+H]+.

Step 2: 8-[(1R)-1-aminoethyl]-2-ethylsulfanyl-3,6-dimethyl-chromen-4-one. Prepared in the same manner as 8-(1-aminoethyl)-2-ethylsulfanyl-6-methyl-chromen-4-one to give the product as a solid (yield: 99%, ee: 98%). MS ES+ m/z 278 [M+H]+.

Step 3: methyl 6-chloro-3-[[(1R)-1-(2-ethylsulfanyl-3,6-dimethyl-4-oxo-chromen-8-yl)ethyl]amino]pyridine-2-carboxylate. Prepared in the same manner as methyl 6-chloro-3-[[(1R)-1-(2-ethylsulfanyl-6-methyl-4-oxo-chromen-8-yl)ethyl]amino]pyridine-2-carboxylate to give the product as a solid (3 g, yield: 96%, ee: 97%). MS ES+ m/z 447 [M+H]+.

Step 4: methyl 6-chloro-3-[[(1R)-1-(2-ethylsulfinyl-3,6-dimethyl-4-oxo-chromen-8-yl)ethyl]amino]pyridine-2-carboxylate. Prepared in the same manner as methyl 6-chloro-3-[[(1R)-1-(2-ethylsulfinyl-6-methyl-4-oxo-chromen-8-yl)ethyl]amino]pyridine-2-carboxylate to give methyl 6-chloro-3-[[(1R)-1-(2-ethylsulfinyl-3,6-dimethyl-4-oxo-chromen-8-yl)ethyl]amino]pyridine-2-carboxylate as a solid (yield: 90%). MS ES+ m/z 463 [M+H]+.

Intermediate 24: 2-[1-(2-Ethylsulfinyl-6-fluoro-4-oxo-chromen-8-yl)ethylamino]benzoic acid

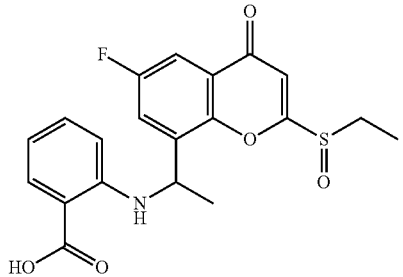 [SMILES: CCS(=O)c1cc(=O)c2cc(F)cc(C(C)Nc3ccccc3C(=O)O)c2o1]

Step 1: (2-bromo-4-fluoro-phenyl) acetate. Prepared in the same manner as 2-bromo-4-methylphenyl acetate to give the product as oil (crude).
Step 2: 1-(3-bromo-5-fluoro-2-hydroxy-phenyl)ethanone. Prepared in the same manner as 1-(3-bromo-2-hydroxy-5-methyl-phenyl)ethanone to give the product as a solid (yield: 79%).
Step 3: 8-bromo-6-fluoro-4-hydroxy-chromene-2-thione. Prepared in the same manner as 8-bromo-4-hydroxy-6-methyl-chromene-2-thione to give the product as a solid (yield: 43%).
Step 4: 8-bromo-2-ethylsulfanyl-6-fluoro-chromen-4-one. Prepared in the same manner as 8-bromo-2-ethylsulfanyl-6-methyl-chromen-4-one to give the product as a solid (yield: 45%). MS ES+ m/z 305 [M+H]+.
Step 5: 8-acetyl-2-ethylsulfanyl-6-fluoro-chromen-4-one. Prepared in the same manner as 8-acetyl-2-ethylsulfanyl-6-methyl-chromen-4-one to give the product as a solid (yield: 36%). MS ES+ m/z 267 [M+H]+.
Step 6: 2-ethylsulfanyl-6-fluoro-8-(1-hydroxyethyl)chromen-4-one. Prepared in the same manner as 2-ethylsulfanyl-8-(1-hydroxyethyl)-6-methyl-chromen-4-one to give the product as a solid (crude). MS ES+ m/z 269 [M+H]+.
Step 7: 8-(1-bromoethyl)-2-ethylsulfanyl-6-fluoro-chromen-4-one. Prepared in the same manner as 8-(1-bromoethyl)-2-ethylsulfanyl-6-methyl-chromen-4-one to give the product as a solid (yield: 35%). MS ES+ m/z 333 [M+H]+.
Step 8: 2-[1-(2-ethylsulfanyl-6-fluoro-4-oxo-chromen-8-yl)ethylamino]benzoic acid. Prepared in the same manner as 2-[1-(2-ethylsulfanyl-6-methyl-4-oxo-chromen-8-yl)ethylamino]benzoic acid to give the product as a solid (yield: 73%). MS ES+ m/z 388 [M+H]+.
Step 9: 2-[1-(2-ethylsulfinyl-6-fluoro-4-oxo-chromen-8-yl)ethylamino]benzoic acid. A mixture of 2-[1-(2-ethylsulfanyl-6-fluoro-4-oxo-chromen-8-yl)ethylamino]benzoic acid (2.80 g, 7.23 mmol) in DCM (30 mL) was added m-CPBA (2.03 g, 9.40 mmol, 85% purity) at 0° C., and stirred at 25° C. for 2 h. The mixture was quenched with sat.Na2S2O3 (50 mL), extracted with DCM (50 mL×3), washed with brine (50 mL), dried over anhydrous Na2SO4, filtered, concentrated. The residue was purified by silica gel chromatography eluted with 0%-70% EtOAc in petroleum ether to give 2-[1-(2-ethylsulfinyl-6-fluoro-4-oxo-chromen-8-yl)ethylamino]benzoic acid as a solid (600 mg, yield: 19%). MS ES+ m/z 404 [M+H]+.

Intermediate 25: 2-[1-(2-Ethylsulfinyl-6-fluoro-3-methyl-4-oxo-chromen-8-yl)ethylamino]benzoic acid

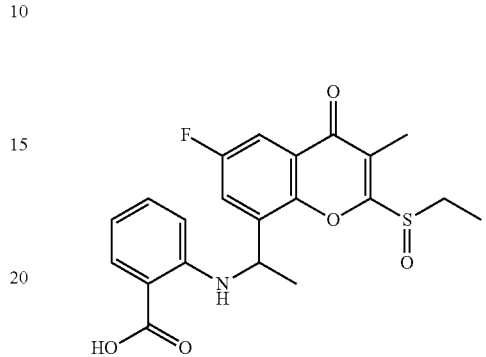

Step 1: (2-bromo-4-fluoro-phenyl) propanoate. Prepared in the same manner as 2-bromo-4-methylphenyl acetate to give the product as oil (crude).
Step 2: 1-(3-bromo-5-fluoro-2-hydroxy-phenyl)propan-1-one. Prepared in the same manner as 1-(3-bromo-2-hydroxy-5-methyl-phenyl)ethanone to give the product as a solid (crude).
Step 3: 8-bromo-6-fluoro-4-hydroxy-3-methyl-chromene-2-thione. Prepared in the same manner as 8-bromo-4-hydroxy-6-methyl-chromene-2-thione to give the product as a solid (yield: 64%).
Step 4: 8-bromo-2-ethylsulfanyl-6-fluoro-3-methyl-chromen-4-one. Prepared in the same manner as 8-bromo-2-ethylsulfanyl-6-methyl-chromen-4-one to give the product as a solid (yield: 45%). MS ES+ m/z 319 [M+H]+.
Step 5: 8-acetyl-2-ethylsulfanyl-6-fluoro-3-methyl-chromen-4-one. Prepared in the same manner as 8-acetyl-2-ethylsulfanyl-6-methyl-chromen-4-one to give the product as a solid (yield: 59%). MS ES+ m/z 281 [M+H]+.
Step 6: 2-ethylsulfanyl-6-fluoro-8-(1-hydroxyethyl)-3-methyl-chromen-4-one. Prepared in the same manner as 2-ethylsulfanyl-8-(1-hydroxyethyl)-6-methyl-chromen-4-one to give the product as a solid (crude). MS ES+ m/z 283 [M+H]+.
Step 7: 8-(1-bromoethyl)-2-ethylsulfanyl-6-fluoro-3-methyl-chromen-4-one. Prepared in the same manner as 8-(1-bromoethyl)-2-ethylsulfanyl-6-methyl-chromen-4-one to give the product as a solid (yield: 81%). MS ES+ m/z 347 [M+H]+.
Step 8: 2-[1-(2-ethylsulfanyl-6-fluoro-3-methyl-4-oxo-chromen-8-yl)ethylamino]benzoic acid. Prepared in the same manner as 2-[1-(2-ethylsulfanyl-6-methyl-4-oxo-chromen-8-yl)ethylamino]benzoic acid to give the product as a solid (yield: 31%). MS ES+ m/z 402 [M+H]+.
Step 9: 2-[1-(2-ethylsulfinyl-6-fluoro-3-methyl-4-oxo-chromen-8-yl)ethylamino]benzoic acid. Prepared in the same manner as 2-[1-(2-ethylsulfinyl-6-fluoro-4-oxo-chromen-8-yl)ethylamino]benzoic acid to give 2-[1-(2-ethylsulfinyl-6-fluoro-3-methyl-4-oxo-chromen-8-yl)ethylamino]benzoic acid as a solid (yield: 66%). MS ES+ m/z 418 [M+H]+.

Intermediate 26: 2-[1-(2-Ethylsulfinyl-4-oxo-chromen-8-yl)ethylamino]benzoic acid

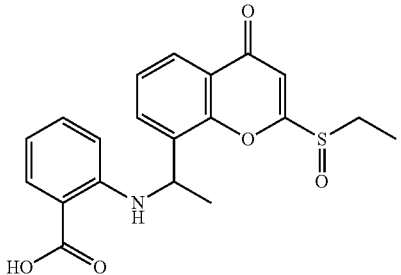

Step 1: 8-bromo-4-hydroxy-chromene-2-thione. A mixture of 1-(3-bromo-2-hydroxy-phenyl) ethanone (19.6 g, 91.1 mmol) and CS$_2$ (8.33 g, 109 mmol) in THF (100 mL) was slowly added to a stirred mixture of t-BuOK (30.7 g, 273 mmol) in THF (100 mL) at 0° C., then stirred at 25° C. under N$_2$ for 16 h. The mixture was diluted with water (100 mL) and EtOAc (80 mL) and adjusted to pH=3 with HCl (2 M). The aqueous layer was extracted with EtOAc (80 mL×2). The combined extracts were washed with brine (80 mL), dried over Na$_2$SO$_4$, filtered and concentrated. The residue was triturated with DCM (40 mL) to give the product as a solid (15.5 g, yield: 66%).

Step 2: 8-bromo-2-ethylsulfanyl-chromen-4-one. Prepared in the same manner as 8-bromo-2-ethylsulfanyl-6-methyl-chromen-4-one to give the product as a solid (12 g, yield: 62%). MS ES+ m/z 285 [M+H]$^+$.

Step 3: 8-acetyl-2-ethylsulfanyl-chromen-4-one. Prepared in the same manner as 8-acetyl-2-ethylsulfanyl-6-methyl-chromen-4-one to give the product as a solid (8.7 g, yield: 83%). MS ES+ m/z 249 [M+H]$^+$.

Step 4: 2-ethylsulfanyl-8-(1-hydroxyethyl)chromen-4-one. Prepared in the same manner as 2-ethylsulfanyl-8-(1-hydroxyethyl)-6-methyl-chromen-4-one to give the product as a solid (5.48 g, crude). MS ES+ m/z 251 [M+H]$^+$.

Step 5: 8-(1-bromoethyl)-2-ethylsulfanyl-chromen-4-one. Prepared in the same manner as 8-(1-bromoethyl)-2-ethylsulfanyl-6-methyl-chromen-4-one to give the product as oil (4.1 g, 60%, purity: 100%). MS ES+ m/z 315 [M+H]$^+$.

Step 6: 2-[1-(2-ethylsulfanyl-4-oxo-chromen-8-yl)ethylamino]benzoic acid. Prepared in the same manner as 2-[1-(2-ethylsulfanyl-6-methyl-4-oxo-chromen-8-yl)ethylamino]benzoic acid to give the product as a solid (crude). MS ES+ m/z 370 [M+H]$^+$.

Step 7: 2-[1-(2-ethylsulfinyl-4-oxo-chromen-8-yl)ethylamino]benzoic acid. Prepared in the same manner as 2-[1-(2-ethylsulfinyl-6-fluoro-4-oxo-chromen-8-yl)ethylamino]benzoic acid to give 2-[1-(2-ethylsulfinyl-4-oxo-chromen-8-yl)ethylamino]benzoic acid as a solid (yield: 51%). MS ES+ m/z 386 [M+H]$^+$.

Intermediate 27: 2-[1-[2-Ethylsulfinyl-4-oxo-6-(trifluoromethyl)chromen-8-yl]ethylamino]benzoic acid

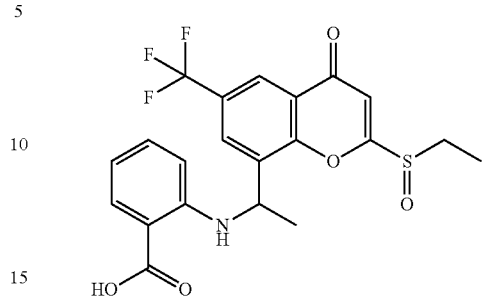

Step 1: 1-[2-hydroxy-5-(trifluoromethyl)phenyl]ethanone. To a mixture of 2-bromo-4-(trifluoromethyl)phenol (50.0 g, 207 mmol) in dioxane (400 mL) was added Pd(PPh$_3$)$_2$Cl$_2$ (7.28 g, 10.37 mmol) and tributyl(1-ethoxyvinyl)stannane (90.0 g, 249 mmol) under N$_2$ atmosphere, and stirred at 95° C. for 16 h. To the reaction was added HCl (1 M, 207 mL) and stirred at 50° C. for 1 h. When cooled to rt, to the mixture was added sat. KF (200 mL), stirred for 0.5 h and filtered. The aqueous layer was extracted with DCM (100 mL×2). The combined organic layer was washed with brine (150 mL×2), dried over anhydrous Na$_2$SO$_4$, filtered and concentrated to give the product as light yellow oil (31 g, crude).

Step 2: 1-[3-bromo-2-hydroxy-5-(trifluoromethyl)phenyl]ethanone. A mixture of Br$_2$ (29.0 g, 182 mmol) in AcOH (50 mL) was added to a mixture of 1-[2-hydroxy-5-(trifluoromethyl)phenyl]ethanone (31.0 g, 152 mmol) and NaOAc (15.0 g, 182 mmol) in AcOH (250 mL) dropwise at 0° C., and stirred at 20° C. for 16 h. The reaction mixture was poured into ice and water (500 mL) and filtered. The filter cake was dried in vacuum to give the product as solid (31 g, yield: 72%).

Step 3: 8-bromo-4-hydroxy-6-(trifluoromethyl)chromene-2-thione. Prepared in the same manner as 8-bromo-4-hydroxy-chromene-2-thione to give the product as a solid (yield: 64%). MS ES+m/z 326 [M+H]$^+$.

Step 4: 8-bromo-2-ethylsulfanyl-6-(trifluoromethyl)chromen-4-one. Prepared in the same manner as 8-bromo-2-ethylsulfanyl-6-methyl-chromen-4-one to give the product as a solid (yield: 70.7%). MS ES+ m/z 354 [M+H]$^+$.

Step 5: 8-acetyl-2-ethylsulfanyl-6-(trifluoromethyl)chromen-4-one. Prepared in the same manner as 8-acetyl-2-ethylsulfanyl-6-methyl-chromen-4-one to give the product (crude) as a solid. MS ES+ m/z 317 [M+H]$^+$.

Step 6: 2-ethylsulfanyl-8-(1-hydroxyethyl)-6-(trifluoromethyl)chromen-4-one. Prepared in the same manner as 2-ethylsulfanyl-8-(1-hydroxyethyl)-6-methyl-chromen-4-one to give the product as a gum (yield: 78%). MS ES+ m/z 319 [M+H]$^+$.

Step 7: 8-(1-bromoethyl)-2-ethylsulfanyl-6-(trifluoromethyl)chromen-4-one. Prepared in the same manner as 8-(1-bromoethyl)-2-ethylsulfanyl-6-methyl-chromen-4-one to give the product as a solid (yield: 99%). MS ES+ m/z 382 [M+H]$^+$.

Step 8: 2-[1-[2-ethylsulfanyl-4-oxo-6-(trifluoromethyl)chromen-8-yl]ethylamino]benzoic acid. Prepared in the same manner as 2-[1-(2-ethylsulfanyl-6-methyl-4-oxo-chromen-8-yl)ethylamino]benzoic acid to give the product as a solid (yield: 93%). MS ES+ m/z 438 [M+H]$^+$.

Step 9: 2-[1-[2-ethylsulfinyl-4-oxo-6-(trifluoromethyl)chromen-8-yl]ethylamino]benzoic acid. Prepared in the same manner as 2-[1-(2-ethylsulfinyl-6-fluoro-4-oxo-chromen-8-yl)ethylamino]benzoic acid to give 2-[1-[2-ethylsulfinyl-4-oxo-6-(trifluoromethyl)chromen-8-yl]ethylamino]benzoic acid as a solid (yield: 89%). MS ES+ m/z 454 [M+H]+.

Intermediate 28: 2-[1-[2-Ethylsulfinyl-3-methyl-4-oxo-6-(trifluoromethyl)chromen-8-yl]ethylamino]benzoic acid

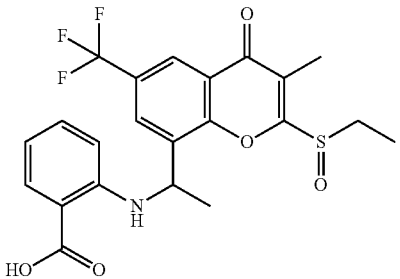 [SMILES: CCS(=O)c1oc2c(C(C)Nc3ccccc3C(=O)O)cc(C(F)(F)F)cc2c(=O)c1C]

Step 1: 2-[4-(trifluoromethyl)phenoxy]tetrahydropyran. A mixture of 4-(trifluoromethyl)phenol (50 g, 308 mmol), 3,4-dihydro-2H-pyran (64.9 g, 771 mmol) and 4-methylbenzenesulfonic acid; pyridine (77.5 g, 308 mmol) in DCM (500 mL) was stirred at rt for 4 h. The reaction mixture was diluted with H$_2$O (500 mL) and extracted with DCM (500 mL×3). The combined organic phase was washed with brine (500 mL×2), dried over anhydrous Na$_2$SO$_4$, filtered and concentrated. The residue was purified by silica gel column eluted with 0-10% EtOAc in petroleum ether to give the product as oil (62 g, yield: 82%).

Step 2: 1-[2-tetrahydropyran-2-yloxy-5-(trifluoromethyl)phenyl]propan-1-one. n-BuLi (2.5 M in hexane, 151 mL) was placed in a 1000 mL round-bottomed flask and while stirring tetramethylethylenediamine (TMEDA) (43.9 g, 378 mmol) was added dropwise at −10° C. After stirring 0.25 h, 2-[4-(trifluoromethyl)phenoxy]tetrahydropyran (62.0 g, 252 mmol) was added dropwise at −10° C., whereupon the lithium complex precipitated. After stirring 1 h, N-methoxy-N-methyl-propanamide (44.3 g, 378 mmol) was added, then the mixture was stirred at −10° C. for 1 h. To the mixture was added H$_2$O (300 mL) dropwise and extracted with EtOAc (200 mL×2). The combined organic phase was washed with brine (200 mL×2), dried over anhydrous Na$_2$SO$_4$, filtered and concentrated. The residue was purified by a silica gel column eluted with 0-10% EtOAc in petroleum ether to give the product as oil (15.5 g, yield: 20%).

Step 3: 1-[2-hydroxy-5-(trifluoromethyl)phenyl]propan-1-one. To a solution of 1-[2-tetrahydropyran-2-yloxy-5-(trifluoromethyl)phenyl]propan-1-one (14.5 g, 48.0 mmol) in MeOH (50 mL) was added HCl (10 mL, 12 M), and stirred at 20° C. for 16 h. The mixture was adjusted to pH=7 with sat.NaHCO$_3$, extracted with EtOAc (40 mL×3). The combined extracts were washed with brine (30 mL×2), dried over anhydrous Na$_2$SO$_4$, filtered and concentrated to give the product as oil (9.70 g, crude).

Step 4: 1-[3-bromo-2-hydroxy-5-(trifluoromethyl)phenyl]propan-1-one. A mixture of Br$_2$ (8.53 g, 53.3 mmol) in HOAc (18 mL) was added to a mixture of 1-[2-hydroxy-5-(trifluoromethyl)phenyl]propan-1-one (9.70 g, 44.5 mmol), NaOAc (4.38 g, 53.3 mmol) in HOAc (80 mL) dropwise at 0° C., and stirred at 20° C. for 16 h. The mixture was poured into ice and water (140 mL) and filtered. The filter cake was dried in vacuum to give the product as oil (7.81 g, crude).

Step 5: 8-bromo-4-hydroxy-3-methyl-6-(trifluoromethyl)chromene-2-thione. Prepared in the same manner as 8-bromo-4-hydroxy-chromene-2-thione to give the product as a solid (crude). MS ES+ m/z 340 [M+H]+.

Step 6: 8-bromo-2-ethylsulfanyl-3-methyl-6-(trifluoromethyl)chromen-4-one. Prepared in the same manner as 8-bromo-2-ethylsulfanyl-6-methyl-chromen-4-one to give the product as a solid (yield: 54%). MS ES+ m/z 368 [M+H]+.

Step 7: 8-acetyl-2-ethylsulfanyl-3-methyl-6-(trifluoromethyl)chromen-4-one. Prepared in the same manner as 8-acetyl-2-ethylsulfanyl-6-methyl-chromen-4-one to give the product as a solid (yield: 78%). MS ES+ m/z 331 [M+H]+.

Step 8: 2-ethylsulfanyl-8-(1-hydroxyethyl)-3-methyl-6-(trifluoromethyl)chromen-4-one. Prepared in the same manner as 2-ethylsulfanyl-8-(1-hydroxyethyl)-6-methyl-chromen-4-one to give the product as a solid (crude). MS ES+ m/z 333 [M+H]+.

Step 9: 8-(1-bromoethyl)-2-ethylsulfanyl-3-methyl-6-(trifluoromethyl)chromen-4-one. Prepared in the same manner as 8-(1-bromoethyl)-2-ethylsulfanyl-6-methyl-chromen-4-one to give the product as a solid (yield: 53%). MS ES+ m/z 396 [M+H]+.

Step 10: 2-[1-[2-ethylsulfanyl-3-methyl-4-oxo-6-(trifluoromethyl)chromen-8-yl]ethylamino]benzoic acid. Prepared in the same manner as 2-[1-(2-ethylsulfanyl-6-methyl-4-oxo-chromen-8-yl)ethylamino]benzoic acid to give the product as a solid (crude). MS ES+ m/z 452 [M+H]+.

Step 11: 2-[1-[2-ethylsulfinyl-3-methyl-4-oxo-6-(trifluoromethyl)chromen-8-yl]ethylamino]benzoic acid. Prepared in the same manner as 2-[1-(2-ethylsulfinyl-6-fluoro-4-oxo-chromen-8-yl)ethylamino]benzoic acid to give 2-[1-[2-ethylsulfinyl-3-methyl-4-oxo-6-(trifluoromethyl)chromen-8-yl]ethylamino]benzoic acid (yield: 55%) as a solid. MS ES+ m/z 468 [M+H]+.

Intermediate 29: 2-[1-(2-Ethylsulfinyl-6-methyl-4-oxo-chromen-8-yl)ethylamino]-5-fluoro-benzoic acid

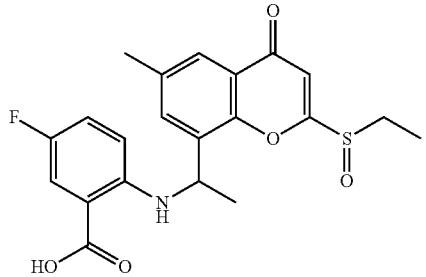 [SMILES: CCS(=O)c1cc(=O)c2cc(C)cc(C(C)Nc3ccc(F)cc3C(=O)O)c2o1]

Step 1: 2-[1-(2-ethylsulfanyl-6-methyl-4-oxo-chromen-8-yl)ethylamino]-5-fluoro-benzoic acid. Prepared in the same manner as 2-[1-(2-ethylsulfanyl-6-methyl-4-oxo-chromen-8-yl)ethylamino]benzoic acid to give the product as a solid (1.5 g, yield: 76%). MS ES+ m/z 402 [M+H]+.

Step 2: 2-[1-(2-ethylsulfinyl-6-methyl-4-oxo-chromen-8-yl)ethylamino]-5-fluoro-benzoic acid Prepared in the same manner as 2-[1-(2-ethylsulfinyl-6-fluoro-4-oxo-chromen-8-yl)ethylamino]benzoic acid to give 2-[1-(2-ethylsulfinyl-6- methyl-4-oxo-chromen-8-yl)ethylamino]-5-fluoro-benzoic acid as a solid (700 mg, yield: 45%). MS ES+ m/z 418 [M+H]+.

Intermediate 30: 8-(1-Bromopropyl)-2-(4,4-dimethyl-1-piperidyl)-6-methyl-chromen-4-one

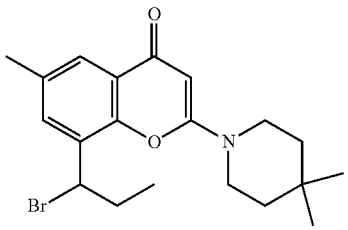

Step 1: 2-(4,4-dimethyl-1-piperidyl)-8-(1-hydroxypropyl)-6-methyl-chromen-4-one. To a solution of 8-bromo-2-(4,4-dimethyl-1-piperidyl)-6-methyl-chromen-4-one (370.0 mg, 1 eq., 1.056 mmol) in THF (25 mL) at −78° C. was added n-butyllithium (74.44 mg, 464.8 µL, 2.5 molar in hexanes, 1.1 eq., 1.162 mmol) dropwise and the resulting mixture was stirred for 20 minutes. After that propionaldehyde (92.03 mg, 1.5 eq., 1.585 mmol) in THF (1 mL) was added dropwise to the reaction mixture and the resulting mixture was allowed to warm at room temperature and stirred for 1 hour. The reaction was quenched with sat. NH4Cl solution (10 mL) and extracted with ethyl acetate (2×50 mL). The organic layer was dried over sodium sulfate and concentrated and purified using silica column (10-100% ethyl acetate in heptane) to give the product (65.0 mg, 197 µmol, 18.7%). MS ES+ m/z 330.4 [M+H]+.

Step 2: 8-(1-bromopropyl)-2-(4,4-dimethyl-1-piperidyl)-6-methyl-chromen-4-one. To a mixture of 2-(4,4-dimethyl-1-piperidyl)-8-(1-hydroxypropyl)-6-methyl-chromen-4-one (65.0 mg, 1 eq., 197 µmol) in DCM (6 mL) was added PBr3 (80.1 mg, 27.9 µL, 1.5 eq., 296 µmol) at 0° C., and stirred at 20° C. for 2 h. The reaction mixture was quenched with aq. NaHCO3 (50 mL), extracted with DCM (60 mL×3). The combined extract was washed with brine (50 mL), dried over anhydrous Na2SO4 and filtered. The filtrate was concentrated and purified on a silica gel column eluted with 0-50% ethyl acetate in heptane to give 8-(1-bromopropyl)-2-(4,4-dimethyl-1-piperidyl)-6-methyl-chromen-4-one (26 mg, 66 µmol, 34%). MS ES+ m/z 394.2 [M+2H]+.

Intermediate 31: tert-Butyl 6-chloro-3-[1-[2-ethylsulfanyl-4-oxo-6-(trifluoromethyl)chromen-8-yl]ethylamino]pyridine-2-carboxylate

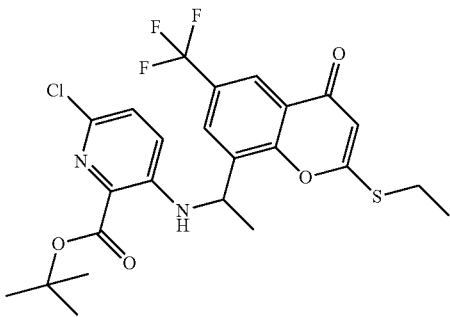 [SMILES: CCSc1cc(=O)c2cc(C(F)(F)F)cc(C(C)Nc3ccc(Cl)nc3C(=O)OC(C)(C)C)c2o1]

Step 1: 8-(1-azidoethyl)-2-ethylsulfanyl-6-(trifluoromethyl)chromen-4-one. Sodium azide (0.36 mg, 3 eq., 5.6 µmol) was added to a stirred solution of 8-(1-bromoethyl)-2-ethylsulfanyl-6-(trifluoromethyl)chromen-4-one (0.71 mg, 1 eq., 1.9 µmol) in DMF (20 mL) at 25° C., and then heated to 80° C. for 1.25 hours. The reaction was diluted with water (220 ml) and EtOAc (75 ml). The aqueous layer was extracted with EtOAc (2×75 ml) and then washed the combined organic with brine (50 ml). The organic layer was dried over Na2SO4, filtered, and concentrated to give the product (0.63 g, 99% yield) as an amber oil. MS ES+ m/z 344 [M+H]+.

Step 2: 8-(1-aminoethyl)-2-ethylsulfanyl-6-(trifluoromethyl)chromen-4-one. Triphenylphosphine-polymer bound (963 mg, 2 eq., 3.67 mmol) (resin bound ~3 mmol/g, 2 eq. added 1.4 g) was added to a solution of 8-(1-azidoethyl)-2-ethylsulfanyl-6-(trifluoromethyl)chromen-4-one (630 mg, 1 eq., 1.84 mmol) in THF (18 mL) and water (4.25 mL) and stirred at 25° C. for 3 days. The reaction mixture was filtered, and resin washed with THF/water (1/1, 10 ml) and then MeOH (10 ml). The filtrate was concentrated to give the product (0.39 g, 67% yield). MS ES+ m/z 318 [M+H]+.

Step 3: tert-butyl 6-chloro-3-fluoropicolinate. 6-Chloro-3-fluoropicolinic acid (2.0 g, 1 eq., 11 mmol), DCC (2.8 g, 1.2 eq., 14 mmol), DMAP (0.35 g, 0.25 eq., 2.8 mmol), and tBuOH (1.7 g, 2.2 mL, 2 eq., 23 mmol) in DCM (15 mL) were stirred at 25° C. for 30 minutes. The reaction mixture was filtered, concentrated, and purified using a silica column (0-50% ethyl acetate in heptane) to give the product (2.4 g, 91% yield) as an off white solid. MS ES+ m/z 254.2 [M+Na]+.

Step 4: tert-butyl 6-chloro-3-[1-[2-ethylsulfanyl-4-oxo-6-(trifluoromethyl)chromen-8-yl]ethylamino]pyridine-2-carboxylate. 8-(1-aminoethyl)-2-ethylsulfanyl-6-(trifluoromethyl)chromen-4-one (390 mg, 1 eq., 1.24 mmol), tert-butyl 6-chloro-3-fluoropicolinate (288 mg, 1 eq., 1.24 mmol), and DIEA (322 mg, 434 µL, 2 eq., 2.49 mmol) in DMSO (5 mL) were heated at 100° C. for 12 hours. The reaction was diluted with water (200 ml) and extracted with EtOAc (3×75 ml). The combined organic layers were washed with brine (50 ml), dried over Na2SO4, filtered, concentrated and purified by silica chromatography (10-75% EtOAc/Heptanes) to give tert-butyl 6-chloro-3-[1-[2-ethylsulfanyl-4-oxo-6-(trifluoromethyl)chromen-8-yl]ethylamino]pyridine-2-carboxylate (180 mg, 28% yield) MS ES+m/z 529 [M+H]+.

Intermediate 32: tert-Butyl 6-chloro-3-[1-(2-ethylsulfanyl-6-fluoro-4-oxo-chromen-8-yl)ethylamino]pyridine-2-carboxylate

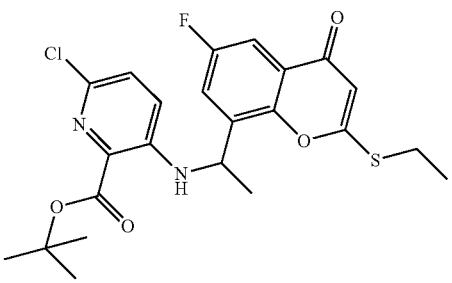 [SMILES: CCSc1cc(=O)c2cc(F)cc(C(C)Nc3ccc(Cl)nc3C(=O)OC(C)(C)C)c2o1]

Step 1: 8-(1-azidoethyl)-2-ethylsulfanyl-6-fluoro-chromen-4-one. Prepared in the same manner as 8-(1-azidoethyl)-2-ethylsulfanyl-6-(trifluoromethyl)chromen-4-one to give the product (0.33 g, yield: 93%). MS ES+ m/z 294 [M+H]+.

Step 2: 8-(1-aminoethyl)-2-ethylsulfanyl-6-fluoro-chromen-4-one. Prepared in the same manner as 8-(1-aminoethyl)-2-ethylsulfanyl-6-(trifluoromethyl)chromen-4-one to give the product (0.13 g, yield: 44%). MS ES+ m/z 268 [M+H]+.

Step 3: tert-butyl 6-chloro-3-[1-(2-ethylsulfanyl-6-fluoro-4-oxo-chromen-8-yl)ethylamino]pyridine-2-carboxylate. Prepared in the same manner as tert-butyl 6-chloro-3-[1-[2-ethylsulfanyl-4-oxo-6-(trifluoromethyl)chromen-8-yl]ethylamino]pyridine-2-carboxylate to give tert-butyl 6-chloro-3-[1-(2-ethylsulfanyl-6-fluoro-4-oxo-chromen-8-yl)ethylamino]pyridine-2-carboxylate (0.13 g, yield: 56%). MS ES+ m/z 479 [M+H]+.

Intermediate 33: Methyl 5-amino-2-(trifluoromethyl)pyrimidine-4-carboxylate

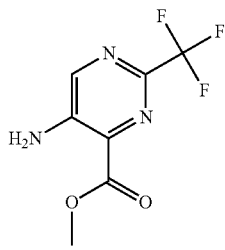

Step 1: 4-bromo-2-(trifluoromethyl)pyrimidin-5-amine. To a solution of 2-(trifluoromethyl)pyrimidin-5-amine (3 g, 1 eq., 18.4 mmol) in acetonitrile (30 mL) was added 1-bromopyrrolidine-2,5-dione (3.93 g, 1.2 eq., 22.1 mmol). The mixture was stirred at room temperature for 16 h. Acetonitrile was evaporated, the residue was partitioned in water and ethyl acetate (100 mL), the layers separated, and the aqueous layer was extracted (2×50 mL) with ethyl acetate. The combined organic layers were washed with brine (50 mL), dried over anhydrous $Na_2SO_4$, and concentrated. The reaction was repeated at 2 g scale (13.7 mmol). The resulting crude materials from both experiments were combined and purified by silica gel chromatography eluted with 0-30% ethyl acetate in heptane to give the product (4.42 g, 54%) as a yellow solid. MS ES+ m/z 242.0, 244.0 [M+H]+.

Step 2: methyl 5-amino-2-(trifluoromethyl)pyrimidine-4-carboxylate. A solution of 4-bromo-2-(trifluoromethyl)pyrimidin-5-amine (2 g, 1 eq., 8.26 mmol) in triethylamine (16 mL) was treated with methanol (7.94 g, 10.0 mL, 30 eq., 247.9 mmol). The mixture was degassed and flushed with argon, the process was repeated three times. Xantphos (286.9 mg, 0.06 eq., 495.9 µmol) and Pd(OAc)$_2$ (55.66 mg, 0.03 eq., 247.9 µmol) was added. The mixture was degassed and flushed with argon (3×) followed with carbon monoxide (3×). The mixture was stirred at 70° C. under CO atmosphere (balloon) for 16 h. After cooling down to room temperature, the mixture was diluted with ethyl acetate (50 mL) and water (50 mL) and filtered over a pad of celite. The filtrate was separated, the aqueous layer was extracted with ethyl acetate (2×50 mL). The combined organic layers were washed with brine (100 mL), dried over anhydrous $Na_2SO_4$, and concentrated. The residue was purified by silica gel chromatography and eluted with 0-30% ethyl acetate in heptane to give methyl 5-amino-2-(trifluoromethyl)pyrimidine-4-carboxylate (1.12 g, 61%) as an off-white solid. MS ES+ m/z 222.0 [M+H]+.

Intermediate 34: 8-(1-Bromoethyl)-6-chloro-2-isoindolin-2-yl-chromen-4-one

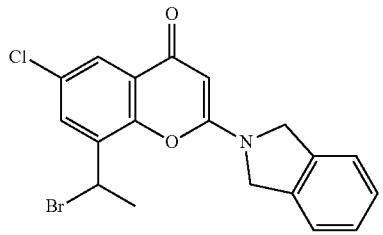 [SMILES: CC(Br)c1cc(Cl)cc2c(=O)cc(N3Cc4ccccc4C3)oc12]

Step 1: 8-bromo-6-chloro-4-hydroxy-chromene-2-thione. Prepared in the same manner as 8-bromo-4-hydroxy-6-methyl-chromene-2-thione to give the product (0.80 g). MS ES+ m/z 291, 293 [M+H]+.

Step 2: 8-bromo-6-chloro-2-ethylsulfanyl-chromen-4-one. Prepared in the same manner as 8-bromo-2-ethylsulfanyl-6-methyl-chromen-4-one to give the product (0.50 g). MS ES+ m/z 319, 321 [M+H]+

Step 3: 8-bromo-6-chloro-2-ethylsulfonyl-chromen-4-one. Prepared in the same manner as 8-bromo-2-ethylsulfonyl-3,6-dimethyl-chromen-4-one to give the product.

Step 4: 8-bromo-6-chloro-2-isoindolin-2-yl-chromen-4-one. Prepared in the same manner as 8-bromo-2-(4,4-dimethyl-1-piperidyl)-3,6-dimethyl-chromen-4-one to give the product (0.35 g). MS ES+ m/z 376, 378 [M+H]+.

Step 5: 8-acetyl-6-chloro-2-isoindolin-2-yl-chromen-4-one. Prepared in the same manner as 8-acetyl-2-(4,4-dimethyl-1-piperidyl)-3,6-dimethyl-chromen-4-one to give the product. MS ES+m/z 340 [M+H]+.

Step 6: 6-chloro-8-(1-hydroxyethyl)-2-isoindolin-2-yl-chromen-4-one. Prepared in the same manner as 2-(4,4-dimethyl-1-piperidyl)-8-(1-hydroxyethyl)-3,6-dimethyl-chromen-4-one to give the product. MS ES+ m/z 342 [M+H]+.

Step 7: 8-(1-bromoethyl)-6-chloro-2-isoindolin-2-yl-chromen-4-one. Prepared in the same manner as 8-(1-bromoethyl)-2-(4,4-dimethyl-1-piperidyl)-3,6-dimethyl-chromen-4-one to give 8-(1-bromoethyl)-6-chloro-2-isoindolin-2-yl-chromen-4-one (0.12 g). MS ES+ m/z 404, 406 [M+H]+.

Intermediate 35: 8-(1-Bromoethyl)-3-cyclopropyl-2-(4,4-dimethyl-1-piperidyl)-6-methyl-chromen-4-one

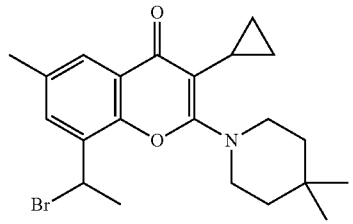

Step 1: 8-acetyl-3-bromo-2-(4,4-dimethyl-1-piperidyl)-6-methyl-chromen-4-one. A mixture of 8-acetyl-2-(4,4-dimethyl-1-piperidyl)-6-methyl-chromen-4-one (3.00 g, 9.57 mmol) and NBS (1.70 g, 9.57 mmol) in DCM (30 mL) was stirred at 25° C. for 0.5 h. The mixture was concentrated and purified on a silica gel column eluted with 0-100% EtOAc in petroleum ether and 0-50% (EtOAc/DCM (3/1)) in petroleum ether. The impure product was diluted with DCM (80 mL), washed with aq. NaOH (0.1 M, 100 mL×4), dried over $Na_2SO_4$, filtered and concentrated to give the product as a solid (2.98 g, 79%). MS ES+ m/z 392 [M+H]+.

Step 2: 8-acetyl-2-(4,4-dimethyl-1-piperidyl)-6-methyl-3-vinyl-chromen-4-one. A mixture of 8-acetyl-3-bromo-2-(4,4-dimethyl-1-piperidyl)-6-methyl-chromen-4-one (1.00 g, 2.55 mmol), tributyl(vinyl)stannane (1.21 g, 3.82 mmol), $Pd(PPh_3)_4$ (295 mg, 0.255 mmol), CuI (146 mg, 0.765 mmol) and CsF (1.16 g, 7.65 mmol) in toluene (10 mL) was stirred at 130° C. under $N_2$ for 16 h. When cooled to rt the mixture was quenched with sat. aq. KF (30 mL) and stirred for 1 h, then filtered and the filter cake was rinsed with DCM (50 mL). The filtrate was extracted with DCM (50 mL×3), washed with brine (80 mL), dried over $Na_2SO_4$, filtered, concentrated and purified on a silica gel column eluted with 0-40% EtOAc in petroleum ether to give the product as a solid (670 mg, 77%). MS ES+ m/z 340 [M+H]+.

Step 3: 8-acetyl-3-cyclopropyl-2-(4,4-dimethyl-1-piperidyl)-6-methyl-chromen-4-one. A mixture of 8-acetyl-2-(4,4-dimethyl-1-piperidyl)-6-methyl-3-vinyl-chromen-4-one (300 mg, 0.884 mmol) in DCM (6 mL) was added $ZnEt_2$ (1 M, 4.42 mmol) and $CH_2I_2$ (2.37 g, 8.84 mmol) dropwise at 0° C. under $N_2$, and stirred at 25° C. for 16 h. The mixture was quenched with sat.aq.$NH_4Cl$ (10 mL), extracted with DCM (20 mL×3), washed with brine (30 mL), dried over $Na_2SO_4$, filtered, concentrated and purified on a silica gel column eluted with 0-35% EtOAc in petroleum ether to give the product as gum (320 mg, crude). MS ES+ m/z 354 [M+H]+.

Step 4: 3-cyclopropyl-2-(4,4-dimethyl-1-piperidyl)-8-(1-hydroxyethyl)-6-methyl-chromen-4-one. Prepared in the same manner as 2-(4,4-dimethyl-1-piperidyl)-8-(1-hydroxyethyl)-3,6-dimethyl-chromen-4-one to give the product. MS ES+ m/z 356 [M+H]+.

Step 5: 8-(1-bromoethyl)-3-cyclopropyl-2-(4,4-dimethyl-1-piperidyl)-6-methyl-chromen-4-one. Prepared in the same manner as 8-(1-bromoethyl)-2-(4,4-dimethyl-1-piperidyl)-3,6-dimethyl-chromen-4-one to give 8-(1-bromoethyl)-3-cyclopropyl-2-(4,4-dimethyl-1-piperidyl)-6-methyl-chromen-4-one as a solid. MS ES+ m/z 417, 419 [M+H]+.

Intermediate 36: 8-(1-Bromoethyl)-2-(4,4-dimethyl-1-piperidyl)-3-isoxazol-4-yl-6-methyl-chromen-4-one

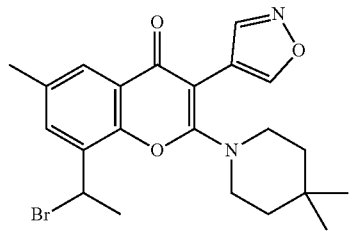

Step 1: 8-acetyl-2-(4,4-dimethyl-1-piperidyl)-3-isoxazol-4-yl-6-methyl-chromen-4-one. A mixture of 8-acetyl-3-bromo-2-(4,4-dimethyl-1-piperidyl)-6-methyl-chromen-4-one (300 mg, 0.765 mmol), 4-(4,4,5,5-tetramethyl-1,3,2-dioxaborolan-2-yl)isoxazole (224 mg, 1.15 mmol), ditertbutyl(cyclopentyl)phosphane; dichloropalladium; iron (50 mg, 0.76 mmol), and TEA (232 mg, 2.29 mmol) in $H_2O$ (2 mL) and THF (10 mL) was stirred at 25° C. under $N_2$ for 40 h. The mixture was quenched with $H_2O$ (20 mL), extracted with EtOAc (100 mL×3), washed with brine (100 mL×2), dried with $Na_2SO_4$, filtered and concentrated. The residue was purified by silica gel chromatography eluted with 0%-28% EtOAc in petroleum ether to give 8-acetyl-2-(4,4-dimethyl-1-piperidyl)-3-isoxazol-4-yl-6-methyl-chromen-4-one as a solid (220 mg, 76%). MS ES+ m/z 381 [M+H]+.

Step 2: 2-(4,4-dimethyl-1-piperidyl)-8-(1-hydroxyethyl)-3-isoxazol-4-yl-6-methyl-chromen-4-one. Prepared in the same manner as 2-(4,4-dimethyl-1-piperidyl)-8-(1-hydroxyethyl)-3,6-dimethyl-chromen-4-one to give the product. MS ES+ m/z 383 [M+H]+.

Step 3: 8-(1-bromoethyl)-2-(4,4-dimethyl-1-piperidyl)-3-isoxazol-4-yl-6-methyl-chromen-4-one. Prepared in the same manner as 8-(1-bromoethyl)-2-(4,4-dimethyl-1-piperidyl)-3,6-dimethyl-chromen-4-one to give 8-(1-bromoethyl)-2-(4,4-dimethyl-1-piperidyl)-3-isoxazol-4-yl-6-methyl-chromen-4-one as a solid. MS ES+ m/z 444, 446 [M+H]+.

The following compounds in Table 6 were prepared essentially as described for 8-(1-bromoethyl)-2-(4,4-dimethyl-1-piperidyl)-3,6-dimethyl-chromen-4-one, Steps 1-9.

TABLE 6

| Intermediate # | Chemical Name | Structure | ES/MS m/z (M + H) |
|---|---|---|---|
| 37 | 8-(1-bromoethyl)-2-(4,4-dimethyl-1-piperidyl)-3-ethyl-6-methyl-chromen-4-one | 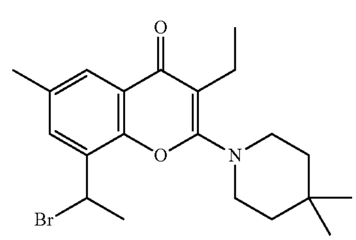 | 406 |

TABLE 6-continued

| Intermediate # | Chemical Name | Structure | ES/MS m/z (M + H) |
|---|---|---|---|
| 38 | 8-(1-bromoethyl)-2-(4,4-dimethyl-1-piperidyl)-6-fluoro-chromen-4-one | 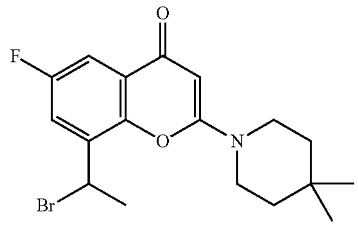 [SMILES: CC(Br)c1cc(F)cc2c(=O)cc(N3CCC(C)(C)CC3)oc12] | 382 |
| 39 | 8-(1-bromoethyl)-2-(4,4-dimethyl-1-piperidyl)-6-(trifluoromethyl)chromen-4-one | 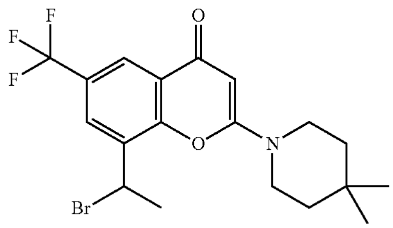 [SMILES: CC(Br)c1cc(C(F)(F)F)cc2c(=O)cc(N3CCC(C)(C)CC3)oc12] | 432 |
| 40 | 8-(1-bromoethyl)-2-(4,4-dimethyl-1-piperidyl)-6-methoxy-chromen-4-one | 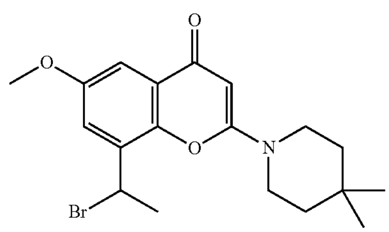 | 394 |

Example 1: 2-[1-[2-(4,4-Dimethyl-1-piperidyl)-6-methyl-4-oxo-chromen-8-yl]ethyl amino]-4-fluoro-5-methoxy-benzoic acid

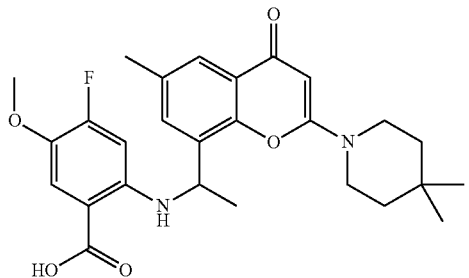 [SMILES: COc1cc(C(=O)O)c(NC(C)c2cc(C)cc3c(=O)cc(N4CCC(C)(C)CC4)oc23)cc1F]

A mixture of 8-(1-bromoethyl)-2-(4,4-dimethyl-1-piperidyl)-6-methyl-chromen-4-one (40 mg, 0.11 mmol) and 2-amino-4-fluoro-5-methoxy-benzoic acid (39 mg, 0.21 mmol) in DMF (1 mL) was stirred at 80° C. for 12 h. When cooled to rt the mixture was adjusted to pH=12 with NaOH (aq 2M), diluted with H$_2$O (15 mL) and washed with EtOAc (20 mL×2). The aqueous phase was adjusted to pH=2 with HCl (aq 1M) and extracted with EtOAc (20 mL×2). The combined extract was washed with brine (10 mL), dried over anhydrous Na$_2$SO$_4$, filtered, concentrated and purified by preparative HPLC to give 2-[1-[2-(4,4-dimethyl-1-piperidyl)-6-methyl-4-oxo-chromen-8-yl]ethylamino]-4-fluoro-5-methoxy-benzoic acid as a solid (11.6 mg, 22%). $^1$H NMR (400 MHz, DMSO-d$_6$) δ ppm 0.98 (s, 6H), 1.38-1.43 (m, 4H), 1.56 (d, J=6.8 Hz, 3H), 2.31 (s, 3H), 3.54 (dd, J=6.8, 4.4 Hz, 4H), 3.72 (s, 3H), 5.01 (s, 1H), 5.52 (s, 1H), 6.37 (d, J=14.0 Hz, 1H), 7.35 (d, J=2.0 Hz, 1H), 7.51 (d, J=10.0 Hz, 1H), 7.60 (d, J=1.6 Hz, 1H), 8.26 (s, 1H). MS ES+ m/z 483 [M+H]$^+$.

The following compounds in Table 7 were prepared essentially as described for 2-[1-[2-(4,4-dimethyl-1-piperidyl)-6-methyl-4-oxo-chromen-8-yl]ethylamino]-4-fluoro-5-methoxy-benzoic acid. If the Example was purified with chiral SFC, the chiral column and eluent are listed in the final column (see Tables 4 and 5).

TABLE 7

| Example # | Chemical Name | Structure | ES/MS m/z (M + H) & Chiral Method |
|---|---|---|---|
| 2 | 2-(4,4-Dimethyl-1-piperidyl)-6-methyl-8-[1-[(2-methylpyrazol-3-yl)amino]ethyl]chromen-4-one | 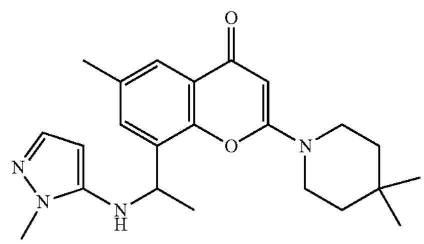 [SMILES: Cc1cc(C(C)Nc2ccnn2C)c2oc(N3CCC(C)(C)CC3)cc(=O)c2c1] | 395 |
| 3 | 2-[1-[2-(4,4-Dimethyl-1-piperidyl)-6-methyl-4-oxo-chromen-8-yl]ethylamino]-5-(trifluoromethyl)benzoic acid | 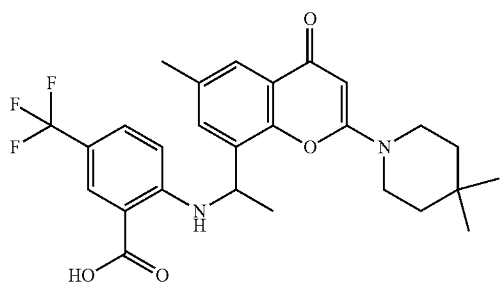 [SMILES: Cc1cc(C(C)Nc2ccc(C(F)(F)F)cc2C(=O)O)c2oc(N3CCC(C)(C)CC3)cc(=O)c2c1] | 503 |
| 4 | 2-[1-[2-(4,4-Dimethyl-1-piperidyl)-6-methyl-4-oxo-chromen-8-yl]ethylamino]benzenesulfonic acid | 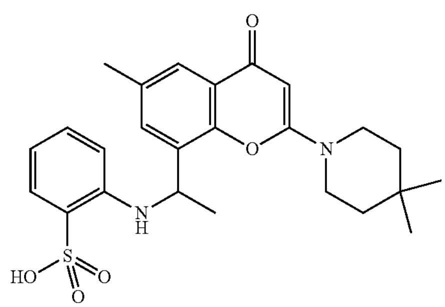 [SMILES: Cc1cc(C(C)Nc2ccccc2S(=O)(=O)O)c2oc(N3CCC(C)(C)CC3)cc(=O)c2c1] | 471 |
| 5 | 2-[1-[2-(4,4-Dimethyl-1-piperidyl)-6-methyl-4-oxo-chromen-8-yl]ethyl-methyl-amino]benzoic acid | 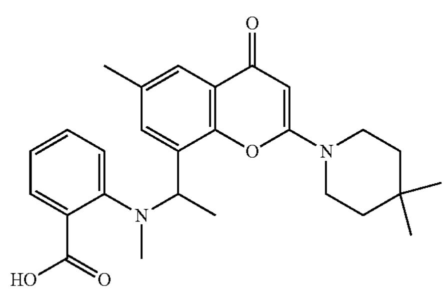 [SMILES: Cc1cc(C(C)N(C)c2ccccc2C(=O)O)c2oc(N3CCC(C)(C)CC3)cc(=O)c2c1] | 449 |
| 6 | 5-Cyano-2-[1-[2-(4,4-dimethyl-1-piperidyl)-6-methyl-4-oxo-chromen-8-yl]ethylamino]benzoic acid | 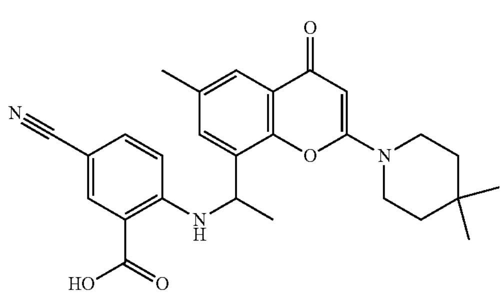 [SMILES: Cc1cc(C(C)Nc2ccc(C#N)cc2C(=O)O)c2oc(N3CCC(C)(C)CC3)cc(=O)c2c1] | 460 |

TABLE 7-continued

| Example # | Chemical Name | Structure | ES/MS m/z (M + H) & Chiral Method |
|---|---|---|---|
| 7 | 5-Bromo-2-[1-[2-(4,4-dimethyl-1-piperidyl)-6-methyl-4-oxo-chromen-8-yl]ethylamino]benzoic acid | 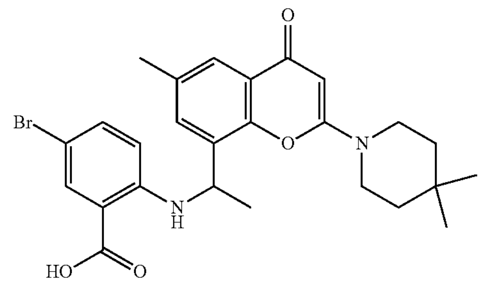 [SMILES: Cc1cc(C(C)Nc2ccc(Br)cc2C(=O)O)c2oc(N3CCC(C)(C)CC3)cc(=O)c2c1] | 513 |
| 8 | 2-(4,4-Dimethyl-1-piperidyl)-8-[1-(5-fluoro-2-nitro-anilino)ethyl]-6-methyl-chromen-4-one | 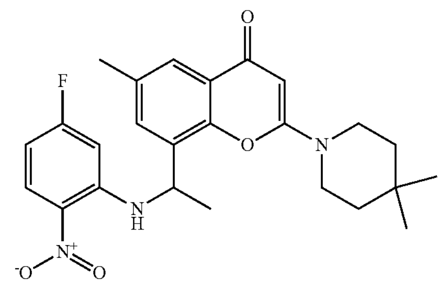 | 454 |
| 9 | 4-[1-[2-(4,4-Dimethyl-1-piperidyl)-6-methyl-4-oxo-chromen-8-yl]ethylamino]-1,3-dihydrobenzimidazol-2-one | 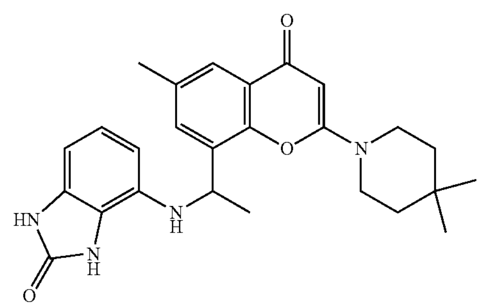 [SMILES: Cc1cc(C(C)Nc2cccc3[nH]c(=O)[nH]c23)c2oc(N3CCC(C)(C)CC3)cc(=O)c2c1] | 447 |
| 10 | 4-Chloro-2-[1-[2-(4,4-dimethyl-1-piperidyl)-6-methyl-4-oxo-chromen-8-yl]ethylamino]benzoic acid | 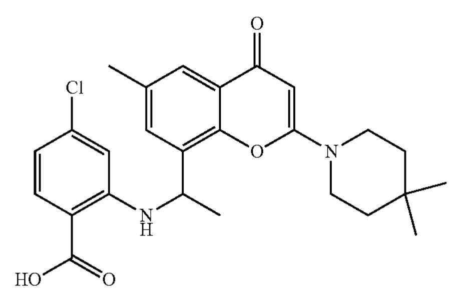 [SMILES: Cc1cc(C(C)Nc2cc(Cl)ccc2C(=O)O)c2oc(N3CCC(C)(C)CC3)cc(=O)c2c1] | 469 |
| 11 | 3-Chloro-2-[1-[2-(4,4-dimethyl-1-piperidyl)-6-methyl-4-oxo-chromen-8-yl]ethylamino]benzoic acid | 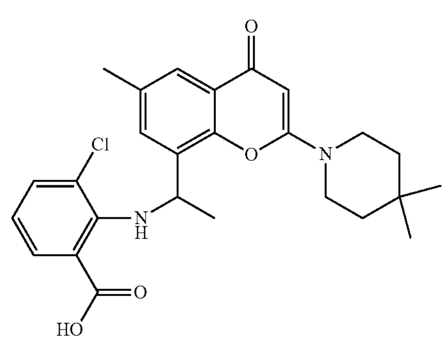 [SMILES: Cc1cc(C(C)Nc2c(Cl)cccc2C(=O)O)c2oc(N3CCC(C)(C)CC3)cc(=O)c2c1] | 469 |

TABLE 7-continued

| Example # | Chemical Name | Structure | ES/MS m/z (M + H) & Chiral Method |
|---|---|---|---|
| 12 | 2-[1-[2-(4,4-Dimethyl-1-piperidyl)-6-methyl-4-oxo-chromen-8-yl]ethylamino]-4,5-dimethyl-benzoic acid | 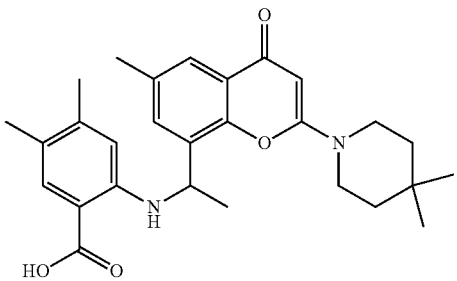 | 463 |
| 13 | 2-[1-[2-(4,4-Dimethyl-1-piperidyl)-6-methyl-4-oxo-chromen-8-yl]ethylamino]-4,5-difluoro-benzoic acid | 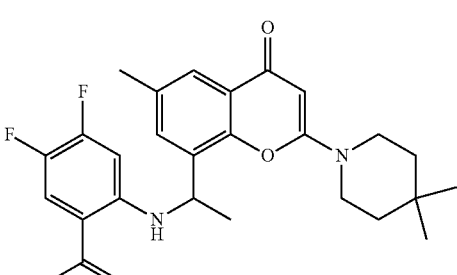 | 470 |
| 14 | 2-[1-[2-(4,4-Dimethyl-1-piperidyl)-6-methyl-4-oxo-chromen-8-yl]ethylamino]-5-fluoro-benzoic acid | 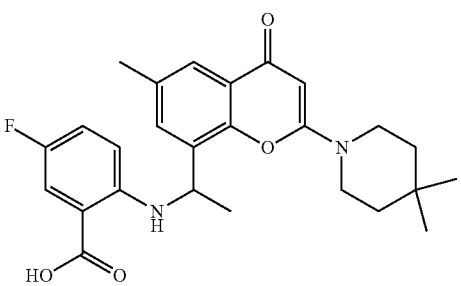 [SMILES: Cc1cc(C(C)Nc2ccc(F)cc2C(=O)O)c2oc(N3CCC(C)(C)CC3)cc(=O)c2c1] | 453 |
| 15 | 2-[1-[2-(4,4-Dimethyl-1-piperidyl)-6-methyl-4-oxo-chromen-8-yl]ethylamino]-5-methoxy-benzoic acid | 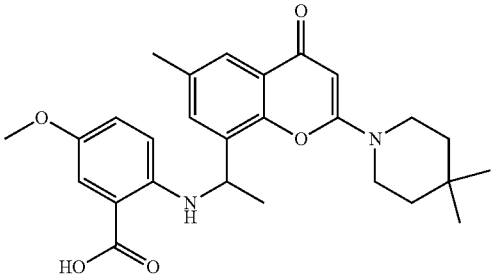 | 465 |
| 16 | 2-[1-[2-(4,4-Dimethyl-1-piperidyl)-6-methyl-4-oxo-chromen-8-yl]ethylamino]-4,5-dimethoxy-benzoic acid | 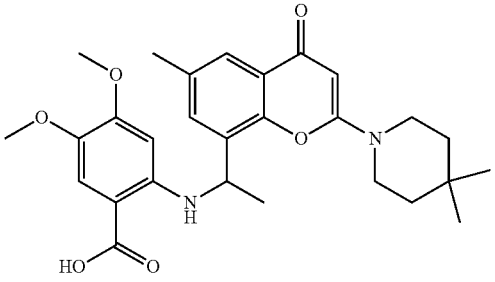 | 495 |

TABLE 7-continued

| Example # | Chemical Name | Structure | ES/MS m/z (M + H) & Chiral Method |
|---|---|---|---|
| 17 | 2-[1-[2-(4,4-Dimethyl-1-piperidyl)-6-methyl-4-oxo-chromen-8-yl]ethylamino]-3-methyl-benzoic acid | 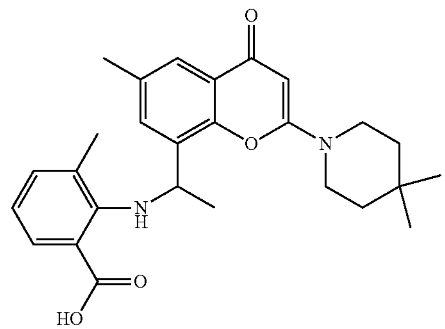 [SMILES: Cc1cc(C(C)Nc2c(C)cccc2C(=O)O)c2oc(N3CCC(C)(C)CC3)cc(=O)c2c1] | 467 |
| 18 | 2-[1-[2-(4,4-Dimethyl-1-piperidyl)-6-methyl-4-oxo-chromen-8-yl]ethylamino]-4-fluoro-5-methyl-benzoic acid | 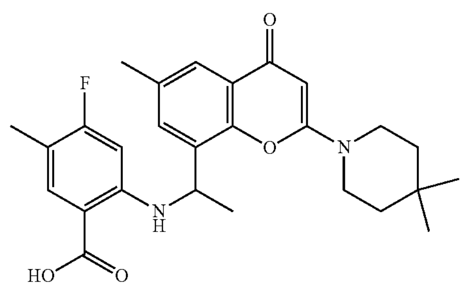 | 467 |
| 19 | 2-[1-[2-(4,4-Dimethyl-1-piperidyl)-6-methyl-4-oxo-chromen-8-yl]ethylamino]-N-methoxy-benzamide | 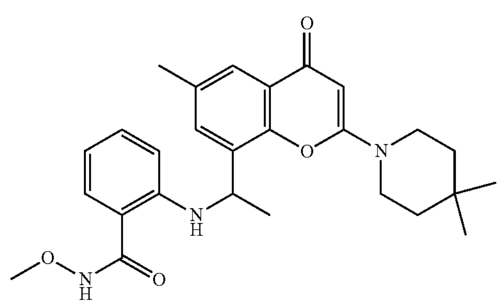 | 464 |
| 20 | 2-(4,4-Dimethyl-1-piperidyl)-6-methyl-8-[1-[2-(1H-tetrazol-5-yl)anilino]ethyl]chromen-4-one | 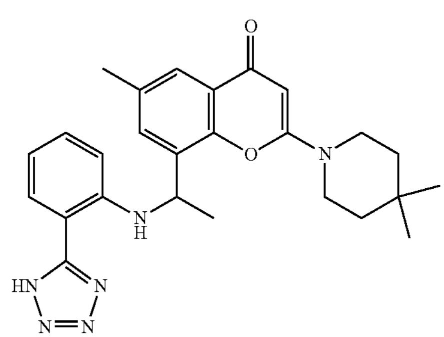 [SMILES: Cc1cc(C(C)Nc2ccccc2-c2nnn[nH]2)c2oc(N3CCC(C)(C)CC3)cc(=O)c2c1] | 459 |

TABLE 7-continued

| Example # | Chemical Name | Structure | ES/MS m/z (M + H) & Chiral Method |
|---|---|---|---|
| 21 | 2-[1-[2-(4,4-Dimethyl-1-piperidyl)-6-methyl-4-oxo-chromen-8-yl]ethylamino]benzenesulfonamide | 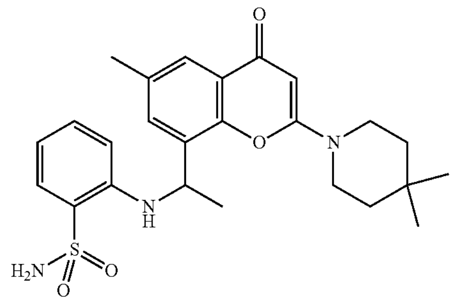 [SMILES: Cc1cc(C(C)Nc2ccccc2S(N)(=O)=O)c2oc(N3CCC(C)(C)CC3)cc(=O)c2c1] | 470 |
| 22 | 2-(4,4-Dimethyl-1-piperidyl)-8-[1-(indan-4-ylamino)ethyl]-6-methyl-chromen-4-one | 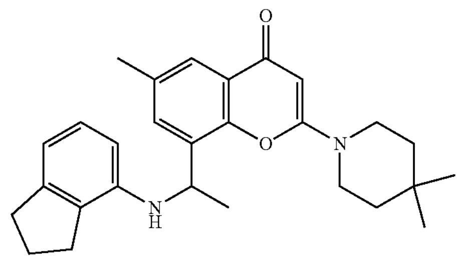 [SMILES: Cc1cc(C(C)Nc2cccc3c2CCC3)c2oc(N3CCC(C)(C)CC3)cc(=O)c2c1] | 431 |
| 23 | 2-[1-[2-(4,4-Dimethyl-1-piperidyl)-6-methyl-4-oxo-chromen-8-yl]ethylamino]-6-fluoro-benzoic acid | 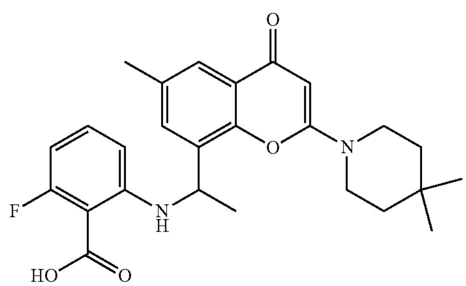 [SMILES: Cc1cc(C(C)Nc2cccc(F)c2C(=O)O)c2oc(N3CCC(C)(C)CC3)cc(=O)c2c1] | 453 |
| 24 | 2-Chloro-6-[1-[2-(4,4-dimethyl-1-piperidyl)-6-methyl-4-oxo-chromen-8-yl]ethylamino]benzoic acid | 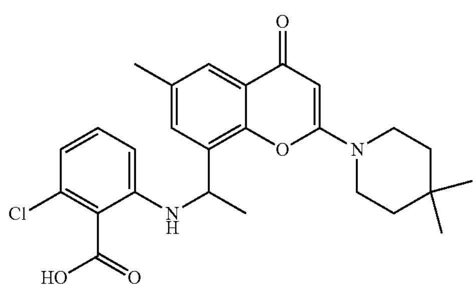 [SMILES: Cc1cc(C(C)Nc2cccc(Cl)c2C(=O)O)c2oc(N3CCC(C)(C)CC3)cc(=O)c2c1] | 469 |
| 25 | 2-[1-[2-(4,4-Dimethyl-1-piperidyl)-6-methyl-4-oxo-chromen-8-yl]ethylamino]-6-methyl-benzoic acid | 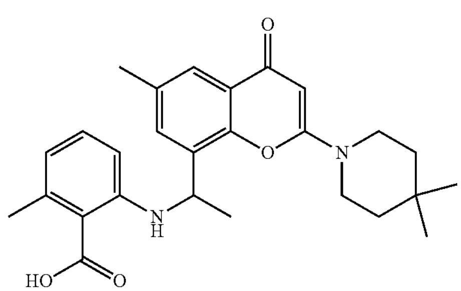 | 349 |

TABLE 7-continued

| Example # | Chemical Name | Structure | ES/MS m/z (M + H) & Chiral Method |
|---|---|---|---|
| 26 | 2-[1-[2-(4,4-Dimethyl-1-piperidyl)-6-methyl-4-oxo-chromen-8-yl]ethylamino]-3-methoxy-benzoic acid | 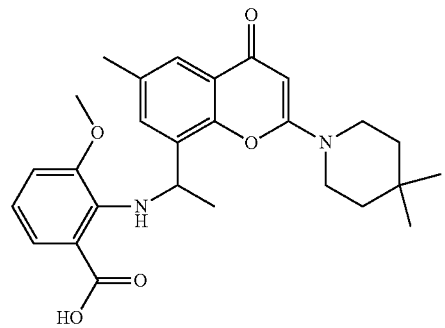 [SMILES: COc1cccc(C(=O)O)c1NC(C)c1cc(C)cc2c(=O)cc(N3CCC(C)(C)CC3)oc12] | 465 |
| 27 | 2-[1-[2-(4,4-Dimethyl-1-piperidyl)-6-methyl-4-oxo-chromen-8-yl]ethylamino]-4-methyl-benzoic acid | 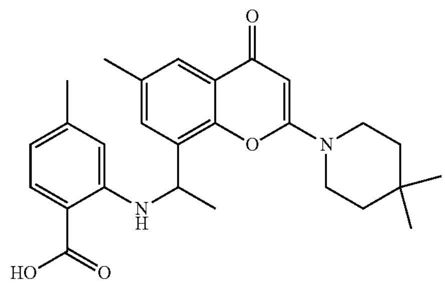 [SMILES: Cc1ccc(C(=O)O)c(NC(C)c2cc(C)cc3c(=O)cc(N4CCC(C)(C)CC4)oc23)c1] | 467 |
| 28 | 5-Chloro-2-[1-[2-(4,4-dimethyl-1-piperidyl)-6-methyl-4-oxo-chromen-8-yl]ethylamino]benzoic acid | 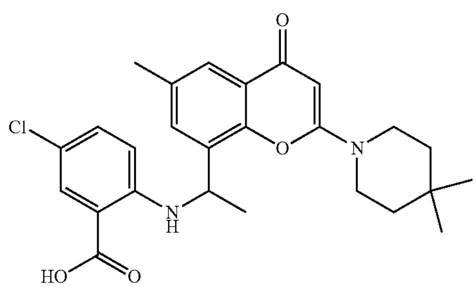 [SMILES: Cc1cc(C(C)Nc2ccc(Cl)cc2C(=O)O)c2oc(N3CCC(C)(C)CC3)cc(=O)c2c1] | 469 |
| 29 | 7-[1-[2-(4,4-Dimethyl-1-piperidyl)-6-methyl-4-oxo-chromen-8-yl]ethylamino]isoindolin-1-one | 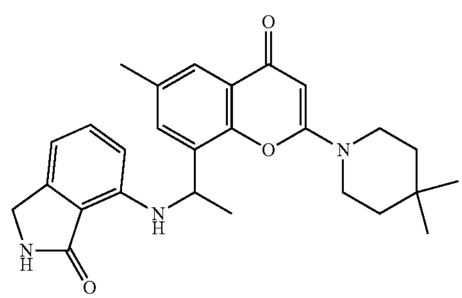 [SMILES: Cc1cc(C(C)Nc2cccc3c2C(=O)NC3)c2oc(N3CCC(C)(C)CC3)cc(=O)c2c1] | 446 |
| 30 | 2-[1-[2-(4,4-Dimethyl-1-piperidyl)-6-methyl-4-oxo-chromen-8-yl]ethylamino]benzonitrile | 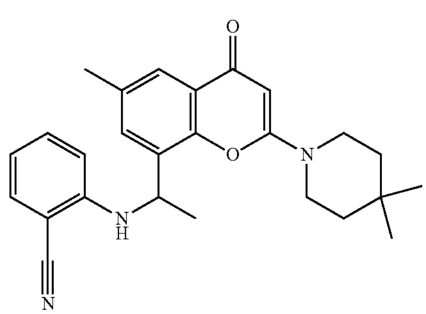 [SMILES: Cc1cc(C(C)Nc2ccccc2C#N)c2oc(N3CCC(C)(C)CC3)cc(=O)c2c1] | 416 |

TABLE 7-continued

| Example # | Chemical Name | Structure | ES/MS m/z (M + H) & Chiral Method |
|---|---|---|---|
| 31 | Methyl 2-[1-[2-(4,4-dimethyl-1-piperidyl)-6-methyl-4-oxo-chromen-8-yl]ethylamino]benzoate | 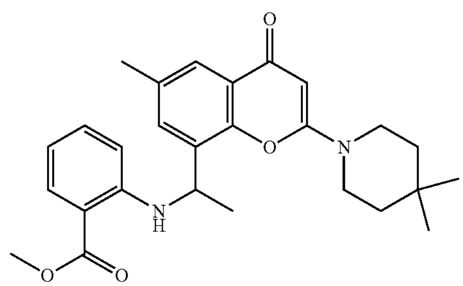 | 449 |
| 32 | 4-((1-(2-(4,4-Dimethylpiperidin-1-yl)-6-methyl-4-oxo-4H-chromen-8-yl)ethyl)amino)isoindoline-1,3-dione | 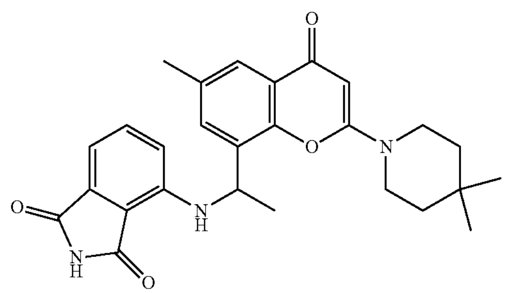 [SMILES: Cc1cc(C(C)Nc2cccc3c2C(=O)NC3=O)c2oc(N3CCC(C)(C)CC3)cc(=O)c2c1] | 460 |
| 33 | 6-[1-[2-(4,4-Dimethyl-1-piperidyl)-6-methyl-4-oxo-chromen-8-yl]ethylamino]-1,3-benzodioxole-5-carboxylic acid | 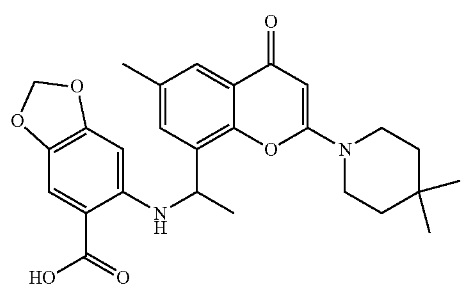 [SMILES: Cc1cc(C(C)Nc2cc3c(cc2C(=O)O)OCO3)c2oc(N3CCC(C)(C)CC3)cc(=O)c2c1] | 479 |
| 34 | 2-[1-[2-(4,4-Dimethyl-1-piperidyl)-6-methyl-4-oxo-chromen-8-yl]ethylamino]-5-ethyl-benzoic acid | 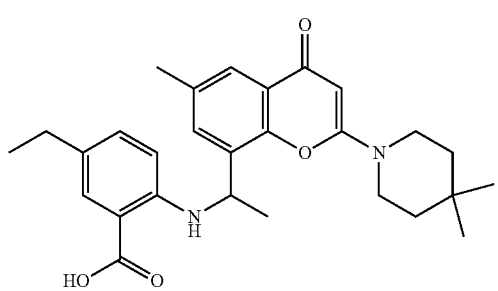 [SMILES: CCc1ccc(NC(C)c2cc(C)cc3c(=O)cc(N4CCC(C)(C)CC4)oc23)c(C(=O)O)c1] | 463 |
| 35 | 6-[1-[2-(4,4-Dimethyl-1-piperidyl)-6-methyl-4-oxo-chromen-8-yl]ethylamino]-3-fluoro-2-methyl-benzoic acid | 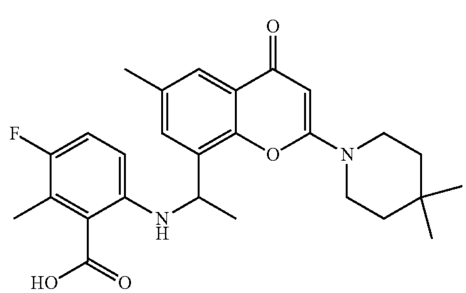 [SMILES: Cc1cc(C(C)Nc2ccc(F)c(C)c2C(=O)O)c2oc(N3CCC(C)(C)CC3)cc(=O)c2c1] | 467 |

TABLE 7-continued

| Example # | Chemical Name | Structure | ES/MS m/z (M + H) & Chiral Method |
|---|---|---|---|
| 36 | 2-[1-[2-(4,4-Dimethyl-1-piperidyl)-6-methyl-4-oxo-chromen-8-yl]ethylamino]-4-fluoro-benzoic acid | 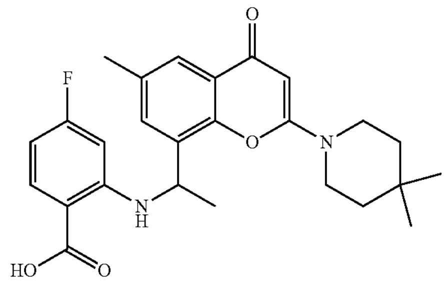 | 453 |
| 37 | 2-[1-[2-(4,4-Dimethyl-1-piperidyl)-6-methyl-4-oxo-chromen-8-yl]ethylamino]-6-methyl-benzoic acid | 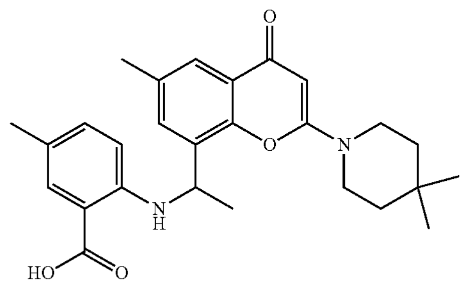 | 449 |
| 38 | 8-[1-[2-(Difluoromethylsulfonyl)anilino]ethyl]-2-(4,4-dimethyl-1-piperidyl)-6-methyl-chromen-4-one | 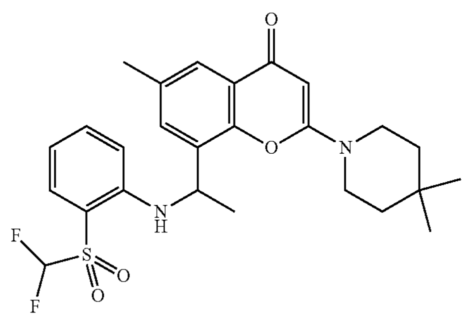 [SMILES: Cc1cc(C(C)Nc2ccccc2S(=O)(=O)C(F)F)c2oc(N3CCC(C)(C)CC3)cc(=O)c2c1] | 505 |
| 39 | 3-[1-[2-(4,4-Dimethyl-1-piperidyl)-6-methyl-4-oxo-chromen-8-yl]ethylamino]thiophene-2-carboxylic acid | 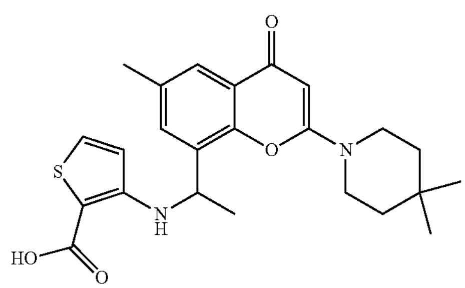 [SMILES: Cc1cc(C(C)Nc2ccsc2C(=O)O)c2oc(N3CCC(C)(C)CC3)cc(=O)c2c1] | 441 |
| 40 | 4-[1-[2-(4,4-Dimethyl-1-piperidyl)-6-methyl-4-oxo-chromen-8-yl]ethylamino]-1-methyl-pyrazole-3-carboxylic acid | 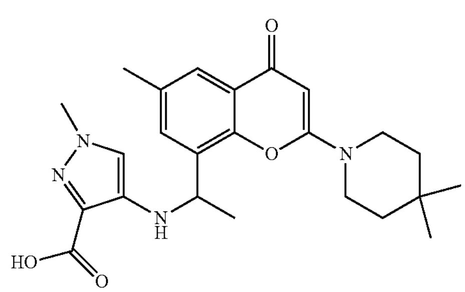 [SMILES: Cc1cc(C(C)Nc2cn(C)nc2C(=O)O)c2oc(N3CCC(C)(C)CC3)cc(=O)c2c1] | 439 |

TABLE 7-continued

| Example # | Chemical Name | Structure | ES/MS m/z (M + H) & Chiral Method |
|---|---|---|---|
| 41 | 2-[1-[2-(4,4-Dimethyl-1-piperidyl)-6-methyl-4-oxo-chromen-8-yl]ethylamino]-5-ethynyl-benzoic acid | 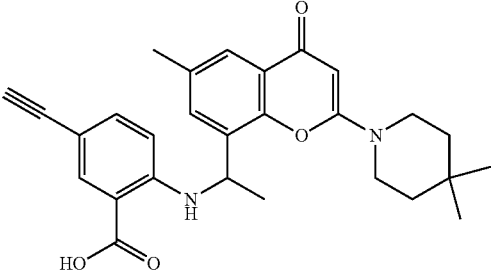 [SMILES: C#Cc1ccc(NC(C)c2cc(C)cc3c(=O)cc(N4CCC(C)(C)CC4)oc23)c(C(=O)O)c1] | 459 |
| 42 | 6-[1-[2-(4,4-Dimethyl-1-piperidyl)-6-methyl-4-oxo-chromen-8-yl]ethylamino]-2,3-difluoro-benzoic acid | 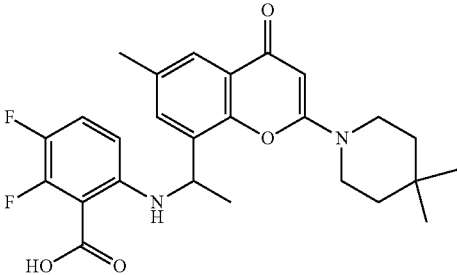 [SMILES: Cc1cc(C(C)Nc2ccc(F)c(F)c2C(=O)O)c2oc(N3CCC(C)(C)CC3)cc(=O)c2c1] | 471 |
| 43 | 3-Chloro-6-[1-[2-(4,4-dimethyl-1-piperidyl)-6-methyl-4-oxo-chromen-8-yl]ethylamino]-2-fluoro-benzoic acid | 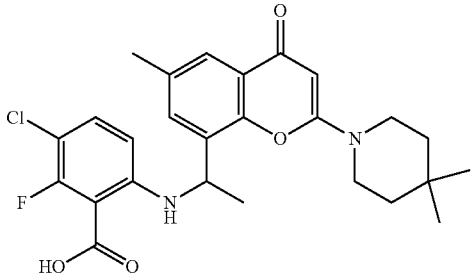 [SMILES: Cc1cc(C(C)Nc2ccc(Cl)c(F)c2C(=O)O)c2oc(N3CCC(C)(C)CC3)cc(=O)c2c1] | 487 |
| 44 | 3-Bromo-6-[1-[2-(4,4-dimethyl-1-piperidyl)-6-methyl-4-oxo-chromen-8-yl]ethylamino]-2-fluoro-benzoic acid | 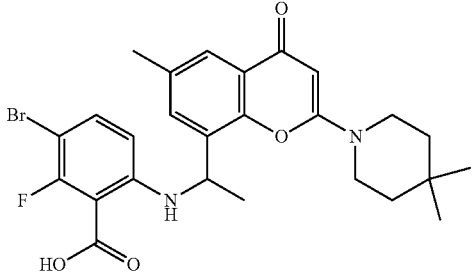 [SMILES: Cc1cc(C(C)Nc2ccc(Br)c(F)c2C(=O)O)c2oc(N3CCC(C)(C)CC3)cc(=O)c2c1] | 531 |
| 45 | 3-[2-[1-[2-(4,4-Dimethyl-1-piperidyl)-6-methyl-4-oxo-chromen-8-yl]ethylamino]phenyl]-4H-1,2,4-oxadiazol-5-one | 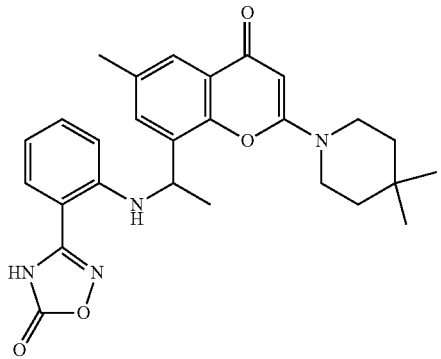 [SMILES: Cc1cc(C(C)Nc2ccccc2-c2noc(=O)[nH]2)c2oc(N3CCC(C)(C)CC3)cc(=O)c2c1] | 475 |

TABLE 7-continued

| Example # | Chemical Name | Structure | ES/MS m/z (M + H) & Chiral Method |
|---|---|---|---|
| 46 | 7-[1-[2-(4,4-Dimethyl-1-piperidyl)-6-methyl-4-oxo-chromen-8-yl]ethylamino]benzothiophene-2-carboxylic acid | 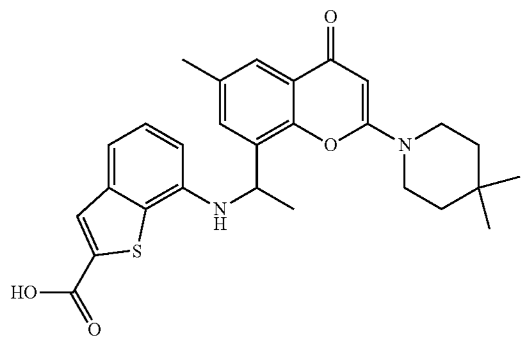 [SMILES: Cc1cc(C(C)Nc2cccc3cc(C(=O)O)sc23)c2oc(N3CCC(C)(C)CC3)cc(=O)c2c1] | 491 |
| 47 | 4-[1-[2-(4,4-Dimethyl-1-piperidyl)-6-methyl-4-oxo-chromen-8-yl]ethylamino]-1,3-benzoxazole-2-carboxylic acid | 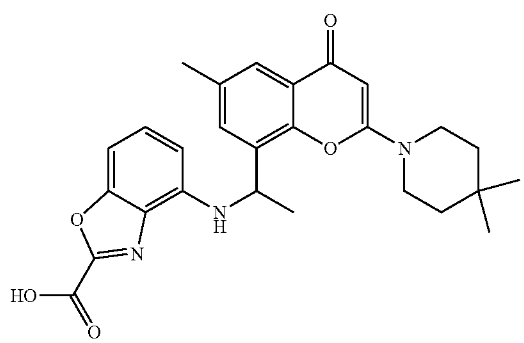 [SMILES: Cc1cc(C(C)Nc2cccc3oc(C(=O)O)nc23)c2oc(N3CCC(C)(C)CC3)cc(=O)c2c1] | 476 |
| 48 | 2-[1-[2-(4,4-Dimethyl-1-piperidyl)-6-methyl-4-oxo-chromen-8-yl]ethylamino]-4,6-difluoro-benzoic acid | 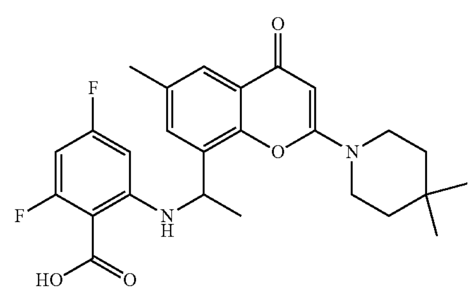 [SMILES: Cc1cc(C(C)Nc2cc(F)cc(F)c2C(=O)O)c2oc(N3CCC(C)(C)CC3)cc(=O)c2c1] | 504 |
| 49 | 3-[1-[2-(4,4-Dimethyl-1-piperidyl)-6-methyl-4-oxo-chromen-8-yl]ethylamino]-6-methyl-pyridine-2-carboxylic acid | 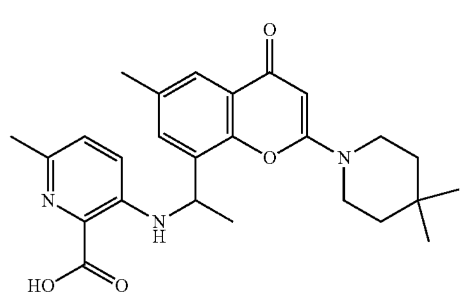 | 450 |

TABLE 7-continued

| Example # | Chemical Name | Structure | ES/MS m/z (M + H) & Chiral Method |
|---|---|---|---|
| 50 | 6-Cyclopropyl-3-[1-[2-(4,4-dimethyl-1-piperidyl)-6-methyl-4-oxo-chromen-8-yl]ethylamino]pyridine-2-carboxylic acid | 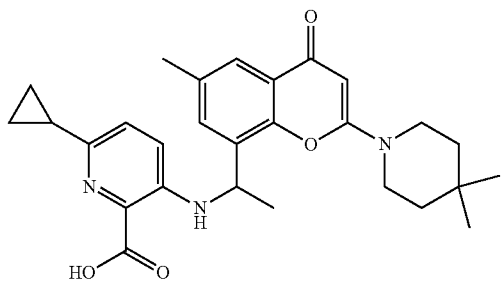 [SMILES: Cc1cc(C(C)Nc2ccc(C3CC3)nc2C(=O)O)c2oc(N3CCC(C)(C)CC3)cc(=O)c2c1] | 476 |
| 51 | 2-[1-[3-Cyclopropyl-2-(4,4-dimethyl-1-piperidyl)-6-methyl-4-oxo-chromen-8-yl]ethylamino]benzoic acid, Isomer 1 | 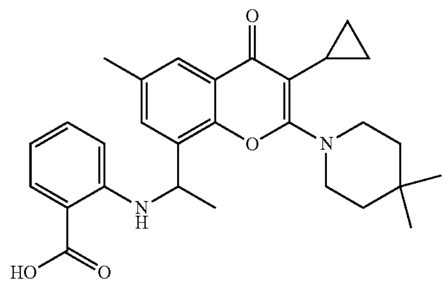 [SMILES: Cc1cc(C(C)Nc2ccccc2C(=O)O)c2oc(N3CCC(C)(C)CC3)c(C3CC3)c(=O)c2c1] | 475 R, 14 |
| 52 | 2-[1-[3-Cyclopropyl-2-(4,4-dimethyl-1-piperidyl)-6-methyl-4-oxo-chromen-8-yl]ethylamino]benzoic acid, Isomer 2 | 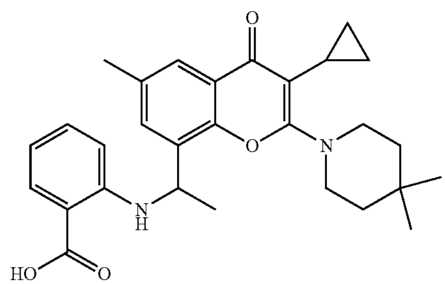 [SMILES: Cc1cc(C(C)Nc2ccccc2C(=O)O)c2oc(N3CCC(C)(C)CC3)c(C3CC3)c(=O)c2c1] | 475 R, 14 |
| 53 | 2-[1-[2-(4,4-Dimethyl-1-piperidyl)-6-isoxazol-4-yl-6-methyl-4-oxo-chromen-8-yl]ethylamino]benzoic acid, Isomer 1 | 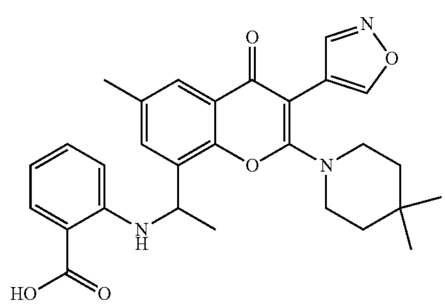 [SMILES: Cc1cc(C(C)Nc2ccccc2C(=O)O)c2oc(N3CCC(C)(C)CC3)c(-c3cnoc3)c(=O)c2c1] | 502 W, 24 |
| 54 | 2-[1-[2-(4,4-Dimethyl-1-piperidyl)-3-isoxazol-4-yl-6-methyl-4-oxo-chromen-8-yl]ethylamino]benzoic acid, Isomer 2 | 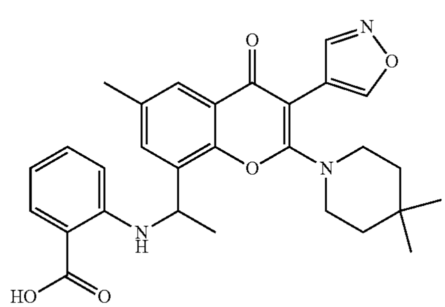 [SMILES: Cc1cc(C(C)Nc2ccccc2C(=O)O)c2oc(N3CCC(C)(C)CC3)c(-c3cnoc3)c(=O)c2c1] | 502 W, 24 |

TABLE 7-continued

| Example # | Chemical Name | Structure | ES/MS m/z (M + H) & Chiral Method |
|---|---|---|---|
| 55 | 2-[1-[2-(4,4-dimethyl-1-piperidyl)-3-ethyl-6-methyl-4-oxo-chromen-8-yl]ethylamino]benzoic acid | 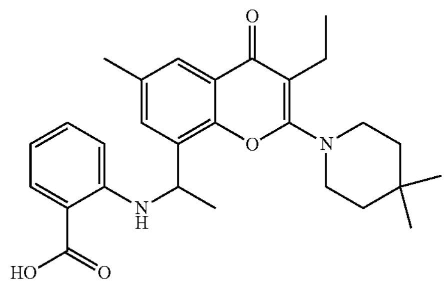 [SMILES: CCc1c(N2CCC(C)(C)CC2)oc2c(C(C)Nc3ccccc3C(=O)O)cc(C)cc2c1=O] | 463 |
| 56 | 2-[1-[2-(4,4-dimethyl-1-piperidyl)-6-fluoro-4-oxo-chromen-8-yl]ethylamino]benzoic acid | 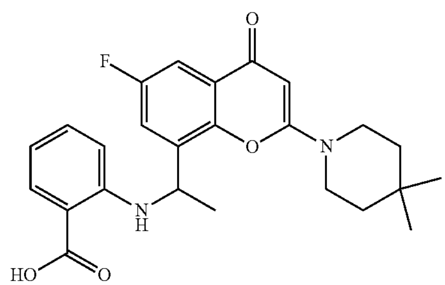 [SMILES: CC(Nc1ccccc1C(=O)O)c1cc(F)cc2c(=O)cc(N3CCC(C)(C)CC3)oc12] | 439 |
| 57 | 2-[1-[2-(4,4-dimethyl-1-piperidyl)-4-oxo-6-(trifluoromethyl)chromen-8-yl]ethylamino]benzoic acid | 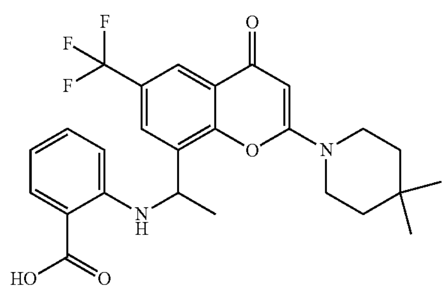 [SMILES: CC(Nc1ccccc1C(=O)O)c1cc(C(F)(F)F)cc2c(=O)cc(N3CCC(C)(C)CC3)oc12] | 489 |
| 58 | 2-[1-[2-(4,4-dimethyl-1-piperidyl)-6-methoxy-4-oxo-chromen-8-yl]ethylamino]benzoic acid | 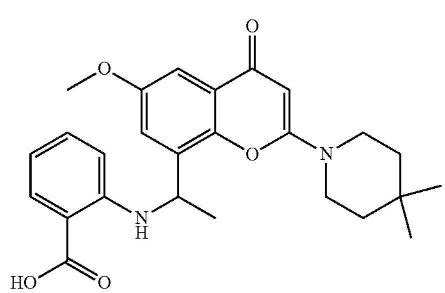 [SMILES: COc1cc(C(C)Nc2ccccc2C(=O)O)c2oc(N3CCC(C)(C)CC3)cc(=O)c2c1] | 451 |

Example 59: 2-[1-[2-[(3S)-3-Methoxy-1-piperidyl]-6-methyl-4-oxo-chromen-8-yl]ethylamino]benzoic acid

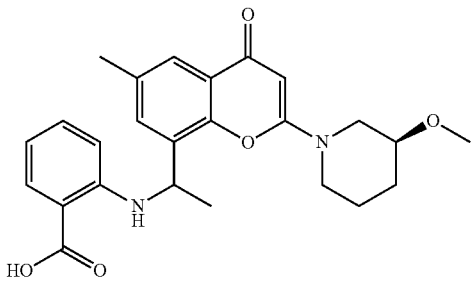 [SMILES: CO[C@H]1CCCN(c2cc(=O)c3cc(C)cc(C(C)Nc4ccccc4C(=O)O)c3o2)C1]

Step 1. A mixture of methyl 2-[1-(2-ethylsulfinyl-6-methyl-4-oxo-chromen-8-yl)ethylamino]benzoate (50 mg, 0.12 mmol), (3S)-3-methoxypiperidine (37 mg, 0.24 mmol, HCl salt) and DIPEA (156 mg, 1.21 mmol) in DCM (1.5 mL) was stirred at 40° C. for 46 h. The mixture was diluted with water (15 mL) and extracted with DCM (20 mL×2). The combined extract was washed with brine (20 mL), dried over anhydrous $Na_2SO_4$, filtered, concentrated and purified by silica gel chromatography eluted with 0-5% MeOH in DCM to give methyl 2-[1-[2-[(3S)-3-methoxy-1-piperidyl]-6-methyl-4-oxo-chromen-8-yl]ethylamino]benzoate as gum (40 mg, 73%). MS ES+ m/z 451 [M+H]$^+$.

Step 2. A mixture of methyl 2-[1-[2-[(3S)-3-methoxy-1-piperidyl]-6-methyl-4-oxo-chromen-8-yl]ethylamino]benzoate (40 mg, 0.089 mmol) and NaOH (14 mg, 0.36 mmol) in MeOH (2 mL) and $H_2O$ (2 mL) was stirred at 40° C. for 16 h. The mixture was concentrated and purified by preparative HPLC to give 2-[1-[2-[(3S)-3-methoxy-1-piperidyl]-6-methyl-4-oxo-chromen-8-yl]ethylamino]benzoic acid as a solid (14.82 mg, 38%). $^1$H NMR (400 MHz, DMSO-d$_6$) δ 1.45-1.58 (m, 1H), 1.58 (d, J=6.8 Hz, 3H), 1.57-1.69 (m, 1H), 1.69-1.80 (m, 1H), 1.80-1.92 (m, 1H), 2.30 (s, 3H), 3.28 (d, J=5.6 Hz, 3H), 3.45-3.60 (m, 4H), 3.65-3.75 (m, 1H), 5.00-5.12 (m, 1H), 5.56 (s, 1H), 6.38 (t, J=9.2 Hz, 1H), 6.53 (t, J=7.2 Hz, 1H), 7.19 (t, J=8.0 Hz, 1H), 7.36 (d, J=2.0 Hz, 1H), 7.60 (d, J=2.0 Hz, 1H), 7.81 (dd, J=8.0, 1.6 Hz, 1H), 8.65 (brs, 1H). MS ES+ m/z 437 [M+H]$^+$.

The following compounds in Table 8 were prepared essentially as described for 2-[1-[2-[(3S)-3-methoxy-1-piperidyl]-6-methyl-4-oxo-chromen-8-yl]ethylamino]benzoic acid. If the Example was purified with chiral SFC, the chiral column and eluent are listed in the final column (see Tables 4 and 5).

TABLE 8

| Example # | Chemical Name | Structure | ES/MS m/z (M + H) & Chiral Method |
|---|---|---|---|
| 60 | 1-[8-[1-(2-Carboxyanilino)ethyl]-6-methyl-4-oxo-chromen-2-yl]-3-methyl-azetidine-3-carboxylic acid | 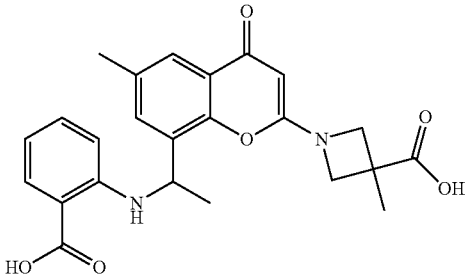 [SMILES: Cc1cc(C(C)Nc2ccccc2C(=O)O)c2oc(N3CC(C)(C(=O)O)C3)cc(=O)c2c1] | 437 |
| 61 | 2-[1-[6-Methyl-4-oxo-2-(3-oxo-2,7-diazaspiro[4.5]decan-7-yl)chromen-8-yl]ethylamino]benzoic acid | 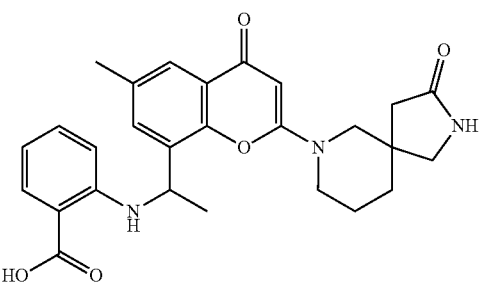 [SMILES: Cc1cc(C(C)Nc2ccccc2C(=O)O)c2oc(N3CCCC4(CNC(=O)C4)C3)cc(=O)c2c1] | 476 |

TABLE 8-continued

| Example # | Chemical Name | Structure | ES/MS m/z (M + H) & Chiral Method |
|---|---|---|---|
| 62 | 2-[1-[2-(3-Carbamoyl-3-methyl-azetidin-1-yl)-6-methyl-4-oxo-chromen-8-yl]ethylamino]benzoic acid | 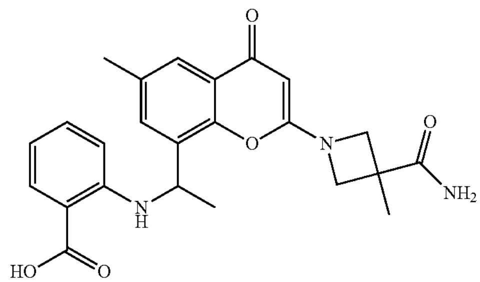 [SMILES: Cc1cc(C(C)Nc2ccccc2C(=O)O)c2oc(N3CC(C)(C(N)=O)C3)cc(=O)c2c1] | 436 |
| 63 | 2-[1-[2-(3-Chloroazetidin-1-yl)-6-methyl-4-oxo-chromen-8-yl]ethylamino]benzoic acid | 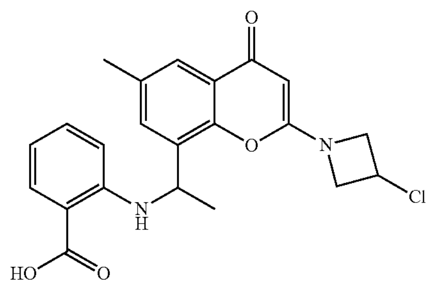 [SMILES: Cc1cc(C(C)Nc2ccccc2C(=O)O)c2oc(N3CC(Cl)C3)cc(=O)c2c1] | 413 |
| 64 | 2-[1-[2-(6-Azaspiro[2.5]octan-6-yl)-6-methyl-4-oxo-chromen-8-yl]ethylamino]benzoic acid | 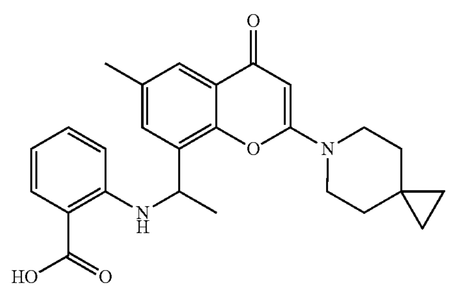 [SMILES: Cc1cc(C(C)Nc2ccccc2C(=O)O)c2oc(N3CCC4(CC3)CC4)cc(=O)c2c1] | 433 |
| 65 | 2-[1-[2-(3,3-Dimethyl-1-piperidyl)-6-methyl-4-oxo-chromen-8-yl]ethylamino]benzoic acid | 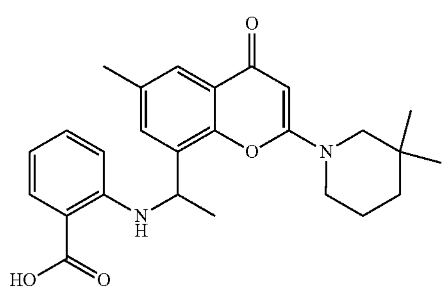 [SMILES: Cc1cc(C(C)Nc2ccccc2C(=O)O)c2oc(N3CCCC(C)(C)C3)cc(=O)c2c1] | 435 |
| 66 | 2-[1-[2-(4-Ethyl-4-methyl-1-piperidyl)-6-methyl-4-oxo-chromen-8-yl]ethylamino]benzoic acid | 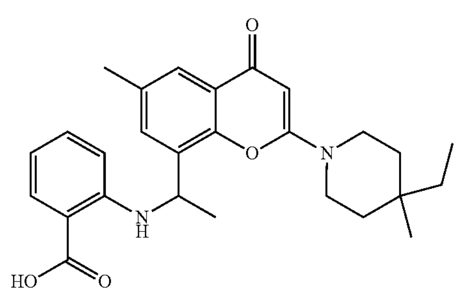 [SMILES: CCC1(C)CCN(c2cc(=O)c3cc(C)cc(C(C)Nc4ccccc4C(=O)O)c3o2)CC1] | 449 |

TABLE 8-continued

| Example # | Chemical Name | Structure | ES/MS m/z (M + H) & Chiral Method |
|---|---|---|---|
| 67 | 2-[1-[6-Methyl-4-oxo-2-(5-oxospiro[3,4-dihydro-1,4-benzoxazepine-2,4'-piperidine]-1'-yl)chromen-8-yl]ethylamino]benzoic acid | 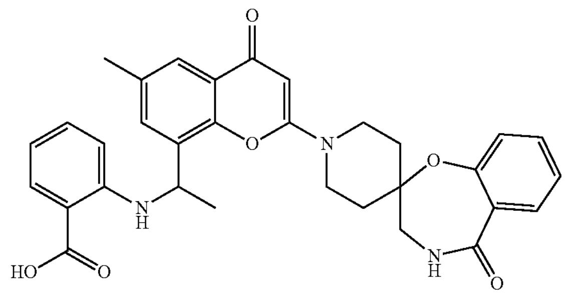 [SMILES: Cc1cc(C(C)Nc2ccccc2C(=O)O)c2oc(N3CCC4(CC3)CNC(=O)c3ccccc3O4)cc(=O)c2c1] | 554 |
| 68 | 2-[1-[2-[3-(Dimethylamino)azetidin-1-yl]-6-methyl-4-oxo-chromen-8-yl]ethylamino]benzoic acid | 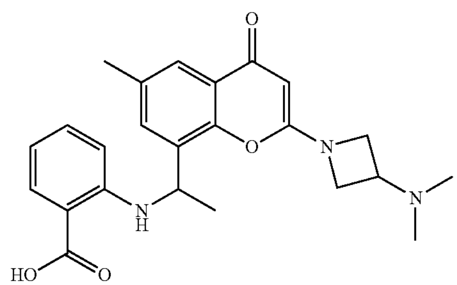 [SMILES: Cc1cc(C(C)Nc2ccccc2C(=O)O)c2oc(N3CC(N(C)C)C3)cc(=O)c2c1] | 422 |
| 69 | 2-[1-[2-(3-Fluoroazetidin-1-yl)-6-methyl-4-oxo-chromen-8-yl]ethylamino]benzoic acid | 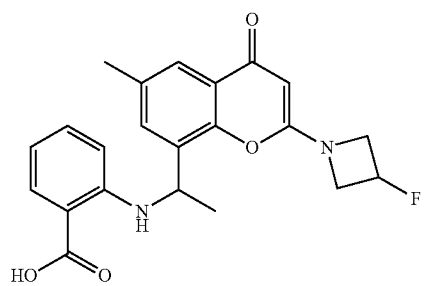 [SMILES: Cc1cc(C(C)Nc2ccccc2C(=O)O)c2oc(N3CC(F)C3)cc(=O)c2c1] | 397 |
| 70 | 2-[1-[2-(3,3-Dimethylazetidin-1-yl)-6-methyl-4-oxo-chromen-8-yl]ethylamino]benzoic acid | 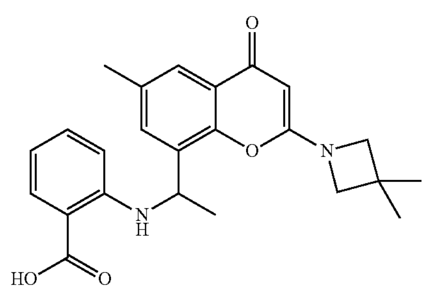 [SMILES: Cc1cc(C(C)Nc2ccccc2C(=O)O)c2oc(N3CC(C)(C)C3)cc(=O)c2c1] | 407 |
| 71 | 2-[1-[2-(4-Isopropyl-4-methyl-1-piperidyl)-6-methyl-4-oxo-chromen-8-yl]ethylamino]benzoic acid | 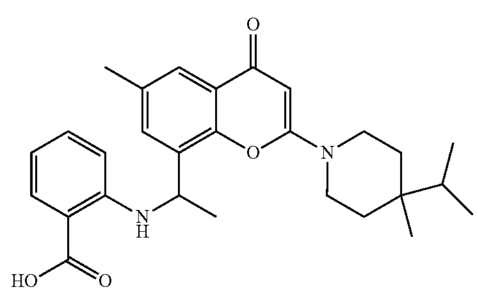 [SMILES: Cc1cc(C(C)Nc2ccccc2C(=O)O)c2oc(N3CCC(C)(C(C)C)CC3)cc(=O)c2c1] | 463 |

TABLE 8-continued

| Example # | Chemical Name | Structure | ES/MS m/z (M + H) & Chiral Method |
|---|---|---|---|
| 72 | 2-[1-[6-Methyl-2-(2-oxa-8-azaspiro[4.5]decan-8-yl)-4-oxo-chromen-8-yl]ethylamino]benzoic acid | 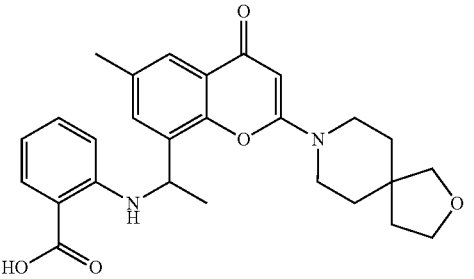 [SMILES: Cc1cc(C(C)Nc2ccccc2C(=O)O)c2oc(N3CCC4(CCOC4)CC3)cc(=O)c2c1] | 463 |
| 73 | 2-[1-[2-[4-(Methoxymethyl)-4-methyl-1-piperidyl]-6-methyl-4-oxo-chromen-8-yl]ethylamino]benzoic acid | 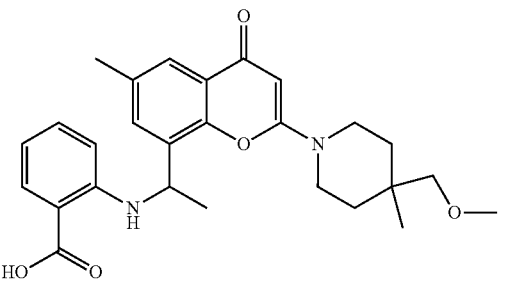 [SMILES: COCC1(C)CCN(c2cc(=O)c3cc(C)cc(C(C)Nc4ccccc4C(=O)O)c3o2)CC1] | 465 |
| 74 | 2-[1-[6-Methyl-4-oxo-2-[4-(trifluoromethyl)-1-piperidyl]chromen-8-yl]ethylamino]benzoic acid | 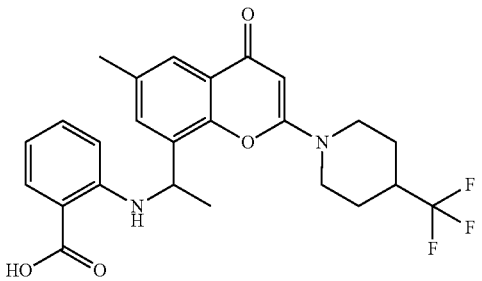 [SMILES: Cc1cc(C(C)Nc2ccccc2C(=O)O)c2oc(N3CCC(C(F)(F)F)CC3)cc(=O)c2c1] | 475 |
| 75 | 2-[1-[2-(6,6-Dimethyl-3-azabicyclo[3.1.0]hexan-3-yl)-6-methyl-4-oxo-chromen-8-yl]ethylamino]benzoic acid | 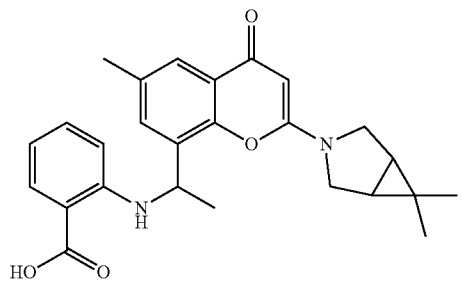 [SMILES: Cc1cc(C(C)Nc2ccccc2C(=O)O)c2oc(N3CC4C(C3)C4(C)C)cc(=O)c2c1] | 433 |
| 76 | 2-[1-[6-Methyl-2-(9-oxa-2-azaspiro[5.5]undecan-2-yl)-4-oxo-chromen-8-yl]ethylamino]benzoic acid | 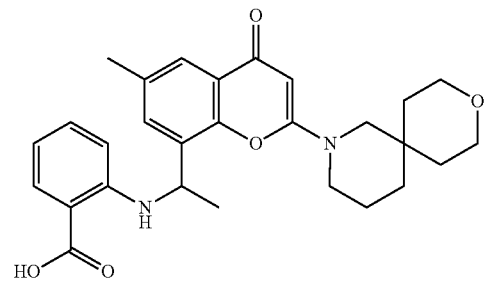 [SMILES: Cc1cc(C(C)Nc2ccccc2C(=O)O)c2oc(N3CCCC4(CCOCC4)C3)cc(=O)c2c1] | 477 |

TABLE 8-continued

| Example # | Chemical Name | Structure | ES/MS m/z (M + H) & Chiral Method |
|---|---|---|---|
| 77 | 2-[1-[2-(Isobutylamino)-6-methyl-4-oxo-chromen-8-yl]ethylamino]benzoic acid | 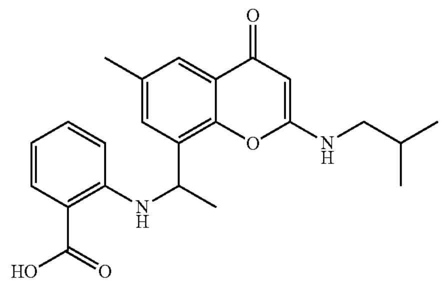 [SMILES: Cc1cc(C(C)Nc2ccccc2C(=O)O)c2oc(NCC(C)C)cc(=O)c2c1] | 395 |
| 78 | 2-[1-[2-(Dimethylamino)-6-methyl-4-oxo-chromen-8-yl]ethylamino]benzoic acid | 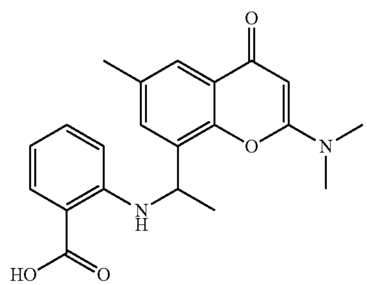 [SMILES: Cc1cc(C(C)Nc2ccccc2C(=O)O)c2oc(N(C)C)cc(=O)c2c1] | 367 |
| 79 | 2-[1-[6-Methyl-2-(3-methyl-1-piperidyl)-4-oxo-chromen-8-yl]ethylamino]benzoic acid | 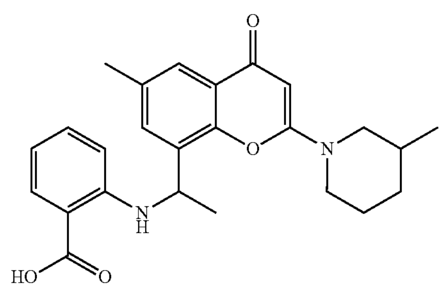 [SMILES: Cc1cc(C(C)Nc2ccccc2C(=O)O)c2oc(N3CCCC(C)C3)cc(=O)c2c1] | 421 |
| 80 | 2-[1-[2-(3-Ethyl-1-piperidyl)-6-methyl-4-oxo-chromen-8-yl]ethylamino]benzoic acid | 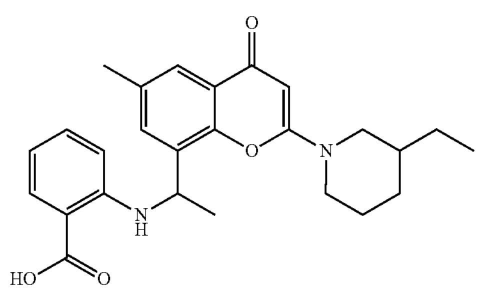 [SMILES: CCC1CCCN(c2cc(=O)c3cc(C)cc(C(C)Nc4ccccc4C(=O)O)c3o2)C1] | 435 |
| 81 | 2-[1-[6-Methyl-4-oxo-2-(1-oxo-2,8-diazaspiro[4.5]decan-8-yl)chromen-8-yl]ethylamino]benzoic acid | 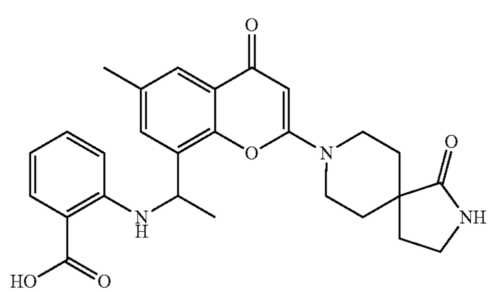 [SMILES: Cc1cc(C(C)Nc2ccccc2C(=O)O)c2oc(N3CCC4(CCNC4=O)CC3)cc(=O)c2c1] | 476 |

TABLE 8-continued

| Example # | Chemical Name | Structure | ES/MS m/z (M + H) & Chiral Method |
|---|---|---|---|
| 82 | 2-[1-[6-Methyl-2-(8-oxa-3-azabicyclo[3.2.1]octan-3-yl)-4-oxo-chromen-8-yl]ethylamino]benzoic acid | 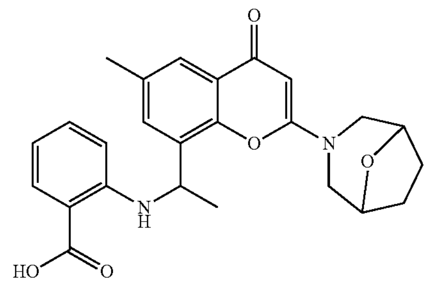 [SMILES: Cc1cc(C(C)Nc2ccccc2C(=O)O)c2oc(N3CC4CCC(C3)O4)cc(=O)c2c1] | 435 |
| 83 | 2-[1-[2-(4-Isobutyl-4-methyl-1-piperidyl)-6-methyl-4-oxo-chromen-8-yl]ethylamino]benzoic acid | 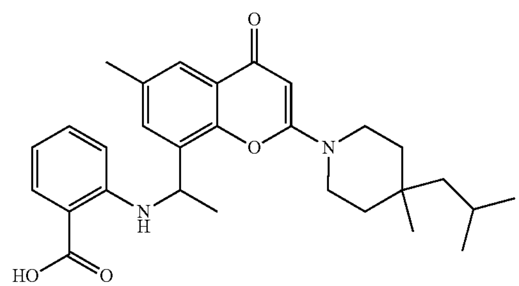 [SMILES: Cc1cc(C(C)Nc2ccccc2C(=O)O)c2oc(N3CCC(C)(CC(C)C)CC3)cc(=O)c2c1] | 477 |
| 84 | 2-[1-[2-(4-Cyano-4-methyl-1-piperidyl)-6-methyl-4-oxo-chromen-8-yl]ethylamino]benzoic acid[a] | 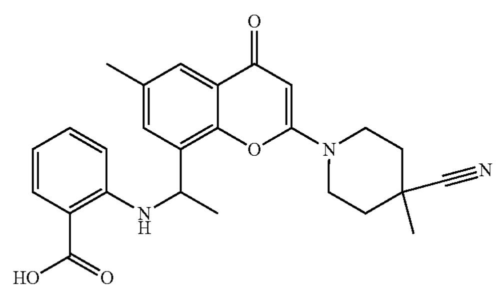 [SMILES: Cc1cc(C(C)Nc2ccccc2C(=O)O)c2oc(N3CCC(C)(C#N)CC3)cc(=O)c2c1] | 446 |
| 85 | 2-[1-[6-Methyl-2-[2-(4-methylsulfonylphenyl)morpholin-4-yl]-4-oxo-chromen-8-yl]ethylamino]benzoic acid | 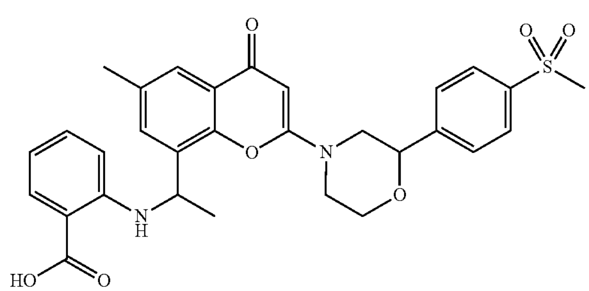 [SMILES: Cc1cc(C(C)Nc2ccccc2C(=O)O)c2oc(N3CCOC(c4ccc(S(C)(=O)=O)cc4)C3)cc(=O)c2c1] | 563 |
| 86 | 2-[1-[2-(3-Acetyl-3,9-diazaspiro[5.5]undecan-9-yl)-6-methyl-4-oxo-chromen-8-yl]ethylamino]benzoic acid | 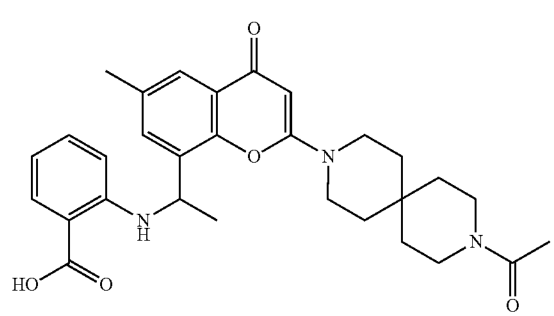 [SMILES: CC(=O)N1CCC2(CC1)CCN(c1cc(=O)c3cc(C)cc(C(C)Nc4ccccc4C(=O)O)c3o1)CC2] | 518 |

TABLE 8-continued

| Example # | Chemical Name | Structure | ES/MS m/z (M + H) & Chiral Method |
|---|---|---|---|
| 87 | 2-[1-[6-Methyl-2-[4-(2-methylpropanoyl)piperazin-1-yl]-4-oxo-chromen-8-yl]ethylamino]benzoic acid | 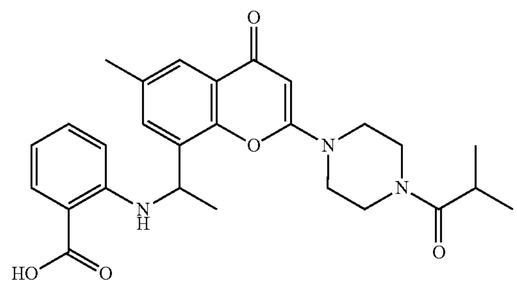 | 478 |
| 88 | 2-[1-[2-(2-Azaspiro[3.5]nonan-2-yl)-6-methyl-4-oxo-chromen-8-yl]ethylamino]benzoic acid | 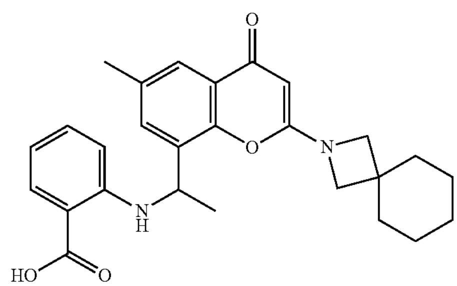 [SMILES: Cc1cc(C(C)Nc2ccccc2C(=O)O)c2oc(N3CC4(CCCCC4)C3)cc(=O)c2c1] | 447 |
| 89 | 2-[1-[2-(3,9-Diazaspiro[5.5]undecan-3-yl)-6-methyl-4-oxo-chromen-8-yl]ethylamino]benzoic acid | 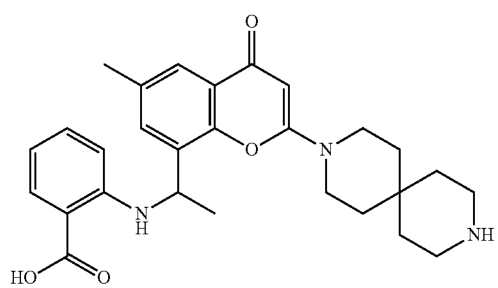 [SMILES: Cc1cc(C(C)Nc2ccccc2C(=O)O)c2oc(N3CCC4(CCNCC4)CC3)cc(=O)c2c1] | 476 |
| 90 | 2-[1-[2-(4-tert-Butoxycarbonylpiperazin-1-yl)-6-methyl-4-oxo-chromen-8-yl]ethylamino]benzoic acid | 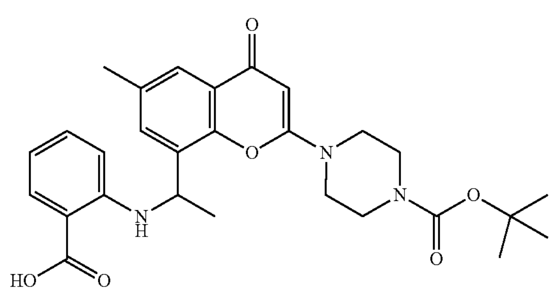 [SMILES: Cc1cc(C(C)Nc2ccccc2C(=O)O)c2oc(N3CCN(C(=O)OC(C)(C)C)CC3)cc(=O)c2c1] | 508 |
| 91 | 2-[1-(6-Methyl-4-oxo-2-piperazin-1-yl-chromen-8-yl)ethylamino]benzoic acid | 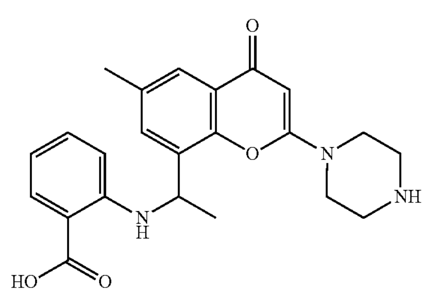 [SMILES: Cc1cc(C(C)Nc2ccccc2C(=O)O)c2oc(N3CCNCC3)cc(=O)c2c1] | 408 |

TABLE 8-continued

| Example # | Chemical Name | Structure | ES/MS m/z (M + H) & Chiral Method |
|---|---|---|---|
| 92 | 2-[1-[6-Methyl-2-(4-methylpiperazin-1-yl)-4-oxo-chromen-8-yl]ethylamino]benzoic acid | 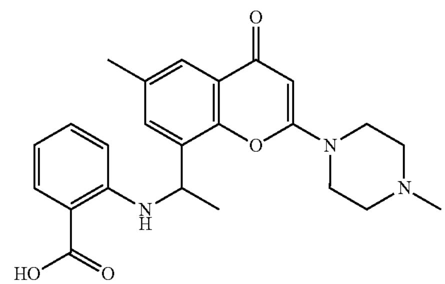 [SMILES: Cc1cc(C(C)Nc2ccccc2C(=O)O)c2oc(N3CCN(C)CC3)cc(=O)c2c1] | 422 |
| 93 | 2-[1-[6-Methyl-2-(1-oxa-9-azaspiro[5.5]undecan-9-yl)-4-oxo-chromen-8-yl]ethylamino]benzoic acid | 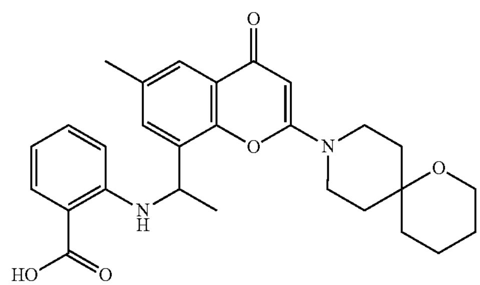 [SMILES: Cc1cc(C(C)Nc2ccccc2C(=O)O)c2oc(N3CCC4(CCCCO4)CC3)cc(=O)c2c1] | 477 |
| 94 | 2-[1-[6-Methyl-2-(3-oxa-9-azaspiro[5.5]undecan-9-yl)-4-oxo-chromen-8-yl]ethylamino]benzoic acid | 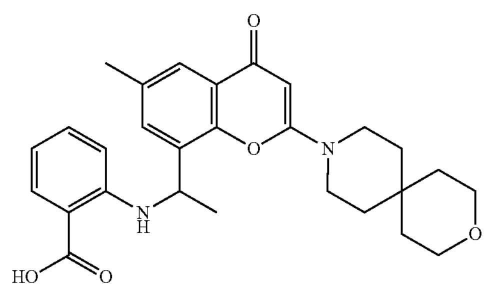 [SMILES: Cc1cc(C(C)Nc2ccccc2C(=O)O)c2oc(N3CCC4(CCOCC4)CC3)cc(=O)c2c1] | 477 |
| 95 | 2-[1-[6-Methyl-4-oxo-2-(1-oxo-2,9-diazaspiro[4.5]decan-9-yl)chromen-8-yl]ethylamino]benzoic acid | 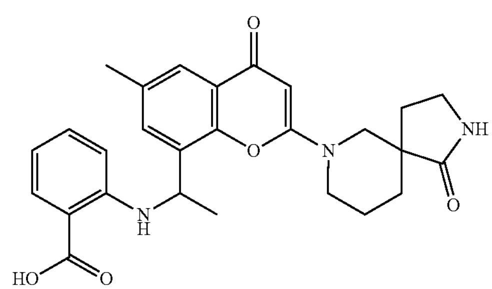 [SMILES: Cc1cc(C(C)Nc2ccccc2C(=O)O)c2oc(N3CCCC4(CCNC4=O)C3)cc(=O)c2c1] | 476 |
| 96 | 2-[1-[2-(8-Azaspiro[4.5]decan-8-yl)-6-methyl-4-oxo-chromen-8-yl]ethylamino]benzoic acid | 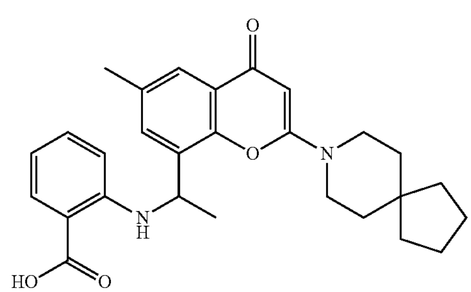 [SMILES: Cc1cc(C(C)Nc2ccccc2C(=O)O)c2oc(N3CCC4(CCCC4)CC3)cc(=O)c2c1] | 461 |

TABLE 8-continued

| Example # | Chemical Name | Structure | ES/MS m/z (M + H) & Chiral Method |
|---|---|---|---|
| 97 | 2-[1-[2-(3-Carbamoyl-1-piperidyl)-6-methyl-4-oxo-chromen-8-yl]ethylamino]benzoic acid | 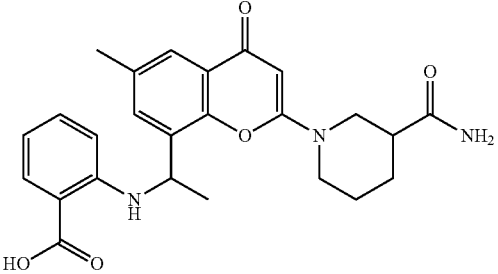 [SMILES: Cc1cc(C(C)Nc2ccccc2C(=O)O)c2oc(N3CCCC(C(N)=O)C3)cc(=O)c2c1] | 450 |
| 98 | 2-[1-[6-Methyl-2-(2-oxa-7-azaspiro[3.5]nonan-7-yl)-4-oxo-chromen-8-yl]ethylamino]benzoic acid | 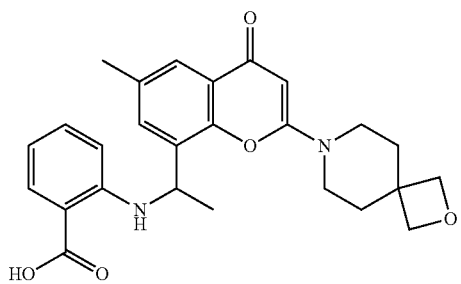 [SMILES: Cc1cc(C(C)Nc2ccccc2C(=O)O)c2oc(N3CCC4(CC3)COC4)cc(=O)c2c1] | 449 |
| 99 | 2-[1-[2-(Diethylamino)-6-methyl-4-oxo-chromen-8-yl]ethylamino]benzoic acid | 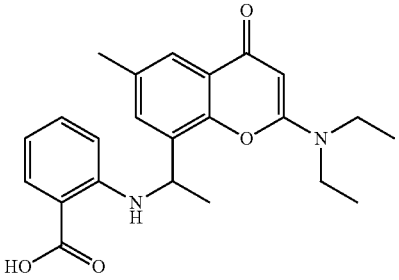 [SMILES: CCN(CC)c1cc(=O)c2cc(C)cc(C(C)Nc3ccccc3C(=O)O)c2o1] | 395 |
| 100 | 2-[1-[2-(5,7-Dihydropyrrolo[3,4-b]pyridin-6-yl)-6-methyl-4-oxo-chromen-8-yl]ethylamino]benzoic acid | 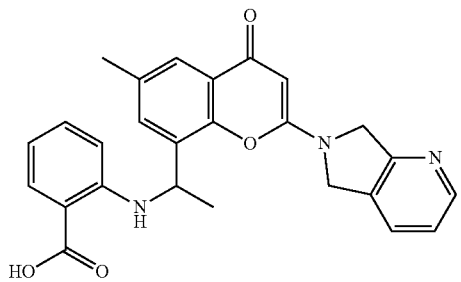 | 442 |
| 101 | 2-[1-[2-(1,3-Dihydropyrrolo[3,4-c]pyridin-2-yl)-6-methyl-4-oxo-chromen-8-yl]ethylamino]benzoic acid | 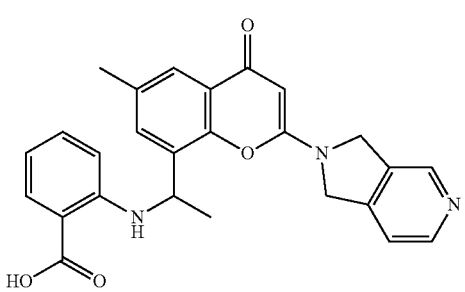 | 442 |

TABLE 8-continued

| Example # | Chemical Name | Structure | ES/MS m/z (M + H) & Chiral Method |
|---|---|---|---|
| 102 | 2-[1-[2-(5,7-Dihydropyrrolo[3,4-d]pyrimidin-6-yl)-6-methyl-4-oxo-chromen-8-yl]ethylamino]benzoic acid | 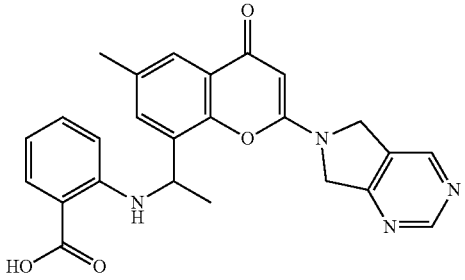 [SMILES: Cc1cc(C(C)Nc2ccccc2C(=O)O)c2oc(N3Cc4cncnc4C3)cc(=O)c2c1] | 443 |
| 103 | 2-[1-[6-Methyl-4-oxo-2-[4-(trifluoromethyl)isoindolin-2-yl]chromen-8-yl]ethylamino]benzoic acid | 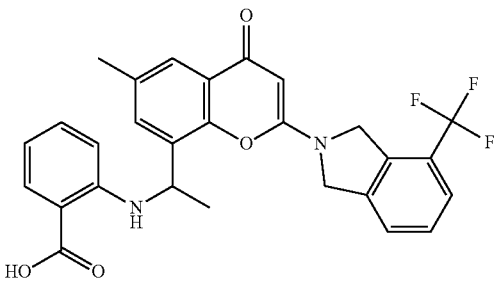 [SMILES: Cc1cc(C(C)Nc2ccccc2C(=O)O)c2oc(N3Cc4cccc(C(F)(F)F)c4C3)cc(=O)c2c1] | 509 |
| 104 | 2-[1-[2-(4-Fluoroisoindolin-2-yl)-6-methyl-4-oxo-chromen-8-yl]ethylamino]benzoic acid | 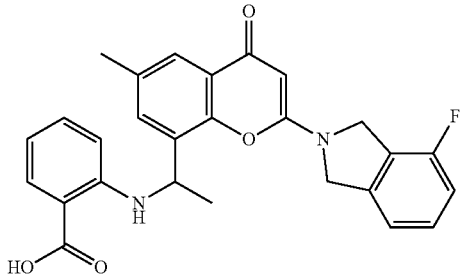 | 459 |
| 105 | 2-[1-[2-(5-Fluoroisoindolin-2-yl)-6-methyl-4-oxo-chromen-8-yl]ethylamino]benzoic acid | 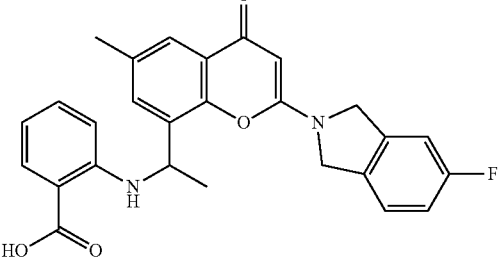 | 459 |
| 106 | 2-[1-[2-[2-[4-(Difluoromethoxy)phenyl]morpholin-4-yl]-6-methyl-4-oxo-chromen-8-yl]ethylamino]benzoic acid | 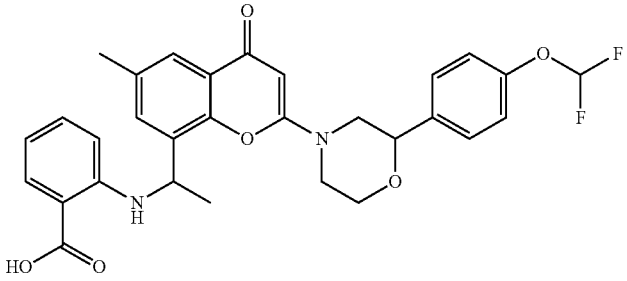 [SMILES: Cc1cc(C(C)Nc2ccccc2C(=O)O)c2oc(N3CCOC(c4ccc(OC(F)F)cc4)C3)cc(=O)c2c1] | 551 |

TABLE 8-continued

| Example # | Chemical Name | Structure | ES/MS m/z (M + H) & Chiral Method |
|---|---|---|---|
| 107 | 2-[1-[2-[2-(Dimethylcarbamoyl)spiro[4,7-dihydropyrazolo[5,1-c][1,4]oxazine-6,4'-piperidine]-1'-yl]-6-methyl-4-oxo-chromen-8-yl]ethylamino]benzoic acid | 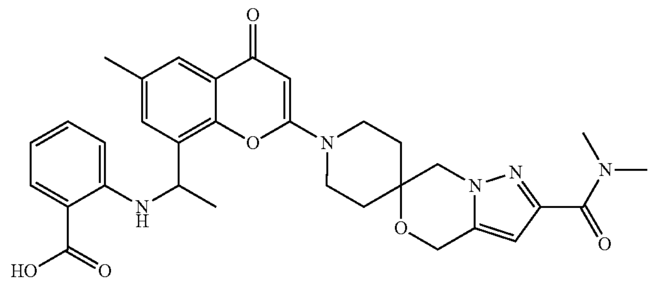 [SMILES: Cc1cc(C(C)Nc2ccccc2C(=O)O)c2oc(N3CCC4(CC3)Cn3nc(C(=O)N(C)C)cc3CO4)cc(=O)c2c1] | 586 |
| 108 | 2-[1-[6-Methyl-2-[(1R,5R)-1-methyl-2-azabicyclo[3.2.0]heptan-2-yl]-4-oxo-chromen-8-yl]ethylamino]benzoic acid | 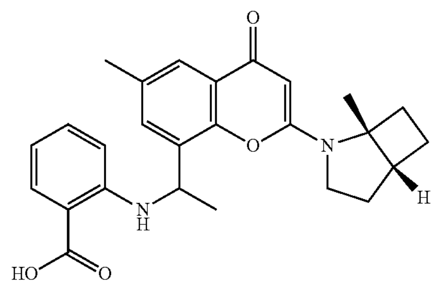 [SMILES: Cc1cc(C(C)Nc2ccccc2C(=O)O)c2oc(N3CC[C@H]4CC[C@]43C)cc(=O)c2c1] | 433 |
| 109 | 2-[1-[6-Methyl-2-(6-oxa-2-azaspiro[4.5]decan-2-yl)-4-oxo-chromen-8-yl]ethylamino]benzoic acid | 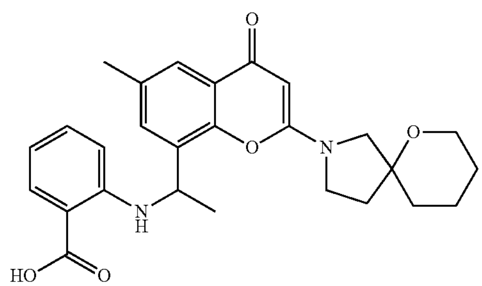 [SMILES: Cc1cc(C(C)Nc2ccccc2C(=O)O)c2oc(N3CCC4(CCCCO4)C3)cc(=O)c2c1] | 463 |
| 110 | 2-[1-[2-(3-Cyano-1-piperidyl)-6-methyl-4-oxo-chromen-8-yl]ethylamino]benzoic acid | 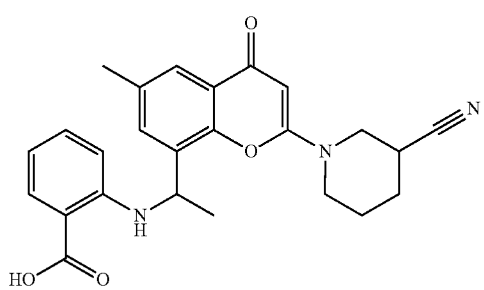 [SMILES: Cc1cc(C(C)Nc2ccccc2C(=O)O)c2oc(N3CCCC(C#N)C3)cc(=O)c2c1] | 432 |
| 111 | 2-[1-[2-(4-Methoxy-2-azabicyclo[2.1.1]hexan-2-yl)-6-methyl-4-oxo-chromen-8-yl]ethylamino]benzoic acid, Isomer 1 | 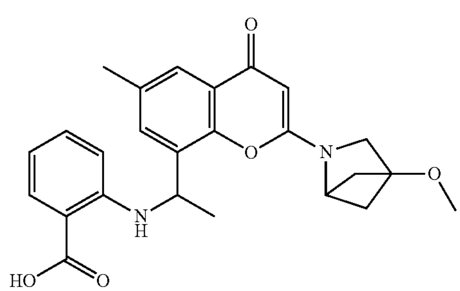 [SMILES: COC12CC(C1)N(c1cc(=O)c3cc(C)cc(C(C)Nc4ccccc4C(=O)O)c3o1)C2] | 435 X, 38 |

TABLE 8-continued

| Example # | Chemical Name | Structure | ES/MS m/z (M + H) & Chiral Method |
|---|---|---|---|
| 112 | 2-[1-[2-(4-Methoxy-2-azabicyclo[2.1.1]hexan-2-yl)-6-methyl-4-oxo-chromen-8-yl]ethylamino]benzoic acid, Isomer 2 | 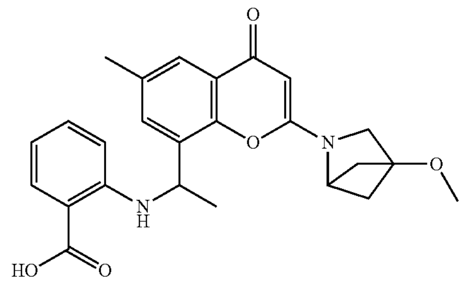 [SMILES: COC12CC(C1)N(c1cc(=O)c3cc(C)cc(C(C)Nc4ccccc4C(=O)O)c3o1)C2] | 435 X, 38 |
| 113 | 2-[1-[2-[(3aS,7aS)-3,3a,4,6,7,7a-Hexahydro-2H-furo[3,2-c]pyridin-5-yl]-6-methyl-4-oxo-chromen-8-yl]ethylamino]benzoic acid | 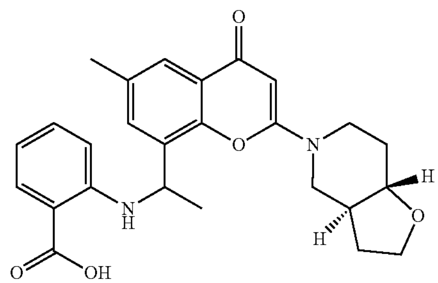 [SMILES: Cc1cc(C(C)Nc2ccccc2C(=O)O)c2oc(N3CC[C@@H]4OCC[C@H]4C3)cc(=O)c2c1] | 449 |
| 114 | 2-[1-[2-(2-Isopropylmorpholin-4-yl)-6-methyl-4-oxo-chromen-8-yl]ethylamino]benzoic acid | 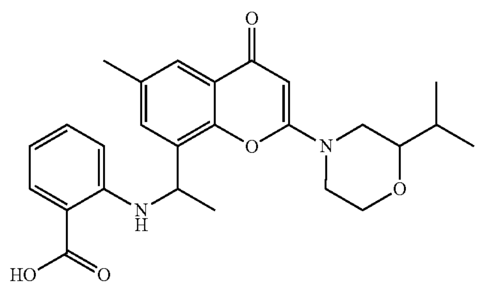 [SMILES: Cc1cc(C(C)Nc2ccccc2C(=O)O)c2oc(N3CCOC(C(C)C)C3)cc(=O)c2c1] | 451 |
| 115 | 2-[1-[2-[4-[(6-Methoxypyrimidin-4-yl)amino]-1-piperidyl]-6-methyl-4-oxo-chromen-8-yl]ethylamino]benzoic acid | 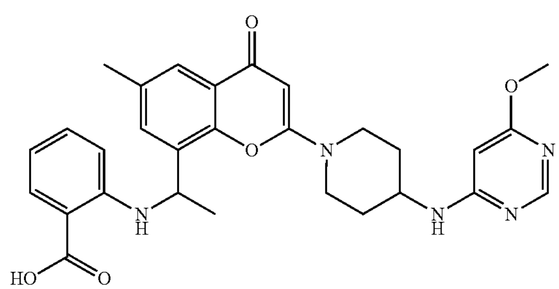 [SMILES: COc1cc(NC2CCN(c3cc(=O)c4cc(C)cc(C(C)Nc5ccccc5C(=O)O)c4o3)CC2)ncn1] | 530 |
| 116 | 2-[1-[6-Methyl-2-(4-methyl-4-morpholino-1-piperidyl)-4-oxo-chromen-8-yl]ethylamino]benzoic acid | 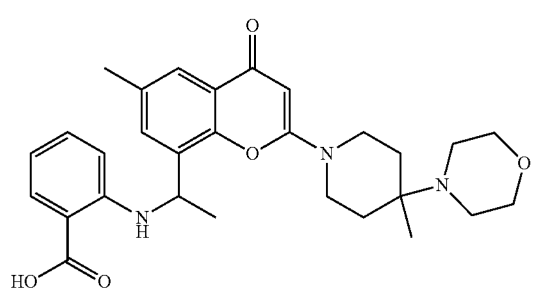 [SMILES: Cc1cc(C(C)Nc2ccccc2C(=O)O)c2oc(N3CCC(C)(N4CCOCC4)CC3)cc(=O)c2c1] | 506 |

TABLE 8-continued

| Example # | Chemical Name | Structure | ES/MS m/z (M + H) & Chiral Method |
|---|---|---|---|
| 117 | 2-[1-[2-(1,1-Dioxo-1,4-thiazinan-4-yl)-6-methyl-4-oxo-chromen-8-yl]ethylamino]benzoic acid | 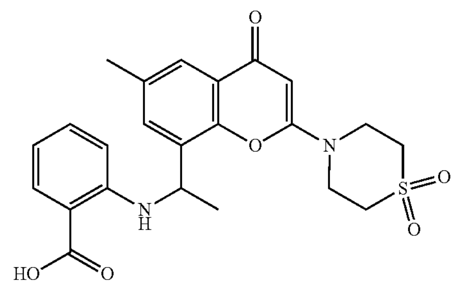 [SMILES: Cc1cc(C(C)Nc2ccccc2C(=O)O)c2oc(N3CCS(=O)(=O)CC3)cc(=O)c2c1] | 457 |
| 118 | 2-[1-[6-Methyl-4-oxo-2-(1-oxo-1,4-thiazinan-4-yl)chromen-8-yl]ethylamino]benzoic acid | 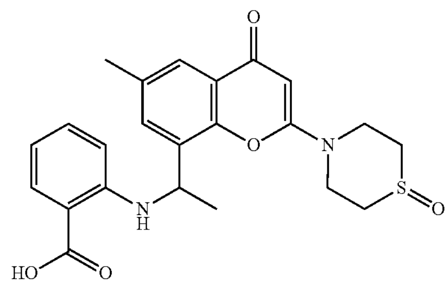 [SMILES: Cc1cc(C(C)Nc2ccccc2C(=O)O)c2oc(N3CCS(=O)CC3)cc(=O)c2c1] | 441 |
| 119 | 2-[1-[2-(5-Cyanoisoindolin-2-yl)-6-methyl-4-oxo-chromen-8-yl]ethylamino]benzoic acid, Isomer 1 | 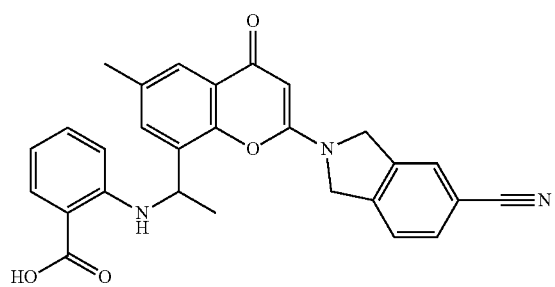 [SMILES: Cc1cc(C(C)Nc2ccccc2C(=O)O)c2oc(N3Cc4ccc(C#N)cc4C3)cc(=O)c2c1] | 466 J, 18 |
| 120 | 2-[1-[2-(5-Cyanoisoindolin-2-yl)-6-methyl-4-oxo-chromen-8-yl]ethylamino]benzoic acid, Isomer 2 | 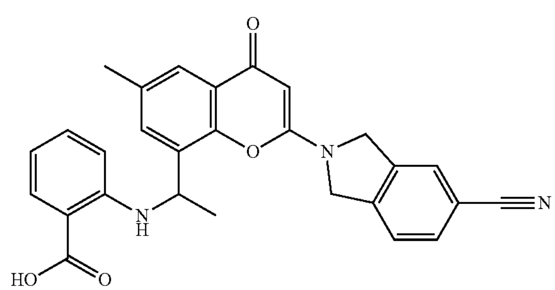 | 466 J, 18 |
| 121 | 2-[1-[6-Methyl-4-oxo-2-[2-[4-(trifluoromethyl)phenyl]morpholin-4-yl]chromen-8-yl]ethylamino]benzoic acid | 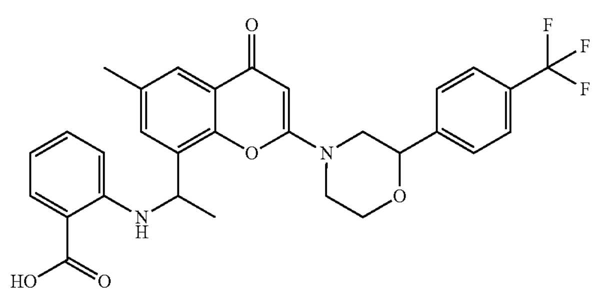 [SMILES: Cc1cc(C(C)Nc2ccccc2C(=O)O)c2oc(N3CCOC(c4ccc(C(F)(F)F)cc4)C3)cc(=O)c2c1] | 553 |

TABLE 8-continued

| Example # | Chemical Name | Structure | ES/MS m/z (M + H) & Chiral Method |
|---|---|---|---|
| 122 | 2-[1-[6-Methyl-2-[2-(2-methylpyrazol-3-yl)morpholin-4-yl]-4-oxo-chromen-8-yl]ethylamino]benzoic acid | 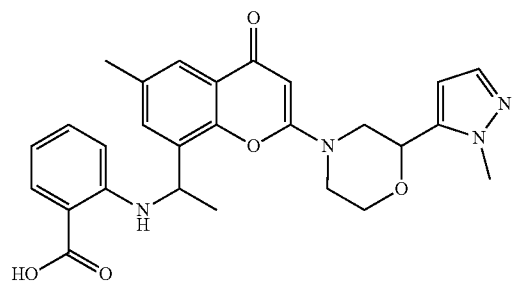 [SMILES: Cc1cc(C(C)Nc2ccccc2C(=O)O)c2oc(N3CCOC(c4ccnn4C)C3)cc(=O)c2c1] | 489 |
| 123 | 2-[1-[2-(5-Fluoroisoindolin-2-yl)-6-methyl-4-oxo-chromen-8-yl]ethylamino]benzoic acid, Isomer 1 | 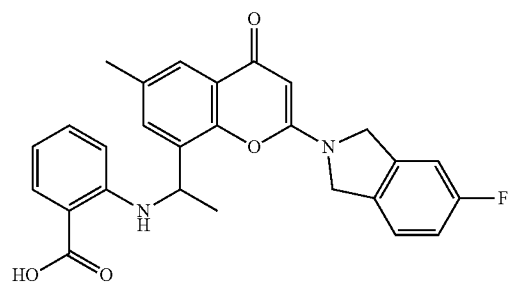 | 459 |
| 124 | 2-[1-[2-(5-Fluoroisoindolin-2-yl)-6-methyl-4-oxo-chromen-8-yl]ethylamino]benzoic acid, Isomer 2 | 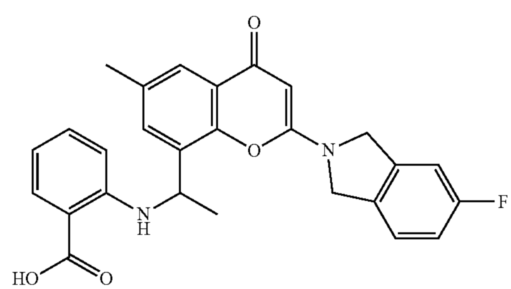 | 459 |
| 125 | 2-[1-[2-(5-Cyanoisoindolin-2-yl)-6-methyl-4-oxo-chromen-8-yl]ethylamino]benzoic acid | 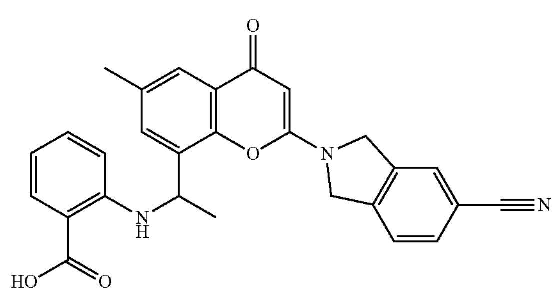 [SMILES: Cc1cc(C(C)Nc2ccccc2C(=O)O)c2oc(N3Cc4ccc(C#N)cc4C3)cc(=O)c2c1] | 466 |

[a] Used LiOH—H$_2$O instead of NaOH as the base.

Example 126: 2-[1-[2-(Ethylamino)-6-methyl-4-oxo-chromen-8-yl]ethylamino]benzoic acid

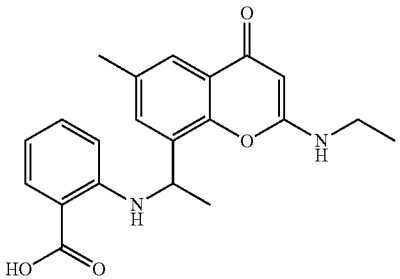 [SMILES: CCNc1cc(=O)c2cc(C)cc(C(C)Nc3ccccc3C(=O)O)c2o1]

A mixture of 2-[1-(2-ethylsulfinyl-6-methyl-4-oxo-chromen-8-yl)ethylamino]benzoic acid (30 mg, 0.075 mmol), ethanamine (25 mg, 0.30 mmol, HCl) and DIPEA (68 mg, 0.53 mmol) in DCM (2 mL) was stirred at 35° C. for 20 h. The mixture was diluted with water (10 mL) and DCM (20 mL), adjusted to pH=4 with HCl (aq 1 M), and extracted with DCM (20 mL). The extract was dried over anhydrous $Na_2SO_4$, filtered, concentrated and purified by preparative HPLC to give 2-[1-[2-(ethylamino)-6-methyl-4-oxo-chromen-8-yl]ethylamino]benzoic acid as a solid (11 mg, 40%). $^1$H NMR (400 MHz, DMSO-$d_6$) δ ppm 1.21 (t, J=7.2 Hz, 3H), 1.56 (d, J=6.8 Hz, 3H), 2.28 (s, 3H), 3.26-3.29 (m, 2H), 5.10-5.13 (m, 1H), 5.25 (s, 1H), 6.43 (d, J=8.8 Hz, 1H), 6.54 (t, J=7.6 Hz, 1H), 7.22-7.26 (m, 1H), 7.32 (d, J=2.0 Hz, 1H), 7.58 (d, J=1.2 Hz, 1H), 7.80 (dd, J=8.0, 1.6 Hz, 1H), 8.08 (s, 1H), 8.37 (d, J=6.4 Hz, 1H), 12.77 (br s, 1H). MS ES+ m/z 367 [M+H]$^+$.

The following compounds in Table 9 were prepared essentially as described for 2-[1-[2-(ethyl amino)-6-methyl-4-oxo-chromen-8-yl]ethylamino]benzoic acid. If the Example was purified with chiral SFC, the chiral column and eluent are listed in the final column (see Tables 4 and 5).

TABLE 9

| Example # | Chemical Name | Structure | ES/MS m/z (M + H) & Chiral Method |
|---|---|---|---|
| 127 | 2-[1-[2-(4-Methoxycarbonylpiperazin-1-yl)-6-methyl-4-oxo-chromen-8-yl]ethylamino]benzoic acid, Isomer 1 | 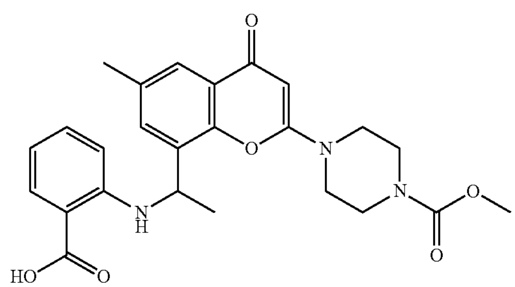 | 466 T, 35 |
| 128 | 2-[1-[2-(4-Methoxycarbonylpiperazin-1-yl)-6-methyl-4-oxo-chromen-8-yl]ethylamino]benzoic acid, Isomer 2 | 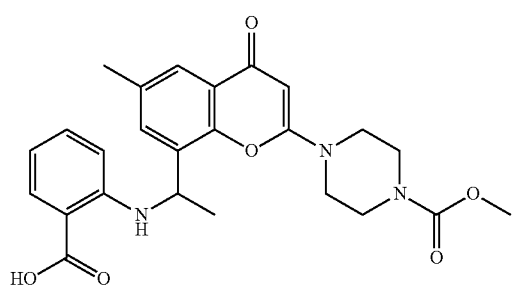 | 466 T, 35 |
| 129 | 2-[1-[2-(4,4-Difluoro-1-piperidyl)-6-methyl-4-oxo-chromen-8-yl]ethylamino]benzoic acid, Isomer 1 | 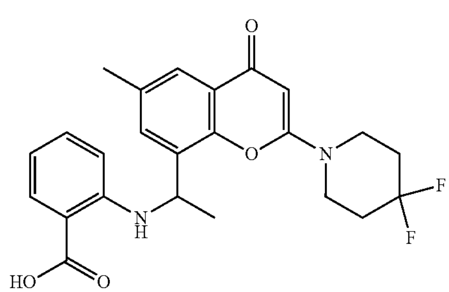 [SMILES: Cc1cc(C(C)Nc2ccccc2C(=O)O)c2oc(N3CCC(F)(F)CC3)cc(=O)c2c1] | 443 U, 5 |

TABLE 9-continued

| Example # | Chemical Name | Structure | ES/MS m/z (M + H) & Chiral Method |
|---|---|---|---|
| 130 | 2-[1-[2-(4,4-Difluoro-1-piperidyl)-6-methyl-4-oxo-chromen-8-yl]ethylamino]benzoic acid, Isomer 2 | 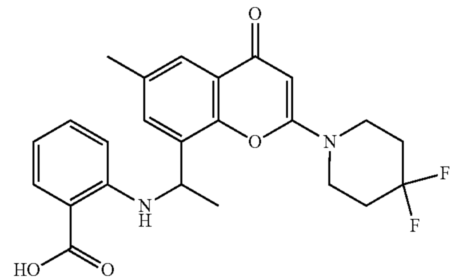 [SMILES: Cc1cc(C(C)Nc2ccccc2C(=O)O)c2oc(N3CCC(F)(F)CC3)cc(=O)c2c1] | 443 U, 5 |
| 131 | 2-[1-[2-(3-Cyanoazetidin-1-yl)-6-methyl-4-oxo-chromen-8-yl]ethylamino]benzoic acid | 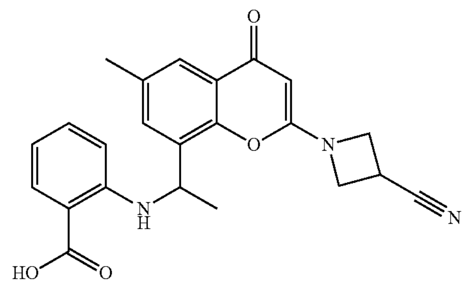 [SMILES: Cc1cc(C(C)Nc2ccccc2C(=O)O)c2oc(N3CC(C#N)C3)cc(=O)c2c1] | 404 |
| 132 | 2-[1-[2-(6,8-Dihydro-[1,3]dioxolo[4,5-e]isoindol-7-yl)-6-methyl-4-oxo-chromen-8-yl]ethylamino]benzoic acid, Isomer 1 | 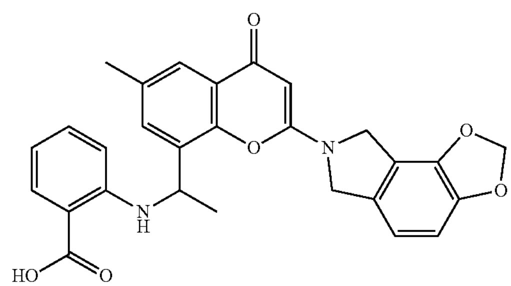 [SMILES: Cc1cc(C(C)Nc2ccccc2C(=O)O)c2oc(N3Cc4ccc5c(c4C3)OCO5)cc(=O)c2c1] | 485 J, 35 |
| 133 | 2-[1-[2-(6,8-Dihydro-[1,3]dioxolo[4,5-e]isoindol-7-yl)-6-methyl-4-oxo-chromen-8-yl]ethylamino]benzoic acid, Isomer 2 | 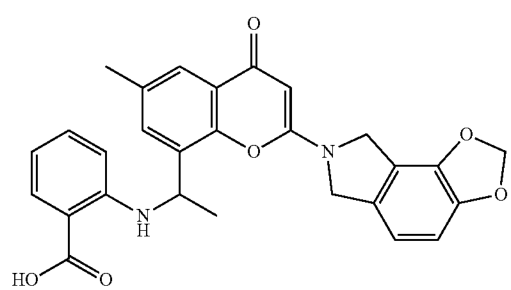 [SMILES: Cc1cc(C(C)Nc2ccccc2C(=O)O)c2oc(N3Cc4ccc5c(c4C3)OCO5)cc(=O)c2c1] | 485 J, 35 |
| 134 | 2-[1-[2-(3,3-Dimethyl-3a,4,6,6a-tetrahydro-2H-furo[3,4-b]pyrrol-1-yl)-6-methyl-4-oxo-chromen-8-yl]ethylamino]benzoic acid, Isomer 1 | 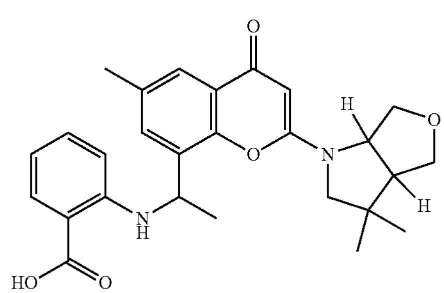 [SMILES: Cc1cc(C(C)Nc2ccccc2C(=O)O)c2oc(N3CC(C)(C)C4COCC43)cc(=O)c2c1] | 463 AF, 38 then AG, 36 |

TABLE 9-continued

| Example # | Chemical Name | Structure | ES/MS m/z (M + H) & Chiral Method |
|---|---|---|---|
| 135 | 2-[1-[2-(3,3-Dimethyl-3a,4,6,6a-tetrahydro-2H-furo[3,4-b]pyrrol-1-yl)-6-methyl-4-oxo-chromen-8-yl]ethylamino]benzoic acid, Isomer 2 | 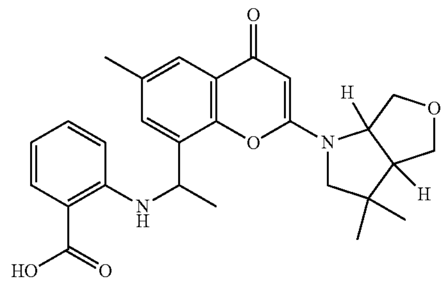 [SMILES: Cc1cc(C(C)Nc2ccccc2C(=O)O)c2oc(N3CC(C)(C)C4COCC43)cc(=O)c2c1] | 463 AF, 38 then AG, 36 |
| 136 | 2-[1-[2-(3,3-Dimethyl-3a,4,6,6a-tetrahydro-2H-furo[3,4-b]pyrrol-1-yl)-6-methyl-4-oxo-chromen-8-yl]ethylamino]benzoic acid, Isomer 3 | 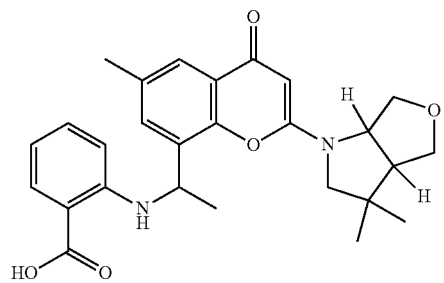 [SMILES: Cc1cc(C(C)Nc2ccccc2C(=O)O)c2oc(N3CC(C)(C)C4COCC43)cc(=O)c2c1] | 463 AF, 38 then AG, 36 |
| 137 | 2-[1-[2-(3,3-Dimethyl-3a,4,6,6a-tetrahydro-2H-furo[3,4-b]pyrrol-1-yl)-6-methyl-4-oxo-chromen-8-yl]ethylamino]benzoic acid, Isomer 4 | 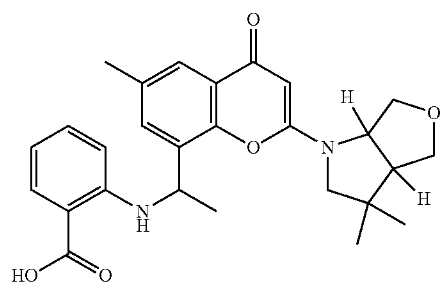 [SMILES: Cc1cc(C(C)Nc2ccccc2C(=O)O)c2oc(N3CC(C)(C)C4COCC43)cc(=O)c2c1] | 463 AF, 38 then AG, 36 |
| 138 | 2-[1-(6-Methyl-4-oxo-2-spiro[3a,4,6,6a-tetrahydro-2H-furo[3,4-b]pyrrole-3,1'-cyclobutane]-1-yl-chromen-8-yl)ethylamino]benzoic acid, Isomer 1 | 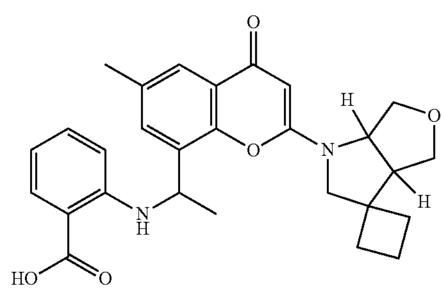 [SMILES: Cc1cc(C(C)Nc2ccccc2C(=O)O)c2oc(N3CC4(CCC4)C4COCC43)cc(=O)c2c1] | 475 U, 28 then Y, 36 |
| 139 | 2-[1-(6-Methyl-4-oxo-2-spiro[3a,4,6,6a-tetrahydro-2H-furo[3,4-b]pyrrole-3,1'-cyclobutane]-1-yl-chromen-8-yl)ethylamino]benzoic acid, Isomer 2 | 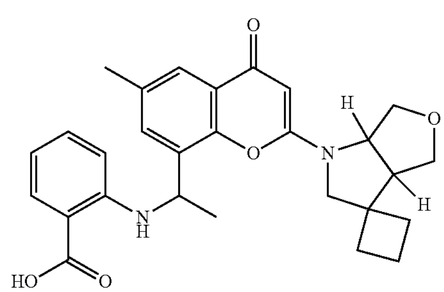 [SMILES: Cc1cc(C(C)Nc2ccccc2C(=O)O)c2oc(N3CC4(CCC4)C4COCC43)cc(=O)c2c1] | 475 U, 28 then Y, 36 |

TABLE 9-continued

| Example # | Chemical Name | Structure | ES/MS m/z (M + H) & Chiral Method |
|---|---|---|---|
| 140 | 2-[1-(6-Methyl-4-oxo-2-spiro[3a,4,6,6a-tetrahydro-2H-furo[3,4-b]pyrrole-3,1'-cyclobutane]-1-yl-chromen-8-yl)ethylamino]benzoic acid, Isomer 3 | 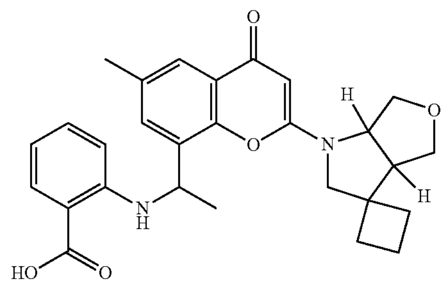 [SMILES: Cc1cc(C(C)Nc2ccccc2C(=O)O)c2oc(N3CC4(CCC4)C4COCC43)cc(=O)c2c1] | 475 U, 28 then Y, 36 |
| 141 | 2-[1-(6-Methyl-4-oxo-2-spiro[3a,4,6,6a-tetrahydro-2H-furo[3,4-b]pyrrole-3,1'-cyclobutane]-1-yl-chromen-8-yl)ethylamino]benzoic acid, Isomer 4 | 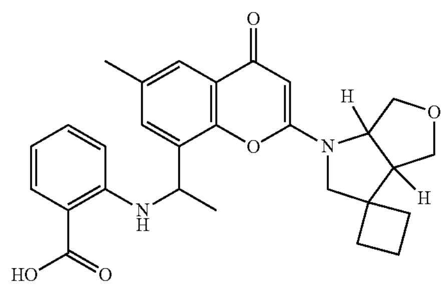 [SMILES: Cc1cc(C(C)Nc2ccccc2C(=O)O)c2oc(N3CC4(CCC4)C4COCC43)cc(=O)c2c1] | 475 U, 28 then Y, 36 |
| 142 | 2-[1-[2-(2-Azabicyclo[4.2.0]octan-2-yl)-6-methyl-4-oxo-chromen-8-yl]ethylamino]benzoic acid, Isomer 1 | 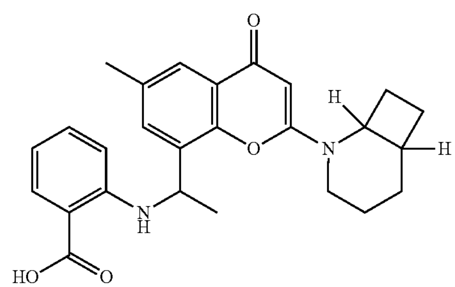 [SMILES: Cc1cc(C(C)Nc2ccccc2C(=O)O)c2oc(N3CCCC4CCC43)cc(=O)c2c1] | 433 J, 18 |
| 143 | 2-[1-[2-(2-Azabicyclo[4.2.0]octan-2-yl)-6-methyl-4-oxo-chromen-8-yl]ethylamino]benzoic acid, Isomer 2 | 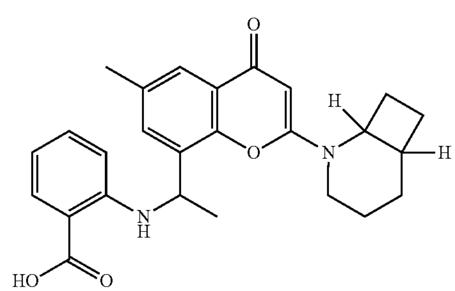 [SMILES: Cc1cc(C(C)Nc2ccccc2C(=O)O)c2oc(N3CCCC4CCC43)cc(=O)c2c1] | 433 J, 18 |
| 144 | 2-[1-[2-(3,3-Difluoroazetidin-1-yl)-6-methyl-4-oxo-chromen-8-yl]ethylamino]benzoic acid | 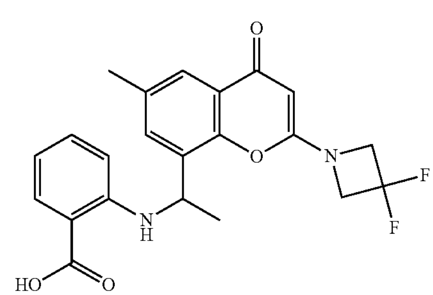 [SMILES: Cc1cc(C(C)Nc2ccccc2C(=O)O)c2oc(N3CC(F)(F)C3)cc(=O)c2c1] | 415 |

TABLE 9-continued

| Example # | Chemical Name | Structure | ES/MS m/z (M + H) & Chiral Method |
|---|---|---|---|
| 145 | 2-[1-[6-Methyl-2-[4-methyl-4-(trifluoromethyl)-1-piperidyl]-4-oxo-chromen-8-yl]ethylamino]benzoic acid, Isomer 1 | 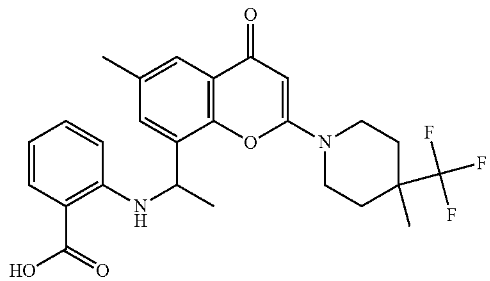 [SMILES: Cc1cc(C(C)Nc2ccccc2C(=O)O)c2oc(N3CCC(C)(C(F)(F)F)CC3)cc(=O)c2c1] | 489 Y, 35 |
| 146 | 2-[1-[6-Methyl-2-[4-methyl-4-(trifluoromethyl)-1-piperidyl]-4-oxo-chromen-8-yl]ethylamino]benzoic acid, Isomer 2 | 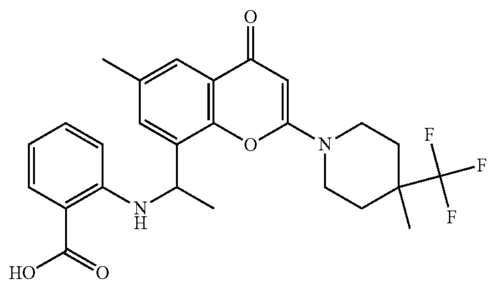 [SMILES: Cc1cc(C(C)Nc2ccccc2C(=O)O)c2oc(N3CCC(C)(C(F)(F)F)CC3)cc(=O)c2c1] | 489 Y, 35 |
| 147 | 2-[1-[2-[4-Methoxy-4-(trifluoromethyl)-1-piperidyl]-6-methyl-4-oxo-chromen-8-yl]ethylamino]benzoic acid, Isomer 1 | 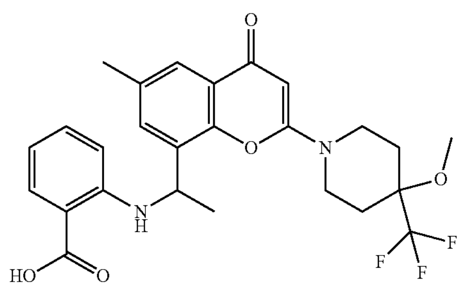 [SMILES: COC1(C(F)(F)F)CCN(c2cc(=O)c3cc(C)cc(C(C)Nc4ccccc4C(=O)O)c3o2)CC1] | 505 Y, 5 |
| 148 | 2-[1-[2-[4-Methoxy-4-(trifluoromethyl)-1-piperidyl]-6-methyl-4-oxo-chromen-8-yl]ethylamino]benzoic acid, Isomer 2 | 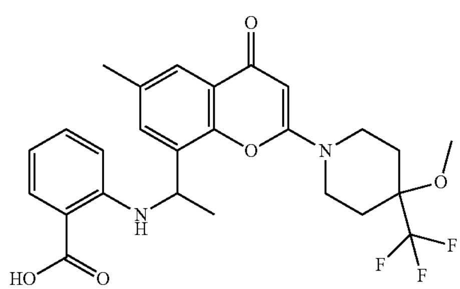 [SMILES: COC1(C(F)(F)F)CCN(c2cc(=O)c3cc(C)cc(C(C)Nc4ccccc4C(=O)O)c3o2)CC1] | 505 Y, 5 |
| 149 | 2-[1-[2-(3,4-Dihydro-1H-isoquinolin-2-yl)-6-methyl-4-oxo-chromen-8-yl]ethylamino]benzoic acid, Isomer 1 | 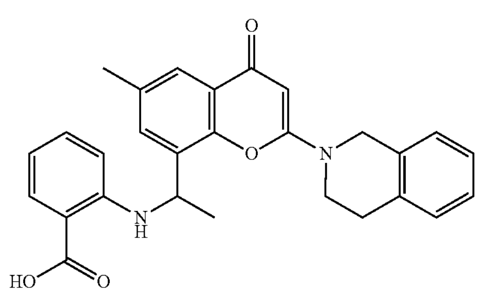 [SMILES: Cc1cc(C(C)Nc2ccccc2C(=O)O)c2oc(N3CCc4ccccc4C3)cc(=O)c2c1] | 455 W, 28 |

TABLE 9-continued

| Example # | Chemical Name | Structure | ES/MS m/z (M + H) & Chiral Method |
|---|---|---|---|
| 150 | 2-[1-[2-(3,4-Dihydro-1H-isoquinolin-2-yl)-6-methyl-4-oxo-chromen-8-yl]ethylamino]benzoic acid, Isomer 2 | 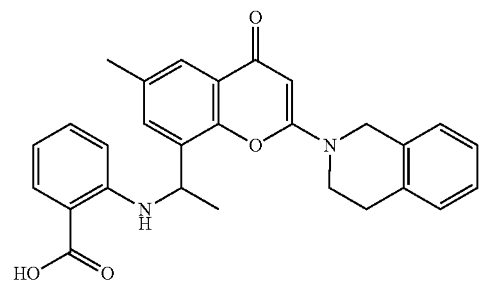 [SMILES: Cc1cc(C(C)Nc2ccccc2C(=O)O)c2oc(N3CCc4ccccc4C3)cc(=O)c2c1] | 455 W, 28 |
| 151 | 2-[1-[6-Methyl-2-(1,4-oxazepan-4-yl)-4-oxo-chromen-8-yl]ethylamino]benzoic acid | 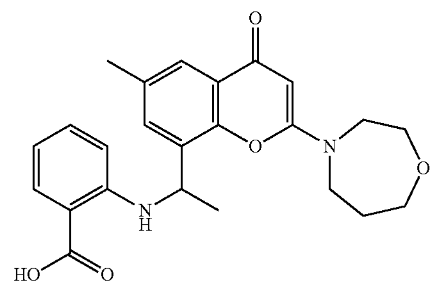 [SMILES: Cc1cc(C(C)Nc2ccccc2C(=O)O)c2oc(N3CCCOCC3)cc(=O)c2c1] | 423 |
| 152 | 2-[1-[2-[4-(Cyclobutoxy)-1-piperidyl]-6-methyl-4-oxo-chromen-8-yl]ethylamino]benzoic acid, Isomer 1 | 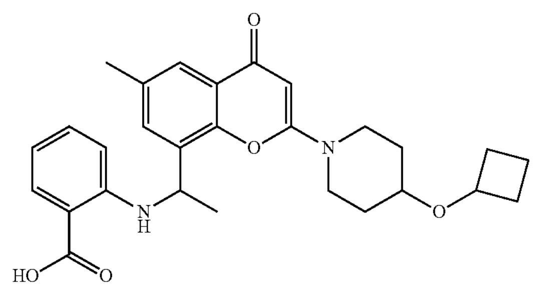 [SMILES: Cc1cc(C(C)Nc2ccccc2C(=O)O)c2oc(N3CCC(OC4CCC4)CC3)cc(=O)c2c1] | 477 X, 35 |
| 153 | 2-[1-[2-[4-(Cyclobutoxy)-1-piperidyl]-6-methyl-4-oxo-chromen-8-yl]ethylamino]benzoic acid, Isomer 2 | 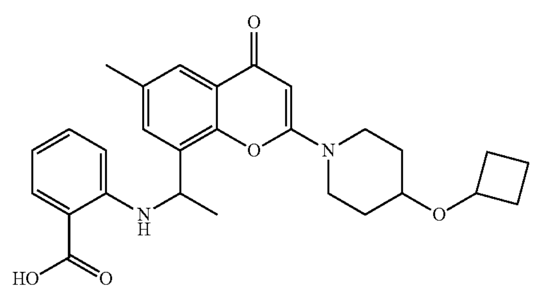 [SMILES: Cc1cc(C(C)Nc2ccccc2C(=O)O)c2oc(N3CCC(OC4CCC4)CC3)cc(=O)c2c1] | 477 X, 35 |
| 154 | 2-[1-[6-Methyl-4-oxo-2-(4-phenoxy-1-piperidyl)chromen-8-yl]ethylamino]benzoic acid | 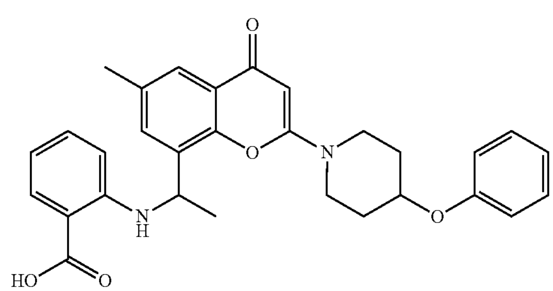 [SMILES: Cc1cc(C(C)Nc2ccccc2C(=O)O)c2oc(N3CCC(Oc4ccccc4)CC3)cc(=O)c2c1] | 499 |

TABLE 9-continued

| Example # | Chemical Name | Structure | ES/MS m/z (M + H) & Chiral Method |
|---|---|---|---|
| 155 | 2-[1-[6-Methyl-4-oxo-2-(2-oxo-1,7-diazaspiro[3.5]nonan-7-yl)chromen-8-yl]ethylamino]benzoic acid | 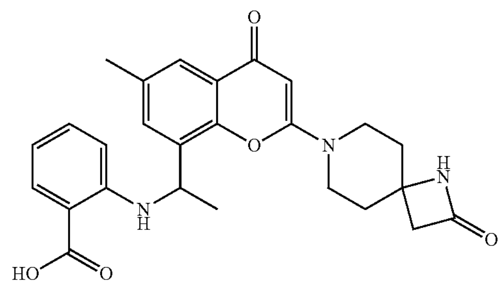 [SMILES: Cc1cc(C(C)Nc2ccccc2C(=O)O)c2oc(N3CCC4(CC3)CC(=O)N4)cc(=O)c2c1] | 462 |
| 156 | 2-[1-[2-(3-Methoxycarbonyl-3,9-diazaspiro[5.5]undecan-9-yl)-6-methyl-4-oxo-chromen-8-yl]ethylamino]benzoic acid | 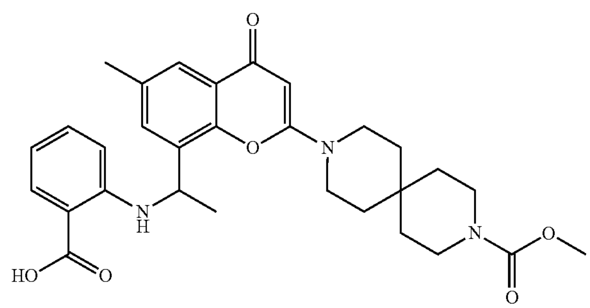 [SMILES: COC(=O)N1CCC2(CC1)CCN(c1cc(=O)c3cc(C)cc(C(C)Nc4ccccc4C(=O)O)c3o1)CC2] | 534 |
| 157 | 2-[1-[6-Methyl-4-oxo-2-(2-oxospiro[1H-pyrido[2,3-d][1,3]oxazine-4,4'-piperidine]-1'-yl)chromen-8-yl]ethylamino]benzoic acid | 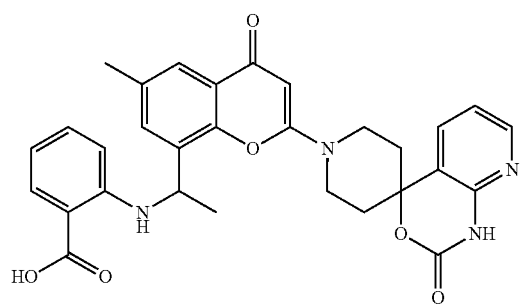 [SMILES: Cc1cc(C(C)Nc2ccccc2C(=O)O)c2oc(N3CCC4(CC3)OC(=O)Nc3ncccc34)cc(=O)c2c1] | 541 |
| 158 | 2-[1-[6-Methyl-4-oxo-2-[4-(1H-pyrrolo[2,3-b]pyridin-3-yl)-1-piperidyl]chromen-8-yl]ethylamino]benzoic acid | 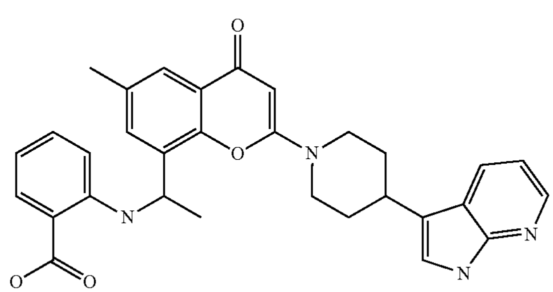 [SMILES: Cc1cc(C(C)Nc2ccccc2C(=O)O)c2oc(N3CCC(c4c[nH]c5ncccc45)CC3)cc(=O)c2c1] | 523 |
| 159 | 2-[1-(6-Methyl-4-oxo-2-spiro[4,5-dihydro-2H-1,5-benzoxazepine-3,4'-piperidine]-1'-yl-chromen-8-yl)ethylamino]benzoic acid | 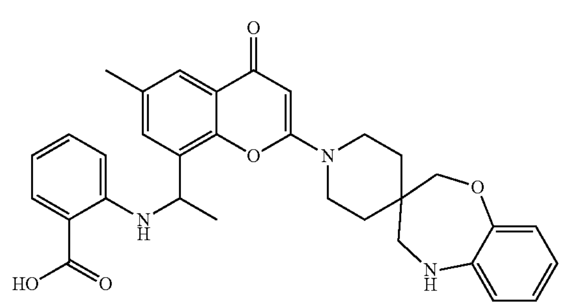 [SMILES: Cc1cc(C(C)Nc2ccccc2C(=O)O)c2oc(N3CCC4(CC3)CNc3ccccc3OC4)cc(=O)c2c1] | 540 |

TABLE 9-continued

| Example # | Chemical Name | Structure | ES/MS m/z (M + H) & Chiral Method |
|---|---|---|---|
| 160 | 2-[1-[2-(6,8-Dihydro-5H-imidazo[1,2-a]pyrazin-7-yl)-6-methyl-4-oxo-chromen-8-yl]ethylamino]benzoic acid | 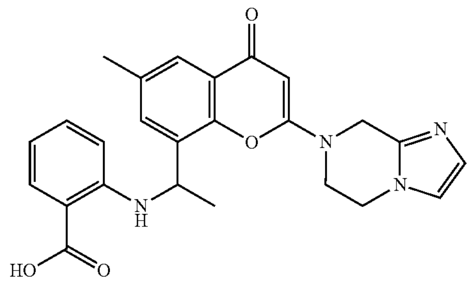 [SMILES: Cc1cc(C(C)Nc2ccccc2C(=O)O)c2oc(N3CCn4ccnc4C3)cc(=O)c2c1] | 445 |
| 161 | 2-[1-[2-(3,4-Dihydro-1H-benzofuro[3,2-c]pyridin-2-yl)-6-methyl-4-oxo-chromen-8-yl]ethylamino]benzoic acid | 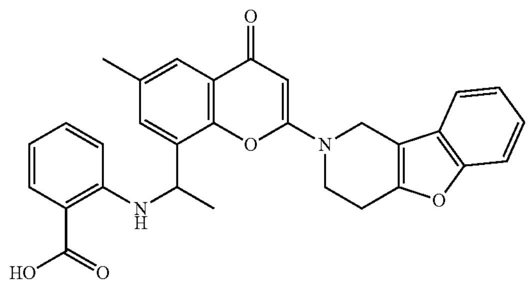 [SMILES: Cc1cc(C(C)Nc2ccccc2C(=O)O)c2oc(N3CCc4oc5ccccc5c4C3)cc(=O)c2c1] | 495 |
| 162 | 2-[1-[2-(6,7-Dihydro-4H-furo[3,2-c]pyridin-5-yl)-6-methyl-4-oxo-chromen-8-yl]ethylamino]benzoic acid | 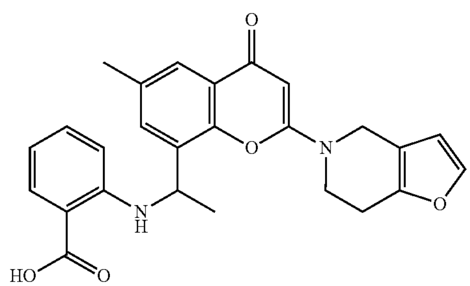 [SMILES: Cc1cc(C(C)Nc2ccccc2C(=O)O)c2oc(N3CCc4occc4C3)cc(=O)c2c1] | 445 |
| 163 | 2-[1-[2-(6,8-Dihydro-5H-[1,2,4]triazolo[4,3-a]pyrazin-7-yl)-6-methyl-4-oxo-chromen-8-yl]ethylamino]benzoic acid | 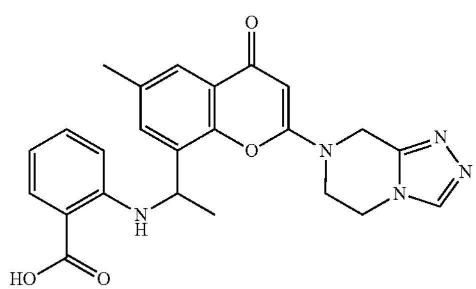 [SMILES: Cc1cc(C(C)Nc2ccccc2C(=O)O)c2oc(N3CCn4cnnc4C3)cc(=O)c2c1] | 446 |
| 164 | 2-[1-[6-Methyl-2-(3-methyl-6,8-dihydro-5H-[1,2,4]triazolo[4,3-a]pyrazin-7-yl)-4-oxo-chromen-8-yl]ethylamino]benzoic acid | 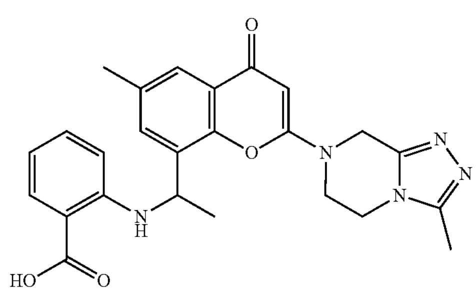 [SMILES: Cc1cc(C(C)Nc2ccccc2C(=O)O)c2oc(N3CCn4c(C)nnc4C3)cc(=O)c2c1] | 460 |

TABLE 9-continued

| Example # | Chemical Name | Structure | ES/MS m/z (M + H) & Chiral Method |
|---|---|---|---|
| 165 | 2-[1-[2-(3-Cyclopropyl-6,8-dihydro-5H-[1,2,4]triazolo[4,3-a]pyrazin-7-yl)-6-methyl-4-oxo-chromen-8-yl]ethylamino]benzoic acid | 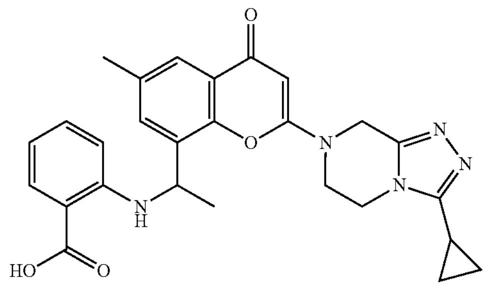 [SMILES: Cc1cc(C(C)Nc2ccccc2C(=O)O)c2oc(N3CCn4c(nnc4C4CC4)C3)cc(=O)c2c1] | 486 |
| 166 | 2-[1-[2-(3,3-Dimethylpyrrolidin-1-yl)-6-methyl-4-oxo-chromen-8-yl]ethylamino]benzoic acid | 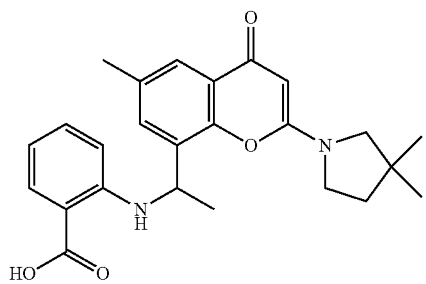 [SMILES: Cc1cc(C(C)Nc2ccccc2C(=O)O)c2oc(N3CCC(C)(C)C3)cc(=O)c2c1] | 421 |
| 167 | 2-[1-[2-(4-Chloro-1-piperidyl)-6-methyl-4-oxo-chromen-8-yl]ethylamino]benzoic acid, Isomer 1 | 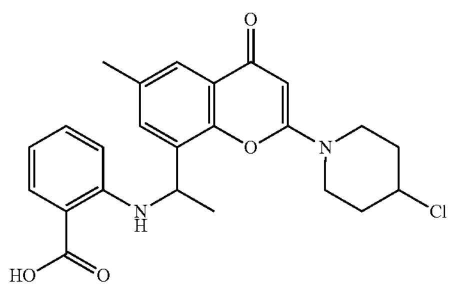 [SMILES: Cc1cc(C(C)Nc2ccccc2C(=O)O)c2oc(N3CCC(Cl)CC3)cc(=O)c2c1] | 441 |
| 168 | 2-[1-[2-(4-Chloro-1-piperidyl)-6-methyl-4-oxo-chromen-8-yl]ethylamino]benzoic acid, Isomer 2 | 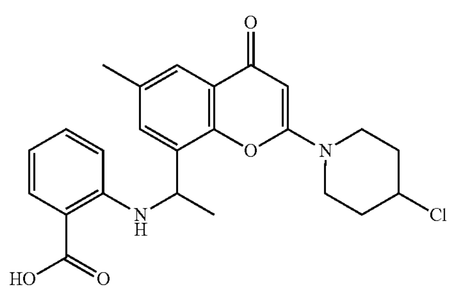 [SMILES: Cc1cc(C(C)Nc2ccccc2C(=O)O)c2oc(N3CCC(Cl)CC3)cc(=O)c2c1] | 441 |
| 169 | 2-[1-[2-[3-(Hydroxymethyl)-1-adamantyl]amino]-6-methyl-4-oxo-chromen-8-yl]ethylamino]benzoic acid | 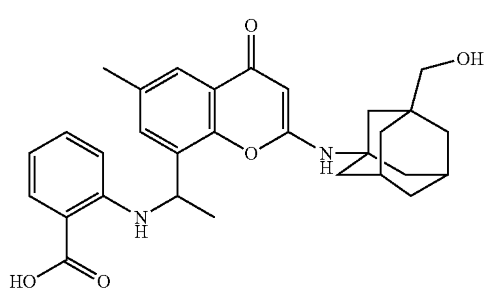 [SMILES: Cc1cc(C(C)Nc2ccccc2C(=O)O)c2oc(NC34CC5CC(CC(CO)(C5)C3)C4)cc(=O)c2c1] | 503 |

TABLE 9-continued

| Example # | Chemical Name | Structure | ES/MS m/z (M + H) & Chiral Method |
|---|---|---|---|
| 170 | 2-[1-[2-(4-Cyano-4-ethyl-1-piperidyl)-6-methyl-4-oxo-chromen-8-yl]ethylamino]benzoic acid | 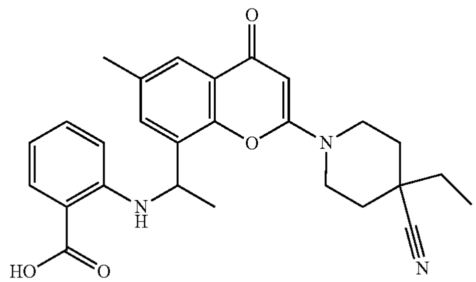 [SMILES: CCC1(C#N)CCN(c2cc(=O)c3cc(C)cc(C(C)Nc4ccccc4C(=O)O)c3o2)CC1] | 460 |
| 171 | 2-[1-[2-(3,4-Dihydro-1H-pyrrolo[1,2-a]pyrazin-2-yl)-6-methyl-4-oxo-chromen-8-yl]ethylamino]benzoic acid | 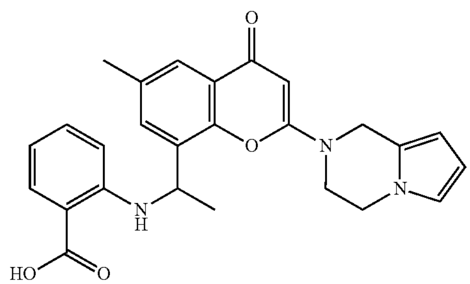 [SMILES: Cc1cc(C(C)Nc2ccccc2C(=O)O)c2oc(N3CCn4cccc4C3)cc(=O)c2c1] | 444 |
| 172 | 2-[1-[6-Methyl-2-(3-methyl-3-phenyl-azetidin-1-yl)-4-oxo-chromen-8-yl]ethylamino]benzoic acid 2,2,2-trifluoroacetic acid | 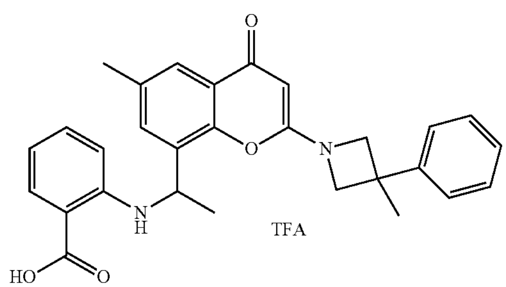 [SMILES: Cc1cc(C(C)Nc2ccccc2C(=O)O)c2oc(N3CC(C)(c4ccccc4)C3)cc(=O)c2c1] | 469 |
| 173 | 2-[1-[2-[3-(Methoxymethyl)-3-phenyl-azetidin-1-yl]-6-methyl-4-oxo-chromen-8-yl]ethylamino]benzoic acid | 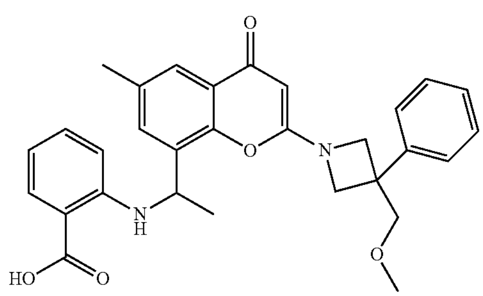 [SMILES: COCC1(c2ccccc2)CN(c2cc(=O)c3cc(C)cc(C(C)Nc4ccccc4C(=O)O)c3o2)C1] | 499 |
| 174 | 2-[1-[2-(3-Benzyl-3-methyl-azetidin-1-yl)-6-methyl-4-oxo-chromen-8-yl]ethylamino]benzoic acid | 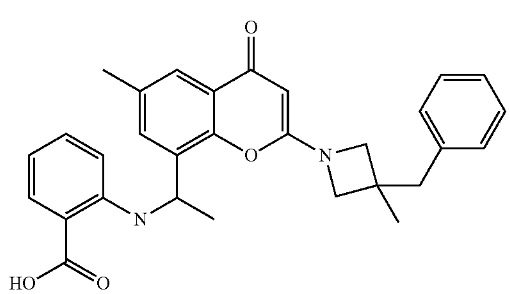 [SMILES: Cc1cc(C(C)Nc2ccccc2C(=O)O)c2oc(N3CC(C)(Cc4ccccc4)C3)cc(=O)c2c1] | 483 |

TABLE 9-continued

| Example # | Chemical Name | Structure | ES/MS m/z (M + H) & Chiral Method |
|---|---|---|---|
| 175 | 2-[1-[2-(1H-Indol-3-ylmethylamino)-6-methyl-4-oxo-chromen-8-yl]ethylamino]benzoic acid | 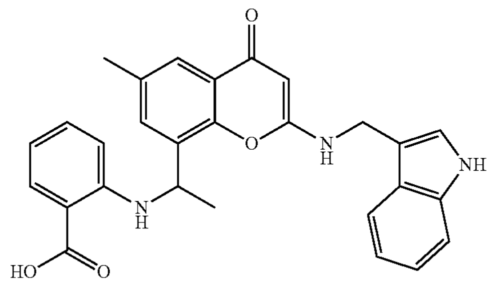 [SMILES: Cc1cc(C(C)Nc2ccccc2C(=O)O)c2oc(NCc3c[nH]c4ccccc34)cc(=O)c2c1] | 468 |
| 176 | 2-[1-[2-(1H-Indol-2-ylmethylamino)-6-methyl-4-oxo-chromen-8-yl]ethylamino]benzoic acid | 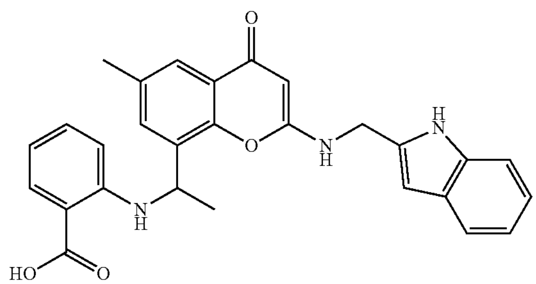 [SMILES: Cc1cc(C(C)Nc2ccccc2C(=O)O)c2oc(NCc3cc4ccccc4[nH]3)cc(=O)c2c1] | 468 |
| 177 | 2-[1-[2-(3-Azabicyclo[3.1.1]heptan-3-yl)-6-methyl-4-oxo-chromen-8-yl]ethylamino]benzoic acid 2,2,2-trifluoroacetic acid | 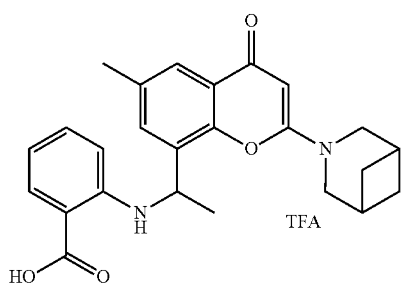 [SMILES: Cc1cc(C(C)Nc2ccccc2C(=O)O)c2oc(N3CC4CC(C4)C3)cc(=O)c2c1] | 419 |
| 178 | 2-[1-[2-(3-Carbamoyl-3-phenyl-azetidin-1-yl)-6-methyl-4-oxo-chromen-8-yl]ethylamino]benzoic acid 2,2,2-trifluoroacetic acid | 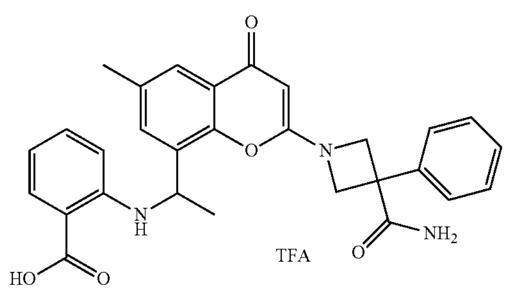 [SMILES: Cc1cc(C(C)Nc2ccccc2C(=O)O)c2oc(N3CC(C(N)=O)(c4ccccc4)C3)cc(=O)c2c1] | 498 |
| 179 | 2-[1-[6-Methyl-4-oxo-2-[(3S)-3-phenylpyrrolidin-1-yl]chromen-8-yl]ethylamino]benzoic acid 2,2,2-trifluoroacetic acid | 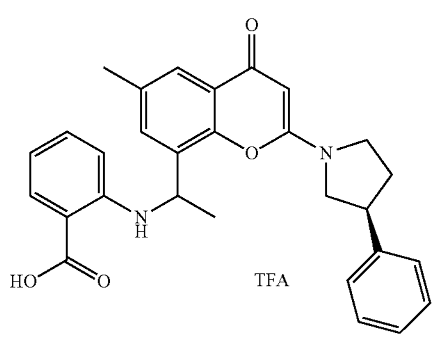 [SMILES: Cc1cc(C(C)Nc2ccccc2C(=O)O)c2oc(N3CC[C@@H](c4ccccc4)C3)cc(=O)c2c1] | 469 |

TABLE 9-continued

| Example # | Chemical Name | Structure | ES/MS m/z (M + H) & Chiral Method |
|---|---|---|---|
| 180 | 2-[1-[6-Methyl-4-oxo-2-[(3R)-3-phenylpyrrolidin-1-yl]chromen-8-yl]ethylamino]benzoic acid 2,2,2-trifluoroacetic acid | 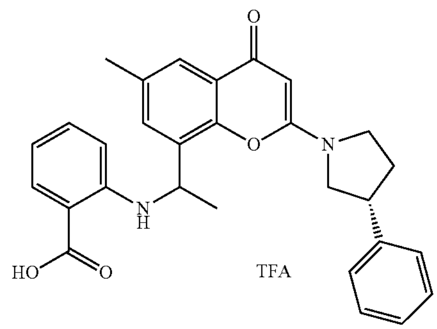 [SMILES: Cc1cc(C(C)Nc2ccccc2C(=O)O)c2oc(N3CC[C@H](c4ccccc4)C3)cc(=O)c2c1] | 469 |
| 181 | 2-[1-[2-(6,6-Difluoro-3-azabicyclo[3.1.1]heptan-3-yl)-6-methyl-4-oxo-chromen-8-yl]ethylamino]benzoic acid 2,2,2-trifluoroacetic acid | 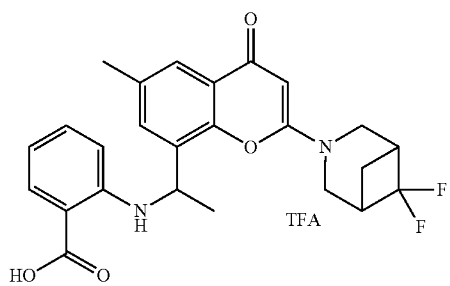 [SMILES: Cc1cc(C(C)Nc2ccccc2C(=O)O)c2oc(N3CC4CC(C3)C4(F)F)cc(=O)c2c1] | 455 |
| 182 | 2-[1-[2-(6-Azabicyclo[3.1.1]heptan-6-yl)-6-methyl-4-oxo-chromen-8-yl]ethylamino]benzoic acid 2,2,2-trifluoroacetic acid | 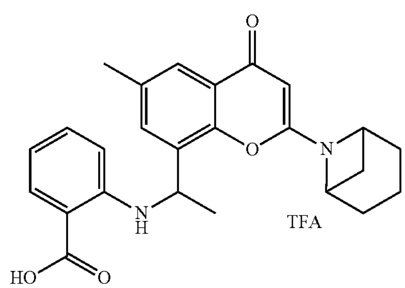 [SMILES: Cc1cc(C(C)Nc2ccccc2C(=O)O)c2oc(N3C4CCCC3C4)cc(=O)c2c1] | 419 |
| 183 | 2-[1-[2-[(3R,4S)-3,4-Difluoropyrrolidin-1-yl]-6-methyl-4-oxo-chromen-8-yl]ethylamino]benzoic acid 2,2,2-trifluoroacetic acid | 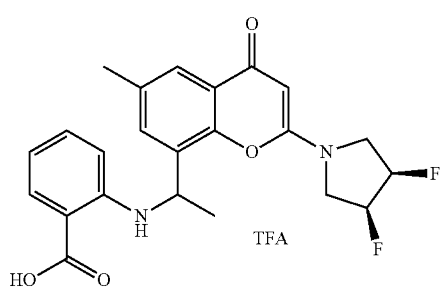 [SMILES: Cc1cc(C(C)Nc2ccccc2C(=O)O)c2oc(N3C[C@@H](F)[C@@H](F)C3)cc(=O)c2c1] | 429 |
| 184 | 2-[1-[2-[(3S)-3-Fluoro-1-piperidyl]-6-methyl-4-oxo-chromen-8-yl]ethylamino]benzoic acid 2,2,2-trifluoroacetic acid | 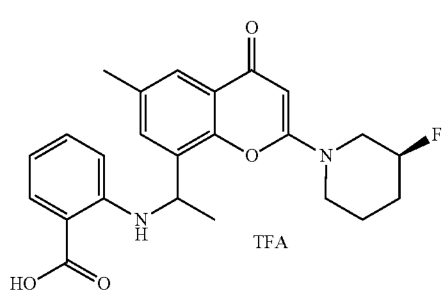 [SMILES: Cc1cc(C(C)Nc2ccccc2C(=O)O)c2oc(N3CCC[C@H](F)C3)cc(=O)c2c1] | 425 |

TABLE 9-continued

| Example # | Chemical Name | Structure | ES/MS m/z (M + H) & Chiral Method |
|---|---|---|---|
| 185 | 2-[1-[2-[(3R)-3-Fluoro-1-piperidyl]-6-methyl-4-oxo-chromen-8-yl]ethylamino]benzoic acid 2,2,2-trifluoroacetic acid | 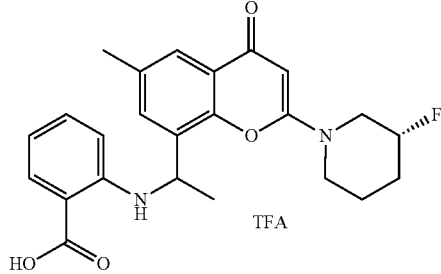 [SMILES: Cc1cc(C(C)Nc2ccccc2C(=O)O)c2oc(N3CCC[C@@H](F)C3)cc(=O)c2c1] | 425 |
| 186 | 2-[1-[2-[(3R,4R)-3,4-Difluoropyrrolidin-1-yl]-6-methyl-4-oxo-chromen-8-yl]ethylamino]benzoic acid 2,2,2-trifluoroacetic acid | 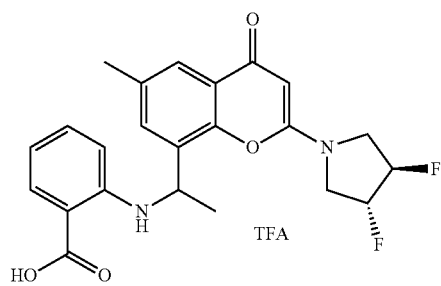 | 429 |
| 187 | 2-[1-[6-Methyl-4-oxo-2-[(3R)-3-(trifluoromethyl)pyrrolidin-1-yl]chromen-8-yl]ethylamino]benzoic acid 2,2,2-trifluoroacetic acid | 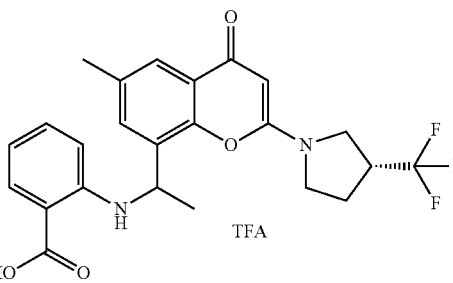 | 461 |
| 188 | 2-[1-[6-Methyl-4-oxo-2-[(3S)-3-(trifluoromethyl)-1-piperidyl]chromen-8-yl]ethylamino]benzoic acid 2,2,2-trifluoroacetic acid | 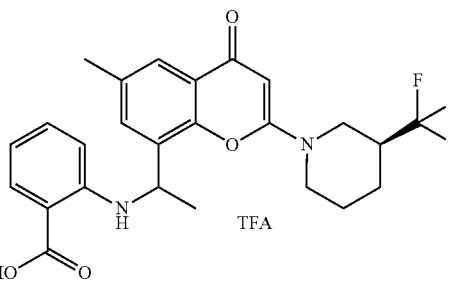 | 475 |
| 189 | 2-[1-[2-[3-(1,1-Difluoroethyl)azetidin-1-yl]-6-methyl-4-oxo-chromen-8-yl]ethylamino]benzoic acid 2,2,2-trifluoroacetic acid | 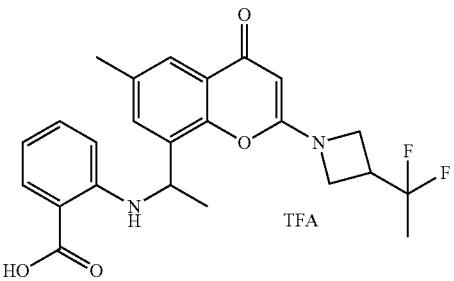 [SMILES: Cc1cc(C(C)Nc2ccccc2C(=O)O)c2oc(N3CC(C(C)(F)F)C3)cc(=O)c2c1] | 443 |

TABLE 9-continued

| Example # | Chemical Name | Structure | ES/MS m/z (M + H) & Chiral Method |
|---|---|---|---|
| 190 | 2-[1-[2-(11-Azatricyclo[6.2.1.02,7]undeca-2(7),3,5-trien-11-yl)-6-methyl-4-oxo-chromen-8-yl]ethylamino]benzoic acid 2,2,2-trifluoroacetic acid, Isomer 1 | 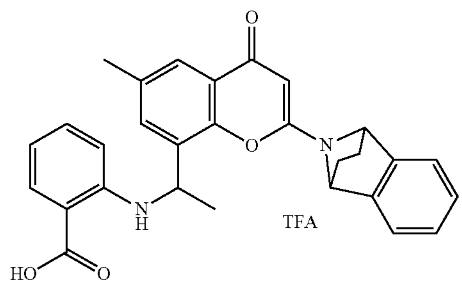 [SMILES: Cc1cc(C(C)Nc2ccccc2C(=O)O)c2oc(N3C4CCC3c3ccccc34)cc(=O)c2c1] | 467 |
| 191 | 2-[1-[2-[3-(4-Methoxyphenyl)azetidin-1-yl]-6-methyl-4-oxo-chromen-8-yl]ethylamino]benzoic acid 2,2,2-trifluoroacetic acid, Isomer 1 | 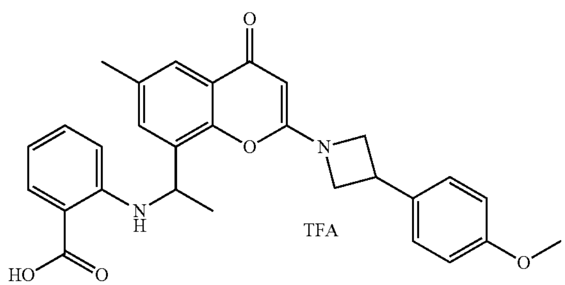 [SMILES: COc1ccc(C2CN(c3cc(=O)c4cc(C)cc(C(C)Nc5ccccc5C(=O)O)c4o3)C2)cc1] | 485 |
| 192 | 2-[1-[2-[3-[(6-Methoxy-3-pyridyl)amino]-3-methyl-azetidin-1-yl]-6-methyl-4-oxo-chromen-8-yl]ethylamino]benzoic acid 2,2,2-trifluoroacetic acid, Isomer 1 | 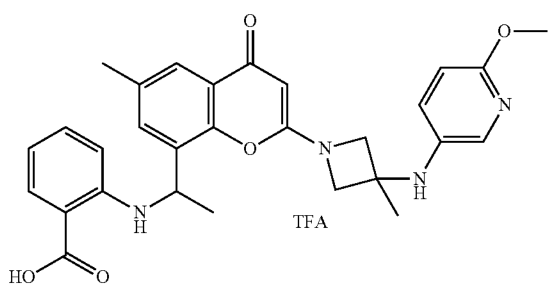 [SMILES: COc1ccc(NC2(C)CN(c3cc(=O)c4cc(C)cc(C(C)Nc5ccccc5C(=O)O)c4o3)C2)cn1] | 515 |
| 193 | 2-[1-[2-(3-Anilino-3-methyl-azetidin-1-yl)-6-methyl-4-oxo-chromen-8-yl]ethylamino]benzoic acid 2,2,2-trifluoroacetic acid, Isomer 1 | 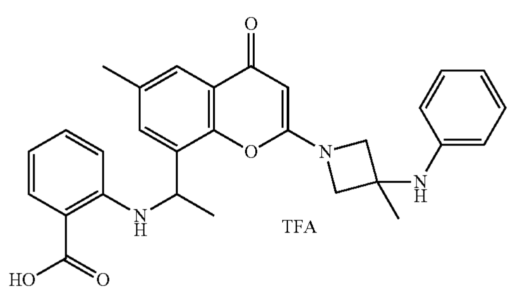 [SMILES: Cc1cc(C(C)Nc2ccccc2C(=O)O)c2oc(N3CC(C)(Nc4ccccc4)C3)cc(=O)c2c1] | 484 |
| 194 | 2-[1-[6-Methyl-4-oxo-2-[3-(4-pyridyl)pyrrolidin-1-yl]chromen-8-yl]ethylamino]benzoic acid 2,2,2-trifluoroacetic acid, Isomer 1 | 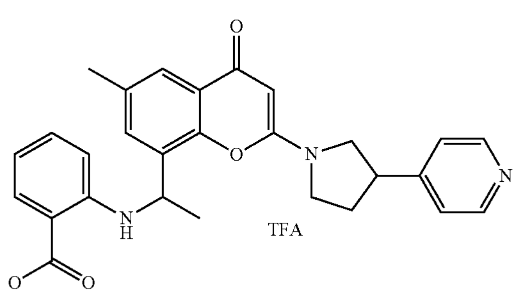 [SMILES: Cc1cc(C(C)Nc2ccccc2C(=O)O)c2oc(N3CCC(c4ccncc4)C3)cc(=O)c2c1] | 470 |

TABLE 9-continued

| Example # | Chemical Name | Structure | ES/MS m/z (M + H) & Chiral Method |
|---|---|---|---|
| 195 | 2-[1-[6-Methyl-4-oxo-2-[3-(4-pyridyl)azetidin-1-yl]chromen-8-yl]ethylamino]benzoic acid 2,2,2-trifluoroacetic acid, Isomer 1 | 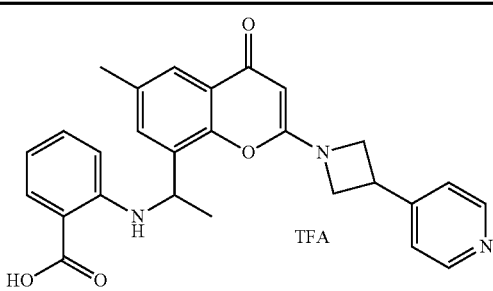 | 456 |
| 196 | 2-[1-[2-[3-(6-Methoxypyridazin-3-yl)oxy-3-methyl-azetidin-1-yl]-6-methyl-4-oxo-chromen-8-yl]ethylamino]benzoic acid 2,2,2-trifluoroacetic acid, Isomer 1 | 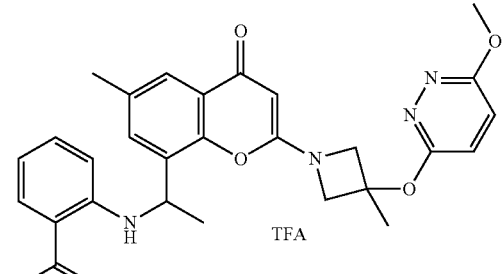 | 517 |
| 197 | 2-[1-[6-Methyl-2-(3-methyl-3-phenoxy-azetidin-1-yl)-4-oxo-chromen-8-yl]ethylamino]benzoic acid 2,2,2-trifluoroacetic acid, Isomer 1 | 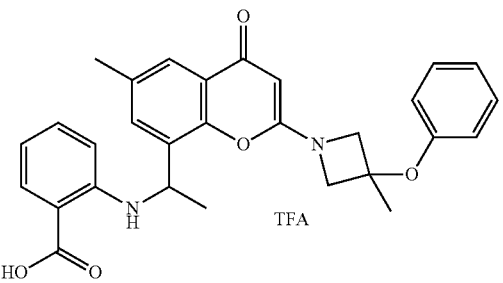 [SMILES: Cc1cc(C(C)Nc2ccccc2C(=O)O)c2oc(N3CC(C)(Oc4ccccc4)C3)cc(=O)c2c1] | 485 |
| 198 | 2-[1-[2-(3-Methoxy-3-phenyl-azetidin-1-yl)-6-methyl-4-oxo-chromen-8-yl]ethylamino]benzoic acid 2,2,2-trifluoroacetic acid, Isomer 1 | 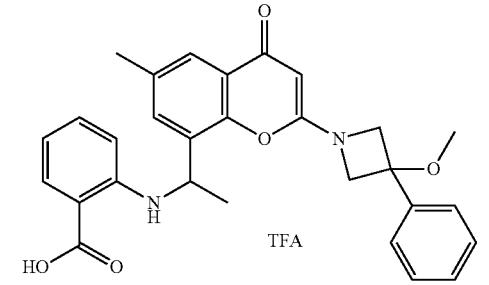 [SMILES: COC1(c2ccccc2)CN(c2cc(=O)c3cc(C)cc(C(C)Nc4ccccc4C(=O)O)c3o2)C1] | 485 |
| 199 | 2-[1-[2-[3-(Hydroxymethyl)-3-phenyl-pyrrolidin-1-yl]-6-methyl-4-oxo-chromen-8-yl]ethylamino]benzoic acid 2,2,2-trifluoroacetic acid, Isomer 1 | 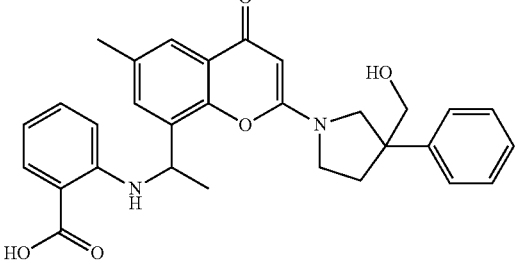 | 499 |

TABLE 9-continued

| Example # | Chemical Name | Structure | ES/MS m/z (M + H) & Chiral Method |
|---|---|---|---|
| 200 | 2-[1-[2-[4-(Hydroxymethyl)-4-phenyl-1-piperidyl-6-methyl-4-oxo-chromen-8-yl]ethylamino]benzoic acid 2,2,2-trifluoroacetic acid, Isomer 1 | 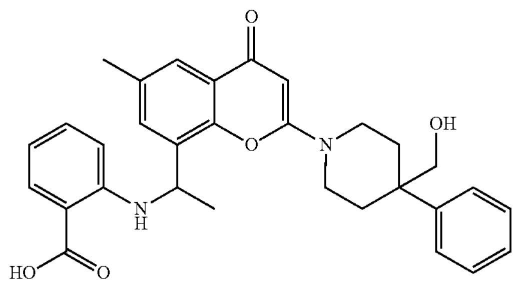 [SMILES: Cc1cc(C(C)Nc2ccccc2C(=O)O)c2oc(N3CCC(CO)(c4ccccc4)CC3)cc(=O)c2c1] | 513 |
| 201 | 2-[1-[2-(4-Hydroxy-4-phenyl-1-piperidyl)-6-methyl-4-oxo-chromen-8-yl]ethylamino]benzoic acid 2,2,2-trifluoroacetic acid, Isomer 1 | 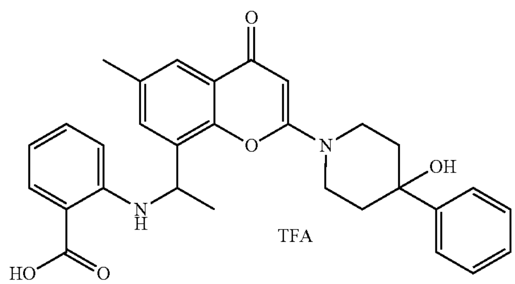 [SMILES: Cc1cc(C(C)Nc2ccccc2C(=O)O)c2oc(N3CCC(O)(c4ccccc4)CC3)cc(=O)c2c1] | 496 |
| 202 | 2-[1-[2-(3-Hydroxy-3-phenyl-azetidin-1-yl)-6-methyl-4-oxo-chromen-8-yl]ethylamino]benzoic acid 2,2,2-trifluoroacetic acid, Isomer 1 | 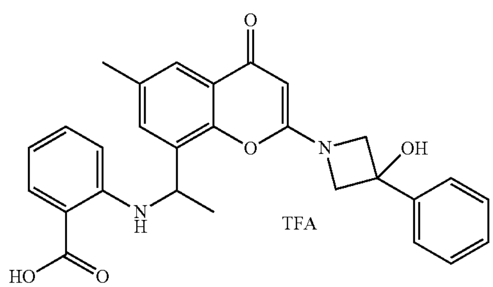 [SMILES: Cc1cc(C(C)Nc2ccccc2C(=O)O)c2oc(N3CC(O)(c4ccccc4)C3)cc(=O)c2c1] | 471 |
| 203 | 2-[1-[6-Methyl-4-oxo-2-(1-phenyl-1,6-diazaspiro[3.3]heptan-6-yl)chromen-8-yl]ethylamino]benzoic acid 2,2,2-trifluoroacetic acid, Isomer 1 | 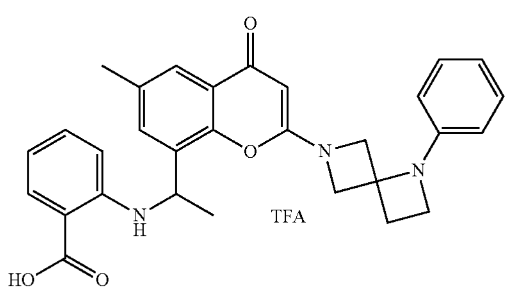 [SMILES: Cc1cc(C(C)Nc2ccccc2C(=O)O)c2oc(N3CC4(CCN4c4ccccc4)C3)cc(=O)c2c1] | 496 |
| 204 | 2-[1-[2-[4-(Hydroxymethyl)-4-methyl-1-piperidyl]-6-methyl-4-oxo-chromen-8-yl]ethylamino]benzoic acid, Isomer 1 | 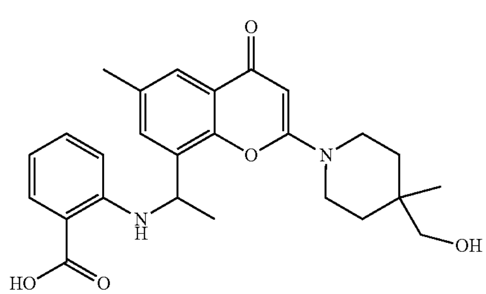 [SMILES: Cc1cc(C(C)Nc2ccccc2C(=O)O)c2oc(N3CCC(C)(CO)CC3)cc(=O)c2c1] | 451 |

TABLE 9-continued

| Example # | Chemical Name | Structure | ES/MS m/z (M + H) & Chiral Method |
|---|---|---|---|
| 205 | 2-[1-[6-Methyl-4-oxo-2-[3-(2-pyridyl)pyrrolidin-1-yl]chromen-8-yl]ethylamino]benzoic acid 2,2,2-trifluoroacetic acid, Isomer 1 | 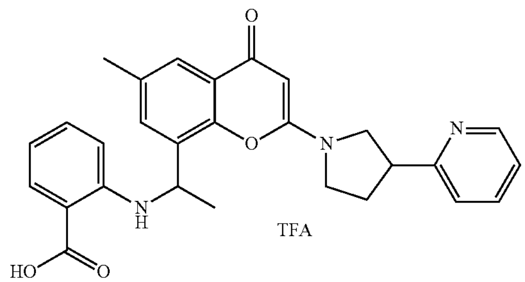 [SMILES: Cc1cc(C(C)Nc2ccccc2C(=O)O)c2oc(N3CCC(c4ccccn4)C3)cc(=O)c2c1] | 470 |
| 206 | 2-[1-[2-[4-Cyano-4-(4-fluorophenyl)-1-piperidyl]-4-oxo-chromen-8-yl]ethylamino]benzoic acid 2,2,2-trifuoroacetic acid, Isomer 1 | 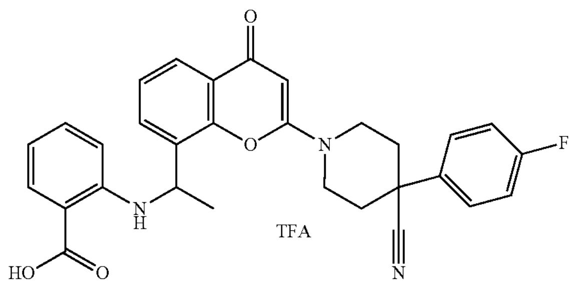 [SMILES: CC(Nc1ccccc1C(=O)O)c1cccc2c(=O)cc(N3CCC(C#N)(c4ccc(F)cc4)CC3)oc12] | 526 |
| 207 | 2-[1-[2-(4-Cyano-4-phenyl-1-piperidyl)-6-methyl-4-oxo-chromen-8-yl]ethylamino]benzoic acid 2,2,2-trifluoroacetic acid, Isomer 1 | 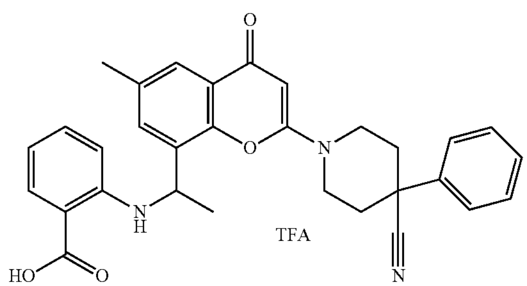 [SMILES: Cc1cc(C(C)Nc2ccccc2C(=O)O)c2oc(N3CCC(C#N)(c4ccccc4)CC3)cc(=O)c2c1] | 508 |
| 208 | 2-[1-[6-Methyl-4-oxo-2-(6-phenyl-3,6-diazabicyclo[3.1.1]heptan-3-yl)chromen-8-yl]ethylamino]benzoic acid 2,2,2-trifluoroacetic acid, Isomer 1 | 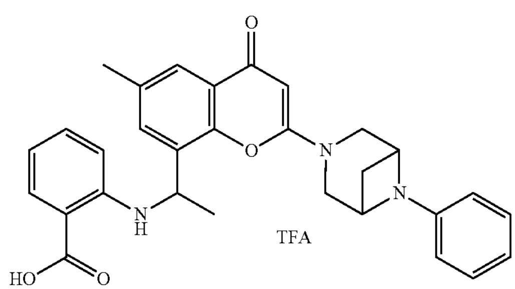 [SMILES: Cc1cc(C(C)Nc2ccccc2C(=O)O)c2oc(N3CC4CC(C3)N4c3ccccc3)cc(=O)c2c1] | 496 |
| 209 | 2-[1-[6-Methyl-2-[3-(1-methylpyrazol-3-yl)pyrrolidin-1-yl]-4-oxo-chromen-8-yl]ethylamino]benzoic acid 2,2,2-trifluoroacetic acid, Isomer 1 | 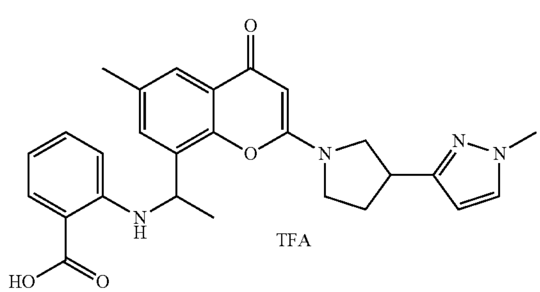 [SMILES: Cc1cc(C(C)Nc2ccccc2C(=O)O)c2oc(N3CCC(c4ccn(C)n4)C3)cc(=O)c2c1] | 473 |

TABLE 9-continued

| Example # | Chemical Name | Structure | ES/MS m/z (M + H) & Chiral Method |
|---|---|---|---|
| 210 | 2-[1-[6-Methyl-2-[3-(2-methylpyrazol-3-yl)pyrrolidin-1-yl]-4-oxo-chromen-8-yl]ethylamino]benzoic acid 2,2,2-trifluoroacetic acid, Isomer 1 | 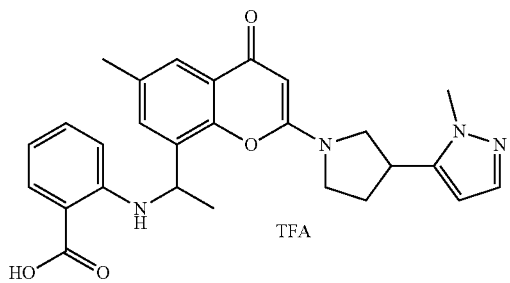 [SMILES: Cc1cc(C(C)Nc2ccccc2C(=O)O)c2oc(N3CCC(c4ccnn4C)C3)cc(=O)c2c1] | 473 |
| 211 | 2-[1-[2-[3-(2-Fluorophenyl)-3-methyl-azetidin-1-yl]-6-methyl-4-oxo-chromen-8-yl]ethylamino]benzoic acid 2,2,2-trifluoroacetic acid, Isomer 1 | 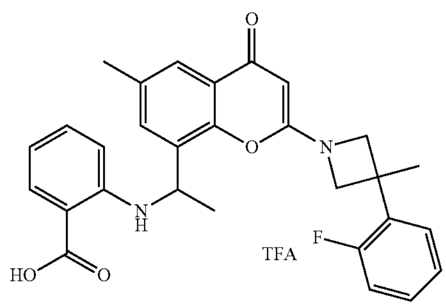 [SMILES: Cc1cc(C(C)Nc2ccccc2C(=O)O)c2oc(N3CC(C)(c4ccccc4F)C3)cc(=O)c2c1] | 487 |
| 212 | 2-[1-[2-(3-Ethyl-3-phenyl-azetidin-1-yl)-6-methyl-4-oxo-chromen-8-yl]ethylamino]benzoic acid 2,2,2-trifluoroacetic acid, Isomer 1 | 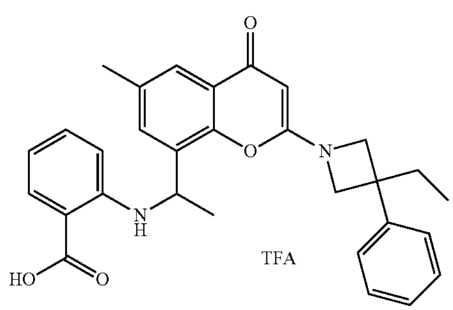 [SMILES: CCC1(c2ccccc2)CN(c2cc(=O)c3cc(C)cc(C(C)Nc4ccccc4C(=O)O)c3o2)C1] | 483 |
| 213 | 2-[1-[2-[3-(4-Fluorophenyl)-3-methyl-azetidin-1-yl]-6-methyl-4-oxo-chromen-8-yl]ethylamino]benzoic acid 2,2,2-trifluoroacetic acid, Isomer 1 | 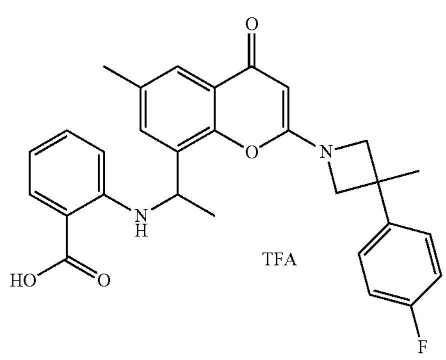 [SMILES: Cc1cc(C(C)Nc2ccccc2C(=O)O)c2oc(N3CC(C)(c4ccc(F)cc4)C3)cc(=O)c2c1] | 487 |

TABLE 9-continued

| Example # | Chemical Name | Structure | ES/MS m/z (M + H) & Chiral Method |
|---|---|---|---|
| 214 | 2-[1-[2-(3-Isopropyl-3-phenyl-azetidin-1-yl)-6-methyl-4-oxo-chromen-8-yl]ethylamino]benzoic acid 2,2,2-trifluoroacetic acid, Isomer 1 | 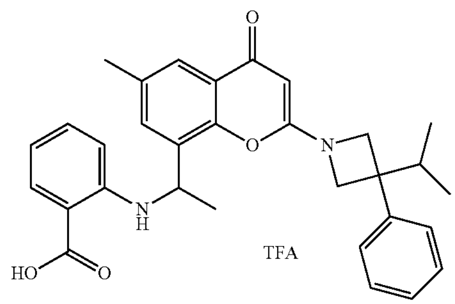 [SMILES: Cc1cc(C(C)Nc2ccccc2C(=O)O)c2oc(N3CC(c4ccccc4)(C(C)C)C3)cc(=O)c2c1] | 497 |
| 215 | 2-[1-[2-[3-(2,2-Difluoroethyl)-3-phenyl-azetidin-1-yl]-6-methyl-4-oxo-chromen-8-yl]ethylamino]benzoic acid 2,2,2-trifluoroacetic acid, Isomer 1 | 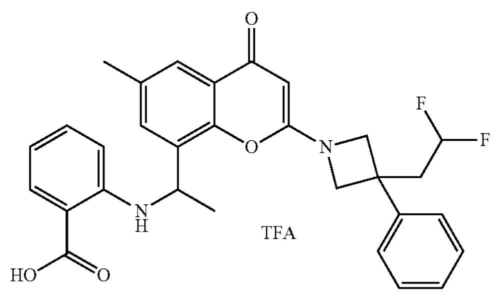 [SMILES: Cc1cc(C(C)Nc2ccccc2C(=O)O)c2oc(N3CC(CC(F)F)(c4ccccc4)C3)cc(=O)c2c1] | 519 |
| 216 | 2-[1-[6-Methyl-4-oxo-2-[3-(2-pyridyl)azetidin-1-yl]chromen-8-yl]ethylamino]benzoic acid 2,2,2-trifluoroacetic acid, Isomer 1 | 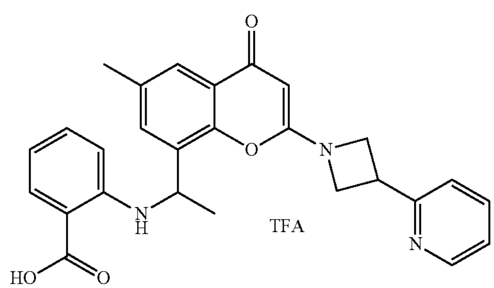 [SMILES: Cc1cc(C(C)Nc2ccccc2C(=O)O)c2oc(N3CC(c4ccccn4)C3)cc(=O)c2c1] | 456 |
| 217 | 2-[1-[2-[3-Fluoro-3-(3-pyridyl)azetidin-1-yl]-6-methyl-4-oxo-chromen-8-yl]ethylamino]benzoic acid 2,2,2-trifluoroacetic acid, Isomer 1 | 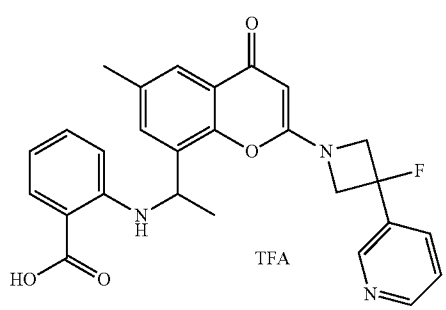 [SMILES: Cc1cc(C(C)Nc2ccccc2C(=O)O)c2oc(N3CC(F)(c4cccnc4)C3)cc(=O)c2c1] | 474 |
| 218 | 2-[1-[6-Methyl-2-(4-methyl-4-phenyl-1-piperidyl)-4-oxo-chromen-8-yl]ethylamino]benzoic acid 2,2,2-trifluoroacetic acid, Isomer 1 | 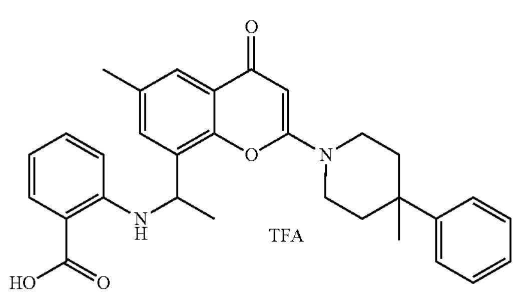 [SMILES: Cc1cc(C(C)Nc2ccccc2C(=O)O)c2oc(N3CCC(C)(c4ccccc4)CC3)cc(=O)c2c1] | 497 |

TABLE 9-continued

| Example # | Chemical Name | Structure | ES/MS m/z (M + H) & Chiral Method |
|---|---|---|---|
| 219 | 2-[1-[2-[3-(Hydroxymethyl)-3-phenyl-azetidin-1-yl]-6-methyl-4-oxo-chromen-8-yl]ethylamino]benzoic acid 2,2,2-trifluoroacetic acid, Isomer 1 | 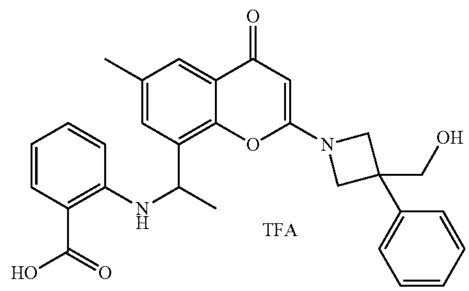 [SMILES: Cc1cc(C(C)Nc2ccccc2C(=O)O)c2oc(N3CC(CO)(c4ccccc4)C3)cc(=O)c2c1] | 485 |
| 220 | 2-[1-[2-(7,7-Difluoro-2-azaspiro[3.3]heptan-2-yl)-6-methyl-4-oxo-chromen-8-yl]ethylamino]benzoic acid 2,2,2-trifluoroacetic acid, Isomer 1 | 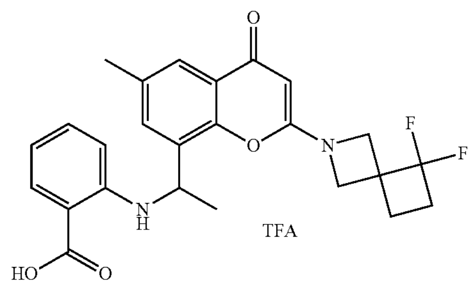 [SMILES: Cc1cc(C(C)Nc2ccccc2C(=O)O)c2oc(N3CC4(CCC4(F)F)C3)cc(=O)c2c1] | 455 |
| 221 | 2-[1-[6-Methyl-4-oxo-2-[6-(trifluoromethyl)-2-azaspiro[3.3]heptan-2-yl]chromen-8-yl]ethylamino]benzoic acid 2,2,2-trifluoroacetic acid, Isomer 1 | 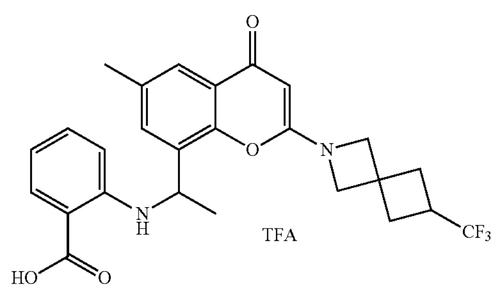 [SMILES: Cc1cc(C(C)Nc2ccccc2C(=O)O)c2oc(N3CC4(CC(C(F)(F)F)C4)C3)cc(=O)c2c1] | 487 |
| 222 | 2-[1[2-(6,6-Difluoro-2-azaspiro[3.3]heptan-2-yl)-6-methyl-4-oxo-chromen-8-yl]ethylamino]benzoic acid 2,2,2-trifluoroacetic acid, Isomer 1 | 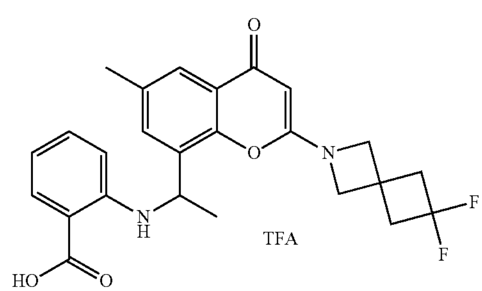 [SMILES: Cc1cc(C(C)Nc2ccccc2C(=O)O)c2oc(N3CC4(C3)CC(F)(F)C4)cc(=O)c2c1] | 455 |
| 223 | 2-[1-[2-[(3R)-3-Fluoropyrrolidin-1-yl]-6-methyl-4-oxo-chromen-8-yl]ethylamino]benzoic acid 2,2,2-trifluoroacetic acid, Isomer 1 | 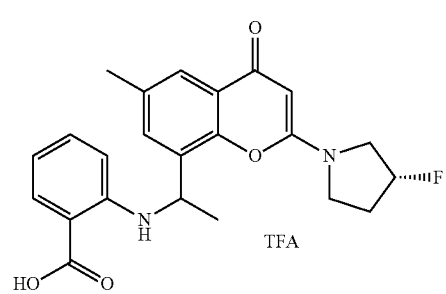 [SMILES: Cc1cc(C(C)Nc2ccccc2C(=O)O)c2oc(N3CC[C@@H](F)C3)cc(=O)c2c1] | 411 |

TABLE 9-continued

| Example # | Chemical Name | Structure | ES/MS m/z (M + H) & Chiral Method |
|---|---|---|---|
| 224 | 2-[1-[2-[(3S)-3-Fluoropyrrolidin-1-yl]-6-methyl-4-oxo-chromen-8-yl]ethylamino]benzoic acid 2,2,2-trifluoroacetic acid, Isomer 1 | 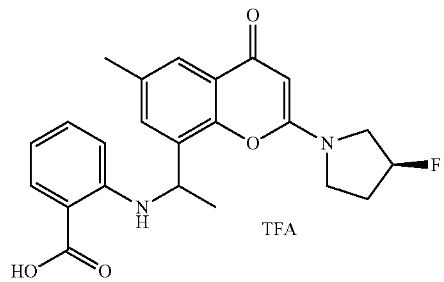 [SMILES: Cc1cc(C(C)Nc2ccccc2C(=O)O)c2oc(N3CC[C@H](F)C3)cc(=O)c2c1] | 411 |
| 225 | 2-[1-[2-[3-Fluoro-3-(trifluoromethyl)azetidin-1-yl]-6-methyl-4-oxo-chromen-8-yl]ethylamino]benzoic acid 2,2,2-trifluoroacetic acid, Isomer 1 | 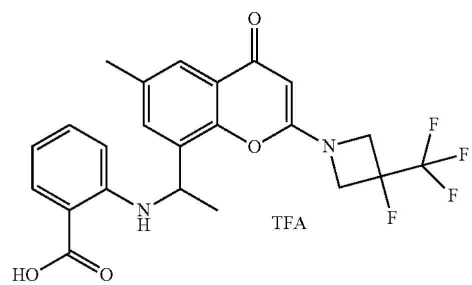 [SMILES: Cc1cc(C(C)Nc2ccccc2C(=O)O)c2oc(N3CC(F)(C(F)(F)F)C3)cc(=O)c2c1] | 465 |
| 226 | 2-[1-[2-(3,3-Difluoropyrrolidin-1-yl)-6-methyl-4-oxo-chromen-8-yl]ethylamino]benzoic acid 2,2,2-trifluoroacetic acid, Isomer 1 | 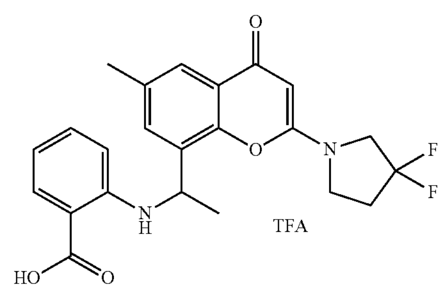 [SMILES: Cc1cc(C(C)Nc2ccccc2C(=O)O)c2oc(N3CCC(F)(F)C3)cc(=O)c2c1] | 429 |
| 227 | 2-[1-[2-(3,3-Difluoro-1-piperidyl)-6-methyl-4-oxo-chromen-8-yl]ethylamino]benzoic acid 2,2,2-trifluoroacetic acid, Isomer 1 | 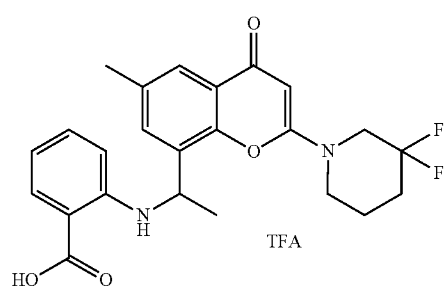 [SMILES: Cc1cc(C(C)Nc2ccccc2C(=O)O)c2oc(N3CCCC(F)(F)C3)cc(=O)c2c1] | 443 |
| 228 | 2-[1-[2-(1-Fluoro-3-azabicyclo[3.1.1]heptan-3-yl)-6-methyl-4-oxo-chromen-8-yl]ethylamino]benzoic acid, Isomer 1 | 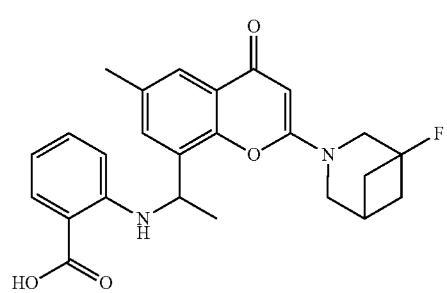 [SMILES: Cc1cc(C(C)Nc2ccccc2C(=O)O)c2oc(N3CC4CC(F)(C4)C3)cc(=O)c2c1] | 437 |

TABLE 9-continued

| Example # | Chemical Name | Structure | ES/MS m/z (M + H) & Chiral Method |
|---|---|---|---|
| 229 | 2-[1-[6-Methyl-4-oxo-2-[(3R)-3-phenylpyrrolidin-1-yl]chromen-8-yl]ethylamino]benzoic acid, Isomer 1 | 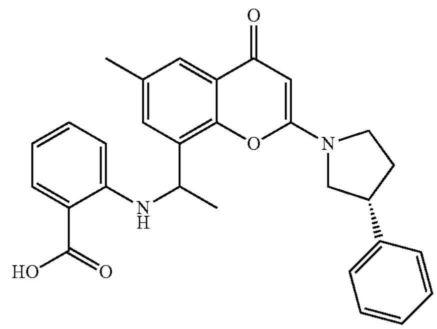 [SMILES: Cc1cc(C(C)Nc2ccccc2C(=O)O)c2oc(N3CC[C@H](c4ccccc4)C3)cc(=O)c2c1] | 469 |
| 230 | 2-[1-[6-Methyl-2-(4-methylisoindolin-2-yl)-4-oxo-chromen-8-yl]ethylamino]benzoic acid 2,2,2-trifluoroacetic acid, Isomer 1 | 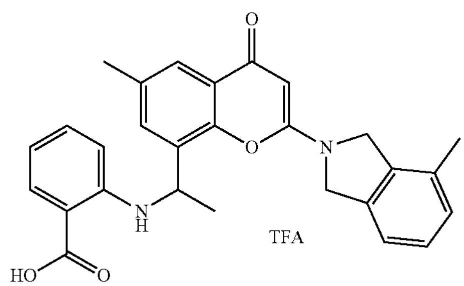 [SMILES: Cc1cc(C(C)Nc2ccccc2C(=O)O)c2oc(N3Cc4cccc(C)c4C3)cc(=O)c2c1] | 455 |
| 231 | 2-[1-[2-(4-Chloroisoindolin-2-yl)-6-methyl-4-oxo-chromen-8-yl]ethylamino]benzoic acid 2,2,2-trifluoroacetic acid, Isomer 1 | 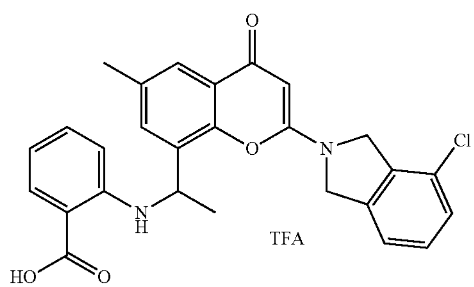 [SMILES: Cc1cc(C(C)Nc2ccccc2C(=O)O)c2oc(N3Cc4cccc(Cl)c4C3)cc(=O)c2c1] | 475 |
| 232 | 2-[1-[2-(5-Chloroisoindolin-2-yl)-6-methyl-4-oxo-chromen-8-yl]ethylamino]benzoic acid 2,2,2-trifluoroacetic acid, Isomer 1 | 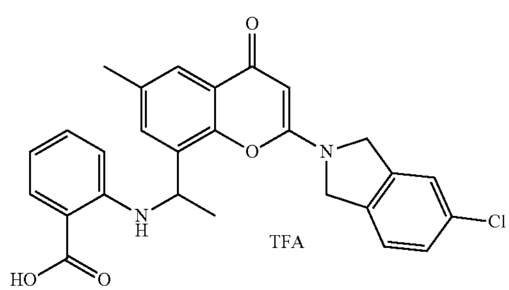 [SMILES: Cc1cc(C(C)Nc2ccccc2C(=O)O)c2oc(N3Cc4ccc(Cl)cc4C3)cc(=O)c2c1] | 475 |
| 233 | 2-[1-[2-(3,4-Dihydro-1H-isoquinolin-2-yl)-6-methyl-4-oxo-chromen-8-yl]ethylamino]benzoic acid | 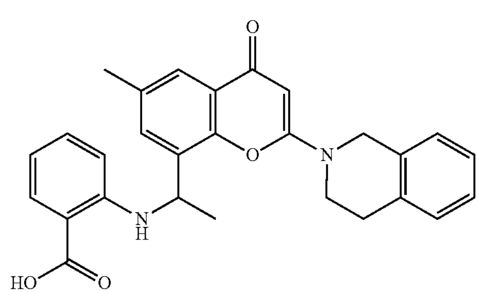 [SMILES: Cc1cc(C(C)Nc2ccccc2C(=O)O)c2oc(N3CCc4ccccc4C3)cc(=O)c2c1] | 455 |

TABLE 9-continued

| Example # | Chemical Name | Structure | ES/MS m/z (M + H) & Chiral Method |
|---|---|---|---|
| 234 | 2-[1-[2-[(1R,6S)-2-Azabicyclo[4.2.0]octan-2-yl]-6-methyl-4-oxo-chromen-8-yl]ethylamino]benzoic acid | 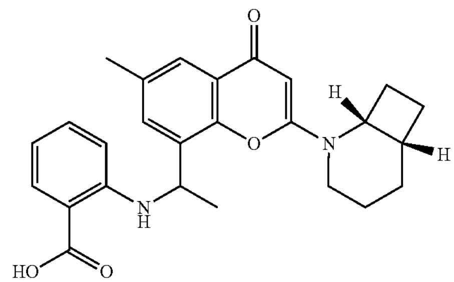 [SMILES: Cc1cc(C(C)Nc2ccccc2C(=O)O)c2oc(N3CCC[C@H]4CC[C@H]43)cc(=O)c2c1] | 433 |
| 235 | 2-[1-[2-(6,8-Dihydro-[1,3]dioxolo[4,5-e]isoindol-7-yl)-6-methyl-4-oxo-chromen-8-ylethylamino]benzoic acid | 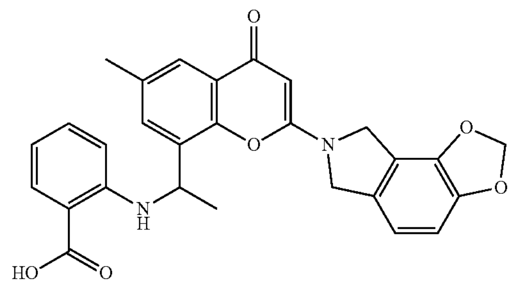 [SMILES: Cc1cc(C(C)Nc2ccccc2C(=O)O)c2oc(N3Cc4ccc5c(c4C3)OCO5)cc(=O)c2c1] | 485 |

Example 236: 2-[1-[6-Methyl-4-oxo-2-(3-phenylazetidin-1-yl)chromen-8-yl]ethylamino]benzoic acid 2,2,2-trifluoroacetic acid, Isomer 1

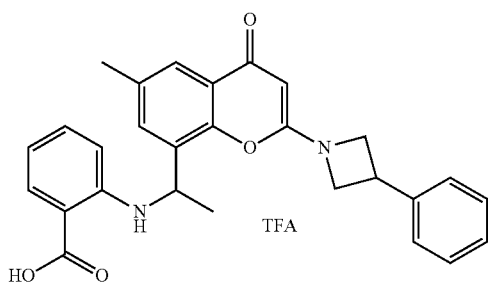 [SMILES: Cc1cc(C(C)Nc2ccccc2C(=O)O)c2oc(N3CC(c4ccccc4)C3)cc(=O)c2c1]

Example 237: 3-[1-(2-Isoindolin-2-yl-6-methyl-4-oxo-chromen-8-yl)ethylamino]-6-methoxy-pyridine-2-carboxylic acid

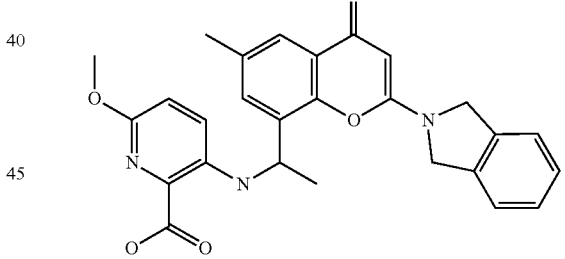

A mixture of 3-phenylazetidine hydrochloride (46 mg, 1.1 eq., 0.27 mmol), 2-[1-(2-ethylsulfinyl-6-methyl-4-oxo-chromen-8-yl)ethylamino]benzoic acid, Isomer 1 (98 mg, 1 eq., 0.25 mmol) and DIPEA (0.13 g, 0.17 mL, 4 eq., 0.98 mmol) in acetonitrile (10 mL) was stirred at 80° C. for 16 h. After cooling to room temperature, the solvent was removed under reduced pressure. The residue was then purified by preparative HPLC (5-95% ACN[0.1% TFA]/Water[0.1% TFA]) to give 2-[1-[6-methyl-4-oxo-2-(3-phenylazetidin-1-yl)chromen-8-yl]ethylamino]benzoic acid 2,2,2-trifluoroacetic acid, Isomer 1 (93 mg, 0.16 mmol, 66%). MS ES+ m/z 455.2 [M+H]+.

Step 1. A mixture of 8-(1-bromoethyl)-2-ethylsulfanyl-6-methyl-chromen-4-one (150 mg, 458 umol, 1 eq) and 3-amino-6-methoxy-pyridine-2-carboxylic acid (92 mg, 550 umol, 1.2 eq) in DMF (3 mL) was stirred at 80° C. for 5 h to give a brown solution. The mixture was diluted with water (20 mL), extracted with ethyl acetate (3×20 mL), washed with brine (2×40 mL), dried over sodium sulfate, filtered, and concentrated. The residue was purified by silica gel chromatography (0~3% methanol in dichloromethane).

Step 2. The product from Step 1 (100 mg, 241 umol, 1 eq) in dichloromethane (2 mL) was treated with m-CPBA (88. mg, 434 umol, 85% purity, 1.8 eq) at 0° C., and stirred at 20° C. for 3 h. The mixture was quenched with sat. Na₂S₂O₃ (10 mL), extracted with dichloromethane (2×20 mL), dried over sodium sulfate, filtered, and concentrated.

Step 3. The product from Step 2 (70 mg, 162 umol, 1 eq), isoindoline-HCl (38 mg, 244 umol, 36 uL, 1.5 eq), and DIEA (105 mg, 813 umol, 141 uL, 5 eq) in dichloromethane (2 mL) were stirred at 45° C. for 14 h to give a brown solution. The mixture was diluted with water (15 mL), extracted with DCM (2×15 mL), dried over sodium sulfate, filtered, and concentrated. The residue was purified by reverse phase HPLC (C18 column, water:acetonitrile gradient, with 0.05% ammonium hydroxide) to give 3-[1-(2-isoindolin-2-yl-6-methyl-4-oxo-chromen-8-yl)ethylamino]-6-methoxy-pyridine-2-carboxylic acid. MS ES+ m/z 472.3 [M+H]+.

The following compounds in Table 10 were prepared essentially as described for 3-[1-(2-isoindolin-2-yl-6-methyl-4-oxo-chromen-8-yl)ethylamino]-6-methoxy-pyridine-2-carboxylic acid. In some instances, Steps 2 and 3 were combined in a two-step one-pot manner.

TABLE 10

| Example # | Chemical Name | Structure | ES/MS m/z (M + H) |
|---|---|---|---|
| 238 | 2-Fluoro-6-[1-[2-(5-fluoroisoindolin-2-yl)-6-methyl-4-oxo-chromen-8-yl]ethylamino]benzoic acid | 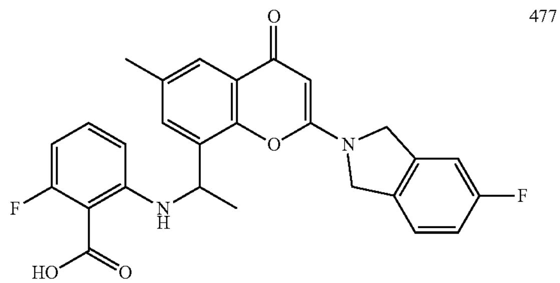 | 477 |
| 239 | 2-Isoindolin-2-yl-8-[1-(2-isoxazol-5-ylanilino)ethyl]-6-methyl-chromen-4-one 2,2,2-trifluoroacetic acid | 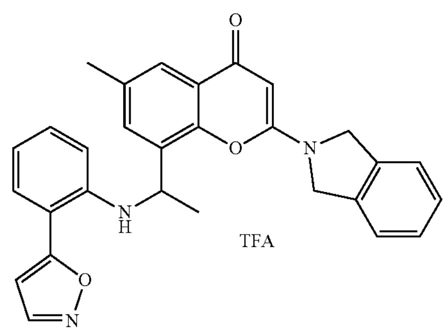 [SMILES: Cc1cc(C(C)Nc2ccccc2-c2ccno2)c2oc(N3Cc4ccccc4C3)cc(=O)c2c1] | 464 |
| 240 | 2-Isoindolin-2-yl-6-methyl-8-[1-[2-(tetrazol-1-yl)anilino]ethyl]chromen-4-one | 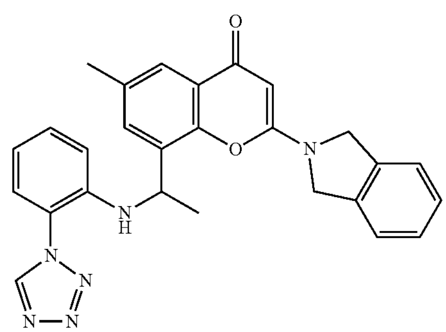 [SMILES: Cc1cc(C(C)Nc2ccccc2-n2cnnn2)c2oc(N3Cc4ccccc4C3)cc(=O)c2c1] | 465 |
| 241 | 2-[1-(2-Isoindolin-2-yl-6-methyl-4-oxo-chromen-8-yl)ethylamino]benzenecarbohydroxamic 2,2,2-trifluoroacetic acid | 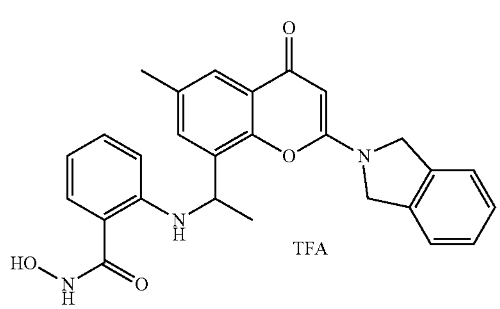 [SMILES: Cc1cc(C(C)Nc2ccccc2C(=O)NO)c2oc(N3Cc4ccccc4C3)cc(=O)c2c1] | 456 |

TABLE 10-continued

| Example # | Chemical Name | Structure | ES/MS m/z (M + H) |
|---|---|---|---|
| 242 | 2-[1-(2-Isoindolin-2-yl-6-methyl-4-oxo-chromen-8-yl)ethylamino]benzenesulfonamide 2,2,2-trifluoroacetic acid | 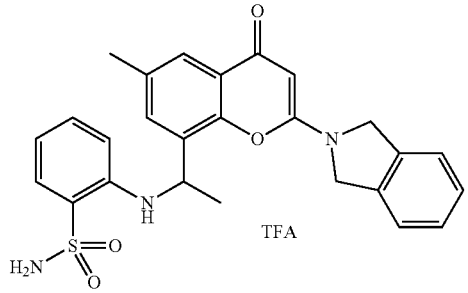 [SMILES: Cc1cc(C(C)Nc2ccccc2S(N)(=O)=O)c2oc(N3Cc4ccccc4C3)cc(=O)c2c1] | 476 |

Example 243: (Isomer 1) and Example 244: (Isomer 2): 2-Fluoro-6-[1-[2-(5-fluoroisoindolin-2-yl)-3,6-dimethyl-4-oxo-chromen-8-yl]ethyl amino]benzoic acid

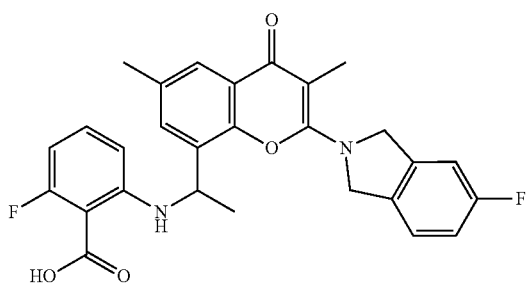 [SMILES: Cc1cc(C(C)Nc2cccc(F)c2C(=O)O)c2oc(N3Cc4ccc(F)cc4C3)c(C)c(=O)c2c1]

Step 1. A mixture of 8-(1-bromoethyl)-2-ethylsulfanyl-3,6-dimethyl-chromen-4-one (1 g, 2.9 mmol, 1 eq) and methyl 2-amino-6-fluoro-benzoate (1.49 g, 8.79 mmol, 3 eq) in DMF (10 mL) was stirred at 80° C. for 16 h to give a yellow solution. The mixture was concentrated and purified by silica gel chromatography (0-10% ethyl acetate/petroleum ether).

Step 2. The product from Step 1 (1.24 g, 2.89 mmol, 1 eq) in dichloromethane (15 mL) was treated with m-CPBA (935 mg, 4.3 mmol, 80% purity, 1.5 eq) at 0° C. and stirred at 25° C. for 2 h. The mixture was quenched with saturated aq. Na$_2$SO$_3$ (20 mL), extracted with DCM (3×50 mL), dried over sodium sulfate, and concentrated in vacuo. The residue was purified by silica gel chromatography (0-40% ethyl acetate/petroleum ether).

Step 3. A mixture of the product from Step 2 (500 mg, 1.12 mmol, 1 eq), 5-fluoroisoindoline-HCl (292 mg, 1.7 mmol, 1.5 eq), and DIEA (725 mg, 5.6 mmol, 977 uL, 5 eq) in chloroform (3 mL) were stirred at 60° C. for 32 h to give a dark solution. The mixture was concentrated and purified by silica gel chromatography (0-46% ethyl acetate/petroleum ether).

Step 4. A mixture of the product from Step 3 (772 mg, 1.5 mmol, 1 eq), NaOH (244 mg, 6.1 mmol, 4 eq), water (1 mL) and methanol (10 mL) was stirred at 60° C. for 16 h. The mixture was concentrated and purified by reverse phase HPLC (C$_{18}$ column, water:acetonitrile gradient, with 0.05% ammonium hydroxide as an additive). The racemic product was purified by chiral SFC (U, 28; See Tables 4 and 5 for chiral column and eluent) to give 2-fluoro-6-[1-[2-(5-fluoroisoindolin-2-yl)-3,6-dimethyl-4-oxo-chromen-8-yl]ethylamino]benzoic acid, Isomer 1 and 2-fluoro-6-[1-[2-(5-fluoroisoindolin-2-yl)-3,6-dimethyl-4-oxo-chromen-8-yl]ethylamino]benzoic acid, Isomer 2. For both products: ee>99%; MS ES+ m/z 491.4 [M+H]$^+$.

The following compounds in Table 11 were prepared essentially as described for 2-fluoro-6-[1-[2-(5-fluoroisoindolin-2-yl)-3,6-dimethyl-4-oxo-chromen-8-yl]ethylamino] benzoic acid. Ester hydrolysis may alternatively have been achieved with boron tribromide in dichloromethane.

TABLE 11

| Example # | Chemical Name | Structure | ES/MS m/z (M + H) |
|---|---|---|---|
| 245 | 2-Chloro-5-[1-(2-isoindolin-2-yl-6-methyl-4-oxo-chromen-8-yl)ethylamino]thiazole-4-carboxylic acid 2,2,2-trifluoroacetic acid | 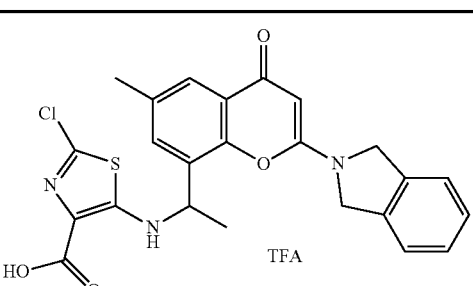 | 482 |

TABLE 11-continued

| Example # | Chemical Name | Structure | ES/MS m/z (M + H) |
|---|---|---|---|
| 246 | 5-[1-(2-Isoindolin-2-yl-6-methyl-4-oxo-chromen-8-yl)ethylamino]-2-(trifluoromethyl)pyrimidine-4-carboxylic acid 2,2,2-trifluoroacetic acid | 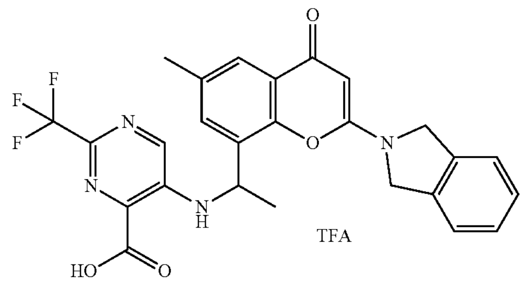 [SMILES: Cc1cc(C(C)Nc2cnc(C(F)(F)F)nc2C(=O)O)c2oc(N3Cc4ccccc4C3)cc(=O)c2c1] | 511 |

Example 247: 2-[1-[6-Methyl-4-oxo-2-[3-(trifluoromethyl)-6,8-dihydro-5H-[1,2,4]triazolo[4,3-a]pyrazin-7-yl]chromen-8-yl]ethylamino]benzoic acid

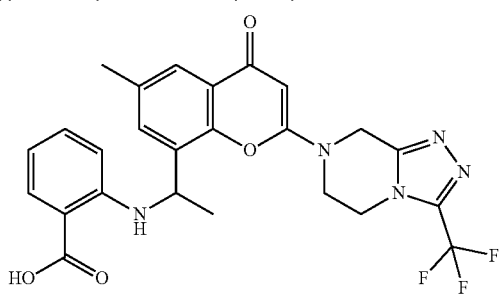

A mixture of 2-[1-(2-ethylsulfonyl-6-methyl-4-oxo-chromen-8-yl)ethylamino]benzoic acid (50 mg, 120 umol, 1 eq), 3-(trifluoromethyl)-5,6,7,8-tetrahydro-[1,2,4]triazolo[4,3-a]pyrazine (46 mg, 241 umol, 2 eq), and DIEA (78 mg, 602 umol, 105 uL, 5 eq) in chloroform (2.5 mL) was stirred at 60° C. for 16 h. The mixture was diluted with water, adjusted to pH 6 with HCl (1M. aq.), and extracted with dichloromethane (3×10 mL). The combined organic phase was dried with anhydrous sodium sulfate, filtered, and concentrated in vacuo. The residue was purified by reverse phase HPLC ($C_{18}$ column, water:acetonitrile gradient, with 0.225% formic acid as an additive) to give 2-[1-[6-methyl-4-oxo-2-[3-(trifluoromethyl)-6,8-dihydro-5H-[1,2,4]triazolo[4,3-a]pyrazin-7-yl]chromen-8-yl]ethylamino]benzoic acid. MS ES+ m/z 514.4 [M+H]+.

Example 248: 1-[8-[1-(2-Carboxyanilino)ethyl]-6-methyl-4-oxo-chromen-2-yl]azetidine-3-carboxylic acid

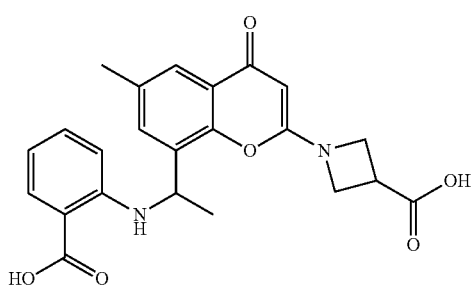 [SMILES: Cc1cc(C(C)Nc2ccccc2C(=O)O)c2oc(N3CC(C(=O)O)C3)cc(=O)c2c1]

Step 1. A mixture of methyl 2-[1-(2-ethylsulfonyl-6-methyl-4-oxo-chromen-8-yl)ethylamino]benzoate (0.05 g, 116 umol, 1 eq), azetidine-3-carbonitrile-HCl (27 mg, 233 umol, 2 eq), and DIEA (150 mg, 1.16 mmol, 203 uL, 10 eq) in dichloromethane (1 mL) was stirred at 45° C. for 4 h. The mixture was extracted with dichloromethane (2×15 mL), washed with brine (15 mL), and concentrated in vacuo.

Step 2. The product from Step 1 (0.04 g, 96 umol, 1 eq) was dissolved in a mixture of methanol (1 mL) and water (1 mL) and treated with $LiOH.H_2O$ (16 mg, 383 umol, 4 eq). The mixture was stirred at 45° C. for 16 hr and concentrated in vacuo. The residue was purified by reverse phase HPLC (C18 column, water:acetonitrile gradient, with 0.225% formic acid as an additive) to give 1-[8-[1-(2-carboxyanilino)ethyl]-6-methyl-4-oxo-chromen-2-yl]azetidine-3-carboxylic acid. MS ES+ m/z 423.1 [M+H]+.

Example 249: 6-Bromo-3-[[(1R)-1-[2-(4,4-dimethyl-1-piperidyl)-6-methyl-4-oxo-chromen-8-yl]ethyl]amino]pyridine-2-carboxylic acid

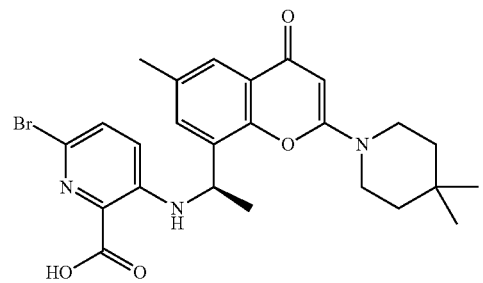

Step 1. A mixture of 8-[(1R)-1-aminoethyl]-2-(4,4-dimethyl-1-piperidyl)-6-methyl-chromen-4-one (50 mg, 159 umol, 1 eq), methyl 6-bromo-3-fluoro-pyridine-2-carboxylate (74 mg, 318 umol, 2 eq), and DIEA (62 mg, 477 umol, 83 uL, 3 eq) in DMF (1 mL) was stirred at 100° C. under nitrogen for 16 h. The mixture was quenched with water (10 mL) and extracted with ethyl acetate (2×10 mL). The combined organic layer was washed with brine (3×10 mL), dried over anhydrous sodium sulfate, filtered, and concentrated in vacuo.

Step 2. The product from Step 1 (20 mg, 37.85 umol, 1 eq) was dissolved in a mixture of methanol (0.5 mL) and water (0.05 mL) and treated with NaOH (3 mg, 76 umol, 2 eq). The mixture was stirred at 25° C. for 16 hr and concentrated. The residue was purified by reverse phase HPLC (Column: Xtimate C18 100×30 mm, 10 um; Mobile phase: [A: Water (0.225% FA); B: ACN]; B %: 45%-75% in 10 min) to give 6-bromo-3-[[(1R)-1-[2-(4,4-dimethyl-1-piperidyl)-6-methyl-4-oxo-chromen-8-yl]ethyl]amino]pyridine-2-carboxylic acid. MS ES+ m/z 514.3, 516.0 [M+H]⁺.

The following compounds in Table 12 were prepared essentially as described for 6-bromo-3-[[(1R)-1-[2-(4,4-dimethyl-1-piperidyl)-6-methyl-4-oxo-chromen-8-yl]ethyl]amino]pyridine-2-carboxylic acid.

TABLE 12

| Example # | Chemical Name | Structure | ES/MS m/z (M + H) |
|---|---|---|---|
| 250 | 2-[[(1R)-1-[2-(4,4-Dimethyl-1-piperidyl)-6-methyl-4-oxo-chromen-8-yl]ethyl]amino]-5-methylsulfonyl-benzoic acid | 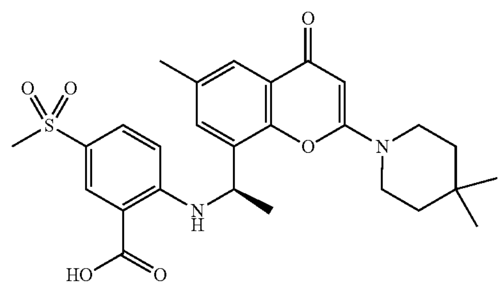 | 513 |
| 251 | 4-[[(1R)-142-(4,4-Dimethyl-1-piperidyl)-6-methyl-4-oxo-chromen-8-yl]ethyl]amino]pyridazine-3-carboxylic acid | 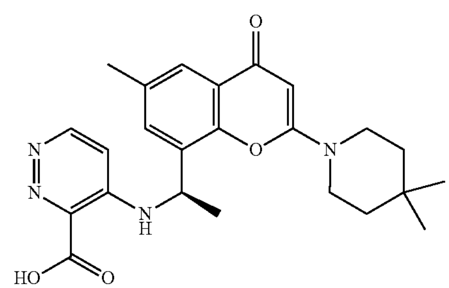 [SMILES: Cc1cc([C@@H](C)Nc2ccnnc2C(=O)O)c2oc(N3CCC(C)(C)CC3)cc(=O)c2c1] | 437 |
| 252 | 2-[[(1R)-1-[2-(4,4-Dimethyl-1-piperidyl)-6-methyl-4-oxo-chromen-8-yl]ethyl]amino]pyridine-3-carboxylic acid | 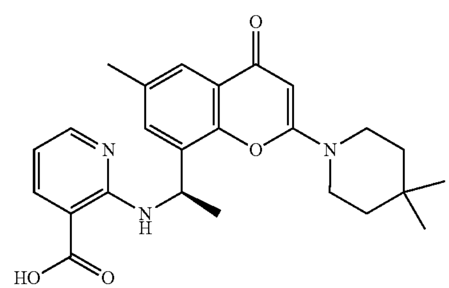 [SMILES: Cc1cc([C@@H](C)Nc2ncccc2C(=O)O)c2oc(N3CCC(C)(C)CC3)cc(=O)c2c1] | 436 |
| 253 | 3-[[(1R)-1-[2-(4,4-Dimethyl-1-piperidyl)-6-methyl-4-oxo-chromen-8-yl]ethyl]amino]-5-fluoro-pyridine-2-carboxylic acid | 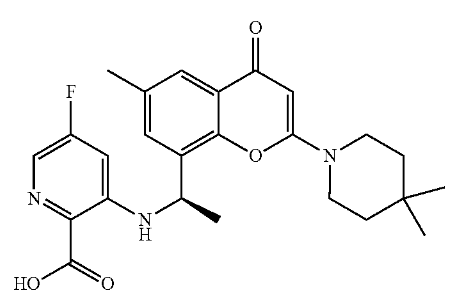 [SMILES: Cc1cc([C@@H](C)Nc2cc(F)cnc2C(=O)O)c2oc(N3CCC(C)(C)CC3)cc(=O)c2c1] | 454 |

TABLE 12-continued

| Example # | Chemical Name | Structure | ES/MS m/z (M + H) |
|---|---|---|---|
| 254 | 5-Chloro-3-[[(1R)-1-[2-(4,4-dimethyl-1-piperidyl)-6-methyl-4-oxo-chromen-8-yl]ethyl]amino]pyridine-2-carboxylic acid | 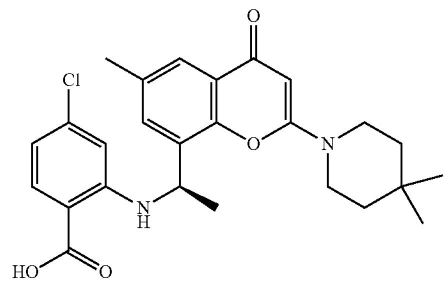 [SMILES: Cc1cc([C@@H](C)Nc2cc(Cl)ccc2C(=O)O)c2oc(N3CCC(C)(C)CC3)cc(=O)c2c1] | 470 |
| 255 | 3-[[(1R)-142-(4,4-Dimethyl-1-piperidyl)-6-methyl-4-oxo-chromen-8-yl]ethyl]amino]-6-(trifluoromethyppyridine-2-carboxylic acid | 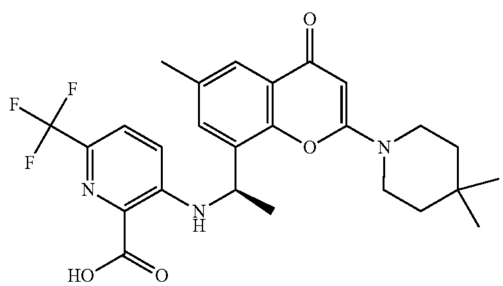 [SMILES: Cc1cc([C@@H](C)Nc2ccc(C(F)(F)F)nc2C(=O)O)c2oc(N3CCC(C)(C)CC3)cc(=O)c2c1] | 504 |
| 256 | 6-Chloro-3-[[(1R)-1-[2-(4,4-dimethyl-1-piperidyl)-6-methyl-4-oxo-chromen-8-yl]ethyl]amino]pyridine-2-carboxylic acid | 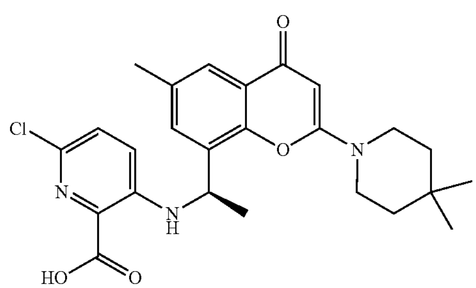 [SMILES: Cc1cc([C@@H](C)Nc2ccc(Cl)nc2C(=O)O)c2oc(N3CCC(C)(C)CC3)cc(=O)c2c1] | 470 |
| 257 | 2-Cyano-6-[[(1R)-1-[2-(4,4-dimethyl-1-piperidyl)-6-methyl-4-oxo-chromen-8-yl]ethyl]amino]benzoic acid | 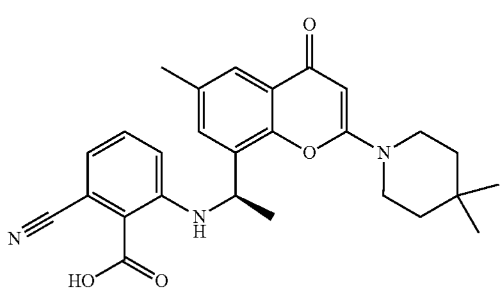 [SMILES: Cc1cc([C@@H](C)Nc2cccc(C#N)c2C(=O)O)c2oc(N3CCC(C)(C)CC3)cc(=O)c2c1] | 460 |

Example 258: (Isomer 1) and Example 259: (Isomer 2): 2-[I-[3,6-Dimethyl-4-oxo-2-(1-piperidyl)chromen-8-yl]ethyl amino]benzoic acid

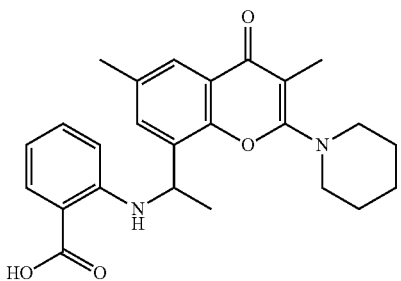 [SMILES: Cc1cc(C(C)Nc2ccccc2C(=O)O)c2oc(N3CCCCC3)c(C)c(=O)c2c1]

Step 1. A mixture of methyl 2-[1-(2-ethylsulfinyl-3,6-dimethyl-4-oxo-chromen-8-yl)ethylamino]benzoate (680 mg, 1.59 mmol, 1 eq) in chloroform (8 mL), piperidine (271 mg, 3.2 mmol, 314 uL, 2 eq), and DIEA (1.23 g, 9.5 mmol, 1.7 mL, 6 eq) was stirred at 60° C. for 48 hr to give a yellow solution. The mixture was diluted with water (30 mL) and extracted with dichloromethane (2×30 mL). The combined extracts were washed with brine (2×30 mL), dried over sodium sulfate, filtered, and concentrated in vacuo. The residue was purified by silica gel chromatography (0-30% ethyl acetate/petroleum ether).

Step 2. The product from Step 1 was dissolved in a mixture of methanol (2 mL) and water (0.5 mL) and treated with NaOH (28 mg, 690 umol, 3 eq). The mixture was stirred at 45° C. for 16 h and concentrated. The residue was purified by reverse phase HPLC (C18 column, water:acetonitrile gradient, with 0.225% formic acid as an additive). The resulting racemic mixture was purified by chiral SFC (U, 24; See Tables 4 and 5 for chiral columns and eluents) to give 2-[1-[3,6-dimethyl-4-oxo-2-(1-piperidyl)chromen-8-yl]ethylamino]benzoic acid, Isomer 1 and 2-[1-[3,6-dimethyl-4-oxo-2-(1-piperidyl)chromen-8-yl]ethylamino]benzoic acid, Isomer 2; both >97%; MS ES+ m/z 435.4 [M+H]+.

The following compounds in Table 13 were prepared essentially as described for 2-[1-[3,6-dimethyl-4-oxo-2-(1-piperidyl)chromen-8-yl]ethylamino]benzoic acid. If the Example was purified with chiral SFC, the chiral column and eluent are listed in the final column (see Tables 4 and 5).

TABLE 13

| Example # | Chemical Name | Structure | ES/MS m/z (M + H) & Chiral Method |
|---|---|---|---|
| 260 | Methyl 2-[1-[3,6-dimethyl-4-oxo-2-(1-piperidyl)chromen-8-yl]ethylamino]benzoate, Isomer 1 | 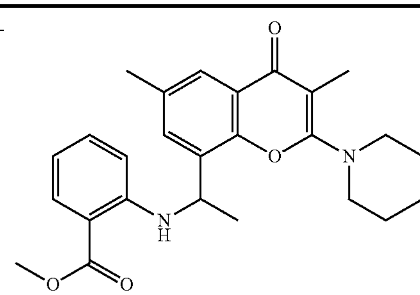 | 435 U, 24 |
| 261 | Methyl 2-[1-[3,6-dimethyl-4-oxo-2-(1-piperidyl)chromen-8-yl]ethylamino]benzoate, Isomer 2 | 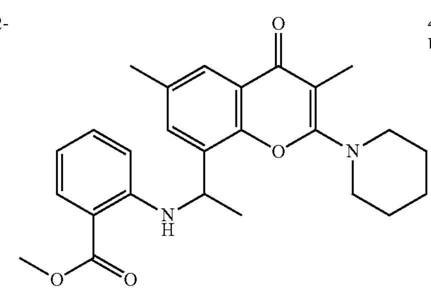 | 435 U, 24 |
| 262 | 2-[1-[3,6-Dimethyl-4-oxo-2-(1-piperidyl)chromen-8-yl]ethylamino]benzoic acid | 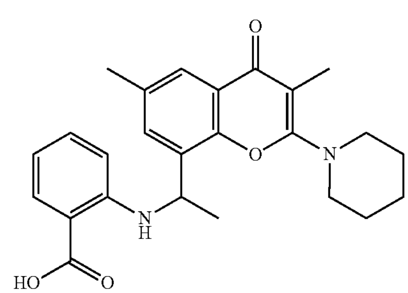 [SMILES: Cc1cc(C(C)Nc2ccccc2C(=O)O)c2oc(N3CCCCC3)c(C)c(=O)c2c1] | 421 |

Example 263: (Isomer 1) and Example 264: (Isomer 2): 2-[1-[2-(6,8-Dihydro-[1,3]dioxolo[4,5-e]isoindol-7-yl)-3,6-dimethyl-4-oxo-chromen-8-yl]ethylamino]benzoic acid

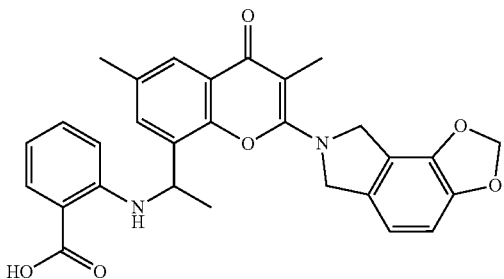 [SMILES: Cc1cc(C(C)Nc2ccccc2C(=O)O)c2oc(N3Cc4ccc5c(c4C3)OCO5)c(C)c(=O)c2c1]

A mixture of 2-[1-(2-ethylsulfinyl-3,6-dimethyl-4-oxo-chromen-8-yl)ethylamino]benzoic acid (100 mg, 242 umol, 1 eq), 7,8-dihydro-6H-[1,3]dioxolo[4,5-e]isoindole·HCl (72.42 mg, 362.77 umol, 1.5 eq), and DIEA (156 mg, 1.2 mmol, 211 uL, 5 eq) in DMSO (2 mL) was stirred at 80° C. for 16 h to give a dark solution. The mixture was diluted with water (30 mL) and extracted with DCM (3×50). The combined organic phase was washed with brine (2×30 mL), dried with anhydrous sodium sulfate, filtered, and concentrated in vacuo. The crude residue was purified by trituration with acetonitrile (2 mL). This racemic mixture was purified by chiral SFC (J, 5; See Tables 4 and 5 for chiral columns and eluents) to give 2-[1-[2-(6,8-dihydro-[1,3]dioxolo[4,5-e]isoindol-7-yl)-3,6-dimethyl-4-oxo-chromen-8-yl]ethylamino]benzoic acid, Isomer 1 and 2-[1-[2-(6,8-dihydro-[1,3]dioxolo[4,5-e]isoindol-7-yl)-3,6-dimethyl-4-oxo-chromen-8-yl]ethylamino]benzoic acid, Isomer 2. For each enantiomer: ee>96%; MS ES+ m/z 499.3 [M+H]⁺.

The following compounds in Table 14 were prepared essentially as described for 2-[1-[2-(6,8-dihydro-[1,3]dioxolo[4,5-e]isoindol-7-yl)-3,6-dimethyl-4-oxo-chromen-8-yl]ethylamino]benzoic acid. If the Example was purified with chiral SFC, the chiral column and eluent are listed in the final column (see Tables 4 and 5).

TABLE 14

| Example # | Chemical Name | Structure | ES/MS m/z (M + H) & Chiral Method |
|---|---|---|---|
| 265 | 2-[1-(2-Isoindolin-2-yl-3,6-dimethyl-4-oxo-chromen-8-yl)ethylamino]benzoic acid, Isomer 1 | 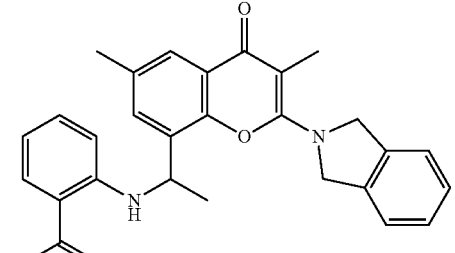 | 455 W, 5 then AD, 37 |
| 266 | 2-[1-(2-Isoindolin-2-yl-3,6-dimethyl-4-oxo-chromen-8-yl)ethylamino]benzoic acid, Isomer 2 | 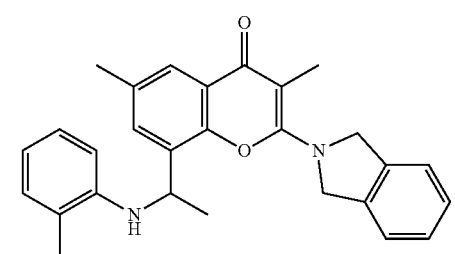 | 455 W, 5 then AD, 37 |
| 267 | 2-[1-[2-(5-Carbamoylisoindolin-2-yl)-3,6-dimethyl-4-oxo-chromen-8-yl]ethylamino]benzoic acid, Isomer 1 | 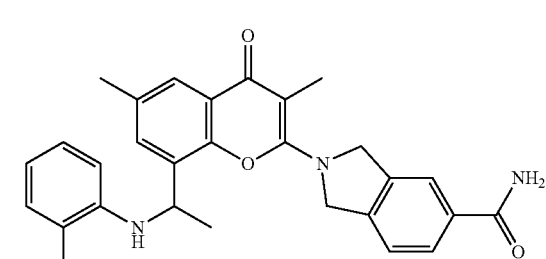 | 498 J, 5 |

TABLE 14-continued

| Example # | Chemical Name | Structure | ES/MS m/z (M + H) & Chiral Method |
|---|---|---|---|
| 268 | 2-[1-[2-(5-Carbamoylisoindolin-2-yl)-3,6-dimethyl-4-oxo-chromen-8-yl]ethylamino]benzoic acid, Isomer 2 | 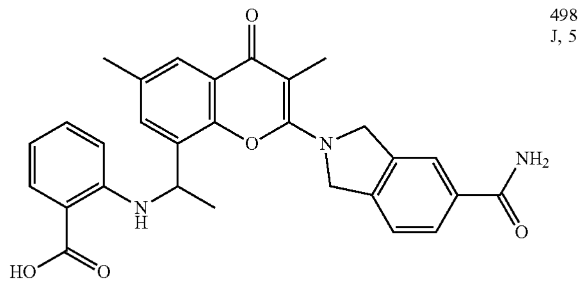 | 498 J, 5 |
| 269 | 2-[1-[2-(5-Cyanoisoindolin-2-yl)-3,6-dimethyl-4-oxo-chromen-8-yl]ethylamino]benzoic acid, Isomer 1 | 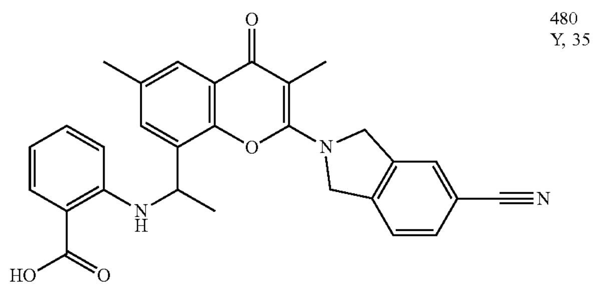 | 480 Y, 35 |
| 270 | 2-[1-[2-(5-Cyanoisoindolin-2-yl)-3,6-dimethyl-4-oxo-chromen-8-yl] ethylamino]benzoic acid, Isomer 2 | 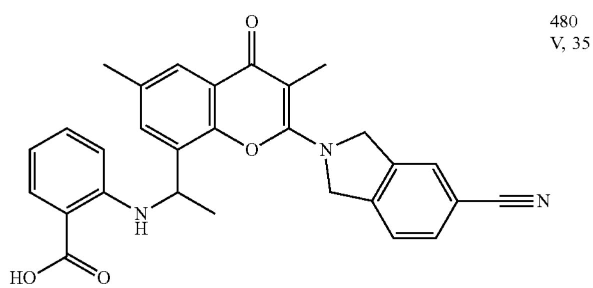 | 480 V, 35 |
| 271 | 2-[1-(2-Isoindolin-2-yl-3,6-dimethyl-4-oxo-chromen-8-yl)ethylamino]benzoic acid | 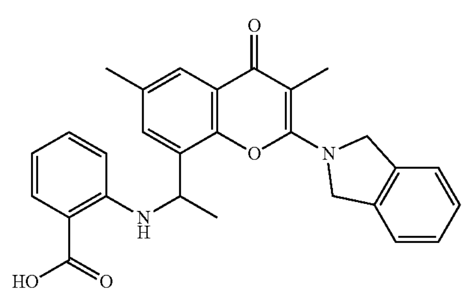 [SMILES: Cc1cc(C(C)Nc2ccccc2C(=O)O)c2oc(N3Cc4ccccc4C3)c(C)c(=O)c2c1] | 455 |

Example 272: (Isomer 1) and Example 273: (Isomer 2): 2-[1-[2-(5-Fluoroisoindolin-2-yl)-3,6-dimethyl-4-oxo-chromen-8-yl]ethyl amino]benzoic acid

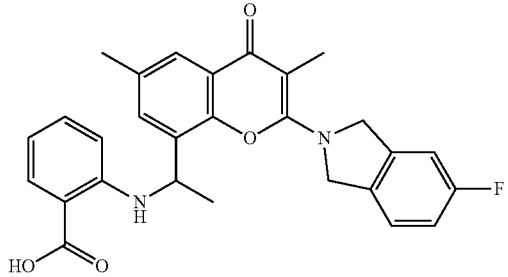

A mixture of 2-[1-(2-ethylsulfinyl-3,6-dimethyl-4-oxo-chromen-8-yl)ethylamino]benzoic acid (500 mg, 1.2 mmol, 1 eq), 5-fluoroisoindoline-HCl (315 mg, 1.8 mmol, 1.5 eq), and DIEA (625 mg, 4.8 mmol, 842 uL, 4 eq) in chloroform (10 mL) was stirred at 60° C. for 120 hours. The mixture was treated with water (30 mL) and extracted with dichloromethane (3×50 mL). The combined organic phase was dried with anhydrous sodium sulfate, filtered, and concentrated in vacuo. This racemic mixture was purified by chiral SFC (J, 5; See Tables 4 and 5 for chiral columns and eluents) to give 2-[1-[2-(5-fluoroisoindolin-2-yl)-3,6-dimethyl-4-oxo-chromen-8-yl]ethylamino]benzoic acid, Isomer 1 (>96% ee) and 2-[1-[2-(5-fluoroisoindolin-2-yl)-3,6-dimethyl-4-oxo-chromen-8-yl]ethylamino]benzoic acid, Isomer 2 (>99% ee). For both enantiomers: MS ES+ m/z 473.3 [M+H]+.

Example 274: 2-[[(1R)-1-[3,6-Dimethyl-2-(3-methyl-3-phenyl-azetidin-1-yl)-4-oxo-chromen-8-yl]ethyl]amino]benzoic acid

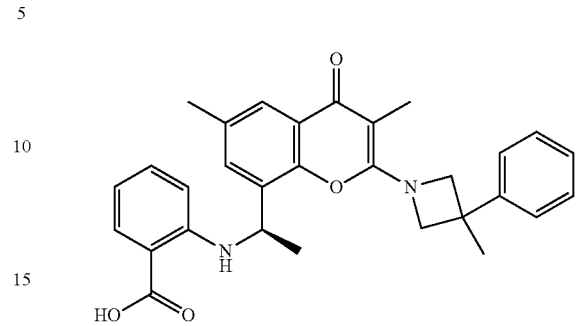

A mixture of 2-[[(1R)-1-(2-ethylsulfinyl-3,6-dimethyl-4-oxo-chromen-8-yl)ethyl]amino]benzoic acid (50 mg, 121 umol, 1 eq), 3-methyl-3-phenyl-azetidine-HCl (33 mg, 181 umol, 1.5 eq), and DIEA (78 mg, 605 umol, 105 uL, 5 eq) in DMSO (1.5 mL) was stirred at 80° C. for 16 h to give a dark solution. The mixture was filtered and purified by reverse phase HPLC (C18 column, water:acetonitrile gradient, with 0.225% formic acid as an additive) to give 2-[[(1R)-1-[3,6-dimethyl-2-(3-methyl-3-phenyl-azetidin-1-yl)-4-oxo-chromen-8-yl]ethyl]amino]benzoic acid. MS ES+ m/z 483.3 [M+H]+.

The following compounds in Table 15 were prepared essentially as described for 2-[[(1R)-1-[3,6-dimethyl-2-(3-methyl-3-phenyl-azetidin-1-yl)-4-oxo-chromen-8-yl]ethyl]amino]benzoic acid.

TABLE 15

| Example # | Chemical Name | Structure | ES/MS m/z (M + H) |
|---|---|---|---|
| 275 | 2-[[(1R)-1-[2-[3-(1,1-Difluoroethyl)azetidin-1-yl]-3,6-dimethyl-4-oxo-chromen-8-yl]ethyl]amino]benzoic acid | 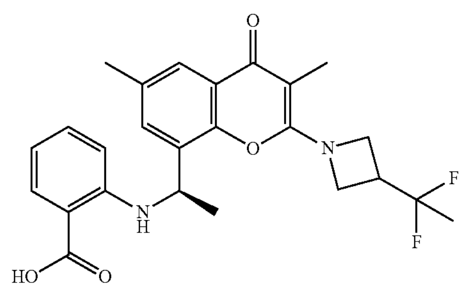 [SMILES: Cc1cc([C@@H](C)Nc2ccccc2C(=O)O)c2oc(N3CC(C(C)(F)F)C3)c(C)c(=O)c2c1] | 457 |
| 276 | 2-[[(1R)-1-[2-(6,6-Difluoro-2-azaspiro[3.3]heptan-2-yl)-3,6-dimethyl-4-oxo-chromen-8-yl]ethyl]amino]benzoic acid | 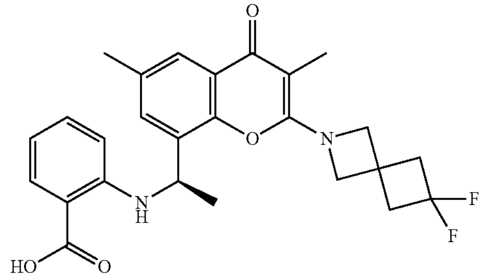 [SMILES: Cc1cc([C@@H](C)Nc2ccccc2C(=O)O)c2oc(N3CC4(C3)CC(F)(F)C4)c(C)c(=O)c2c1] | 469 |

TABLE 15-continued

| Example # | Chemical Name | Structure | ES/MS m/z (M + H) |
|---|---|---|---|
| 277 | 2-[[(1R)-1-[2-[3-(2-Fluorophenyl)-3-methyl-azetidin-1-yl]-3,6-dimethyl-4-oxo-chromen-8-yl]ethyl]amino]benzoic acid | 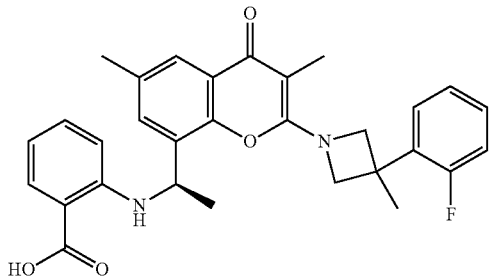 [SMILES: Cc1cc([C@@H](C)Nc2ccccc2C(=O)O)c2oc(N3CC(C)(c4ccccc4F)C3)c(C)c(=O)c2c1] | 501 |
| 278 | 2-[[(1R)-1-[3,6-Dimethyl-4-oxo-2-[3-(2-pyridyl)azetidin-1-yl]chromen-8-yl]ethyl]amino]benzoic acid | 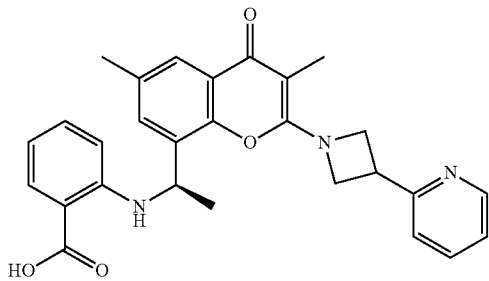 [SMILES: Cc1cc([C@@H](C)Nc2ccccc2C(=O)O)c2oc(N3CC(c4ccccn4)C3)c(C)c(=O)c2c1] | 470 |
| 279 | 2-[[(1R)-1-[3,6-Dimethyl-4-oxo-2-[6-(trifluoromethyl)-2-azaspiro[3.3]heptan-2-yl]chromen-8-yl]ethyl]amino]benzoic acid | 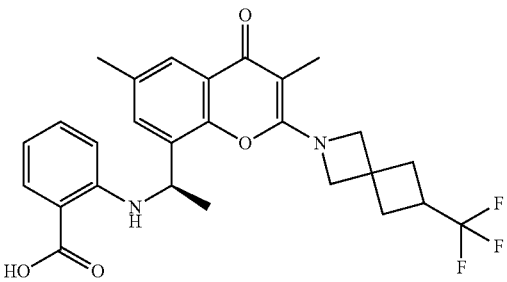 [SMILES: Cc1cc([C@@H](C)Nc2ccccc2C(=O)O)c2oc(N3CC4(CC(C(F)(F)F)C4)C3)c(C)c(=O)c2c1] | 501 |
| 280 | 2-[[(1R)-1-[2-[3-(4-Fluorophenyl)-3-methyl-azetidin-1-yl]-3,6-dimethyl-4-oxo-chromen-8-yl]ethyl]amino]benzoic acid | 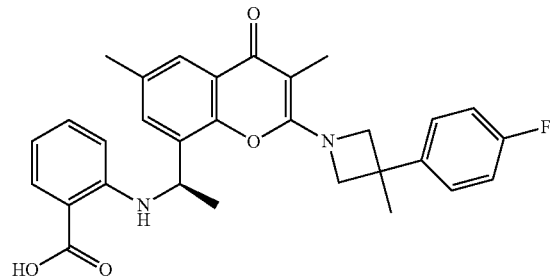 [SMILES: Cc1cc([C@@H](C)Nc2ccccc2C(=O)O)c2oc(N3CC(C)(c4ccc(F)cc4)C3)c(C)c(=O)c2c1] | 501 |
| 281 | 2-[[(1R)-1-[2-(3,3-Difluoropyrrolidin-l-yl)-3,6-dimethyl-4-oxo-chromen-8-yl]ethyl]amino]benzoic acid | 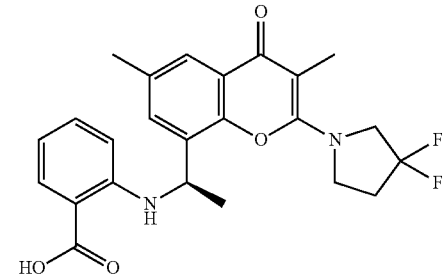 [SMILES: Cc1cc([C@@H](C)Nc2ccccc2C(=O)O)c2oc(N3CCC(F)(F)C3)c(C)c(=O)c2c1] | 443 |

TABLE 15-continued

| Example # | Chemical Name | Structure | ES/MS m/z (M + H) |
|---|---|---|---|
| 282 | 2-[[(1R)-1-[2-(4,4-Difluoro-1-piperidyl)-3,6-dimethyl-4-oxo-chromen-8-yl]ethyl]amino]benzoic acid | 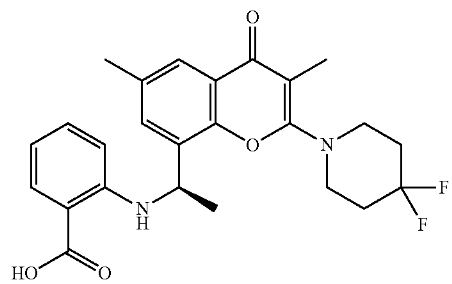 [SMILES: Cc1cc([C@@H](C)Nc2ccccc2C(=O)O)c2oc(N3CCC(F)(F)CC3)c(C)c(=O)c2c1] | 457 |
| 283 | 2-[[(1R)-1-[2-(4-Fluoro-1-piperidyl)-3,6-dimethyl-4-oxo-chromen-8-yl]ethyl]amino]benzoic acid | 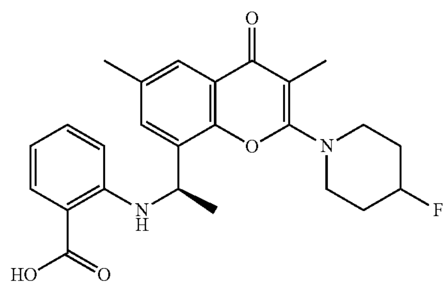 [SMILES: Cc1cc([C@@H](C)Nc2ccccc2C(=O)O)c2oc(N3CCC(F)CC3)c(C)c(=O)c2c1] | 439 |
| 284 | 2-[[(1R)-1-[2-[(3S,4R)-3,4-Difluoropyrrolidin-l-yl]-3,6-dimethyl-4-oxo-chromen-8-yl]ethyl]amino]benzoic acid | 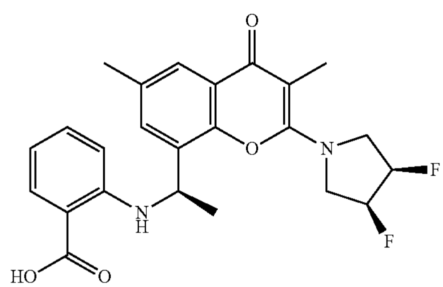 [SMILES: Cc1cc([C@@H](C)Nc2ccccc2C(=O)O)c2oc(N3C[C@@H](F)[C@@H](F)C3)c(C)c(=O)c2c1] | 443 |
| 285 | 2-[[(1R)-1-[2-(6-Azaspiro[2.5]octan-6-yl)-3,6-dimethyl-4-oxo-chromen-8-yl]ethyl]amino]benzoicacid | 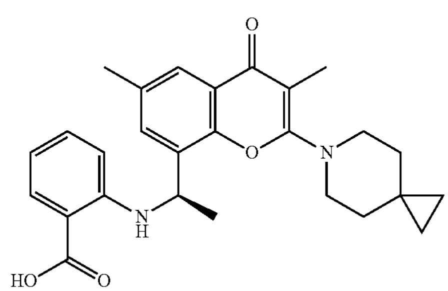 [SMILES: Cc1cc([C@@H](C)Nc2ccccc2C(=O)O)c2oc(N3CCC4(CC3)CC4)c(C)c(=O)c2c1] | 447 |
| 286 | 2-[[(1R)-1-[3,6-dimethyl-4-oxo-2-[(3R)-3-phenylpyrrolidin-1-yl]chromen-8-yl]ethyl]amino]benzoic acid | 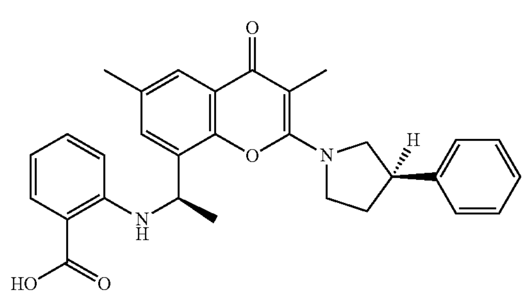 [SMILES: Cc1cc([C@@H](C)Nc2ccccc2C(=O)O)c2oc(N3CC[C@H](c4ccccc4)C3)c(C)c(=O)c2c1] | 483 |

TABLE 15-continued

| Example # | Chemical Name | Structure | ES/MS m/z (M + H) |
|---|---|---|---|
| 287 | 2-[[(1R)-1-[3,6-dimethyl-4-oxo-2-[(3S)-3-phenylpyrrolidin-1-yl]chromen-8-yl]ethyl]amino]benzoic acid | 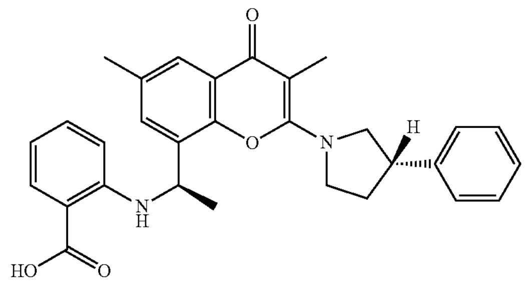 [SMILES: Cc1cc([C@@H](C)Nc2ccccc2C(=O)O)c2oc(N3CC[C@@H](c4ccccc4)C3)c(C)c(=O)c2c1] | 483 |

Example 288: 2-[[(1R)-1-[2-(4-Cyano-4-phenyl-1-piperidyl)-3,6-dimethyl-4-oxo-chromen-8-yl]ethyl]amino]benzoic acid

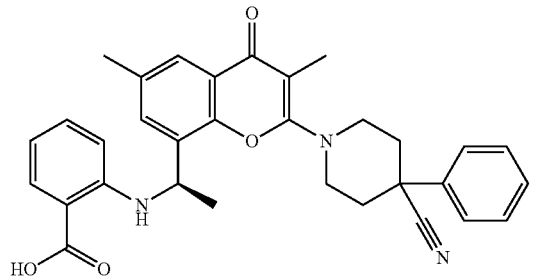 [SMILES: Cc1cc([C@@H](C)Nc2ccccc2C(=O)O)c2oc(N3CCC(C#N)(c4ccccc4)CC3)c(C)c(=O)c2c1]

A mixture of 2-[[(1R)-1-(2-ethylsulfinyl-3,6-dimethyl-4-oxo-chromen-8-yl)ethyl]amino]benzoic acid (50 mg, 121 umol, 1 eq), 4-phenylpiperidine-4-carbonitrile (34 mg, 181 umol, 1.5 eq), and DIEA (78 mg, 605 umol, 105 uL, 5 eq) in DMSO (1 mL) was stirred at 80° C. for 3 d. The mixture was filtered and the filtrate was purified by reverse phase HPLC ($C_{18}$ column, water:acetonitrile gradient with 0.225% formic acid as an additive) to give 2-[[(1R)-1-[2-(4-cyano-4-phenyl-1-piperidyl)-3,6-dimethyl-4-oxo-chromen-8-yl]ethyl]amino]benzoic acid. MS ES+ m/z 522.3 [M+H]$^+$.

Example 289: 2-[[(1R)-1-[2-(7,7-Difluoro-2-azaspiro[3.3]heptan-2-yl)-3,6-dimethyl-4-oxo-chromen-8-yl]ethyl]amino]benzoic acid

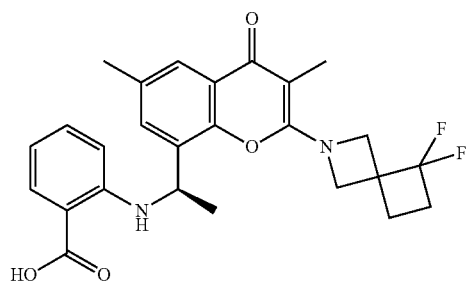 [SMILES: Cc1cc([C@@H](C)Nc2ccccc2C(=O)O)c2oc(N3CC4(CCC4(F)F)C3)c(C)c(=O)c2c1]

A mixture of 2-[[(1R)-1-(2-ethylsulfinyl-3,6-dimethyl-4-oxo-chromen-8-yl)ethyl]amino]benzoic acid (50 mg, 121 umol, 1 eq), 7,7-difluoro-2-azaspiro[3.3]heptane-HCl (31 mg, 181 umol, 1.5 eq), and DIEA (78 mg, 605 umol, 105 uL, 5 eq) in DMSO (1 mL) was stirred at 80° C. for 16 h. The mixture was filtered, and the filtrate was purified by reverse phase HPLC ($C_{18}$ column, water:acetonitrile gradient with 0.225% formic acid as an additive) to give 2-[[(1R)-1-[2-(7,7-difluoro-2-azaspiro[3.3]heptan-2-yl)-3,6-dimethyl-4-oxo-chromen-8-yl]ethyl]amino]benzoic acid as an off-white solid. MS ES+ m/z 469.3 [M+H]$^+$.

Example 290: 2-[1-[2-(5-Fluoroisoindolin-2-yl)-6-methyl-4-oxo-chromen-8-yl]ethylamino]benzamide

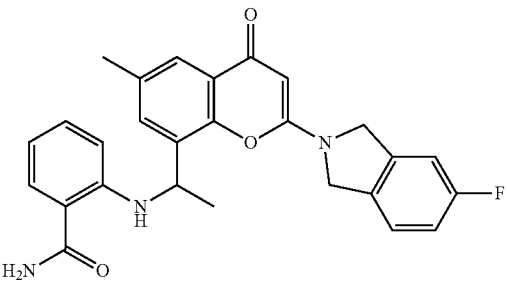 [SMILES: Cc1cc(C(C)Nc2ccccc2C(N)=O)c2oc(N3Cc4ccc(F)cc4C3)cc(=O)c2c1]

A mixture of 8-(1-bromoethyl)-2-(5-fluoroisoindolin-2-yl)-6-methyl-chromen-4-one (40 mg, 99 umol, 1 eq) and 2-amino-N-methyl-benzamide (27 mg, 199 umol, 2 eq) in DMF (1 mL) was stirred at 80° C. for 14 h and purified by reverse phase HPLC (C18 column, water:acetonitrile gradient, with 0.225% formic acid as an additive) to give 2-[1-[2-(5-fluoroisoindolin-2-yl)-6-methyl-4-oxo-chromen-8-yl]ethylamino]benzamide as a white solid. MS ES+ m/z 458.4 [M+H]$^+$.

The following compounds in Table 16 were prepared essentially as described for 2-[1-[2-(5-fluoroisoindolin-2-yl)-6-methyl-4-oxo-chromen-8-yl]ethyl amino]benzamide.

TABLE 16

| Example # | Chemical Name | Structure | ES/MS m/z (M + H) |
|---|---|---|---|
| 291 | 2-[1-[2-(5-Fluoroisoindolin-2-yl)-6-methyl-4-oxo-chromen-8-yl]ethylamino]-N-methyl-benzamide | 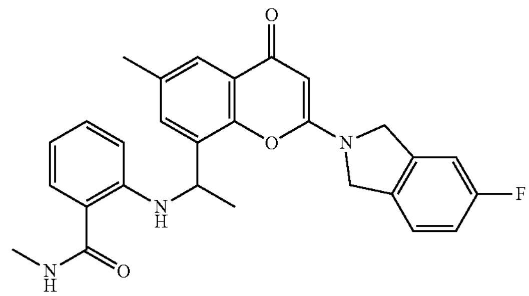 [SMILES: CNC(=O)c1ccccc1NC(C)c1cc(C)cc2c(=O)cc(N3Cc4ccc(F)cc4C3)oc12] | 472 |
| 292 | 2-[1-[2-(5-Fluoroisoindolin-2-yl)-6-methyl-4-oxo-chromen-8-yl]ethylamino]-N,N-dimethyl-benzamide | 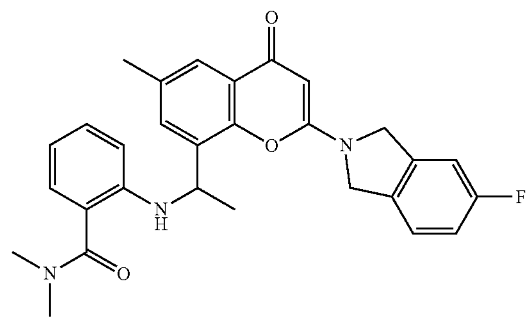 [SMILES: Cc1cc(C(C)Nc2ccccc2C(=O)N(C)C)c2oc(N3Cc4ccc(F)cc4C3)cc(=O)c2c1] | 486 |
| 293 | 2-[1-[2-(5-Fluoroisoindolin-2-yl)-6-methyl-4-oxo-chromen-8-yl]ethylamino]-6-methoxy-benzoic acid, Isomer 1 | 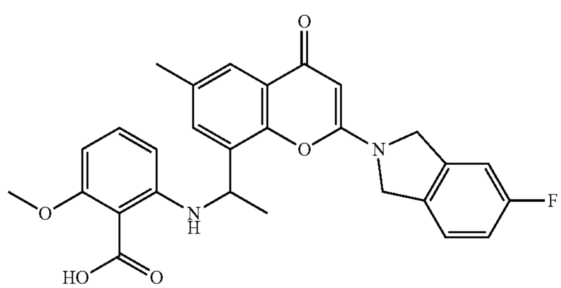 [SMILES: COc1cccc(NC(C)c2cc(C)cc3c(=O)cc(N4Cc5ccc(F)cc5C4)oc23)c1C(=O)O] | 489 |
| 294 | 2-[1-[2-(5-Fluoroisoindolin-2-yl)-6-methyl-4-oxo-chromen-8-yl]ethylamino]-6-methoxy-benzoic acid, Isomer 2 | 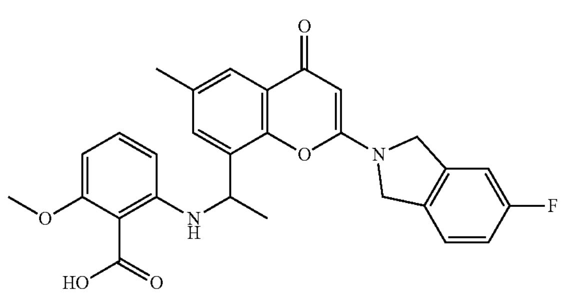 [SMILES: COc1cccc(NC(C)c2cc(C)cc3c(=O)cc(N4Cc5ccc(F)cc5C4)oc23)c1C(=O)O] | 489 |

381

Example 295: 3-[1-[2-(5-Carbamoylisoindolin-2-yl)-6-methyl-4-oxo-chromen-8-yl]ethylamino]-6-chloro-pyridine-2-carboxylic acid

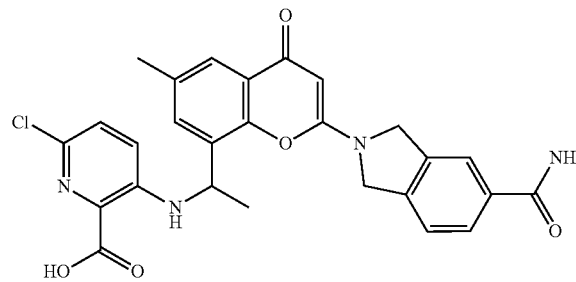

A mixture of 6-chloro-3-[1-(2-ethylsulfinyl-6-methyl-4-oxo-chromen-8-yl)ethylamino]pyridine-2-carboxylic acid (150 mg, 344.9 mmol, 1 eq), isoindoline-5-carboxamide (102.8 mg, 517.37 umol, 1.5 eq, HCl), and DIEA (222.9 mg, 1.7 mmol, 300 uL, 5 eq) in DMSO (1 mL) was stirred at 80° C. for 16 hours to give a dark suspension. The mixture was poured into water (20 mL) and EtOAc (20 mL) was added. The aqueous phase was adjusted pH to 2 with HCl (aq 1M), and then the solid crude product was collected by filtration. The crude product was treated with DMF (3 mL) and aqueous ammonia (0.25 mL), and the mixture was purified by reverse phase HPLC (C-18 column, Water-acetonitrile gradient with 0.2% ammonium hydroxide) to give 3-[1-[2-(5-carbamoylisoindolin-2-yl)-6-methyl-4-oxo-chromen-8-yl]ethylamino]-6-chloro-pyridine-2-carboxylic acid. MS ES+ m/z 519 [M+H]+.

The following compounds in Table 17 were prepared essentially as described for 3-[1-[2-(5-carbamoylisoindolin-2-yl)-6-methyl-4-oxo-chromen-8-yl]ethylamino]-6-chloro-pyridine-2-carboxylic acid.

Example 297: 6-Chloro-3-[1-[2-(5-fluoroisoindolin-2-yl)-6-methyl-4-oxo-chromen-8-yl]ethylamino]pyridine-2-carboxylic acid

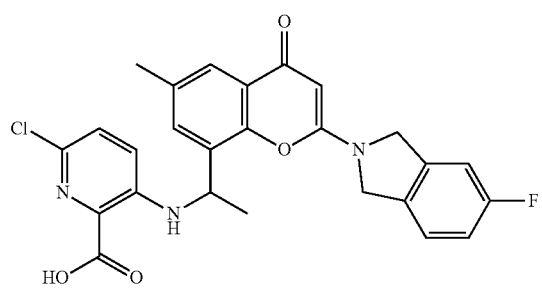 [SMILES: Cc1cc(C(C)Nc2ccc(Cl)nc2C(=O)O)c2oc(N3Cc4ccc(F)cc4C3)cc(=O)c2c1]

382

A mixture of 6-chloro-3-[1-(2-ethylsulfinyl-6-methyl-4-oxo-chromen-8-yl)ethylamino]pyridine-2-carboxylic acid (150 mg, 345 umol, 1 eq), 5-fluoroisoindoline-HCl (120 mg, 690 umol, 2 eq), and DIEA (223 mg, 1.7 mmol, 300 uL, 5 eq) in chloroform (2 mL) was stirred at 60° C. for 16 hours to give a brown suspension. The mixture was concentrated, and the residue was triturated with DMF (3 mL) and aqueous ammonium hydroxide (0.5 mL). 6-Chloro-3-[1-[2-(5-fluoroisoindolin-2-yl)-6-methyl-4-oxo-chromen-8-yl]ethylamino]pyridine-2-carboxylic acid was collected by filtration. MS ES+ m/z 494.1 [M+H]+.

Example 298: 3-[1-[2-(6-Azaspiro[2.5]octan-6-yl)-6-methyl-4-oxo-chromen-8-yl]ethylamino]-6-chloro-pyridine-2-carboxylic acid

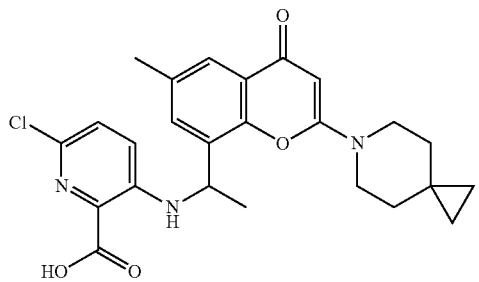 [SMILES: Cc1cc(C(C)Nc2ccc(Cl)nc2C(=O)O)c2oc(N3CCC4(CC3)CC4)cc(=O)c2c1]

A mixture of 6-chloro-3-[1-(2-ethylsulfinyl-6-methyl-4-oxo-chromen-8-yl)ethylamino]pyridine-2-carboxylic acid (100 mg, 230 umol, 1 eq) and 6-azaspiro[2.5]octane-HCl (68 mg, 460 umol, 2 eq), and DIEA (149 mg, 1.15 mmol, 200 uL, 5 eq) in chloroform (2 mL) was stirred at 60° C. for 16 h to give a dark suspension. The mixture was diluted with water (20 mL), then extracted with dichloromethane (2×20 mL), washed with brine (20 mL×2), dried over sodium sulfate, filtered, and concentrated. The residue was triturated with acetonitrile (1.5 mL) and purified by reverse phase HPLC (C-18 column, water-acetonitrile gradient, 36-76% acetonitrile, with 0.225% formic acid as an additive) to give 3-[1-[2-(6-azaspiro[2.5]octan-6-yl)-6-methyl-4-oxo-chromen-8-yl]ethylamino]-6-chloro-pyridine-2-carboxylic acid. MS ES+ m/z 468.3 [M+H]+.

TABLE 17

| Example # | Chemical Name | Structure | ES/MS m/z (M + H) |
|---|---|---|---|
| 296 | 6-Chloro-3-[1-(2-isoindolin-2-yl-6-methyl-4-oxo-chromen-8-yl)ethylamino]pyridine-2-carboxylic acid | 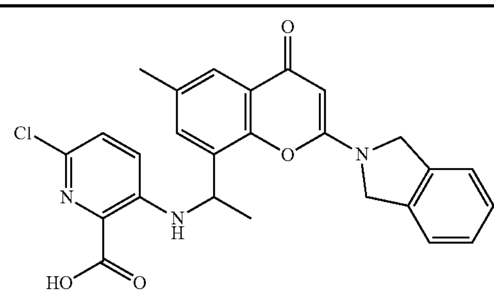 | 476 |

Example 299: 6-Chloro-3-[1-[2-(6,8-dihydro-[1,3]dioxolo[4,5-e]isoindol-7-yl)-6-methyl-4-oxo-chromen-8-yl]ethylamino]pyridine-2-carboxylic acid

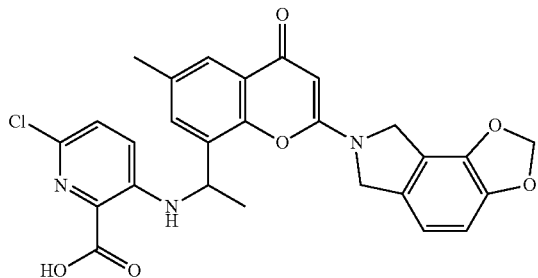 [SMILES: Cc1cc(C(C)Nc2ccc(Cl)nc2C(=O)O)c2oc(N3Cc4ccc5c(c4C3)OCO5)cc(=O)c2c1]

A mixture of 6-chloro-3-[1-(2-ethylsulfinyl-6-methyl-4-oxo-chromen-8-yl)ethylamino]pyridine-2-carboxylic acid (100 mg, 223 umol, 1 eq), 7,8-dihydro-6H-[1,3]dioxolo[4,5-e]isoindole-HCl (69 mg, 345 umol, 1.50 eq), and DIEA (149 mg, 1.15 mmol, 200 uL, 5 eq) in chloroform (2 mL) was stirred at 60° C. for 16 h to give a dark suspension. The mixture was diluted with water (10 mL), extracted with dichloromethane (3×10 mL), dried over sodium sulfate, filtered, and concentrated. The residue was triturated with acetonitrile (3 mL) and purified by reverse phase HPLC (C-18 column, water-acetonitrile gradient with 0.225% formic acid) to give 6-chloro-3-[1-[2-(6,8-dihydro-[1,3]dioxolo[4,5-e]isoindol-7-yl)-6-methyl-4-oxo-chromen-8-yl]ethylamino]pyridine-2-carboxylic acid. MS ES+ m/z 520.3 [M+H]+.

Example 300: 6-Chloro-3-[[(1R)-1-(2-isoindolin-2-yl-6-methyl-4-oxo-chromen-8-yl)ethyl]amino]pyridine-2-carboxylic acid

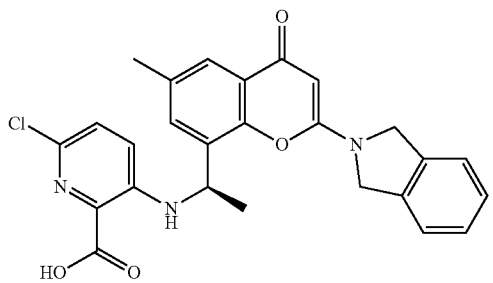 [SMILES: Cc1cc([C@@H](C)Nc2ccc(Cl)nc2C(=O)O)c2oc(N3Cc4ccccc4C3)cc(=O)c2c1]

Step 1: A mixture of methyl 6-chloro-3-[[(1R)-1-(2-ethylsulfinyl-6-methyl-4-oxo-chromen-8-yl)ethyl]amino]pyridine-2-carboxylate (200 mg, 445.5 umol, 1 eq), isoindoline-HCl (139 mg, 891 umol, 132 uL, 2 eq), and DIEA (288 mg, 2.2 mmol, 388 uL, 5 eq) in chloroform (2 mL) was stirred at 60° C. for 16 hours to give a brown solution. The mixture was poured into water (10 mL) and DCM (10 mL), the aqueous phase was adjusted pH to 2 with HCl (1M), the layers were separated, and the aqueous layer was extracted again with DCM (3×10 mL). The combined organic layer was washed with brine (20 mL), dried over anhydrous sodium sulfate, and concentrated in vacuum.

Step 2: The crude material (200 mg, ~408.21 umol, 1 eq) was treated with a solution of NaOH (33 mg, 816 umol, 2 eq) and H2O (0.2 mL) in MeOH (2 mL). The mixture was stirred at 50° C. for 1 hour to give a brown solution. The mixture was poured into water (20 mL), adjusted to pH 2 with HCl (1M), and extracted with DCM (3×20 mL). The combined organic layer was washed with brine (30 mL), dried over anhydrous sodium sulfate, and concentrated in vacuo. The residue was dissolved in a mixture of MeOH (2 mL), DMF (2 mL) and ammonia water (0.5 mL) and purified by HPLC (Column: YMC Triart C18, 7 um, 250×50 mm; mobile phase: [A: Water with 0.05% ammonia hydroxide v/v)-B: Acetonitrile]; B %: 0%-40%, 9 min) to give 6-chloro-3-[[(1R)-1-(2-isoindolin-2-yl-6-methyl-4-oxo-chromen-8-yl)ethyl]amino]pyridine-2-carboxylic acid. MS ES+ m/z 476.1 [M+H]+.

Example 301: 6-Chloro-3-[[(1R)-1-[2-(6,8-dihydro-[1,3]dioxolo[4,5-e]isoindol-7-yl)-6-methyl-4-oxo-chromen-8-yl]ethyl]amino]pyridine-2-carboxylic acid

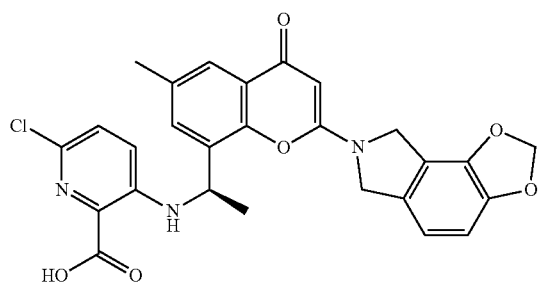 [SMILES: Cc1cc([C@@H](C)Nc2ccc(Cl)nc2C(=O)O)c2oc(N3Cc4ccc5c(c4C3)OCO5)cc(=O)c2c1]

Step 1: A mixture of methyl 6-chloro-3-[[(1R)-1-(2-ethylsulfinyl-6-methyl-4-oxo-chromen-8-yl)ethyl]amino]pyridine-2-carboxylate (276 mg, 615 umol, 1 eq), 7,8-dihydro-6H-[1,3]dioxolo[4,5-e]isoindole-HCl (196 mg, 982 umol, 1.6 eq), and DIEA (397 mg, 3.1 mmol, 536 uL, 5 eq) in CHCl3 (4 mL) was stirred at 60° C. for 16 hours to give a black-brown solution. The mixture was concentrated in vacuo to give a crude residue.

Step 2: The crude material was treated with a solution of NaOH (90 mg) and H2O (0.6 mL) in MeOH (6 mL). The mixture was stirred at 50° C. for 1.5 hours to give a black-brown solution. The mixture was poured into water (20 mL), adjusted to pH 2 with HCl (1M), and extracted with DCM (3×20 mL). The combined organic layer was washed with brine (30 mL), dried over anhydrous sodium sulfate, and concentrated in vacuo. The residue was triturated from DMF (4 mL) and 6-chloro-3-[[(1R)-1-[2-(6,8-dihydro-[1,3]dioxolo[4,5-e]isoindol-7-yl)-6-methyl-4-oxo-chromen-8-yl]ethyl]amino]pyridine-2-carboxylic acid was collected by filtration. MS ES+ m/z 520 [M+H]+.

Example 302: 3-[1-[2-(6-Azaspiro[2.5]octan-6-yl)-3,6-dimethyl-4-oxo-chromen-8-yl]ethylamino]-6-chloro-pyridine-2-carboxylic acid

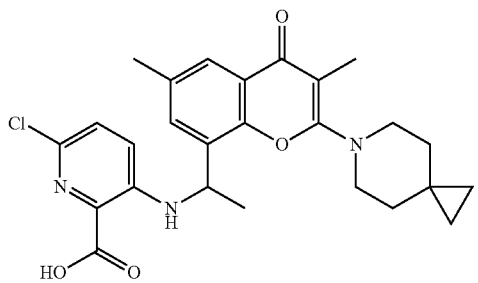 [SMILES: Cc1cc(C(C)Nc2ccc(Cl)nc2C(=O)O)c2oc(N3CCC4(CC3)CC4)c(C)c(=O)c2c1]

A mixture of 6-chloro-3-[1-(2-ethylsulfinyl-3,6-dimethyl-4-oxo-chromen-8-yl)ethylamino]pyridine-2-carboxylic acid (150.00 mg, 334.14 umol, 1 eq), 6-azaspiro[2.5]octane-HCl (74 mg, 501 umol, 1.5 eq), and DIEA (216 mg, 1.67 mmol, 291 uL, 5 eq) in chloroform (2 mL) was stirred at 60° C. for 16 h to give a black solution. To complete the reaction, the mixture was treated with additional 6-azaspiro[2.5]octane-HCl (74 mg, 501 umol, 1.5 eq). The mixture was stirred for 16 h at 60° C. then concentrated and purified by reverse phase HPLC (water-acetonitrile gradient, 0.2% formic acid or ammonium hydroxide as additive) to give 3-[1-[2-(6-azaspiro[2.5]octan-6-yl)-3,6-dimethyl-4-oxo-chromen-8-yl]ethylamino]-6-chloro-pyridine-2-carboxylic acid. MS ES+ m/z 482.2 [M+H]$^+$.

The following compounds in Table 18 were prepared essentially as described for 3-[1-[2-(6-azaspiro[2.5]octan-6-yl)-3,6-dimethyl-4-oxo-chromen-8-yl]ethylamino]-6-chloro-pyridine-2-carboxylic acid.

TABLE 18

| Example # | Chemical Name | Structure | ES/MS m/z (M + H) |
|---|---|---|---|
| 303 | 6-Chloro-3-[1-(2-isoindolin-2-yl-3,6-dimethyl-4-oxo-chromen-8-yl)ethylamino]pyridine-2-carboxylic acid | 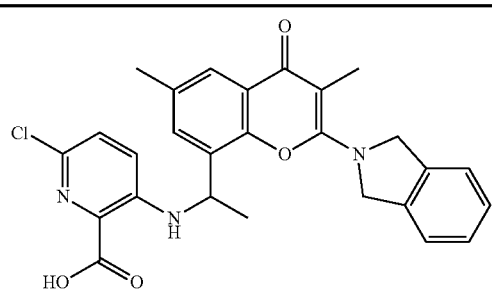 | 490 |
| 304 | 3-[1-[2-(5-Carbamoylisoindolin-2-yl)-3,6-dimethyl-4-oxo-chromen-8-yl]ethylamino]-6-chloro-pyridine-2-carboxylic acid | 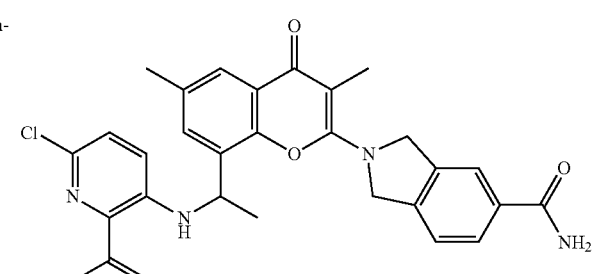 | 533 |
| 305 | 6-Chloro-3-[1-[3,6-dimethyl-4-oxo-2-(1-piperidyl)chromen-8-yl]ethylamino]pyridine-2-carboxylic acid | 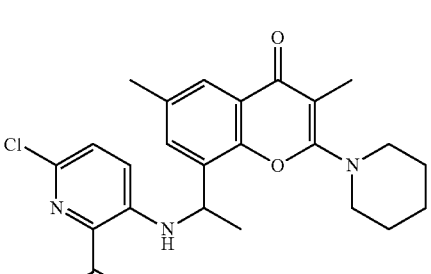 | 456 |

Example 306: 3-[[(1R)-1-[2-(6-Azaspiro[2.5]octan-6-yl)-3,6-dimethyl-4-oxo-chromen-8-yl]ethyl]amino]-6-chloro-pyridine-2-carboxylic acid

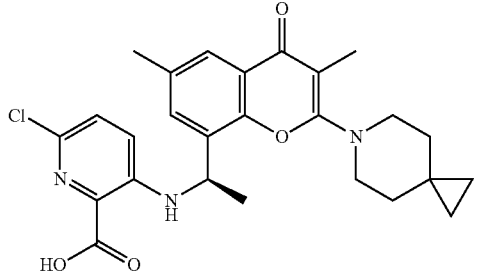 [SMILES: Cc1cc([C@@H](C)Nc2ccc(Cl)nc2C(=O)O)c2oc(N3CCC4(CC3)CC4)c(C)c(=O)c2c1]

Step 1. A mixture of methyl 6-chloro-3-[[(1R)-1-(2-ethylsulfinyl-3,6-dimethyl-4-oxo-chromen-8-yl)ethyl]amino]pyridine-2-carboxylate (350 mg, 756 umol, 1 eq), 6-azaspiro[2.5]octane-HCl (134 mg, 907 umol, 1.2 eq), and DIEA (489 mg, 3.8 mmol, 658 uL, 5 eq) in DMSO (10 mL) was stirred at 80° C. for 54 h to give a dark solution. The mixture was diluted with water (30 mL) and extracted with ethyl acetate (2×50 mL). The combined organic phase was washed with brine (50 mL), dried with anhydrous sodium sulfate, filtered, and concentrated in vacuo.

Step 2. The product from Step 1 (~400 mg, 807 umol, 1 eq), NaOH (161 mg, 4.0 mmol, 5 eq), methanol (15 mL) and water (3 mL) were stirred at 45° C. for 1 h. The mixture was treated with HCl (20 mL, 1M, aq) and extracted with dichloromethane (2×50 mL). The combined organic phase was washed with brine (30 mL), dried with anhydrous sodium sulfate, filtered, and concentrated in vacuo. The residue was purified by reverse phase HPLC (C18 column; water-acetonitrile gradient, with 0.225% formic acid as an additive) to give 3-[[(1R)-1-[2-(6-azaspiro[2.5]octan-6-yl)-3,6-dimethyl-4-oxo-chromen-8-yl]ethyl]amino]-6-chloro-pyridine-2-carboxylic acid as a yellow solid. MS ES+ m/z 482.1 [M+H]$^+$.

The following compounds in Table 19 were prepared essentially as described for 3-[[(1R)-1-[2-(6-azaspiro[2.5]octan-6-yl)-3,6-dimethyl-4-oxo-chromen-8-yl]ethyl]amino]-6-chloro-pyridine-2-carboxylic acid.

Example 308: 6-Chloro-3-[[(1R)-1-[2-(5-fluoroisoindolin-2-yl)-3,6-dimethyl-4-oxo-chromen-8-yl]ethyl]amino]pyridine-2-carboxylic acid

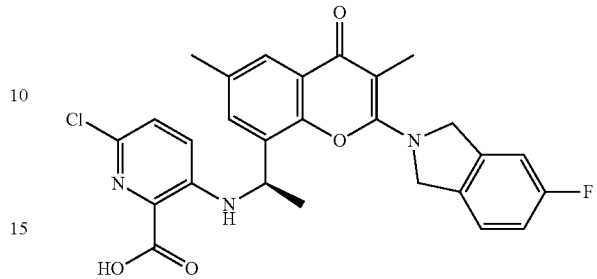

Step 1. A mixture of methyl 6-chloro-3-[[(1R)-1-(2-ethylsulfinyl-3,6-dimethyl-4-oxo-chromen-8-yl)ethyl]amino]pyridine-2-carboxylate (350 mg, 756 umol, 1 eq), 5-fluoroisoindoline-HCl (158 mg, 907 umol, 1.2 eq), and DIEA (489 mg, 3.78 mmol, 658 uL, 5 eq) in DMSO (10 mL) was stirred at 80° C. for 54 h to give a dark solution. The mixture was treated with water (30 mL) and extracted with ethyl acetate (2×50 mL). The combined organic phase was washed with brine (50 mL), dried with anhydrous sodium sulfate, filtered, and concentrated in vacuo.

Step 2. The product from Step 1 (400 mg, 766 umol, 1 eq) was dissolved in a mixture of methanol (15 mL) and water (3 mL) and treated with NaOH (153 mg, 3.8 mmol, 5 eq). The mixture was stirred at 45° C. for 1 h., treated with HCl (20 mL, 1M, aq), and extracted with dichloromethane (2×50 mL). The combined organic phase was washed with brine (30 mL), dried with anhydrous sodium sulfate, filtered, and concentrated in vacuo. The residue was purified by reverse phase HPLC (Column: Boston Prime C18 150×30 mm, 5 um; Mobile phase: [A: Water (with 0.225% formic acid), B: Acetonitrile]; B %: 43%-73% in 9 min) to give 6-chloro-3-[[(1R)-1-[2-(5-fluoroisoindolin-2-yl)-3,6-dimethyl-4-oxo-chromen-8-yl]ethyl]amino]pyridine-2-carboxylic acid as a yellow solid. ES+ m/z 508.1 [M+H]$^+$.

TABLE 19

| Example # | Chemical Name | Structure | ES/MS m/z (M + H) |
|---|---|---|---|
| 307 | 6-Chloro-3-[[(1R)-1-[2-(4,4-dimethyl-1-piperidyl)-3,6-dimethyl-4-oxo-chromen-8-yl]ethyl]amino]pyridine-2-carboxylic acid | 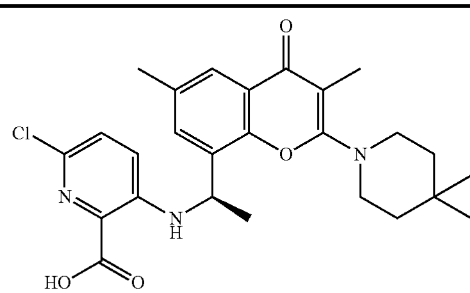 | 484 |

Example 309: 6-Chloro-3-[[(1R)-1-[3,6-dimethyl-4-oxo-2-(1-piperidyl)chromen-8-yl]ethyl]amino]pyridine-2-carboxylic acid

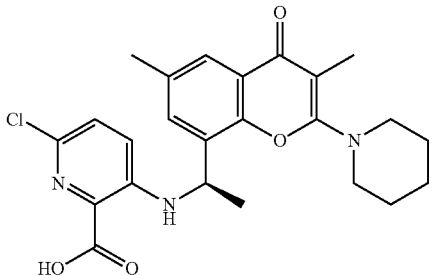 [SMILES: Cc1cc([C@@H](C)Nc2ccc(Cl)nc2C(=O)O)c2oc(N3CCCCC3)c(C)c(=O)c2c1]

Step 1. A mixture of methyl 6-chloro-3-[[(1R)-1-(2-ethylsulfinyl-3,6-dimethyl-4-oxo-chromen-8-yl)ethyl]amino]pyridine-2-carboxylate (200 mg, 432 umol, 2.4 mL, 1 eq), piperidine-HCl (63 mg, 518 umol, 73 uL, 1.2 eq), and DIEA (279 mg, 2.2 mmol, 376 uL, 5 eq) in DMSO (5 mL) was stirred at 80° C. for 16 hr. The reaction mixture was treated with brine (30 mL) and extracted with ethyl acetate (3×20 mL). The combined organic phase was dried over anhydrous sodium sulfate, filtered, and concentrated in vacuo.

Step 2. The product from Step 1 (~200 mg, 425 umol, 2.4 mL, 1 eq) and NaOH (85 mg, 2.1 mmol, 5 eq) in a mixture of methanol (10 mL) and water (4 mL) was stirred at 45° C. for 1 hr. The mixture was treated with HCl (1 M, 5 mL, aq) and extracted with dichloromethane (2×40 mL). The combined organic layer was washed with brine (40 mL), dried over anhydrous sodium sulfate, filtered, and concentrated in vacuo. The residue was purified by reverse phase HPLC (Column: Phenomenex Luna C18 100×30 mm, 3 um; mobile phase: [A: water (with 0.225% formic acid); B: acetonitrile]; B %: 50%-80% in 8 min. to give 6-chloro-3-[[(1R)-1-[3,6-dimethyl-4-oxo-2-(1-piperidyl)chromen-8-yl]ethyl]amino]pyridine-2-carboxylic acid as a white solid. MS ES+ m/z 456.0 [M+H]$^+$.

Example 310: 6-Chloro-3-[[(1R)-1-[2-(4,4-difluoro-1-piperidyl)-3,6-dimethyl-4-oxo-chromen-8-yl]ethyl]amino]pyridine-2-carboxylic acid

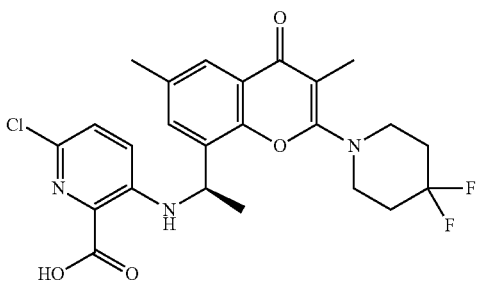 [SMILES: Cc1cc([C@@H](C)Nc2ccc(Cl)nc2C(=O)O)c2oc(N3CCC(F)(F)CC3)c(C)c(=O)c2c1]

Step 1. A mixture of methyl 6-chloro-3-[[(1R)-1-(2-ethylsulfinyl-3,6-dimethyl-4-oxo-chromen-8-yl)ethyl]amino]pyridine-2-carboxylate (75 mg, 162 umol, 1 eq), 4,4-difluoropiperidine (39 mg, 324 umol, 2 eq), and DIEA (104 mg, 810 umol, 141 uL, 5 eq) in DMSO (1.5 mL) was stirred at 80° C. for 3 d. The mixture was diluted with water (20 mL) and extracted with ethyl acetate (3×20 mL). The combined organic phase was washed with brine (2×20 mL), dried over sodium sulfate, filtered, and concentrated. The residue was purified by silica gel chromatography (0-50% ethyl acetate in petroleum ether).

Step 2. The product from Step 1 (~40 mg, 79 umol, 1 eq) was dissolved in a mixture of methanol (1 mL) and water (0.1 mL), treated with NaOH (9 mg, 237 umol, 3 eq), and stirred at 45° C. for 1 h. The mixture was concentrated and purified by reverse phase HPLC (C18 column, water:acetonitrile gradient with 0.1% ammonium hydroxide as an additive) to give 6-chloro-3-[[(1R)-1-[2-(4,4-difluoro-1-piperidyl)-3,6-dimethyl-4-oxo-chromen-8-yl]ethyl]amino]pyridine-2-carboxylic acid. MS ES+ m/z 492.3 [M+H]$^+$.

Example 311: (Isomer 1) and Example 312: (Isomer 2): 2-[1-[6-Fluoro-2-(5-fluoroisoindolin-2-yl)-4-oxo-chromen-8-yl]ethylamino]benzoic acid

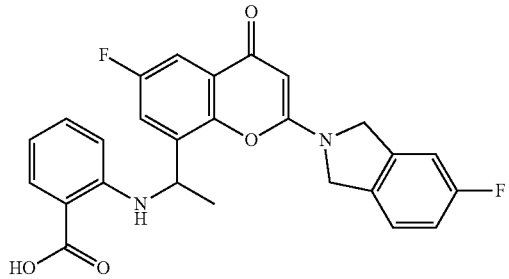 [SMILES: CC(Nc1ccccc1C(=O)O)c1cc(F)cc2c(=O)cc(N3Cc4ccc(F)cc4C3)oc12]

A mixture of 2-[1-(2-ethylsulfinyl-6-fluoro-4-oxo-chromen-8-yl)ethylamino]benzoic acid (150 mg, 372 umol, 1 eq), DIEA (240 mg, 1.86 mmol, 324 uL, 5 eq) and 5-fluoroisoindoline-HCl (97 mg, 558 umol, 1.5 eq) in chloroform (2 mL) was stirred at 60° C. for 16 hours to give a yellow solution. The mixture was diluted with water (20 mL) and extracted with dichloromethane (3×20 mL). The combined extracts were dried with sodium sulfate, filtered, and concentrated. The residue was triturated with acetonitrile (1 mL) to yield a solid. This was purified by SFC (Y, 36; See Tables 4 and 5 for chiral columns and eluents) to give 2-[1-[6-fluoro-2-(5-fluoroisoindolin-2-yl)-4-oxo-chromen-8-yl]ethylamino]benzoic acid, Isomer 1 and 2-[1-[6-fluoro-2-(5-fluoroisoindolin-2-yl)-4-oxo-chromen-8-yl]ethylamino]benzoic acid, Isomer 2; both >96% ee. Each enantiomer: MS ES+ m/z 463.3 [M+H]$^+$.

The following compounds in Table 20 were prepared essentially as described for 2-[1-[6-fluoro-2-(5-fluoroisoindolin-2-yl)-4-oxo-chromen-8-yl]ethylamino]benzoic acid. If the Example was purified with chiral SFC, the chiral column and eluent are listed in the final column (see Tables 4 and 5).

TABLE 20

| Example # | Chemical Name | Structure | ES/MS m/z (M + H) & Chiral Method |
|---|---|---|---|
| 313 | 2-[1-[2-(5-Cyanoisoindolin-2-yl)-6-fluoro-4-oxo-chromen-8-yl]ethylamino]benzoic acid, Isomer 1 | 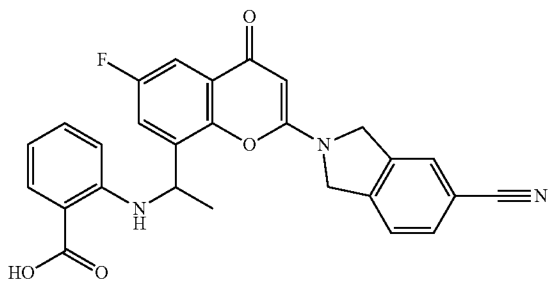 | 470 J, 5 |
| 314 | 2-[1-[2-(5-Cyanoisoindolin-2-yl)-6-fluoro-4-oxo-chromen-8-yl]ethylamino]benzoic acid, Isomer 2 | 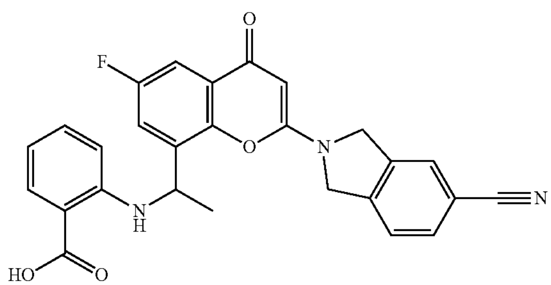 | 470 J, 5 |
| 315 | 2-[1-(6-fluoro-2-isoindolin-2-yl-4-oxo-chromen-8-yl)ethylamino]benzoic acid, Isomer 1 | 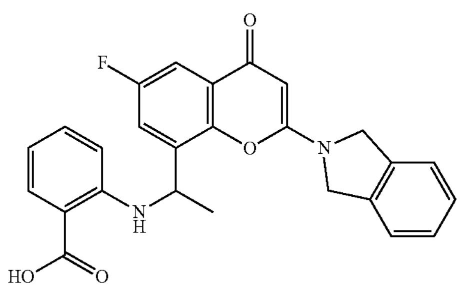 | 445 AA, 38 |
| 316 | 2-[1-(6-fluoro-2-isoindolin-2-yl-4-oxo-chromen-8-yl)ethylamino]benzoic acid, Isomer 2 | 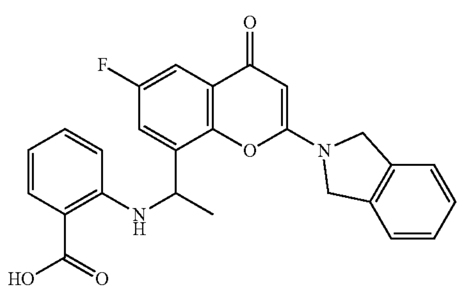 [SMILES: CC(Nc1ccccc1C(=O)O)c1cc(F)cc2c(=O)cc(N3Cc4ccccc4C3)oc12] | 445 AA, 38 |
| 317 | 2-[1-[2-(4,4-dimethyl-1-piperidyl)-6-fluoro-4-oxo-chromen-8-yl]ethylamino]benzoic acid, Isomer 1 | 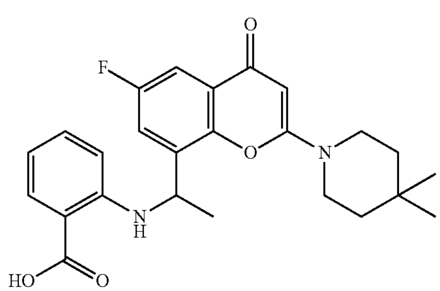 [SMILES: CC(Nc1ccccc1C(=O)O)c1cc(F)cc2c(=O)cc(N3CCC(C)(C)CC3)oc12] | 439 Y, 5 |

TABLE 20-continued

| Example # | Chemical Name | Structure | ES/MS m/z (M + H) & Chiral Method |
|---|---|---|---|
| 318 | 2-[1-[2-(4,4-dimethyl-1-piperidyl)-6-fluoro-4-oxo-chromen-8-yl]ethylamino]benzoic acid, Isomer 2 | 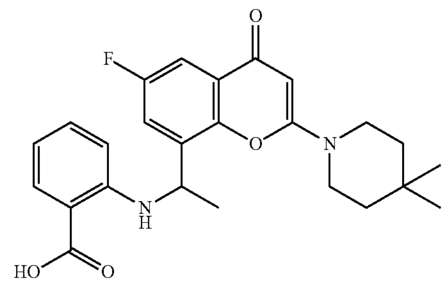 [SMILES: CC(Nc1ccccc1C(=O)O)c1cc(F)cc2c(=O)cc(N3CCC(C)(C)CC3)oc12] | 439 Y, 5 |

Example 319: (Isomer 1) and Example 320: (Isomer 2): 2-[1-[6-Fluoro-2-(5-fluoroisoindolin-2-yl)-3-methyl-4-oxo-chromen-8-yl]ethylamino]benzoic acid

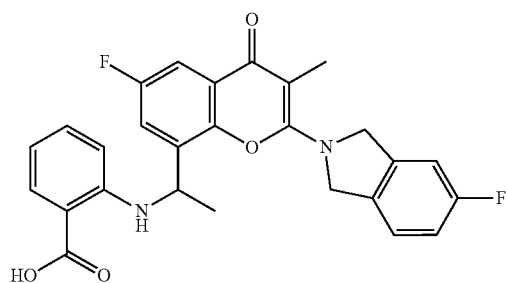

A mixture of 2-[1-(2-ethylsulfinyl-6-fluoro-3-methyl-4-oxo-chromen-8-yl)ethylamino]benzoic acid (400 mg, 958 umol, 1 eq), 5-fluoroisoindoline-HCl (299 mg, 1.72 mmol, 1.8 eq, HCl), and DIEA (619 mg, 4.8 mmol, 834 uL, 5 eq) in DMSO (8 mL) was stirred at 80° C. for 20 h to give a dark solution. The mixture was diluted with water (40 mL) and EtOAc (40 mL), adjusted to pH 3 with aqueous HCl (2 M), and extracted with ethyl acetate (3×50 mL). The combined organic phase was washed with brine (2×100 mL), dried over sodium sulfate, filtered, and concentrated to a solid. This was purified by SFC (X, 34; See Tables 4 and 5 for chiral columns and eluents) to give 2-[1-[6-fluoro-2-(5-fluoroisoindolin-2-yl)-3-methyl-4-oxo-chromen-8-yl]ethylamino]benzoic acid, Isomer 1 and 2-[1-[6-fluoro-2-(5-fluoroisoindolin-2-yl)-3-methyl-4-oxo-chromen-8-yl]ethylamino]benzoic acid, Isomer 2; both >98% ee. For both: MS ES+ m/z 477.1 [M+H]+.

The following compounds in Table 21 were prepared essentially as described for 2-[1-[6-fluoro-2-(5-fluoroisoindolin-2-yl)-3-methyl-4-oxo-chromen-8-yl]ethylamino]benzoic acid If the Example was purified with chiral SFC, the chiral column and eluent are listed in the final column (see Tables 4 and 5).

TABLE 21

| Example # | Chemical Name | Structure | ES/MS m/z (M + H) & Chiral Method |
|---|---|---|---|
| 321 | 2-[1-[2-(5-Cyanoisoindolin-2-yl)-6-fluoro-3-methyl-4-oxo-chromen-8-yl]ethylamino]benzoic acid, Isomer 1 | 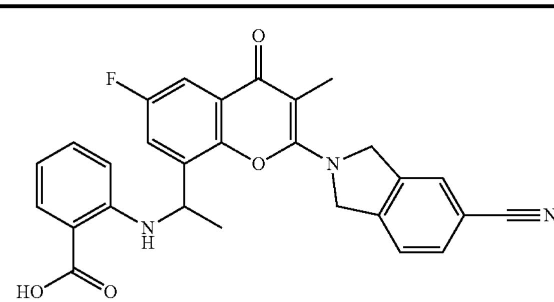 | 484 Y, 36 |

TABLE 21-continued

| Example # | Chemical Name | Structure | ES/MS m/z (M + H) & Chiral Method |
|---|---|---|---|
| 322 | 2-[1-[2-(5-Cyanoisoindolin-2-yl)-6-fluoro-3-methyl-4-oxo-chromen-8-yl]ethylamino]benzoic acid, Isomer 2 | 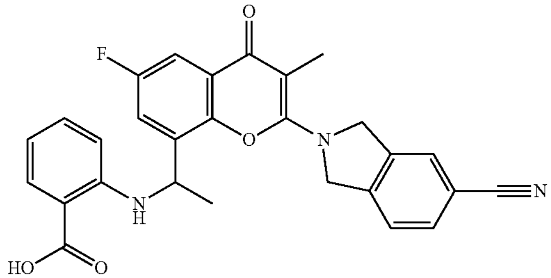 | 484 Y, 36 |

Example 323: (Isomer 1) and Example 324: (Isomer 2): 2-[1-(6-Fluoro-2-isoindolin-2-yl-3-methyl-4-oxo-chromen-8-yl)ethylamino]benzoic acid Example 325: (Isomer 1) and Example 326: (Isomer 2): 2-[1-[2-(4,4-Difluoro-1-piperidyl)-6-fluoro-3-methyl-4-oxo-chromen-8-yl]ethylamino]benzoic acid

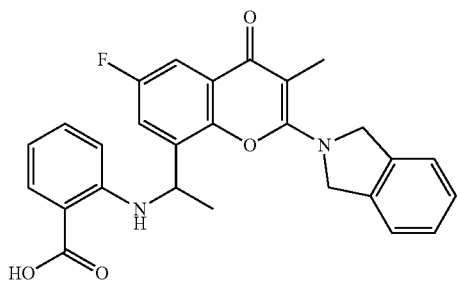

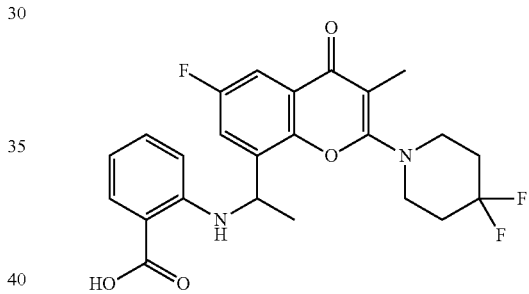

A mixture of 2-[1-(2-ethylsulfinyl-6-fluoro-3-methyl-4-oxo-chromen-8-yl)ethylamino]benzoic acid (150 mg, 359 umol, 1 eq), isoindoline-HCl (84 mg, 539 umol, 80 uL, 1.5 eq), and DIEA (232 mg, 1.8 mmol, 313 uL, 5 eq) in chloroform (3 mL) was stirred at 60° C. for 16 h under a nitrogen atmosphere. The mixture was diluted with water (20 mL) and extracted with dichloromethane (2×20 mL). The combined organic phase was washed with brine (2×20 mL), dried over sodium sulfate, filtered, concentrated in vacuo, and triturated with acetonitrile (1 mL) to give a solid. This racemic mixture was purified by SFC (U, 5; See Tables 4 and 5 for chiral columns and eluents) to give 2-[1-(6-fluoro-2-isoindolin-2-yl-3-methyl-4-oxo-chromen-8-yl)ethylamino]benzoic acid, Isomer 1 (99% ee) and 2-[1-(6-fluoro-2-isoindolin-2-yl-3-methyl-4-oxo-chromen-8-yl)ethylamino]benzoic acid, Isomer 2 (98% ee). For each enantiomer: MS ES+m/z 459.3 [M+H]+.

A mixture of 2-[1-(2-ethylsulfinyl-6-fluoro-3-methyl-4-oxo-chromen-8-yl)ethylamino]benzoic acid (150 mg, 359 umol, 1 eq), 4,4-difluoropiperidine (65 mg, 539 umol, 1.5 eq), and DIEA (232 mg, 1.8 mmol, 313 uL, 5 eq) in DMSO (1 mL) was stirred at 80° C. for 18 h. The mixture was purified by reverse phase HPLC (Column: Boston Prime C18 150×30 mm, 5 um; Mobile phase: [A: Water with 0.05% ammonium hydroxide; B: Acetonitrile]; B %: 14%-44% in 9 min). The racemic product was purified by SFC (W, 31; See Tables 4 and 5 for chiral columns and eluents) to give 2-[1-[2-(4,4-difluoro-1-piperidyl)-6-fluoro-3-methyl-4-oxo-chromen-8-yl]ethylamino]benzoic acid, Isomer 1 (100% ee) and 2-[1-[2-(4,4-difluoro-1-piperidyl)-6-fluoro-3-methyl-4-oxo-chromen-8-yl]ethylamino]benzoic acid, Isomer 2 (97% ee). For both enantiomers MS ES+ m/z 461.2 [M+H]+.

Example 327: (Isomer 1) and Example 328: (Isomer 2): 2-[1-[2-(6-Azaspiro[2.5]octan-6-yl)-6-fluoro-3-methyl-4-oxo-chromen-8-yl]ethylamino]benzoic acid

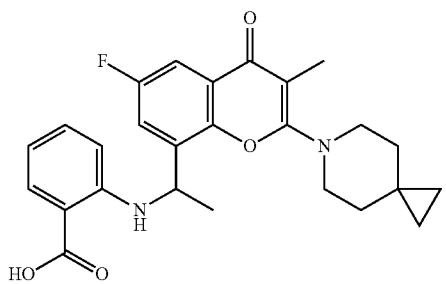 [SMILES: Cc1c(N2CCC3(CC2)CC3)oc2c(C(C)Nc3ccccc3C(=O)O)cc(F)cc2c1=O]

A mixture of 2-[1-(2-ethylsulfinyl-6-fluoro-3-methyl-4-oxo-chromen-8-yl)ethylamino]benzoic acid (151 mg, 363 umol, 1 eq) and 6-azaspiro[2.5]octane-HCl (100 mg, 544 umol, 1.5 eq), DIEA (234 mg, 1.8 mmol, 316 uL, 5 eq) in DMSO (2 mL) was stirred at 80° C. for 16 h. The mixture was diluted with water (10 mL) and extracted with ethyl acetate (3×10 mL). The combined organic phase was dried over sodium sulfate and concentrated in vacuo. The residue was purified by reverse phase HPLC (Column: Boston Prime C18 150×30 mm, 5 um; Mobile phase: [A: Water (with 0.225% formic acid); B: Acetonitrile] B %: 49%-79% in 9 min). The racemic mixture was purified by SFC (W, 14; See Tables 4 and 5 for chiral columns and eluents) to give 2-[1-[2-(6-azaspiro[2.5]octan-6-yl)-6-fluoro-3-methyl-4-oxo-chromen-8-yl]ethylamino]benzoic acid, Isomer 1 (100% ee) and 2-[1-[2-(6-azaspiro[2.5]octan-6-yl)-6-fluoro-3-methyl-4-oxo-chromen-8-yl]ethylamino]benzoic acid, Isomer 2 (100% ee). For both enantiomers MS ES+ m/z 451.3 [M+H]$^+$.

Example 329: (Isomer 1) and Example 330: (Isomer 2): 2-[1-[2-(5-Fluoroisoindolin-2-yl)-4-oxo-chromen-8-yl]ethylamino]benzoic acid

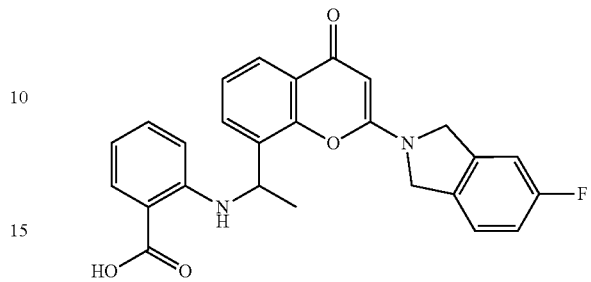

A mixture of 2-[1-(2-ethylsulfinyl-4-oxo-chromen-8-yl)ethylamino]benzoic acid (100 mg, 259 umol, 1 eq), 5-fluoroisoindoline-HCl (81 mg, 467 umol, 1.80 eq), and DIEA (168 mg, 1.30 mmol, 226 uL, 5 eq) in CHCl$_3$ (2 mL) was stirred at 60° C. for 15 h to give an orange suspension. The mixture was diluted with water (20 mL), adjusted to pH 2 with aqueous 1 M HCl, extracted with dichloromethane (3×20 mL), dried over sodium sulfate, filtered, and concentrated in vacuo. The residue was triturated with acetonitrile (2 mL) to yield a pink solid.

This solid was purified by SFC (Y, 21; See Tables 4 and 5 for chiral columns and eluents) to give 2-[1-[2-(5-fluoroisoindolin-2-yl)-4-oxo-chromen-8-yl]ethylamino]benzoic acid, Isomer 1 and 2-[1-[2-(5-fluoroisoindolin-2-yl)-4-oxo-chromen-8-yl]ethylamino]benzoic acid, Isomer 2; both >98% ee. For both: MS ES+ m/z 445.0 [M+H]$^+$.

The following compounds in Table 22 were prepared essentially as described for 2-[1-[2-(5-fluoroisoindolin-2-yl)-4-oxo-chromen-8-yl]ethylamino]benzoic acid. If the Example was purified with chiral SFC, the chiral column and eluent are listed in the final column (see Tables 4 and 5).

TABLE 22

| Example # | Chemical Name | Structure | ES/MS m/z (M + H) & Chiral Method |
|---|---|---|---|
| 331 | 2-[1-[2-(4,4-Dimethyl-1-piperidyl)-4-oxo-chromen-8-yl]ethylamino]benzoic acid, Isomer 1 | 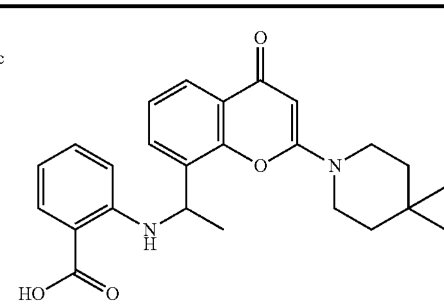 | 421 W, 24 |

TABLE 22-continued

| Example # | Chemical Name | Structure | ES/MS m/z (M + H) & Chiral Method |
|---|---|---|---|
| 332 | 2-[1-[2-(4,4-Dimethyl-1-piperidyl)-4-oxo-chromen-8-yl]ethylamino]benzoic acid, Isomer 2 | 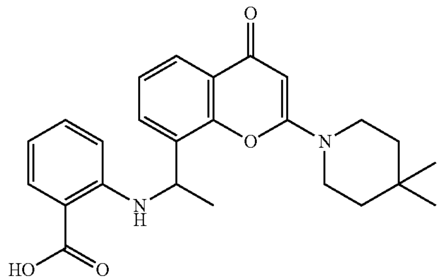 [SMILES: CC(Nc1ccccc1C(=O)O)c1cccc2c(=O)cc(N3CCC(C)(C)CC3)oc12] | 421 W, 24 |
| 333 | 2-[1-[4-Oxo-2-(1-piperidyl)chromen-8-yl]ethylamino]benzoic acid, Isomer 1 | 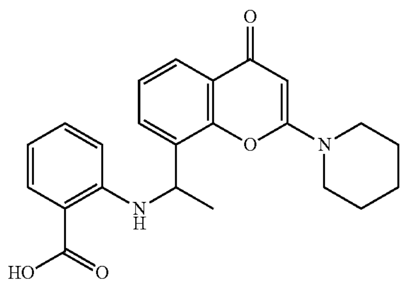 [SMILES: CC(Nc1ccccc1C(=O)O)c1cccc2c(=O)cc(N3CCCCC3)oc12] | 393 Y, 15 |
| 334 | 2-[1-[4-Oxo-2-(1-piperidyl)chromen-8-yl]ethylamino]benzoic acid, Isomer 2 | 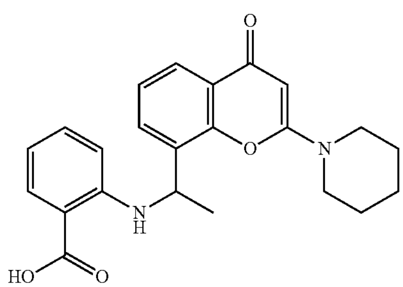 [SMILES: CC(Nc1ccccc1C(=O)O)c1cccc2c(=O)cc(N3CCCCC3)oc12] | 393 Y, 15 |

Example 335: (Isomer 1) and Example 336: (Isomer 2): 2-[1-[2-(5-Fluoroisoindolin-2-yl)-4-oxo-6-(trifluoromethyl)chromen-8-yl]ethylamino]benzoic acid

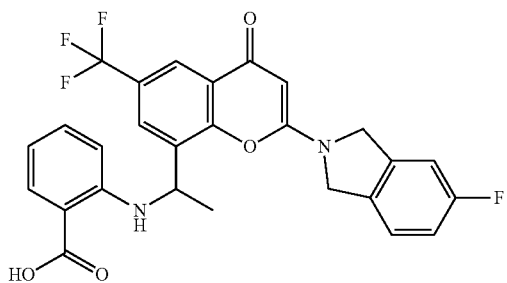 [SMILES: CC(Nc1ccccc1C(=O)O)c1cc(C(F)(F)F)cc2c(=O)cc(N3Cc4ccc(F)cc4C3)oc12]

A mixture of 2-[1-[2-ethylsulfinyl-4-oxo-6-(trifluoromethyl)chromen-8-yl]ethylamino]benzoic acid (600 mg, 1.18 mmol, 1 eq), DIEA (763 mg, 5.9 mmol, 1.0 mL, 5 eq), and 5-fluoroisoindoline-HCl (410.10 mg, 2.36 mmol, 2 eq) in chloroform (6 mL) was stirred at 60° C. for 16 hours to give a yellow solution. The mixture was diluted with water (20 mL), adjusted to pH 3 with 1 M HCl, and extracted with DCM (3×20 mL). The combined organic phase was dried over sodium sulfate, filtered, and concentrated to give a solid residue. This was purified by SFC (Z, 35; See Tables 4 and 5 for chiral columns and eluents) to give 2-[1-[2-(5-fluoroisoindolin-2-yl)-4-oxo-6-(trifluoromethyl)chromen-8-yl]ethylamino]benzoic acid, Isomer 1 and 2-[1-[2-(5-fluoroisoindolin-2-yl)-4-oxo-6-(trifluoromethyl)chromen-8-yl]ethylamino]benzoic acid, Isomer 2; both >95% ee. For both enantiomers: MS ES+ m/z 513.1 [M+H]+.

The following compounds in Table 23 were prepared essentially as described for 2-[1-[2-(5-fluoroisoindolin-2-yl)-4-oxo-6-(trifluoromethyl)chromen-8-yl]ethylamino] benzoic acid. If the Example was purified with chiral SFC, the chiral column and eluent are listed in the final column (see Tables 4 and 5).

TABLE 23

| Example # | Chemical Name | Structure | ES/MS m/z (M + H) & Chiral Method |
|---|---|---|---|
| 337 | 2-[1-[2-(5-Cyanoisoindolin-2-yl)-4-oxo-6-(trifluoromethyl)chromen-8-yl]ethylamino]benzoic acid, Isomer 1 | 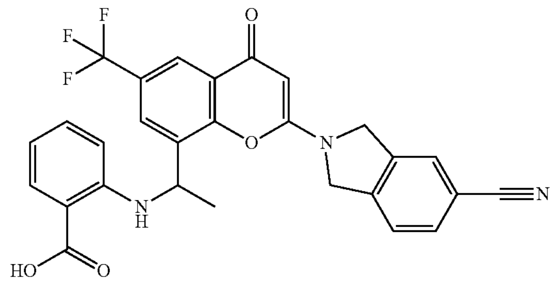 [SMILES: CC(Nc1ccccc1C(=O)O)c1cc(C(F)(F)F)cc2c(=O)cc(N3Cc4ccc(C#N)cc4C3)oc12] | 520 AA, 5 |
| 338 | 2-[1-[2-(5-Cyanoisoindolin-2-yl)-4-oxo-6-(trifluoromethyl)chromen-8-yl]ethylamino]benzoic acid, Isomer 2 | 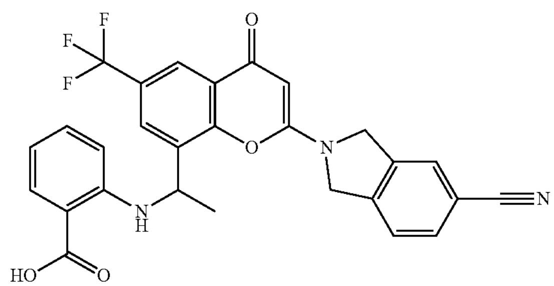 [SMILES: CC(Nc1ccccc1C(=O)O)c1cc(C(F)(F)F)cc2c(=O)cc(N3Cc4ccc(C#N)cc4C3)oc12] | 520 AA, 5 |
| 339 | 2-[1-[2-(4,4-dimethyl-1-piperidyl)-4-oxo-6-(trifluoromethyl)chromen-8-yl]ethylamino]benzoic acid, Isomer 1 | 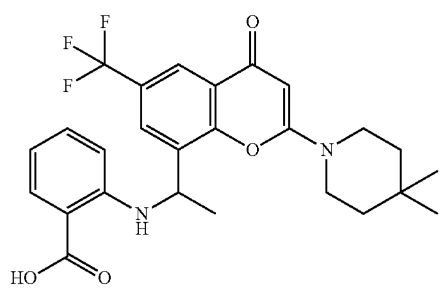 [SMILES: CC(Nc1ccccc1C(=O)O)c1cc(C(F)(F)F)cc2c(=O)cc(N3CCC(C)(C)CC3)oc12] | 489 |
| 340 | 2-[1-[2-(4,4-dimethyl-1-piperidyl)-4-oxo-6-(trifluoromethyl)chromen-8-yl]ethylamino]benzoic acid, Isomer 2 | 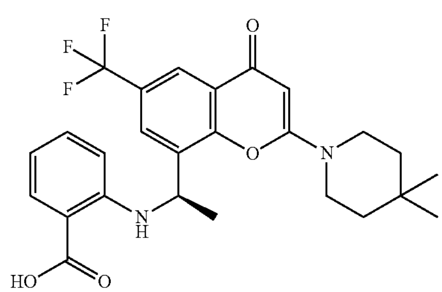 [SMILES: C[C@@H](Nc1ccccc1C(=O)O)c1cc(C(F)(F)F)cc2c(=O)cc(N3CCC(C)(C)CC3)oc12] | 489 |

Example 341: (Isomer 1) and Example 342: (Isomer 2): 2-[1-[2-Isoindolin-2-yl-4-oxo-6-(trifluoromethyl)chromen-8-yl]ethyl amino]benzoic acid

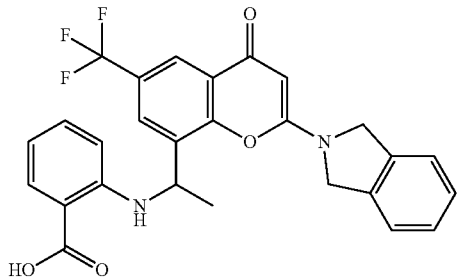 [SMILES: CC(Nc1ccccc1C(=O)O)c1cc(C(F)(F)F)cc2c(=O)cc(N3Cc4ccccc4C3)oc12]

A mixture of 2-[1-[2-ethyl sulfinyl-4-oxo-6-(trifluoromethyl)chromen-8-yl]ethyl amino]benzoic acid (600 mg, 1.18 mmol, 1 eq), DIEA (763 mg, 5.9 mmol, 1.0 mL, 5 eq), and isoindoline-HCl (367 mg, 2.36 mmol, 2 eq) in chloroform (6 mL) was stirred at 60° C. for 16 hours. The mixture was diluted with water (20 mL), and extracted with dichloromethane (3×20 mL). The combined organic phase was dried over sodium sulfate, filtered, concentrated in vacuo, and triturated with acetonitrile (5 mL) to give a solid residue. This was purified by SFC (Z, 34; See Tables 4 and 5 for chiral columns and eluents) to give 2-[1-[2-isoindolin-2-yl-4-oxo-6-(trifluoromethyl)chromen-8-yl]ethylamino]benzoic acid, Isomer 1 (ee=100%) and 2-[1-[2-isoindolin-2-yl-4-oxo-6-(trifluoromethyl)chromen-8-yl]ethylamino]benzoic acid, Isomer 2 (ee=100%). For both enantiomers MS ES+ m/z 495.1 [M+H]+.

Example 343: (Isomer 1) and Example 344: (Isomer 2): 2-[1-[2-(5-Fluoroisoindolin-2-yl)-3-methyl-4-oxo-6-(trifluoromethyl)chromen-8-yl]ethylamino]benzoic acid

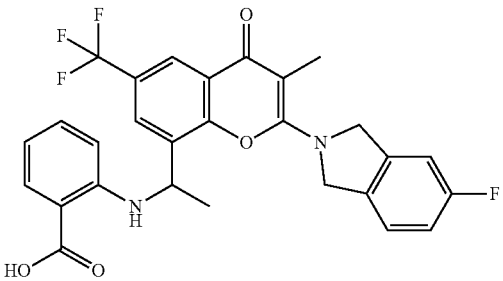 [SMILES: Cc1c(N2Cc3ccc(F)cc3C2)oc2c(C(C)Nc3ccccc3C(=O)O)cc(C(F)(F)F)cc2c1=O]

A mixture of 2-[1-[2-ethylsulfinyl-3-methyl-4-oxo-6-(trifluoromethyl)chromen-8-yl]ethylamino]benzoic acid (100 mg, 214 umol, 1 eq), 5-fluoroisoindoline-HCl (56 mg, 321 umol, 1.5 eq), and DIEA (138 mg, 1.07 mmol, 186 uL, 5 eq) in DMSO (5 mL) was stirred at 80° C. for 16 h. The mixture was diluted with water (15 mL) and extracted with EtOAc (3×20 mL). The combined organic layer was washed with brine (3×30 mL), dried over anhydrous sodium sulfate, filtered, and concentrated in vacuo. The residue was purified by prep-HPLC: Column: Phenomenex Luna C18 100×30 mm, 3 um; Mobile phase: [A: Water (0.225% FA); B: ACN]; B %: 50%-80% in 8 min., then purified by SFC (X, 5; See Tables 4 and 5 for chiral columns and eluents) to give 2-[1-[2-(5-fluoroisoindolin-2-yl)-3-methyl-4-oxo-6-(trifluoromethyl)chromen-8-yl]ethylamino]benzoic acid, Isomer 1 and 2-[1-[2-(5-fluoroisoindolin-2-yl)-3-methyl-4-oxo-6-(trifluoromethyl)chromen-8-yl]ethylamino]benzoic acid, Isomer 2; both >99% ee. For both enantiomers: MS ES+ m/z 527.3 [M+H]+.

The following compounds in Table 24 were prepared essentially as described for 2-[1-[2-(5-fluoroisoindolin-2-yl)-3-methyl-4-oxo-6-(trifluoromethyl)chromen-8-yl]ethylamino]benzoic acid. If the Example was purified with chiral SFC, the chiral column and eluent are listed in the final column (see Tables 4 and 5).

TABLE 24

| Example # | Chemical Name | Structure | ES/MS m/z (M + H) & Chiral Method |
|---|---|---|---|
| 345 | 2-[1-[2-(5-Cyanoisoindolin-2-yl)-3-methyl-4-oxo-6-(trifluoromethyl)chromen-8-yl]ethylamino]benzoic acid, Isomer 1 | 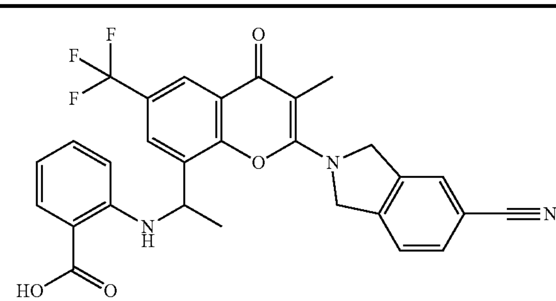 | 534 AE, 5 |

TABLE 24-continued

| Example # | Chemical Name | Structure | ES/MS m/z (M + H) & Chiral Method |
|---|---|---|---|
| 346 | 2-[1-[2-(5-Cyanoisoindolin-2-yl)-3-methyl-4-oxo-6-(trifluoromethyl)chromen-8-yl]ethylamino]benzoic acid, Isomer 2 | 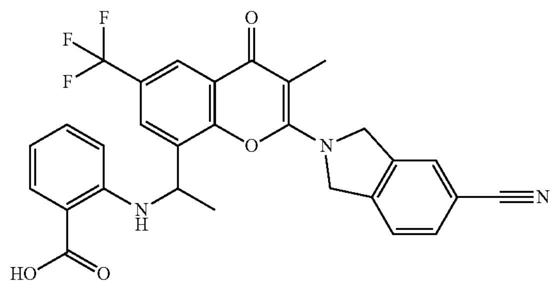 | 534 AE, 5 |

Example 347: (Isomer 1) and Example 348: (Isomer 2): 2-[1-[2-Isoindolin-2-yl-3-methyl-4-oxo-6-(trifluoromethyl)chromen-8-yl]ethylamino]benzoic acid Example 349: (Isomer 1) and Example 350: (Isomer 2): 5-Fluoro-2-[1-[2-(5-fluoroisoindolin-2-yl)-6-methyl-4-oxo-chromen-8-yl]ethylamino]benzoic acid A mixture of 2-[1-[2-ethylsulfinyl-3-methyl-4-oxo-6-(trifluoromethyl)chromen-8-yl]ethylamino]benzoic acid (100 mg, 214 umol, 1 eq), isoindoline-HCl (50 mg, 321 umol, 1.5 eq), and DIEA (138 mg, 1.07 mmol, 186 uL, 5 eq) in DMSO (5 mL) was stirred at 80° C. for 16h. The mixture was diluted with water (15 mL) and extracted with EtOAc (3×20 mL). The combined organic layer was washed with brine (3×30 mL), dried over anhydrous sodium sulfate, filtered, and concentrated in vacuo. The residue was purified by reverse phase HPLC (Column: Phenomenex Luna C18 100×30 mm, 3 um; Mobile phase: [A: Water (0.225% FA); B: ACN]; B %: 50%-80% in 8 min., then purified by SFC (AB, 21; See Tables 4 and 5 for chiral columns and eluents) to give 2-[1-[2-isoindolin-2-yl-3-methyl-4-oxo-6-(trifluoromethyl)chromen-8-yl]ethylamino]benzoic acid, Isomer 1 (ee=100%) and 2-[1-[2-isoindolin-2-yl-3-methyl-4-oxo-6-(trifluoromethyl)chromen-8-yl]ethylamino]benzoic acid, Isomer 2 (ee=100%). For both enantiomers: MS ES+ m/z 509.3 [M+H]$^+$.

A mixture of 2-[1-(2-ethylsulfinyl-6-methyl-4-oxo-chromen-8-yl)ethylamino]-5-fluoro-benzoic acid (150 mg, 359 umol, 1 eq), DIEA (232 mg, 1.80 mmol, 312.94 uL, 5 eq), and 5-fluoroisoindoline (74 mg, 539 umol, 1.5 eq) in chloroform (2 mL) was stirred at 60° C. for 16 hours. The mixture was diluted with water (20 mL) and extracted with DCM (3×20 mL). The combined organic phase was dried over sodium sulfate, filtered, and concentrated to give a residue that was triturated with acetonitrile (1 mL) to yield the racemic product as a solid. This was purified by SFC (Z, 5; See Tables 4 and 5 for chiral columns and eluents) to give 5-fluoro-2-[1-[2-(5-fluoroisoindolin-2-yl)-6-methyl-4-oxo-chromen-8-yl]ethylamino]benzoic acid, Isomer 1 and 5-fluoro-2-[1-[2-(5-fluoroisoindolin-2-yl)-6-methyl-4-oxo-chromen-8-yl]ethylamino]benzoic acid, Isomer 2; both >98% ee. For both enantiomers: MS ES+ m/z 477.3 [M+H]$^+$.

The following compounds in Table 25 were prepared essentially as described for 5-fluoro-2-[1-[2-(5-fluoroisoindolin-2-yl)-6-methyl-4-oxo-chromen-8-yl]ethylamino]benzoic acid. If the Example was purified with chiral SFC, the chiral column and eluent are listed in the final column (see Tables 4 and 5).

TABLE 25

| Example # | Chemical Name | Structure | ES/MS m/z (M + H) & Chiral Method |
|---|---|---|---|
| 351 | 2-[1-[2-(5-Cyanoisoindolin-2-yl)-6-methyl-4-oxo-chromen-8-yl]ethylamino]-5-fluoro-benzoic acid, Isomer 1 | 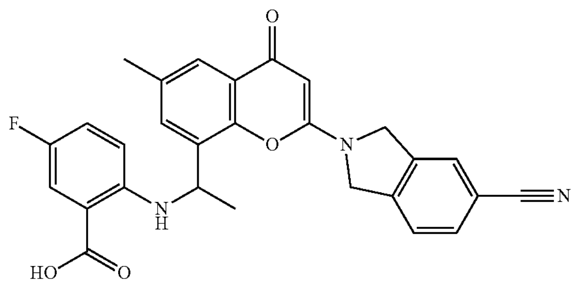 [SMILES: Cc1cc(C(C)Nc2ccc(F)cc2C(=O)O)c2oc(N3Cc4ccc(C#N)cc4C3)cc(=O)c2c1] | 484 Z, 35 |
| 352 | 2-[1-[2-(5-Cyanoisoindolin-2-yl)-6-methyl-4-oxo-chromen-8-yl]ethylamino]-5-fluoro-benzoic acid, Isomer 2 | 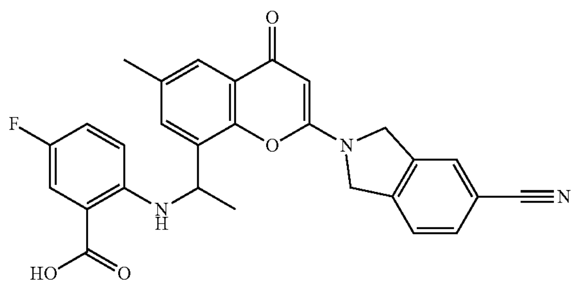 [SMILES: Cc1cc(C(C)Nc2ccc(F)cc2C(=O)O)c2oc(N3Cc4ccc(C#N)cc4C3)cc(=O)c2c1] | 484 Z, 35 |
| 353 | 5-Fluoro-2-[1-[2-(4-methoxycarbonylpiperazin-1-yl)-6-methyl-4-oxo-chromen-8-yl]ethylamino]benzoic acid | 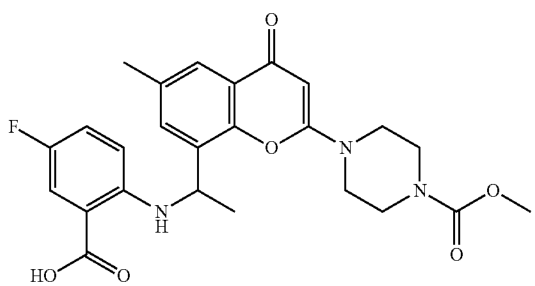 [SMILES: COC(=O)N1CCN(c2cc(=O)c3cc(C)cc(C(C)Nc4ccc(F)cc4C(=O)O)c3o2)CC1] | 484 |
| 354 | 5-Fluoro-2-[1-(2-isoindolin-2-yl-6-methyl-4-oxo-chromen-8-yl)ethylamino]benzoic acid, Isomer 1 | 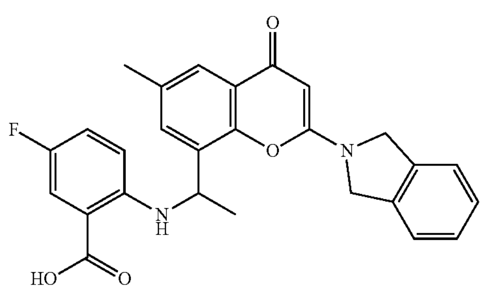 [SMILES: Cc1cc(C(C)Nc2ccc(F)cc2C(=O)O)c2oc(N3Cc4ccccc4C3)cc(=O)c2c1] | 459 AD, 28 |
| 355 | 5-Fluoro-2-[1-(2-isoindolin-2-yl-6-methyl-4-oxo-chromen-8-yl)ethylamino]benzoic acid, Isomer 2 | 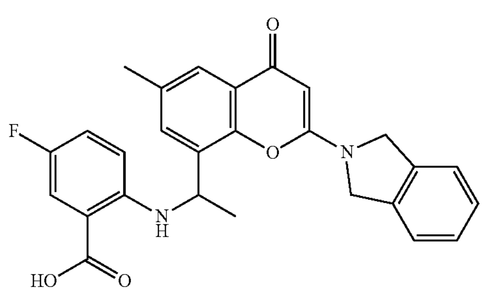 [SMILES: Cc1cc(C(C)Nc2ccc(F)cc2C(=O)O)c2oc(N3Cc4ccccc4C3)cc(=O)c2c1] | 459 AD, 28 |

Example 356: [2-[1-[2-(4,4-Dimethyl-1-piperidyl)-6-methyl-4-oxo-chromen-8-yl]ethylamino]phenyl]boronic acid

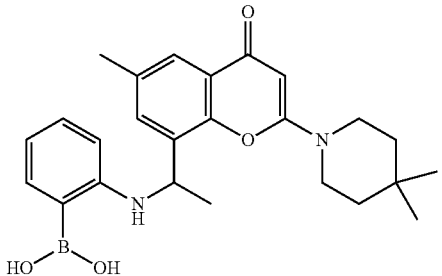 [SMILES: Cc1cc(C(C)Nc2ccccc2B(O)O)c2oc(N3CCC(C)(C)CC3)cc(=O)c2c1]

A mixture of 8-(1-bromoethyl)-2-(4,4-dimethyl-1-piperidyl)-6-methyl-chromen-4-one (200 mg, 0.529 mmol) and (2-aminophenyl)boronic acid (145 mg, 1.06 mmol) in DMF (4 mL) was stirred at 80° C. for 16 h. When cooled to rt the mixture was filtered, the filtrate was purified by preparative HPLC to give [2-[1-[2-(4,4-dimethyl-1-piperidyl)-6-methyl-4-oxo-chromen-8-yl]ethylamino]phenyl]boronic acid as a solid (59 mg, 25%). $^1$H NMR (400 MHz, DMSO-d$_6$) δ ppm 0.98 (s, 6H), 1.41-1.45 (m, 4H), 1.51 (d, J=6.8 Hz, 3H), 2.29 (s, 3H), 3.52-3.56 (m, 4H), 4.87-4.97 (m, 1H), 5.51 (s, 1H), 6.18 (d, J=8.4 Hz, 1H), 6.43-6.51 (m, 1H), 6.98-7.07 (m, 2H), 7.37 (d, J=2.0 Hz, 1H), 7.55-7.61 (m, 2H), 8.28 (s, 2H). MS ES+ m/z 435 [M+H]$^+$.

Example 357: 5-Borono-2-[1-[2-(4,4-dimethyl-1-piperidyl)-6-methyl-4-oxo-chromen-8-yl]ethylamino]benzoic acid

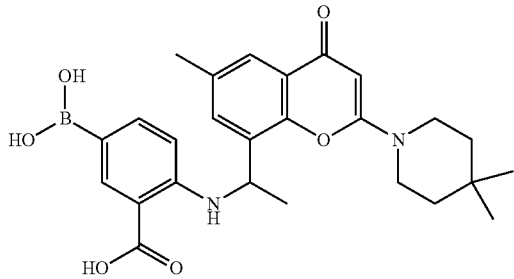 [SMILES: Cc1cc(C(C)Nc2ccc(B(O)O)cc2C(=O)O)c2oc(N3CCC(C)(C)CC3)cc(=O)c2c1]

Step 1: methyl 2-amino-5-(4,4,5,5-tetramethyl-1,3,2-dioxaborolan-2-yl)benzoate. A mixture of methyl 2-amino-5-bromo-benzoate (500 mg, 2.17 mmol), 4,4,5,5-tetramethyl-2-(4,4,5,5-tetramethyl-1,3,2-dioxaborolan-2-yl)-1,3,2-dioxaborolane (828 mg, 3.26 mmol), Pd(dppf)Cl$_2$ (159 mg, 0.22 mmol), KOAc (640 mg, 6.52 mmol) in dioxane (10 mL) was stirred at 100° C. for 16 h under N$_2$. When cooled to rt the mixture was filtered, the filtrate was concentrated and purified on a silica gel column eluted with 0-15% EtOAc in petroleum ether to give the product as a solid (490 mg, 81%). $^1$H NMR (400 MHz, CDCl$_3$-d) δ ppm 1.21-1.37 (m, 12H), 3.81-3.96 (m, 3H), 5.97 (s, 2H), 6.64 (d, J=8.4 Hz, 1H), 7.68 (dd, J=8.4, 1.2 Hz, 1H), 8.34 (d, J=1.2 Hz, 1H).

Step 2: 5-borono-2-[1-[2-(4,4-dimethyl-1-piperidyl)-6-methyl-4-oxo-chromen-8-yl]ethylamino]benzoic acid. A mixture of 8-(1-bromoethyl)-2-(4,4-dimethyl-1-piperidyl)-6-methyl-chromen-4-one (60.0 mg, 0.16 mmol) and methyl 2-amino-5-(4,4,5,5-tetramethyl-1,3,2-dioxaborolan-2-yl)benzoate (87.9 mg, 0.32 mmol) in DMF (1 mL) was stirred in 80° C. for 12 h. When cooled to rt the mixture was added H$_2$O (10 mL) and extracted with EtOAc (20 mL×3). The combined extract was washed with brine (15 mL), dried over anhydrous Na$_2$SO$_4$, filtered, concentrated and purified on a silica gel column eluted with 0-10% MeOH in DCM to give methyl 2-[1-[2-(4,4-dimethyl-1-piperidyl)-6-methyl-4-oxo-chromen-8-yl]ethylamino]-5-(4,4,5,5-tetramethyl-1,3,2-dioxaborolan-2-yl)benzoate as a solid (100 mg, crude). A mixture of methyl 2-[1-[2-(4,4-dimethyl-1-piperidyl)-6-methyl-4-oxo-chromen-8-yl]ethylamino]-5-(4,4,5,5-tetramethyl-1,3,2-dioxaborolan-2-yl)benzoate (100 mg, 0.17 mmol) and NaOH (28 mg, 0.70 mmol) in MeOH (1 mL) and H$_2$O (0.4 mL) was stirred at 25° C. for 16 h, then stirred at 35° C. for 7 h. The mixture was added NaOH (14 mg, 0.35 mmol) and stirred at 35° C. for another 16 h. The mixture was added H$_2$O (15 mL) and washed with EtOAc (20 mL×2). The aqueous phase was adjusted to pH=2 with HCl (1 M), extracted with DCM (20 mL×2). The combined extract was dried over anhydrous Na$_2$SO$_4$, filtered, concentrated and purified by preparative HPLC to give 5-borono-2-[1-[2-(4,4-dimethyl-1-piperidyl)-6-methyl-4-oxo-chromen-8-yl]ethylamino]benzoic acid as a solid (8.6 mg, 17%). $^1$H NMR (400 MHz, DMSO-d$_6$) δ ppm 0.98 (s, 6H), 1.39-1.44 (m, 4H), 1.59 (d, J=6.8 Hz, 3H), 2.30 (s, 3H), 3.51-3.57 (m, 4H), 5.09 (d, J=7.6 Hz, 1H), 5.52 (s, 1H), 6.43 (d, J=8.4 Hz, 1H), 7.35 (s, 1H), 7.59-7.66 (m, 2H), 7.71 (s, 1H), 8.32 (d, J=1.6 Hz, 1H), 8.49 (d, J=6.4 Hz, 1H), 12.51-12.79 (m, 1H). MS ES+ m/z 479 [M+H]$^+$.

Example 358:, Example 359: (Isomer 1), and Example 360: (Isomer 2): 2-[1-[2-(4,4-Dimethyl-1-piperidyl)-3,6-dimethyl-4-oxo-chromen-8-yl]ethylamino]benzoic acid

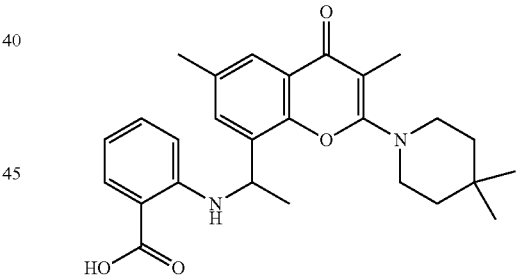

A mixture of 8-(1-bromoethyl)-2-(4,4-dimethyl-1-piperidyl)-3,6-dimethyl-chromen-4-one (300 mg, 0.765 mmol) and 2-aminobenzoic acid (210 mg, 1.53 mmol) in DMF (6 mL) was stirred at 25° C. for 16 h and at 35° C. for 6 h. The mixture was diluted with EtOAc (20 mL), water (20 mL) and adjusted to pH=11 with NaOH (2 M). The aqueous layer was washed with EtOAc (40 mL×2), then adjusted to pH 4 with HCl (2 M), white solid was precipitated out and filtered. The filter cake was triturated with MeCN (2 mL) to give 2-[1-[2-(4,4-dimethyl-1-piperidyl)-3,6-dimethyl-4-oxo-chromen-8-yl]ethylamino]benzoic acid as a solid (150 mg, 43%). MS ES+ m/z 449 [M+H]$^+$.

2-[1-[2-(4,4-Dimethyl-1-piperidyl)-3,6-dimethyl-4-oxo-chromen-8-yl]ethylamino]benzoic acid was purified by chiral SFC (W, 14; See Tables 4 and 5 for chiral column and eluent) to give 2-[1-[2-(4,4-dimethyl-1-piperidyl)-3,6-dimethyl-4-oxo-chromen-8-yl]ethylamino]benzoic acid, Isomer 1 as a solid (61.8 mg, 41%, $^1$H NMR (400 MHz, DMSO-$d_6$) δ ppm 0.98 (s, 6H), 1.41-1.50 (m, 4H), 1.60 (d, J=6.8 Hz, 3H), 1.92 (s, 3H), 2.31 (s, 3H), 3.37-3.45 (m, 4H), 5.03-5.15 (m, 1H), 6.48 (d, J=8.4 Hz, 1H), 6.54 (t, J=7.6 Hz, 1H), 7.20-7.28 (m, 1H), 7.40 (d, J=2.0 Hz, 1H), 7.64 (d, J=1.2 Hz, 1H), 7.80 (dd, J=8.0, 1.6 Hz, 1H), 8.35 (d, J=5.6 Hz, 1H), 12.73 (brs, 1H), MS ES+ m/z 449 [M+H]$^+$) and 2-[1-[2-(4,4-dimethyl-1-piperidyl)-3,6-dimethyl-4-oxo-chromen-8-yl]ethylamino]benzoic acid, Isomer 2 as a solid (61.2 mg, 40%, $^1$H NMR (400 MHz, DMSO-$d_6$) δ ppm 0.98 (s, 6H), 1.42-1.50 (m, 4H), 1.60 (d, J=6.4 Hz, 3H), 1.92 (s, 3H), 2.31 (s, 3H), 3.37-3.45 (m, 4H), 5.03-5.14 (m, 1H), 6.48 (d, J=8.4 Hz, 1H), 6.54 (t, J=7.6 Hz, 1H), 7.18-7.29 (m, 1H), 7.40 (d, J=2.0 Hz, 1H), 7.64 (d, J=1.2 Hz, 1H), 7.80 (dd, J=8.0, 1.6 Hz, 1H), 8.35 (d, J=5.6 Hz, 1H), 12.72 (s, 1H), MS ES+ m/z 449 [M+H]$^+$).

Example 361: N-[2-[1-[2-(4,4-Dimethyl-1-piperidyl)-6-methyl-4-oxo-chromen-8-yl]ethylamino]phenyl]sulfonylacetamide

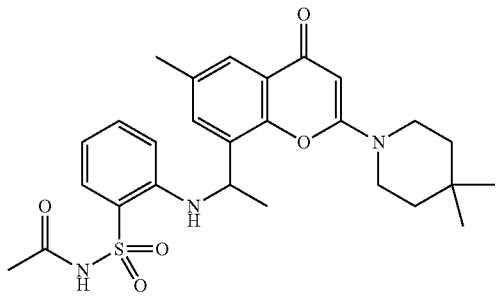 [SMILES: CC(=O)NS(=O)(=O)c1ccccc1NC(C)c1cc(C)cc2c(=O)cc(N3CCC(C)(C)CC3)oc12]

Step 1: N-(2-aminophenyl)sulfonylacetamide. A mixture of 2-aminobenzenesulfonamide (200 mg, 1.16 mmol) and DMAP (284 mg, 2.32 mmol) in THF (4 mL) was added Ac$_2$O (130 mg, 1.28 mmol) at 0° C. under N$_2$, and stirred at 20° C. for 1 h. The mixture was diluted with water (20 mL), extracted with EtOAc (30 mL×3), dried over anhydrous Na$_2$SO$_4$, filtered, concentrated and purified on a silica gel column eluted with 0-50% EtOAc in petroleum ether to give the product as gum (120 mg, 48%). $^1$H NMR (400 MHz, DMSO-$d_6$) δ ppm 1.92 (s, 3H), 6.02 (brs, 2H), 6.58-6.67 (m, 1H), 6.76-6.84 (m, 1H), 7.25-7.33 (m, 1H), 7.56 (dd, J=8.0, 1.6 Hz, 1H), 11.86 (brs, 1H). MS ES+ m/z 215 [M+H]$^+$.

Step 2: N-[2-[1-[2-(4,4-dimethyl-1-piperidyl)-6-methyl-4-oxo-chromen-8-yl]ethylamino]phenyl]sulfonylacetamide. A mixture of 8-(1-bromoethyl)-2-(4,4-dimethyl-1-piperidyl)-6-methyl-chromen-4-one (50 mg, 0.13 mmol) and N-(2-aminophenyl)sulfonylacetamide (57 mg, 0.26 mmol) in DMF (1 mL) was stirred at 80° C. for 16 h. When cooled to rt the mixture was filtered. The filtrate was combined with another batch (50 mg) and purified by preparative HPLC to give N-[2-[1-[2-(4,4-dimethyl-1-piperidyl)-6-methyl-4-oxo-chromen-8-yl]ethylamino]phenyl]sulfonylacetamide as a solid (9.12 mg, 7%). $^1$H NMR (400 MHz, DMSO-$d_6$) δ ppm 0.98 (s, 6H), 1.38-1.46 (m, 4H), 1.57 (d, J=6.4 Hz, 3H), 1.92 (s, 3H), 2.28 (s, 3H), 3.48-3.57 (m, 4H), 5.10 (q, J=6.4 Hz, 1H), 5.51 (s, 1H), 6.42 (d, J=8.4 Hz, 1H), 6.54 (d, J=5.6 Hz, 1H), 6.63 (t, J=7.6 Hz, 1H), 6.77-7.38 (m, 2H), 7.45 (d, J=2.0 Hz, 1H), 7.59 (d, J=2.0 Hz, 1H), 7.64 (dd, J=8.0, 1.6 Hz, 1H). MS ES+ m/z 512 [M+H]$^+$.

Example 362: (Isomer 1) and Example 363: (Isomer 2): 2-[1-(2-Isoindolin-2-yl-6-methyl-4-oxo-chromen-8-yl)ethylamino]benzoic acid

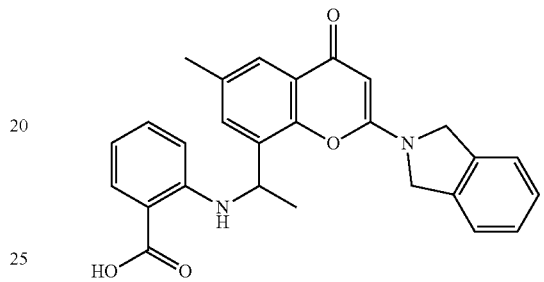

A mixture of methyl 2-[1-(2-ethylsulfinyl-6-methyl-4-oxo-chromen-8-yl)ethylamino]benzoate (500 mg, 1.21 mmol) in DCM (10 mL) was added isoindoline (753 mg, 4.84 mmol, HCl) and DIPEA (1.56 g, 12.1 mmol) at 10° C., then stirred at 40° C. for 20 h. The mixture was diluted with water (20 mL), extracted with DCM (40 mL×3). The combined extract was washed with brine (60 mL×2), dried over anhydrous Na$_2$SO$_4$, filtered and concentrated to give methyl 2-[1-(2-isoindolin-2-yl-6-methyl-4-oxo-chromen-8-yl)ethylamino]benzoate as gum (500 mg).

A mixture of methyl 2-[1-(2-isoindolin-2-yl-6-methyl-4-oxo-chromen-8-yl)ethylamino]benzoate (500 mg, 1.10 mmol) and NaOH (176 mg, 4.40 mmol) in MeOH (3 mL), H$_2$O (5 mL) and THF (4 mL) was stirred at 40° C. for 16 h. The mixture was diluted with EtOAc (50 mL) and water (50 mL), some pink solid was precipitated out and filtered. The filter cake was diluted with DCM (50 mL) and water (50 mL), adjusted to pH=4 with HCl (2 M), pink solid was precipitated out and filtered. The filter cake was purified by preparative HPLC and then by chiral SFC (U, 5; See Tables 4 and 5 for chiral column and eluent) to give 2-[1-(2-isoindolin-2-yl-6-methyl-4-oxo-chromen-8-yl)ethylamino]benzoic acid, Isomer 1 as a solid (48.9 mg, 20%, $^1$H NMR (400 MHz, DMSO-$d_6$) δ ppm 1.67 (d, J=6.8 Hz, 3H), 2.32 (s, 3H), 4.50-5.12 (m, 4H), 5.14-5.23 (m, 1H), 5.31 (s, 1H), 6.52-6.62 (m, 2H), 7.23-7.29 (m, 1H), 7.33-7.39 (m, 2H), 7.39-7.46 (m, 3H), 7.65 (d, J=1.6 Hz, 1H), 7.81 (dd, J=8.0, 1.6 Hz, 1H), 8.42 (d, J=6.0 Hz, 1H), 12.74 (brs, 1H), MS ES+ m/z 441 [M+H]$^+$) and 2-[1-(2-isoindolin-2-yl-6-methyl-4-oxo-chromen-8-yl)ethylamino]benzoic acid, Isomer 2 as a solid (39.7 mg, 17%, $^1$H NMR (400 MHz, DMSO-$d_6$) δ ppm 1.67 (d, J=6.4 Hz, 3H), 2.32 (s, 3H), 4.61-5.09 (m, 4H), 5.16-5.26 (m, 1H), 5.31 (s, 1H), 6.51-6.62 (m, 2H), 7.23-7.30 (m, 1H), 7.32-7.39 (m, 2H), 7.39-7.47 (m, 3H), 7.65 (s, 1H), 7.81 (dd, J=8.0, 1.6 Hz, 1H), 8.41 (d, J=6.4 Hz, 1H), 12.73 (brs, 1H), MS ES+ m/z 441 [M+H]$^+$).

Example 364: 2-(4,4-Dimethyl-1-piperidyl)-6-methyl-8-[1-[2-(2,2,2-trifluoro-1-hydroxy-ethyl)anilino]ethyl]chromen-4-one

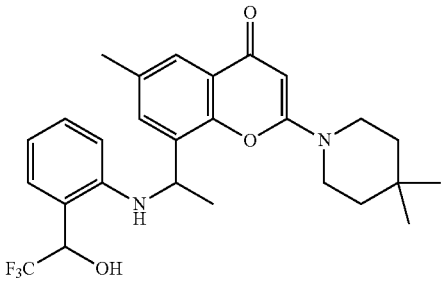 [SMILES: Cc1cc(C(C)Nc2ccccc2C(O)C(F)(F)F)c2oc(N3CCC(C)(C)CC3)cc(=O)c2c1]

A mixture of 2-(4,4-dimethyl-1-piperidyl)-6-methyl-8-[1-[2-(2,2,2-trifluoroacetyl)anilino]ethyl]chromen-4-one (20 mg, 0.041 mmol) and NaBH$_4$ (2.0 mg, 0.049 mmol) in MeOH (3 mL) was stirred at 15° C. for 2 h. The mixture was added water (0.3 mL), concentrated and purified by preparative HPLC to give 2-(4,4-dimethyl-1-piperidyl)-6-methyl-8-[1-[2-(2,2,2-trifluoro-1-hydroxy-ethyl)anilino]ethyl]chromen-4-one as a solid (8.5 mg, 42%). $^1$H NMR (400 MHz, DMSO-d$_6$) δ ppm 0.98-0.99 (m, 6H), 1.41-1.46 (m, 4H), 1.52 (d, J=6.4 Hz, 3H), 2.27 (d, J=8.8 Hz, 3H), 3.53-3.55 (m, 4H), 4.96-5.01 (m, 1H), 5.52 (s, 1H), 5.53-5.55 (m, 1H), 6.01 (d, J=6.0 Hz, 0.5H), 6.08 (d, J=6.8 Hz, 0.5H), 6.26 (d, J=8.0 Hz, 1H), 6.56 (t, J=7.2 Hz, 1H), 6.98-7.02 (m, 2H), 7.26 (d, J=7.6 Hz, 1H), 7.34 (d, J=2.0 Hz, 0.5H), 7.41 (d, J=2.4 Hz, 0.5H), 7.57 (s, 1H). MS ES+ m/z 489 [M+H]$^+$.

Example 365: 2-(4,4-Dimethyl-1-piperidyl)-6-methyl-8-[1-[2-(2,2,2-trifluoroacetyl)anilino]ethyl]chromen-4-one

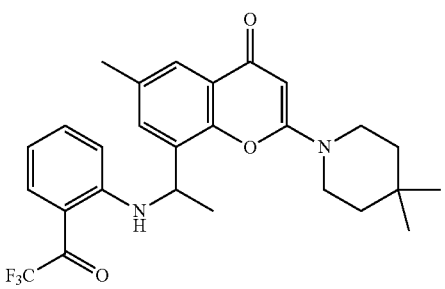 [SMILES: Cc1cc(C(C)Nc2ccccc2C(=O)C(F)(F)F)c2oc(N3CCC(C)(C)CC3)cc(=O)c2c1]

Step 1: 2,2,2-trifluoro-1-(2-nitrophenyl)ethanol. A mixture of 2-nitrobenzaldehyde (1.00 g, 6.62 mmol), K$_2$CO$_3$ (2.74 g, 19.9 mmol) and TMSCF$_3$ (1.88 g, 13.2 mmol) in DMF (20 mL) was stirred at 20° C. for 12 h. The mixture was added 2 N HCl (30 mL), and stirred for 2 h. The mixture was extracted with EtOAc (20 mL×3). The combined extract was washed with sat. NaHCO$_3$ (30 mL) and brine (15 mL×3), dried over anhydrous Na$_2$SO$_4$, filtered and concentrated to give the product (1.4 g, 96%) as oil. $^1$H NMR (400 MHz, DMSO-d$_6$) δ ppm 5.85-5.92 (m, 1H), 7.34 (d, J=6.0 Hz, 1H), 7.66-7.74 (m, 1H), 7.83-7.87 (m, 1H), 7.92-7.92 (m, 1H), 8.05 (dd, J=8.0, 1.2 Hz, 1H).

Step 2: 2,2,2-trifluoro-1-(2-nitrophenyl)ethanone. A mixture of 2,2,2-trifluoro-1-(2-nitrophenyl)ethanol (700 mg, 3.17 mmol) and 2-iodoxybenzoic acid (1.77 g, 6.33 mmol) in EtOAc (20 mL) was stirred at 77° C. for 14 h. When cooled to rt the mixture was filtered, and filter cake was washed with EtOAc (20 mL). The filtrate was washed with sat. Na$_2$S$_2$O$_3$ (30 mL), sat.NaHCO$_3$ (30 mL) and brine (30 mL×3), dried over anhydrous Na$_2$SO$_4$, filtered, concentrated and purified by silica gel chromatography eluted with 0%-10% EtOAc in petroleum ether to give the product (500 mg, 72%) as oil. $^1$H NMR (400 MHz, DMSO-d$_6$) δ ppm 7.92 (dd, J=7.2, 1.2 Hz, 1H), 8.00-8.04 (m, 1H), 8.08-8.10 (m, 1H), 8.43 (dd, J=8.4, 1.2 Hz, 1H).

Step 3: 1-(2-aminophenyl)-2,2,2-trifluoro-ethanone. A mixture of 2,2,2-trifluoro-1-(2-nitrophenyl)ethanone (200 mg, 0.913 mmol), NH$_4$Cl (391 mg, 7.30 mmol) and Fe (408 mg, 7.30 mmol) in EtOH (8 mL) and H$_2$O (2 mL) was stirred at 80° C. for 6 h. The mixture was filtered, the filter cake was washed with EtOH (10 mL). The filtrate was concentrated. The residue was diluted with water (15 mL), extracted with DCM (15 mL×3). The combined extract was washed with brine (30 mL), dried over anhydrous Na$_2$SO$_4$, filtered, concentrated and purified by silica gel chromatography eluted with 0%-22% EtOAc in petroleum ether to give the product (100 mg, 56%) as a solid. MS ES+ m/z 190 [M+H]$^+$.

Step 4: 2-(4,4-dimethyl-1-piperidyl)-6-methyl-8-[1-[2-(2,2,2-trifluoroacetyl)anilino]ethyl]chromen-4-one. A mixture of 8-(1-bromoethyl)-2-(4,4-dimethyl-1-piperidyl)-6-methyl-chromen-4-one (60 mg, 0.16 mmol) and 1-(2-aminophenyl)-2,2,2-trifluoro-ethanone (45 mg, 0.24 mmol) in DMF (1 mL) was stirred at 80° C. for 34 h. When cooled to rt the reaction mixture was purified by preparative HPLC to give 2-(4,4-dimethyl-1-piperidyl)-6-methyl-8-[1-[2-(2,2,2-trifluoroacetyl)anilino]ethyl]chromen-4-one as a solid (25.79 mg, 33%). $^1$H NMR (400 MHz, DMSO-d$_6$) δ ppm 0.97 (s, 6H), 1.36-1.39 (m, 4H), 1.65 (d, J=6.8 Hz, 3H), 2.32 (s, 3H), 3.50-3.53 (m, 4H), 5.22-5.29 (m, 1H), 5.52 (s, 1H), 6.72-6.77 (m, 2H), 7.43 (d, J=2.0 Hz, 1H), 7.50 (t, J=8.0 Hz, 1H), 7.63-7.64 (m, 1H), 7.73 (d, J=8.4 Hz, 1H), 9.02 (d, J=6.0 Hz, 1H). MS ES+ m/z 487 [M+H]$^+$.

Example 366: (Isomer 1) and Example 367: (Isomer 2): 2-[1-[2-(4,4-Dimethyl-1-piperidyl)-6-methyl-4-oxo-chromen-8-yl]ethylamino]benzoic acid

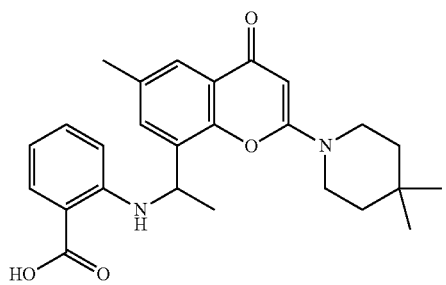 [SMILES: Cc1cc(C(C)Nc2ccccc2C(=O)O)c2oc(N3CCC(C)(C)CC3)cc(=O)c2c1]

A mixture of 8-(1-bromoethyl)-2-(4,4-dimethyl-1-piperidyl)-6-methyl-chromen-4-one (4.00 g, 10.6 mmol) and 2-aminobenzoic acid (2.90 g, 21.1 mmol) in DMF (40 mL) was stirred at 80° C. for 16 h. When cooled to rt the mixture was diluted with EtOAc (120 mL), water (120 mL) and adjusted to pH=11 with NaOH (2 M). The aqueous layer was washed with EtOAc (200 mL×2), adjusted to pH=4 with HCl (2 M), white solid was precipitated out and filtered. The filter cake was diluted with DCM/MeOH (10/1, 400 mL), dried over anhydrous Na$_2$SO$_4$, filtered, concentrated and purified by SFC to give 2-[1-[2-(4,4-dimethyl-1-piperidyl)-6-methyl-4-oxo-chromen-8-yl]ethylamino]benzoic acid, Isomer 1 as a solid (1.73 g, 39%, $^1$H NMR (400 MHz, DMSO-d$_6$) δ ppm 0.97 (s, 6H), 1.37-1.45 (m, 4H), 1.57 (d, J=6.4 Hz, 3H), 2.30 (s, 3H), 3.49-3.60 (m, 4H), 5.00-5.10 (m, 1H), 5.52 (s, 1H), 6.43 (d, J=8.4 Hz, 1H), 6.54 (t, J=7.6 Hz, 1H), 7.17-7.27 (m, 1H), 7.36 (d, J=2.0 Hz, 1H), 7.60 (d, J=1.6 Hz, 1H), 7.81 (dd, J=8.0, 1.6 Hz, 1H), 8.44 (brs, 1H), MS ES+ m/z 435 [M+H]$^+$) and 2-[1-[2-(4,4-dimethyl-1-piperidyl)-6-methyl-4-oxo-chromen-8-yl]ethylamino]benzoic acid, Isomer 2 as a solid (1.76 g, 39%, $^1$H NMR (400 MHz, DMSO-d$_6$) δ ppm 0.98 (s, 6H), 1.36-1.47 (m, 4H), 1.58 (d, J=6.4 Hz, 3H), 2.30 (s, 3H), 3.47-3.61 (m, 4H), 5.00-5.11 (m, 1H), 5.51 (s, 1H), 6.45 (d, J=8.4 Hz, 1H), 6.55 (t, J=7.6 Hz, 1H), 7.19-7.29 (m, 1H), 7.36 (d, J=2.0 Hz, 1H), 7.60 (d, J=1.6 Hz, 1H), 7.81 (dd, J=8.0, 1.6 Hz, 1H), 8.35 (d, J=5.6 Hz, 1H), 12.59 (brs, 1H), MS ES+ m/z 435 [M+H]$^+$).

Example 368: 2-[1-(6-Methyl-4-oxo-2-pyrrolidin-1-yl-chromen-8-yl)ethylamino]benzoic acid

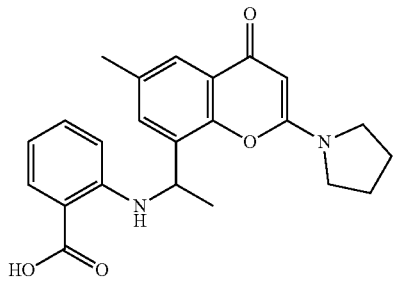 [SMILES: Cc1cc(C(C)Nc2ccccc2C(=O)O)c2oc(N3CCCC3)cc(=O)c2c1]

A mixture of methyl 2-[1-(2-ethylsulfanyl-6-methyl-4-oxo-chromen-8-yl)ethylamino]benzoate (30 mg, 0.075 mmol) and pyrrolidine (16 mg, 0.23 mmol) in EtOH (3 mL) was stirred at 78° C. for 32 h. When cooled to rt the mixture was concentrated to give methyl 2-[1-(6-methyl-4-oxo-2-pyrrolidin-1-yl-chromen-8-yl)ethylamino]benzoate as a solid (30 mg, crude). MS ES+ m/z 407 [M+H]$^+$. A mixture of methyl 2-[1-(6-methyl-4-oxo-2-pyrrolidin-1-yl-chromen-8-yl)ethylamino]benzoate (30 mg, 0.074 mmol) and LiOH.H$_2$O (9.3 mg, 0.22 mmol) in MeOH (2 mL) and H$_2$O (0.2 mL) was stirred at 30° C. for 20 h. The mixture was added NaOH (24 mg, 0.59 mmol) and stirred at 30° C. for another 40 h. The mixture was adjusted to pH=4 with HCl (1 M), concentrated and purified by preparative HPLC to give 2-[1-(6-methyl-4-oxo-2-pyrrolidin-1-yl-chromen-8-yl) ethylamino]benzoic acid as a solid (16.07 mg, 55%). $^1$H NMR (400 MHz, DMSO-d$_6$) δ ppm 1.60 (d, J=6.4 Hz, 3H), 1.97-2.00 (m, 4H), 2.30 (s, 3H), 3.55-3.75 (m, 4H), 5.06-5.09 (m, 1H), 5.22 (s, 1H), 6.46 (d, J=8.8 Hz, 1H), 6.55 (t, J=7.2 Hz, 1H), 7.22-7.25 (m, 1H), 7.35 (d, J=2.4 Hz, 1H), 7.61 (d, J=1.6 Hz, 1H), 7.80 (dd, J=8.0, 1.6 Hz, 1H), 8.36 (br, J=6.0 Hz, 1H), 12.78 (br s, 1H). MS ES+ m/z 393 [M+H]$^+$.

Example 369: 2-[[2-(4,4-Dimethyl-1-piperidyl)-6-methyl-4-oxo-chromen-8-yl]methylamino]benzoic acid

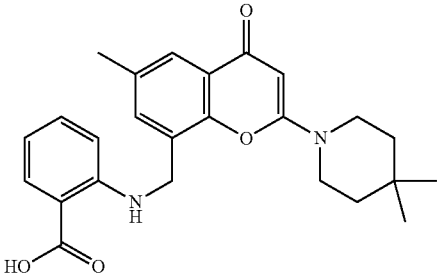 [SMILES: Cc1cc(CNc2ccccc2C(=O)O)c2oc(N3CCC(C)(C)CC3)cc(=O)c2c1]

Step 1: 2-[1-[2-(4,4-dimethyl-1-piperidyl)-6-methyl-4-oxo-chromen-8-yl]ethylamino]-N-methoxy-benzamide. A mixture of 8-bromo-2-(4,4-dimethylpiperidin-1-yl)-6-methyl-4H-chromen-4-one (220 mg, 0.628 mmol), DPPF (35 mg, 0.063 mmol), TEA (953 mg, 9.42 mmol) and Pd(OAc)$_2$ (21 mg, 0.094 mmol) in DMF (5 mL) and MeOH (8 mL) was stirred at 80° C. under CO atmosphere (50 psi) for 5 h. When cooled to rt the mixture was concentrated, diluted with water (20 mL), extracted with EtOAc (20 mL×3). The combined extract was washed with brine (30 mL), dried over anhydrous Na$_2$SO$_4$, filtered and concentrated to give the product as a solid (200 mg, crude). MS ES+ m/z 330 [M+H]$^+$.

Step 2: 2-(4,4-dimethyl-1-piperidyl)-8-(hydroxymethyl)-6-methyl-chromen-4-one. A mixture of methyl 2-(4,4-dimethyl-1-piperidyl)-6-methyl-4-oxo-chromene-8-carboxylate (200 mg, 0.607 mmol) in THF (3 mL) was added LiAlH$_4$ (23 mg, 0.61 mmol) in portions at 0° C. and stirred at 20° C. for 2 h. The reaction mixture was quenched with sat.NH$_4$Cl (15 mL) and extracted with EtOAc (20 mL×2). The combined extract was washed with brine (20 mL×2), dried over anhydrous Na$_2$SO$_4$, filtered, concentrated and purified on a silica gel column eluted with 30-100% EtOAc in petroleum ether to give the product as a solid (140 mg, 77%). MS ES+ m/z 302 [M+H]$^+$.

Step 3: 8-(bromomethyl)-2-(4,4-dimethyl-1-piperidyl)-6-methyl-chromen-4-one. A mixture of 2-(4,4-dimethyl-1-piperidyl)-8-(hydroxymethyl)-6-methyl-chromen-4-one (140 mg, 0.465 mmol) in DCM (4 mL) was added PBr$_3$ (251 mg, 0.929 mmol) at 0° C., then stirred at 20° C. for 16 h. The mixture was quenched with sat. NaHCO$_3$ (10 mL). The aqueous layer was extracted with DCM (15 mL×2). The combined extract was washed with brine (20 mL×2), dried over anhydrous Na$_2$SO$_4$, filtered, concentrated and purified on a silica gel chromatography eluted with 30-70% EtOAc in petroleum ether to give the product as a solid (90 mg, 53%). MS ES+ m/z 366 [M+H]$^+$.

Step 4: 2-[[2-(4,4-dimethyl-1-piperidyl)-6-methyl-4-oxo-chromen-8-yl]methylamino]benzoic acid. A mixture of 8-(bromomethyl)-2-(4,4-dimethyl-1-piperidyl)-6-methyl-chromen-4-one (70 mg, 0.19 mmol) and 2-aminobenzoic acid (53 mg, 0.38 mmol) in DMF (1 mL) was at 80° C. under N$_2$ for 16 h. When cooled to rt the mixture was diluted with H$_2$O (5 mL) and adjusted to pH=10 with aq. NaOH (1 M), then washed with DCM (10 mL×2). The aqueous phase was adjusted to pH=5 with aq. HCl (2 M) and extracted with DCM (10 mL×2). The combined extract was dried over anhydrous Na$_2$SO$_4$, filtered, concentrated and purified by preparative HPLC to give 2-[[2-(4,4-dimethyl-1-piperidyl)-

6-methyl-4-oxo-chromen-8-yl]methylamino]benzoic acid as a solid (18.1 mg, 22%). $^1$H NMR (400 MHz, DMSO-d$_6$) δ ppm 0.96 (s, 6H), 1.35-1.38 (m, 4H), 2.07 (s, 3H), 3.47-3.50 (m, 4H), 4.63-4.64 (m, 2H), 5.50 (s, 1H), 6.59 (t, J=6.4 Hz, 1H), 6.74 (d, J=6.8 Hz, 1H), 7.32 (t, J=5.6 Hz, 1H), 6.35 (d, J=1.6 Hz, 1H), 7.35 (d, J=1.6 Hz, 1H), 7.81 (d, J=6.4 Hz, 1H), 8.26 (brs, 1H). MS ES+ m/z 421 [M+H]$^+$.

Example 370: 2-[1-[6-Methyl-2-(4-methyl-1-piperidyl)-4-oxo-chromen-8-yl]ethylamino]benzoic acid

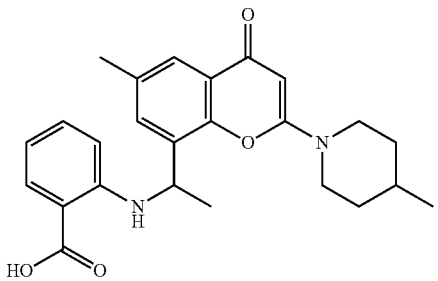 [SMILES: Cc1cc(C(C)Nc2ccccc2C(=O)O)c2oc(N3CCC(C)CC3)cc(=O)c2c1]

Step 1: 8-bromo-6-methyl-2-(4-methyl-1-piperidyl) chromen-4-one. A mixture of 4-methylpiperidine (72 mg, 0.72 mmol) and DIPEA (312 mg, 2.42 mmol) in DCM (3 mL) was added dropwise to a solution of 8-bromo-2-ethylsulfonyl-6-methyl-chromen-4-one (200 mg, 0.604 mmol) in DCM (3 mL) at 10° C. under N$_2$ atmosphere, and stirred at 25° C. for 4 h. The mixture was diluted with water (20 mL), extracted with DCM (20 mL×2). The combined extract was washed with brine (20 mL×2), dried over anhydrous Na$_2$SO$_4$, filtered and concentrated to give the product as a solid (203 mg, 80%). MS ES+ m/z 338 [M+2+H]$^+$.

Step 2: 8-acetyl-6-methyl-2-(4-methyl-1-piperidyl) chromen-4-one. A mixture of 8-bromo-6-methyl-2-(4-methyl-1-piperidyl)chromen-4-one (200 mg, 0.595 mmol), tributyl(1-ethoxyvinyl)stannane (430 mg, 1.19 mmol) and Pd(PPh$_3$)$_2$Cl$_2$ (42 mg, 0.059 mmol) in dioxane (10 mL) was stirred at 95° C. under N$_2$ for 16 h. The mixture was added aq. HCl (2 mL, 2 M) and stirred at 50° C. for 1 h. When cooled to rt the mixture was added sat. KF (30 mL), stirred for 1 h, extracted with EtOAc (30 mL×3). The combined extract was washed with brine (20 mL), dried over anhydrous Na$_2$SO$_4$, filtered and concentrated. The residue was purified by silica gel chromatography eluted with 0%-10% MeOH in DCM to give the product (178 mg, 97%) as a solid. MS ES+ m/z 300 [M+H]$^+$.

Step 3: 8-(1-hydroxyethyl)-6-methyl-2-(4-methyl-1-piperidyl)chromen-4-one. A mixture of 8-acetyl-6-methyl-2-(4-methyl-1-piperidyl)chromen-4-one (170 mg, 0.568 mmol) in DCM (2 mL) and MeOH (2 mL) was added NaBH$_4$ (26 mg, 0.68 mmol) at 0° C., then stirred at 15° C. for 1 h. The mixture was diluted with water (10 mL), extracted with DCM (20 mL×2). The combined extract was washed with brine (20 mL), dried over anhydrous Na$_2$SO$_4$, filtered and concentrated. The residue was purified by silica gel chromatography eluted with 0%-3% MeOH in DCM to give the product (160 mg, crude) as a solid. MS ES+ m/z 302 [M+H]$^+$.

Step 4: 8-(1-bromoethyl)-6-methyl-2-(4-methyl-1-piperidyl)chromen-4-one. A mixture of 8-(1-hydroxyethyl)-6-methyl-2-(4-methyl-1-piperidyl)chromen-4-one (160 mg, 0.531 mmol) in DCM (3 mL) was added PBr$_3$ (287 mg, 1.06 mmol) at 0° C., stirred at 15° C. for 15 h. The mixture was adjusted with sat.NaHCO$_3$ to pH=9, extracted with DCM (20 mL×2). The combined extract was washed with brine (20 mL), dried over anhydrous Na$_2$SO$_4$, filtered and concentrated. The residue was purified by silica gel chromatography eluted with 0%-8% MeOH in DCM to give the product (160 mg, crude) as oil. MS ES+ m/z 364 [M+H]$^+$.

Step 5: 2-[1-[6-methyl-2-(4-methyl-1-piperidyl)-4-oxo-chromen-8-yl]ethylamino]benzoic acid. A mixture of 8-(1-bromoethyl)-6-methyl-2-(4-methyl-1-piperidyl)chromen-4-one (70.0 mg, 0.192 mmol) and 2-aminobenzoic acid (79.1 mg, 0.576 mmol) in DMF (1 mL) was stirred at 80° C. for 14 h. When cooled to rt the mixture was diluted with water (10 mL) and EtOAc (20 mL), then adjusted with aq. NaOH (1 M) to pH=12, the mixture was extracted with EtOAc (20 mL). The aqueous layer was adjusted with aq. HCl (1 M) to pH=4, then extracted with DCM (20 mL×3). The combined extract was dried over anhydrous Na$_2$SO$_4$, filtered and concentrated. The residue was purified by preparative HPLC to give 2-[1-[6-methyl-2-(4-methyl-1-piperidyl)-4-oxo-chromen-8-yl]ethylamino]benzoic acid as a solid (6.74 mg, 8%). $^1$H NMR (400 MHz, DMSO-d$_6$) δ ppm 0.92 (d, J=6.4 Hz, 3H), 1.16-1.23 (m, 2H), 1.58 (d, J=6.4 Hz, 3H), 1.63-1.73 (m, 3H), 2.30 (s, 3H), 3.02 (t, J=12.4 Hz, 2H), 4.05-4.08 (m, 2H), 5.05-5.08 (m, 1H), 5.52 (s, 1H,), 6.45 (d, J=8.4 Hz, 1H), 6.55 (t, J=7.6 Hz, 1H), 7.24 (t, J=7.6 Hz, 1H), 7.36 (d, J=2.0 Hz, 1H), 7.60 (d, J=1.6 Hz, 1H), 7.81 (dd, J=8.0, 1.6 Hz, 1H), 8.37 (br s, 1H), 12.73 (s, 1H). MS ES+ m/z 421 [M+H]$^+$. MS ES+ m/z 421 [M+H]$^+$.

Example 371: 2-[1-[6-Methyl-2-[4-(methylcarbamoyl)-1-piperidyl]-4-oxo-chromen-8-yl]ethylamino] benzoic acid

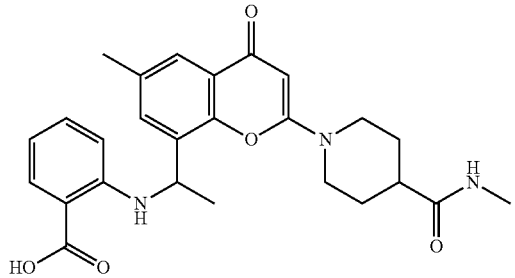 [SMILES: CNC(=O)C1CCN(c2cc(=O)c3cc(C)cc(C(C)Nc4ccccc4C(=O)O)c3o2)CC1]

Step 1: 1-(8-bromo-6-methyl-4-oxo-chromen-2-yl)-N-methyl-piperidine-4-carboxamide. A mixture of 8-bromo-2-ethylsulfonyl-6-methyl-chromen-4-one (300 mg, 0.906 mmol) in DCM (6 mL) was added N-methylpiperidine-4-carboxamide (322 mg, 2.26 mmol) and DIPEA (702 mg, 5.44 mmol) at 10° C., and stirred at 25° C. for 3 h. The mixture was quenched with HCl (1M, 2 mL), extracted with DCM (20 mL×3). The combined extract was washed with brine (30 mL×2), dried over anhydrous Na$_2$SO$_4$, filtered and concentrated to give the product as gum (400 mg, crude). MS ES+ m/z 381 [M+H]$^+$.

Step 2: 1-(8-acetyl-6-methyl-4-oxo-chromen-2-yl)-N-methyl-piperidine-4-carboxamide. A mixture of 1-(8-bromo-6-methyl-4-oxo-chromen-2-yl)-N-methyl-piperidine-4-carboxamide (350 mg, 0.923 mmol), Pd(PPh$_3$)$_2$Cl$_2$ (65 mg, 0.092 mmol) and tributyl(1-ethoxyvinyl)stannane (400 mg, 1.11 mmol) in dioxane (7 mL) was stirred at 95° C. under N$_2$ for 16 h. The mixture was added HCl (1.5 mL, 2 M) and stirred at 50° C. for 0.5 h. When cooled to rt the mixture was combined with another batch (50 mg), added sat. aq. KF (10 mL) and stirred for 1 h, filtered and the filter cake was rinsed with DCM (30 mL). The aqueous phase was extracted with DCM (30 mL×3). The combined extract was dried over anhydrous $Na_2SO_4$, filtered, concentrated and purified on a silica gel column eluted with 0-10% MeOH in DCM to give the product as a solid (130 mg, 36%). MS ES+ m/z 343 [M+H]+.

Step 3: 1-[8-(1-hydroxyethyl)-6-methyl-4-oxo-chromen-2-yl]-N-methyl-piperidine-4-carboxamide. A mixture of 1-(8-acetyl-6-methyl-4-oxo-chromen-2-yl)-N-methyl-piperidine-4-carboxamide (110 mg, 0.321 mmol) in DCM (1 mL) and MeOH (1 mL) was added $NaBH_4$ (15 mg, 0.39 mmol) at −10° C., and stirred at −10° C. for 1.5 h. The mixture was combined with another batch (20 mg), quenched with water (30 mL), extracted with DCM/MeOH (30 mL×3, 10/1). The combined extract was dried over anhydrous $Na_2SO_4$, filtered and concentrated to give the product as gum (130 mg, crude). MS ES+ m/z 345 [M+H]+.

Step 4: 1-[8-(1-bromoethyl)-6-methyl-4-oxo-chromen-2-yl]-N-methyl-piperidine-4-carboxamide. A mixture of 1-[8-(1-hydroxyethyl)-6-methyl-4-oxo-chromen-2-yl]-N-methyl-piperidine-4-carboxamide (110 mg, 0.319 mmol) in DCM (3 mL) was added $PBr_3$ (173 mg, 0.639 mmol) at 0° C., and stirred at 20° C. for 16 h. The reaction mixture was quenched with sat.aq.$NaHCO_3$ (10 mL), extracted with DCM (30 mL×3). The combined extract was washed with brine (50 mL×2), dried over anhydrous $Na_2SO_4$, filtered, concentrated and purified on a silica gel column eluted with 0-8% MeOH in DCM to give the product as a solid (45 mg, 35%). 1H NMR (400 MHz, DMSO-$d_6$) δ ppm 1.59-1.67 (m, 2H), 1.77-1.83 (m, 2H), 2.10 (d, J=7.2 Hz, 3H), 2.39 (s, 3H), 2.54-2.60 (m, 4H), 3.09-3.18 (m, 2H), 4.10-4.21 (m, 2H), 5.55 (s, 1H), 5.85 (q, J=6.8 Hz, 1H), 7.66-7.71 (m, 2H), 7.76-7.82 (m, 1H). MS ES+ m/z 407 [M+H]+.

Step 5: 2-[1-[6-methyl-2-[4-(methylcarbamoyl)-1-piperidyl]-4-oxo-chromen-8-yl]ethylamino]benzoic acid. A mixture of 1-[8-(1-bromoethyl)-6-methyl-4-oxo-chromen-2-yl]-N-methyl-piperidine-4-carboxamide (40 mg, 0.098 mmol) and 2-aminobenzoic acid (27 mg, 0.20 mmol) in DMF (1 mL) was stirred at 80° C. for 16 h. When cooled to rt the mixture was filtered. The filtrate was purified by preparative HPLC to give 2-[1-[6-methyl-2-[4-(methylcarbamoyl)-1-piperidyl]-4-oxo-chromen-8-yl]ethylamino]benzoic acid as a solid (8.37 mg, 18%). 1H NMR (400 MHz, DMSO-$d_6$) δ 1.58 (d, J=6.4 Hz, 3H), 1.60-1.68 (m, 2H), 1.72-1.82 (m, 2H), 2.30 (s, 3H), 2.54-2.61 (m, 4H), 3.00-3.14 (m, 2H), 4.01-4.16 (m, 2H), 5.08 (q, J=6.4 Hz, 1H), 5.54 (s, 1H), 6.46 (d, J=8.4 Hz, 1H), 6.55 (t, J=7.6 Hz, 1H), 7.20-7.28 (m, 1H), 7.36 (d, J=2.4 Hz, 1H), 7.60 (d, J=1.6 Hz, 1H), 7.74-7.85 (m, 2H), 8.34 (d, J=6.0 Hz, 1H), 12.68 (brs, 1H). MS ES+ m/z 464 [M+H]+.

Example 372: 2-[1-[6-Methyl-4-oxo-2-(1-piperidyl)chromen-8-yl]ethylamino]benzamide

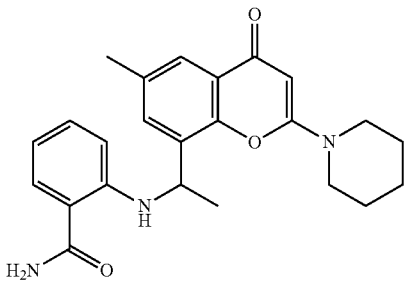 [SMILES: Cc1cc(C(C)Nc2ccccc2C(N)=O)c2oc(N3CCCCC3)cc(=O)c2c1]

A mixture of 8-(1-bromoethyl)-6-methyl-2-(1-piperidyl)chromen-4-one (80 mg, 0.23 mmol) and 2-aminobenzamide (62 mg, 0.46 mmol) in DMF (1 mL) was stirred at 80° C. for 16 h. When cooled to rt the mixture was quenched with $H_2O$ (20 mL), extracted with DCM (20 mL×2). The combined extracted was washed with brine (40 mL×2), dried over anhydrous $Na_2SO_4$, filtered and concentrated. The residue was purified by preparative HPLC to give 2-[1-[6-methyl-4-oxo-2-(1-piperidyl)chromen-8-yl]ethylamino]benzamide as a solid (90 mg, 97%). 1H NMR (400 MHz, DMSO-$d_6$) δ ppm 1.53-1.62 (m, 9H), 2.33 (s, 3H), 3.54-3.56 (m, 4H), 5.00 (t, J=6.8 Hz, 1H), 5.51 (s, 1H), 6.38 (d, J=8.0 Hz, 1H), 6.52 (t, J=7.6 Hz, 1H), 7.13 (t, J=7.2 Hz, 1H), 7.14 (brs, 1H), 7.36 (d, J=2.0 Hz, 1H), 7.59-7.63 (m, 2H), 7.91 (brs, 1H), 8.72 (d, J=6.0 Hz, 1H). MS ES+ m/z 406 [M+H]+.

Example 373: 2-[1-[2-(4-Methoxy-1-piperidyl)-6-methyl-4-oxo-chromen-8-yl]ethylamino]benzoic acid

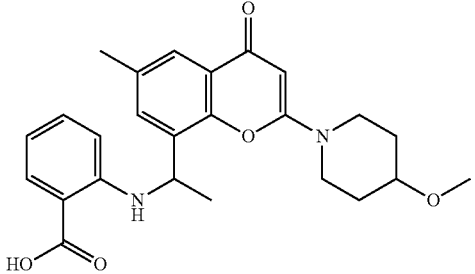 [SMILES: COC1CCN(c2cc(=O)c3cc(C)cc(C(C)Nc4ccccc4C(=O)O)c3o2)CC1]

Step 1: 8-bromo-2-(4-methoxy-1-piperidyl)-6-methyl-chromen-4-one. A mixture of 8-bromo-2-ethylsulfonyl-6-methyl-chromen-4-one (200 mg, 0.604 mmol), DIPEA (312 mg, 2.42 mmol) and 4-methoxypiperidine (153 mg, 1.33 mmol) in DCM (25 mL) was stirred at 20° C. for 2 h. The mixture was quenched with HCl (1M, 2 mL), extracted with DCM (20 mL×2). The combined extract was washed with brine (20 mL×2), dried over anhydrous $Na_2SO_4$, filtered and concentrated to give the product as a solid (213 mg, crude). MS ES+ m/z 436 [M+H]+.

Step 2: 8-acetyl-2-(4-methoxy-1-piperidyl)-6-methyl-chromen-4-one. A mixture of 8-bromo-2-(4-methoxy-1-piperidyl)-6-methyl-chromen-4-one (200 mg, 0.568 mmol), $Pd(PPh_3)_2Cl_2$ (40 mg, 0.057 mmol) and tributyl(1-ethoxyvinyl)stannane (246 mg, 0.681 mmol) in dioxane (20 mL) was stirred at 95° C. under $N_2$ for 16 h. HCl (2 M, 5.68 mL) was added to the mixture and stirred at 50° C. for 1 h. When cooled to rt the mixture was quenched with sat.aq. KF (10 mL) and stirred for 0.5 h, filtered, the filtrate was adjusted to pH=8 and extracted with DCM (30 mL×2). The combined extract was washed with brine (30 mL×2), dried over anhydrous $Na_2SO_4$, filtered, concentrated and purified on a silica gel column eluted with 0-10% MeOH in DCM to give the product as a solid (179 mg, crude). MS ES+ m/z 316 [M+H]$^+$.

Step 3: 8-(1-hydroxyethyl)-2-(4-methoxy-1-piperidyl)-6-methyl-chromen-4-one. A mixture of 8-acetyl-2-(4-methoxy-1-piperidyl)-6-methyl-chromen-4-one (179 mg, 0.567 mmol) in DCM (2 mL) and MeOH (2 mL) was added $NaBH_4$ (32 mg, 0.85 mmol) in one portion at −10° C. under $N_2$ and stirred at −10° C. for 1 h. The reaction mixture was quenched with water (15 mL), extracted with DCM/MeOH (20 mL×2, 10/1). The combined extract was washed with brine (20 mL), dried over anhydrous $Na_2SO_4$, filtered, concentrated and purified on a silica gel chromatography eluted with 0%-10% MeOH in DCM to give the product as a solid (190 mg, crude). MS ES+ m/z 318 [M+H]$^+$.

Step 4: 8-(1-bromoethyl)-2-(4-methoxy-1-piperidyl)-6-methyl-chromen-4-one. A mixture of 8-(1-hydroxyethyl)-2-(4-methoxy-1-piperidyl)-6-methyl-chromen-4-one (190 mg, 0.598 mmol) in DCM (5 mL) was added $PBr_3$ (162 mg, 0.598 mmol) dropwise at 0° C. and stirred at 20° C. for 2 h. The reaction mixture was quenched with sat.aq.$NaHCO_3$ (20 mL), extracted with DCM (20 mL×2). The combined extract was washed with brine (30 mL×2), dried over anhydrous $Na_2SO_4$ (30 mL), filtered and concentrated to give the product as a solid (200 mg, 88%). MS ES+ m/z 352 [M+H]$^+$.

Step 5: 2-[1-[2-(4-methoxy-1-piperidyl)-6-methyl-4-oxo-chromen-8-yl]ethylamino]benzoic acid. A mixture of 8-(1-bromoethyl)-2-(4-methoxy-1-piperidyl)-6-methyl-chromen-4-one (200 mg, 0.526 mmol) and methyl 2-aminobenzoate (159 mg, 1.05 mmol) in DMF (1 mL) was stirred at 80° C. for 16 h. When cooled to rt the mixture was quenched with $H_2O$ (20 mL), extracted with DCM (20 mL×2). The combined extract was washed with brine (40 mL×2), dried over anhydrous $Na_2SO_4$, filtered, concentrated and purified on a silica gel chromatography eluted with 0%-10% MeOH in DCM to give methyl 2-[1-[2-(4-methoxy-1-piperidyl)-6-methyl-4-oxo-chromen-8-yl]ethylamino]benzoate as a solid (100 mg, 42%). A mixture of methyl 2-[1-[2-(4-methoxy-1-piperidyl)-6-methyl-4-oxo-chromen-8-yl]ethylamino]benzoate (100 mg, 0.222 mmol) and $LiOH \cdot H_2O$ (19 mg, 0.44 mmol) in THF (2 mL), EtOH (1 mL) and $H_2O$ (4 mL) was stirred at 20° C. for 18 h. Then the reaction mixture was added NaOH (17.8 mg, 0.444 mol) in $H_2O$ (4 mL) and stirred at 20° C. for 4 h. The mixture was concentrated to remove most of EtOH and THF, then purified by preparative HPLC to give 2-[1-[2-(4-methoxy-1-piperidyl)-6-methyl-4-oxo-chromen-8-yl]ethylamino]benzoic acid as a solid (20 mg, 21%). $^1$H NMR (400 MHz, DMSO-$d_6$) δ ppm 1.52-1.57 (m, 5H), 1.90-1.91 (m, 2H), 2.29 (s, 3H), 3.27 (s, 3H), 3.45-3.48 (m, 3H), 3.74-3.77 (m, 2H), 5.01-5.05 (m, 1H), 5.54 (s, 1H), 6.37 (d, J=8.8 Hz, 1H), 6.49 (t, J=7.6 Hz, 1H), 7.12-7.16 (m, 1H), 7.37 (d, J=1.6 Hz, 1H), 7.59 (d, J=1.6 Hz, 1H), 7.79 (d, J=7.6 Hz, 1H), 8.83 (brs, 1H). MS ES+ m/z 437 [M+H]$^+$.

Example 374: 2-[1-[2-(4-Cyano-1-piperidyl)-6-methyl-4-oxo-chromen-8-yl]ethylamino]benzoic acid

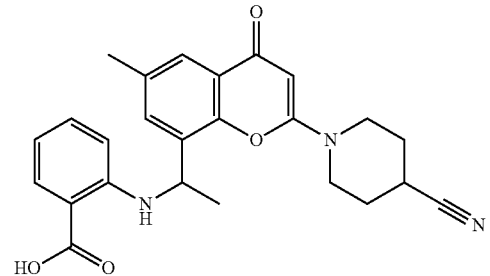 [SMILES: Cc1cc(C(C)Nc2ccccc2C(=O)O)c2oc(N3CCC(C#N)CC3)cc(=O)c2c1]

Step 1: 1-(8-bromo-6-methyl-4-oxo-chromen-2-yl)piperidine-4-carbonitrile. A mixture of piperidine-4-carbonitrile (80 mg, 0.72 mmo) and DIPEA (312 mg, 2.42 mmol) in DCM (3 mL) was added dropwise to a solution of 8-bromo-2-ethylsulfonyl-6-methyl-chromen-4-one (200 mg, 0.604 mmol) in DCM (3 mL) at 10° C. under $N_2$ atmosphere, and stirred at 20° C. for 14 h. The mixture was diluted with water (20 mL), extracted with DCM (20 mL×2). The combined extract was washed with brine (20 mL×2), dried over anhydrous $Na_2SO_4$, filtered and concentrated to give the product as oil (209 mg, 100%). MS ES+ m/z 349 [M+2+H]$^+$.

Step 2: 1-(8-acetyl-6-methyl-4-oxo-chromen-2-yl)piperidine-4-carbonitrile. A mixture of 1-(8-bromo-6-methyl-4-oxo-chromen-2-yl)piperidine-4-carbonitrile (200 mg, 0.576 mmol), tributyl(1-ethoxyvinyl)stannane (416 mg, 1.15 mmol) and $Pd(PPh_3)_2Cl_2$ (40 mg, 0.58 mmol) in dioxane (2 mL) was stirred at 95° C. under $N_2$ for 16 h. HCl (0.5 mL, 2 M) was added to the mixture and stirred at 50° C. for 0.5 h. When cooled to rt the mixture was quenched with sat. aq. KF (10 mL) and stirred for 0.5 h, filtered, the filtrate was adjusted to pH=8 and extracted with DCM (30 mL×2). The combined extract was washed with brine (30 mL×2), dried over anhydrous $Na_2SO_4$, filtered, concentrated and purified on a silica gel column eluted with 0%-2% MeOH in DCM to give the product as oil (222 mg, 93%). MS ES+ m/z 311 [M+H]$^+$.

Step 3: 1-[8-(1-hydroxyethyl)-6-methyl-4-oxo-chromen-2-yl]piperidine-4-carbonitrile. A mixture of 1-(8-acetyl-6-methyl-4-oxo-chromen-2-yl)piperidine-4-carbonitrile (200 mg, 0.483 mmol) in DCM (3 mL) and MeOH (3 mL) was added $NaBH_4$ (22 mg, 0.58 mmol) at 0° C., and stirred at 20° C. for 1 h. The mixture was diluted with water (15 mL), extracted with DCM (20 mL×2). The combined extract was washed with brine (20 mL×2), dried over anhydrous $Na_2SO_4$, filtered, concentrated and purified on a silica gel column eluted with 0%-4% MeOH in DCM to give the product as a solid (140 mg, 88%). MS ES+ m/z 313 [M+H]$^+$.

Step 4: 1-[8-(1-bromoethyl)-6-methyl-4-oxo-chromen-2-yl]piperidine-4-carbonitrile. A mixture of 1-[8-(1-hydroxyethyl)-6-methyl-4-oxo-chromen-2-yl]piperidine-4-carbonitrile (140 mg, 0.448 mmol) in DCM (3 mL) was added $PBr_3$ (182 mg, 0.672 mmol) at 0° C., and stirred at 15° C. for 3 h. The reaction mixture was adjusted to pH=9 with sat.$NaHCO_3$, extracted with DCM (20 mL×2). The combined extract was washed with brine (20 mL×2), dried over anhydrous $Na_2SO_4$, filtered, concentrated and purified on a silica gel column eluted with 0%-9% MeOH in DCM to give the product as a solid (100 mg, 54%). MS ES+ m/z 375 [M+H]$^+$.

Step 5: 2-[1-[2-(4-cyano-1-piperidyl)-6-methyl-4-oxo-chromen-8-yl]ethylamino]benzoic acid. A mixture of 1-[8-(1-bromoethyl)-6-methyl-4-oxo-chromen-2-yl]piperidine-4-carbonitrile (50 mg, 0.13 mmol) and 2-aminobenzoic acid (55 mg, 0.40 mmol) in DMF (1 mL) was stirred at 80° C. for 14 h. The mixture was diluted with water (10 mL), adjusted to pH=12 with aq. NaOH (1 M) and extracted with EtOAc (20 mL×2). The aqueous layer was adjusted to pH=4 with HCl (1 M), extracted with DCM (20 mL×3). The combined extract was washed with brine (20 mL), dried over anhydrous Na$_2$SO$_4$, filtered, concentrated and purified by preparative HPLC to give 2-[1-[2-(4-cyano-1-piperidyl)-6-methyl-4-oxo-chromen-8-yl]ethylamino]benzoic acid as a solid (25.41 mg, 44%). $^1$H NMR (400 MHz, DMSO-d$_6$) δ ppm 1.58 (d, J=6.8 Hz, 3H), 1.80-1.85 (m, 2H), 1.95-2.02 (m, 2H), 2.30 (s, 3H), 3.16-3.20 (m, 1H), 3.41-3.44 (m, 2H), 3.76-3.79 (m, 2H), 5.06-5.09 (m, 1H), 5.58 (s, 1H), 6.46 (d, J=8.8 Hz, 1H), 6.55 (t, J=7.2 Hz, 1H), 7.24 (t, J=7.2 Hz, 1H), 7.37 (d, J=1.6 Hz, 1H), 7.60 (s, 1H), 7.81 (dd, J=8.0, 1.6 Hz, 1H), 8.38 (br s, 1H). MS ES+ m/z 432 [M+H]$^+$.

Example 375: 2-[1-[2-(Azetidin-1-yl)-6-methyl-4-oxo-chromen-8-yl]ethylamino]benzoic acid

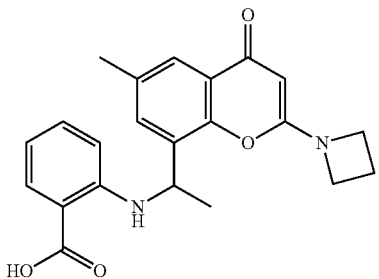 [SMILES: Cc1cc(C(C)Nc2ccccc2C(=O)O)c2oc(N3CCC3)cc(=O)c2c1]

Step 1: 2-(azetidin-1-yl)-8-bromo-6-methyl-chromen-4-one. A mixture of 8-bromo-2-ethylsulfonyl-6-methyl-chromen-4-one (200 mg, 0.604 mmol), azetidine (85 mg, 0.91 mmol, HCl salt) and DIPEA (78 mg, 0.60 mmol) in DCM (10 mL) was stirred at 25° C. for 4 h. The reaction mixture was concentrated and purified on a silica gel column eluted with 0-10% MeOH in DCM to give the product as a solid (177 mg, 99%). MS ES+ m/z 294 [M+H]$^+$.

Step 2: 8-acetyl-2-(azetidin-1-yl)-6-methyl-chromen-4-one. A mixture of 2-(azetidin-1-yl)-8-bromo-6-methyl-chromen-4-one (110 mg, 0.374 mmol), tributyl(1-ethoxyvinyl)stannane (270 mg, 0.748 mmol) and Pd(PPh$_3$)$_2$Cl$_2$ (26 mg, 0.037 mmol) in dioxane (5 mL) was stirred at 95° C. under N$_2$ for 16 h. HCl (4 mL, 1 M) was added and stirred at 50° C. for 1 h. The mixture was combined with another batch (50 mg), quenched with sat. KF (30 mL) and filtered. The filtrate was diluted with sat.NaHCO$_3$ (30 mL), extracted with EtOAc (30 mL×3). The combined extract was washed with brine (30 mL), dried over anhydrous Na$_2$SO$_4$, filtered, concentrated and purified on a silica gel column eluted with 0-10% MeOH in DCM to give the product as a solid (139 mg, 99%). MS ES+ m/z 258 [M+H]$^+$.

Step 3: 2-(azetidin-1-yl)-8-(1-hydroxyethyl)-6-methyl-chromen-4-one. A mixture of 8-acetyl-2-(azetidin-1-yl)-6-methyl-chromen-4-one (139 mg, 0.540 mmol) in DCM (5 mL) and MeOH (5 mL) was added NaBH$_4$ (31 mg, 0.81 mmol) at −10° C. and stirred for 1 h. The reaction mixture was quenched with water (20 mL), extracted with DCM/MeOH (20 mL×2, 10/1). The combined extract was washed with brine (30 mL), dried over anhydrous Na$_2$SO$_4$, filtered and concentrated to give the product as a solid (140 mg, crude). MS ES+ m/z 260 [M+H]$^+$.

Step 4: 2-(azetidin-1-yl)-8-(1-bromoethyl)-6-methyl-chromen-4-one. A mixture of 2-(azetidin-1-yl)-8-(1-hydroxyethyl)-6-methyl-chromen-4-one (140 mg, 0.540 mmol) in DCM (5 mL) was added PBr$_3$ (219 mg, 0.810 mmol) at 0° C. and stirred at 20° C. for 2 h. The mixture was quenched with sat.NaHCO$_3$ (30 mL), extracted with DCM (30 mL×3). The combined extract was washed with brine (30 mL×2), dried over anhydrous Na$_2$SO$_4$, filtered, concentrated and purified on a silica gel column eluted with 0-10% MeOH in DCM to give the product as a solid (100 mg, 57%). MS ES+ m/z 322 [M+H]$^+$.

Step 5: 2-[1-[2-(azetidin-1-yl)-6-methyl-4-oxo-chromen-8-yl]ethylamino]benzoic acid. A mixture of 2-(azetidin-1-yl)-8-(1-bromoethyl)-6-methyl-chromen-4-one (75 mg, 0.23 mmol), methyl 2-aminobenzoate (70 mg, 0.46 mmol) and KI (42 mg, 0.26 mmol) in DCM (4 mL) and MeOH (1 mL) was stirred at 20° C. for 24 h. The reaction mixture was concentrated and purified by preparative TLC to give methyl 2-[1-[2-(azetidin-1-yl)-6-methyl-4-oxo-chromen-8-yl]ethylamino]benzoate as a solid (70 mg, 77%). A mixture of methyl 2-[1-[2-(azetidin-1-yl)-6-methyl-4-oxo-chromen-8-yl]ethylamino]benzoate (70 mg, 0.18 mmol) and LiOH.H$_2$O (26 mg, 0.16 mmol) in THF (3 mL) and H$_2$O (1 mL) was stirred at 25° C. for 16 h. The reaction mixture was concentrated and purified by preparative HPLC to give 2-[1-[2-(azetidin-1-yl)-6-methyl-4-oxo-chromen-8-yl]ethylamino]benzoic acid as a solid (4.43 mg, 7%). $^1$H NMR (400 MHz, DMSO-d6) δ 1.59 (d, J=6.8 Hz, 3H), 2.31 (s, 3H), 2.36-2.45 (m, 2H), 4.13-4.23 (m, 4H), 4.98-5.06 (m, 2H), 6.48-6.58 (m, 2H), 7.21-7.29 (m, 1H), 7.39 (d, J=2.0 Hz, 1H), 7.61 (d, J=1.2 Hz, 1H), 7.80 (dd, J=8.0, 1.2 Hz, 1H), 8.37 (d, J=6.8 Hz, 1H), 12.78 (brs, 1H). MS ES+ m/z 379 [M+H]$^+$.

Example 376: 2-[[(1R)-1-[6-Methyl-4-oxo-2-(1-piperidyl)chromen-8-yl]ethyl]amino]benzoic acid

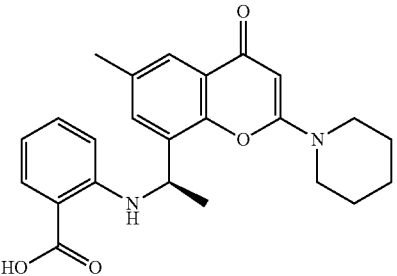 [SMILES: Cc1cc([C@@H](C)Nc2ccccc2C(=O)O)c2oc(N3CCCCC3)cc(=O)c2c1]

A mixture of 8-[(1R)-1-aminoethyl]-6-methyl-2-(1-piperidyl)chromen-4-one (150 mg, 0.524 mmol), 2-iodobenzoic acid (234 mg, 0.943 mmol), CuI (10 mg, 0.052 mmol), 2-(methylamino)acetic acid (9.0 mg, 0.10 mmol) and K$_2$CO$_3$ (145 mg, 1.05 mmol) in DMSO (3 mL) was stirred at 45° C. under N$_2$ for 96 h. When cooled to rt the mixture was combined with another batch (50 mg), extracted with DCM (20 mL×3). The combined extract was dried over anhydrous Na$_2$SO$_4$, filtered, concentrated, purified by preparative HPLC and SFC to give 2-[[(1R)-1-[6-methyl-4-oxo-2-(1-piperidyl)chromen-8-yl]ethyl]amino]benzoic acid as a solid (14.78 mg, 14%). $^1$H NMR (400 MHz, DMSO-d$_6$) δ ppm 1.54-1.65 (m, 9H), 2.30 (s, 3H), 3.48-3.62 (m, 4H), 5.00-5.11 (m, 1H), 5.51 (s, 1H), 6.44 (d, J=8.4 Hz, 1H), 6.54 (t, J=7.2 Hz, 1H), 7.17-7.28 (m, 1H), 7.36 (d, J=1.6 Hz, 1H), 7.60 (d, J=1.2 Hz, 1H), 7.81 (dd, J=8.0, 1.6 Hz, 1H), 8.46 (brs, 1H). MS ES+ m/z 407 [M+H]⁺.

Example 377: 2-(2-Methoxyethoxy)ethyl 2-[[(1R)-1-[6-methyl-4-oxo-2-(1-piperidyl)chromen-8-yl]ethyl]amino]benzoate

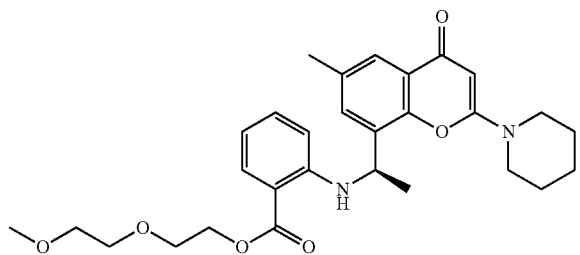 [SMILES: COCCOCCOC(=O)c1ccccc1N[C@H](C)c1cc(C)cc2c(=O)cc(N3CCCCC3)oc12]

A mixture of 2-[[(1R)-1-[6-methyl-4-oxo-2-(1-piperidyl)chromen-8-yl]ethyl]amino]benzoic acid (30 mg, 0.074 mmol) and K₂CO₃ (20 mg, 0.15 mmol) in DMF (2 mL) was added 1-(2-bromoethoxy)-2-methoxy-ethane (20 mg, 0.11 mmol) under N₂ and stirred at 20° C. for 48 h. The reaction mixture was filtered and purified by preparative HPLC to give 2-(2-methoxyethoxy)ethyl 2-[[(1R)-1-[6-methyl-4-oxo-2-(1-piperidyl)chromen-8-yl]ethyl]amino]benzoate as a solid (10 mg, 27%). ¹H NMR (400 MHz, DMSO-d₆) δ ppm 1.59-1.60 (m, 9H), 2.30 (s, 3H), 3.23 (s, 3H), 3.44-3.47 (m, 2H), 2.54-3.55 (m, 4H), 3.59-3.61 (m, 2H), 3.75-3.76 (m, 2H), 4.38-4.39 (m, 2H), 5.07-5.13 (m, 1H), 5.52 (s, 1H), 6.50 (d, J=8.4 Hz, 1H), 6.60 (t, J=7.6 Hz, 1H), 7.29 (t, J=8.0 Hz, 1H), 7.37 (d, J=2.0 Hz, 1H), 7.60 (d, J=1.6 Hz, 1H), 7.84 (dd, J=8.0, 1.6 Hz, 1H), 8.08 (d, J=6.4 Hz, 1H). MS ES+ m/z 509 [M+H]⁺.

Example 378: 2-[1-[2-(4-Acetylpiperazin-1-yl)-6-methyl-4-oxo-chromen-8-yl]ethylamino]benzoic acid

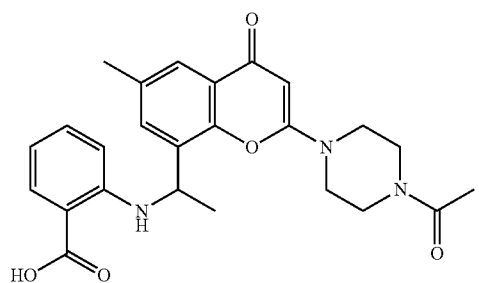 [SMILES: CC(=O)N1CCN(c2cc(=O)c3cc(C)cc(C(C)Nc4ccccc4C(=O)O)c3o2)CC1]

Step 1: 2-(4-acetylpiperazin-1-yl)-8-bromo-6-methyl-chromen-4-one. A mixture of 1-piperazin-1-ylethanone (348 mg, 2.72 mmol) and DIPEA (585 mg, 4.53 mmol) in DCM (3 mL) was added dropwise to a solution of 8-bromo-2-ethylsulfonyl-6-methyl-chromen-4-one (300 mg, 906 μmol) in DCM (5 mL) at 10° C. under N₂ atmosphere, and stirred at 20° C. for 4 h. The mixture was quenched with HCl (1M, 2 mL), extracted with DCM (20 mL×2). The combined extract was washed with brine (20 mL×2), dried over anhydrous Na₂SO₄, filtered, concentrated and purified on a silica gel column eluted with 1%-9% MeOH in DCM to give the product as a solid (250 mg, 76%). MS ES+ m/z 367 [M+2+H]⁺.

Step 2: 8-acetyl-2-(4-acetylpiperazin-1-yl)-6-methyl-chromen-4-one. A mixture of 2-(4-acetylpiperazin-1-yl)-8-bromo-6-methyl-chromen-4-one (200 mg, 0.548 mmol), tributyl(1-ethoxyvinyl)stannane (237 mg, 0.657 mmol) and Pd(PPh₃)₂Cl₂ (384 mg, 0.548 mmol) in dioxane (8 mL) was stirred at 95° C. under N₂ for 16 h. HCl (0.5 mL, 2 M) was added to the mixture and stirred at 50° C. for 0.5 h. When cooled to rt the mixture was quenched with sat. aq. KF (10 mL) and stirred for 0.5 h, filtered, the filtrate was adjusted to pH=8 and extracted with DCM (30 mL×2). The combined extract was washed with brine (30 mL×2), dried over anhydrous Na₂SO₄, filtered, concentrated and purified on a silica gel column eluted with 1%-9% MeOH in DCM to give the product as a solid (180 mg, 92%). MS ES+ m/z 329 [M+H]⁺.

Step 3: 2-(4-acetylpiperazin-1-yl)-8-(1-hydroxyethyl)-6-methyl-chromen-4-one. A mixture of 8-acetyl-2-(4-acetylpiperazin-1-yl)-6-methyl-chromen-4-one (180 mg, 0.548 mmol) in DCM (2 mL) and MeOH (2 mL) was added NaBH₄ (25 mg, 0.66 mmol) at 0° C., and stirred at 25° C. for 2 h. The mixture was adjusted to pH=8 with sat.NaHCO₃, extracted with DCM (20 mL×2). The combined extract was washed with brine (20 mL×2), dried over anhydrous Na₂SO₄, filtered, concentrated and purified on a silica gel column eluted with 1%-9% MeOH in DCM to give the product as a solid (80 mg, 42%). MS ES+ m/z 331 [M+H]⁺.

Step 4: 2-(4-acetylpiperazin-1-yl)-8-(1-bromoethyl)-6-methyl-chromen-4-one. A mixture of 2-(4-acetylpiperazin-1-yl)-8-(1-hydroxyethyl)-6-methyl-chromen-4-one (80 mg, 0.24 mmol) in DCM (2 mL) was added PBr₃ (98 mg, 0.36 mmol) at 0° C., and stirred at 25° C. for 16 h. The mixture was adjusted to pH=9 with sat.Na₂CO₃, extracted with DCM (20 mL×2). The combined extract was washed with brine (20 mL×2), dried over anhydrous Na₂SO₄, filtered, concentrated and purified on a silica gel column eluted with 1%-9% MeOH in DCM to give the product as a solid (73 mg, 63%). MS ES+ m/z 395 [M+2+H]⁺.

Step 5: 2-[1-[2-(4-acetylpiperazin-1-yl)-6-methyl-4-oxo-chromen-8-yl]ethylamino]benzoic acid. A mixture of 2-(4-acetylpiperazin-1-yl)-8-(1-bromoethyl)-6-methyl-chromen-4-one (35 mg, 0.089 mmol), methyl 2-aminobenzoate (27 mg, 0.18 mmol) and KI (19 mg, 0.12 mmol) in DCM/MeOH (4/1, 2.5 mL) was stirred at 25° C. for 48 h. The mixture was concentrated and purified on a silica gel column eluted with 1%-9% MeOH in DCM to give methyl 2-[1-[2-(4-acetylpiperazin-1-yl)-6-methyl-4-oxo-chromen-8-yl]ethylamino]benzoate as a solid (47 mg, 88%). MS ES+ m/z 464 [M+H]⁺. A mixture of methyl 2-[1-[2-(4-acetylpiperazin-1-yl)-6-methyl-4-oxo-chromen-8-yl]ethylamino]benzoate (50 mg, 0.11 mmol) and LiOH.H₂O (11 mg, 0.27 mmol) in EtOH (1 mL) and H₂O (1 mL) was stirred at 20° C. for 24 h. The mixture was concentrated and purified by preparative HPLC to give 2-[1-[2-(4-acetylpiperazin-1-yl)-6-methyl-4-oxo-chromen-8-yl]ethylamino]benzoic acid as a solid (6.3 mg, 13%). ¹H NMR (400 MHz, DMSO-d₆) δ ppm 1.60 (d, J=6.4 Hz, 3H), 2.05 (s, 3H), 2.31 (s, 3H), 3.56-3.62 (m, 8H), 5.10-5.13 (m, 1H), 5.56 (s, 1H), 6.47 (d, J=8.4 Hz, 1H), 6.57 (t, J=7.6 Hz, 1H), 7.24-7.28 (m, 1 H), 7.39 (d, J=1.6 Hz, 1H), 7.62 (s, 1H), 7.82 (dd, J=8.0, 1.6 Hz, 1H), 8.36 (d, J=6.0 Hz, 1H). MS ES+ m/z 450 [M+H]⁺.

Example 379: Methyl 2-[[(1R)-1-[6-methyl-4-oxo-2-(1-piperidyl)chromen-8-yl]ethyl]amino]benzoate

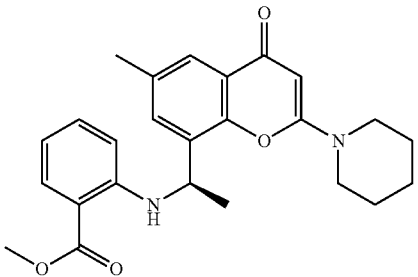 [SMILES: COC(=O)c1ccccc1N[C@H](C)c1cc(C)cc2c(=O)cc(N3CCCCC3)oc12]

A mixture of 2-[[(1R)-1-[6-methyl-4-oxo-2-(1-piperidyl)chromen-8-yl]ethyl]amino]benzoic acid (20 mg, 0.049 mmol), $K_2CO_3$ (10 mg, 0.074 mmol) and MeI (11 mg, 0.074 mmol) in DMF (2 mL) was stirred at 20° C. for 2 h. The reaction mixture was filtered. The filtrate was concentrated and purified by preparative HPLC to give methyl 2-[[(1R)-1-[6-methyl-4-oxo-2-(1-piperidyl)chromen-8-yl]ethyl]amino]benzoate as a solid (5.4 mg, 26%). $^1$H NMR (400 MHz, DMSO-$d_6$) δ ppm 1.58-1.60 (m, 9H), 2.29 (s, 3H), 3.53-3.54 (m, 4H), 3.83 (s, 3H), 5.07-5.10 (m, 1H), 5.51 (s, 1H), 6.50 (d, J=8.8 Hz, 1H), 6.58 (t, J=7.2 Hz, 1H), 7.28 (td, J=8.4, 1.6 Hz, 1H), 7.36 (d, J=2.0 Hz, 1H), 7.60 (d, J=1.6 Hz, 1H), 7.70 (dd, J=7.6, 1.6 Hz, 1H), 8.15 (d, J=6.0 Hz, 1H). MS ES+ m/z 421 [M+H]$^+$.

Example 380: 2-[1-[6-Methyl-2-(3-methyl-2-oxo-1-oxa-3,8-diazaspiro[4.5]decan-8-yl)-4-oxo-chromen-8-yl]ethylamino]benzoic acid

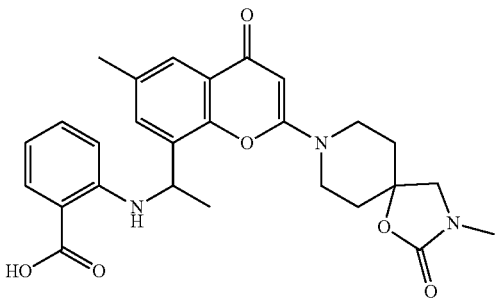 [SMILES: Cc1cc(C(C)Nc2ccccc2C(=O)O)c2oc(N3CCC4(CC3)CN(C)C(=O)O4)cc(=O)c2c1]

Step 1: tert-butyl 4-(2-ethoxy-2-oxo-ethyl)-4-hydroxy-piperidine-1-carboxylate. A mixture of ethyl acetate (4.95 g, 56.2 mmol) in THF (60 mL) was added LiHMDS (55 mL, 1 M in THF) dropwise at −65° C. over 2 h, then stirred at −65° C. for 30 min. Then tert-butyl 4-(2-ethoxy-2-oxo-ethyl)-4-hydroxy-piperidine-1-carboxylate (10.0 g, 50.2 mmol) in THF (60 mL) was added dropwise at −65° C. and stirred for 1 h, then stirred at 0° C. for 14 h. The mixture was quenched with sat.NH$_4$Cl (100 mL) and extracted with EtOAc (150 mL×2). The combined extract was concentrated and purified by silica gel chromatography eluted with 10-25% EtOAc in petroleum ether to give the product as oil (8.8 g, 61%). $^1$H NMR (400 MHz, CDCl$_3$) δ ppm 1.30 (t, J=7.2 Hz, 3H), 1.47 (s, 9H), 1.43-1.55 (m, 2H), 1.63-1.75 (m, 2H), 2.48 (s, 2H), 3.10-3.30 (m, 2H), 3.62 (brs, 1H), 3.75-3.86 (m, 2H), 4.20 (q, J=7.2 Hz, 2H).

Step 2: 2-(1-tert-butoxycarbonyl-4-hydroxy-4-piperidyl)acetic acid. A mixture of tert-butyl 4-(2-ethoxy-2-oxo-ethyl)-4-hydroxy-piperidine-1-carboxylate (8.80 g, 30.6 mmol) and LiOH.H$_2$O (1.54 g, 36.7 mmol) in MeOH (100 mL) and H$_2$O (50 mL) was stirred at 25° C. for 16 h. The mixture was concentrated, diluted with water (50 mL) and adjusted to pH=7 with HCl (3 M). The mixture was washed with DCM (100 mL×2). The aqueous phase was lyophilized to give the product as a solid (7.94 g, contained LiCl). $^1$H NMR (400 MHz, DMSO-$d_6$) δ ppm 1.15-1.30 (m, 2H), 1.38 (s, 9H), 1.35-1.55 (m, 2H), 1.98 (s, 2H), 2.95-3.20 (m, 2H), 3.50-3.70 (m, 2H), 6.80-8.00 (brs, 1H).

Step 3: tert-butyl 2-oxo-1-oxa-3,8-diazaspiro[4.5]decane-8-carboxylate. A mixture of 2-(1-tert-butoxycarbonyl-4-hydroxy-4-piperidyl)acetic acid (7.94 g, crude) (200 mL), DPPA (9.27 g, 33.7 mmol) and TEA (3.41 g, 33.7 mmol) in toluene was stirred at 120° C. for 16 h. When cooled to rt the mixture was diluted with water (100 mL) and extracted with EtOAc (80 mL×2). The combined extract was washed with brine (100 mL×2), dried over anhydrous Na$_2$SO$_4$, filtered and concentrated. The residue was purified by silica gel chromatography eluted with 20-85% EtOAc in petroleum ether to give the product as an solid (3.8 g, yield for two steps: 48%). $^1$H NMR (400 MHz, CDCl$_3$) δ ppm 1.48 (s, 9H), 1.60-1.75 (m, 2H), 1.90-2.00 (m, 2H), 3.20-3.38 (m, 4H), 3.79-3.92 (m, 2H), 5.23 (brs, 1H).

Step 4: 3-methyl-1-oxa-3,8-diazaspiro[4.5]decan-2-one. A mixture of tert-butyl 2-oxo-1-oxa-3,8-diazaspiro[4.5]decane-8-carboxylate (3.80 g, 14.8 mmol) in DMF (40 mL) was added NaH (890 mg, 22.2 mmol, 60% dispersed in mineral oil) in portions at 0° C. and stirred for 0.5 h, then added CH$_3$I (3.16 g, 22.2 mmol) dropwise at 0° C. and stirred at 25° C. for 16 h. The mixture was quenched with sat.NH$_4$Cl (60 mL) and extracted with EtOAc (60 mL×3). The combined extract was washed with brine (80 mL×3), dried over anhydrous Na$_2$SO$_4$, filtered and concentrated to give tert-butyl 3-methyl-2-oxo-1-oxa-3,8-diazaspiro[4.5]decane-8-carboxylate (3.5 g, 87%) as a solid. $^1$H NMR (400 MHz, DMSO-$d_6$) δ ppm 1.41 (s, 9H), 1.65-1.78 (m, 4H), 2.75 (s, 2H), 3.15-3.30 (m, 2H), 3.34 (s, 3H), 3.50-3.59 (m, 2H). A mixture of tert-butyl 3-methyl-2-oxo-1-oxa-3,8-diazaspiro[4.5]decane-8-carboxylate (500 mg, 1.85 mmol) in FA (15 mL) was stirred at 100° C. for 1 h. The mixture was concentrated. Water (40 mL) was added and lyophilized to give the product as a solid (400 mg, FA salt). $^1$H NMR (400 MHz, DMSO-$d_6$) δ ppm 1.68-1.85 (m, 4H), 2.76 (s, 3H), 2.85-3.00 (m, 4H), 3.34 (s, 2H).

Step 5: 8-(8-bromo-6-methyl-4-oxo-chromen-2-yl)-3-methyl-1-oxa-3,8-diazaspiro[4.5]decan-2-one. A mixture of 8-bromo-2-ethylsulfonyl-6-methyl-chromen-4-one (350 mg, 1.06 mmol), 3-methyl-1-oxa-3,8-diazaspiro[4.5]decan-2-one (388 mg, 1.80 mmol, FA salt) and DIPEA (742 mg, 5.74 mmol) in DCM (14 mL) was stirred at 25° C. for 14 h. The mixture was quenched with HCl (1 M, 2 mL), extracted with DCM (40 mL×2). The combined extract was washed with brine (40 mL×2), dried over anhydrous Na$_2$SO$_4$, filtered and concentrated. The residue was purified by silica gel chromatography eluted with 0-10% MeOH in DCM to give the product as a solid (420 mg, 98%). $^1$H NMR (400 MHz, DMSO-$d_6$) δ 1.83-1.95 (4H, m), 2.38 (3H, s), 2.77 (3H, s), 3.37 (2H, s), 3.40-3.55 (2H, m), 3.80-3.91 (2H, m), 5.63 (1H, s), 7.70 (1H, d, J=2.0 Hz), 7.80 (1H, d, J=2.0 Hz). MS ES+ m/z 407 [M+H]$^+$.

Step 6: 8-(8-acetyl-6-methyl-4-oxo-chromen-2-yl)-3-methyl-1-oxa-3,8-diazaspiro[4.5]decan-2-one. A mixture of 8-(8-bromo-6-methyl-4-oxo-chromen-2-yl)-3-methyl-1-oxa-3,8-diazaspiro[4.5]decan-2-one (420 mg, 1.03 mmol), Pd(PPh$_3$)$_2$Cl$_2$ (72 mg, 0.103 mmol) and tributyl(1-ethoxyvinyl)stannane (447 mg, 1.24 mmol) in dioxane (10 mL) was stirred at 95° C. under N$_2$ for 16 h. HCl (1 mL, 2 M) was added and stirred at 50° C. for 0.5 h. When cooled to rt the mixture was added sat. KF (10 mL), stirred for 1 h, extracted with EtOAc (10 mL×3). The combined extract was washed with brine (10 mL), dried over anhydrous Na$_2$SO$_4$, filtered and concentrated. The residue was purified by silica gel chromatography eluted with 0-10% MeOH in DCM to give the product as a solid (350 mg, 92%). MS ES+ m/z 371 [M+H]$^+$.

Step 7: 8-[8-(1-hydroxyethyl)-6-methyl-4-oxo-chromen-2-yl]-3-methyl-1-oxa-3,8-diazaspiro[4.5]decan-2-one. A mixture of 8-(8-acetyl-6-methyl-4-oxo-chromen-2-yl)-3-methyl-1-oxa-3,8-diazaspiro[4.5]decan-2-one (100 mg, 0.270 mmol) in MeOH (5 mL) and DCM (5 mL) was added NaBH$_4$ (12 mg, 0.32 mmol) at −10° C., then stirred at 0° C. for 2 h. The mixture was quenched with water (15 mL), extracted with DCM (15 mL×2). The combined extract was washed with brine (20 mL×2), dried over anhydrous Na$_2$SO$_4$, filtered and concentrated to give the product as gum (100 mg, crude). MS ES+ m/z 373 [M+H]$^+$.

Step 8: 8-[8-(1-bromoethyl)-6-methyl-4-oxo-chromen-2-yl]-3-methyl-1-oxa-3,8-diazaspiro[4.5]decan-2-one. A mixture of 8-[8-(1-hydroxyethyl)-6-methyl-4-oxo-chromen-2-yl]-3-methyl-1-oxa-3,8-diazaspiro[4.5]decan-2-one (100 mg, 0.268 mmol) in DCM (5 mL) was added PBr$_3$ (109 mg, 0.403 mmol) dropwise at 0° C., then stirred at 25° C. for 2 h. The mixture was adjusted to pH=8 with sat.NaHCO$_3$, extracted with DCM (20 mL×2). The combined extract was concentrated and purified by silica gel chromatography eluted with 0-5% MeOH in DCM to give the product as a solid (75 mg, yield for two steps: 64%). MS ES+ m/z 435 [M+H]$^+$.

Step 9: 2-[1-[6-methyl-2-(3-methyl-2-oxo-1-oxa-3,8-diazaspiro[4.5]decan-8-yl)-4-oxo-chromen-8-yl]ethylamino]benzoic acid. A mixture of 8-[8-(1-bromoethyl)-6-methyl-4-oxo-chromen-2-yl]-3-methyl-1-oxa-3,8-diazaspiro[4.5]decan-2-one (75 mg, 0.17 mmol), methyl 2-aminobenzoate (52 mg, 0.34 mmol) and KI (31 mg, 0.19 mmol) in DCM (4 mL) and MeOH (1 mL) was stirred at 25° C. for 16 h. The mixture was quenched with water (15 mL), extracted with DCM (20 mL×2). The combined extract was concentrated and purified by silica gel chromatography eluted with 0-10% MeOH in DCM to give methyl 2-[1-[6-methyl-2-(3-methyl-2-oxo-1-oxa-3,8-diazaspiro[4.5]decan-8-yl)-4-oxo-chromen-8-yl]ethylamino]benzoate (50 mg, 34%). A mixture of methyl 2-[1-[6-methyl-2-(3-methyl-2-oxo-1-oxa-3,8-diazaspiro[4.5]decan-8-yl)-4-oxo-chromen-8-yl]ethylamino]benzoate (30 mg, crude) and LiOH.H$_2$O (5 mg, 0.1 mmol) in EtOH (1 mL) and water (1 mL) was stirred at 25° C. for 16 h. The mixture was concentrated and adjusted to pH=5 with HCl (1 M) and filtered. The filter cake was purified by preparative HPLC to give 2-[1-[6-methyl-2-(3-methyl-2-oxo-1-oxa-3,8-diazaspiro[4.5]decan-8-yl)-4-oxo-chromen-8-yl]ethylamino]benzoic acid as a solid (7.0 mg, 24%). $^1$H NMR (400 MHz, DMSO-d$_6$) δ 1.59 (d, J=6.8 Hz, 3H), 1.81-1.98 (m, 4H), 2.33 (s, 3H), 2.77 (s, 3H), 3.36 (s, 2H), 3.40-3.55 (m, 2H), 3.80-3.91 (m, 2H), 5.00-5.13 (m, 1H), 5.62 (s, 1H), 6.47 (d, J=8.8 Hz, 1H), 6.56 (t, J=8.0 Hz, 1H), 7.23 (t, J=7.2 Hz, 1H), 7.39 (d, J=2.0 Hz, 1H), 7.62 (d, J=2.0 Hz, 1H), 7.81 (dd, J=8.0, 1.6 Hz, 1H), 8.37 (brs, 1H), 12.78 (brs, 1H). MS ES+ m/z 492 [M+H]$^+$.

Example 381: 2-[1-[6-Methyl-2-(2-methyl-1-oxo-2,8-diazaspiro[4.5]decan-8-yl)-4-oxo-chromen-8-yl]ethylamino]benzoic acid

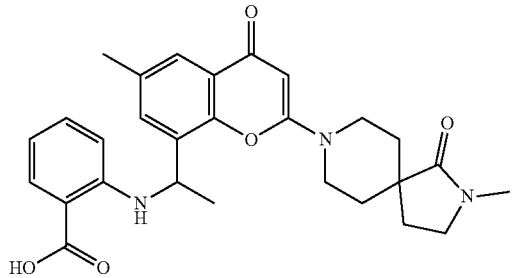 [SMILES: Cc1cc(C(C)Nc2ccccc2C(=O)O)c2oc(N3CCC4(CCN(C)C4=O)CC3)cc(=O)c2c1]

Step 1: 2-methyl-2,8-diazaspiro[4.5]decan-1-one. A mixture of tert-butyl 1-oxo-2,8-diazaspiro[4.5]decane-8-carboxylate (1.50 g, 5.90 mmol) in DMF (20 mL) was added NaH (354 mg, 8.85 mmol, 60% dispersed in mineral oil) in portions at 0° C. and stirred for 0.5 h, then added CH$_3$I (1.26 g, 8.85 mmol) dropwise at 0° C., then stirred at 25° C. for 16 h. The mixture was quenched with sat.NH$_4$Cl (40 mL) and extracted with DCM (40 mL×6). The combined extract was washed with brine (100 mL×3), dried over anhydrous Na$_2$SO$_4$, filtered and concentrated to give tert-butyl 2-methyl-1-oxo-2,8-diazaspiro[4.5]decane-8-carboxylate as oil (1.58 g, crude). $^1$H NMR (400 MHz, DMSO-d$_6$) δ ppm 1.20-1.40 (m, 2H), 1.40 (s, 9H), 1.45-1.60 (m, 2H), 1.80-1.95 (m, 2H), 2.72 (s, 3H), 2.75-2.90 (m, 2H), 3.25-3.33 (m, 2H), 3.74-3.90 (m, 2H). A mixture of tert-butyl 2-methyl-1-oxo-2,8-diazaspiro[4.5]decane-8-carboxylate (500 mg, crude) was added FA (3 mL) and stirred at 100° C. for 1 h. The mixture was concentrated and diluted with DCM/MeOH (10/1, 30 mL), then adjusted to pH=8 with NaHCO$_3$ solid. The mixture was filtered. The filtrate was concentrated to give the product as a pale yellow oil (520 mg, crude).

Step 2: 8-(8-bromo-6-methyl-4-oxo-chromen-2-yl)-2-methyl-2,8-diazaspiro[4.5]decan-1-one. A mixture of 8-bromo-2-ethylsulfonyl-6-methyl-chromen-4-one (200 mg, 0.604 mmol), 2-methyl-2,8-diazaspiro[4.5]decan-1-one (259 mg, crude), DIPEA (390 mg, 3.02 mmol) in DCM (12 mL) was stirred at 25° C. for 14 h. The mixture and another batch (100 mg) were diluted with water (25 mL), extracted with DCM (25 mL×2). The combined extract was concentrated and purified silica gel chromatography eluted with 0-10% MeOH in DCM to give the product as gum (300 mg, 82%). MS ES+ m/z 405 [M+H]$^+$.

Step 3: 8-(8-acetyl-6-methyl-4-oxo-chromen-2-yl)-2-methyl-2,8-diazaspiro[4.5]decan-1-one. A mixture of 8-(8-bromo-6-methyl-4-oxo-chromen-2-yl)-2-methyl-2,8-diazaspiro[4.5]decan-1-one (300 mg, crude), Pd(PPh$_3$)$_2$Cl$_2$ (52 mg, 0.074 mmol) and tributyl(1-ethoxyvinyl)stannane (321 mg, 0.889 mmol) in dioxane (10 mL) was stirred at 95° C. under N$_2$ atmosphere for 16 h. HCl (1 mL, 2 M) was added and stirred at 50° C. for 0.5 h. When cooled to rt the mixture was added sat. KF (10 mL), stirred for 1 h, extracted with EtOAc (10 mL×3), the combined extract was washed with brine (10 mL), dried over anhydrous Na$_2$SO$_4$, filtered and concentrated. The residue was purified by silica gel chromatography eluted with 0-10% MeOH in DCM to give the product as a solid (265 mg, 97%). MS ES+ m/z 369 [M+H]$^+$.

Step 4: 8-[8-(1-hydroxyethyl)-6-methyl-4-oxo-chromen-2-yl]-2-methyl-2,8-diazaspiro[4.5]decan-1-one. A mixture of 8-(8-acetyl-6-methyl-4-oxo-chromen-2-yl)-2-methyl-2,8- diazaspiro[4.5]decan-1-one (150 mg, 0.407 mmol) in DCM (5 mL) and MeOH (5 mL) was added NaBH₄ (18 mg, 0.49 mmol) in portions at −10° C., then stirred at 0° C. for 2 h. The mixture was quenched with water (15 mL), extracted with DCM (20 mL×2). The combined extract was washed with brine (20 mL×2), dried over anhydrous Na₂SO₄, filtered and concentrated. The residue was purified by silica gel chromatography eluted with 0-10% MeOH in DCM to give the product as a solid (110 mg, 73%). MS ES+ m/z 371 [M+H]⁺.

Step 5: 8-[8-(1-bromoethyl)-6-methyl-4-oxo-chromen-2-yl]-2-methyl-2,8-diazaspiro[4.5]decan-1-one. A mixture of 8-[8-(1-hydroxyethyl)-6-methyl-4-oxo-chromen-2-yl]-2-methyl-2,8-diazaspiro[4.5]decan-1-one (110 mg, 0.297 mmol) in DCM (8 mL) was added PBr₃ (127 mg, 0.468 mmol) at 0° C., then stirred at 25° C. for 16 h. The mixture was adjusted to pH=8 with sat.NaHCO₃, extracted with DCM (20 mL×2) The combined extract was washed with brine (20 mL×2), dried over anhydrous Na₂SO₄, filtered and concentrated. The residue was purified by silica gel chromatography eluted with 0-7% MeOH in DCM to give the product as gum (100 mg, 78%). MS ES+ m/z 433 [M+H]⁺.

Step 6: 2-[1-[6-methyl-2-(2-methyl-1-oxo-2,8-diazaspiro[4.5]decan-8-yl)-4-oxo-chromen-8-yl]ethylamino]benzoic acid. A mixture of 8-[8-(1-bromoethyl)-6-methyl-4-oxo-chromen-2-yl]-2-methyl-2,8-diazaspiro[4.5]decan-1-one (100 mg, 0.231 mmol), methyl 2-aminobenzoate (70 mg, 0.46 mmol) and KI (57 mg, 0.35 mmol) in DCM (4 mL) and MeOH (0.5 mL) was stirred at 25° C. for 4 h. The mixture was diluted with water (15 mL) and extracted with DCM (20 mL×2). The combined extract was washed with brine (20 mL×2), dried over anhydrous Na₂SO₄, filtered and concentrated. The residue was purified by silica gel chromatography eluted with 0-10% MeOH in DCM to give methyl 2-[1-[6-methyl-2-(2-methyl-1-oxo-2,8-diazaspiro[4.5]decan-8-yl)-4-oxo-chromen-8-yl]ethylamino]benzoate as yellow gum (30 mg, 17%). A mixture of methyl 2-[1-[6-methyl-2-(2-methyl-1-oxo-2,8-diazaspiro[4.5]decan-8-yl)-4-oxo-chromen-8-yl]ethylamino]benzoate (30 mg, crude) and LiOH.H₂O (8 mg, 0.2 mmol) in THF (0.5 mL), EtOH (0.5 mL) and water (0.5 mL) was stirred at 25° C. for 16 h. The mixture was diluted with water (10 mL) and washed with EtOAc (15 mL×2). The aqueous phase was lyophilized and purified by preparative HPLC to give 2-[1-[6-methyl-2-(2-methyl-1-oxo-2,8-diazaspiro[4.5]decan-8-yl)-4-oxo-chromen-8-yl]ethylamino]benzoic acid as a solid (2.1 mg, yield: 7%). ¹H NMR (400 MHz, DMSO-d₆) δ 1.40-1.52 (m, 2H), 1.58 (d, J=6.8 Hz, 3H), 1.70-1.82 (m, 2H), 1.99 (t, J=6.8 Hz, 2H), 2.31 (s, 3H), 2.74 (s, 3H), 3.20-3.40 (m, 4H), 3.90-4.11 (m, 2H), 5.00-5.11 (m, 1H), 5.58 (s, 1H), 6.46 (d, J=8.4 Hz, 1H), 6.55 (t, J=7.6 Hz, 1H), 7.24 (t, J=7.2 Hz, 1H), 7.37 (d, J=2.0 Hz, 1H), 7.61 (d, J=2.0 Hz, 1H), 7.82 (d, J=7.6 Hz, 1H), 8.40 (brs, 1H), 12.50 (brs, 1H). MS ES+ m/z 490 [M+H]⁺.

Example 382: N-[2-(2-Methoxyethoxy)ethyl]-2-[[(1R)-1-[6-methyl-4-oxo-2-(1-piperidyl)chromen-8-yl]ethyl]amino]benzamide

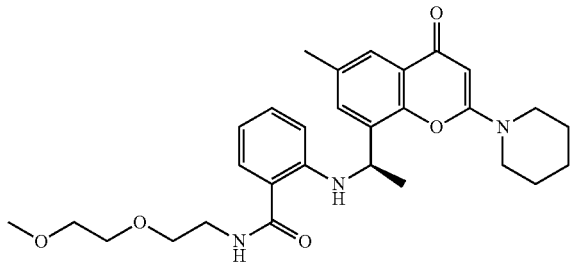 [SMILES: COCCOCCNC(=O)c1ccccc1N[C@H](C)c1cc(C)cc2c(=O)cc(N3CCCCC3)oc12]

A mixture of 2-[[(1R)-1-[6-methyl-4-oxo-2-(1-piperidyl)chromen-8-yl]ethyl]amino]benzoic acid (30 mg, 0.074 mmol), 2-(2-methoxyethoxy)ethanamine (13 mg, 0.11 mmol) and EDCI (28 mg, 0.15 mmol) in pyridine (1 mL) was stirred at 25° C. for 4 h. The reaction mixture was concentrated to remove most of pyridine and purified by preparative HPLC to give N-[2-(2-methoxyethoxy)ethyl]-2-[[(1R)-1-[6-methyl-4-oxo-2-(1-piperidyl)chromen-8-yl]ethyl]amino]benzamide as a solid (3.6 mg, 9.4%). ¹H NMR (400 MHz, DMSO-d₆) δ ppm 1.53 (d, J=6.8 Hz, 3H), 1.61 (s, 6H), 2.28 (s, 3H), 3.23 (s, 3H), 2.43-3.46 (m, 4H), 3.52-3.55 (m, 8H), 4.99 (t, J=6.4 Hz, 1H), 5.50 (s, 1H), 6.39 (d, J=8.4 Hz, 1H), 6.54 (t, J=7.6 Hz, 1H), 7.14 (t, J=7.2 Hz, 1H), 7.35 (d, J=1.6 Hz, 1H), 7.55-7.57 (m, 2H), 8.42 (d, J=6.4 Hz, 2H). MS ES+m/z 508 [M+H]⁺.

Example 383: 2-[[(1R)-1-[2-(4-Chloro-1-piperidyl)-6-methyl-4-oxo-chromen-8-yl]ethyl]amino]benzoic acid

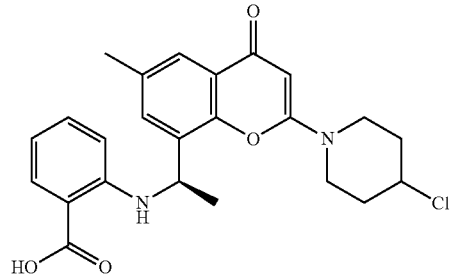 [SMILES: Cc1cc([C@@H](C)Nc2ccccc2C(=O)O)c2oc(N3CCC(Cl)CC3)cc(=O)c2c1]

Step 1: -(3-bromo-2-hydroxy-5-methylphenyl)-3-(4-chloropiperidin-1-yl)propane-1,3-dione. A mixture of 4-chloropiperidine (1 g, 6 mmol, HCl), TEA (972 mg, 9.61 mmol) in DCM (10 mL) was added dropwise to a solution of triphosgene (950 mg, 3.20 mmol) in DCM (10 mL) at −10° C., and stirred at −10° C. for 1 h, then stirred at 0° C. for another 3 h. The mixture was concentrated, added EtOAc (20 mL) and stirred for 30 min, then filtered. The filter cake was washed with EtOAc (10 mL×2). The filtrate was concentrated and purified by silica gel chromatography eluted with 0%-25% EtOAc in petroleum ether to give 1-(3-bromo-2-hydroxy-5-methylphenyl)-3-(4-chloropiperidin-1-yl)propane-1,3-dione (1.07 g, 81%) as a solid. A mixture of 1-(3-bromo-2-hydroxy-5-methylphenyl)ethanone (1.12 g, 4.90 mmol) in THF (10 mL) was added LiHMDS (1 M, 17.14 mL) dropwise at −65° C., stirred at 0° C. for 2 h. The mixture was added a mixture of 4-chloropiperidine-1-carbonyl chloride (1.07 g, 5.88 mmol) in THF(5 mL) dropwise. The mixture was stirred at 25° C. for another 14 h, quenched with sat.NH$_4$Cl (40 mL) dropwise, then adjusted to pH=7 with HCl (2 M), extracted with EtOAc (20 mL×2). The combined extract was washed with brine (30 mL×2), dried over anhydrous Na$_2$SO$_4$, filtered and concentrated. The residue was purified by silica gel chromatography eluted with 16%-75% EtOAc in petroleum ether to give the product (1.44 g, 75%) as oil. MS ES+ m/z 374 [M+H]$^+$.

Step 2: 8-bromo-2-(4-chloro-1-piperidyl)-6-methyl-chromen-4-one. A mixture of 1-(3-bromo-2-hydroxy-5-methylphenyl)-3-(4-chloropiperidin-1-yl)propane-1,3-dione (800 mg, 2.41 mmol) and Tf$_2$O (2.41 g, 8.54 mmol) in DCE (20 mL) was stirred at 50° C. for 4 h. When cooled to rt the mixture was concentrated, diluted with DCM (20 mL), adjusted to pH=7 with sat.NaHCO$_3$, and extracted with DCM (30 mL×2). The combined extract was washed with brine (30 mL×2), dried over anhydrous Na$_2$SO$_4$, filtered and concentrated. The residue was purified by silica gel chromatography eluted with 0%-33% EtOAc in petroleum ether to give the product (435 mg, 57%) as a solid. MS ES+ m/z 358 [M+2+H]$^+$.

Step 3: 8-acetyl-2-(4-chloro-1-piperidyl)-6-methyl-chromen-4-one. A mixture of 8-bromo-2-(4-chloro-1-piperidyl)-6-methyl-chromen-4-one (380 mg, 1.07 mmol), tributyl (1-ethoxyvinyl) stannane (770 mg, 2.13 mmol) and Pd(PPh$_3$)$_2$Cl$_2$ (74.8 mg, 0.107 mmol) in dioxane (10 mL) was stirred at 95° C. under N$_2$ for 16 h. HCl (0.5 mL, 2 M) was added to the mixture and stirred at 50° C. for 0.5 h. When cooled to rt the mixture was added sat. KF (30 mL), stirred for 1 h, extracted with EtOAc (30 mL×3). The combined extract was washed with brine (20 mL), dried over anhydrous Na$_2$SO$_4$, filtered and concentrated. The residue was purified by silica gel chromatography eluted with 66%-100% EtOAc in petroleum ether to give the product (300 mg, 85%) as a solid. MS ES+ m/z 320 [M+H]$^+$.

Step 4: (R,E)-N-(1-(2-(4-chloropiperidin-1-yl)-6-methyl-4-oxo-4H-chromen-8-yl)ethylidene)-2-methylpropane-2-sulfinamide. A mixture of 8-acetyl-2-(4-chloro-1-piperidyl)-6-methyl-chromen-4-one (305 mg, 887 μmol), 2-methylpropane-2-sulfinamide (537 mg, 4.44 mmol) and tetraisopropoxytitanium (2.02 g, 7.10 mmol) in THF (8 mL) was stirred at 80° C. for 32 h. When cooled to rt the mixture was quenched with brine (20 mL) and stirred for 0.5 h, then filtered. The filter cake was washed with EtOAc (20 mL×3). The aqueous phase was extracted with EtOAc (30 mL×2). The combined extract was washed with brine (40 mL×2), dried over anhydrous Na$_2$SO$_4$, filtered and concentrated to give the product as a gum (375 mg, 100%). MS ES+ m/z 423 [M+H]$^+$.

Step 5: N-[(1R)-1-[2-(4-chloro-1-piperidyl)-6-methyl-4-oxo-chromen-8-yl]ethyl]-2-methyl-propane-2-sulfinamide. A mixture of (R,E)-N-(1-(2-(4-chloropiperidin-1-yl)-6-methyl-4-oxo-4H-chromen-8-yl)ethylidene)-2-methylpropane-2-sulfinamide (375 mg, 0.887 mmol) in MeOH (8 mL) and DCM (8 mL) was added NaBH$_3$CN (445 mg, 7.09 mmol) and AcOH (213 mg, 3.55 mmol) at 0° C., then stirred at 25° C. for 14 h. The mixture was adjusted to pH=8 with sat.NaHCO$_3$, then extracted with DCM (25 mL×2). The combined extract was washed with brine (30 mL×2), dried over anhydrous Na$_2$SO$_4$, filtered and concentrated. The residue was purified by preparative HPLC to give the product as oil (250 mg, 64%). MS ES+ m/z 425 [M+H]$^+$.

Step 6: 8-[(1S)-1-aminoethyl]-2-(4-chloro-1-piperidyl)-6-methyl-chromen-4-one. A mixture of N-[(1R)-1-[2-(4-chloro-1-piperidyl)-6-methyl-4-oxo-chromen-8-yl]ethyl]-2-methyl-propane-2-sulfinamide (250 mg, 588 μmol) and HCl/dioxane (0.50 mL, 4M) in dioxane (2 mL) was stirred at 25° C. for 1 h. The mixture was concentrated, diluted with DCM/MeOH (1/1, 15 mL), added excess NaHCO$_3$ solid and stirred for 1 h to give an off-white suspension. The mixture was filtered, the filter cake was washed with DCM (10 mL×2). The filtrate was concentrated and purified by silica gel chromatography eluted with 1%-10% MeOH in DCM to give the product (150 mg, 72%) as oil. MS ES+ m/z 321 [M+H]$^+$.

Step 7: 2-[[(1R)-1-[2-(4-chloro-1-piperidyl)-6-methyl-4-oxo-chromen-8-yl]ethyl]amino]benzoic acid. A mixture of 8-[(1R)-1-aminoethyl]-2-(4-chloro-1-piperidyl)-6-methyl-chromen-4-one (125 mg, 0.389 mmol), 2-iodobenzoic acid (289 mg, 1.17 mmol) and 2-(methylamino) acetic acid (6.94 mg, 0.0779 mmol), K$_2$CO$_3$ (134 mg, 0.974 mmol) and CuI (14.8 mg, 0.0779 mmol) in DMSO (1 mL) was stirred at 95° C. under N$_2$ for 16 h. When cooled to rt the mixture was filtered, the filter cake was washed with DCM (10 mL×2). The filtrate was diluted with water (20 mL) and extracted with DCM (30 mL×2). The combined extract was washed with brine (30 mL×2), dried over anhydrous Na$_2$SO$_4$, filtered and concentrated. The residue was purified by preparative HPLC to give 2-[[(1R)-1-[2-(4-chloro-1-piperidyl)-6-methyl-4-oxo-chromen-8-yl]ethyl]amino]benzoic acid as a solid (18 mg, 10%). $^1$H NMR (400 MHz, DMSO-d$_6$) δ ppm 1.59 (d, J=6.4 Hz, 3H), 1.79-1.88 (m, 2H), 2.08-2.20 (m, 2H), 2.31-2.34 (m, 3H), 3.45-3.53 (m, 2H), 3.80 (s, 2H), 4.48-4.53 (m, 1H), 5.06-5.12 (m, 1H), 5.61 (s, 1H), 6.48 (d, J=8.8 Hz, 1H), 6.57 (t, J=7.6 Hz, 1H), 7.26 (t, J=7.2 Hz, 1H), 7.39 (d, J=2.0 Hz, 1H), 7.62 (d, J=1.2 Hz, 1H), 7.82 (dd, J=7.6, 1.2 Hz, 1H), 8.34 (d, J=5.2 Hz, 1H), 12.78 (s, 1H). MS ES+m/z 441 [M+H]$^+$.

Example 384: 2-[[(1R)-1-(6-Methyl-4-oxo-2-thio-morpholino-chromen-8-yl)ethyl]amino]benzoic acid

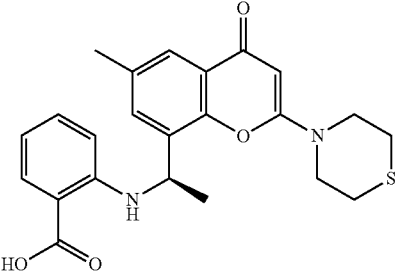 [SMILES: Cc1cc([C@@H](C)Nc2ccccc2C(=O)O)c2oc(N3CCSCC3)cc(=O)c2c1]

A mixture of 8-[(1R)-1-aminoethyl]-6-methyl-2-thiomorpholino-chromen-4-one (100 mg, 0.329 mmol), 2-iodobenzoic acid (163 mg, 0.657 mmol), CuI (6 mg, 0.03 mmol), K$_2$CO$_3$ (91 mg, 0.66 mmol) and 2-(methylamino) acetic acid (6 mg, 0.07 mmol) in DMSO (1.5 mL) was stirred at 45° C. under O2 atmosphere for 168 h. When cooled to rt the mixture was diluted with water (15 mL) and adjusted to pH=5 with HCl (2M). The mixture was extracted with DCM (20 mL×3), the combined extract was concentrated and purified by preparative HPLC, SFC to give 2-[[(1R)-1-(6-methyl-4-oxo-2-thiomorpholino-chromen-8-yl)ethyl] amino]benzoic acid as a solid (7.32 mg, 8%, ee>99%). $^1$H NMR (400 MHz, DMSO-d$_6$) δ 1.57 (d, J=6.8 Hz, 3H), 2.30 (s, 3H), 2.59-2.70 (m, 4H), 3.81-3.92 (m, 4H), 4.95-5.12 (m, 1H), 5.58 (s, 1H), 6.45 (d, J=8.4 Hz, 1H), 6.54 (t, J=7.6 Hz, 1H), 7.23 (td, J=8.8, 1.6 Hz, 1H), 7.37 (d, J=2.0 Hz, 1H), 7.61 (d, J=1.6 Hz, 1H), 7.81 (dd, J=8.4, 1.2 Hz, 1H), 8.35-8.55 (m, 1H). MS ES+ m/z 425 [M+H]⁺.

Example 385: 2-[[(1R)-1-[2-[(2S,6R)-2,6-Dimethylmorpholin-4-yl]-6-methyl-4-oxo-chromen-8-yl]ethyl]amino]benzoic acid

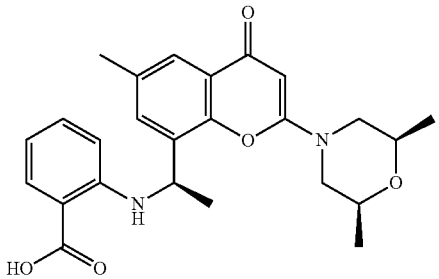 [SMILES: Cc1cc([C@@H](C)Nc2ccccc2C(=O)O)c2oc(N3C[C@@H](C)O[C@@H](C)C3)cc(=O)c2c1]

A mixture of 8-[(1R)-1-aminoethyl]-2-[(2S,6R)-2,6-dimethylmorpholin-4-yl]-6-methyl-chromen-4-one (200 mg, 0.632 mmol), 2-iodobenzoic acid (282 mg, 1.14 mmol), CuI (12 mg, 0.06 mmol), K₂CO₃ (175 mg, 1.26 mmol) and 2-(methylamino) acetic acid (11 mg, 0.13 mmol) in DMSO (1.5 mL) was stirred at 45° C. under N₂ for 136 h. The mixture and another batch (200 mg) were diluted with water (30 mL), adjusted to pH=9 with NaOH (1 M). The mixture was washed with DCM (20 mL). The aqueous phase was adjusted to pH=5 with HCl (2 M) and extracted with DCM (20 mL×3), the combined extract was concentrated and purified by preparative HPLC, SFC to give 2-[[(1R)-1-[2-[(2S,6R)-2,6-dimethylmorpholin-4-yl]-6-methyl-4-oxo-chromen-8-yl]ethyl]amino]benzoic acid as a solid (43.81 mg, ee>99%). ¹H NMR (400 MHz, DMSO-d₆) δ 1.00-1.20 (m, 6H), 1.58 (d, J=6.4 Hz, 3H), 2.31 (s, 3H), 2.52-2.71 (m, 2H), 3.55-3.70 (m, 2H), 3.89-4.01 (m, 2H), 5.05-5.15 (m, 1H), 5.58 (s, 1H), 6.48 (d, J=8.4 Hz, 1H), 6.56 (td, J=8.0, 0.8 Hz, 1H), 7.26 (td, J=8.8, 1.2 Hz, 1H), 7.39 (d, J=2.0 Hz, 1H), 7.62 (d, J=1.6 Hz, 1H), 7.82 (dd, J=8.0, 1.6 Hz, 1H), 8.34 (d, J=6.4 Hz, 1H), 12.76 (brs, 1H). MS ES+ m/z 437 [M+H]⁺.

Example 386: 8-[(1R)-1-Anilinoethyl]-2-(4,4-dimethyl-1-piperidyl)-6-methyl-chromen-4-one

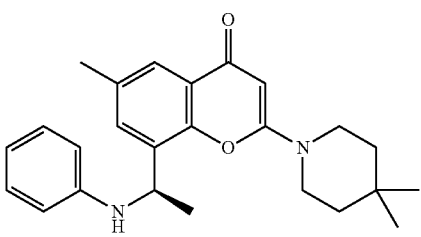 [SMILES: Cc1cc([C@@H](C)Nc2ccccc2)c2oc(N3CCC(C)(C)CC3)cc(=O)c2c1]

Step 1: -(3-bromo-2-hydroxy-5-methyl-phenyl)-3-(4,4-dimethyl-1-piperidyl)propane-1,3-dione. A solution of triphosgene (2.08 g, 7.02 mmol) in DCM (30 mL) was added dropwise a solution of TEA (3.55 g, 35.1 mmol) and 4,4-dimethylpiperidine (2.10 g, 14.0 mmol, HCl salt) in DCM (10 mL) at −10° C. and stirred for 1 h, then stirred at 0° C. for another 3 h. The mixture was concentrated, added EtOAc (50 mL) and filtered. The filter cake was washed with EtOAc (10 mL×3). The filtrate was concentrated and purified by silica gel chromatography eluted with 0-5% EtOAc in petroleum ether to give 4,4-dimethylpiperidine-1-carbonyl chloride as oil (1.20 g, 49%). A mixture of 1-(3-bromo-2-hydroxy-5-methyl-phenyl)ethanone (2.00 g, 8.73 mmol) in THF (25 mL) was added LiHMDS (29.7 mL, 1 M in THF) dropwise at −65° C., and stirred at 0° C. for 2 h. Then cooled to −65° C. and added a solution of 4,4-dimethylpiperidine-1-carbonyl chloride (2.20 g, 12.5 mmol) in THF (5 mL) dropwise, and stirred at 25° C. for another 14 h. The mixture was quenched with water (15 mL), adjusted to pH=7 with HCl (2 M), extracted with EtOAc (30 mL×2). The combined extract was washed with brine (30 mL×2), dried over anhydrous Na₂SO₄, filtered and concentrated. The residue was purified by silica gel chromatography eluted with 10%-50% EtOAc in petroleum ether to the product as a brown solid (2.60 g, 81%). MS ES+ m/z 368 [M+H]⁺

Step 2: 8-bromo-2-(4,4-dimethyl-1-piperidyl)-6-methyl-chromen-4-one. A mixture of 1-(3-bromo-2-hydroxy-5-methyl-phenyl)-3-(4,4-dimethyl-1-piperidyl)propane-1,3-dione (2.60 g, 7.06 mmol) and Tf₂O (7.97 g, 28.2 mmol) in DCE (30 mL) was stirred at 50° C. for 4 h. When cooled to rt the mixture was quenched with MeOH (20 mL), adjusted to pH=7 with sat.NaHCO₃, extracted with EtOAc (30 mL×2). The combined extract was washed with brine (30 mL×2), dried over anhydrous Na₂SO₄, filtered and concentrated. The residue was purified by silica gel chromatography eluted with 0-70% EtOAc in petroleum ether to give the product as a solid (1.83 g, 74%). ¹H NMR (400 MHz, CDCl₃) δ 1.04 (s, 6H), 1.49-1.54 (m, 4H), 2.40 (s, 3H), 3.56-3.60 (m, 4H), 5.52 (s, 1H), 7.56 (d, J=2.0 Hz, 1H), 7.88 (d, J=1.2 Hz, 1H)

Step 3: 8-acetyl-2-(4,4-dimethyl-1-piperidyl)-6-methyl-chromen-4-one. A mixture of 8-bromo-2-(4,4-dimethyl-1-piperidyl)-6-methyl-chromen-4-one (800 mg, 2.28 mmol), tributyl(1-ethoxyvinyl)stannane (990 mg, 2.74 mmol) and Pd(dppf)Cl₂ (167 mg, 0.228 mmol) in dioxane (8 mL) was stirred at 95° C. under N₂ for 14 h. HCl (1 mL) was added into the mixture and stirred at 50° C. for 0.5 h. When cooled to rt the mixture was added sat. KF (100 mL), stirred for 1 h, extracted with EtOAc (100 mL×3). The combined extract was washed with brine (100 mL), dried over anhydrous Na₂SO₄, filtered and concentrated. The residue was purified by silica gel chromatography eluted with 0-10% MeOH in DCM to give the product as a solid (450 mg, 63%). ¹H NMR (400 MHz, CDCl₃) 1.04 (s, 6H), 1.49-1.53 (m, 4H), 2.46 (s, 3H), 2.68 (s, 3H), 3.56-3.60 (m, 4H), 5.55 (s, 1H), 7.74 (d, J=2.0 Hz, 1H), 8.16 (d, J=1.6 Hz, 1H). MS ES+m/z 314 [M+H]⁺.

Step 4: (NE)-N-[1-[2-(4,4-dimethyl-1-piperidyl)-6-methyl-4-oxo-chromen-8-yl]ethylidene]-2-methyl-propane-2-sulfinamide. A mixture of 8-acetyl-2-(4,4-dimethyl-1-piperidyl)-6-methyl-chromen-4-one (450 mg, 1.44 mmol), (R)-2-tert-butyl-2-sulfinamide (348 mg, 2.87 mmol), titanium(IV) isopropoxide (2.04 g, 7.18 mmol) in THF (20 mL) was stirred at 70° C. for 32 h. When cooled to rt the mixture was quenched with brine (20 mL) and filtered. The filter cake was washed with EtOAc (20 mL×3). The aqueous phase was extracted with EtOAc (30 mL×2), the combined extract was washed with brine (40 mL×2), dried over anhydrous Na₂SO₄, filtered and concentrated to give the product as a gum (590 mg, crude).

Step 5: N-[(1R)-1-[2-(4,4-dimethyl-1-piperidyl)-6-methyl-4-oxo-chromen-8-yl]ethyl]-2-methyl-propane-2-sulfinamide. NaBH₃CN (267 mg, 4.25 mmol) and AcOH (680 mg, 11.3 mmol) was added into a solution of (NE)-N-[1-[2-(4,4-dimethyl-1-piperidyl)-6-methyl-4-oxo-chromen-8-yl]ethylidene]-2-methyl-propane-2-sulfinamide (590 mg, crude) in DCM (10 mL) and MeOH (10 mL) at 0° C., then stirred at 25° C. for 16 h. The mixture was adjusted to pH=8 with sat.NaHCO₃, extracted with DCM (25 mL×2). The combined extract was washed with brine (30 mL×2), dried over anhydrous Na₂SO₄, filtered and concentrated to give the product as gum (590 mg, crude).

Step 6: 8-[(1R)-1-aminoethyl]-2-(4,4-dimethyl-1-piperidyl)-6-methyl-chromen-4-one. A mixture of N-[(1R)-1-[2-(4,4-dimethyl-1-piperidyl)-6-methyl-4-oxo-chromen-8-yl]ethyl]-2-methyl-propane-2-sulfinamide (590 mg, 1.41 mmol) in EtOAc (10 mL) was added HCl/EtOAc (1 mL, 4 M) and stirred at 25° C. for 16 h. The mixture was concentrated, then diluted with DCM/MeOH (1/1, 15 mL), added excess NaHCO₃ solid and filtered. The filter cake was washed with DCM (10 mL×2). The filtrate was concentrated and purified by silica gel chromatography eluted with 0-10% MeOH in EtOAc (5% TEA) to give the product as a solid (400 mg, yield for three steps: 86%). MS ES+ m/z 315 [M+H]⁺.

Step 7: 8-[(1R)-1-anilinoethyl]-2-(4,4-dimethyl-1-piperidyl)-6-methyl-chromen-4-one. A mixture of 8-[(1R)-1-aminoethyl]-2-(4,4-dimethyl-1-piperidyl)-6-methyl-chromen-4-one (400 mg, 1.27 mmol), phenylboronic acid (388 mg, 3.18 mmol), Cu(OAc)₂ (254 mg, 1.40 mmol), 4A MS (100 mg) and pyridine (253 mg, 3.20 mmol) in DCE (20 mL) was stirred at 35° C. under O2 atmosphere (15 psi) for 16 h. The mixture was filtered, the filter cake was washed with DCM (10 mL×2). The filtrate was washed with brine (30 mL×2), dried over anhydrous Na₂SO₄, filtered and concentrated. The residue was purified by silica gel chromatography eluted with 30%-100% EtOAc in petroleum ether, then 0-10% MeOH in DCM to give a crude product. The crude product was triturated with CH₃CN (10 mL) to give the product (230 mg, 44%, ee: 79.2%). Then further purified by SFC to give 8-[(1R)-1-anilinoethyl]-2-(4,4-dimethyl-1-piperidyl)-6-methyl-chromen-4-one as a solid (134.88 mg, ee>99%). ¹H NMR (400 MHz, DMSO-d6) δ 0.99 (s, 6H), 1.39-1.45 (m, 4H), 1.49 (d, J=6.8 Hz, 3H), 2.29 (s, 3H), 3.51-3.60 (m, 4H), 4.85-4.95 (m, 1H), 5.52 (s, 1H), 6.26 (brs, 1H), 6.45-6.52 (m, 3H), 6.96-7.04 (m, 2H), 7.42 (d, J=2.0 Hz, 1H), 7.56 (d, J=1.2 Hz, 1H). MS ES+ m/z 391 [M+H]⁺.

Example 387: (8-[(1R)-1-Anilinoethyl]-2-[(2S,6R)-2,6-dimethylmorpholin-4-yl]-6-methyl-chromen-4-one

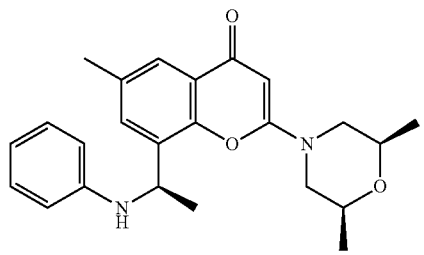 [SMILES: Cc1cc([C@@H](C)Nc2ccccc2)c2oc(N3C[C@@H](C)O[C@@H](C)C3)cc(=O)c2c1]

Step 1: -(3-bromo-2-hydroxy-5-methyl-phenyl)-3-[(2S,6R)-2,6-dimethylmorpholin-4-yl]propane-1,3-dione. A solution of (2S,6R)-2,6-dimethylmorpholine (1.80 g, 15.6 mmol), TEA (2.37 g, 23.4 mmol) in DCM (10 mL) was added dropwise into a solution of triphosgene (2.32 g, 7.81 mmol) in DCM (15 mL) at −10° C., and stirred at −10° C. for 1 h, then stirred at 0° C. for another 3 h. The mixture was concentrated, added EtOAc (20 mL) and filtered. The filter cake was washed with EtOAc (10 mL×2). The filtrate was concentrated and purified by silica gel chromatography eluted with 0-5% EtOAc in petroleum ether to give (2S,6R)-2,6-dimethylmorpholine-4-carbonyl chloride as oil (1.80 g, 65%). A mixture of 1-(3-bromo-2-hydroxy-5-methyl-phenyl)ethanone (1.90 g, 8.29 mmol) in THF (25 mL) was added LiHMDS (29 mL, 1M in THF) dropwise at −65° C., then warmed to 0° C. and stirred for 1 h. Then cooled to −65° C. and added a solution of (2S,6R)-2,6-dimethylmorpholine-4-carbonyl chloride (1.77 g, 9.95 mmol) in THF (5 mL) dropwise, then slowly warmed to rt and stirred for another 5 h. The mixture was quenched with sat.NH₄Cl (30 mL), adjusted to pH=7 with HCl (2 M), extracted with EtOAc (40 mL×2). The combined extract washed with brine (50 mL×2), dried over anhydrous Na₂SO₄ and concentrated. The residue was triturated with PE/EtOAc (8/1, 50 mL) to give the product as a solid (2.1 g). The filtrate was further purified by silica gel chromatography eluted with 25%-70% EtOAc in petroleum ether to give the product (430 mg). Totally (2.53 g, 82%). ¹H NMR (400 MHz, DMSO-d6) δ 1.06-1.12 (m, 6H), 2.25-2.36 (m, 4H), 2.65-2.76 (m, 1H), 2.40-2.49 (m, 1H), 3.50-3.61 (m, 1H), 3.72-3.77 (m, 1H), 4.19-4.26 (m, 1H), 4.34 (s, 2H), 7.73-7.78 (m, 2H), 12.22 (brs, 1H).

Step 2: 8-bromo-2-[(2S,6R)-2,6-dimethylmorpholin-4-yl]-6-methyl-chromen-4-one. A mixture of 1-(3-bromo-2-hydroxy-5-methyl-phenyl)-3-[(2S,6R)-2,6-dimethylmorpholin-4-yl]propane-1,3-dione (2.53 g, 6.83 mmol) and Tf₂O (7.71 g, 27.3 mmol) in DCE (30 mL) was stirred at 50° C. for 14 h. When cooled to rt the mixture was concentrated and quenched with MeOH (20 mL), adjusted to pH=7 with sat.NaHCO₃. The mixture was extracted with DCM (40 mL×2), washed with brine (40 mL×2), dried over anhydrous Na₂SO₄, filtered and concentrated. The residue was triturated with PE/EtOAc (50 mL, 5/1) to give the product as a solid (1.70 g, 71%).

Step 3: 8-acetyl-2-[(2S,6R)-2,6-dimethylmorpholin-4-yl]-6-methyl-chromen-4-one. A mixture of 8-bromo-2-[(2S,6R)-2,6-dimethylmorpholin-4-yl]-6-methyl-chromen-4-one (1.00 g, 2.84 mmol), tributyl(1-ethoxyvinyl)stannane (1.29 g, 3.58 mmol) and Pd(PPh₃)₂Cl₂ (199 mg, 0.284 mmol) in dioxane (20 mL) was stirred at 95° C. under N₂ for 16 h. HCl (1 mL, 2 M) was added into the mixture and stirred at 50° C. for 0.5 h. When cooled to rt the mixture was diluted with sat. KF (20 mL), stirred for 1 h and extracted with EtOAc (40 mL×2). The combined extract washed with brine (40 mL×2), dried over anhydrous Na₂SO₄, filtered and concentrated. The residue was triturated with PE/EtOAc (8/1, 40 mL) to give the product as a solid (850 mg, 95%). MS ES+m/z 316 [M+H]+

Step 4: (NE)-N—[i-[2-[(2S,6R)-2,6-dimethylmorpholin-4-yl]-6-methyl-4-oxo-chromen-8-yl]ethylidene]-2-methyl-propane-2-sulfinamide. A mixture of 8-acetyl-2-[(2S,6R)-2,6-dimethylmorpholin-4-yl]-6-methyl-chromen-4-one (500 mg, 1.59 mmol), (R)-2-tert-butyl-2-sulfinamide (384 mg, 3.17 mmol), Ti(i-PrO)₄ (1.80 g, 6.34 mmol) in THF (20 mL) was stirred at 70° C. under N₂ for 32 h. When cooled to rt the mixture was quenched with brine (30 mL) and filtered. The filter cake was washed with EtOAc (20 mL×3). The aqueous phase was extracted with EtOAc (30 mL×2), the combined extract was washed with brine (30 mL×2), dried over anhydrous Na₂SO₄, filtered and concentrated to give the product as gum (660 mg, crude).

Step 5: N-[(1R)-1-[2-[(2S,6R)-2,6-dimethylmorpholin-4-yl]-6-methyl-4-oxo-chromen-8-yl]ethyl]-2-methyl-propane-2-sulfinamide. A mixture of (NE)-N-[1-[2-[(2S,6R)-2,6-dimethylmorpholin-4-yl]-6-methyl-4-oxo-chromen-8-yl]ethylidene]-2-methyl-propane-2-sulfinamide (660 mg, crude) in DCM (10 mL) and MeOH (10 mL) was added AcOH (840 mg, 14.0 mmol) and NaBH₃CN (297 mg, 4.73 mmol) at 0° C., then stirred at 20° C. for 16 h. The mixture was adjusted to pH=8 with sat.NaHCO₃, then extracted with DCM (30 mL×2), washed with brine (40 mL×2), dried over anhydrous Na₂SO₄, filtered, concentrated to give the product as gum (660 mg, crude).

Step 6: 8-[(1R)-1-aminoethyl]-2-[(2S,6R)-2,6-dimethyl-morpholin-4-yl]-6-methyl-chromen-4-one. A mixture of N-[(1R)-1-[2-[(2S,6R)-2,6-dimethylmorpholin-4-yl]-6-methyl-4-oxo-chromen-8-yl]ethyl]-2-methyl-propane-2-sulfinamide (500 mg, crude) in dioxane (10 mL) was added HCl/dioxane (2 mL, 4 M) and stirred at 20° C. for 1 h. The mixture was concentrated, diluted with DCM/MeOH (1/1, 15 mL), added excess NaHCO₃ solid and filtered. The filter cake was washed with DCM (10 mL×2). The filtrate was concentrated and purified by silica gel chromatography eluted with 0-10% MeOH in EtOAc (5% TEA) to give the product as a solid (150 mg, yield for three steps: 39%). MS ES+ m/z 317 [M+H]⁺.

Step 7: 8-[(1R)-1-anilinoethyl]-2-[(2S,6R)-2,6-dimethyl-morpholin-4-yl]-6-methyl-chromen-4-one. A mixture of 8-[(1R)-1-aminoethyl]-2-[(2S,6R)-2,6-dimethylmorpholin-4-yl]-6-methyl-chromen-4-one (150 mg, 0.474 mmol), phenylboronic acid (144 mg, 1.19 mmol), Cu(OAc)₂ (95 mg, 0.52 mmol), 4A MS (100 mg) and pyridine (98 mg, 1.24 mmol) in DCE (20 mL) was stirred at 30° C. under O2 atmosphere (15 psi) for 24 h. The mixture was filtered. The filter cake was washed with DCM (10 mL×2). The filtrate was diluted with water (15 mL) and extracted with DCM (20 mL×2). The combined extract was washed with brine (30 mL×2), dried over anhydrous Na₂SO₄, filtered and concentrated. The residue was purified by preparative HPLC to give the product (80 mg, 43%, ee: 78%). Then further purified by SFC to give (8-[(1R)-1-anilinoethyl]-2-[(2S,6R)-2,6-dimethylmorpholin-4-yl]-6-methyl-chromen-4-one as a solid (46.38 mg, ee>99%). ¹H NMR (400 MHz, DMSO-d6) δ 1.13 (d, J=6.0 Hz, 3H), 1.15 (d, J=6.0 Hz, 3H), 1.49 (d, J=6.4 Hz, 3H), 2.30 (s, 3H), 2.65-2.74 (m, 2H), 3.62-3.73 (m, 2H), 3.89-4.00 (m, 2H), 4.90-4.99 (m, 1H), 5.57 (s, 1H), 6.22 (brs, 1H), 6.45-6.52 (m, 3H), 6.96-7.04 (m, 2H), 7.43 (d, J=2.0 Hz, 1H), 7.58 (d, J=1.6 Hz, 1H). MS ES+ m/z 393 [M+H]⁺.

Example 388: 8-[(1R)-1-Anilinoethyl]-6-methyl-2-(1-piperidyl)chromen-4-one

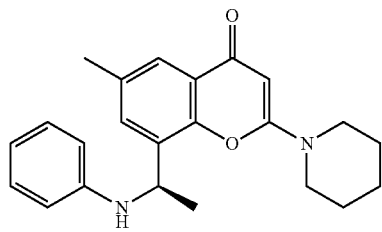 [SMILES: Cc1cc([C@@H](C)Nc2ccccc2)c2oc(N3CCCCC3)cc(=O)c2c1]

Step 1: 1-(3-bromo-2-hydroxy-5-methyl-phenyl)-3-(1-piperidyl)propane-1,3-dione. A solution of piperidine (2.00 g, 23.5 mmol), TEA (3.57 g, 35.2 mmol) in DCM (20 mL) was added dropwise into a solution of triphosgene (3.49 g, 11.7 mmol) in DCM (10 mL) at −10° C. and stirred at -10° C. for 1 h, then stirred at 0° C. for another 3 h. The mixture was concentrated, added EtOAc (20 mL) and filtered. The filter cake was washed with EtOAc (10 mL×2). The filtrate was concentrated and purified by silica gel chromatography eluted with 0-2% EtOAc in petroleum ether to give piperidine-1-carbonyl chloride as oil (3.0 g, 87%). A mixture of 1-(3-bromo-2-hydroxy-5-methyl-phenyl)ethanone (2.1 g, 9.17 mmol) in THF (15 mL) was added LiHMDS (29.3 mL, 1M in THF) dropwise at −65° C., warmed to 0° C. and stirred for 2 h. Then cooled to -65° C. and added a solution of piperidine-1-carbonyl chloride (1.96 g, 13.3 mmol) in THF (5 mL) dropwise, then stirred at 25° C. for another 4 h. The mixture was quenched with sat.NH₄Cl (30 mL), adjusted to pH=7 with HCl (2 M), extracted with EtOAc (40 mL×2). The combined extract was washed with brine (50 mL×2), dried over anhydrous Na₂SO₄ and concentrated. The residue was triturated with PE/EtOAc (5/1, 60 mL) to give the product as a solid (3.0 g, 96%). ¹H NMR (400 MHz, DMSO-d6) δ 1.44-1.65 (m, 8H), 2.29 (s, 3H), 3.43-3.50 (m, 2H), 4.29 (s, 2H), 7.73-7.76 (m, 2H), 12.27 (brs, 1H).

Step 2: 8-bromo-6-methyl-2-(1-piperidyl)chromen-4-one. A mixture of 1-(3-bromo-2-hydroxy-5-methyl-phenyl)-3-(1-piperidyl)propane-1,3-dione (3.00 g, 8.82 mmol) and Tf₂O (9.95 g, 35.3 mmol) in DCE (30 mL) was stirred at 50° C. for 14 h. When cooled to rt the mixture was concentrated and quenched with MeOH (30 mL), adjusted to pH=7 with sat.NaHCO₃, extracted with DCM (40 mL×2). The combined extract was washed with brine (50 mL×2), dried over anhydrous Na₂SO₄, filtered and concentrated. The residue was triturated with EtOAc (20 mL) to give the product as a solid (1.8 g, 63%). ¹H NMR (400 MHz, DMSO-d6) δ 1.55-1.68 (m, 6H), 2.38 (s, 3H), 3.55-3.62 (m, 4H), 5.53 (s, 1H), 7.69 (d, J=1.6 Hz, 1H), 7.78 (d, J=2.0 Hz, 1H). MS ES+ m/z 323 [M+H]⁺.

Step 3: 8-acetyl-6-methyl-2-(1-piperidyl)chromen-4-one. A mixture of 8-bromo-6-methyl-2-(1-piperidyl)chromen-4-one (1.00 g, 3.10 mmol), tributyl(1-ethoxyvinyl)stannane (1.41 g, 3.91 mmol) and Pd(PPh₃)₂Cl₂ (218 mg, 0.310 mmol) in dioxane (20 mL) was stirred at 95° C. under N₂ for 16 h. HCl (1.0 mL, 2 M) was added into the mixture and stirred at 50° C. for 0.5 h. When cooled to rt the mixture was added sat. KF (100 mL), stirred for 1 h, extracted with EtOAc (100 mL×3). The combined extract was washed with brine (100 mL), dried over anhydrous Na₂SO₄, filtered and concentrated. The residue was purified by silica gel chromatography eluted with 50%-100% EtOAc in petroleum ether to give the product as a solid (700 mg, 79%). MS ES+ m/z 286 [M+H]⁺.

Step 4: (NE)-2-methyl-N-[1-[6-methyl-4-oxo-2-(1-piperidyl)chromen-8-yl]ethylidene]propane-2-sulfinamide. A mixture of 8-acetyl-6-methyl-2-(1-piperidyl)chromen-4-one (500 mg, 1.75 mmol), (R)-2-tert-butyl-2-sulfinamide (425 mg, 3.50 mmol), Ti(i-PrO)₄ (1.99 g, 7.01 mmol) in THF (20 mL) was stirred at 70° C. for 32 h. When cooled to rt the mixture was quenched with brine (30 mL) and filtered. The filter cake was washed with EtOAc (20 mL×3). The aqueous phase was extracted with EtOAc (30 mL×2), the combined extract was washed with brine (30 mL×2), dried over anhydrous Na₂SO₄, filtered and concentrated to give the product as gum (680 mg, crude).

Step 5: 2-methyl-N-[(1R)-1-[6-methyl-4-oxo-2-(1-piperidyl)chromen-8-yl]ethyl]propane-2-sulfinamide. A mixture of (NE)-2-methyl-N-[1-[6-methyl-4-oxo-2-(1-piperidyl)chromen-8-yl]ethylidene]propane-2-sulfinamide (680 mg, crude) in DCM (10 mL) and MeOH (10 mL) was added AcOH (840 mg, 14.0 mmol) and NaBH₃CN (330 mg, 5.25 mmol) at 0° C. and stirred at 25° C. for 16 h. The mixture was adjusted to pH=8 with sat.NaHCO₃, extracted with DCM (25 mL×2). The combined extract was washed with brine (30 mL×2), dried over anhydrous Na$_2$SO$_4$, filtered and concentrated under to give the product as gum (680 mg, crude).

Step 6: 8-[(1R)-1-aminoethyl]-6-methyl-2-(1-piperidyl)chromen-4-one. A mixture of 2-methyl-N-[(1R)-1-[6-methyl-4-oxo-2-(1-piperidyl)chromen-8-yl]ethyl]propane-2-sulfinamide (450 mg, crude) in dioxane (20 mL) was added HCl/dioxane (2 mL, 4 M) and stirred at 25° C. for 1 h. The mixture was concentrated and diluted with DCM/MeOH (1/1, 15 mL), added excess NaHCO$_3$ solid and filtered. The filter cake was washed with DCM (10 mL×2). The filtrate was concentrated and purified by silica gel chromatography eluted with 0-10% MeOH in EtOAc (5% TEA) to give the product as a solid (280 mg, yield for three steps: 85%). MS ES+ m/z 287 [M+H]$^+$.

Step 7: 8-[(1R)-1-anilinoethyl]-6-methyl-2-(1-piperidyl)chromen-4-one. A mixture of 8-[(1R)-1-aminoethyl]-6-methyl-2-(1-piperidyl)chromen-4-one (280 mg, 0.978 mmol), phenylboronic acid (298 mg, 2.44 mmol), copper(II) acetate (195 mg, 1.08 mmol), 4A MS (100 mg) and pyridine (194 mg, 2.46 mmol) in DCE (20 mL) was stirred at 30° C. under O2 atmosphere (15 psi) for 24 h. The mixture was filtered. The filter cake was washed with DCM (10 mL×2). The filtrate was diluted with water (20 mL), extracted with DCM (30 mL×2), the combined extract was washed with brine (30 mL×2), dried over anhydrous Na$_2$SO$_4$, filtered and concentrated. The residue was purified by silica gel chromatography eluted with 50-100% EtOAc in petroleum ether, then 0-10% MeOH in DCM to give an impure product. The impure product was further purified by preparative HPLC to give the product (25 mg, 7%, ee: 68.32%). Then further purified by SFC to give 8-[(1R)-1-anilinoethyl]-6-methyl-2-(1-piperidyl)chromen-4-one as a solid (17.7 mg, ee>99%). $^1$H NMR (400 MHz, DMSO-d6) δ 1.49 (d, J=6.8 Hz, 3H), 1.55-1.70 (m, 6H), 2.29 (s, 3H), 3.51-3.59 (m, 4H), 4.85-4.95 (m, 1H), 5.51 (s, 1H), 6.26 (brs, 1H), 6.44-6.52 (m, 3H), 6.96-7.04 (m, 2H), 7.42 (d, J=2.0 Hz, 1H), 7.58 (d, J=1.6 Hz, 1H). MS ES+ m/z 363 [M+H]$^+$.

Example 389: 8-[(1R)-1-Anilinoethyl]-6-methyl-2-thiomorpholino-chromen-4-one

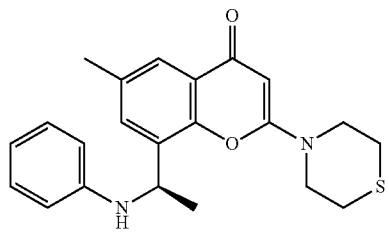 [SMILES: Cc1cc([C@@H](C)Nc2ccccc2)c2oc(N3CCSCC3)cc(=O)c2c1]

Step 1: -(3-bromo-2-hydroxy-5-methyl-phenyl)-3-thiomorpholino-propane-1,3-dione. A solution of thiomorpholine (1.09 g, 10.6 mmol), TEA (1.60 g, 15.8 mmol) in DCM (10 mL) was added dropwise into a solution of triphosgene (1.57 g, 5.28 mmol) in DCM (10 mL) at −10° C., stirred for 1 h, and then stirred at 0° C. for another 3 h. The mixture was concentrated and diluted with EtOAc (15 mL) and filtered. The filter cake was washed with EtOAc (5 mL×2). The filtrate was concentrated to give thiomorpholine-4-carbonyl chloride as yellow oil (1.50 g, crude). A mixture of 1-(3-bromo-2-hydroxy-5-methyl-phenyl)ethanone (1.70 g, 7.42 mmol) in THF (15 mL) was added LiHMDS (26 mL, 1 M in THF) dropwise at −65° C., warmed to 0° C. and stirred for 2 h. Then cooled to −65° C. and added a solution of thiomorpholine-4-carbonyl chloride (1.50 g, crude) in THF (5 mL) dropwise, warmed to rt and stirred for another 14 h. The mixture was quenched with sat.NH$_4$Cl (40 mL), adjusted to pH=7 with HCl (2 M), extracted with EtOAc (50 mL×2). The combined extract was washed with brine (50 mL×2), dried over anhydrous Na$_2$SO$_4$, filtered and concentrated. The residue was purified by silica gel chromatography eluted with 20%-80% EtOAc in petroleum ether to give the product as a solid (2.66 g, 100%). $^1$H NMR (400 MHz, DMSO-d6) δ 2.29 (s, 3H), 2.53-2.59 (m, 2H), 2.64-2.69 (m, 2H), 3.66-3.71 (m, 2H), 3.71-3.77 (m, 2H), 4.34 (s, 2H), 7.73-7.79 (m, 2H), 12.20 (brs, 1H). MS ES+ m/z 361 [M+H]$^+$.

Step 2: 8-bromo-6-methyl-2-thiomorpholino-chromen-4-one. A mixture of 1-(3-bromo-2-hydroxy-5-methyl-phenyl)-3-thiomorpholino-propane-1,3-dione (2.66 g, 7.42 mmol) and Tf$_2$O (8.38 g, 29.7 mmol) in DCE (30 mL) was stirred at 50° C. for 4 h. When cooled to rt the mixture was concentrated, diluted with DCM (20 mL) and adjusted to pH=7 with sat.NaHCO$_3$. The aqueous phase was extracted with DCM (30 mL×2), the combined extract was washed with brine (30 mL×2), dried over anhydrous Na$_2$SO$_4$, filtered and concentrated. The residue purified by silica gel chromatography eluted with 20% EtOAc in petroleum ether, then 0-2% MeOH in DCM to give an impure product. Then triturated with EtOAc (10 mL) to give the product as a solid (330 mg, 13%). $^1$H NMR (400 MHz, DMSO-d6) δ 2.39 (s, 3H), 2.72-2.80 (m, 4H), 3.87-3.95 (m, 4H), 5.60 (s, 1H), 7.70 (d, J=1.6 Hz, 1H), 7.80 (d, J=1.6 Hz, 1H).

Step 3: 8-acetyl-6-methyl-2-thiomorpholino-chromen-4-one. A mixture of 8-bromo-6-methyl-2-thiomorpholino-chromen-4-one (330 mg, 0.970 mmol), tributyl(1-ethoxyvinyl)stannane (441 mg, 1.22 mmol) and Pd(PPh$_3$)$_2$Cl$_2$ (68 mg, 0.097 mmol) in dioxane (5 mL) was stirred at 95° C. under N$_2$ for 16 h. HCl (1.5 mL, 2 M) was added into the mixture and stirred at 50° C. for 0.5 h. When cooled to rt the mixture was added sat. KF (30 mL), stirred for 1 h, extracted with EtOAc (30 mL×3), the combined extract was washed with brine (20 mL), dried over anhydrous Na$_2$SO$_4$, filtered and concentrated. The residue was purified by silica gel chromatography eluted with 0-10% MeOH in EtOAc to give the product as a solid (273 mg, 93%). MS ES+ m/z 304 [M+H]$^+$.

Step 4: (NE)-2-methyl-N-[1-(6-methyl-4-oxo-2-thiomorpholino-chromen-8-yl)ethylidene]propane-2-sulfinamide. A mixture of 8-acetyl-6-methyl-2-thiomorpholino-chromen-4-one (250 mg, 0.824 mmol), (R)-2-tert-butyl-2-sulfinamide (180 mg, 1.48 mmol), Ti(i-PrO)$_4$ (937 mg, 3.30 mmol) in THF (15 mL) was stirred at 70° C. for 32 h. When cooled to rt the mixture was quenched with brine (20 mL) and filtered. The filter cake was washed with EtOAc (20 mL×3). The filtrate was extracted with EtOAc (30 mL×2). The combined extract was washed with brine (40 mL×2), dried over anhydrous Na$_2$SO$_4$, filtered and concentrated to give the product as gum (300 mg, crude). MS ES+ m/z 407 [M+H]$^+$.

Step 5: 2-methyl-N-[(1R)-1-(6-methyl-4-oxo-2-thiomorpholino-chromen-8-yl)ethyl]propane-2-sulfinamide. A mixture of (NE)-2-methyl-N-[1-(6-methyl-4-oxo-2-thiomorpholino-chromen-8-yl)ethylidene]propane-2-sulfinamide (300 mg, crude) in DCM (15 mL) and MeOH (10 mL) was added AcOH (354 mg, 5.90 mmol), NaBH$_3$CN (139 mg, 2.21 mmol) at −15° C. and stirred for 3 h, then stirred at 0° C. for 10 h. The mixture was adjusted to pH=8 with sat.NaHCO$_3$ and extracted with DCM (25 mL×2). The combined extract was washed with brine (30 mL×2), dried over anhydrous Na$_2$SO$_4$, filtered and concentrated to give the product as a gum (300 mg, crude). MS ES+ m/z 409 [M+H]$^+$.

Step 6: 8-[(1R)-1-aminoethyl]-6-methyl-2-thiomorpholino-chromen-4-one. A mixture of 2-methyl-N-[(1R)-1-(6-methyl-4-oxo-2-thiomorpholino-chromen-8-yl)ethyl]propane-2-sulfinamide (300 mg, crude) in dioxane (2 mL) was added HCl/dioxane (0.3 mL) and stirred at 25° C. for 30 min. The mixture was concentrated and diluted with DCM/MeOH (1/1, 15 mL), added excess NaHCO$_3$ solid and filtered. The filter cake was washed with DCM (10 mL×2). The filtrate was concentrated and purified by silica gel chromatography eluted with 0-10% MeOH in DCM (5% TEA) to give the product as a solid (145 mg, yield for three steps: 75%). MS ES+ m/z 305 [M+H]$^+$.

Step 7: 8-[(1R)-1-anilinoethyl]-6-methyl-2-thiomorpholino-chromen-4-one. A mixture of 8-[(1R)-1-aminoethyl]-6-methyl-2-thiomorpholino-chromen-4-one (145 mg, 0.476 mmol), phenylboronic acid (145 mg, 1.19 mmol), Cu(OAc)$_2$ (95 mg, 0.52 mmol), 4A MS (100 mg) and pyridine (95 mg, 1.20 mmol) in DCE (20 mL) was stirred at 30° C. under 02 atmosphere (15 psi) for 24 h. The mixture was filtered, the filter cake was washed with DCM (10 mL×2). The filtrate was diluted with water (15 mL) and extracted with DCM (20 mL×2), washed with brine (30 mL×2), dried over anhydrous Na$_2$SO$_4$, filtered and concentrated. The residue was purified by silica gel chromatography eluted with 40%-100% EtOAc in petroleum ether, then 0-10% MeOH in DCM. Then further purified by preparative HPLC to give the product (30 mg, 16%, ee: 81.79%). Then further purified by SFC to give 8-[(1R)-1-anilinoethyl]-6-methyl-2-thiomorpholino-chromen-4-one as a solid (16.8 mg, ee>99%). $^1$H NMR (400 MHz, DMSO-d6) δ 1.49 (d, J=6.8 Hz, 3H), 2.30 (s, 3H), 2.69-2.75 (m, 4H), 3.85-3.93 (m, 4H), 4.85-4.95 (m, 1H), 5.57 (s, 1H), 6.51 (brs, 1H), 6.45-6.52 (m, 3H), 6.95-7.05 (m, 2H), 7.43 (d, J=2.0 Hz, 1H), 7.58 (d, J=2.0 Hz, 1H). MS ES+ m/z 381 [M+H]$^+$.

Example 390: 2-[1-[2-(4,4-Dimethyl-1-piperidyl)-6-methyl-4-oxo-chromen-8-yl]propylamino]benzoic acid 2,2,2-trifluoroacetic acid

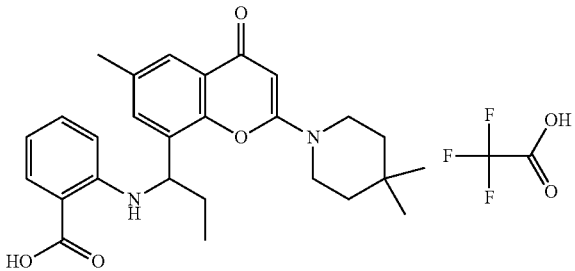

Step 1: methyl 2-[1-[2-(4,4-dimethyl-1-piperidyl)-6-methyl-4-oxo-chromen-8-yl]propylamino]benzoate. A mixture of 8-(1-bromopropyl)-2-(4,4-dimethyl-1-piperidyl)-6-methyl-chromen-4-one (26.0 mg, 1 eq., 66.3 μmol) and methyl 2-aminobenzoate (10.0 mg, 1 eq., 66.3 μmol) in DMF (2 mL) was stirred at 80° C. for 15 h. After completion of the reaction, the reaction mixture was concentrated to give crude product. MS ES+ m/z 463.4 [M+H]$^+$.

Step 2: 2-[1-[2-(4,4-dimethyl-1-piperidyl)-6-methyl-4-oxo-chromen-8-yl]propylamino]benzoic acid 2,2,2-trifluoroacetic acid. A 20 mL vial was charged with methyl 2-[1-[2-(4,4-dimethyl-1-piperidyl)-6-methyl-4-oxo-chromen-8-yl]propylamino]benzoate (35.0 mg, 1 eq., 75.7 μmol) and LiOH (5.44 mg, 227 μL, 1 molar, 3 eq., 227 μmol) in THF (3 mL) and stirred at 50° C. for 5 hours. After completion of the reaction, 1N aq HCl (5 mL) was added to the reaction and the mixture was diluted with water (10 mL) and extracted with ethyl acetate (2×20 mL). The combined organic layers were dried over sodium sulfate and concentrated and purified by reverse phase C18 column using 10-90% acetonitrile in water (0-0.1% TFA as modifier) to afford 2-[1-[2-(4,4-dimethyl-1-piperidyl)-6-methyl-4-oxo-chromen-8-yl]propylamino]benzoic acid 2,2,2-trifluoroacetic acid (4.1 mg, 9.1 μmol, 12%). MS ES+ m/z 449.4 [M+H]$^+$.

The following compounds in Table 26 were prepared essentially as described for 2-[1-[2-(4,4-dimethyl-1-piperidyl)-6-methyl-4-oxo-chromen-8-yl]propylamino]benzoic acid 2,2,2-trifluoroacetic acid.

TABLE 26

| Example # | Chemical Name | Structure | ES/MS m/z (M + H) |
|---|---|---|---|
| 391 | 2-[1-(6-chloro-2-isoindolin-2-yl-4-oxo-chromen-8-yl)ethylamino]benzoic acid 2,2,2-trifluoroacetic acid | 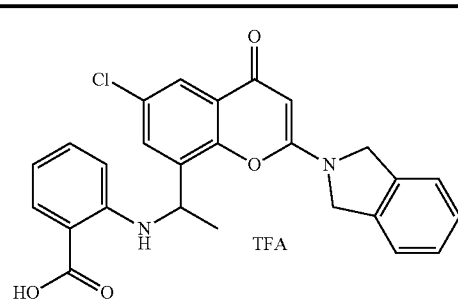 | 461 |

Example 392: 2-[1-[3-Cyano-2-(4,4-dimethyl-1-piperidyl)-6-methyl-4-oxo-chromen-8-yl]ethyl-amino]benzoic acid 2,2,2-trifluoroacetic acid

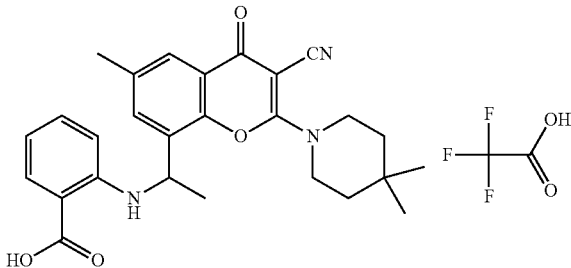

Step 1: 8-bromo-6-methyl-4-oxo-chromene-3-carbaldehyde. 1-(3-bromo-2-hydroxy-5-methyl-phenyl)ethanone (7 g, 1 eq., 0.03 mol) was stirred in DMF (70 mL) at −10° C. for 20 min. POCl$_3$ (9 g, 6 mL, 2 eq., 0.06 mol) was added dropwise. The reaction mixture was allowed to warm to room temperature and stirred for 18 hours. After 18 h, the reaction mixture was diluted with 25 mL water. The reaction mixture was filtered. The collected solid was dissolved in DCM (100 mL), dried (Na$_2$SO$_4$), and concentrated on a rotary evaporator to give crude product (8 g, 0.03 mol, 100%).

Step 2: 2-anilino-8-bromo-6-methyl-4-oxo-chromene-3-carbaldehyde. 8-bromo-6-methyl-4-oxo-chromene-3-carbaldehyde (2.4981 g, 1 eq., 9.3534 mmol) was stirred in anhydrous toluene (50 mL) at room temperature. N-phenylhydroxylamine (1.0207 g, 1 eq., 9.3534 mmol) was added to the reaction mixture. After 15 min at rt, the reaction was heated to 80° C. for 3 h to induce rearrangement. After 3 h, the reaction was concentrated and purified by column chromatography (SiO$_2$, DCM/EtOAc 0-100%) to provide the product (1.5 g, 4.2 mmol, 45%). MS ES+ m/z 358.2, 360.2 [M+H]$^+$.

Step 3: 2-anilino-8-bromo-6-methyl-4-oxo-chromene-3-carbonitrile. Propanephosphonic acid anhydride (8.0 g, 7.3 mL, 50% wt in DMF, 3 eq., 13 mmol) was added to a stirring mixture of 2-anilino-8-bromo-6-methyl-4-oxo-chromene-3-carbaldehyde (1.5 g, 1 eq., 4.2 mmol), hydroxylamine hydrochloride (1.2 g, 4 eq., 17 mmol), and triethylamine (0.42 g, 0.58 mL, 1 eq., 4.2 mmol) in DMF (50 mL). The reaction solution was heated to 60° C. and stirred for 70 min. After 70 min, the reaction was partitioned between water (25 mL) and DCM (200 mL). The organic layer was dried (Na$_2$SO$_4$), concentrated and purified by column chromatography (SiO$_2$, DCM/EtOAc 0-50%) to provide the product (698.9 mg, 1.968 mmol, 47%). MS ES+ m/z 355.2, 357.2 [M+H]$^+$.

Step 4: 8-bromo-6-methyl-2-(N-methylanilino)-4-oxo-chromene-3-carbonitrile. 2-anilino-8-bromo-6-methyl-4-oxo-chromene-3-carbonitrile (698.9 mg, 1 eq., 1.968 mmol), iodomethane (5.586 g, 2.45 mL, 20 eq., 39.35 mmol), and potassium carbonate (1.360 g, 5 eq., 9.838 mmol) in MeCN (75 mL) was heated to 50° C. for 1 hour. After 1 hour, the reaction mixture was partitioned between brine (25 mL) and DCM (100 mL). The organic layer was dried (Na$_2$SO$_4$), concentrated on a rotary evaporator and purified by column chromatography (SiO$_2$, DCM/EtOAc 0-70%) to provide the product (559.6 mg, 1.516 mmol, 77.03%). MS ES+ m/z 370.2, 372.2 [M+H]$^+$.

Step 5: 8-bromo-2-(4,4-dimethyl-1-piperidyl)-6-methyl-4-oxo-chromene-3-carbonitrile. 8-bromo-6-methyl-2-(N-methylanilino)-4-oxo-chromene-3-carbonitrile (559.6 mg, 1 eq., 1.516 mmol), 4,4-dimethylpiperidine, HCl (453.7 mg, 2 eq., 3.031 mmol), and K$_2$CO$_3$ (418.9 mg, 2 eq., 3.031 mmol) were stirred in acetonitrile (100 mL) at 65° C. for 18 h and 80° C. for 48 h. The reaction mixture was then partitioned between brine (50 mL) and DCM (100 mL). The organic layer was dried (Na$_2$SO$_4$), concentrated on a rotary evaporator and purified by column chromatography (SiO$_2$, DCM/EtOAc 0-70%) to provide the product (169.3 mg, 451.1 μmol, 29.77%). MS ES+ m/z 375.2, 377.2 [M+H]$^+$.

Step 6: 8-acetyl-2-(4,4-dimethyl-1-piperidyl)-6-methyl-4-oxo-chromene-3-carbonitrile. 8-bromo-2-(4,4-dimethyl-1-piperidyl)-6-methyl-4-oxo-chromene-3-carbonitrile (169.3 mg, 1 eq., 451.1 μmol), tributyl(1-ethoxyvinyl)stannane (195.5 mg, 183.2 μL, 1.2 eq., 541.4 μmol), and PdCl$_2$(dppf) (16.51 mg, 0.05 eq., 22.56 μmol) were stirred together in 1,4-dioxane (8 mL) at 95° C. for 1 h. After 1 h, reaction was cooled to rt. 2 M HCl (5 mL) was added, the reaction mixture was stirred at 50° C. for 30 minutes. After 30 min, saturated KF (5 mL) was added to the reaction mixture. The suspension was stirred at rt for 30 minutes. After 30 minutes, the reaction mixture was filtered through celite. The filter cake was rinsed with DCM (25 mL). The organic layer was washed with H$_2$O (10 mL), washed with brine (10 mL), dried (Na$_2$SO$_4$), concentrated on a rotary evaporator, and purified by column chromatography (SiO$_2$, DCM/EtOAc 0-40%) to provide the product (96.7 mg, 286 μmol, 63.3%). MS ES+ m/z 339.2 [M+H]$^+$.

Step 7: 2-(4,4-dimethyl-1-piperidyl)-8-(1-hydroxyethyl)-6-methyl-4-oxo-chromene-3-carbonitrile. NaBH$_4$ (13.0 mg, 1.2 eq., 343 μmol) was added to a stirring solution of 8-acetyl-2-(4,4-dimethyl-1-piperidyl)-6-methyl-4-oxo-chromene-3-carbonitrile (96.7 mg, 1 eq., 286 μmol) in methanol (2 mL) and DCM (2 mL) at −10° C. The reaction mixture was let warm to rt and stirred. After 30 minutes, the reaction mixture was quenched with saturated NH$_4$Cl (1 mL) and extracted with DCM (2×5 mL). The combined extracts were washed with brine (3 mL), dried (Na$_2$SO$_4$) and concentrated on a rotary evaporator to provide the product (97.2 mg, 286 μmol, 99.9%) which was taken forward crude. MS ES+ m/z 341.4 [M+H]$^+$.

Step 8: 8-(1-bromoethyl)-2-(4,4-dimethyl-1-piperidyl)-6-methyl-4-oxo-chromene-3-carbonitrile. A solution of PBr$_3$ (85.0 mg, 314 μL, 1 molar, 1.1 eq., 314 μmol) in DCM was added to a stirred solution of 2-(4,4-dimethyl-1-piperidyl)-8-(1-hydroxyethyl)-6-methyl-4-oxo-chromene-3-carbonitrile (97.2 mg, 1 eq., 286 μmol) in DCM (6 mL) at 0° C. The reaction was let warm to rt and stirred for 30 minutes. After 30 minutes, the reaction mixture was adjusted to pH=8 with saturated NaHCO$_3$. The mixture was diluted with DCM (5 mL). The organic layer was separated, dried (Na$_2$SO$_4$) and concentrated to provide the crude product (95.6 mg, 237 μmol, 83.0%). MS ES+ m/z 403.2, 405.2 [M+H]$^+$.

Step 9: tert-butyl 2-[1-[3-cyano-2-(4,4-dimethyl-1-piperidyl)-6-methyl-4-oxo-chromen-8-yl]ethylamino]benzoate. 8-(1-bromoethyl)-2-(4,4-dimethyl-1-piperidyl)-6-methyl-4-oxo-chromene-3-carbonitrile (95.6 mg, 1 eq., 237 μmol) and tert-butyl 2-aminobenzoate (68.7 mg, 64.8 μL, 1.5 eq., 356 μmol) were stirred together in DMF (2 mL) at 80° C. for 18 h. After 18 h, the reaction mixture was concentrated and purified by column chromatography (SiO$_2$, DCM/EtOAc 0-100%) to provide the product (62.3 mg, 121 μmol, 51.0%). MS ES+ m/z 516.4 [M+H]$^+$.

Step 10: 2-[1-[3-cyano-2-(4,4-dimethyl-1-piperidyl)-6-methyl-4-oxo-chromen-8-yl]ethylamino]benzoic acid 2,2,2- trifluoroacetic acid. A trifluoroacetic acid (0.2 mL)/DCM (2 mL) solution was added to tert-butyl 2-[1-[3-cyano-2-(4,4-dimethyl-1-piperidyl)-6-methyl-4-oxo-chromen-8-yl]ethyl-amino]benzoate (62.3 mg, 1 eq., 121 µmol) at room temperature. The clear solution was stirred at 45° C. for 2 h. Reaction was stirred at 35° C. for 18 h. Toluene (2 mL) was added to the reaction mixture. The reaction mixture was concentrated on a rotary evaporator and purified by Preparative HPLC (10-100% 0.1% TFA in MeCN/0.1% TFA in water) to provide 2-[1-[3-cyano-2-(4,4-dimethyl-1-piperidyl)-6-methyl-4-oxo-chromen-8-yl]ethylamino]benzoic acid 2,2,2-trifluoroacetic acid (8 mg, 0.02 mmol, 10%) as a white solid. MS ES+ m/z 460.4 [M+H]$^+$.

Example 393: N-[2-[1-(2-Isoindolin-2-yl-6-methyl-4-oxo-chromen-8-yl)ethylamino]phenyl]sulfonyl-2-phenyl-acetamide 2,2,2-trifluoroacetic acid

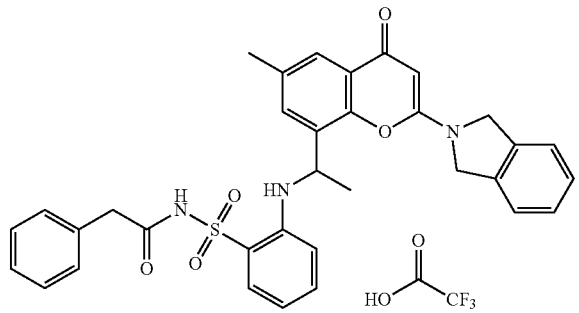 [SMILES: Cc1cc(C(C)Nc2ccccc2S(=O)(=O)NC(=O)Cc2ccccc2)c2oc(N3Cc4ccccc4C3)cc(=O)c2c1 ; O=C(O)C(F)(F)F]

A suspension of 2-[1-(2-isoindolin-2-yl-6-methyl-4-oxo-chromen-8-yl)ethylamino]benzenesulfonamide (50 mg, 0.11 mmol), 2-phenylacetic acid (14 mg, 0.11 mmol), dicyclohexylmethanediimine (33 mg, 0.16 mmol), and N,N-dimethylpyrin-4-amine (13 mg, 0.11 mmol) was stirred in DCM (3 mL) for 16 hours. The mixture was then poured into H$_2$O (5 mL) and DCM (5 mL). The layers were separated and the aqueous layer extracted 3× with DCM (5 mL). The combined organic layers were concentrated and the residue purified via reverse-phase chromatography eluted with 10-100% MeCN (0.1% TFA) in H$_2$O (0.1% TFA) to give N-[2-[1-(2-isoindolin-2-yl-6-methyl-4-oxo-chromen-8-yl)ethylamino]phenyl]sulfonyl-2-phenyl-acetamide 2,2,2-trifluoroacetic acid (49 mg, 66%). MS ES+ m/z 594.4 [M+H].

The following compounds in Table 27 were prepared essentially as described for N-[2-[1-(2-isoindolin-2-yl-6-methyl-4-oxo-chromen-8-yl)ethylamino]phenyl]sulfonyl-2-phenyl-acetamide 2,2,2-trifluoroacetic acid.

TABLE 27

| Example # | Chemical Name | Structure | ES/MS m/z (M + H) |
|---|---|---|---|
| 394 | 2-[1-(2-Isoindolin-2-yl-6-methyl-4-oxo-chromen-8-yl)ethylamino]-N-methylsulfonyl-benzamide 2,2,2-trifluoroacetic acid, Isomer 1 | 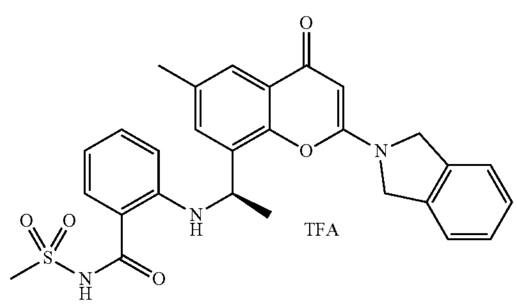 [SMILES: Cc1cc([C@@H](C)Nc2ccccc2C(=O)NS(C)(=O)=O)c2oc(N3Cc4ccccc4C3)cc(=O)c2c1] | 518 |
| 395 | N-(Difluoromethylsulfonyl)-2-[1-(2-isoindolin-2-yl-6-methyl-4-oxo-chromen-8-yl)ethylamino]benzamide 2,2,2-trifluoroacetic acid, Isomer 1 | 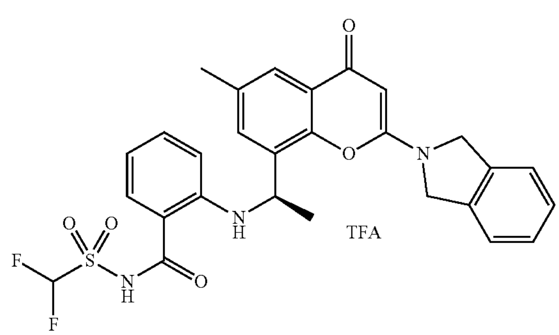 [SMILES: Cc1cc([C@@H](C)Nc2ccccc2C(=O)NS(=O)(=O)C(F)F)c2oc(N3Cc4ccccc4C3)cc(=O)c2c1] | 554 |

Example 396: 2-[1-[2-(4,4-Difluoro-1-piperidyl)-4-oxo-6-(trifluoromethyl)chromen-8-yl]ethylamino]benzoic acid 2,2,2-trifluoroacetic acid

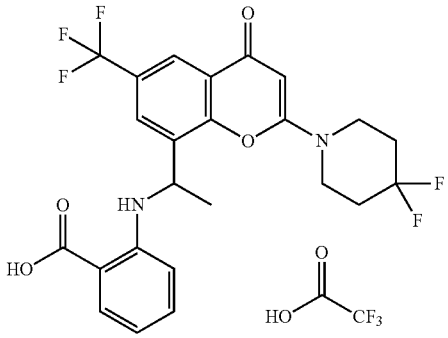 [SMILES: CC(Nc1ccccc1C(=O)O)c1cc(C(F)(F)F)cc2c(=O)cc(N3CCC(F)(F)CC3)oc12 ; O=C(O)C(F)(F)F]

A solution of 2-[1-[2-ethylsulfanyl-4-oxo-6-(trifluoromethyl)chromen-8-yl]ethylamino]benzoic acid (73 mg, 0.19 mmol) in DCM (2.5 mL) was cooled to 0° C. and to this was added 3-chloroperoxybenzoic acid (51 mg, 77% wt, 0.23 mmol). The mixture was warmed to 25° C. and stirred for 3 hrs. The mixture was again cooled to 0° C. and to this was added 4,4-difluoropiperidine (68 mg, 0.57 mmol) and N,N-diisopropylethylamine (0.20 mL, 1.2 mmol). The mixture was warmed to 25° C. and stirred for 3 hrs. The mixture was then concentrated and the residue purified via reverse-phase chromatography eluted with 10-100% MeCN(0.1% TFA) in H₂O (0.1% TFA) to give 2-[1-[2-(4,4-difluoro-1-piperidyl)-4-oxo-6-(trifluoromethyl)chromen-8-yl]ethylamino]benzoic acid 2,2,2-trifluoroacetic acid (40 mg, 39%). MS ES+ m/z 497.6 [M+H].

Example 397: 2-[1-[2-(6-Azaspiro[2.5]octan-6-yl)-4-oxo-6-(trifluoromethyl)chromen-8-yl]ethylamino]benzoic acid 2,2,2-trifluoroacetic acid

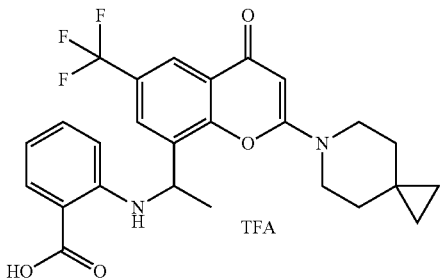 [SMILES: CC(Nc1ccccc1C(=O)O)c1cc(C(F)(F)F)cc2c(=O)cc(N3CCC4(CC3)CC4)oc12]

A solution of 2-[1-[2-ethylsulfanyl-4-oxo-6-(trifluoromethyl)chromen-8-yl]ethylamino]benzoic acid (100 mg, 1 eq., 229 μmol) in DCM (5 mL) was cooled to 0° C. and treated with mCPBA (68.1 mg, 77% wt, 1.33 eq., 304 μmol). The reaction was allowed to slowly warm to 25° C. in ice bath. After 3 hrs the mixture was cooled down again to 0° C. and 6-azaspiro[2.5]octane (25.4 mg, 1 eq., 0.23 mmol) was added followed by triethylamine (69.4 mg, 95.6 μL, 3 eq., 686 μmol). The reaction was allowed to slowly warm to 25° C. and stirred for 16 hrs. The mixture was concentrated and the residue purified by reverse-phase chromatography eluted with 20-100% acetonitrile (with 0.1% TFA) in water (with 0.1% TF) to give 2-[1-[2-(6-azaspiro[2.5]octan-6-yl)-4-oxo-6-(trifluoromethyl)chromen-8-yl]ethylamino]benzoic acid 2,2,2-trifluoroacetic acid (67 mg, 49%) as a solid. MS ES+ m/z 487.4 [M+H].

Example 398: 2-[1-[2-(6-Azaspiro[2.5]octan-6-yl)-6-fluoro-4-oxo-chromen-8-yl]ethylamino]benzoic acid 2,2,2-trifluoroacetic acid

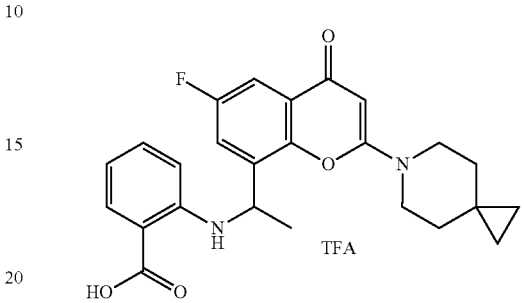

A solution of 2-[1-(2-ethylsulfanyl-6-fluoro-4-oxo-chromen-8-yl)ethylamino]benzoic acid (150 mg, 0.39 mmol) in DCM (2.5 mL) was cooled to 0° C. and to this was added 3-chloroperoxybenzoic acid (100 mg, 77% wt, 0.47 mmol). The mixture was warmed to 25° C. and stirred for 3 hrs. The mixture was again cooled to 0° C. and to this was added 6-azaspiro[2.5]octane (130 mg, 1.2 mmol) and N,N-diisopropylethylamine (0.47 mL, 2.7 mmol). The mixture was warmed to 25° C. and stirred for 3 hrs. The mixture was then concentrated and the residue purified via reverse-phase chromatography eluted with 10-100% MeCN(0.1% TFA) in H₂O (0.1% TFA) to give 2-[1-[2-(6-azaspiro[2.5]octan-6-yl)-6-fluoro-4-oxo-chromen-8-yl]ethylamino]benzoic acid 2,2,2-trifluoroacetic acid (61 mg, 29%). MS ES+ m/z 437.2 [M+H].

Example 399: 2-[1-[2-(4,4-Difluoro-1-piperidyl)-4-oxo-6-(trifluoromethyl)chromen-8-yl]ethylamino]benzoic acid 2,2,2-trifluoroacetic acid

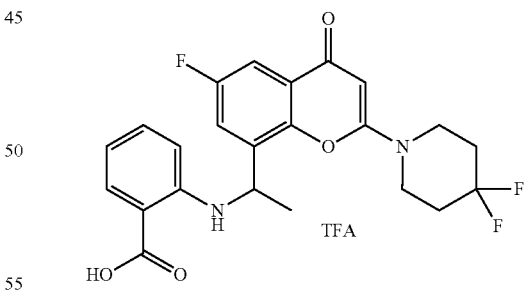

A solution of 2-[1-(2-ethylsulfanyl-6-fluoro-4-oxo-chromen-8-yl)ethylamino]benzoic acid (28 mg, 0.07 mmol) in DCM (2.5 mL) was cooled to 0° C. and to this was added 3-chloroperoxybenzoic acid (24 mg, 77% wt, 0.11 mmol). The mixture was warmed to 25° C. and stirred for 1 hr. The mixture was again cooled to 0° C. and to this was added 4,4-difluoropiperidine (13 mg, 0.22 mmol) and N,N-diisopropylethylamine (0.038 mL, 0.22 mmol). The mixture was warmed to 25° C. and stirred for 4 hrs. The mixture was then concentrated and MeCN (2.5 mL), 4,4-difluoropiperidine (9 mg, 0.07 mmol), and N,N-Diisopropylethylamine (0.051 mL, 0.28 mmol). The mixture was warmed to 60° C. and stirred for 16 hrs. The mixture was concentrated and the residue purified via reverse-phase chromatography eluted with 10-100% MeCN (0.1% TFA) in H₂O (0.1% TFA) to give 2-[1-[2-(4,4-difluoro-1-piperidyl)-4-oxo-6-(trifluoromethyl)chromen-8-yl]ethylamino]benzoic acid 2,2,2-trifluoroacetic acid (24 mg, 56%). MS ES+ m/z 447.4 [M+H].

Example 400: 6-Chloro-3-[1-(6-fluoro-2-isoindolin-2-yl-4-oxo-chromen-8-yl)ethylamino]pyridine-2-carboxylic acid 2,2,2-trifluoroacetic acid

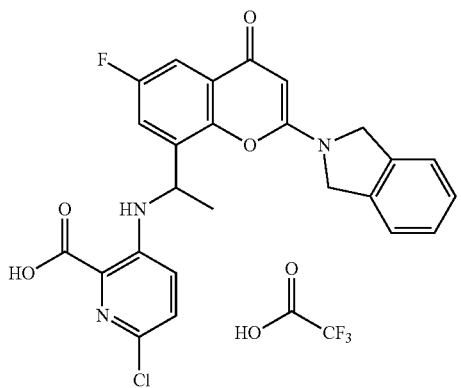 [SMILES: CC(Nc1ccc(Cl)nc1C(=O)O)c1cc(F)cc2c(=O)cc(N3Cc4ccccc4C3)oc12 ; O=C(O)C(F)(F)F]

Step 1: tert-butyl 6-chloro-3-[1-(6-fluoro-2-isoindolin-2-yl-4-oxo-chromen-8-yl)ethylamino]pyridine-2-carboxylate.

tert-butyl 6-chloro-3-[1-(2-ethylsulfanyl-6-fluoro-4-oxo-chromen-8-yl)ethylamino]pyridine-2-carboxylate (73 mg, 0.15 mmol) in DCM (5 mL) was cooled to 0° C. and to this was added 3-chloroperoxybenzoic acid (45 mg, 77% wt, 0.20 mmol). The mixture was warmed to 25° C. and stirred for 3 hrs. The mixture was again cooled to 0° C. and to this was added isoindoline HCl (31 mg, 0.2 mmol) and triethylamine (0.064 mL, 0.46 mmol). The mixture was warmed to 25° C. and stirred for 16 hrs. The mixture was then diluted into H₂O (10 mL) and DCM (10 mL). The organic layer was extracted from the aqueous layer 3×using DCM (5 mL), filtered through a phase separator, and concentrated. The residue purified via normal-phase chromatography eluted with 0-100% EtOAc in Heptane to give the product (68 mg, 83%). MS ES+ m/z 536.4 [M+H].

Step 2: 6-chloro-3-[1-(6-fluoro-2-isoindolin-2-yl-4-oxo-chromen-8-yl)ethylamino]pyridine-2-carboxylic acid 2,2,2-trifluoroacetic acid. A solution of tert-butyl 6-chloro-3-[1-(6-fluoro-2-isoindolin-2-yl-4-oxo-chromen-8-yl)ethylamino]pyridine-2-carboxylate (68 mg, 0.13 mmol) in trifluoroacetic acid (1 mL) and DCM (1.5 mL) was stirred for 1 hour at 30° C. The mixture was concentrated and the residue purified via reverse-phase chromatography eluted with 20-100% acetonitrile (0.1% TFA) in H₂O (0.1% TFA) to give 6-chloro-3-[1-(6-fluoro-2-isoindolin-2-yl-4-oxo-chromen-8-yl)ethylamino]pyridine-2-carboxylic acid 2,2,2-trifluoroacetic acid (40 mg, 64%). MS ES+ m/z 480.1 [M+H].

The following compounds in Table 28 were prepared essentially as described for 6-chloro-3-[1-(6-fluoro-2-isoindolin-2-yl-4-oxo-chromen-8-yl)ethylamino]pyridine-2-carboxylic acid 2,2,2-trifluoroacetic acid.

TABLE 28

| Example # | Chemical Name | Structure | ES/MS m/z (M + H) |
|---|---|---|---|
| 401 | 6-Chloro-3-[1-[6-fluoro-2-(5-fluoroisoindolin-2-yl)-4-oxo-chromen-8-yl]ethylamino]pyridine-2-carboxylic acid 2,2,2-trifluoroacetic acid | 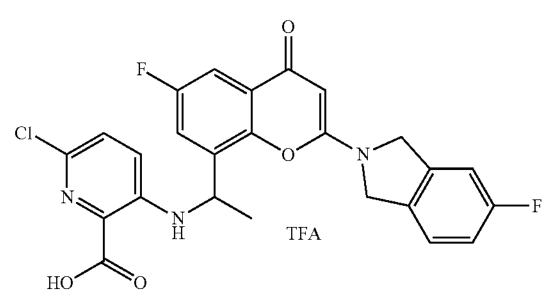 [SMILES: CC(Nc1ccc(Cl)nc1C(=O)O)c1cc(F)cc2c(=O)cc(N3Cc4ccc(F)cc4C3)oc12] | 498 |
| 402 | 3-[1-[2-(6-Azaspiro[2.5]octan-6-yl)-6-fluoro-4-oxo-chromen-8-yl]ethylamino]-6-chloro-pyridine-2-carboxylic acid 2,2,2-trifluoroacetic acid | 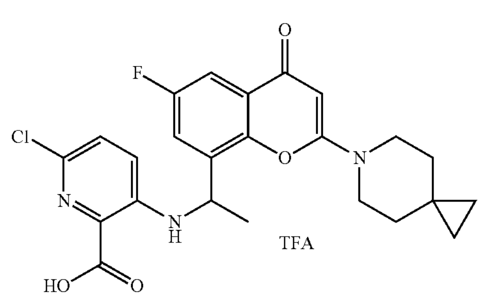 [SMILES: CC(Nc1ccc(Cl)nc1C(=O)O)c1cc(F)cc2c(=O)cc(N3CCC4(CC3)CC4)oc12] | 472 |

TABLE 28-continued

| Example # | Chemical Name | Structure | ES/MS m/z (M + H) |
|---|---|---|---|
| 403 | 3-[1-[2-(6-Azaspiro[2.5]octan-6-yl)-4-oxo-6-(trifluoromethyl)chromen-8-yl]ethylamino]-6-chloro-pyridine-2-carboxylic acid 2,2,2-trifluoroacetic acid | 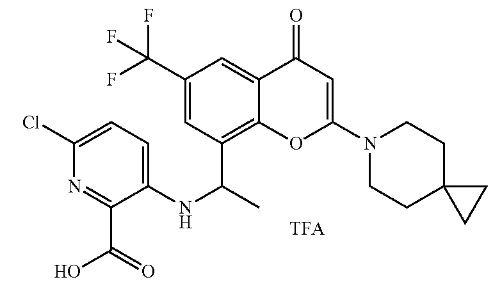 [SMILES: CC(Nc1ccc(Cl)nc1C(=O)O)c1cc(C(F)(F)F)cc2c(=O)cc(N3CCC4(CC3)CC4)oc12] | 522 |
| 404 | 6-Chloro-3-[1-[2-isoindolin-2-yl-4-oxo-6-(trifluoromethyl)chromen-8-yl]ethylamino]pyridine-2-carboxylic acid 2,2,2-trifluoroacetic acid | 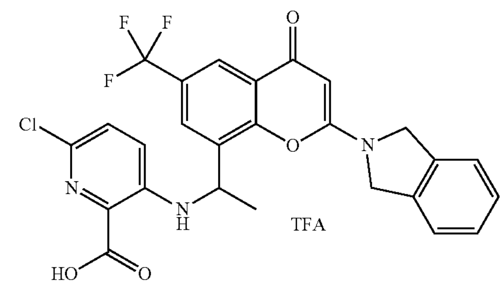 [SMILES: CC(Nc1ccc(Cl)nc1C(=O)O)c1cc(C(F)(F)F)cc2c(=O)cc(N3Cc4ccccc4C3)oc12] | 530 |
| 405 | 6-Chloro-3-[1-[2-(5-fluoroisoindolin-2-yl)-4-oxo-6-(trifluoromethyl)chromen-8-yl]ethylamino]pyridine-2-carboxylic acid 2,2,2-trifluoroacetic acid | 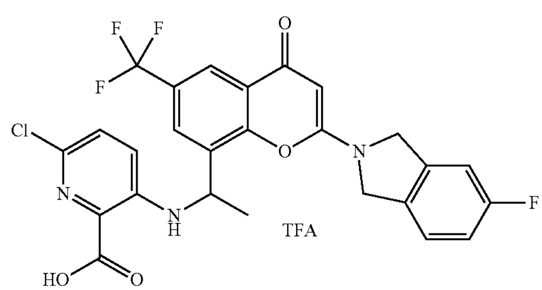 [SMILES: CC(Nc1ccc(Cl)nc1C(=O)O)c1cc(C(F)(F)F)cc2c(=O)cc(N3Cc4ccc(F)cc4C3)oc12] | 548 |

Example 406: 2-[1-[6-Methyl-2-(1-methyl-4,6-dihydropyrrolo[3,4-c]pyrazol-5-yl)-4-oxo-chromen-8-yl]ethylamino]benzoic acid 2,2,2-trifluoroacetic acid, Isomer 1

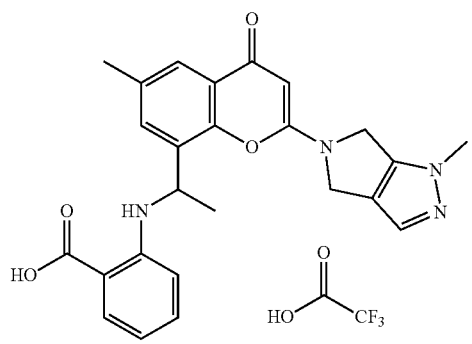 [SMILES: Cc1cc(C(C)Nc2ccccc2C(=O)O)c2oc(N3Cc4cnn(C)c4C3)cc(=O)c2c1 ; O=C(O)C(F)(F)F]

A solution of 2-[1-(2-ethylsulfanyl-6-methyl-4-oxo-chromen-8-yl)ethylamino]benzoic acid, Isomer 1 (90 mg, 0.23 mmol) in DCM (2 mL) was cooled to 0° C. and to this was added 3-chloroperoxybenzoic acid (58 mg, 77% wt, 0.26 mmol). The mixture was warmed to 25° C. and stirred for 3 hrs. The mixture was again cooled to 0° C. and to this was added 1-methyl-1,4,5,6-tetrahydropyrrolo[3,4-c]pyrazole hydrochloride (94 mg, 0.59 mmol) and triethylamine (0.23 mL, 1.6 mmol). The mixture was warmed to 25° C. and stirred for 13 hrs then poured into H₂O (5 mL). Organics were extracted 3×using DCM (5 mL), passed through a phase separator, and concentrated. The residue purified via reverse-phase chromatography eluted with 10-100% MeCN (0.1% TFA) in H₂O (0.1% TFA) to give 2-[1-[6-methyl-2-(1-methyl-4,6-dihydropyrrolo[3,4-c]pyrazol-5-yl)-4-oxo-chromen-8-yl]ethylamino]benzoic acid 2,2,2-trifluoroacetic acid, Isomer 1 (32 mg, 24%). MS ES+ m/z 445.4 [M+H].

The following compounds in Table 29 were prepared essentially as described for 2-[1-[6-methyl-2-(1-methyl-4,6-dihydropyrrolo[3,4-c]pyrazol-5-yl)-4-oxo-chromen-8-yl] ethyl amino]benzoic acid 2,2,2-trifluoroacetic acid, Isomer 1.

TABLE 29

| Example # | Chemical Name | Structure | ES/MS m/z (M + H) |
|---|---|---|---|
| 407 | 2-[1-[6-Methyl-2-[(1S)-1-methylisoindolin-2-yl]-4-oxo-chromen-8-yl]ethylamino]benzoic acid 2,2,2-trifluoroacetic acid, Isomer 1 | 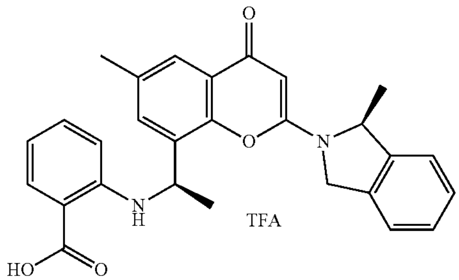 [SMILES: Cc1cc([C@@H](C)Nc2ccccc2C(=O)O)c2oc(N3Cc4ccccc4[C@@H]3C)cc(=O)c2c1] | 455 |
| 408 | 2-[1-[6-Methyl-2-[(1R)-1-methylisoindolin-2-yl]-4-oxo-chromen-8-yl]ethylamino]benzoic acid 2,2,2-trifluoroacetic acid, Isomer 1 | 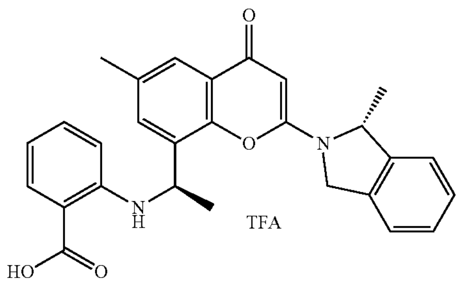 [SMILES: Cc1cc([C@@H](C)Nc2ccccc2C(=O)O)c2oc(N3Cc4ccccc4[C@H]3C)cc(=O)c2c1] | 455 |
| 409 | 2-[1-[6-Methyl-2-(3-methyl-3-phenyl-pyrrolidin-1-yl)-4-oxo-chromen-8-yl]ethylamino]benzoic acid 2,2,2-trifluoroacetic acid, Isomer 1 | 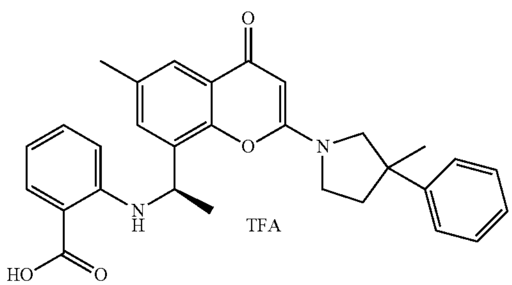 [SMILES: Cc1cc([C@@H](C)Nc2ccccc2C(=O)O)c2oc(N3CCC(C)(c4ccccc4)C3)cc(=O)c2c1] | 483 |

The following compounds in Table 30 were purified from racemic examples with chiral SFC.

TABLE 30

| Example # | Chemical Name | Chiral Column, Eluent (see Tables 4 and 5) | ES/MS m/z (M + H) |
|---|---|---|---|
| 410 | 2-[1-[6-Methyl-4-oxo-2-[3-(4-pyridyl)pyrrolidin-1-yl]chromen-8-yl]ethylamino]benzoic acid, Isomer 1 | G, 16 | 470 |
| 411 | 2-[1-[6-Methyl-4-oxo-2-[3-(4-pyridyl)pyrrolidin-1-yl]chromen-8-yl]ethylamino]benzoic acid, Isomer 2 | G, 16 | 470 |
| 412 | 2-[1-[6-Methyl-2-[3-(2-methylpyrazol-3-yl)pyrrolidin-1-yl]-4-oxo-chromen-8-yl]ethylamino]benzoic acid, Isomer 1 | B, 20 | 473 |
| 413 | 2-[1-[6-Methyl-2-[3-(2-methylpyrazol-3-yl)pyrrolidin-1-yl]-4-oxo-chromen-8-yl]ethylamino]benzoic acid, Isomer 2 | B, 20 | 473 |
| 414 | 2-[1-[6-Methyl-2-[3-(1-methylpyrazol-3-yl)pyrrolidin-1-yl]-4-oxo-chromen-8-yl]ethylamino]benzoic acid, Isomer 1 | C, 3 | 473 |
| 415 | 2-[1-[6-Methyl-2-[3-(1-methylpyrazol-3-yl)pyrrolidin-1-yl]-4-oxo-chromen-8-yl]ethylamino]benzoic acid, Isomer 2 | C, 3 | 473 |
| 416 | 2-[1-[6-Methyl-2-(3-methyl-3-phenyl-pyrrolidin-1-yl)-4-oxo-chromen-8-yl]ethylamino]benzoic acid, Isomer 1 | H, 20 | 483 |
| 417 | 2-[1-[6-Methyl-2-(3-methyl-3-phenyl-pyrrolidin-1-yl)-4-oxo-chromen-8-yl]ethylamino]benzoic acid, Isomer 2 | H, 20 | 483 |
| 418 | 2-[1-(2-Isoindolin-2-yl-6-methyl-4-oxo-chromen-8-yl)ethylamino]benzenecarbohydroxamic acid, Isomer 1 | A, 30 | 456 |

TABLE 30-continued

| Example # | Chemical Name | Chiral Column, Eluent (see Tables 4 and 5) | ES/MS m/z (M + H) |
|---|---|---|---|
| 419 | 2-[1-(2-Isoindolin-2-yl-6-methyl-4-oxo-chromen-8-yl)ethylamino]benzenecarbohydroxamic acid, Isomer 2 | A, 30 | 456 |
| 420 | N-[2-[1-(2-Isoindolin-2-yl-6-methyl-4-oxo-chromen-8-yl)ethylamino]phenyl]sulfonyl-2-phenyl-acetamide, Isomer 1 | F, 33 | 594 |
| 421 | N-[2-[1-(2-Isoindolin-2-yl-6-methyl-4-oxo-chromen-8-yl)ethylamino]phenyl]sulfonyl-2-phenyl-acetamide, Isomer 2 | F, 33 | 594 |
| 422 | 2-Isoindolin-2-yl-6-methyl-8-[1-[2-(tetrazol-1-yl)anilino]ethyl]chromen-4-one, Isomer 1 | E, 6 | 465 |
| 423 | 2-Isoindolin-2-yl-6-methyl-8-[1-[2-(tetrazol-1-yl)anilino]ethyl]chromen-4-one, Isomer 2 | E, 6 | 465 |
| 424 | 2-[1-[2-(6-Azabicyclo[3.1.1]heptan-6-yl)-6-methyl-4-oxo-chromen-8-yl]ethylamino]benzoic acid, Isomer 1 | A, 8 | 419 |
| 425 | 2-[1-[2-(6-Azabicyclo[3.1.1]heptan-6-yl)-6-methyl-4-oxo-chromen-8-yl]ethylamino]benzoic acid, Isomer 2 | A, 8 | 419 |
| 426 | 2-Isoindolin-2-yl-8-[1-(2-isoxazol-5-ylanilino)ethyl]-6-methyl-chromen-4-one, Isomer 1 | C, 33 | 464 |
| 427 | 2-Isoindolin-2-yl-8-[1-(2-isoxazol-5-ylanilino)ethyl]-6-methyl-chromen-4-one, Isomer 2 | C, 33 | 464 |
| 428 | 2-[1-[2-[3-(1,1-Difluoroethyl)azetidin-1-yl]-6-methyl-4-oxo-chromen-8-yl]ethylamino]benzoic acid, Isomer 1 | C, 7 | 443 |
| 429 | 2-[1-[2-[3-(1,1-Difluoroethyl)azetidin-1-yl]-6-methyl-4-oxo-chromen-8-yl]ethylamino]benzoic acid, Isomer 2 | C, 7 | 443 |
| 430 | 2-[1-[2-[(3R,4S)-3,4-Difluoropyrrolidin-1-yl]-6-methyl-4-oxo-chromen-8-yl]ethylamino]benzoic acid, Isomer 1 | A, 19 | 429 |
| 431 | 2-[1-[2-[(3R,4S)-3,4-Difluoropyrrolidin-1-yl]-6-methyl-4-oxo-chromen-8-yl]ethylamino]benzoic acid, Isomer 2 | A, 19 | 429 |
| 432 | 2-[1-[6-Methyl-4-oxo-2-[(3S)-3-(trifluoromethyl)-1-piperidyl]chromen-8-yl]ethylamino]benzoic acid, Isomer 1 | A, 23 | 475 |
| 433 | 2-[1-[6-Methyl-4-oxo-2-[(3S)-3-(trifluoromethyl)-1-piperidyl]chromen-8-yl]ethylamino]benzoic acid, Isomer 2 | A, 23 | 475 |
| 434 | 2-[1-[6-Methyl-4-oxo-2-[(3R)-3-(trifluoromethyl)pyrrolidin-1-yl]chromen-8-yl]ethylamino]benzoic acid, Isomer 1 | A, 23 | 461 |
| 435 | 2-[1-[6-Methyl-4-oxo-2-[(3R)-3-(trifluoromethyl)pyrrolidin-1-yl]chromen-8-yl]ethylamino]benzoic acid, Isomer 2 | A, 23 | 461 |
| 436 | 2-[1-[2-[(3R,4R)-3,4-Difluoropyrrolidin-1-yl]-6-methyl-4-oxo-chromen-8-yl]ethylamino]benzoic acid, Isomer 1 | A, 32 | 429 |
| 437 | 2-[1-[2-[(3R,4R)-3,4-Difluoropyrrolidin-1-yl]-6-methyl-4-oxo-chromen-8-yl]ethylamino]benzoic acid, Isomer 2 | A, 32 | 429 |
| 438 | 2-[1-[2-[(3R)-3-Fluoro-1-piperidyl]-6-methyl-4-oxo-chromen-8-yl]ethylamino]benzoic acid, Isomer 1 | A, 32 | 425 |
| 439 | 2-[1-[2-[(3R)-3-Fluoro-1-piperidyl]-6-methyl-4-oxo-chromen-8-yl]ethylamino]benzoic acid, Isomer 2 | A, 32 | 425 |
| 440 | 2-[1-[2-[(3S)-3-Fluoro-1-piperidyl]-6-methyl-4-oxo-chromen-8-yl]ethylamino]benzoic acid, Isomer 1 | A, 32 | 425 |
| 441 | 2-[1-[2-[(3S)-3-Fluoro-1-piperidyl]-6-methyl-4-oxo-chromen-8-yl]ethylamino]benzoic acid, Isomer 2 | A, 32 | 425 |
| 442 | 2-[1-[2-(6,6-Difluoro-3-azabicyclo[3.1.1]heptan-3-yl)-6-methyl-4-oxo-chromen-8-yl]ethylamino]benzoic acid, Isomer 1 | A, 6 | 455 |
| 443 | 2-[1-[2-(6,6-Difluoro-3-azabicyclo[3.1.1]heptan-3-yl)-6-methyl-4-oxo-chromen-8-yl]ethylamino]benzoic acid, Isomer 2 | A, 6 | 455 |
| 444 | 2-[1-[2-(3-Carbamoyl-3-phenyl-azetidin-1-yl)-6-methyl-4-oxo-chromen-8-yl]ethylamino]benzoic acid, Isomer 1 | D, 4 | 498 |
| 445 | 2-[1-[2-(3-Carbamoyl-3-phenyl-azetidin-1-yl)-6-methyl-4-oxo-chromen-8-yl]ethylamino]benzoic acid, Isomer 2 | D, 4 | 498 |
| 446 | 2-[1-[6-Methyl-4-oxo-2-[(3S)-3-phenylpyrrolidin-1-yl]chromen-8-yl]ethylamino]benzoic acid, Isomer 1 | A, 20 | 469 |
| 447 | 2-[1-[6-Methyl-4-oxo-2-[(3S)-3-phenylpyrrolidin-1-yl]chromen-8-yl]ethylamino]benzoic acid, Isomer 2 | A, 20 | 469 |

Example 448: 2-[[1-[2-(4,4-Dimethyl-1-piperidyl)-6-methyl-4-oxo-chromen-8-yl]-2,2,2-trifluoro-ethyl]amino]benzoic acid 2,2,2-trifluoroacetic acid

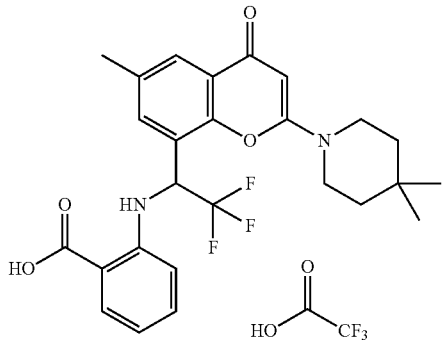 [SMILES: Cc1cc(C(Nc2ccccc2C(=O)O)C(F)(F)F)c2oc(N3CCC(C)(C)CC3)cc(=O)c2c1 ; O=C(O)C(F)(F)F]

Step 1: 2-(4,4-dimethyl-1-piperidyl)-6-methyl-8-(2,2,2-trifluoro-1-hydroxy-ethyl)chromen-4-one. A solution of 8-bromo-2-(4,4-dimethyl-1-piperidyl)-6-methyl-chromen-4-one (1.40 g, 1 eq, 4.00 mmol) in THF (20 mL) was cooled to 0° C. under argon. Isopropylmagnesium chloride (2.30 mL, 2 M in THF, 1.15 eq, 4.60 mmol) was added dropwise. This mixture was stirred at 0° C. for 30 min, then cooled to −78° C. 2,2,2-trifluoro-N-methoxy-N-methylacetamide (785 mg, 1.25 eq, 5.00 mmol) was added in portions. This mixture was stirred from −78° C. to room temperature for 12 h. The reaction was quenched with water and concentrated to dryness under reduced pressure. Purification by silica gel flash column chromatography (3% MeOH/DCM) afforded a crude mixture of 2-(4,4-dimethyl-1-piperidyl)-6-methyl-8-(2,2,2-trifluoro-1,1-dihydroxy-ethyl)chromen-4-one and 2-(4,4-dimethyl-1-piperidyl)-6-methyl-8-(2,2,2-trifluoro-1-hydroxy-1-methoxy-ethyl)chromen-4-one as a pale orange solid (1.17 g). MS ES+ m/z 386, 400 [M+H]. The crude mixture was dissolved in MeOH/DCM (1:1, 10 mL) and cooled to 0° C. NaBH$_4$ (103 mg, 1.5 eq, 2.72 mmol) was added in portions over 10 min. This mixture was stirred at 0° C. for 30 min, then at room temperature for 12 h. The reaction was quenched with water and concentrated to dryness under reduced pressure. Purification by silica gel flash column chromatography (3% MeOH/DCM) gave the product as a white solid (570 mg, 72%). MS ES+m/z 370 [M+H].

Step 2: 8-(1-bromo-2,2,2-trifluoro-ethyl)-2-(4,4-dimethyl-1-piperidyl)-6-methyl-chromen-4-one. To a solution of 2-(4,4-dimethyl-1-piperidyl)-6-methyl-8-(2,2,2-trifluoro-1-hydroxy-ethyl)chromen-4-one (120 mg, 1 eq, 325 μmol) in DCM (2 mL) was added triphenyl phosphite (202 mg, 2 eq, 650 μmol) and NBS (116 mg, 2 eq, 650 μmol). The mixture was stirred at 40° C.; after 3.5 h, another equivalent of NBS was added (108 mg, 1 eq, 325 μmol), then stirred at this temperature for a total of 12 h. The reaction was quenched with water and concentrated to dryness under reduced pressure. Purification by silica gel flash column chromatography (3% MeOH/DCM) gave the product as a pale orange solid (70 mg, 35%). MS ES+ m/z 432 434 [M+H].

Step 3: 2-[[1-[2-(4,4-dimethyl-1-piperidyl)-6-methyl-4-oxo-chromen-8-yl]-2,2,2-trifluoro-ethyl]amino]benzoic acid 2,2,2-trifluoroacetic acid. To a solution of 8-(1-bromo-2,2,2-trifluoro-ethyl)-2-(4,4-dimethyl-1-piperidyl)-6-methyl-chromen-4-one (70 mg, 1 eq, 0.16 mmol) in DMF (2 mL) was added 2-aminobenzoic acid (44 mg, 2 eq, 0.32 mmol). This mixture was stirred at 125° C. for 2 h. The reaction was quenched with water and concentrated to dryness under reduced pressure. Purification by preparative reverse phase HPLC (CH$_3$CN/H$_2$O/TFA) gave 2-[[1-[2-(4,4-dimethyl-1-piperidyl)-6-methyl-4-oxo-chromen-8-yl]-2,2,2-trifluoro-ethyl]amino]benzoic acid 2,2,2-trifluoroacetic acid as a white solid (9 mg, 9%). MS ES+ m/z 489 [M+H].

PI3K-Alpha kinase (PIK3CA) activity, wild-type and H1047R mutant and determining IC50 values for inhibitors Recombinant, catalytically active human full length PIK3KA Wild-type and H1047R mutant were purchased as 1:1 complex of N-terminal 6×his tagged p110<(catalytic) and untagged p85<(regulatory subunit) from EMD Millipore Sigma (cat. no. 14-602M and 14-792M, respectively). The enzyme stocks were diluted to 5× stocks in buffer (20 mM HEPES pH 7.4, 100 mM NaCl, 0.5 mM EGTA, 0.01% triton-x-100) just before use. PIP2diC8 (Avanti Polar Lipids Inc., cat. no. 850185) or phosphoinositol-4,5-bisphosphate with phosphoserine (PIP2:PS) membrane (Thermo Fisher Scientific, cat. no. PV5100) was used as lipid substrates. PIP2diC8 lyophilized powder and PIP2:PS (1:19) membrane stock (1 mM in PIP2) were separately dissolved in milliQ water to a concentration of 250 uM and stored in −20° C. 10 mM stocks of compounds were serially diluted (3×) in neat DMSO and stored in a dessicator at room temperature. 5× compound stocks in 25% DMSO were prepared fresh from neat DMSO stocks. Wild-type (WT) and H1047R mutant protein, along with buffer components (except ATP), were incubated with or without compound at 27° C. for 1h. After incubation, the reaction was initiated by the addition of 5 uL of 125 uM ATP. A typical assay mixture (25 uL) comprised 40 mM HEPES buffer, pH 7.4, 25 mM MgCl$_2$, 0.01% v/v triton-X-100, 5% v/v DMSO, 20 mM NaCl, 1-5 nM wt or H1047R, 25 uM ATP, and 50 uM PTP2diC8 or PTP2 in membrane. The reaction was allowed to proceed until about 1000 conversion (2.5 uM ADP) after which time, 10 uL of reaction mixture was quenched with 25 uL of transcreener reagent (Transcreener ADP2 FI assay kit, BellBrook labs, Cat. No. 3013). The contents were incubated at rt for 1h and fluorescence was measured using a plate reader (Paradigm, Molecular Devices). The same assay was also run at pH 6.0 or 6.4 using MOPS buffer (Fisher BioReagents, CAS 1132-61-2). A calibration curve was generated under identical buffer conditions with varying ADP amounts. Using that, the observed fluorescence was converted to uM ADP. A plot between [ADP] and log[I] yielded the dose-response curves that enabled the calculation of IC$_{50}$s.

For IC$_{50}$ values shown in Table A, "A" means IC$_{50}$<0.5 μM; "B" means IC$_{50}$ ranging between 0.5 μM and 1.0 μM; "C" means IC$_{50}$ ranging between 1 μM and 5 μM; "D" means IC$_{50}$ ranging between 5 μM and 10 μM; "E" means IC$_{50}$>10 μM.

TABLE A

| PI3K-α (PIK3CA) Biochemical IC$_{50}$ of PI3K wild-type (WT) and H1047R mutant | | |
|---|---|---|
| Example # | IC$_{50}$ WT | IC$_{50}$ H1047R |
| 1 | E | C |
| 4 | C | C |
| 5 | E | E |
| 6 | E | A |
| 8 | E | E |
| 11 | E | E |

TABLE A-continued

PI3K-α (PIK3CA) Biochemical
IC$_{50}$ of PI3K wild-type (WT) and H1047R mutant

| Example # | IC$_{50}$ WT | IC$_{50}$ H1047R |
|---|---|---|
| 19 | B | A |
| 20 | B | A |
| 29 | C | C |
| 33 | E | E |
| 38 | B | B |
| 39 | E | C |
| 45 | C | B |
| 46 | C | B |
| 50 | C | B |
| 51 | C | A |
| 53 | B | A |
| 54 | E | E |
| 55 | C | A |
| 57 | C | B |
| 61 | E | C |
| 63 | E | A |
| 65 | D | A |
| 68 | E | C |
| 74 | D | B |
| 76 | D | B |
| 77 | E | A |
| 82 | E | C |
| 85 | C | C |
| 88 | D | A |
| 93 | D | B |
| 96 | C | B |
| 105 | D | A |
| 107 | D | C |
| 111 | E | E |
| 112 | C | B |
| 117 | E | C |
| 123 | B | A |
| 124 | E | D |
| 126 | E | B |
| 130 | C | A |
| 151 | C | B |
| 163 | E | C |
| 169 | E | C |
| 171 | B | A |
| 177 | C | A |
| 189 | C | A |
| 194 | E | B |
| 203 | C | A |
| 212 | B | A |
| 222 | C | A |
| 233 | C | A |
| 236 | B | A |
| 237 | E | D |
| 238 | E | C |
| 244 | D | E |
| 245 | B | A |
| 251 | C | C |
| 256 | A | A |
| 265 | C | A |
| 272 | B | A |
| 274 | A | A |
| 286 | A | A |
| 288 | B | A |
| 289 | B | A |
| 296 | C | B |
| 297 | C | A |
| 298 | A | A |
| 299 | B | A |
| 300 | A | A |
| 301 | A | A |
| 302 | B | A |
| 305 | A | A |
| 306 | A | A |
| 308 | A | A |
| 309 | A | A |
| 310 | A | A |
| 319 | B | A |
| 324 | A | A |
| 326 | A | A |
| 328 | A | A |
| 335 | B | A |
| 338 | A | A |
| 342 | A | A |
| 343 | B | A |
| 348 | B | A |
| 349 | A | A |
| 357 | E | E |
| 362 | B | A |
| 370 | E | A |
| 371 | E | C |
| 373 | E | B |
| 376* | C | A |
| 380 | E | C |
| 392 | B | B |
| 396 | C | A |
| 398 | C | A |
| 399 | C | A |
| 400 | A | A |
| 425 | C | A |

*For Example 376: IC$_{50}$ WT/IC$_{50}$ H1047R = 13.5

For EC$_{50}$ values shown in Table B, "A" means EC$_{50}$<1.0 μM; "B" means EC$_{50}$ ranging between 1.0 μM and 5.0 μM; "C" means EC$_{50}$ ranging between 5 μM and 15 μM; "D" means EC$_{50}$ ranging between 15 μM and 24 μM; "E" means EC$_{50}$>24 μM.

TABLE B

Cellular Assay

| Example # | Avg T-47D EC$_{50}$ |
|---|---|
| 1 | D |
| 6 | B |
| 7 | C |
| 10 | D |
| 11 | D |
| 12 | E |
| 13 | D |
| 14 | B |
| 15 | C |
| 16 | E |
| 17 | E |
| 18 | D |
| 19 | D |
| 20 | D |
| 21 | C |
| 23 | C |
| 24 | E |
| 32 | E |
| 36 | C |
| 37 | D |
| 77 | E |
| 78 | E |
| 79 | B |
| 89 | E |
| 90 | D |
| 91 | E |
| 92 | E |
| 93 | C |
| 94 | C |
| 95 | E |
| 96 | B |
| 98 | E |
| 126 | E |
| 130 | B |
| 358 | A |
| 363 | B |
| 366 | B |
| 368 | D |
| 369 | E |

TABLE B-continued

| Cellular Assay | |
|---|---|
| Example # | Avg T-47D EC$_{50}$ |
| 370 | B |
| 375 | E |
| 376 | B |
| 377 | E |
| 379 | E |
| 380 | E |
| 381 | E |
| 383 | B |

TABLE C

| | Selectivity against selected lipid kinases | | | | | |
|---|---|---|---|---|---|---|
| Example # | Avg PI3K-B IC50: (nM) | Avg PI3K-D IC50 (nM): | Avg PI3K-G IC50: (nM) | Avg Vps34 IC50: (nM) | Avg DNA-PK IC50: (nM) | Avg mTOR IC50: (nM) |
| 363 | 110 | >10,000 | >10,000 | 450 | 980 | 7800 |
| 366 | >10,000 | >10,000 | >10,000 | >10,000 | >10,000 | >10,000 |

TABLE D

Mouse PK Assays: The compounds show good oral bioavailability in animal models.

| Example # | 363 | | | 366 | |
|---|---|---|---|---|---|
| PK-Mouse: IV Dose (mg/kg) | 1 | | | 1 | |
| PK-Mouse: IV Cl (mL/min/kg) | 8.2 | | | 43 | |
| PK-Mouse: IV-AUC-0-last (ng*h/mL) | 2130 | | | 343 | |
| PK-Mouse: PO Dose (mg/kg) | 10 | 50 | 10 | 50 | 100 |
| PK-Mouse: PO Vehicle | 20% DMSO/ 60% PEG400/ 20% Water Solution | 20% DMSO/ 60% PEG400/ 20% Water Solution | 30% SBE-beta-cyclodextrin Solution | 20% DMSO/ 60% PEG400/ 20% H2O Solution | 20% DMSO/ 60% PEG400/ 20% H2O Solution |
| PK-Mouse: PO Vehicle appearance | | | | | |
| PK-Mouse: PO Cmax (ng/mL) | 1300 | 5100 | 350 | 8.56 | 22.6 |
| PK-Mouse: PO AUC-0-last (ng*h/mL) | 18,000 | 31,000 | 3.9 | 48 | 76 |
| PK-Mouse: PO F (%) | 87 | 33 | | 100 | |
| PK-Mouse: F % Calcd (%) | 86 | 33 | 110 | 280 | 220 |
| PK-Mouse: PO AUC-last/dose | 1800 | 700 | 390 | 960 | 760 |
| PK-Mouse: PO observations | Fed | Fed | Fed | Fed | Fed |

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs.

The foregoing description has been presented only for the purposes of illustration and is not intended to limit the disclosure to the precise form disclosed, but by the claims appended hereto.

The invention claimed is:

1. A compound of the Formula:

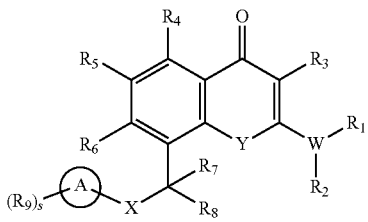

or a prodrug, solvate, enantiomer, stereoisomer, tautomer, or pharmaceutically acceptable salt thereof, wherein:

X is $-NR_{12}-$ or $-O-$;

Y is $-C(R_{11})_2-$, $-O-$, $-NR_{11}-$, or $-S-$;

$WR_1R_2$ is a group of the formula:

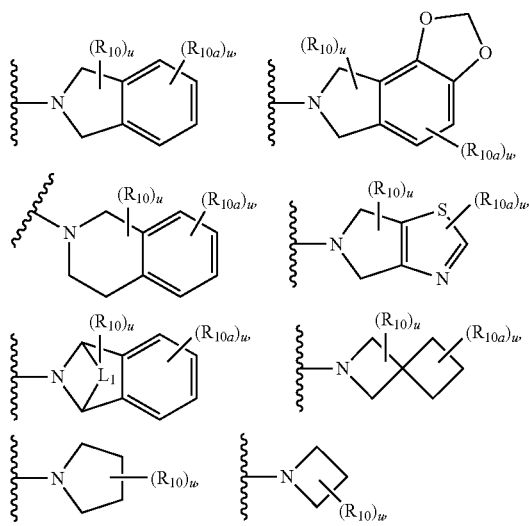

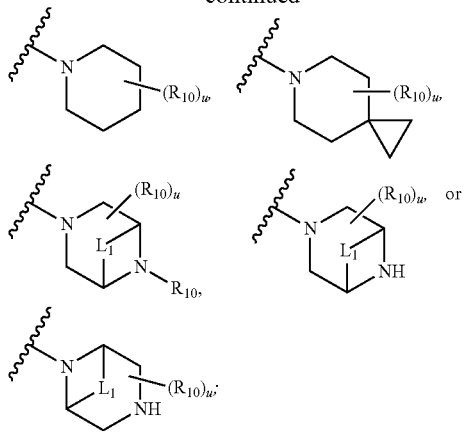

$R_{10}$ at each occurrence is independently oxo, halogen, $-CN$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $-(CH_2)_n-OR_{12}$, $-(CH_2)_n-N(R_{12})_2$, $-(CH_2)_n-C(O)R_{12}$, $-(CH_2)_n-C(O)OR_{12}$, $-(CH_2)_n-C(O)N(R_{12})_2$, $-(CH_2)_n-SO_2R_{12}$, $-(CH_2)_n-O-(CH_2CH_2-O)_rR_{13}$, $C_3$-$C_{10}$ cycloalkyl, heterocycle, $-(CH_2)_n$-aryl, or heteroaryl, wherein the cycloalkyl, heterocycle, aryl, and heteroaryl is optionally substituted with halogen, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, or $-(CH_2)_n-SO_2R_{12}$;

$R_{10a}$ at each occurrence is independently halogen, $-CN$, $C_1$-$C_6$ alkyl, $C_1$-$C_6$ haloalkyl, $C_1$-$C_6$ alkoxy, or $-(CH_2)_n-OR_{12}$;

-$L_1$- is $-(CH_2)-$ or $-(CH_2)_2-$;

u at each occurrence is independently 0, 1, 2, 3 or 4;

each $R_3$, $R_4$, $R_5$, and $R_6$ is independently H, halogen, $-CN$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $-(CH_2)_m-R_{12}$, $-(CH_2)_m-OR_{12}$, $-(CH_2)_m-N(R_{12})_2$, $-(CH_2)_m-C(O)R_{12}$, $-(CH_2)_m-C(O)OR_{12}$, $-(CH_2)_m-C(O)N(R_{12})_2$, $C_3$-$C_{10}$ cycloalkyl, aryl, heterocycle comprising 1-4 heteroatoms selected from O, N, and S, or heteroaryl comprising 1-4 heteroatoms selected from O, N, and S;

each $R_7$ and $R_8$ is independently H, halogen, —CN, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;
at least one $R_9$ is —C(O)OR$_{12}$ and
each of the remaining $R_9$ at each occurrence is independently oxo, =NR$_{11}$, halogen, —CN, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_m$—N(R$_{12}$)$_2$, —(CH$_2$)$_m$—OR$_{12}$, —(CH$_2$)$_m$—CR$_{13}$(OH)—R$_{12}$, —(CH$_2$)$_m$—C(O)R$_{12}$, —(CH$_2$)$_m$—C(O)OR$_{12}$, —(CH$_2$)$_m$—C(O)N(R$_{12}$)$_2$, —(CH$_2$)$_m$—C(O)N(OH)R$_{12}$, —(CH$_2$)$_m$—SO$_2$R$_{12}$, —(CH$_2$)$_m$—SO$_2$—OR$_{12}$, —(CH$_2$)$_m$—SO$_2$N(R$_{12}$)$_2$, —(CH$_2$)$_m$—P(O)(OR$_{12}$)$_2$, —(CH$_2$)$_m$—P(O)(R$_{12}$)$_2$, —(CH$_2$)$_m$—P(O)(OR$_{13}$)R$_{12}$, —(CH$_2$)$_m$—B(OH)$_2$, —(CH$_2$)$_m$—B(R$_{12}$)$_2$, —(CH$_2$)$_m$ O—(CH$_2$CH$_2$—)$_r$R$_{13}$, —(CH$_2$)$_m$—NR$_{12}$—(CH$_2$CH$_2$—)$_r$R$_{13}$, —(CH$_2$)$_m$—C(O)—(CH$_2$CH$_2$—)$_r$R$_{13}$, —(CH$_2$)$_m$—C(O)O—(CH$_2$CH$_2$—O)$_r$R$_{13}$, —(CH$_2$)$_m$—C(O)NR$_{12}$—(CH$_2$CH$_2$—O)$_r$R$_{13}$, —(CH$_2$)$_m$—C(O)—NR$_{12}$—SO$_2$R$_{13}$, —(CH$_2$)$_m$—SO$_2$NR$_{12}$—C(O)R$_{13}$, —(CH$_2$)$_m$—S(O)(NR$_{12}$)—R$_{13}$, $C_3$-$C_{10}$ cycloalkyl, aryl, heterocycle comprising 1-4 heteroatoms selected from O, N, and S, or heteroaryl comprising 1-4 heteroatoms selected from N, O, and S, wherein the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, aryl, heterocycle, or heteroaryl is optionally substituted with one or more oxo, halogen, —CN, —OH, —NH$_2$, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy; or two $R_9$, together with the atoms to which they are attached form a $C_3$-$C_{10}$ cycloalkyl, an aryl, or a heterocycle comprising 1-4 heteroatoms selected from O, N, and S, wherein the cycloalkyl, aryl or heterocycle is optionally substituted with one or more oxo, halogen, —CN, —OH, —NH$_2$, =NH, —NO$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;
$R_{11}$ is H, $C_1$-$C_6$ alkyl, $C_2$-$C_6$ alkenyl, or $C_2$-$C_6$ alkynyl;
each $R_{12}$ and $R_{13}$ at each occurrence is independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —(CH$_2$)$_q$—O—C(O)—(CH$_2$)$_r$—R$_{14}$, —(CH$_2$)$_q$—NH—C(O)—(CH$_2$)$_r$—R$_{14}$, —(CH$_2$)$_q$—O—C(O)—(CH$_2$)$_r$—OR$_{14}$, —(CH$_2$)$_q$—NH—C(O)—(CH$_2$)$_r$—OR$_{14}$, —(CH$_2$)$_q$—O—(CH$_2$)$_r$—R$_{14}$, —(CH$_2$)$_q$—NH—(CH$_2$)$_r$—R$_{14}$, —(CH$_2$)$_q$—O—(CH$_2$)$_r$—OR$_{14}$, —(CH$_2$)$_q$—NH—(CH$_2$)$_r$—OR$_{14}$, $C_3$-$C_{10}$ cycloalkyl, heterocycle comprising 1-4 heteroatoms selected from O, N, and S, —(CH$_2$)$_q$-aryl, or heteroaryl comprising 1-4 heteroatoms selected from N, O, and S, wherein the cycloalkyl, heterocycle, aryl, and heteroaryl are optionally substituted with one or more halogen, $C_1$-$C_6$ alkyl, $C_1$-$C_6$ haloalkyl, $C_1$-$C_6$ alkoxy, or $C_1$-$C_6$ haloalkoxy;
Ring A is $C_3$-$C_{10}$ cycloalkyl, aryl, heterocycle comprising 1-4 heteroatoms selected from N, O, and S, or heteroaryl comprising 1-4 heteroatoms selected from N, O, and S;
$R_{14}$ is

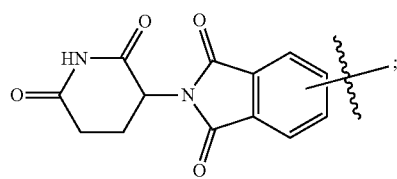

each n, m, q, or r, is independently at each occurrence 0, 1, 2, 3, 4, 5, or 6; and
s is 1, 2, 3, 4, 5, or 6.

2. The compound of claim 1, or a prodrug, solvate, enantiomer, stereoisomer, tautomer, or pharmaceutically acceptable salt thereof, having the Formula:

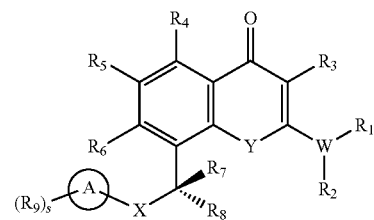

wherein
$R_7$ is halogen, —CN, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy; and
$R_8$ is H.

3. The compound of claim 1, or a prodrug, solvate, enantiomer, stereoisomer, tautomer, or pharmaceutically acceptable salt thereof, wherein X is —NR$_{12}$—, and Y is —O—.

4. The compound of claim 1, or a prodrug, solvate, enantiomer, stereoisomer, tautomer, or pharmaceutically acceptable salt thereof, wherein each $R_3$, $R_4$, $R_5$, and $R_6$ is independently H, halogen, —CN, $C_1$-$C_6$ alkyl, $C_1$-$C_6$ haloalkyl, $C_1$-$C_6$ alkoxy, —(CH$_2$)$_m$—OR$_{12}$, —(CH$_2$)$_m$—N(R$_{12}$)$_2$, —(CH$_2$)$_m$—C(O)R$_{12}$, $C_3$-$C_{10}$ cycloalkyl, aryl, heterocycle comprising 1-4 heteroatoms selected from O, N, and S, or heteroaryl comprising 1-4 heteroatoms selected from O, N, and S.

5. The compound of claim 1, or a prodrug, solvate, enantiomer, stereoisomer, tautomer, or pharmaceutically acceptable salt thereof, wherein $R_3$ is hydrogen.

6. The compound of claim 1, or a prodrug, solvate, enantiomer, stereoisomer, tautomer, or pharmaceutically acceptable salt thereof, wherein $R_3$ is —CN or $C_1$-$C_3$ alkyl.

7. The compound of claim 1, or a prodrug, solvate, enantiomer, stereoisomer, tautomer, or pharmaceutically acceptable salt thereof, wherein $R_4$ is H, halogen, $C_1$-$C_6$ alkyl or $C_1$-$C_6$ haloalkyl.

8. The compound of claim 1, or a prodrug, solvate, enantiomer, stereoisomer, tautomer, or pharmaceutically acceptable salt thereof, wherein $R_5$ is H, halogen, methyl or trifluoromethyl.

9. The compound of claim 1, or a prodrug, solvate, enantiomer, stereoisomer, tautomer, or pharmaceutically acceptable salt thereof, wherein $R_7$ is $C_1$-$C_3$ alkyl and $R_8$ is H.

10. The compound of claim 1, or a prodrug, solvate, enantiomer, stereoisomer, tautomer, or pharmaceutically acceptable salt thereof, wherein Ring A is a group of the formula:

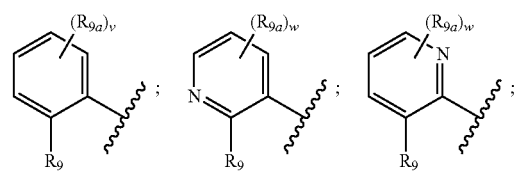

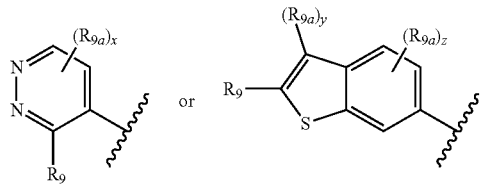

wherein $R_9$ is —C(O)OH, $R_{9a}$ is halogen, $C_1$-$C_3$ alkyl, $C_1$-$C_3$ haloalkyl, $C_1$-$C_3$ alkoxy, or $C_3$-$C_5$ cycloalkyl, v is 0, 1, or 2, w is 0, 1, or 2, x is 0 or 1, y is 0 or 1, and z is 0, 1, or 2.

11. The compound of claim 1, or a prodrug, solvate, enantiomer, stereoisomer, tautomer, or pharmaceutically acceptable salt thereof, wherein Ring A is a group of the formula:

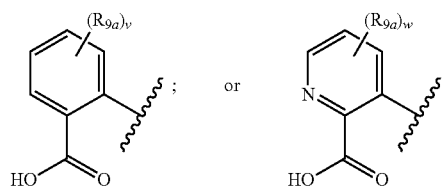

wherein $R_{9a}$ is halogen or trifluoromethyl; v is 0 or 1; and w is 0 or 1.

12. The compound of claim 1 selected from:

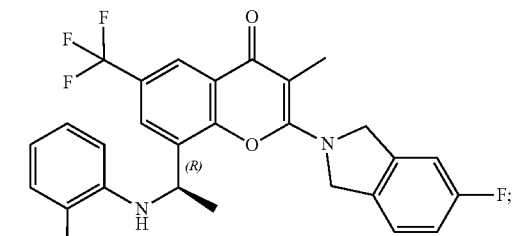

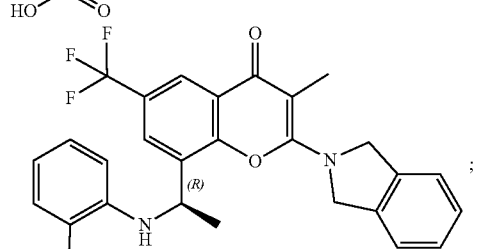

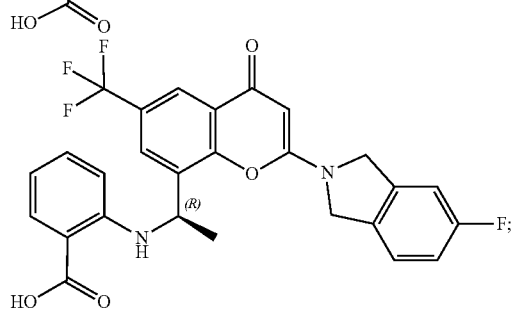

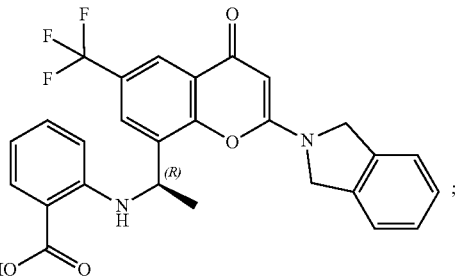

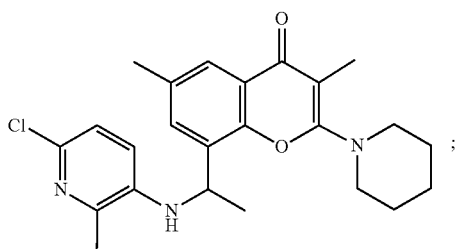

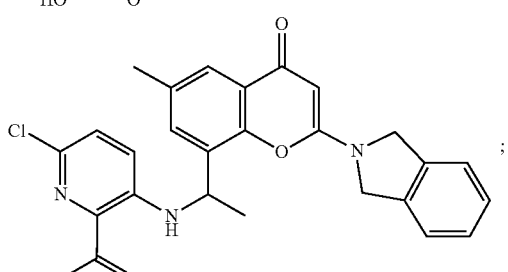

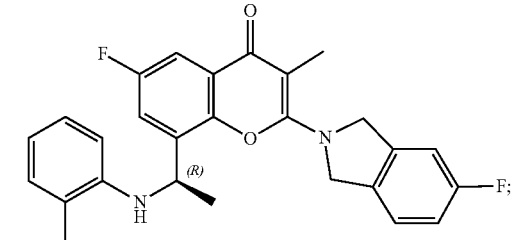

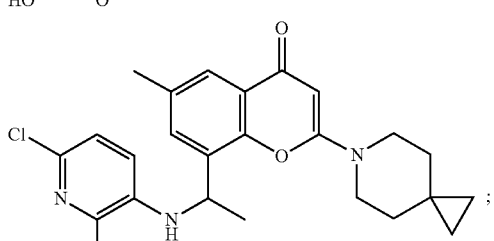

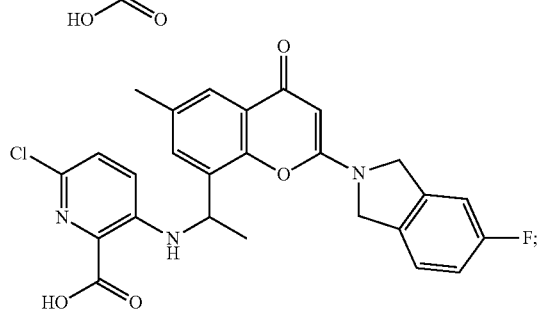

481
-continued
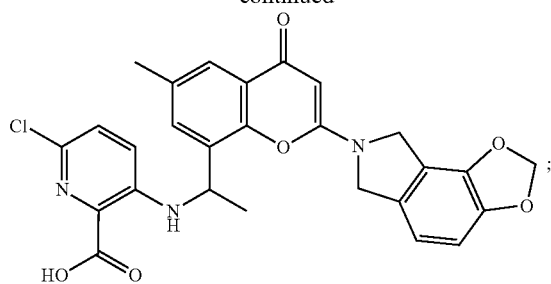
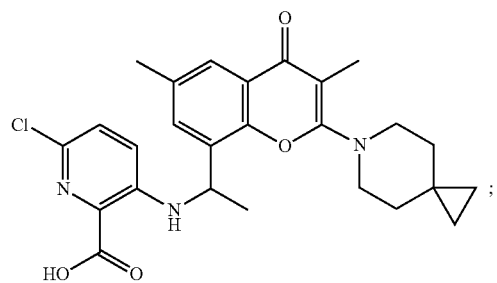
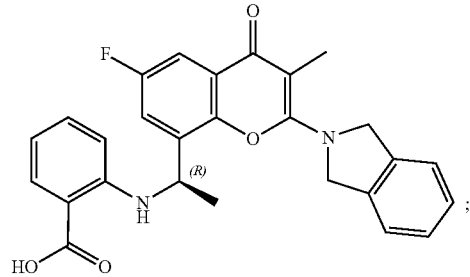
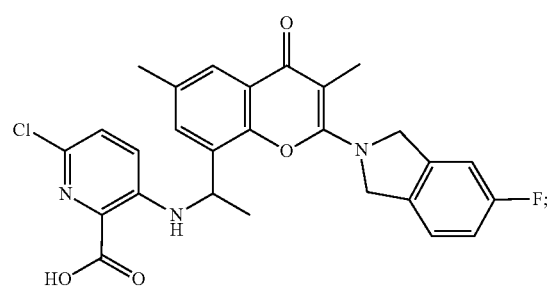
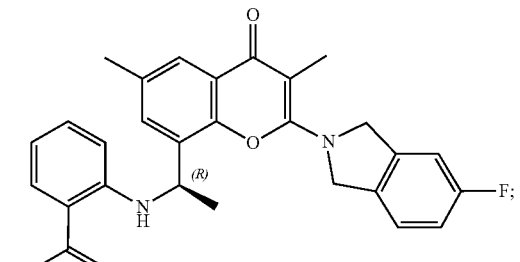
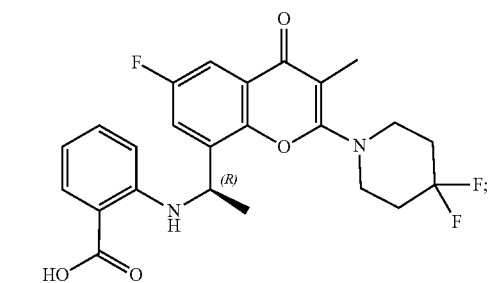
482
-continued
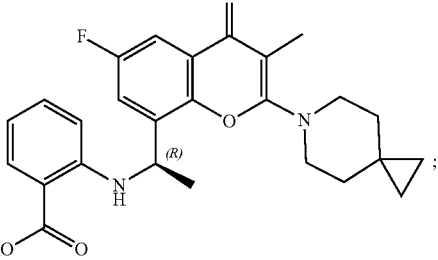
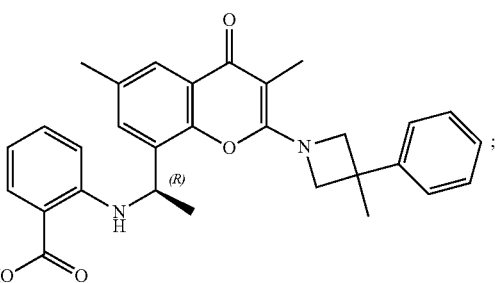
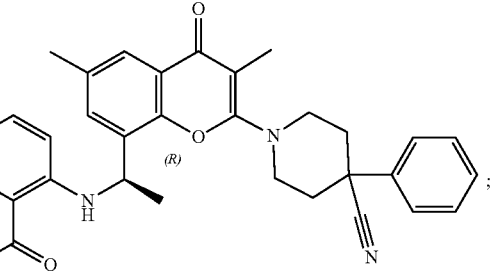
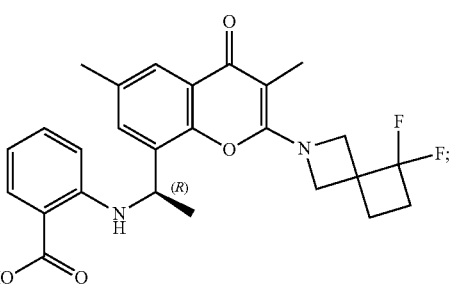
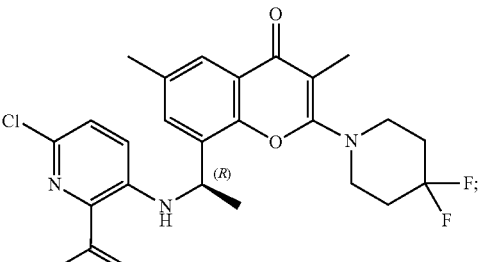
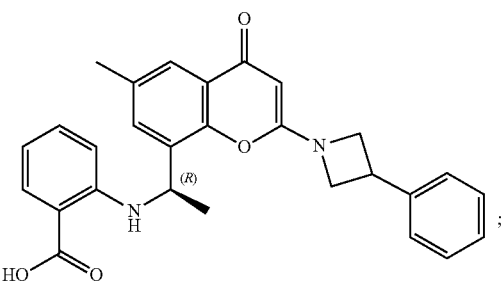

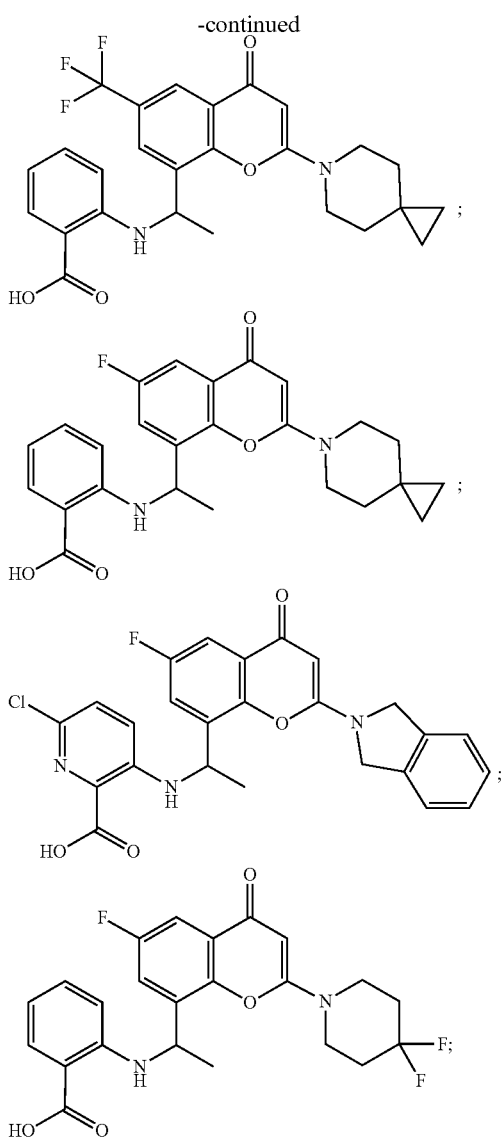

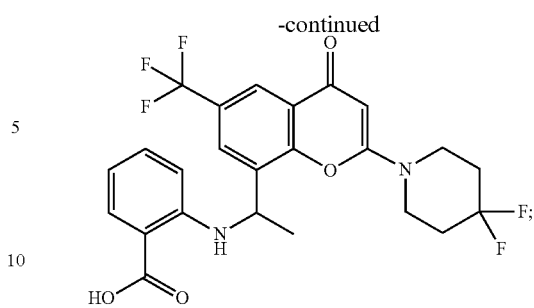

or a prodrug, solvate, enantiomer, stereoisomer, tautomer, or a pharmaceutically acceptable salt thereof.

13. A pharmaceutical composition comprising, a compound of claim 1, and a pharmaceutically acceptable carrier.

14. A method of treating a disease or disorder associated with modulation of phosphoinositide 3-kinase (PI3K), comprising administering to a patient in need thereof a therapeutically effective amount of a compound of claim 1.

15. The method of claim 14, wherein the PI3K is PI3Kα.

16. The method of claim 14, wherein the PI3K associated with the disease or disorder has a H1047R mutation.

17. The method of claim 14, wherein the disease or disorder is a cancer.

18. The method of claim 17 wherein the cancer is endometrial cancer, gastric cancer, leukemia, lymphoma, sarcoma, colorectal cancer, lung cancer, ovarian cancer, skin cancer, head and neck cancer, breast cancer, brain cancer, or prostate cancer.

19. The method of claim 14, wherein the disease or disorder is CLOVES syndrome (congenital lipomatous overgrowth, vascular malformations, epidermal naevi, scoliosis/skeletal and spinal syndrome), or PIK3CA-related overgrowth syndrome (PROS).

20. A method of inhibiting phosphoinositide 3-kinase (PI3K), comprising administering to a patient in need thereof a therapeutically effective amount of a compound of claim 1.

* * * * *

UNITED STATES PATENT AND TRADEMARK OFFICE
CERTIFICATE OF CORRECTION

PATENT NO. : 11,649,227 B2
APPLICATION NO. : 17/221209
DATED : May 16, 2023
INVENTOR(S) : Erin Danielle Anderson et al.

It is certified that error appears in the above-identified patent and that said Letters Patent is hereby corrected as shown below:

On the Title Page

Item (56)
Column 2, Line 5, delete "Biorganic" and insert -- Bioorganic --, therefor.

In the Claims

In Claim 1
Column 477, Line 10 (Approx.), delete "—$(CH_2)_m$ $C(O)N(R_{12})_2$," and insert
-- –$(CH_2)_m$-$C(O)N(R_{12})_2$, --, therefor.

In Claim 1
Column 477, Line 15 (Approx.), delete "—$(CH_2)_m$ O—$(CH_2CH_2$—$)_rR_{13}$," and insert
-- –$(CH_2)_m$-O-$(CH_2CH_2$-O$)_rR_{13}$, --, therefor.

In Claim 1
Column 477, Line 16 (Approx.), delete "—$(CH_2)_m$—$NR_{12}$—$(CH_2CH_2$—$)_rR_{13}$," and insert
-- –$(CH_2)_m$-$NR_{12}$-$(CH_2CH_2$-O$)_rR_{13}$, --, therefor.

In Claim 1
Column 477, Lines 16-17 (Approx.), delete "—$(CH_2)_m$—C(O)—$(CH_2CH_2$—$)_rR_{13}$," and insert
-- –$(CH_2)_m$-C(O)-$(CH_2CH_2$-O$)_rR_{13}$, --, therefor.

In Claim 1
Column 477, Line 44 (Approx.), delete "—$(CH_2)_q$ NH—$(CH_2)_r$—$R_{14}$," and insert
-- –$(CH_2)_q$-NH-$(CH_2)_r$-$R_{14}$, --, therefor.

In Claim 1
Column 477, Line 46 (Approx.), delete "$C_3$- $C_{10}$" and insert -- $C_3$-$C_{10}$ --, therefor.

Signed and Sealed this
Ninth Day of January, 2024

*Katherine Kelly Vidal*

Katherine Kelly Vidal
*Director of the United States Patent and Trademark Office*

CERTIFICATE OF CORRECTION (continued)
U.S. Pat. No. 11,649,227 B2

In Claim 12

Column 483, Line 39 (Approx.), after " 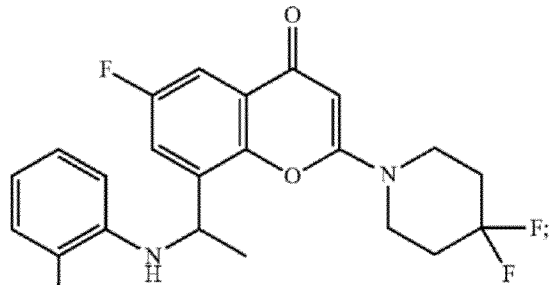 " insert -- or --.